US007947866B2

(12) United States Patent
Sparks

(10) Patent No.: US 7,947,866 B2
(45) Date of Patent: May 24, 2011

(54) GENE DISRUPTIONS, COMPOSITIONS AND METHODS RELATING THERETO

(75) Inventor: Mary Jean Sparks, Magnolia, TX (US)

(73) Assignee: Genentech, Inc., South San Francisco, CA (US)

( * ) Notice: Subject to any disclaimer, the term of this patent is extended or adjusted under 35 U.S.C. 154(b) by 889 days.

(21) Appl. No.: 11/577,547

(22) PCT Filed: Oct. 18, 2005

(86) PCT No.: PCT/US2005/037291
§ 371 (c)(1),
(2), (4) Date: Apr. 19, 2007

(87) PCT Pub. No.: WO2006/049854
PCT Pub. Date: May 11, 2006

(65) Prior Publication Data

US 2009/0196876 A1 Aug. 6, 2009

Related U.S. Application Data

(60) Provisional application No. 60/623,789, filed on Oct. 29, 2004.

(51) Int. Cl.
*G01N 33/00* (2006.01)

(52) U.S. Cl. ................................ 800/3; 800/11; 800/18

(58) Field of Classification Search ................ 800/3, 13, 800/14, 18

See application file for complete search history.

(56) References Cited

U.S. PATENT DOCUMENTS

| | | | | |
|---|---|---|---|---|
| 7,339,029 | B2 * | 3/2008 | Ren et al. | 530/350 |
| 2003/0104545 | A1 | 6/2003 | Baker et al. | |
| 2005/0163766 | A1 * | 7/2005 | Baker et al. | 424/130.1 |

FOREIGN PATENT DOCUMENTS

| | | |
|---|---|---|
| WO | WO 01/90304 | 11/2001 |

OTHER PUBLICATIONS

Yamada D, et al., Disruption of spermatogenic cell adhesion and male infertility in mice lacking TSLC1/IGSF4, an immunoglobulin superfamily cell adhesion molecule Mol Cell Biol. May 2006;26(9):3610-24.*

Result 7 , Score Search Results Details for Application 11577547 and Search Result 20100428_114030_us-11-577-547-13.rni Result 7.*

Sanders Williamset al., Transgenic animals in integrative biology: approaches and interpretations of outcome. Appl Physiol 88: 1119-1126, 2000.*

Sigmund. Viewpoint: are studies in genetically altered mice out of control? Arterioscler Thromb Vasc Biol. Jun. 2000;20(6):1425-9. Review.*

Moreadith RW,Gene targeting in embryonic stem cells: the new physiology and metabolism. J Mol Med. Mar. 1997;75(3):208-16.*

Keefer, Production of bioproducts through the use of transgenic animal models. Anim Reprod Sci. Jul. 2004;82-83:5-12. Review.*

Database Geneseq—Derwent—Jun. 25, 1999—XP002507244.

Database Geneseq—Derwent—Jun. 5, 2000—XP002507245.

Database Geneseq—Derwent—May 24, 2002—XP002507246.

Database Geneseq—Derwent—Nov. 20, 2003—XP002507247.

Abu-Elheiga, L. et al., "Continuous Fatty Acid Oxidation and Reduced Fat Storage in Mice Lacking Acetyl-CoA Carboxylase 2" *Science* 291(5513):2613-16 (Mar. 30, 2001).

The ADHR Consortium, "Autosomal dominant hypophosphataemic rickets is associated with mutations in FGF23" *Nat Genet.* 26(3):345-348 (Nov. 2000).

Agnel et al., "Identification of three novel members of the calcium-dependent chloride channel (CaCC) family predominantly expressed in the digestive tract and trachea" *FEBS Letters* 455(3):295-301 (Jul. 23, 1999).

Arrate et al., "Cloning of human junctional adhesion molecule 3 (JAM3) and its identification as the JAM2 counter-receptor" *J Biol Chem.* 276(49):45826-45832 (Dec. 7, 2001).

Birkenbach et al., "Epstein-Barr virus-induced genes: first lymphocyte-specific G protein-coupled peptide receptors" *J Virol.* 67(4):2209-2220 (Apr. 1993).

Bowe et al., "FGF-23 inhibits renal tubular phosphate transport and is a PHEX substrate" *Biochem Biophys Res Commun.* 284(4):977-981 (Jun. 22, 2001).

Cahir-McFarland et al., "Role of NF-kappa B in cell survival and transcription of latent membrane protein 1-expressing or Epstein-Barr virus latency III-infected cells" *J Virol.* 78(8):4108-4119 (Apr. 2004).

Carson-Walter et al., "Cell surface tumor endothelial markers are conserved in mice and humans" *Cancer Research* 61(18):6649-6655 (Sep. 15, 2001).

Chavakis et al., "Leukocyte trans-endothelial migration: JAMs add new pieces to the puzzle" *Thromb Haemost.* 89(1):13-17 (Jan. 2003).

Choi et al., "Identification and characterization of ADAM32 with testis-predominant gene expression" *Gene* 304:151-62 (Jan. 30, 2003).

Chuang and McMahon, protein"Vertebrate Hedgehog signalling modulated by induction of a Hedgehog-binding protein" *Nature* 397(6720):617-621 (Feb. 18, 1999).

Chuang et al., "Feedback control of mammalian Hedgehog signaling by the Hedgehog-binding protein, Hipl, modulates Fgf signaling during branching morphogenesis of the lung" *Genes Dev.* 17(3):342-327 (Feb. 1, 2003).

(Continued)

*Primary Examiner* — Maria Leavitt

(74) *Attorney, Agent, or Firm* — Bonny Yeung; Christopher De Vry; Arnold & Porter LLP

(57) ABSTRACT

The present invention relates to transgenic animals, as well as compositions and methods relating to the characterization of gene function. Specifically, the present invention provides transgenic mice comprising disruptions in PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 genes. Such in vivo studies and characterizations may provide valuable identification and discovery of therapeutics and/or treatments useful in the prevention, amelioration or correction of diseases or dysfunctions associated with gene disruptions such as neurological disorders; cardiovascular, endothelial or angiogenic disorders; eye abnormalities; immunological disorders; oncological disorders; bone metabolic abnormalities or disorders; lipid metabolic disorders; or developmental abnormalities.

3 Claims, 84 Drawing Sheets

OTHER PUBLICATIONS

Clark et al., "The secreted protein discovery initiative (SPDI), a large-scale effort to identify novel human secreted and transmembrane proteins: a bioinformatics assessment" *Genome Research* 13(10):2265-2270 (Oct. 2003).
Coulombe et al., "Hedgehog interacting protein in the mature brain: membrane-associated and soluble forms" *Mol Cell Neurosci.* 25(2):323-333 (Feb. 2004).
Cunningham et al., "Cloning of an epithelial chloride channel from bovine trachea" *J Biol Chem.* 270(52):31016-31026 (Dec. 29, 1995).
Cunningham et al., "JAM2 interacts with alpha4betal. Facilitation by JAM3" *J Biol Chem.* 277(31):27589-27592 (Aug. 2, 2002).
Dandoy-Dron et al., "Gene expression in scrapie. Cloning of a new scrapie-responsive gene and the identification of increased levels of seven other mRNA transcripts" *Biol Chem.* 273(13):7691-7697 (Mar. 27, 1998).
Dandoy-Dron et al., "Scrgl, a novel protein of the CNS is targeted to the large dense-core vesicles in neuronal cells" *Eur J Neurosci.* 18(9):2449-2459 (Nov. 2003).
Davis et al., "Identification of a family of Fc receptor homologs with preferential B cell expression" *Proc Natl Acad Sci U S A.* 98(17):9772-9777 (Aug. 14, 2001).
DeLorey, T.M. et al., "Mice lacking the β3 subunit of the GABAA receptor have the epilepsy phenotype and many of the behavorial characteristics of Angelman syndrome" *J Neurosci.* 18(20):8505-14 (Oct. 15, 1998).
Dron et al., "Characterization of the human analogue of a Scrapie-responsive gene" *J Biol Chem.* 273(29):18015-18018 (Jul. 17, 1998).
Dron et al., "Mouse scrapie responsive gene 1 (Scrgl): genomic organization, physical linkage to sap30, genetic mapping on chromosome 8, and expression in neuronal primary cell cultures" *Genomics* 70(1):140-149 (Nov. 15, 2000).
Duffy et al., "The ADAMs family of proteins: from basic studies to potential clinical applications" *Thromb Haemost.* 89(4):622-631 (Apr. 2003).
Escarceller et al., "Identification and expression analysis of C3orf1, a novel human gene homologous to the Drosophila RP140-upstream gene" *DNA Seg.* 11(3-4):335-338 (2000).
Esther, R.C. et al., "Mice Lacking angiotensin-converting enzyme have low blood pressure, renal pathology, and reduced male fertility" *Laboratory Investigation* 74(5):953-65 (May 1996).
Evers et al., "Molecular cloning and characterization of a dermatan-specific N-acetylgalactosamine 4-O-sulfotransferase" *J Biol Chem.* 276(39):36344-36353 (Sep. 28, 2001).
Feinberg et al., "Transport of dsRNA into cells by the transmembrane protein SID-1" *Science* 301(5639):1545-1547 (Sep. 12, 2003).
Fransson et al., "Glypicans" *Int J Biochem Cell Biol.* 35(2):125-129 (Feb. 2003).
Fu et al., "Fibroblast Growth Factor 19 Increases Metabolic Rate and Reverses Dietry and Leptin-Deficient Diabetes" *Endocrinology* 145(6):2594-2603 (Jun. 2004).
Fukamachi et al., "Neuronal leucine-rich repeat protein-3 amplifies MAPK activation by epidermal growth factor through a carboxyl-terminal region containing endocytosis motifs" *J Biol Chem.* 277(46):43549-43552 (Nov. 15, 2002).
Fukuhara et al., "Association of a lung tumor suppressor TSLC1 with MPP3, a human homologue of Drosophila tumor suppressor Dlg" *Oncogene* 22(40):6160-6165 (Sep. 18, 2003).
Galli et al., "Glypican 4 modulates FGF signalling and regulates dorsoventral forebrain patterning in Xenopus embryos" *Development* 130(20):4919-4929 (Oct. 2003).
Grigorenko et al., "Novel class of polytopic proteins with domains associated with putative protease activity" *Biochemistry (Mosc)* 67(7):826-35 (Jul. 2002).
Guselnikov et al., "A family of highly diverse human and mouse genes structurally links leukocyte FcR, gp42 and PECAM-1" *Immunogenetics* 54(2):87-95 (May 2002).
Harmer et al., "The Crystal Structure of Fibroblast Growth Factor (FGF) 19 Reveals Novel Features of the FGF Family and Offers a Structural Basis for its Unusual Receptor Affinity" *Biochemistry* 43(3):629-640 (Jan. 27, 2004).
Henry et al., "Expression pattern and gene characterization of asporin. a newly discovered member of the leucine-rich repeat protein family" *J Biol Chem.* 276(15):12212-12221 (Apr. 13, 2001).
Hickling et al., "Collectins and their role in lung immunity" *J Leukoc Biol.* 75(1):27-33 (Jan. 2004).
Himmelfarb et al., "ITIH5, a novel member of the inter-alpha-trypsin inhibitor heavy chain family is downregulated in breast cancer" *Cancer Lett.* 204(1):69-77 (Feb. 10, 2004).
Hochstrasser, "Evolution and function of ubiquitin-like protein-conjugation systems" *Nat Cell Biol.* 2(8):E153-157 (Aug. 2000).
Hochstrasser, "SP-RING for SUMO: new functions bloom for a ubiquitin-like protein" *Cell* 107(1):5-8 (Oct. 5, 2001).
Holt et al., "Definition of a novel growth factor-dependent signal cascade for the suppression of bile acid biosynthesis" *Genes Dev.* 17(13):1581-1591 (Jul. 1, 2003).
Ishii et al., "Carboxy-terminal cytoplasmic domain of mouse butyrophilin specifically associates with a 150-kDa protein of mammary epithelial cells and milk fat globule membrane" *Biochim Biophys Acta* . 1245(3):285-292 (Dec. 14, 1995).
Ishii et al., "Increased expression of NLRR-3 mRNA after cortical brain injury in mouse" *Brain Res Mol Brain Res.* 40(1):148-152 (Aug. 1996).
Ito et al., "Identification of a novel mouse membrane-bound family 1 glycosidase-like protein, which carries an atypical active site structure" *Biochim Biophys Acta.* 1576(3):341-345 (Jul. 19, 2002).
Ito at al., "Involvement of TSLC1 in progression of esophageal squamous cell carcinoma" *Cancer Research* 63(19):6320-6326 (Oct. 1, 2003).
Jack and Mather, "Cloning and analysis of cDNA encoding bovine butyrophilin, an apical glycoprotein expressed in mammary tissue and secreted in association with the milk-fat globule membrane during la" *J Biol Chem.* 265(24):14481-14486 (Aug. 25, 1990).
Jonsson et al., "Fibroblast growth factor 23 in oncogenic osteomalacia and X-linked hypophosphatemia" *N Engl J Med.* 348(17):1656-1663 (Apr. 24, 2003).
Karumanchi et al., "Cell surface glypicans are low-affinity endostatin receptors" *Mol Cell* 7(4):811-822 (Apr. 2001).
Kawahira et al., "Combined activities of hedgehog signaling inhibitors regulate pancreas development" *Development* 130(20):4871-4879 (Oct. 2003).
Komatsuzaki et al., "Modulation of G(ialpha(2)) signaling by the axonal guidance molecule UNC5H2" *Biochem Biophys Res Commun.* 297(4):898-905 (Oct. 4, 2002).
Kunjathoor et al., "Scavenger receptors class A-I/II and CD36 are the principal receptors responsible for the uptake of modified low density lipoprotein leading to lipid loading in macrophages" *J Biol Chem.* 275(51):49982-499988 (Dec. 20, 2002).
Ladher at al., "Identification of synergistic signals initiating inner ear development" *Science* 290(5498):1965-1967 (Dec. 8, 2000).
Lai et al., "Identification of novel human genes evolutionarily conserved in *Caenorhabditis elegans* by comparative proteomics" *Genome Res.* 10(5):703-713 (May 2000).
Langenbach, R. et al., "Prostaglandin Synthase 1 Gene Disruption in Mice Reduces Arachidonic Acid-Induced Inflammation and Indomethancin-Induced Gastric Ulceration" *Cell* 83(3):483-92 (Nov. 3, 1995).
Leonardo at al., "Vertebrate homologues of *C.elegans* UNC-5 are candidate netrin receptors" *Nature* 386(6627):833-838 (Apr. 24, 1997).
Liang at al., "Vascular endothelial-junctional adhesion molecule (VE-JAM)/JAM 2 interacts with T, NK, and dendritic cells through JAM 3" *J Immunol.* 168(4):1618-1626 (Feb. 15, 2002).
Lin et al., "The netrin-G1 ligand NGL-1 promotes the outgrowth of thalamocortical axons" *Nat Neurosci.* 6(12):1270-1276 (Dec. 2003).
Llambi et al., "Netrin-1 acts as a survival factor via its receptors UNC5H and DCC" *EMBO Journal* 20(11):2715-2722 (Jun. 1, 2001).
Lorenzo et al., "Identification and characterization of asporin. A novel member of the leucine-rich repeat protein family closely related to decorin and biglycan" *J Biol Chem.* 276(15):12201-12211 (Apr. 13, 2001).
Mao et al., "The cytoplasmic domain is critical to the tumor suppressor activity of TSLC1 in non-small cell lung cancer" *Cancer Research* 63(22):7979-7985 (Nov. 15, 2003).

Mazzocchi et al, "Cerebellin enhances in vitro secretory activity of human adrenal gland" *J Clin Endocrinol Metab.* 84(2):632-635 (Feb. 1999).
Mikami et al., "Specificities of three distinct human chondroitin/dermatan N-acetylgalactosamine 4-O-sulfotransferases demonstrated using partially desulfated dermatan sulfate as an acceptor" *J Biol Chem.* 278(38):36115-36127 (Sep. 19, 2003).
Miller et al, "IRTAs: A new family of immunoglobulinlike receptors differentially expressed in B cells" *Blood* 99(8):2662-2669 (Apr. 15, 2002).
Miyaoka et al., "Transgenic overexpression of Reg protein caused gastric cell proliferation and differentiation along parietal cell and chief cell lineages" *Oncogene* 23(20):3572-3579 (Apr. 29, 2004).
Morimoto-Tomita et al., "Cloning and characterization of two extracellular heparin-degrading endosulfatases in mice and humans" *J Biol Chem.* 277(51):49175-49185 (Dec. 20, 2002).
Nicholes et al., "Animal Model: A mouse model of hepatocellular carcinoma, ectopic expression of fibroblast growth factor 19 in skeletal muscle of transgenic mice" *American Journal of Pathology* 160(6):2295-2307 (Jun. 2002).
Nishimura et al., "Structure and expression of a novel human FGF, FGF-19, expressed in the fetal brain" *Biochimica et Biophysica Acta* 1444(1):148-151 (Jan. 18, 1999).
Nishioka et al., "Identification of a 428-kb homozygously deleted region disrupting the SEZ6L gene at 22q12.1 in a lung cancer cell line" *Oncogene* 19(54):6251-6260 (Dec. 2000).
Nobuhisa et al., "Characterization and evolution of a gene encoding a *Trimeresurus flavoviridis* serum protein that inhibits basic phospholipase A2 isozymes in the snake's venom" *Eur J Biochem.* 249(3):838-845 (Nov. 1, 1997).
Ota et al., "Complete sequencing and characterization of 21,243 full-length human cDNAs" *Nat Genet.* 36(1):40-5 (Jan. 2004).
Palmeri et al., "Vascular endothelial junction-associated molecule, a novel member of the immunoglobulin superfamily, is localized to intercellular boundaries of endothelial cells" *J Biol Chem.* 275(25):19139-19145 (Jun. 23, 2000).
Pang et al., "Cbln3, a novel member of the precerebellin family that binds specifically to Cbln1" *J Neurosci.* 20(17):6333-6339 (Sep. 1, 2000).
Pauli et al., "Molecular characteristics and functional diversity of CLCA family members" *Clin Exp Pharmacol Physiol.* 27(11):901-905 (Nov. 2000).
Saito et al., "Human fibroblast growth factor-23 mutants suppress Na+-dependent phosphate co-transport activity and 1alpha,25-dihydroxyvitamin D3 production" *J Biol Chem.* 278(4):2206-2211 (Jan. 24, 2003).
Salier et al., "The inter-alpha-inhibitor family: from structure to regulation" *Biochemical Journal* 315(Pt 1):1-9 (Apr. 1, 1996).
Santoso et al., "The junctional adhesion molecule 3 (JAM-3) on human platelets is a counterreceptor for the leukocyte integrin Mac-1" *J Exp Med.* 196(5):679-691 (Sep. 2, 2002).
Sheu et al., "Use of a phage display technique to identify potential osteoblast binding sites within osteoclast lacunae" *J Bone Miner Res.* 17(5):915-922 (May 2002).
Shimada et al., "Cloning and characterization of FGF23 as a causative factor of tumor-induced osteomalacia" *Proc Natl Acad Sci U S A* 98(11):6500-6505 (May 22, 2001).
Shimada et al., "Targeted ablation of Fgf23 demonstrates an essential physiological role of FGF23 in phosphate and vitamin D metabolism" *J Clin Invest.* 113(4):561-568 (Feb. 2004).
St. Croix et al., "Genes expressed in human tumor endothelium" *Science* 289(5482):1197-1202 (Aug. 18, 2000).
Talbot et al., "Cell adhesion and fertilization: steps in oocyte transport, sperm-zona pellucida interactions, and sperm-egg fusion" *Biol. Reprod.* 68(1):1-9 (Jan. 2003).
Taniguchi et al., "Cloning and expression of a novel gene for a protein with leucine-rich repeats in the developing mouse nervous system" *Brain Res Mol Brain Res.* 36(1):45-52 (Feb. 1996).
Tanikawa et al., "p53RDL1 regulates p53-dependent apoptosis" *Nat Cell Biol.* 5(3):216-223 (Mar. 2003).
Thiebault et al., "The netrin-1 receptors UNC5H are putative tumor suppressors controlling cell death commitment" *Proc Natl Acad Sci U S A* 100(7):4173-8 (Apr. 1, 2003).
Tomlinson et al., "Transgenic Mice Expressing Human Fibroblast Growth Factor-19 Display Increased Metabolic Rate and Decreased Adiposity" *Endocrinology* 143(5):1741-1747 (May 2002).
Urny et al., "Expression of the presenilin-like signal peptide peptidase (SPP) in mouse adult brain and during development" *Gene Expr Patterns* 3(5):685-691 (Oct. 2003).
Watabe et al., "IGSF4: a new intercellular adhesion molecule that is called by three names, TSLC1, SgIGSF and SynCAM, by virtue of its diverse function" *Histol Histopathol.* 18(4):1321-1329 (Oct. 2003).
Watanabe et al., "K-glypican: a novel GPI-anchored heparan sulfate proteoglycan that is highly expressed in developing brain and kidney" *J Cell Biol.* 130(5):1207-1218 (Sep. 1995).
Weihofen et al., "Identification of signal peptide peptidase, a presenilin-type aspartic protease" *Science* 296(5576):2215-2218 (Jun. 21, 2002).
White et al., "ADAMs: modulators of cell-cell and cell-matrix interactions" *Curr Opin Cell Biol.* 15(5):598-606 (Oct. 2003).
Winston at al., "Systemic RNAi in *C. elegans* requires the putative transmembrane protein SID-1" *Science* 295(5564):2456-2459 (Mar 29, 2002).
Wright et al., "Mouse FGF15 is the ortholog of human and chick FGF19, but is not uniquely required for otic induction" *Dev Biol.* 269(1):264-275 (May 1, 2004).
Wu, H. et al., "Generation of Committed Erythroid BFU-E and CFU-E Progenitors Does Not Require Erythropoietin or the Erythropoietin Receptor" *Cell* 83(1):59-67 (Oct. 6, 1995).
Xia and Wolfe, "Intramembrane proteolysis by presenilin and presenilin-like proteases" *Cell Sci.* 116(Pt 14):2839-2844 (Jul. 15, 2003).
Xie et al., "FGF-19, a novel fibroblast growth factor with unique specificity for FGFR4" *Cytokine* 11(10):729-735 (Oct. 1999).
Xu et al., "SPAP2, an Ig family receptor containing both ITIMs and ITAMs" *Biochem Biophys Res Commun.* 293(3):1037-1046 (May 10, 2002).
Yamada et al., "Expression profile of active genes in human periodontal ligament and isolation of PLAP-1, a novel SLRP family gene" *Gene* 275(2):279-286 (Sep. 19, 2001).
Yamashita et al., "Identification of a novel fibroblast growth factor, FGF-23, preferentially expressed in the ventrolateral thalamic nucleus of the brain" *Biochem Biophys Res Commun.* 277(2):494-498 (Oct. 22, 2000).
Yamazaki et al., "Increased circulatory level of biologically active full-length FGF-23 in patients with hypophosphatemic rickets/osteomalacia" *J Clin Endocrinol Metab.* 87(11):4957-4960 (Nov. 2002).
Yeh et al., "Ubiquitin-like proteins: new wines in new bottles" *Gene* 248(1-2):1-14 (May 2, 2000).
Zannettino et al., "Novel mesenchymal and haematopoietic cell isoforms of the SHP-2 docking receptor, PZR: identification, molecular cloning and effects on cell migration" *Biochemical Journal* 370(Pt 2):537-549 (Mar. 1, 2003).
Zhao et al., "Cell surface glycoprotein PZR is a major mediator of concanavalin A-induced cell signaling" *J Biol Chem.* 277(10):7882-7888 (Mar. 8, 2002).
Zhao et al., "Dissecting the interaction of SHP-2 with PZR, an immunoglobulin family protein containing immunoreceptor tyrosine-based inhibitory motifs" *J Biol Chem.* 275(8):5453-5459 (Feb. 25, 2000).
Zhao et al., "Purification and Cloning of PZR, a Binding Protein and Putative Physiological Substrate of Tyrosine Phosphatase SHP-2" *Journal of Biological Chemistry* 273(45):29367-29372 (Nov. 6, 1998).
Jeppesen, et al., "Triglyceride concentration and ischemic heart disease an eight-year follow-up in the Copenhagen male study", Circulation, 97: 1029-1036, (1998).
Pennacchio, et al., "An apolipoprotein influencing triglycerides in humans and mice revealed by comparative sequencing", Science, vol. 294, pp. 169-173, (2001).

* cited by examiner

FIGURE 1

CCCACGCGTCCGCCCGCCGCTGCGTCCCGGAGTGCAAGTGAGCTTCTCGGCTGCCCCGCGGGCCGGGGTGCGGA
GCCGACATGCGCCCGCTTCTCGGCCTCCTTCTGGTCTTCGCCGGCTGCACCTTCGCCTTGTACTTGCTGTCGAC
GCGACTGCCCCGCGGGCGGAGACTGGGCTCCACCGAGGAGGCTGGAGGCAGGTCGCTGTGGTTCCCCTCCGACC
TGGCAGAGCTGCGGGAGCTCTCTGAGGTCCTTCGAGAGTACCGGAAGGAGCACCAGGCCTACGTGTTCCTGCTC
TTCTGCGGCGCCTACCTCTACAAACAGGGCTTTGCCATCCCCGGCTCCAGCTTCCTGAATGTTTTAGCTGGTGC
CTTGTTTGGGCCATGGCTGGGGCTTCTGCTGTGCTGTGTGTTGACCTCGGTGGGTGCCACATGCTGCTACCTGC
TCTCCAGTATTTTTGGCAAACAGTTGGTGGTGTCCTACTTTCCTGATAAAGTGGCCCTGCTGCAGAGAAAGGTG
GAGGAGAACAGAAACAGCTTGTTTTTTTTCTTATTGTTTTTGAGACTTTTCCCCATGACACCAAACTGGTTCTT
GAACCTCTCGGCCCCAATTCTGAACATTCCCATCGTGCAGTTCTTCTTCTCAGTTCTTATCGGTTTGATCCCAT
ATAATTTCATCTGTGTGCAGACAGGGTCCATCCTGTCAACCCTAACCTCTCTGGATGCTCTTTTCTCCTGGGAC
ACTGTCTTTAAGCTGTTGGCCATTGCCATGGTGGCATTAATTCCTGGAACCCTCATTAAAAAATTTAGTCAGAA
ACATCTGCAATTGAATGAAACAAGTACTGCTAATCATATACACAGTAGAAAAGACACATGATCTGGATTTTCTG
TTTGCCACATCCCTGGACTCAGTTGCTTATTTGTGTAATGGATGTGGTCCTCTAAAGCCCCTCATTGTTTTTGA
TTGCCTTCTATAGGTGATGTGGACACTGTGCATCAATGTGCAGTGTCTTTTCAGAAAGGACACTCTGCTCTTGA
AGGTGTATTACATCAGGTTTTCAAACCAGCCCTGGTGTAGCAGACACTGCAACAGATGCCTCCTAGAAAATGCT
GTTTGTGGCCGGGCGCGGTGGCTCACGCCTGTAATCCCAGCACTTTGGGAGGCCGAGGCCGGTGATTCACAAGG
TCAGGAGTTCAAGACCAGCCTGGCCAAGATGGTGAAATCCTGTCTCTAATAAAAATACAAAAATTAGCCAGGCG
TGGTGGCAGGCACCTGTAATCCCAGCTACTCGGGAGGCTGAGGCAGGAGAATTGCTTGAACCAAGGTGGCAGAG
GTTGCAGTAAGCCAAGATCACACCACTGCACTCCAGCCTGGGTGATAGAGTGAGACACTGTCTTGAC

FIGURE 2

MRPLLGLLLVFAGCTFALYLLSTRLPRGRRLGSTEEAGGRSLWFPSDLAELRELSEVLREYRKEHQAYVFLLFC
GAYLYKQGFAIPGSSFLNVLAGALFGPWLGLLLCCVLTSVGATCCYLLSSIFGKQLVVSYFPDKVALLQRKVEE
NRNSLFFFLLFLRLFPMTPNWFLNLSAPILNIPIVQFFFSVLIGLIPYNFICVQTGSILSTLTSLDALFSWDTV
FKLLAIAMVALIPGTLIKKFSQKHLQLNETSTANHIHSRKDT

Important features:

Signal peptide:

amino acids 1-17

Transmembrane domains:

amino acids 101-123, 189-211

N-glycosylation sites.

amino acids 172-176, 250-254 cAMP- and cGMP-dependent protein kinase phosphorylation site.

amino acids 240-244, 261-265

N-myristoylation site.

amino acids 13-19, 104-110, 115-121, 204-210

Amidation site.

amino acids 27-31

Prokaryotic membrane lipoprotein lipid attachment site.

amino acids 4-15

Protein splicing proteins.

amino acids 25-31

Sugar transport proteins.

amino acids 162-172

FIGURE 3

GACATCGGAGGTGGGCTAGCACTGAAACTGCTTTTCAAGACGAGGAAGAGGAGGAGAAAGAGAAAGAAGAGGAA
GATGTTGGGCAACATTTATTTAACATGCTCCACAGCCCGGACCCTGGCATCATGCTGCTATTCCTGCAAATACT
GAAGAAGCATGGGATTTAAATATTTTACTTCTAAATAAATGAATTACTCAATCTCCTATGACCATCTATACATA
CTCCACCTTCAAAAAGTACATCAATATTATATCATTAAGGAAATAGTAACCTTCTCTTCTCCAATATGCATGAC
ATTTTTGGACAATGCAATTGTGGCACTGGCACTTATTTCAGTGAAGAAAAACTTTGTGGTTCTATGGCATTCAT
CATTTGACAAATGCAAGCATCTTCCTTATCAATCAGCTCCTATTGAACTTACTAGCACTGACTGTGGAATCCTT
AAGGGCCCATTACATTTCTGAAGAAGAAAGCTAAGATGAAGGACATGCCACTCCGAATTCATGTGCTACTTGGC
CTAGCTATCACTACACTAGTACAAGCTGTAGATAAAAAAGTGGATTGTCCACGGTTATGTACGTGTGAAATCAG
GCCTTGGTTTACACCCAGATCCATTTATATGGAAGCATCTACAGTGGATTGTAATGATTTAGGTCTTTTAACTT
TCCCAGCCAGATTGCCAGCTAACACACAGATTCTTCTCCTACAGACTAACAATATTGCAAAAATTGAATACTCC
ACAGACTTTCCAGTAAACCTTACTGGCCTGGATTTATCTCAAAACAATTTATCTTCAGTCACCAATATTAATGT
AAAAAAGATGCCTCAGCTCCTTTCTGTGTACCTAGAGGAAAACAAACTTACTGAACTGCCTGAAAAATGTCTGT
CCGAACTGAGCAACTTACAAGAACTCTATATTAATCACAACTTGCTTTCTACAATTTCACCTGGAGCCTTTATT
GGCCTACATAATCTTCTTCGACTTCATCTCAATTCAAATAGATTGCAGATGATCAACAGTAAGTGGTTTGATGC
TCTTCCAAATCTAGAGATTCTGATGATTGGGGAAAATCCAATTATCAGAATCAAAGACATGAACTTTAAGCCTC
TTATCAATCTTCGCAGCCTGGTTATAGCTGGTATAAACCTCACAGAAATACCAGATAACGCCTTGGTTGGACTG
GAAAACTTAGAAAGCATCTCTTTTTACGATAACAGGCTTATTAAAGTACCCCATGTTGCTCTTCAAAAAGTTGT
AAATCTCAAATTTTTGGATCTAAATAAAAATCCTATTAATAGAATACGAAGGGGTGATTTTAGCAATATGCTAC
ACTTAAAAGAGTTGGGGATAAATAATATGCCTGAGCTGATTTCCATCGATAGTCTTGCTGTGGATAACCTGCCA
GATTTAAGAAAAATAGAAGCTACTAACAACCCTAGATTGTCTTACATTCACCCCAATGCATTTTTCAGACTCCC
CAAGCTGGAATCACTCATGCTGAACAGCAATGCTCTCAGTGCCCTGTACCATGGTACCATTGAGTCTCTGCCAA
ACCTCAAGGAAATCAGCATACACAGTAACCCCATCAGGTGTGACTGTGTCATCCGTTGGATGAACATGAACAAA
ACCAACATTCGATTCATGGAGCCAGATTCACTGTTTTGCGTGGACCCACCTGAATTCCAAGGTCAGAATGTTCG
GCAAGTGCATTTCAGGGACATGATGGAAATTTGTCTCCCTCTTATAGCTCCTGAGAGCTTTCCTTCTAATCTAA
ATGTAGAAGCTGGGAGCTATGTTTCCTTTCACTGTAGAGCTACTGCAGAACCACAGCCTGAAATCTACTGGATA
ACACCTTCTGGTCAAAAACTCTTGCCTAATACCCTGACAGACAAGTTCTATGTCCATTCTGAGGGAACACTAGA
TATAAATGGCGTAACTCCCAAAGAAGGGGGTTTATATACTTGTATAGCAACTAACCTAGTTGGCGCTGACTTGA
AGTCTGTTATGATCAAAGTGGATGGATCTTTTCCACAAGATAACAATGGCTCTTTGAATATTAAAATAAGAGAT
ATTCAGGCCAATTCAGTTTTGGTGTCCTGGAAAGCAAGTTCTAAAATTCTCAAATCTAGTGTTAAATGGACAGC
CTTTGTCAAGACTGAAAATTCTCATGCTGCGCAAAGTGCTCGAATACCATCTGATGTCAAGGTATATAATCTTA
CTCATCTGAATCCATCAACTGAGTATAAAATTTGTATTGATATTCCCACCATCTATCAGAAAAACAGAAAAAAA
TGTGTAAATGTCACCACCAAAGGTTTGCACCCTGATCAAAAAGAGTATGAAAAGAATAATACCACAACACTTAT
GGCCTGTCTTGGAGGCCTTCTGGGGATTATTGGTGTGATATGTCTTATCAGCTGCCTCTCTCCAGAAATGAACT
GTGATGGTGGACACAGCTATGTGAGGAATTACTTACAGAAACCAACCTTTGCATTAGGTGAGCTTTATCCTCCT
CTGATAAATCTCTGGGAAGCAGGAAAAGAAAAAAGTACATCACTGAAAGTAAAAGCAACTGTTATAGGTTTACC
AACAAATATGTCCTAAAAACCACCAAGGAAACCTACTCCAAAAATGAAC

FIGURE 4

MKDMPLRIHVLLGLAITTLVQAVDKKVDCPRLCTCEIRPWFTPRSIYMEASTVDCNDLGLL
TFPARLPANTQILLLQTNNIAKIEYSTDFPVNLTGLDLSQNNLSSVTNINVKKMPQLLSVY
LEENKLTELPEKCLSELSNLQELYINHNLLSTISPGAFIGLHNLLRLHLNSNRLQMINSKW
FDALPNLEILMIGENPIIRIKDMNFKPLINLRSLVIAGINLTEIPDNALVGLENLESISFY
DNRLIKVPHVALQKVVNLKFLDLNKNPINRIRRGDFSNMLHLKELGINNMPELISIDSLAV
DNLPDLRKIEATNNPRLSYIHPNAFFRLPKLESLMLNSNALSALYHGTIESLPNLKEISIH
SNPIRCDCVIRWMNMNKTNIRFMEPDSLFCVDPPEFQGQNVRQVHFRDMMEICLPLIAPES
FPSNLNVEAGSYVSFHCRATAEPQPEIYWITPSGQKLLPNTLTDKFYVHSEGTLDINGVTP
KEGGLYTCIATNLVGADLKSVMIKVDGSFPQDNNGSLNIKIRDIQANSVLVSWKASSKILK
SSVKWTAFVKTENSHAAQSARIPSDVKVYNLTHLNPSTEYKICIDIPTIYQKNRKKCVNVT
TKGLHPDQKEYEKNNTTTLMACLGGLLGIIGVICLISCLSPEMNCDGGHSYVRNYLQKPTF
ALGELYPPLINLWEAGKEKSTSLKVKATVIGLPTNMS

Important features:

Signal sequence:
amino acids 1-22

Transmembrane domain:
amino acids 633-650

N-glycosylation site.
amino acids 93-97, 103-107, 223-227, 382-386, 522-526, 579-583, 608-612, 624-628, 625-629

Casein kinase II phosphorylation site.
amino acids 51-55, 95-99, 242-246, 468-472, 487-491

Tyrosine kinase phosphorylation site.
amino acids 570-579

N-myristoylation site.
amino acids 13-19, 96-102, 158-164, 221-227, 352-358, 437-443, 491-497, 492-498, 634-640, 702-708

Cell attachment sequence.
amino acids 277-280

FIGURE 5

GGACTAATCTGTGGGAGCAGTTTATTCCAGTATCACCCAGGGTGCAGCCACACCAGGACTG
TGTTGAAGGGTGTTTTTTTTCTTTTAAATGTAATACCTCCTCATCTTTTCTTCTTACACAG
TGTCTGAGAACATTTACATTATAGATAAGTAGTACATGGTGGATAACTTCTACTTTTAGGA
GGACTACTCTCTTCTGACAGTCCTAGACTGGTCTTCTACACTAAGACACCATGAAGGAGTA
TGTGCTCCTATTATTCCTGGCTTTGTGCTCTGCCAAACCCTTCTTTAGCCCTTCACACATC
GCACTGAAGAATATGATGCTGAAGGATATGGAAGACACAGATGATGATGATGATGATGATG
ATGATGATGATGATGATGAGGACAACTCTCTTTTTCCAACAAGAGAGCCAAGAAGCCATTT
TTTTCCATTTGATCTGTTTCCAATGTGTCCATTTGGATGTCAGTGCTATTCACGAGTTGTA
CATTGCTCAGATTTAGGTTTGACCTCAGTCCCAACCAACATTCCATTTGATACTCGAATGC
TTGATCTTCAAAACAATAAAATTAAGGAAATCAAAGAAAATGATTTTAAAGGACTCACTTC
ACTTTATGGTCTGATCCTGAACAACAACAAGCTAACGAAGATTCACCCAAAAGCCTTTCTA
ACCACAAAGAAGTTGCGAAGGCTGTATCTGTCCCACAATCAACTAAGTGAAATACCACTTA
ATCTTCCCAAATCATTAGCAGAACTCAGAATTCATGAAAATAAAGTTAAGAAAATACAAAA
GGACACATTCAAAGGAATGAATGCTTTACACGTTTTGGAAATGAGTGCAAACCCTCTTGAT
AATAATGGGATAGAGCCAGGGGCATTTGAAGGGGTGACGGTGTTCCATATCAGAATTGCAG
AAGCAAAACTGACCTCAGTTCCTAAAGGCTTACCACCAACTTTATTGGAGCTTCACTTAGA
TTATAATAAAATTTCAACAGTGGAACTTGAGGATTTTAAACGATACAAAGAACTACAAAGG
CTGGGCCTAGGAAACAACAAAATCACAGATATCGAAAATGGGAGTCTTGCTAACATACCAC
GTGTGAGAGAAATACATTTGGAAAACAATAAACTAAAAAAAATCCCTTCAGGATTACCAGA
GTTGAAATACCTCCAGATAATCTTCCTTCATTCTAATTCAATTGCAAGAGTGGGAGTAAAT
GACTTCTGTCCAACAGTGCCAAAGATGAAGAAATCTTTATACAGTGCAATAAGTTTATTCA
ACAACCCGGTGAAATACTGGGAAATGCAACCTGCAACATTTCGTTGTGTTTTGAGCAGAAT
GAGTGTTCAGCTTGGGAACTTTGGAATGTAATAATTAGTAATTGGTAATGTCCATTTAATA
TAAGATTCAAAAATCCCTACATTTGGAATACTTGAACTCTATTAATAATGGTAGTATTATA
TATACAAGCAAATATCTATTCTCAAGTGGTAAGTCCACTGACTTATTTTATGACAAGAAAT
TTCAACGGAATTTTGCCAAACTATTGATACATAAGGGGTTGAGAGAAACAAGCATCTATTG
CAGTTTCCTTTTTGCGTACAAATGATCTTACATAAATCTCATGCTTGACCATTCCTTTCTT
CATAACAAAAAAGTAAGATATTCGGTATTTAACACTTTGTTATCAAGCACATTTTAAAAAG
AACTGTACTGTAAATGGAATGCTTGACTTAGCAAAATTTGTGCTCTTTCATTTGCTGTTAG
AAAAACAGAATTAACAAAGACAGTAATGTGAAGAGTGCATTACACTATTCTTATTCTTTAG
TAACTTGGGTAGTACTGTAATATTTTTAATCATCTTAAAGTATGATTTGATATAATCTTAT
TGAAATTACCTTATCATGTCTTAGAGCCCGTCTTTATGTTTAAAACTAATTTCTTAAAATA
AAGCCTTCAGTAAATGTTCATTACCAACTTGATAAATGCTACTCATAAGAGCTGGTTTGGG
GCTATAGCATATGCTTTTTTTTTTTTAATTATTACCTGATTTAAAAATCTCTGTAAAAACG
TGTAGTGTTTCATAAAATCTGTAACTCGCATTTTAATGATCCGCTATTATAAGCTTTTAAT
AGCATGAAAATTGTTAGGCTATATAACATTGCCACTTCAACTCTAAGGAATATTTTTGAGA
TATCCCTTTGGAAGACCTTGCTTGGAAGAGCCTGGACACTAACAATTCTACACCAAATTGT
CTCTTCAAATACGTATGGACTGGATAACTCTGAGAAACACATCTAGTATAACTGAATAAGC
AGAGCATCAAATTAAACAGACAGAAACCGAAAGCTCTATATAAATGCTCAGAGTTCTTTAT
GTATTTCTTATTGGCATTCAACATATGTAAAATCAGAAAACAGGGAAATTTTCATTAAAAA
TATTGGTTTGAAAT

FIGURE 6

</usr/seqdb2/sst/DNA/Dnaseqs.min/ss.DNA34392
<subunit 1 of 1, 379 aa, 1 stop
<MW: 43302, pI: 7.30, NX(S/T): 1
MKEYVLLLFLALCSAKPFFSPSHIALKNMMLKDMEDTDDDDDDDDDDDDEDNSLFPTREP
RSHFFPFDLFPMCPFGCQCYSRVVHCSDLGLTSVPTNIPFDTRMLDLQNNKIKEIKENDFK
GLTSLYGLILNNNKLTKIHPKAFLTTKKLRRLYLSHNQLSEIPLNLPKSLAELRIHENKVK
KIQKDTFKGMNALHVLEMSANPLDNNGIEPGAFEGVTVFHIRIAEAKLTSVPKGLPPTLLE
LHLDYNKISTVELEDFKRYKELQRLGLGNNKITDIENGSLANIPRVREIHLENNKLKKIPS
GLPELKYLQIIFLHSNSIARVGVNDFCPTVPKMKKSLYSAISLFNNPVKYWEMQPATFRCV
LSRMSVQLGNFGM

Signal sequence.
amino acids 1-15

N-glycosylation site.
amino acids 281-285

N-myristoylation sites.
amino acids 129-135, 210-216, 214-220, 237-243, 270-276, 282-288

Leucine zipper pattern.
amino acids 154-176

FIGURE 7

GAGCGAGGCCGGGGACTGAAGGTGTGGGTGTCGAGCCCTCTGGCAGAGGGTTAACCTGGGTCAAATGCACGGAT
TCTCACCTCGTACAGTTACGCTCTCCCGCGGCACGTCCGCGAGGACTTGAAGTCCTGAGCGCTCAAGTTTGTCC
GTAGGTCGAGAGAAGGCCATGGAGGTGCCGCCACCGGCACCGCGGAGCTTTCTCTGTAGAGCATTGTGCCTATT
TCCCCGAGTCTTTGCTGCCGAAGCTGTGACTGCCGATTCGGAAGTCCTTGAGGAGCGTCAGAAGCGGCTTCCCT
ACGTCCCAGAGCCCTATTACCCGGAATCTGGATGGGACCGCCTCCGGGAGCTGTTTGGCAAAGATGAACAGCAG
AGAATTTCAAAGGACCTTGCTAATATCTGTAAGACGGCAGCTACAGCAGGCATCATTGGCTGGGTGTATGGGGG
AATACCAGCTTTTATTCATGCTAAACAACAATACATTGAGCAGAGCCAGGCAGAAATTTATCATAACCGGTTTG
ATGCTGTGCAATCTGCACATCGTGCTGCCACACGAGGCTTCATTCGTTATGGCTGGCGCTGGGGTTGGAGAACT
GCAGTGTTTGTGACTATATTCAACACAGTGAACACTAGTCTGAATGTATACCGAAATAAAGATGCCTTAAGCCA
TTTTGTAATTGCAGGAGCTGTCACGGGAAGTCTTTTTAGGATAAACGTAGGCCTGCGTGGCCTGGTGGCTGGTG
GCATAATTGGAGCCTTGCTGGGCACTCCTGTAGGAGGCCTGCTGATGGCATTTCAGAAGTACGCTGGTGAGACT
GTTCAGGAAAGAAAACAGAAGGATCGAAAGGCACTCCATGAGCTAAAACTGGAAGAGTGGAAAGGCAGACTACA
AGTTACTGAGCACCTCCCTGAGAAAATTGAAAGTAGTTTACGGGAAGATGAACCTGAGAATGATGCTAAGAAAA
TTGAAGCACTGCTAAACCTTCCTAGAAACCCTTCAGTAATAGATAAACAAGACAAGGACTGAAAGTGCTCTGAA
CTTGAAACTCACTGGAGAGCTGAAGGGAGCTGCCATGTCCGATGAATGCCAACAGACAGGCCACTCTTTGGTCA
GCCTGCTGACAAATTTAAGTGCTGGTACCTGTGGTGGCAGTGGCTTGCTCTTGTCTTTTTCTTTTCTTTTTAAC
TAAGAATGGGGCTGTTGTACTCTCACTTTACTTATCCTTAAATTTAAATACATACTTATGTTTGTATTAATCTA
TCAATATATGCATACATGGATATATCCACCCACCTAGATTTTAAGCAGTAAATAAAACATTTCGCAAAAGATTA
AAGTTGAATTTTACAGTTT

FIGURE 8

></usr/seqdb2/sst/DNA/Dnaseqs.min/ss.DNA23318
><subunit 1 of 1, 285 aa, 1 stop
><MW: 32190, pI: 9.03, NX(S/T): 2
MEVPPPAPRSFLCRALCLFPRVFAAEAVTADSEVLEERQKRLPYVPEPYYPESGWDRLRELFGKDEQQRISKDL
ANICKTAATAGIIGWVYGGIPAFIHAKQQYIEQSQAEIYHNRFDAVQSAHRAATRGFIRYGWRWGWRTAVFVTI
FNTVNTSLNVYRNKDALSHFVIAGAVTGSLFRINVGLRGLVAGGIIGALLGTPVGGLLMAFQKYAGETVQERKQ
KDRKALHELKLEEWKGRLQVTEHLPEKIESSLREDEPENDAKKIEALLNLPRNPSVIDKQDKD

Important Features:
Signal Peptide:
amino acids 1-24

Transmembrane domains:
amino acids 76-96 and 171-195

N-glycosylation site:
amino acids 153-156

FIGURE 9

GGGGAGAGGAATTGACCATGTAAAAGGAGACTTTTTTTTTTGGTGGTGGTGGCTGTTGGGTGCCTTGCAAAAAT
GAAGGATGCAGGACGCAGCTTTCTCCTGGAACCGAACGCAATGGATAAACTGATTGTGCAAGAGAGAAGGAAGA
ACGAAGCTTTTTCTTGTGAGCCCTGGATCTTAACACAAATGTGTATATGTGCACACAGGGAGCATTCAAGAATG
AAATAAACCAGAGTTAGACCCGCGGGGGTTGGTGTGTTCTGACATAAATAAATAATCTTAAAGCAGCTGTTCCC
CTCCCCACCCCCAAAAAAAAGGATGATTGGAAATGAAGAACCGAGGATTCACAAAGAAAAAAGTATGTTCATTT
TTCTCTATAAAGGAGAAAGTGAGCCAAGGAGATATTTTTGGAATGAAAAGTTTGGGGCTTTTTTAGTAAAGTAA
AGAACTGGTGTGGTGGTGTTTTCCTTTCTTTTTGAATTTCCCACAAGAGGAGAGGAAATTAATAATACATCTGC
AAAGAAATTTCAGAGAAGAAAAGTTGACCGCGGCAGATTGAGGCATTGATTGGGGGAGAGAAACCAGCAGAGCA
CAGTTGGATTTGTGCCTATGTTGACTAAAATTGACGGATAATTGCAGTTGGATTTTTCTTCATCAACCTCCTTT
TTTTTAAATTTTTATTCCTTTTGGTATCAAGATCATGCGTTTTCTCTTGTTCTTAACCACCTGGATTTCCATCT
GGATGTTGCTGTGATCAGTCTGAAATACAACTGTTTGAATTCCAGAAGGACCAACACCAGATAAATTATGAATG
TTGAACAAGATGACCTTACATCCACAGCAGATAATGATAGGTCCTAGGTTTAACAGGGCCCTATTTGACCCCCT
GCTTGTGGTGCTGCTGGCTCTTCAACTTCTTGTGGTGGCTGGTCTGGTGCGGGCTCAGACCTGCCCTTCTGTGT
GCTCCTGCAGCAACCAGTTCAGCAAGGTGATTTGTGTTCGGAAAAACCTGCGTGAGGTTCCGGATGGCATCTCC
ACCAACACACGGCTGCTGAACCTCCATGAGAACCAAATCCAGATCATCAAAGTGAACAGCTTCAAGCACTTGAG
GCACTTGGAAATCCTACAGTTGAGTAGGAACCATATCAGAACCATTGAAATTGGGGCTTTCAATGGTCTGGCGA
ACCTCAACACTCTGGAACTCTTTGACAATCGTCTTACTACCATCCCGAATGGAGCTTTTGTATACTTGTCTAAA
CTGAAGGAGCTCTGGTTGCGAAACAACCCCATTGAAAGCATCCCTTCTTATGCTTTTAACAGAATTCCTTCTTT
GCGCCGACTAGACTTAGGGGAATTGAAAAGACTTTCATACATCTCAGAAGGTGCCTTTGAAGGTCTGTCCAACT
TGAGGTATTTGAACCTTGCCATGTGCAACCTTCGGGAAATCCCTAACCTCACACCGCTCATAAAACTAGATGAG
CTGGATCTTTCTGGGAATCATTTATCTGCCATCAGGCCTGGCTCTTTCCAGGGTTTGATGCACCTTCAAAAACT
GTGGATGATACAGTCCCAGATTCAAGTGATTGAACGGAATGCCTTTGACAACCTTCAGTCACTAGTGGAGATCA
ACCTGGCACACAATAATCTAACATTACTGCCTCATGACCTCTTCACTCCCTTGCATCATCTAGAGCGGATACAT
TTACATCACAACCCTTGGAACTGTAACTGTGACATACTGTGGCTCAGCTGGTGGATAAAAGACATGGCCCCCTC
GAACACAGCTTGTTGTGCCCGGTGTAACACTCCTCCCAATCTAAAGGGGAGGTACATTGGAGAGCTCGACCAGA
ATTACTTCACATGCTATGCTCCGGTGATTGTGGAGCCCCCTGCAGACCTCAATGTCACTGAAGGCATGGCAGCT
GAGCTGAAATGTCGGGCCTCCACATCCCTGACATCTGTATCTTGGATTACTCCAAATGGAACAGTCATGACACA
TGGGGCGTACAAAGTGCGGATAGCTGTGCTCAGTGATGGTACGTTAAATTTCACAAATGTAACTGTGCAAGATA
CAGGCATGTACACATGTATGGTGAGTAATTCCGTTGGGAATACTACTGCTTCAGCCACCCTGAATGTTACTGCA
GCAACCACTACTCCTTTCTCTTACTTTTCAACCGTCACAGTAGAGACTATGGAACCGTCTCAGGATGAGGCACG
GACCACAGATAACAATGTGGGTCCCACTCCAGTGGTCGACTGGGAGACCACCAATGTGACCACCTCTCTCACAC
CACAGAGCACAAGGTCGACAGAGAAAACCTTCACCATCCCAGTGACTGATATAAACAGTGGGATCCCAGGAATT
GATGAGGTCATGAAGACTACCAAAATCATCATTGGGTGTTTTGTGGCCATCACACTCATGGCTGCAGTGATGCT
GGTCATTTTCTACAAGATGAGGAAGCAGCACCATCGGCAAAACCATCACGCCCCAACAAGGACTGTTGAAATTA
TTAATGTGGATGATGAGATTACGGGAGACACACCCATGGAAAGCCACCTGCCCATGCCTGCTATCGAGCATGAG
CACCTAAATCACTATAACTCATACAAATCTCCCTTCAACCACACAACAACAGTTAACACAATAAATTCAATACA
CAGTTCAGTGCATGAACCGTTATTGATCCGAATGAACTCTAAAGACAATGTACAAGAGACTCAAATCTAAAACA
TTTACAGAGTTACAAAAAACAAACAATCAAAAAAAAAGACAGTTTATTAAAAATGACACAAATGACTGGGCTAA
ATCTACTGTTTCAAAAAAGTGTCTTTACAAAAAAACAAAAAAGAAAAGAAATTTATTTATTAAAAATTCTATTG
TGATCTAAAGCAGACAAAAA

FIGURE 10

MLNKMTLHPQQIMIGPRFNRALFDPLLVVLLALQLLVVAGLVRAQTCPSVCSCSNQFSKVI
CVRKNLREVPDGISTNTRLLNLHENQIQIIKVNSFKHLRHLEILQLSRNHIRTIEIGAFNG
LANLNTLELFDNRLTTIPNGAFVYLSKLKELWLRNNPIESIPSYAFNRIPSLRRLDLGELK
RLSYISEGAFEGLSNLRYLNLAMCNLREIPNLTPLIKLDELDLSGNHLSAIRPGSFQGLMH
LQKLWMIQSQIQVIERNAFDNLQSLVEINLAHNNLTLLPHDLFTPLHHLERIHLHHNPWNC
NCDILWLSWWIKDMAPSNTACCARCNTPPNLKGRYIGELDQNYFTCYAPVIVEPPADLNVT
EGMAAELKCRASTSLTSVSWITPNGTVMTHGAYKVRIAVLSDGTLNFTNVTVQDTGMYTCM
VSNSVGNTTASATLNVTAATTTPFSYFSTVTVETMEPSQDEARTTDNNVGPTPVVDWETTN
VTTSLTPQSTRSTEKTFTIPVTDINSGIPGIDEVMKTTKIIIGCFVAITLMAAVMLVIFYK
MRKQHHRQNHHAPTRTVEIINVDDEITGDTPMESHLPMPAIEHEHLNHYNSYKSPFNHTTT
VNTINSIHSSVHEPLLIRMNSKDNVQETQI

Signal sequence:
amino acids 1-44

Transmembrane domain:
amino acids 523-543

N-glycosylation site.
amino acids 278-282, 364-368, 390-394, 412-416, 415-419, 434-438, 442-446, 488-492, 606-610 cAMP- and cGMP-dependent protein kinase phosphorylation site.
amino acids 183-187

Casein kinase II phosphorylation site.
amino acids 268-272, 417-421, 465-469, 579-583, 620-624

N-myristoylation site.
amino acids 40-46, 73-79, 118-124, 191-197, 228-234, 237-243, 391-397, 422-428, 433-439, 531-537

FIGURE 11

CGGACGCGTGGGCTGGGCGCTGCAAAGCGTGTCCCGCCGGGTCCCCGAGCGTCCCGCGCCCTCGCCCCGCCATG
CTCCTGCTGCTGGGGCTGTGCCTGGGGCTGTCCCTGTGTGTGGGGTCGCAGGAAGAGGCGCAGAGCTGGGGCCA
CTCTTCGGAGCAGGATGGACTCAGGGTCCCGAGGCAAGTCAGACTGTTGCAGAGGCTGAAAACCAAACCTTTGA
TGACAGAATTCTCAGTGAAGTCTACCATCATTTCCCGTTATGCCTTCACTACGGTTTCCTGCAGAATGCTGAAC
AGAGCTTCTGAAGACCAGGACATTGAGTTCCAGATGCAGATTCCAGCTGCAGCTTTCATCACCAACTTCACTAT
GCTTATTGGAGACAAGGTGTATCAGGGCGAAATTACAGAGAGAGAAAAGAAGAGTGGTGATAGGGTAAAAGAGA
AAAGGAATAAAACCACAGAAGAAAATGGAGAGAAGGGGACTGAAATATTCAGAGCTTCTGCAGTGATTCCCAGC
AAGGACAAAGCCGCCTTTTTCCTGAGTTATGAGGAGCTTCTGCAGAGGCGCCTGGGCAAGTACGAGCACAGCAT
CAGCGTGCGGCCCCAGCAGCTGTCCGGGAGGCTGAGCGTGGACGTGAATATCCTGGAGAGCGCGGGCATCGCAT
CCCTGGAGGTGCTGCCGCTTCACAACAGCAGGCAGAGGGGCAGTGGGCGCGGGGAAGATGATTCTGGGCCTCCC
CCATCTACTGTCATTAACCAAAATGAAACATTTGCCAACATAATTTTTAAACCTACTGTAGTACAACAAGCCAG
GATTGCCCAGAATGGAATTTTGGGAGACTTTATCATTAGATATGACGTCAATAGAGAACAGAGCATTGGGGACA
TCCAGGTTCTAAATGGCTATTTTGTGCACTACTTTGCTCCTAAAGACCTTCCTCCTTTACCCAAGAATGTGGTA
TTCGTGCTTGACAGCAGTGCTTCTATGGTGGGAACCAAACTCCGGCAGACCAAGGATGCCCTCTTCACAATTCT
CCATGACCTCCGACCCCAGGACCGTTTCAGTATCATTGGATTTTCCAACCGGATCAAAGTATGGAAGGACCACT
TGATATCAGTCACTCCAGACAGCATCAGGGATGGGAAAGTGTACATTCACCATATGTCACCCACTGGAGGCACA
GACATCAACGGGGCCCTGCAGAGGGCCATCAGGCTCCTCAACAAGTACGTGGCCCACAGTGGCATTGGAGACCG
GAGCGTGTCCCTCATCGTCTTCCTGACGGATGGGAAGCCCACGGTCGGGGAGACGCACACCCTCAAGATCCTCA
ACAACACCCGAGAGGCCGCCCGAGGCCAAGTCTGCATCTTCACCATTGGCATCGGCAACGACGTGGACTTCAGG
CTGCTGGAGAAACTGTCGCTGGAGAACTGTGGCCTCACACGGCGCGTGCACGAGGAGGAGGACGCAGGCTCGCA
GCTCATCGGGTTCTACGATGAAATCAGGACCCCGCTCCTCTCTGACATCCGCATCGATTATCCCCCCAGCTCAG
TGGTGCAGGCCACCAAGACCCTGTTCCCCAACTACTTCAACGGCTCGGAGATCATCATTGCGGGGAAGCTGGTG
GACAGGAAGCTGGATCACCTGCACGTGGAGGTCACCGCCAGCAACAGTAAGAAATTCATCATCCTGAAGACAGA
TGTGCCTGTGCGGCCTCAGAAGGCAGGGAAAGATGTCACAGGAAGCCCCAGGCCTGGAGGCGATGGAGAGGGGG
ACACCAACCACATCGAGCGTCTCTGGAGCTACCTCACCACAAAGGAGCTGCTGAGCTCCTGGCTGCAAAGTGAC
GATGAACCGGAGAAGGAGCGGCTGCGGCAGCGGGCCCAGGCCCTGGCTGTGAGCTACCGCTTCCTCACTCCCTT
CACCTCCATGAAGCTGAGGGGGCCGGTCCCACGCATGGATGGCCTGGAGGAGGCCCACGGCATGTCGGCTGCCA
TGGGACCCGAACCGGTGGTGCAGAGCGTGCGAGGAGCTGGCACGCAGCCAGGACCTTTGCTCAAGAAGCCAAAC
TCCGTCAAAAAAAAACAAAACAAAACAAAAAAAAGACATGGGAGAGATGGTGTTTTTCCTCTCCACCACCTGGG
GATACGATGAGAAGATGGCCACCTGCAAGCCAGGAAGACGGCCCTCACCAGACACCATGTCTGCTGGCACCTTG
ATCTTGGACCTCCCAGCCTCCAGAACTGTGAGAAATAAATGTGTTTTGTTTAAGCTAAAAAAAAAAAAAAAAAA
AAAAAAAAAAAAAAAAAAAAAAAAAAAAAAAAAAAAA

FIGURE 12

</usr/seqdb2/sst/DNA/Dnaseqs.min/ss.DNA44192
<subunit 1 of 1, 694 aa, 1 stop
<MW: 77400, pI: 9.54, NX(S/T): 6
MLLLLGLCLGLSLCVGSQEEAQSWGHSSEQDGLRVPRQVRLLQRLKTKPLMTEFSVKSTIISRYAFTTVSCRML
NRASEDQDIEFQMQIPAAAFITNFTMLIGDKVYQGEITEREKKSGDRVKEKRNKTTEENGEKGTEIFRASAVIP
SKDKAAFFLSYEELLQRRLGKYEHSISVRPQQLSGRLSVDVNILESAGIASLEVLPLHNSRQRGSGRGEDDSGP
PPSTVINQNETFANIIFKPTVVQQARIAQNGILGDFIIRYDVNREQSIGDIQVLNGYFVHYFAPKDLPPLPKNV
VFVLDSSASMVGTKLRQTKDALFTILHDLRPQDRFSIIGFSNRIKVWKDHLISVTPDSIRDGKVYIHHMSPTGG
TDINGALQRAIRLLNKYVAHSGIGDRSVSLIVFLTDGKPTVGETHTLKILNNTREAARGQVCIFTIGIGNDVDF
RLLEKLSLENCGLTRRVHEEEDAGSQLIGFYDEIRTPLLSDIRIDYPPSSVVQATKTLFPNYFNGSEIIIAGKL
VDRKLDHLHVEVTASNSKKFIILKTDVPVRPQKAGKDVTGSPRPGGDGEGDTNHIERLWSYLTTKELLSSWLQS
DDEPEKERLRQRAQALAVSYRFLTPFTSMKLRGPVPRMDGLEEAHGMSAAMGPEPVVQSVRGAGTQPGPLLKKP
NSVKKKQNKTKKRHGRDGVFPLHHLGIR

Signal sequence.
amino acids 1-14

N-glycosylation sites.
amino acids 97-101, 127-131, 231-235, 421-425, 508-512, 674-678

Glycosaminoglycan attachment sites.
amino acids 213-217, 391-395

N-myristoylation sites.
amino acids 6-12, 10-16, 212-218, 370-376, 632-638, 638-644

FIGURE 13

CGGACGCGTGGGGTGCCCGACATGGCGAGTGTAGTGCTGCCGAGCGGATCCCAGTGTGCGG
CGGCAGCGGCGGCGGCGGCGCCTCCCGGGCTCCGGCTTCTGCTGTTGCTCTTCTCCGCCGC
GGCACTGATCCCCACAGGTGATGGGCAGAATCTGTTTACGAAAGACGTGACAGTGATCGAG
GGAGAGGTTGCGACCATCAGTTGCCAAGTCAATAAGAGTGACGACTCTGTGATTCAGCTAC
TGAATCCCAACAGGCAGACCATTTATTTCAGGGACTTCAGGCCTTTGAAGGACAGCAGGTT
TCAGTTGCTGAATTTTTCTAGCAGTGAACTCAAAGTATCATTGACAAACGTCTCAATTTCT
GATGAAGGAAGATACTTTTGCCAGCTCTATACCGATCCCCCACAGGAAAGTTACACCACCA
TCACAGTCCTGGTCCCACCACGTAATCTGATGATCGATATCCAGAAAGACACTGCGGTGGA
AGGTGAGGAGATTGAAGTCAACTGCACTGCTATGGCCAGCAAGCCAGCCACGACTATCAGG
TGGTTCAAAGGGAACACAGAGCTAAAAGGCAAATCGGAGGTGGAAGAGTGGTCAGACATGT
ACACTGTGACCAGTCAGCTGATGCTGAAGGTGCACAAGGAGGACGATGGGGTCCCAGTGAT
CTGCCAGGTGGAGCACCCTGCGGTCACTGGAAACCTGCAGACCCAGCGGTATCTAGAAGTA
CAGTATAAGCCTCAAGTGCACATTCAGATGACTTATCCTCTACAAGGCTTAACCCGGGAAG
GGGACGCGCTTGAGTTAACATGTGAAGCCATCGGGAAGCCCCAGCCTGTGATGGTAACTTG
GGTGAGAGTCGATGATGAAATGCCTCAACACGCCGTACTGTCTGGGCCCAACCTGTTCATC
AATAACCTAAACAAAACAGATAATGGTACATACCGCTGTGAAGCTTCAAACATAGTGGGGA
AAGCTCACTCGGATTATATGCTGTATGTATACGATCCCCCCACAACTATCCCTCCTCCCAC
AACAACCACCACCACCACCACCACCACCACCACCACCATCCTTACCATCATCACAGATTCC
CGAGCAGGTGAAGAAGGCTCGATCAGGGCAGTGGATCATGCCGTGATCGGTGGCGTCGTGG
CGGTGGTGGTGTTCGCCATGCTGTGCTTGCTCATCATTCTGGGGCGCTATTTTGCCAGACA
TAAAGGTACATACTTCACTCATGAAGCCAAAGGAGCCGATGACGCAGCAGACGCAGACACA
GCTATAATCAATGCAGAAGGAGGACAGAACAACTCCGAAGAAAAGAAAGAGTACTTCATCT
AGATCAGCCTTTTTGTTTCAATGAGGTGTCCAACTGGCCCTATTTAGATGATAAAGAGACA
GTGATATTGG

FIGURE 14

</usr/seqdb2/sst/DNA/Dnaseqs.min/ss.DNA39518
<subunit 1 of 1, 440 aa, 1 stop
<MW: 48240, pI: 4.93, NX(S/T): 7
MASVVLPSGSQCAAAAAAAAPPGLRLLLLLFSAAALIPTGDGQNLFTKDVTVIEGEVATIS
CQVNKSDDSVIQLLNPNRQTIYFRDFRPLKDSRFQLLNFSSSELKVSLTNVSISDEGRYFC
QLYTDPPQESYTTITVLVPPRNLMIDIQKDTAVEGEEIEVNCTAMASKPATTIRWFKGNTE
LKGKSEVEEWSDMYTVTSQLMLKVHKEDDGVPVICQVEHPAVTGNLQTQRYLEVQYKPQVH
IQMTYPLQGLTREGDALELTCEAIGKPQPVMVTWVRVDDEMPQHAVLSGPNLFINNLNKTD
NGTYRCEASNIVGKAHSDYMLYVYDPPTTIPPPTTTTTTTTTTTTILTIITDSRAGEEGS
IRAVDHAVIGGVVAVVVFAMLCLLIILGRYFARHKGTYFTHEAKGADDAADADTAIINAEG
GQNNSEEKKEYFI

Signal sequence.
amino acids 1-36

Transmembrane domain.
amino acids 372-393

N-glycosylation sites.
amino acids 65-69, 99-103, 111-115, 163-167, 302-306, 306-310, 430-434

Tyrosine kinase phosphorylation sites.
amino acids 233-240, 319-328

N-myristoylation sites.
amino acids 9-15, 227-233, 307-313, 365-371, 376-382, 402-408, 411-417, 427-433, 428-432

FIGURE 15

GCTCCCAGCCAAGAACCTCGGGGCCGCTGCGCGGTGGGGAGGAGTTCCCCGAAACCCGGCC
GCTAAGCGAGGCCTCCTCCTCCCGCAGATCCGAACGGCCTGGGCGGGGTCACCCCGGCTGG
GACAAGAAGCCGCCGCCTGCCTGCCCGGGCCCGGGGAGGGGGCTGGGGCTGGGGCCGGAGG
CGGGGTGTGAGTGGGTGTGTGCGGGGGGCGGAGGCTTGATGCAATCCCGATAAGAAATGCT
CGGGTGTCTTGGGCACCTACCCGTGGGGCCCGTAAGGCGCTACTATATAAGGCTGCCGGCC
CGGAGCCGCCGCGCCGTCAGAGCAGGAGCGCTGCGTCCAGGATCTAGGGCCACGACCATCC
CAACCCGGCACTCACAGCCCCGCAGCGCATCCCGGTCGCCGCCCAGCCTCCCGCACCCCCA
TCGCCGGAGCTGCGCCGAGAGCCCCAGGGAGGTGCCATGCGGAGCGGGTGTGTGGTGGTCC
ACGTATGGATCCTGGCCGGCCTCTGGCTGGCCGTGGCCGGGCGCCCCCTCGCCTTCTCGGA
CGCGGGGCCCCACGTGCACTACGGCTGGGGCGACCCCATCCGCCTGCGGCACCTGTACACC
TCCGGCCCCCACGGGCTCTCCAGCTGCTTCCTGCGCATCCGTGCCGACGGCGTCGTGGACT
GCGCGCGGGGCCAGAGCGCGCACAGTTTGCTGGAGATCAAGGCAGTCGCTCTGCGGACCGT
GGCCATCAAGGGCGTGCACAGCGTGCGGTACCTCTGCATGGGCGCCGACGGCAAGATGCAG
GGGCTGCTTCAGTACTCGGAGGAAGACTGTGCTTTCGAGGAGGAGATCCGCCCAGATGGCT
ACAATGTGTACCGATCCGAGAAGCACCGCCTCCCGGTCTCCCTGAGCAGTGCCAAACAGCG
GCAGCTGTACAAGAACAGAGGCTTTCTTCCACTCTCTCATTTCCTGCCCATGCTGCCCATG
GTCCCAGAGGAGCCTGAGGACCTCAGGGGCCACTTGGAATCTGACATGTTCTCTTCGCCCC
TGGAGACCGACAGCATGGACCCATTTGGGCTTGTCACCGGACTGGAGGCCGTGAGGAGTCC
CAGCTTTGAGAAGTAACTGAGACCATGCCCGGGCCTCTTCACTGCTGCCAGGGGCTGTGGT
ACCTGCAGCGTGGGGGACGTGCTTCTACAAGAACAGTCCTGAGTCCACGTTCTGTTTAGCT
TTAGGAAGAAACATCTAGAAGTTGTACATATTCAGAGTTTTCCATTGGCAGTGCCAGTTTC
TAGCCAATAGACTTGTCTGATCATAACATTGTAAGCCTGTAGCTTGCCCAGCTGCTGCCTG
GGCCCCCATTCTGCTCCCTCGAGGTTGCTGGACAAGCTGCTGCACTGTCTCAGTTCTGCTT
GAATACCTCCATCGATGGGGAACTCACTTCCTTTGGAAAAATTCTTATGTCAAGCTGAAAT
TCTCTAATTTTTTCTCATCACTTCCCCAGGAGCAGCCAGAAGACAGGCAGTAGTTTTAATT
TCAGGAACAGGTGATCCACTCTGTAAAACAGCAGGTAAATTTCACTCAACCCCATGTGGGA
ATTGATCTATATCTCTACTTCCAGGGACCATTTGCCCTTCCCAAATCCCTCCAGGCCAGAA
CTGACTGGAGCAGGCATGGCCCACCAGGCTTCAGGAGTAGGGGAAGCCTGGAGCCCCACTC
CAGCCCTGGGACAACTTGAGAATTCCCCCTGAGGCCAGTTCTGTCATGGATGCTGTCCTGA
GAATAACTTGCTGTCCCGGTGTCACCTGCTTCCATCTCCCAGCCCACCAGCCCTCTGCCCA
CCTCACATGCCTCCCCATGGATTGGGGCCTCCCAGGCCCCCCACCTTATGTCAACCTGCAC
TTCTTGTTCAAAAATCAGGAAAAGAAAAGATTTGAAGACCCCAAGTCTTGTCAATAACTTG
CTGTGTGGAAGCAGCGGGGGAAGACCTAGAACCCTTTCCCCAGCACTTGGTTTTCCAACAT
GATATTTATGAGTAATTTATTTTGATATGTACATCTCTTATTTTCTTACATTATTTATGCC
CCCAAATTATATTTATGTATGTAAGTGAGGTTTGTTTTGTATATTAAAATGGAGTTTGTTTGT

FIGURE 16

MRSGCVVVHVWILAGLWLAVAGRPLAFSDAGPHVHYGWGDPIRLRHLYTSGPHGLSSCFLR
IRADGVVDCARGQSAHSLLEIKAVALRTVAIKGVHSVRYLCMGADGKMQGLLQYSEEDCAF
EEEIRPDGYNVYRSEKHRLPVSLSSAKQRQLYKNRGFLPLSHFLPMLPMVPEEPEDLRGHL
ESDMFSSPLETDSMDPFGLVTGLEAVRSPSFEK

Signal peptide:
amino acids 1-22

Casein kinase II phosphorylation site.
amino acids 78-82, 116-120, 190-194, 204-208

N-myristoylation site.
amino acids 15-21, 54-60, 66-72, 201-207

Prokaryotic membrane lipoprotein lipid attachment site.
amino acids 48-59

FIGURE 17

GGCGCCTGGTTCTGCGCGTACTGGCTGTACGGAGCAGGAGCAAGAGGTCGCCGCCAGCCTCCGCCGCCGAGCCT
CGTTCGTGTCCCCGCCCCTCGCTCCTGCAGCTACTGCTCAGAAACGCTGGGGCGCCCACCCTGGCAGACTAACG
AAGCAGCTCCCTTCCCACCCCAACTGCAGGTCTAATTTTGGACGCTTTGCCTGCCATTTCTTCCAGGTTGAGGG
AGCCGCAGAGGCGGAGGCTCGCGTATTCCTGCAGTCAGCACCCACGTCGCCCCCGGACGCTCGGTGCTCAGGCC
CTTCGCGAGCGGGGCTCTCCGTCTGCGGTCCCTTGTGAAGGCTCTGGGCGGCTGCAGAGGCCGGCCGTCCGGTT
TGGCTCACCTCTCCCAGGAAACTTCACACTGGAGAGCCAAAAGGAGTGGAAGAGCCTGTCTTGGAGATTTTCCT
GGGGAAATCCTGAGGTCATTCATTATGAAGTGTACCGCGCGGGAGTGGCTCAGAGTAACCACAGTGCTGTTCAT
GGCTAGAGCAATTCCAGCCATGGTGGTTCCCAATGCCACTTTATTGGAGAAACTTTTGGAAAAATACATGGATG
AGGATGGTGAGTGGTGGATAGCCAAACAACGAGGGAAAAGGGCCATCACAGACAATGACATGCAGAGTATTTTG
GACCTTCATAATAAATTACGAAGTCAGGTGTATCCAACAGCCTCTAATATGGAGTATATGACATGGGATGTAGA
GCTGGAAAGATCTGCAGAATCCTGGGCTGAAAGTTGCTTGTGGGAACATGGACCTGCAAGCTTGCTTCCATCAA
TTGGACAGAATTTGGGAGCACACTGGGGAAGATATAGGCCCCCGACGTTTCATGTACAATCGTGGTATGATGAA
GTGAAAGACTTTAGCTACCCATATGAACATGAATGCAACCCATATTGTCCATTCAGGTGTTCTGGCCCTGTATG
TACACATTATACACAGGTCGTGTGGGCAACTAGTAACAGAATCGGTTGTGCCATTAATTTGTGTCATAACATGA
ACATCTGGGGGCAGATATGGCCCAAAGCTGTCTACCTGGTGTGCAATTACTCCCCAAAGGGAAACTGGTGGGGC
CATGCCCCTTACAAACATGGGCGGCCCTGTTCTGCTTGCCCACCTAGTTTTGGAGGGGGCTGTAGAGAAAATCT
GTGCTACAAAGAAGGGTCAGACAGGTATTATCCCCCTCGAGAAGAGGAAACAAATGAAATAGAACGACAGCAGT
CACAAGTCCATGACACCCATGTCCGGACAAGATCAGATGATAGTAGCAGAAATGAAGTCATAAGCGCACAGCAA
ATGTCCCAAATTGTTTCTTGTGAAGTAAGATTAAGAGATCAGTGCAAAGGAACAACCTGCAATAGGTACGAATG
TCCTGCTGGCTGTTTGGATAGTAAAGCTAAAGTTATTGGCAGTGTACATTATGAAATGCAATCCAGCATCTGTA
GAGCTGCAATTCATTATGGTATAATAGACAATGATGGTGGCTGGGTAGATATCACTAGACAAGGAAGAAAGCAT
TATTTCATCAAGTCCAATAGAAATGGTATTCAAACAATTGGCAAATATCAGTCTGCTAATTCCTTCACAGTCTC
TAAAGTAACAGTTCAGGCTGTGACTTGTGAAACAACTGTGGAACAGCTCTGTCCATTTCATAAGCCTGCTTCAC
ATTGCCCAAGAGTATACTGTCCTCGTAACTGTATGCAAGCAAATCCACATTATGCTCGTGTAATTGGAACTCGA
GTTTATTCTGATCTGTCCAGTATCTGCAGAGCAGCAGTACATGCTGGAGTGGTTCGAAATCACGGTGGTTATGT
TGATGTAATGCCTGTGGACAAAAGAAAGACCTACATTGCTTCTTTTCAGAATGGAATCTTCTCAGAAAGTTTAC
AGAATCCTCCAGGAGGAAAGGCATTCAGAGTGTTTGCTGTTGTGTGAAACTGAATACTTGGAAGAGGACCATAA
AGACTATTCCAAATGCAATATTTCTGAATTTTGTATAAAACTGTAACATTACTGTACAGAGTACATCAACTATT
TTCAGCCCAAAAAGGTGCCAAATGCATATAAATCTTGATAAACAAAGTCTATAAAATAAAACATGGGACATTAG
CTTTGGGAAAAGTAATGAAAATATAATGGTTTTAGAAATCCTGTGTTAAATATTGCTATATTTTCTTAGCAGTT
ATTTCTACAGTTAATTACATAGTCATGATTGTTCTACGTTTCATATATTATATGGTGCTTTGTATATGCCACTA
ATAAAATGAATCTAAACATTGAATGTGAATGGCCCTCAGAAAATCATCTAGTGCATTTAAAAATAATCGACTCT
AAAACTGAAAGAAACCTTATCACATTTTCCCCAGTTCAATGCTATGCCATTACCAACTCCAAATAATCTCAAAT
AATTTTCCACTTAATAACTGTAAAGTTTTTTTCTGTTAATTTAGGCATATAGAATATTAAATTCTGATATTGCA
CTTCTTATTTTATATAAAATAATCCTTTAATATCCAAATGAATCTGTTAAAATGTTTGATTCCTTGGGAATGGC
CTTAAAAATAAATGTAATAAAGTCAGAGTGGTGGTATGAAAACATTCCTAGTGATCATGTAGTAAATGTAGGGT
TAAGCATGGACAGCCAGAGCTTTCTATGTACTGTTAAAATTGAGGTCACATATTTTCTTTTGTATCCTGGCAAA
TACTCCTGCAGGCCAGGAAGTATAATAGCAAAAAGTTGAACAAAGATGAACTAATGTATTACATTACCATTGCC
ACTGATTTTTTTAAATGGTAAATGACCTTGTATATAAATATTGCCATATCATGGTACCTATAATGGTGATATA
TTTGTTTCTATGAAAAATGTATTGTGCTTTGATACTAAAAATCTGTAAAATGTTAGTTTTGGTAATTTTTTTTC
TGCTGGTGGATTTACATATTAAATTTTTTCTGCTGGTGGATAAACATTAAAATTAATCATGTTTCAAAAAAAAA
AAAA

FIGURE 18

</usr/seqdb2/sst/DNA/Dnaseqs.min/ss.DNA45417
<subunit 1 of 1, 500 aa, 1 stop
<MW: 56888, pI: 8.53, NX(S/T): 2
MKCTAREWLRVTTVLFMARAIPAMVVPNATLLEKLLEKYMDEDGEWWIAKQRGKRAITDNDMQSILDLHNKLRS
QVYPTASNMEYMTWDVELERSAESWAESCLWEHGPASLLPSIGQNLGAHWGRYRPPTFHVQSWYDEVKDFSYPY
EHECNPYCPFRCSGPVCTHYTQVVWATSNRIGCAINLCHNMNIWGQIWPKAVYLVCNYSPKGNWWGHAPYKHGR
PCSACPPSFGGGCRENLCYKEGSDRYYPPREEETNEIERQQSQVHDTHVRTRSDDSSRNEVISAQQMSQIVSCE
VRLRDQCKGTTCNRYECPAGCLDSKAKVIGSVHYEMQSSICRAAIHYGIIDNDGGWVDITRQGRKHYFIKSNRN
GIQTIGKYQSANSFTVSKVTVQAVTCETTVEQLCPFHKPASHCPRVYCPRNCMQANPHYARVIGTRVYSDLSSI
CRAAVHAGVVRNHGGYVDVMPVDKRKTYIASFQNGIFSESLQNPPGGKAFRVFAVV

Important features:

Signal peptide:

amino acids 1-20

Extracellular proteins SCP/Tpx-1/Ag5/PR-1/Sc7 protein amino acids 165-186, 196-218, 134-146, 96-108 and 58-77

N-glycosylation site amino acids 28-31

FIGURE 19

CCCACGCGTCCGAAGGCAGACAAAGGTTCATTTGTAAAGAAGCTCCTTCCAGCACCTCCTC
TCTTCTCCTTTTGCCCAAACTCACCCAGTGAGTGTGAGCATTTAAGAAGCATCCTCTGCCA
AGACCAAAAGGAAAGAAGAAAAAGGGCCAAAAGCCAAAATGAAACTGATGGTACTTGTTTT
CACCATTGGGCTAACTTTGCTGCTAGGAGTTCAAGCCATGCCTGCAAATCGCCTCTCTTGC
TACAGAAAGATACTAAAAGATCACAACTGTCACAACCTTCCGGAAGGAGTAGCTGACCTGA
CACAGATTGATGTCAATGTCCAGGATCATTTCTGGGATGGGAAGGGATGTGAGATGATCTG
TTACTGCAACTTCAGCGAATTGCTCTGCTGCCCAAAAGACGTTTTCTTTGGACCAAAGATC
TCTTTCGTGATTCCTTGCAACAATCAATGAGAATCTTCATGTATTCTGGAGAACACCATTC
CTGATTTCCCACAAACTGCACTACATCAGTATAACTGCATTTCTAGTTTCTATATAGTGCA
ATAGAGCATAGATTCTATAAATTCTTACTTGTCTAAGACAAGTAAATCTGTGTTAAACAAG
TAGTAATAAAAGTTAATTCAATCTAAAAAAAAAAAAA

FIGURE 20

</usr/seqdb2/sst/DNA/Dnaseqs.min/ss.DNA52758
<subunit 1 of 1, 98 aa, 1 stop
<MW: 11081, pI: 6.68, NX(S/T): 1
MKLMVLVFTIGLTLLLGVQAMPANRLSCYRKILKDHNCHNLPEGVADLTQIDVNVQDHFWD
GKGCEMICYCNFSELLCCPKDVFFGPKISFVIPCNNQ

Important features:

Signal peptide:

amino acids 1-20

N-glycosylation site.

amino acids 72-76

Tyrosine kinase phosphorylation site.

amino acids 63-71

FIGURE 21

GGCACAGCCGCGCGGCGGAGGGCAGAGTCAGCCGAGCCGAGTCCAGCCGGACGAGCGGACCAGCGCAGGGCAGC
CCAAGCAGCGCGCAGCGAACGCCCGCCGCCGCCCACACCCTCTGCGGTCCCCGCGGCGCCTGCCACCCTTCCCT
CCTTCCCCGCGTCCCCGCCTCGCCGGCCAGTCAGCTTGCCGGGTTCGCTGCCCCGCGAAACCCCGAGGTCACCA
GCCCGCGCCTCTGCTTCCCTGGGCCGCGCGCCGCCTCCACGCCCTCCTTCTCCCCTGGCCCGGCGCCTGGCACC
GGGGACCGTTGCCTGACGCGAGGCCCAGCTCTACTTTTCGCCCCGCGTCTCCTCCGCCTGCTCGCCTCTTCCAC
CAACTCCAACTCCTTCTCCCTCCAGCTCCACTCGCTAGTCCCCGACTCCGCCAGCCCTCGGCCCGCTGCCGTAG
CGCCGCTTCCCGTCCGGTCCCAAAGGTGGGAACGCGTCCGCCCCGGCCCGCACCATGGCACGGTTCGGCTTGCC
CGCGCTTCTCTGCACCCTGGCAGTGCTCAGCGCCGCGCTGCTGGCTGCCGAGCTCAAGTCGAAAAGTTGCTCGG
AAGTGCGACGTCTTTACGTGTCCAAAGGCTTCAACAAGAACGATGCCCCCCTCCACGAGATCAACGGTGATCAT
TTGAAGATCTGTCCCCAGGGTTCTACCTGCTGCTCTCAAGAGATGGAGGAGAAGTACAGCCTGCAAAGTAAAGA
TGATTTCAAAAGTGTGGTCAGCGAACAGTGCAATCATTTGCAAGCTGTCTTTGCTTCACGTTACAAGAAGTTTG
ATGAATTCTTCAAAGAACTACTTGAAAATGCAGAGAAATCCCTGAATGATATGTTTGTGAAGACATATGGCCAT
TTATACATGCAAAATTCTGAGCTATTTAAAGATCTCTTCGTAGAGTTGAAACGTTACTACGTGGTGGGAAATGT
GAACCTGGAAGAAATGCTAAATGACTTCTGGGCTCGCCTCCTGGAGCGGATGTTCCGCCTGGTGAACTCCCAGT
ACCACTTTACAGATGAGTATCTGGAATGTGTGAGCAAGTATACGGAGCAGCTGAAGCCCTTCGGAGATGTCCCT
CGCAAATTGAAGCTCCAGGTTACTCGTGCTTTTGTAGCAGCCCGTACTTTCGCTCAAGGCTTAGCGGTTGCGGG
AGATGTCGTGAGCAAGGTCTCCGTGGTAAACCCCACAGCCCAGTGTACCCATGCCCTGTTGAAGATGATCTACT
GCTCCCACTGCCGGGGTCTCGTGACTGTGAAGCCATGTTACAACTACTGCTCAAACATCATGAGAGGCTGTTTG
GCCAACCAAGGGGATCTCGATTTTGAATGGAACAATTTCATAGATGCTATGCTGATGGTGGCAGAGAGGCTAGA
GGGTCCTTTCAACATTGAATCGGTCATGGATCCCATCGATGTGAAGATTTCTGATGCTATTATGAACATGCAGG
ATAATAGTGTTCAAGTGTCTCAGAAGGTTTTCCAGGGATGTGGACCCCCCAAGCCCCTCCCAGCTGGACGAATT
TCTCGTTCCATCTCTGAAAGTGCCTTCAGTGCTCGCTTCAGACCACATCACCCCGAGGAACGCCCAACCACAGC
AGCTGGCACTAGTTTGGACCGACTGGTTACTGATGTCAAGGAGAAACTGAAACAGGCCAAGAAATTCTGGTCCT
CCCTTCCGAGCAACGTTTGCAACGATGAGAGGATGGCTGCAGGAAACGGCAATGAGGATGACTGTTGGAATGGG
AAAGGCAAAAGCAGGTACCTGTTTGCAGTGACAGGAAATGGATTAGCCAACCAGGGCAACAACCCAGAGGTCCA
GGTTGACACCAGCAAACCAGACATACTGATCCTTCGTCAAATCATGGCTCTTCGAGTGATGACCAGCAAGATGA
AGAATGCATACAATGGGAACGACGTGGACTTCTTTGATATCAGTGATGAAAGTAGTGGAGAAGGAAGTGGAAGT
GGCTGTGAGTATCAGCAGTGCCCTTCAGAGTTTGACTACAATGCCACTGACCATGCTGGGAAGAGTGCCAATGA
GAAAGCCGACAGTGCTGGTGTCCGTCCTGGGGCACAGGCCTACCTCCTCACTGTCTTCTGCATCTTGTTCCTGG
TTATGCAGAGAGAGTGGAGATAATTCTCAAACTCTGAGAAAAAGTGTTCATCAAAAAGTTAAAAGGCACCAGTT
ATCACTTTTCTACCATCCTAGTGACTTTGCTTTTTAAATGAATGGACAACAATGTACAGTTTTTACTATGTGGC
CACTGGTTTAAGAAGTGCTGACTTTGTTTTCTCATTCAGTTTTGGGAGGAAAAGGGACTGTGCATTGAGTTGGT
TCCTGCTCCCCCAAACCATGTTAAACGTGGCTAACAGTGTAGGTACAGAACTATAGTTAGTTGTGCATTTGTGA
TTTTATCACTCTATTATTTGTTTGTATGTTTTTTTCTCATTTCGTTTGTGGGTTTTTTTTTCCAACTGTGATCT
CGCCTTGTTTCTTACAAGCAAACCAGGGTCCCTTCTTGGCACGTAACATGTACGTATTTCTGAAATATTAAATA
GCTGTACAGAAGCAGGTTTATTTATCATGTTATCTTATTAAAAGAAAAAGCCCAAAAAGC

FIGURE 22

MARFGLPALLCTLAVLSAALLAAELKSKSCSEVRRLYVSKGFNKNDAPLHEINGDHLKICP
QGSTCCSQEMEEKYSLQSKDDFKSVVSEQCNHLQAVFASRYKKFDEFFKELLENAEKSLND
MFVKTYGHLYMQNSELFKDLFVELKRYYVVGNVNLEEMLNDFWARLLERMFRLVNSQYHFT
DEYLECVSKYTEQLKPFGDVPRKLKLQVTRAFVAARTFAQGLAVAGDVVSKVSVVNPTAQC
THALLKMIYCSHCRGLVTVKPCYNYCSNIMRGCLANQGDLDFEWNNFIDAMLMVAERLEGP
FNIESVMDPIDVKISDAIMNMQDNSVQVSQKVFQGCGPPKPLPAGRISRSISESAFSARFR
PHHPEERPTTAAGTSLDRLVTDVKEKLKQAKKFWSSLPSNVCNDERMAAGNGNEDDCWNGK
GKSRYLFAVTGNGLANQGNNPEVQVDTSKPDILILRQIMALRVMTSKMKNAYNGNDVDFFD
ISDESSGEGSGSGCEYQQCPSEFDYNATDHAGKSANEKADSAGVRPGAQAYLLTVFCILFL
VMQREWR

Important features:

Signal peptide:

amino acids 1-22

ATP/GTP-binding site motif A (P-loop).

amino acids 515-524

N-glycosylation site.

amino acids 514-518

Glycosaminoglycan attachment sites.

amino acids 494-498, 498-502

N-myristoylation sites.

amino acids 63-69, 224-230, 276-282, 438-444, 497-503, 531-537

Glypicans proteins.

amino acids 54-75, 105-157, 238-280, 309-346, 423-460, 468-506

FIGURE 23

AGACAGTACCTCCTCCCTAGGACTACACAAGGACTGAACCAGAAGGAAGAGGACAGAGCAA
AGCCATGAACATCATCCTAGAAATCCTTCTGCTTCTGATCACCATCATCTACTCCTACTTG
GAGTCGTTGGTGAAGTTTTTCATTCCTCAGAGGAGAAAATCTGTGGCTGGGGAGATTGTTC
TCATTACTGGAGCTGGGCATGGAATAGGCAGGCAGACTACTTATGAATTTGCAAAACGACA
GAGCATATTGGTTCTGTGGGATATTAATAAGCGCGGTGTGGAGGAAACTGCAGCTGAGTGC
CGAAAACTAGGCGTCACTGCGCATGCGTATGTGGTAGACTGCAGCAACAGAGAAGAGATCT
ATCGCTCTCTAAATCAGGTGAAGAAAGAAGTGGGTGATGTAACAATCGTGGTGAATAATGC
TGGGACAGTATATCCAGCCGATCTTCTCAGCACCAAGGATGAAGAGATTACCAAGACATTT
GAGGTCAACATCCTAGGACATTTTTGGATCACAAAAGCACTTCTTCCATCGATGATGGAGA
GAAATCATGGCCACATCGTCACAGTGGCTTCAGTGTGCGGCCACGAAGGGATTCCTTACCT
CATCCCATATTGTTCCAGCAAATTTGCCGCTGTTGGCTTTCACAGAGGTCTGACATCAGAA
CTTCAGGCCTTGGGAAAAACTGGTATCAAAACCTCATGTCTCTGCCCAGTTTTTGTGAATA
CTGGGTTCACCAAAAATCCAAGCACAAGATTATGGCCTGTATTGGAGACAGATGAAGTCGT
AAGAAGTCTGATAGATGGAATACTTACCAATAAGAAAATGATTTTTGTTCCATCGTATATC
AATATCTTTCTGAGACTACAGAAGTTTCTTCCTGAACGCGCCTCAGCGATTTTAAATCGTA
TGCAGAATATTCAATTTGAAGCAGTGGTTGGCCACAAAATCAAAATGAAATGAATAAATAA
GCTCCAGCCAGAGATGTATGCATGATAATGATATGAATAGTTTCGAATCAATGCTGCAAAG
CTTTATTTCACATTTTTTCAGTCCTGATAATATTAAAAACATTGGTTTGGCACTAGCAGCA
GTCAAACGAACAAGATTAATTACCTGTCTTCCTGTTTCTCAAGAATATTTACGTAGTTTTT
CATAGGTCTGTTTTTCCTTTCATGCCTCTTAAAAACTTCTGTGCTTACATAAACATACTTA
AAAGGTTTTCTTTAAGATATTTTATTTTTCCATTTAAAGGTGGACAAAAGCTACCTCCCTA
AAAGTAAATACAAAGAGAACTTATTTACACAGGGAAGGTTTAAGACTGTTCAAGTAGCATT
CCAATCTGTAGCCATGCCACAGAATATCAACAAGAACACAGAATGAGTGCACAGCTAAGAG
ATCAAGTTTCAGCAGGCAGCTTTATCTCAACCTGGACATATTTTAAGATTCAGCATTTGAA
AGATTTCCCTAGCCTCTTCCTTTTTCATTAGCCCAAAACGGTGCAACTCTATTCTGGACTT
TATTACTTGATTCTGTCTTCTGTATAACTCTGAAGTCCACCAAAAGTGGACCCTCTATATT
TCCTCCCTTTTTATAGTCTTATAAGATACATTATGAAAGGTGACCGACTCTATTTTAAATC
TCAGAATTTTAAGTTCTAGCCCCATGATAACCTTTTTCTTTGTAATTTATGCTTTCATATA
TCCTTGGTCCCAGAGATGTTTAGACAATTTTAGGCTCAAAAATTAAAGCTAACACAGGAAA
AGGAACTGTACTGGCTATTACATAAGAAACAATGGACCCAAGAGAAGAA

FIGURE 24

</usr/seqdb2/sst/DNA/Dnaseqs.min/ss.DNA56409
<subunit 1 of 1, 300 aa, 1 stop
<MW: 33655, pI: 9.31, NX(S/T): 1

MNIILEILLLLITIIYSYLESLVKFFIPQRRKSVAGEIVLITGAGHGIGRQTTYEFAKRQS
ILVLWDINKRGVEETAAECRKLGVTAHAYVVDCSNREEIYRSLNQVKKEVGDVTIVVNNAG
TVYPADLLSTKDEEITKTFEVNILGHFWITKALLPSMMERNHGHIVTVASVCGHEGIPYLI
PYCSSKFAAVGFHRGLTSELQALGKTGIKTSCLCPVFVNTGFTKNPSTRLWPVLETDEVVR
SLIDGILTNKKMIFVPSYINIFLRLQKFLPERASAILNRMQNIQFEAVVGHKIKMK

Important features:

Signal peptide:

amino acids 1-19 cAMP- and cGMP-dependent protein kinase phosphorylation site.

amino acids 30-33 and 58-61

Short-chain alcohol dehydrogenase family protein amino acids 165-202, 37-49, 112-122 and 210-219

FIGURE 25

CTCGGGCGCGCACAGGCAGCTCGGTTTGCCCTGCGATTGAGCTGCGGGTCGCGGCCGGCGCCGGCCTCTCCAAT
GGCAAATGTGTGTGGCTGGAGGCGAGCGCGAGGCTTTCGGCAAAGGCAGTCGAGTGTTTGCAGACCGGGGCGAG
TCCTGTGAAAGCAGATAAAAGAAAACATTTATTAACGTGTCATTACGAGGGGAGCGCCCGGCCGGGGCTGTCGC
ACTCCCCGCGGAACATTTGGCTCCCTCCAGCTCCGAGAGAGGAGAAGAAGAAAGCGGAAAAGAGGCAGATTCAC
GTCGTTTCCAGCCAAGTGGACCTGATCGATGGCCCTCCTGAATTTATCACGATATTTGATTTATTAGCGATGCC
CCCTGGTTTGTGTGTTACGCACACACACGTGCACACAAGGCTCTGGCTCGCTTCCCTCCCTCGTTTCCAGCTCC
TGGGCGAATCCCACATCTGTTTCAACTCTCCGCCGAGGGCGAGCAGGAGCGAGAGTGTGTCGAATCTGCGAGTG
AAGAGGGACGAGGGAAAAGAAACAAAGCCACAGACGCAACTTGAGACTCCCGCATCCCAAAAGAAGCACCAGAT
CAGCAAAAAAAAGAAGATGGGCCCCCCGAGCCTCGTGCTGTGCTTGCTGTCCGCAACTGTGTTCTCCCTGCTGGG
TGGAAGCTCGGCCTTCCTGTCGCACCACCGCCTGAAAGGCAGGTTTCAGAGGGACCGCAGGAACATCCGCCCCA
ACATCATCCTGGTGCTGACGGACGACCAGGATGTGGAGCTGGGTTCCATGCAGGTGATGAACAAGACCCGGCGC
ATCATGGAGCAGGGCGGGGCGCACTTCATCAACGCCTTCGTGACCACACCCATGTGCTGCCCCTCACGCTCCTC
CATCCTCACTGGCAAGTACGTCCACAACCACAACACCTACACCAACAATGAGAACTGCTCCTCGCCCTCCTGGC
AGGCACAGCACGAGAGCCGCACCTTTGCCGTGTACCTCAATAGCACTGGCTACCGGACAGCTTTCTTCGGGAAG
TATCTTAATGAATACAACGGCTCCTACGTGCCACCCGGCTGGAAGGAGTGGGTCGGACTCCTTAAAAACTCCCG
CTTTTATAACTACACGCTGTGTCGGAACGGGGTGAAAGAGAAGCACGGCTCCGACTACTCCAAGGATTACCTCA
CAGACCTCATCACCAATGACAGCGTGAGCTTCTTCCGCACGTCCAAGAAGATGTACCCGCACAGGCCAGTCCTC
ATGGTCATCAGCCATGCAGCCCCCCACGGCCCTGAGGATTCAGCCCCACAATATTCACGCCTCTTCCCAAACGC
ATCTCAGCACATCACGCCGAGCTACAACTACGCGCCCAACCCGGACAAACACTGGATCATGCGCTACACGGGGC
CCATGAAGCCCATCCACATGGAATTCACCAACATGCTCCAGCGGAAGCGCTTGCAGACCCTCATGTCGGTGGAC
GACTCCATGGAGACGATTTACAACATGCTGGTTGAGACGGGCGAGCTGGACAACACGTACATCGTATACACCGC
CGACCACGGTTACCACATCGGCCAGTTTGGCCTGGTGAAAGGGAAATCCATGCCATATGAGTTTGACATCAGGG
TCCCGTTCTACGTGAGGGGCCCCAACGTGGAAGCCGGCTGTCTGAATCCCCACATCGTCCTCAACATTGACCTG
GCCCCCACCATCCTGGACATTGCAGGCCTGGACATACCTGCGGATATGGACGGGAAATCCATCCTCAAGCTGCT
GGACACGGAGCGGCCGGTGAATCGGTTTCACTTGAAAAAGAAGATGAGGGTCTGGCGGGACTCCTTCTTGGTGG
AGAGAGGCAAGCTGCTACACAAGAGAGACAATGACAAGGTGGACGCCCAGGAGGAGAACTTTCTGCCCAAGTAC
CAGCGTGTGAAGGACCTGTGTCAGCGTGCTGAGTACCAGACGGCGTGTGAGCAGCTGGGACAGAAGTGGCAGTG
TGTGGAGGACGCCACGGGGAAGCTGAAGCTGCATAAGTGCAAGGGCCCCATGCGGCTGGGCGGCAGCAGAGCCC
TCTCCAACCTCGTGCCCAAGTACTACGGGCAGGGCAGCGAGGCCTGCACCTGTGACAGCGGGGACTACAAGCTC
AGCCTGGCCGGACGCCGGAAAAAACTCTTCAAGAAGAAGTACAAGGCCAGCTATGTCCGCAGTCGCTCCATCCG
CTCAGTGGCCATCGAGGTGGACGGCAGGGTGTACCACGTAGGCCTGGGTGATGCCGCCCAGCCCCGAAACCTCA
CCAAGCGGCACTGGCCAGGGGCCCCTGAGGACCAAGATGACAAGGATGGTGGGGACTTCAGTGGCACTGGAGGC
CTTCCCGACTACTCAGCCGCCAACCCCATTAAAGTGACACATCGGTGCTACATCCTAGAGAACGACACAGTCCA
GTGTGACCTGGACCTGTACAAGTCCCTGCAGGCCTGGAAAGACCACAAGCTGCACATCGACCACGAGATTGAAA
CCCTGCAGAACAAAATTAAGAACCTGAGGGAAGTCCGAGGTCACCTGAAGAAAAAGCGGCCAGAAGAATGTGAC
TGTCACAAAATCAGCTACCACACCCAGCACAAAGGCCGCCTCAAGCACAGAGGCTCCAGTCTGCATCCTTTCAG
GAAGGGCCTGCAAGAGAAGGACAAGGTGTGGCTGTTGCGGGAGCAGAAGCGCAAGAAGAAACTCCGCAAGCTGC
TCAAGCGCCTGCAGAACAACGACACGTGCAGCATGCCAGGCCTCACGTGCTTCACCCACGACAACCAGCACTGG
CAGACGGCGCCTTTCTGGACACTGGGGCCTTTCTGTGCCTGCACCAGCGCCAACAATAACACGTACTGGTGCAT
GAGGACCATCAATGAGACTCACAATTTCCTCTTCTGTGAATTTGCAACTGGCTTCCTAGAGTACTTTGATCTCA
ACACAGACCCCTACCAGCTGATGAATGCAGTGAACACACTGGACAGGGATGTCCTCAACCAGCTACACGTACAG
CTCATGGAGCTGAGGAGCTGCAAGGGTTACAAGCAGTGTAACCCCCGGACTCGAAACATGGACCTGGATGGAGG
AAGCTATGAGCAATACAGGCAGTTTCAGCGTCGAAAGTGGCCAGAAATGAAGAGACCTTCTTCCAAATCACTGG
GACAACTGTGGGAAGGCTGGGAAGGTTAAGAAACAACAGAGGTGGACCTCCAAAAACATAGAGGCATCACCTGA
CTGCACAGGCAATGAAAAACCATGTGGGTGATTTCCAGCAGACCTGTGCTATTGGCCAGGAGGCCTGAGAAAGC
AAGCACGCACTCTCAGTCAACATGACAGATTCTGGAGGATAACCAGCAGGAGCAGAGATAACTTCAGGAAGTCC
ATTTTTGCCCCTGCTTTTGCTTTGGATTATACCTCACCAGCTGCACAAAATGCATTTTTTCGTATCAAAAAGTC
ACCACTAACCCTCCCCCAGAAGCTCACAAAGGAAAACGGAGAGAGCGAGCGAGAGAGATTTCCTTGGAAATTTC
TCCCAAGGGCGAAAGTCATTGGAATTTTTAAATCATAGGGGAAAAGCAGTCCTGTTCTAAATCCTCTTATTCTT
TTGGTTTGTCACAAAGAAGGAACTAAGAAGCAGGACAGAGGCAACGTGGAGAGGCTGAAAACAGTGCAGAGACG
TTTGACAATGAGTCAGTAGCACAAAAGAGATGACATTTACCTAGCACTATAAACCCTGGTTGCCTCTGAAGAAA
CTGCCTTCATTGTATATATGTGACTATTTACATGTAATCAACATGGAACTTTTAGGGGAACCTAATAAGAAAT
CCCAATTTTCAGGAGTGGTGGTGTCAATAAACGCTCTGTGGCCAGTGTAAAAGAAAAA

FIGURE 26

MGPPSLVLCLLSATVFSLLGGSSAFLSHHRLKGRFQRDRRNIRPNIILVLTDDQDVELGSM
QVMNKTRRIMEQGGAHFINAFVTTPMCCPSRSSILTGKYVHNHNTYTNNENCSSPSWQAQH
ESRTFAVYLNSTGYRTAFFGKYLNEYNGSYVPPGWKEWVGLLKNSRFYNYTLCRNGVKEKH
GSDYSKDYLTDLITNDSVSFFRTSKKMYPHRPVLMVISHAAPHGPEDSAPQYSRLFPNASQ
HITPSYNYAPNPDKHWIMRYTGPMKPIHMEFTNMLQRKRLQTLMSVDDSMETIYNMLVETG
ELDNTYIVYTADHGYHIGQFGLVKGKSMPYEFDIRVPFYVRGPNVEAGCLNPHIVLNIDLA
PTILDIAGLDIPADMDGKSILKLLDTERPVNRFHLKKKMRVWRDSFLVERGKLLHKRDNDK
VDAQEENFLPKYQRVKDLCQRAEYQTACEQLGQKWQCVEDATGKLKLHKCKGPMRLGGSRA
LSNLVPKYYGQGSEACTCDSGDYKLSLAGRRKKLFKKKYKASYVRSRSIRSVAIEVDGRVY
HVGLGDAAQPRNLTKRHWPGAPEDQDDKDGGDFSGTGGLPDYSAANPIKVTHRCYILENDT
VQCDLDLYKSLQAWKDHKLHIDHEIETLQNKIKNLREVRGHLKKKRPEECDCHKISYHTQH
KGRLKHRGSSLHPFRKGLQEKDKVWLLREQKRKKKLRKLLKRLQNNDTCSMPGLTCFTHDN
QHWQTAPFWTLGPFCACTSANNNTYWCMRTINETHNFLFCEFATGFLEYFDLNTDPYQLMN
AVNTLDRDVLNQLHVQLMELRSCKGYKQCNPRTRNMDLDGGSYEQYRQFQRRKWPEMKRPS
SKSLGQLWEGWEG

Important features:

Signal peptide:

amino acids 1-17

Sulfatases signature 1.

amino acids 86-99

Homologous region to sulfatase:

amino acids 87-106, 133-146, 216-229, 291-320, 365-375

N-glycosylation sites.

amino acids 65-69, 112-116, 132-136, 149-153, 171-175, 198-202, 241-245, 561-565, 608-612, 717-721, 754-758, 764-768

FIGURE 27

GCGACGGGCAGGACGCCCCGTTCGCCTAGCGCGTGCTCAGGAGTTGGTGTCCTGCCTGCGC
TCAGGATGAGGGGGAATCTGGCCCTGGTGGGCGTTCTAATCAGCCTGGCCTTCCTGTCACT
GCTGCCATCTGGACATCCTCAGCCGGCTGGCGATGACGCCTGCTCTGTGCAGATCCTCGTC
CCTGGCCTCAAAGGGGATGCGGGAGAGAAGGGAGACAAAGGCGCCCCCGGACGGCCTGGAA
GAGTCGGCCCCACGGGAGAAAAAGGAGACATGGGGGACAAAGGACAGAAAGGCAGTGTGGG
TCGTCATGGAAAAATTGGTCCCATTGGCTCTAAAGGTGAGAAAGGAGATTCCGGTGACATA
GGACCCCCTGGTCCTAATGGAGAACCAGGCCTCCCATGTGAGTGCAGCCAGCTGCGCAAGG
CCATCGGGGAGATGGACAACCAGGTCTCTCAGCTGACCAGCGAGCTCAAGTTCATCAAGAA
TGCTGTCGCCGGTGTGCGCGAGACGGAGAGCAAGATCTACCTGCTGGTGAAGGAGGAGAAG
CGCTACGCGGACGCCCAGCTGTCCTGCCAGGGCCGCGGGGGCACGCTGAGCATGCCCAAGG
ACGAGGCTGCCAATGGCCTGATGGCCGCATACCTGGCGCAAGCCGGCCTGGCCCGTGTCTT
CATCGGCATCAACGACCTGGAGAAGGAGGGCGCCTTCGTGTACTCTGACCACTCCCCCATG
CGGACCTTCAACAAGTGGCGCAGCGGTGAGCCCAACAATGCCTACGACGAGGAGGACTGCG
TGGAGATGGTGGCCTCGGGCGGCTGGAACGACGTGGCCTGCCACACCACCATGTACTTCAT
GTGTGAGTTTGACAAGGAGAACATGTGAGCCTCAGGCTGGGGCTGCCCATTGGGGGCCCCA
CATGTCCCTGCAGGGTTGGCAGGGACAGAGCCCAGACCATGGTGCCAGCCAGGGAGCTGTC
CCTCTGTGAAGGGTGGAGGCTCACTGAGTAGAGGGCTGTTGTCTAAACTGAGAAAATGGCC
TATGCTTAAGAGGAAAATGAAAGTGTTCCTGGGGTGCTGTCTCTGAAGAAGCAGAGTTTCA
TTACCTGTATTGTAGCCCCAATGTCATTATGTAATTATTACCCAGAATTGCTCTTCCATAA
AGCTTGTGCCTTTGTCCAAGCTATACAATAAAATCTTTAAGTAGTGCAGTAGTTAAGTCCA
AAAAAAAAAAAAAAAAAA

FIGURE 28

MRGNLALVGVLISLAFLSLLPSGHPQPAGDDACSVQILVPGLKGDAGEKGDKGAPGRPGRV
GPTGEKGDMGDKGQKGSVGRHGKIGPIGSKGEKGDSGDIGPPGPNGEPGLPCECSQLRKAI
GEMDNQVSQLTSELKFIKNAVAGVRETESKIYLLVKEEKRYADAQLSCQGRGGTLSMPKDE
AANGLMAAYLAQAGLARVFIGINDLEKEGAFVYSDHSPMRTFNKWRSGEPNNAYDEEDCVE
MVASGGWNDVACHTTMYFMCEFDKENM

FIGURE 29

CGGCAACCAGCCGCCGCCACCACCGCTGCCACTGCCGCCCTGCCGGGGCCATGTTCGCTCTGGGCTTGCCCTTC
TTGGTGCTCTTGGTGGCCTCGGTCGAGAGCCATCTGGGGGTTCTGGGGCCCAAGAACGTCTCGCAGAAAGACGC
CGAGTTTGAGCGCACCTACGTGGACGAGGTCAACAGCGAGCTGGTCAACATCTACACCTTCAACCATACTGTGA
CCCGCAACAGGACAGAGGGCGTGCGTGTGTCTGTGAACGTCCTGAACAAGCAGAAGGGGGCGCCGTTGCTGTTT
GTGGTCCGCCAGAAGGAGGCTGTGGTGTCCTTCCAGGTGCCCCTAATCCTGCGAGGGATGTTTCAGCGCAAGTA
CCTCTACCAAAAAGTGGAACGAACCCTGTGTCAGCCCCCCACCAAGAATGAGTCGGAGATTCAGTTCTTCTACG
TGGATGTGTCCACCCTGTCACCAGTCAACACCACATACCAGCTCCGGGTCAGCCGCATGGACGATTTTGTGCTC
AGGACTGGGGAGCAGTTCAGCTTCAATACCACAGCAGCACAGCCCCAGTACTTCAAGTATGAGTTCCCTGAAGG
CGTGGACTCGGTAATTGTCAAGGTGACCTCCAACAAGGCCTTCCCCTGCTCAGTCATCTCCATTCAGGATGTGC
TGTGTCCTGTCTATGACCTGGACAACAACGTAGCCTTCATCGGCATGTACCAGACGATGACCAAGAAGGCGGCC
ATCACCGTACAGCGCAAAGACTTCCCCAGCAACAGCTTTTATGTGGTGGTGGTGGTGAAGACCGAAGACCAAGC
CTGCGGGGGCTCCCTGCCTTTCTACCCCTTCGCAGAAGATGAACCGGTCGATCAAGGGCACCGCCAGAAAACCC
TGTCAGTGCTGGTGTCTCAAGCAGTCACGTCTGAGGCATACGTCAGTGGGATGCTCTTTTGCCTGGGTATATTT
CTCTCCTTTTACCTGCTGACCGTCCTCCTGGCCTGCTGGGAGAACTGGAGGCAGAAGAAGAAGACCCTGCTGGT
GGCCATTGACCGAGCCTGCCCAGAAAGCGGTCACCCTCGAGTCCTGGCTGATTCTTTTCCTGGCAGTTCCCCTT
ATGAGGGTTACAACTATGGCTCCTTTGAGAATGTTTCTGGATCTACCGATGGTCTGGTTGACAGCGCTGGCACT
GGGGACCTCTCTTACGGTTACCAGGGCCGCTCCTTTGAACCTGTAGGTACTCGGCCCCGAGTGGACTCCATGAG
CTCTGTGGAGGAGGATGACTACGACACATTGACCGACATCGATTCCGACAAGAATGTCATTCGCACCAAGCAAT
ACCTCTATGTGGCTGACCTGGCACGGAAGGACAAGCGTGTTCTGCGGAAAAAGTACCAGATCTACTTCTGGAAC
ATTGCCACCATTGCTGTCTTCTATGCCCTTCCTGTGGTGCAGCTGGTGATCACCTACCAGACGGTGGTGAATGT
CACAGGGAATCAGGACATCTGCTACTACAACTTCCTCTGCGCCCACCCACTGGGCAATCTCAGCGCCTTCAACA
ACATCCTCAGCAACCTGGGGTACATCCTGCTGGGGCTGCTTTTCCTGCTCATCATCCTGCAACGGGAGATCAAC
CACAACCGGGCCCTGCTGCGCAATGACCTCTGTGCCCTGGAATGTGGGATCCCCAAACACTTTGGGCTTTTCTA
CGCCATGGGCACAGCCCTGATGATGGAGGGGCTGCTCAGTGCTTGCTATCATGTGTGCCCCAACTATACCAATT
TCCAGTTTGACACATCGTTCATGTACATGATCGCCGGACTCTGCATGCTGAAGCTCTACCAGAAGCGGCACCCG
GACATCAACGCCAGCGCCTACAGTGCCTACGCCTGCCTGGCCATTGTCATCTTCTTCTCTGTGCTGGGCGTGGT
CTTTGGCAAAGGGAACACGGCGTTCTGGATCGTCTTCTCCATCATTCACATCATCGCCACCCTGCTCCTCAGCA
CGCAGCTCTATTACATGGGCCGGTGGAAACTGGACTCGGGGATCTTCCGCCGCATCCTCCACGTGCTCTACACA
GACTGCATCCGGCAGTGCAGCGGGCCGCTCTACGTGGACCGCATGGTGCTGCTGGTCATGGGCAACGTCATCAA
CTGGTCGCTGGCTGCCTATGGGCTTATCATGCGCCCCAATGATTTCGCTTCCTACTTGTTGGCCATTGGCATCT
GCAACCTGCTCCTTTACTTCGCCTTCTACATCATCATGAAGCTCCGGAGTGGGGAGAGGATCAAGCTCATCCCC
CTGCTCTGCATCGTTTGCACCTCCGTGGTCTGGGGCTTCGCGCTCTTCTTCTTCTTCCAGGGACTCAGCACCTG
GCAGAAAACCCCTGCAGAGTCGAGGGAGCACAACCGGGACTGCATCCTCCTCGACTTCTTTGACGACCACGACA
TCTGGCACTTCCTCTCCTCCATCGCCATGTTCGGGTCCTTCCTGGTGTTGCTGACACTGGATGACGACCTGGAT
ACTGTGCAGCGGGACAAGATCTATGTCTTCTAGCAGGAGCTGGGCCCTTCGCTTCACCTCAAGGGGCCCTGAGC
TCCTTTGTGTCATAGACCGGTCACTCTGTCGTGCTGTGGGGATGAGTCCCAGCACCGCTGCCCAGCACTGGATG
GCAGCAGGACAGCCAGGTCTAGCTTAGGCTTGGCCTGGGACAGCCATGGGGTGGCATGGAACCTTGCAGCTGCC
CTCTGCCGAGGAGCAGGCCTGCTCCCCTGGAACCCCCAGATGTTGGCCAAATTGCTGCTTTCTTCTCAGTGTTG
GGGCCTTCCATGGGCCCCTGTCCTTTGGCTCTCCATTTGTCCCTTTGCAAGAGGAAGGATGGAAGGGACACCCT
CCCCATTTCATGCCTTGCATTTTGCCCGTCCTCCTCCCCACAATGCCCCAGCCTGGGACCTAAGGCCTCTTTTT
CCTCCCATACTCCCACTCCAGGGCCTAGTCTGGGGCCTGAATCTCTGTCCTGTATCAGGGCCCCAGTTCTCTTT
GGGCTGTCCCTGGCTGCCATCACTGCCCATTCCAGTCAGCCAGGATGGATGGGGGTATGAGATTTTGGGGGTTG
GCCAGCTGGTGCCAGACTTTTGGTGCTAAGGCCTGCAAGGGGCCTGGGGCAGTGCGTATTCTCTTCCCTCTGAC
CTGTGCTCAGGGCTGGCTCTTTAGCAATGCGCTCAGCCCAATTTGAGAACCGCCTTCTGATTCAAGAGGCTGAA
TTCAGAGGTCACCTCTTCATCCCATCAGCTCCCAGACTGATGCCAGCACCAGGACTGGAGGGAGAAGCGCCTCA
CCCCTTCCCTTCCTTCTTTCCAGGCCCTTAGTCTTGCCAAACCCCAGCTGGTGGCCTTTCAGTGCCATTGACAC
TGCCCAAGAATGTCCAGGGGCAAAGGAGGGATGATACAGAGTTCAGCCCGTTCTGCCTCCACAGCTGTGGGCAC
CCCAGTGCCTACCTTAGAAAGGGGCTTCAGGAAGGGATGTGCTGTTTCCCTCTACGTGCCCAGTCCTAGCCTCG
CTCTAGGACCCAGGGCTGGCTTCTAAGTTTCCGTCCAGTCTTCAGGCAAGTTCTGTGTTAGTCATGCACACACA
TACCTATGAAACCTTGGAGTTTACAAAGAATTGCCCCAGCTCTGGGCACCCTGGCCACCCTGGTCCTTGGATCC
CCTTCGTCCCACCTGGTCCACCCCAGATGCTGAGGATGGGGGAGCTCAGGCGGGGCCTCTGCTTTGGGGATGGG
AATGTGTTTTTCTCCCAAACTTGTTTTTATAGCTCTGCTTGAAGGGCTGGGAGATGAGGTGGGTCTGGATCTTT
TCTCAGAGCGTCTCCATGCTATGGTTGCATTTCCGTTTTCTATGAATGAATTTGCATTCAATAAACAACCAGAC
TCAAAAAAAAAAAAAAAA

FIGURE 30

></usr/seqdb2/sst/DNA/Dnaseqs.min/ss.DNA66659
><subunit 1 of 1, 832 aa, 1 stop
><MW: 94454, pI: 6.94, NX(S/T): 12

MFALGLPFLVLLVASVESHLGVLGPKNVSQKDAEFERTYVDEVNSELVNIYTFNHTVTRNR
TEGVRVSVNVLNKQKGAPLLFVVRQKEAVVSFQVPLILRGMFQRKYLYQKVERTLCQPPTK
NESEIQFFYVDVSTLSPVNTTYQLRVSRMDDFVLRTGEQFSFNTTAAQPQYFKYEFPEGVD
SVIVKVTSNKAFPCSVISIQDVLCPVYDLDNNVAFIGMYQTMTKKAAITVQRKDFPSNSFY
VVVVVKTEDQACGGSLPFYPFAEDEPVDQGHRQKTLSVLVSQAVTSEAYVSGMLFCLGIFL
SFYLLTVLLACWENWRQKKKTLLVAIDRACPESGHPRVLADSFPGSSPYEGYNYGSFENVS
GSTDGLVDSAGTGDLSYGYQGRSFEPVGTRPRVDSMSSVEEDDYDTLTDIDSDKNVIRTKQ
YLYVADLARKDKRVLRKKYQIYFWNIATIAVFYALPVVQLVITYQTVVNVTGNQDICYYNF
LCAHPLGNLSAFNNILSNLGYILLGLLFLLIILQREINHNRALLRNDLCALECGIPKHFGL
FYAMGTALMMEGLLSACYHVCPNYTNFQFDTSFMYMIAGLCMLKLYQKRHPDINASAYSAY
ACLAIVIFFSVLGVVFGKGNTAFWIVFSIIHIIATLLLSTQLYYMGRWKLDSGIFRRILHV
LYTDCIRQCSGPLYVDRMVLLVMGNVINWSLAAYGLIMRPNDFASYLLAIGICNLLLYFAF
YIIMKLRSGERIKLIPLLCIVCTSVVWGFALFFFFQGLSTWQKTPAESREHNRDCILLDFF
DDHDIWHFLSSIAMFGSFLVLLTLDDDLDTVQRDKIYVF

Important features of the protein:

Signal peptide:

amino acids 1-18

Transmembrane domains:

amino acids 292-317, 451-470, 501-520, 607-627, 751-770

Leucine zipper pattern.

amino acids 497-518

N-glycosylation sites.

amino acids 27-30, 54-57, 60-63, 123-126, 141-144, 165-168, 364-367, 476-479, 496-499, 572-575, 603-606, 699-702

FIGURE 31

GTGAATGTGAGGGTTTGATGACTTTCAGATGTCTAGGAACCAGAGTGGGTGCAGGGGCCCC
AGGCAGGGCTGATTCTTGGGCGGAGGAGAGTAGGGTAAAGGGTTCTGCATGAGCTCCTTAA
AGGACAAAGGTAACAGAGCCAGCGAGAGAGCTCGAGGGGAGACTTTGACTTCAAGCCACAG
AATTGGTGGAAGTGTGCGCGCCGCCGCCGCCGTCGCTCCTGCAGCGCTGTCGACCTAGCCG
CTAGCATCTTCCCGAGCACCGGGATCCCGGGGTAGGAGGCGACGCGGGCGAGCACCAGCGC
CAGCCGGCTGCGGCTGCCCACACGGCTCACCATGGGCTCCGGGCGCCGGGCGCTGTCCGCG
GTGCCGGCCGTGCTGCTGGTCCTCACGCTGCCGGGGCTGCCCGTCTGGGCACAGAACGACA
CGGAGCCCATCGTGCTGGAGGGCAAGTGTCTGGTGGTGTGCGACTCGAACCCGGCCACGGA
CTCCAAGGGCTCCTCTTCCTCCCCGCTGGGGATATCGGTCCGGGCGGCCAACTCCAAGGTC
GCCTTCTCGGCGGTGCGGAGCACCAACCACGAGCCATCCGAGATGAGCAACAAGACGCGCA
TCATTTACTTCGATCAGATCCTGGTGAATGTGGGTAATTTTTTCACATTGGAGTCTGTCTT
TGTAGCACCAAGAAAAGGAATTTACAGTTTCAGTTTTCACGTGATTAAAGTCTACCAGAGC
CAAACTATCCAGGTTAACTTGATGTTAAATGGAAAACCAGTAATATCTGCCTTTGCGGGGG
ACAAAGATGTTACTCGTGAAGCTGCCACGAATGGTGTCCTGCTCTACCTAGATAAAGAGGA
TAAGGTTTACCTAAAACTGGAGAAAGGTAATTTGGTTGGAGGCTGGCAGTATTCCACGTTT
TCTGGCTTTCTGGTGTTCCCCCTATAGGATTCAATTTCTCCATGATGTTCATCCAGGTGAG
GGATGACCCACTCCTGAGTTATTGGAAGATCATTTTTTCATCATTGGATTGATGTCTTTTA
TTGGTTTCTCATGGGTGGATATGGATTCTAAGGATTCTAGCCTGTCTGAACCAATACAAAA
TTTCACAGATTATTTGTGTGTGTCTGTTTCAGTATATTTGGATTGGGACTCTAAGCAGATA
ATACCTATGCTTAAATGTAACAGTCAAAAGCTGTCTGCAAGACTTATTCTGAATTTCATTT
CCTGGGATTACTGAATTAGTTACAGATGTGGAATTTTATTTGTTTAGTTTTAAAAGACTGG
CAACCAGGTCTAAGGATTAGAAAACTCTAAAGTTCTGACTTCAATCAACGGTTAGTGTGAT
ACTGCCAAAGAACTGTATACTGTGTTAATATATTGATTATATTTGTTTTTATTCCTTTGGA
ATTAGTTTGTTTGGTTCTTGTAAAAAACTTGGATTTTTTTTTCAGTAACTGGTATTATGT
TTTCTCTTAAAATAAGGTAATGAATGGCTTGCCCACAAATTTACCTTGACTACGATATCAT
CGACATGACTTCTCTCAAAAAAAAAGAATGCTTCATAGTTGTATTTTAATTGTATATGTGA
AAGAGTCATATTTTCCAAGTTATATTTTCTAAGAAGAAGAATAGATCATAAATCTGACAAG
GAAAAAGTTGCTTACCCAAAATCTAAGTGCTCAATCCCTGAGCCTCAGCAAAACAGCTCCC
CTCCGAGGGAAATCTTATACTTTATTGCTCAACTTTAATTAAAATGATTGATAATAACCAC
TTTATTAAAAACCTAAGGTTTTTTTTTTTCCGTAGACATGACCACTTTATTAACTGGTGG
TGGGATGCTGTTGTTTCTAATTATACCTATTTTTCAAGGCTTCTGTTGTATTTGAAGTATC
ATCTGGTTTTGCCTTAACTCTTTAAATTGTATATATTTATCTGTTTAGCTAATATTAAATT
CAAATATCCCATATCTAAATTTAGTGCAATATCTTGTCTTTTGTATAGGTCATATGAATTC
ATAAAATTATTTATGTCTGTTATAGAATAAAGATTAATATATGTTAAAAAAA

FIGURE 32

MGSGRRALSAVPAVLLVLTLPGLPVWAQNDTEPIVLEGKCLVVCDSNPATDSKGSSSSPLG
ISVRAANSKVAFSAVRSTNHEPSEMSNKTRIIYFDQILVNVGNFFTLESVFVAPRKGIYSF
SFHVIKVYQSQTIQVNLMLNGKPVISAFAGDKDVTREAATNGVLLYLDKEDKVYLKLEKGN
LVGGWQYSTFSGFLVFPL

Signal peptide:

amino acids 1-27

FIGURE 33

GTCGAAGGTTATAAAAGCTTCCAGCCAAACGGCATTGAAGTTGAAGATACAACCTGACAGC
ACAGCCTGAGATCTTGGGGATCCCTCAGCCTAACACCCACAGACGTCAGCTGGTGGATTCC
CGCTGCATCAAGGCCTACCCACTGTCTCCATGCTGGGCTCTCCCTGCCTTCTGTGGCTCCT
GGCCGTGACCTTCTTGGTTCCCAGAGCTCAGCCCTTGGCCCCTCAAGACTTTGAAGAAGAG
GAGGCAGATGAGACTGAGACGGCGTGGCCGCCTTTGCCGGCTGTCCCCTGCGACTACGACC
ACTGCCGACACCTGCAGGTGCCCTGCAAGGAGCTACAGAGGGTCGGGCCGGCGGCCTGCCT
GTGCCCAGGACTCTCCAGCCCCGCCCAGCCGCCCGACCCGCCGCGCATGGGAGAAGTGCGC
ATTGCGGCCGAAGAGGGCCGCGCAGTGGTCCACTGGTGTGCCCCCTTCTCCCCGGTCCTCC
ACTACTGGCTGCTGCTTTGGGACGGCAGCGAGGCTGCGCAGAAGGGGCCCCCGCTGAACGC
TACGGTCCGCAGAGCCGAACTGAAGGGGCTGAAGCCAGGGGGCATTTATGTCGTTTGCGTA
GTGGCCGCTAACGAGGCCGGGGCAAGCCGCGTGCCCCAGGCTGGAGGAGAGGGCCTCGAGG
GGGCCGACATCCCTGCCTTCGGGCCTTGCAGCCGCCTTGCGGTGCCGCCCAACCCCCGCAC
TCTGGTCCACGCGGCCGTCGGGGTGGGCACGGCCCTGGCCCTGCTAAGCTGTGCCGCCCTG
GTGTGGCACTTCTGCCTGCGCGATCGCTGGGGCTGCCCGCGCCGAGCCGCCGCCCGAGCCG
CAGGGGCGCTCTGAAAGGGGCCTGGGGGCATCTCGGGCACAGACAGCCCCACCTGGGGCGC
TCAGCCTGGCCCCCGGGAAAGAGGAAAACCCGCTGCCTCCAGGGAGGGCTGGACGGCGAGC
TGGGAGCCAGCCCCAGGCTCCAGGGCCACGGCGGAGTCATGGTTCTCAGGACTGAGCGCTT
GTTTAGGTCCGGTACTTGGCGCTTTGTTTCCTGGCTGAGGTCTGGGAAGGAATAGAAAGGG
GCCCCCAATTTTTTTTTAAGCGGCCAGATAATAAATAATGTAACCTTTGCGGTTAAAAAAA
AAAAAAAAAAA

FIGURE 34

></usr/seqdb2/sst/DNA/Dnaseqs.min/ss.DNA68874

><subunit 1 of 1, 238 aa, 1 stop

><MW: 25262, pI: 6.44, NX(S/T): 1

MLGSPCLLWLLAVTFLVPRAQPLAPQDFEEEEADETETAWPPLPAVPCDYDHCRHLQVPCK
ELQRVGPAACLCPGLSSPAQPPDPPRMGEVRIAAEEGRAVVHWCAPFSPVLHYWLLLWDGS
EAAQKGPPLNATVRRAELKGLKPGGIYVVCVVAANEAGASRVPQAGGEGLEGADIPAFGPC
SRLAVPPNPRTLVHAAVGVGTALALLSCAALVWHFCLRDRWGCPRRAAARAAGAL

Important features of the protein:

Signal peptide:

amino acids 1-20

Transmembrane domain:

amino acids 194-220

N-glycosylation site.

amino acids 132-135

FIGURE 35

CGGCTCGAGCCCGCCCGGAAGTGCCCGAGGGGCCGCGATGGAGCTGGGGGAGCCGGGCGCT
CGGTAGCGCGGCGGGCAAGGCAGGCGCC<u>ATG</u>ACCCTGATTGAAGGGGTGGGTGATGAGGTG
ACCGTCCTTTTCTCGGTGCTTGCCTGCCTTCTGGTGCTGGCCCTTGCCTGGGTCTCAACGC
ACACCGCTGAGGGCGGGGACCCACTGCCCCAGCCGTCAGGGACCCCAACGCCATCCCAGCC
CAGCGCAGCCATGGCAGCTACCGACAGCATGAGAGGGGAGGCCCCAGGGGCAGAGACCCCC
AGCCTGAGACACAGAGGTCAAGCTGCACAGCCAGAGCCCAGCACGGGGTTCACAGCAACAC
CGCCAGCCCCGGACTCCCCGCAGGAGCCCCTCGTGCTACGGCTGAAATTCCTCAATGATTC
AGAGCAGGTGGCCAGGGCCTGGCCCCACGACACCATTGGCTCCTTGAAAAGGACCCAGTTT
CCCGGCCGGGAACAGCAGGTGCGACTCATCTACCAAGGGCAGCTGCTAGGCGACGACACCC
AGACCCTGGGCAGCCTTCACCTCCCTCCCAACTGCGTTCTCCACTGCCACGTGTCCACGAG
AGTCGGTCCCCCAAATCCCCCCTGCCCGCCGGGGTCCGAGCCCGGCCCCTCCGGGCTGGAA
ATCGGCAGCCTGCTGCTGCCCCTGCTGCTCCTGCTGTTGCTGCTGCTCTGGTACTGCCAGA
TCCAGTACCGGCCCTTCTTTCCCCTGACCGCCACTCTGGGCCTGGCCGGCTTCACCCTGCT
CCTCAGTCTCCTGGCCTTTGCCATGTACCGCCCG<u>TAG</u>TGCCTCCGCGGGCGCTTGGCAGCG
TCGCCGGCCCCTCCGGACCTTGCTCCCCGCGCCGCGGCGGGAGCTGCTGCCTGCCCAGGCC
CGCCTCTCCGGCCTGCCTCTTCCCGCTGCCCTGGAGCCCAGCCCTGCGCCGCAGAGGACTC
CCGGGACTGGCGGAGGCCCCGCCCTGCGACCGCCGGGGCTCGGGGCCACCTCCCGGGGCTG
CTGAACCTCAGCCCGCACTGGGAGTGGGCTCCTCGGGGTCGGGCATCTGCTGTCGCTGCCT
CGGCCCCGGGCAGAGCCGGGCCGCCCCGGGGGCCCGTCTTAGTGTTCTGCCGGAGGACCCA
GCCGCCTCCAATCCCTGACAGCTCCTTGGGCTGAGTTGGGGACGCCAGGTCGGTGGGAGGC
TGGTGAAGGGGAGCGGGGAGGGGCAGAGGAGTTCCCCGGAACCCGTGCAGATTAAAGTAAC
TGTGAAGTTTAAAAAAAAAAAAAAAAAA

FIGURE 36

MTLIEGVGDEVTVLFSVLACLLVLALAWVSTHTAEGGDPLPQPSGTPTPSQPSAAMAATDS
MRGEAPGAETPSLRHRGQAAQPEPSTGFTATPPAPDSPQEPLVLRLKFLNDSEQVARAWPH
DTIGSLKRTQFPGREQQVRLIYQGQLLGDDTQTLGSLHLPPNCVLHCHVSTRVGPPNPPCP
PGSEPGPSGLEIGSLLLPLLLLLLLLLWYCQIQYRPFFPLTATLGLAGFTLLLSLLAFAMYRP

Signal peptide:

amino acids 1-31

Transmembrane domain:

amino acids 195-217

FIGURE 37

GTGACACTATAGAAGAGCTATGACGTCGCATGCACGCGTACGTAAGCTCGGAATTCGGCTCGAGGCTGGTGGGA
AGAAGCCGAGATGGCGGCAGCCAGCGCTGGGGCAACCCGGCTGCTCCTGCTCTTGCTGATGGCGGTAGCAGCGC
CCAGTCGAGCCCGGGGCAGCGGCTGCCGGGCCGGGACTGGTGCGCGAGGGGCTGGGGCGGAAGGTCGAGAGGGC
GAGGCCTGTGGCACGGTGGGGCTGCTGCTGGAGCACTCATTTGAGATCGATGACAGTGCCAACTTCCGGAAGCG
GGGCTCACTGCTCTGGAACCAGCAGGATGGTACCTTGTCCCTGTCACAGCGGCAGCTCAGCGAGGAGGAGCGGG
GCCGACTCCGGGATGTGGCAGCCCTGAATGGCCTGTACCGGGTCCGGATCCCAAGGCGACCCGGGGCCCTGGAT
GGCCTGGAAGCTGGTGGCTATGTCTCCTCCTTTGTCCCTGCGTGCTCCCTGGTGGAGTCGCACCTGTCGGACCA
GCTGACCCTGCACGTGGATGTGGCCGGCAACGTGGTGGGCGTGTCGGTGGTGACGCACCCCGGGGGCTGCCGGG
GCCATGAGGTGGAGGACGTGGACCTGGAGCTGTTCAACACCTCGGTGCAGCTGCAGCCGCCCACCACAGCCCCA
GGCCCTGAGACGGCGGCCTTCATTGAGCGCCTGGAGATGGAACAGGCCCAGAAGGCCAAGAACCCCCAGGAGCA
GAAGTCCTTCTTCGCCAAATACTGGATGTACATCATTCCCGTCGTCCTGTTCCTCATGATGTCAGGAGCGCCAG
ACACCGGGGGCCAGGGTGGGGGTGGGGGTGGGGGTGGTGGTGGGGGTAGTGGCCTTTGCTGTGTGCCACCCTCC
CTGTAAGTCTATTTAAAAACATCGACGATACATTGAAATGTGTGAACGTTTTGAAAAGCTACAGCTTCCAGCAG
CCAAAAGCAACTGTTGTTTTGGCAAGACGGTCCTGATGTACAAGCTTGATTGAAATTCACTGCTCACTTGATAC
GTTATTCAGAAACCCAAGGAATGGCTGTCCCCATCCTCATGTGGCTGTGTGGAGCTCAGCTGTGTTGTGTGGCA
GTTTATTAAACTGTCCCCCAGATCGACACGCAAAAAAAAA

FIGURE 38

MAAASAGATRLLLLLLMAVAAPSRARGSGCRAGTGARGAGAEGREGEACGTVGLLLEHSFEIDDSANFRKRGSL
LWNQQDGTLSLSQRQLSEEERGRLRDVAALNGLYRVRIPRRPGALDGLEAGGYVSSFVPACSLVESHLSDQLTL
HVDVAGNVVGVSVVTHPGGCRGHEVEDVDLELFNTSVQLQPPTTAPGPETAAFIERLEMEQAQKAKNPQEQKSF
FAKYWMYIIPVVLFLMMSGAPDTGGQGGGGGGGGGGGSGLCCVPPSL

Important features:

Signal peptide:

amino acids 1-24

Transmembrane domain:

amino acids 226-243

FIGURE 39

GCGACGCGCGGCGGGGCGGCGAGAGGAAACGCGGCGCCGGGCCGGGCCCGGCCCTGGAGAT
GGTCCCCGGCGCCGCGGGCTGGTGTTGTCTCGTGCTCTGGCTCCCCGCGTGCGTCGCGGCC
CACGGCTTCCGTATCCATGATTATTTGTACTTTCAAGTGCTGAGTCCTGGGGACATTCGAT
ACATCTTCACAGCCACACCTGCCAAGGACTTTGGTGGTATCTTTCACACAAGGTATGAGCA
GATTCACCTTGTCCCCGCTGAACCTCCAGAGGCCTGCGGGGAACTCAGCAACGGTTTCTTC
ATCCAGGACCAGATTGCTCTGGTGGAGAGGGGGGGCTGCTCCTTCCTCTCCAAGACTCGGG
TGGTCCAGGAGCACGGCGGGCGGGCGGTGATCATCTCTGACAACGCAGTTGACAATGACAG
CTTCTACGTGGAGATGATCCAGGACAGTACCCAGCGCACAGCTGACATCCCCGCCCTCTTC
CTGCTCGGCCGAGACGGCTACATGATCCGCCGCTCTCTGGAACAGCATGGGCTGCCATGGG
CCATCATTTCCATCCCAGTCAATGTCACCAGCATCCCCACCTTTGAGCTGCTGCAACCGCC
CTGGACCTTCTGGTAGAAGAGTTTGTCCCACATTCCAGCCATAAGTGACTCTGAGCTGGGA
AGGGGAAACCCAGGAATTTTGCTACTTGGAATTTGGAGATAGCATCTGGGGACAAGTGGAG
CCAGGTAGAGGAAAAGGGTTTGGGCGTTGCTAGGCTGAAAGGGAAGCCACACCACTGGCCT
TCCCTTCCCCAGGGCCCCCAAGGGTGTCTCATGCTACAAGAAGAGGCAAGAGACAGGCCCC
AGGGCTTCTGGCTAGAACCCGAAACAAAAGGAGCTGAAGGCAGGTGGCCTGAGAGCCATCT
GTGACCTGTCACACTCACCTGGCTCCAGCCTCCCCTACCCAGGGTCTCTGCACAGTGACCT
TCACAGCAGTTGTTGGAGTGGTTTAAAGAGCTGGTGTTTGGGGACTCAATAAACCCTCACT
GACTTTTTAGCAATAAAGCTTCTCATCAGGGTTGCAAAAAAAAAAAAAAAAAAAAAAAAA

FIGURE 40

></usr/seqdb2/sst/DNA/Dnaseqs.min/ss.DNA76532

><subunit 1 of 1, 188 aa, 1 stop

><MW: 21042, pI: 5.36, NX(S/T): 2

MVPGAAGWCCLVLWLPACVAAHGFRIHDYLYFQVLSPGDIRYIFTATPAKDFGGIFHTRYE
QIHLVPAEPPEACGELSNGFFIQDQIALVERGGCSFLSKTRVVQEHGGRAVIISDNAVDND
SFYVEMIQDSTQRTADIPALFLLGRDGYMIRRSLEQHGLPWAIISIPVNVTSIPTFELLQP
PWTFW

Signal peptide:

amino acids 1-20

FIGURE 41

GGAGAGCCGCGGCTGGGACCGGAGTGGGGAGCGCGGCGTGGAGGTGCCACCCGGCGCGGGT
GGCGGAGAGATCAGAAGCCTCTTCCCCAAGCCGAGCCAACCTCAGCGGGGACCCGGGCTCA
GGGACGCGGCGGCGGCGGCGGCGACTGCAGTGGCTGGACGATGGCAGCGTCCGCCGGAGCC
GGGGCGGTGATTGCAGCCCCAGACAGCCGGCGCTGGCTGTGGTCGGTGCTGGCGGCGGCGC
TTGGGCTCTTGACAGCTGGAGTATCAGCCTTGGAAGTATATACGCCAAAAGAAATCTTCGT
GGCAAATGGTACACAAGGGAAGCTGACCTGCAAGTTCAAGTCTACTAGTACGACTGGCGGG
TTGACCTCAGTCTCCTGGAGCTTCCAGCCAGAGGGGGCCGACACTACTGTGTCGTTTTTCC
ACTACTCCCAAGGGCAAGTGTACCTTGGGAATTATCCACCATTTAAAGACAGAATCAGCTG
GGCTGGAGACCTTGACAAGAAAGATGCATCAATCAACATAGAAAATATGCAGTTTATACAC
AATGGCACCTATATCTGTGATGTCAAAAACCCTCCTGACATCGTTGTCCAGCCTGGACACA
TTAGGCTCTATGTCGTAGAAAAAGAGAATTTGCCTGTGTTTCCAGTTTGGGTAGTGGTGGG
CATAGTTACTGCTGTGGTCCTAGGTCTCACTCTGCTCATCAGCATGATTCTGGCTGTCCTC
TATAGAAGGAAAAACTCTAAACGGGATTACACTGGCTGCAGTACATCAGAGAGTTTGTCAC
CAGTTAAGCAGGCTCCTCGGAAGTCCCCCTCCGACACTGAGGGTCTTGTAAAGAGTCTGCC
TTCTGGATCTCACCAGGGCCCAGTCATATATGCACAGTTAGACCACTCCGGCGGACATCAC
AGTGACAAGATTAACAAGTCAGAGTCTGTGGTGTATGCGGATATCCGAAAGAATTAAGAGA
ATACCTAGAACATATCCTCAGCAAGAAACAAAACCAAACTGGACTCTCGTGCAGAAAATGT
AGCCCATTACCACATGTAGCCTTGGAGACCCAGGCAAGGACAAGTACACGTGTACTCACAG
AGGGAGAGAAAGATGTGTACAAAGGATATGTATAAATATTCTATTTAGTCATCCTGATATG
AGGAGCCAGTGTTGCATGATGAAAAGATGGTATGATTCTACATATGTACCCATTGTCTTGC
TGTTTTTGTACTTTCTTTTCAGGTCATTTACAATTGGGAGATTTCAGAAACATTCCTTTCA
CCATCATTTAGAAATGGTTTGCCTTAATGGAGACAATAGCAGATCCTGTAGTATTTCCAGT
AGACATGGCCTTTTAATCTAAGGGCTTAAGACTGATTAGTCTTAGCATTTACTGTAGTTGG
AGGATGGAGATGCTATGATGGAAGCATACCCAGGGTGGCCTTTAGCACAGTATCAGTACCA
TTTATTTGTCTGCCGCTTTTAAAAAATACCCATTGGCTATGCCACTTGAAAACAATTTGAG
AAGTTTTTTTGAAGTTTTTCTCACTAAAATATGGGGCAATTGTTAGCCTTACATGTTGTGT
AGACTTACTTTAAGTTTGCACCCTTGAAATGTGTCATATCAATTTCTGGATTCATAATAGC
AAGATTAGCAAAGGATAAATGCCGAAGGTCACTTCATTCTGGACACAGTTGGATCAATACT
GATTAAGTAGAAAATCCAAGCTTTGCTTGAGAACTTTTGTAACGTGGAGAGTAAAAAGTAT
CGGTTTTA

FIGURE 42

></usr/seqdb2/sst/DNA/Dnaseqs.min/ss.DNA76510
><subunit 1 of 1, 269 aa, 1 stop
><MW: 29082, pI: 9.02, NX(S/T): 3
MAASAGAGAVIAAPDSRRWLWSVLAAALGLLTAGVSALEVYTPKEIFVANGTQGKLTCKFK
STSTTGGLTSVSWSFQPEGADTTVSFFHYSQGQVYLGNYPPFKDRISWAGDLDKKDASINI
ENMQFIHNGTYICDVKNPPDIVVQPGHIRLYVVEKENLPVFPVWVVVGIVTAVVLGLTLLI
SMILAVLYRRKNSKRDYTGCSTSESLSPVKQAPRKSPSDTEGLVKSLPSGSHQGPVIYAQL
DHSGGHHSDKINKSESVVYADIRKN

Signal peptide:
amino acids 1-37

Transmembrane domain:
amino acids 161-183

FIGURE 43

GGGACTACAAGCCGCGCCGCGCTGCCGCTGGCCCCTCAGCAACCCTCGACATGGCGCTGAGGCGGCCACCGCGA
CTCCGGCTCTGCGCTCGGCTGCCTGACTTCTTCCTGCTGCTGCTTTTCAGGGGCTGCCTGATAGGGGCTGTAAA
TCTCAAATCCAGCAATCGAACCCCAGTGGTACAGGAATTTGAAAGTGTGGAACTGTCTTGCATCATTACGGATT
CGCAGACAAGTGACCCCAGGATCGAGTGGAAGAAAATTCAAGATGAACAAACCACATATGTGTTTTTTGACAAC
AAAATTCAGGGAGACTTGGCGGGTCGTGCAGAAATACTGGGGAAGACATCCCTGAAGATCTGGAATGTGACACG
GAGAGACTCAGCCCTTTATCGCTGTGAGGTCGTTGCTCGAAATGACCGCAAGGAAATTGATGAGATTGTGATCG
AGTTAACTGTGCAAGTGAAGCCAGTGACCCCTGTCTGTAGAGTGCCGAAGGCTGTACCAGTAGGCAAGATGGCA
ACACTGCACTGCCAGGAGAGTGAGGGCCACCCCCGGCCTCACTACAGCTGGTATCGCAATGATGTACCACTGCC
CACGGATTCCAGAGCCAATCCCAGATTTCGCAATTCTTCTTTCCACTTAAACTCTGAAACAGGCACTTTGGTGT
TCACTGCTGTTCACAAGGACGACTCTGGGCAGTACTACTGCATTGCTTCCAATGACGCAGGCTCAGCCAGGTGT
GAGGAGCAGGAGATGGAAGTCTATGACCTGAACATTGGCGGAATTATTGGGGGGGTTCTGGTTGTCCTTGCTGT
ACTGGCCCTGATCACGTTGGGCATCTGCTGTGCATACAGACGTGGCTACTTCATCAACAATAAACAGGATGGAG
AAAGTTACAAGAACCCAGGGAAACCAGATGGAGTTAACTACATCCGCACTGACGAGGAGGGCGACTTCAGACAC
AAGTCATCGTTTGTGATCTGAGACCCGCGGTGTGGCTGAGAGCGCACAGAGCGCACGTGCACATACCTCTGCTA
GAAACTCCTGTCAAGGCAGCGAGAGCTGATGCACTCGGACAGAGCTAGACACTCATTCAGAAGCTTTTCGTTTT
GGCCAAAGTTGACCACTACTCTTCTTACTCTAACAAGCCACATGAATAGAAGAATTTTCCTCAAGATGGACCCG
GTAAATATAACCACAAGGAAGCGAAACTGGGTGCGTTCACTGAGTTGGGTTCCTAATCTGTTTCTGGCCTGATT
CCCGCATGAGTATTAGGGTGATCTTAAAGAGTTTGCTCACGTAAACGCCCGTGCTGGGCCCTGTGAAGCCAGCA
TGTTCACCACTGGTCGTTCAGCAGCCACGACAGCACCATGTGAGATGGCGAGGTGGCTGGACAGCACCAGCAGC
GCATCCCGGCGGGAACCCAGAAAAGGCTTCTTACACAGCAGCCTTACTTCATCGGCCCACAGACACCACCGCAG
TTTCTTCTTAAAGGCTCTGCTGATCGGTGTTGCAGTGTCCATTGTGGAGAAGCTTTTTGGATCAGCATTTTGTA
AAAACAACCAAAATCAGGAAGGTAAATTGGTTGCTGGAAGAGGGATCTTGCCTGAGGAACCCTGCTTGTCCAAC
AGGGTGTCAGGATTTAAGGAAAACCTTCGTCTTAGGCTAAGTCTGAAATGGTACTGAAATATGCTTTTCTATGG
GTCTTGTTTATTTTATAAAATTTTACATCTAAATTTTTGCTAAGGATGTATTTTGATTATTGAAAAGAAAATTT
CTATTTAAACTGTAAATATATTGTCATACAATGTTAAATAACCTATTTTTTTAAAAAAGTTCAACTTAAGGTAG
AAGTTCCAAGCTACTAGTGTTAAATTGGAAAATATCAATAATTAAGAGTATTTTACCCAAGGAATCCTCTCATG
GAAGTTTACTGTGATGTTCCTTTTCTCACACAAGTTTTAGCCTTTTTCACAAGGGAACTCATACTGTCTACACA
TCAGACCATAGTTGCTTAGGAAACCTTTAAAAATTCCAGTTAAGCAATGTTGAAATCAGTTTGCATCTCTTCAA
AAGAAACCTCTCAGGTTAGCTTTGAACTGCCTCTTCCTGAGATGACTAGGACAGTCTGTACCCAGAGGCCACCC
AGAAGCCCTCAGATGTACATACACAGATGCCAGTCAGCTCCTGGGGTTGCGCCAGGCGCCCCCGCTCTAGCTCA
CTGTTGCCTCGCTGTCTGCCAGGAGGCCCTGCCATCCTTGGGCCCTGGCAGTGGCTGTGTCCCAGTGAGCTTTA
CTCACGTGGCCCTTGCTTCATCCAGCACAGCTCTCAGGTGGGCACTGCAGGGACACTGGTGTCTTCCATGTAGC
GTCCCAGCTTTGGGCTCCTGTAACAGACCTCTTTTTGGTTATGGATGGCTCACAAAATAGGGCCCCCAATGCTA
TTTTTTTTTTTTAAGTTTGTTTAATTATTTGTTAAGATTGTCTAAGGCCAAAGGCAATTGCGAAATCAAGTCTG
TCAAGTACAATAACATTTTTAAAAGAAAATGGATCCCACTGTTCCTCTTTGCCACAGAGAAAGCACCCAGACGC
CACAGGCTCTGTCGCATTTCAAAACAAACCATGATGGAGTGGCGGCCAGTCCAGCCTTTTAAAGAACGTCAGGT
GGAGCAGCCAGGTGAAAGGCCTGGCGGGGAGGAAAGTGAAACGCCTGAATCAAAAGCAGTTTTCTAATTTTGAC
TTTAAATTTTTCATCCGCCGGAGACACTGCTCCCATTTGTGGGGGGACATTAGCAACATCACTCAGAAGCCTGT
GTTCTTCAAGAGCAGGTGTTCTCAGCCTCACATGCCCTGCCGTGCTGGACTCAGGACTGAAGTGCTGTAAAGCA
AGGAGCTGCTGAGAAGGAGCACTCCACTGTGTGCCTGGAGAATGGCTCTCACTACTCACCTTGTCTTTCAGCTT
CCAGTGTCTTGGGTTTTTTATACTTTGACAGCTTTTTTTTAATTGCATACATGAGACTGTGTTGACTTTTTTTA
GTTATGTGAAACACTTTGCCGCAGGCCGCCTGGCAGAGGCAGGAAATGCTCCAGCAGTGGCTCAGTGCTCCCTG
GTGTCTGCTGCATGGCATCCTGGATGCTTAGCATGCAAGTTCCCTCCATCATTGCCACCTTGGTAGAGAGGGAT
GGCTCCCCACCCTCAGCGTTGGGGATTCACGCTCCAGCCTCCTTCTTGGTTGTCATAGTGATAGGGTAGCCTTA
TTGCCCCCTCTTCTTATACCCTAAAACCTTCTACACTAGTGCCATGGGAACCAGGTCTGAAAAAGTAGAGAGAA
GTGAAAGTAGAGTCTGGGAAGTAGCTGCCTATAACTGAGACTAGACGGAAAAGGAATACTCGTGTATTTTAAGA
TATGAATGTGACTCAAGACTCGAGGCCGATACGAGGCTGTGATTCTGCCTTTGGATGGATGTTGCTGTACACAG
ATGCTACAGACTTGTACTAACACACCGTAATTTGGCATTTGTTTAACCTCATTTATAAAAGCTTCAAAAAAACCCA

FIGURE 44

MALRRPPRLRLCARLPDFFLLLLFRGCLIGAVNLKSSNRTPVVQEFESVELSCIITDSQTSDPRIEWKKIQDEQ
TTYVFFDNKIQGDLAGRAEILGKTSLKIWNVTRRDSALYRCEVVARNDRKEIDEIVIELTVQVKPVTPVCRVPK
AVPVGKMATLHCQESEGHPRPHYSWYRNDVPLPTDSRANPRFRNSSFHLNSETGTLVFTAVHKDDSGQYYCIAS
NDAGSARCEEQEMEVYDLNIGGIIGGVLVVLAVLALITLGICCAYRRGYFINNKQDGESYKNPGKPDGVNYIRT
DEEGDFRHKSSFVI

Important features:

Signal peptide:

amino acids 1-30

Transmembrane domain:

amino acids 243-263

N-glycosylation sites.

amino acids 104-107, 192-195 cAMP- and cGMP-dependent protein kinase phosphorylation site.

amino acids 107-110

Casein kinase II phosphorylation site.

amino acids 106-109, 296-299

Tyrosine kinase phosphorylation site.

amino acids 69-77

N-myristoylation sites.

amino acids 26-31, 215-220, 226-231, 243-248, 244-249, 262-267

FIGURE 45

GCCGGCTAGGGCGCCGGAGCCGCACGCAGCCGCGGGGCTCCGAGAGGCGCGCACTGGGGCTGGGACTGCGCGGC
GCCGCCGCTGCGAGCGCCACTGAGCGGTCGCGCAACTTCGGAGGCACAGCGCCGGAGCCAGGCGAGCGCTCAGA
GACCCGGAGCCAGAGGGGCGCGCCGGAGCCTCGTTCGAGAGCCGGCGCCAGGCACCCACCGCGCTCCGAGTGCC
AGGCGGCCCTCCGCGCAGCGTGGCTTCCGCTGCCCCCACGGAAGGCACGGGCTGGCGCTGCCGGGCGCCGGGGA
GGACGGCGAGGAGGAGGCGGCGGCGGCGGAGACGGCGGCGGCGAGACTGGGGCCAGGGAGACAGCCCTGGGGGA
GAGGCGCCCGAACCAGGCCGCGGGAGCATGGGGGCCCGGAGCGGAGCTCGGGGCGCGCTGCTGCTGGCACTGCT
GCTCTGCTGGGACCCGAGGCTGAGCCAAGCAGGCACTGATTCTGGCAGCGAGGTGCTCCCTGACTCCTTCCCGT
CAGCGCCAGCAGAGCCGCTGCCCTACTTCCTGCAGGAGCCACAGGACGCCTACATTGTGAAGAACAAGCCTGTG
GAGCTCCGCTGCCGCGCCTTCCCCGCCACACAGATCTACTTCAAGTGCAACGGCGAGTGGGTCAGCCAGAACGA
CCACGTCACACAGGAAGGCCTGGATGAGGCCACCGGCCTGCGGGTGCGCGAGGTGCAGATCGAGGTGTCGCGGC
AGCAGGTGGAGGAGCTCTTTGGGCTGGAGGATTACTGGTGCCAGTGCGTGGCCTGGAGCTCCGCAGGCACCACC
AAGAGTCGCCGAGCCTACGTCCGCATCGCCTACCTGCGCAAGAACTTCGATCAGGAGCCTCTGGGCAAGGAGGT
GCCCCTGGACCATGAGGTTCTCCTGCAGTGCCGCCCGCCGGAGGGGGTGCCTGTGGCCGAGGTGGAATGGCTCA
AGAATGAGGATGTCATCGACCCCACCCAGGACACCAACTTCCTGCTCACCATCGACCACAACCTCATCATCCGC
CAGGCCCGCCTGTCGGACACTGCCAACTATACCTGCGTGGCCAAGAACATCGTGGCCAAACGCCGGAGCACCAC
TGCCACCGTCATCGTCTACGTGAATGGCGGCTGGTCCAGCTGGGCAGAGTGGTCACCCTGCTCCAACCGCTGTG
GCCGAGGCTGGCAGAAGCGCACCCGGACCTGCACCAACCCCGCTCCACTCAACGGAGGGGCCTTCTGCGAGGGC
CAGGCATTCCAGAAGACCGCCTGCACCACCATCTGCCCAGTCGATGGGGCGTGGACGGAGTGGAGCAAGTGGTC
AGCCTGCAGCACTGAGTGTGCCCACTGGCGTAGCCGCGAGTGCATGGCGCCCCCACCCCAGAACGGAGGCCGTG
ACTGCAGCGGGACGCTGCTCGACTCTAAGAACTGCACAGATGGGCTGTGCATGCAAAATAAGAAAACTCTAAGC
GACCCCAACAGCCACCTGCTGGAGGCCTCAGGGGATGCGGCGCTGTATGCGGGGCTCGTGGTGGCCATCTTCGT
GGTCGTGGCAATCCTCATGGCGGTGGGGGTGGTGGTGTACCGCCGCAACTGCCGTGACTTCGACACAGACATCA
CTGACTCATCTGCTGCCCTGACTGGTGGTTTCCACCCCGTCAACTTTAAGACGGCAAGGCCCAGCAACCCGCAG
CTCCTACACCCCTCTGTGCCTCCTGACCTGACAGCCAGCGCCGGCATCTACCGCGGACCCGTGTATGCCCTGCA
GGACTCCACCGACAAAATCCCCATGACCAACTCTCCTCTGCTGGACCCCTTACCCAGCCTTAAGGTCAAGGTCT
ACAGCTCCAGCACCACGGGCTCTGGGCCAGGCCTGGCAGATGGGGCTGACCTGCTGGGGGTCTTGCCGCCTGGC
ACATACCCTAGCGATTTCGCCCGGGACACCCACTTCCTGCACCTGCGCAGCGCCAGCCTCGGTTCCCAGCAGCT
CTTGGGCCTGCCCCGAGACCCAGGGAGCAGCGTCAGCGGCACCTTTGGCTGCCTGGGTGGGAGGCTCAGCATCC
CCGGCACAGGGGTCAGCTTGCTGGTGCCCAATGGAGCCATTCCCCAGGGCAAGTTCTACGAGATGTATCTACTC
ATCAACAAGGCAGAAAGTACCCTCCCGCTTTCAGAAGGGACCCAGACAGTATTGAGCCCCTCGGTGACCTGTGG
ACCCACAGGCCTCCTGCTGTGCCGCCCCGTCATCCTCACCATGCCCCACTGTGCCGAAGTCAGTGCCCGTGACT
GGATCTTTCAGCTCAAGACCCAGGCCCACCAGGGCCACTGGGAGGAGGTGGTGACCCTGGATGAGGAGACCCTG
AACACACCCTGCTACTGCCAGCTGGAGCCCAGGGCCTGTCACATCCTGCTGGACCAGCTGGGCACCTACGTGTT
CACGGGCGAGTCCTATTCCCGCTCAGCAGTCAAGCGGCTCCAGCTGGCCGTCTTCGCCCCCGCCCTCTGCACCT
CCCTGGAGTACAGCCTCCGGGTCTACTGCCTGGAGGACACGCCTGTAGCACTGAAGGAGGTGCTGGAGCTGGAG
CGGACTCTGGGCGGATACTTGGTGGAGGAGCCGAAACCGCTAATGTTCAAGGACAGTTACCACAACCTGCGCCT
CTCCCTCCATGACCTCCCCCATGCCCATTGGAGGAGCAAGCTGCTGGCCAAATACCAGGAGATCCCCTTCTATC
ACATTTGGAGTGGCAGCCAGAAGGCCCTCCACTGCACTTTCACCCTGGAGAGGCACAGCTTGGCCTCCACAGAG
CTCACCTGCAAGATCTGCGTGCGGCAAGTGGAAGGGGAGGGCCAGATATTCCAGCTGCATACCACTCTGGCAGA
GACACCTGCTGGCTCCCTGGACACTCTCTGCTCTGCCCCTGGCAGCACTGTCACCACCCAGCTGGGACCTTATG
CCTTCAAGATCCCACTGTCCATCCGCCAGAAGATATGCAACAGCCTAGATGCCCCCAACTCACGGGGCAATGAC
TGGCGGATGTTAGCACAGAAGCTCTCTATGGACCGGTACCTGAATTACTTTGCCACCAAAGCGAGCCCCACGGG
TGTGATCCTGGACCTCTGGGAAGCTCTGCAGCAGGACGATGGGGACCTCAACAGCCTGGCGAGTGCCTTGGAGG
AGATGGGCAAGAGTGAGATGCTGGTGGCTGTGGCCACCGACGGGGACTGCTGAGCCTCCTGGGACAGCGGGCTG
GCAGGGACTGGCAGGAGGCAGGTGCAGGGAGGCCTGGGGCAGCCTCCTGATGGGGATGTTTGGCCTCTGCTTCC
TCCCAGTTCACAGCCAGAGTTGCCTCTCCTCCTCCTCTTCCCCAACCCCCAGACCATGACCAGCCTTAGAAAAT
CCATGTACTCTGTTGTTAGAGGGCCCAGAGTTCCTTCTCCACCCCCGCTCTCTCTCTCTTGGCCTGAGATCTCT
GTGCAGGAACCAAGATGGGGCTGAAGCCTCTGGAGGCAGTTGGTTGGGGGCGGGCAGGCAGGAGGCCCTCCCTC
CACCCCCCCACCCTCAGCCCGGCAACTTCTGGGTTCCGTGGGTTTTAGTTCCGTTCTTCGTTTTCTTCCTCCGT
TATTGATTTCTCCTTTCTCCCTAAGCCCCCTTCTGCTTCCACGCCCTTTTCCTCTTTGAAGAGTCAAGTACAAT
TCAGACAAACTGCTTTCTCCTGTCCAAAAGCAAAAAGGCAAAGGAAAGAAAGAAAGCTTCAGACCGCTAGTAAG
GCTCAAAGAAGAAGAAAAACACCAAAACCACAAGGGAAAAGAAAAACCCAGTTTCTTAGGAAACGCAAACGATT
TATTATCCAGATTATTTGGATAAGTCCTTTTTAAAA

FIGURE 46

MGARSGARGALLLALLLCWDPRLSQAGTDSGSEVLPDSFPSAPAEPLPYFLQEPQDAYIVK
NKPVELRCRAFPATQIYFKCNGEWVSQNDHVTQEGLDEATGLRVREVQIEVSRQQVEELFG
LEDYWCQCVAWSSAGTTKSRRAYVRIAYLRKNFDQEPLGKEVPLDHEVLLQCRPPEGVPVA
EVEWLKNEDVIDPTQDTNFLLTIDHNLIIRQARLSDTANYTCVAKNIVAKRRSTTATVIVY
VNGGWSSWAEWSPCSNRCGRGWQKRTRTCTNPAPLNGGAFCEGQAFQKTACTTICPVDGAW
TEWSKWSACSTECAHWRSRECMAPPPQNGGRDCSGTLLDSKNCTDGLCMQNKKTLSDPNSH
LLEASGDAALYAGLVVAIFVVVAILMAVGVVVYRRNCRDFDTDITDSSAALTGGFHPVNFK
TARPSNPQLLHPSVPPDLTASAGIYRGPVYALQDSTDKIPMTNSPLLDPLPSLKVKVYSSS
TTGSGPGLADGADLLGVLPPGTYPSDFARDTHFLHLRSASLGSQQLLGLPRDPGSSVSGTF
GCLGGRLSIPGTGVSLLVPNGAIPQGKFYEMYLLINKAESTLPLSEGTQTVLSPSVTCGPT
GLLLCRPVILTMPHCAEVSARDWIFQLKTQAHQGHWEEVVTLDEETLNTPCYCQLEPRACH
ILLDQLGTYVFTGESYSRSAVKRLQLAVFAPALCTSLEYSLRVYCLEDTPVALKEVLELER
TLGGYLVEEPKPLMFKDSYHNLRLSLHDLPHAHWRSKLLAKYQEIPFYHIWSGSQKALHCT
FTLERHSLASTELTCKICVRQVEGEGQIFQLHTTLAETPAGSLDTLCSAPGSTVTTQLGPY
AFKIPLSIRQKICNSLDAPNSRGNDWRMLAQKLSMDRYLNYFATKASPTGVILDLWEALQQ
DDGDLNSLASALEEMGKSEMLVAVATDGDC

Important features of the protein:

Signal peptide:

amino acids 1-26

Transmembrane domain:

amino acids 374-395

N-glycosylation sites.

amino acids 222-225, 347-350

Glycosaminoglycan attachment site.

amino acids 492-495 cAMP- and cGMP-dependent protein kinase phosphorylation site.

amino acids 233-236, 234-237

Casein kinase II phosphorylation sites.

amino acids 30-33, 87-90, 251-254, 341-344, 359-362, 629-632, 651-654, 706-709, 757-760, 827-830, 925-928, 941-944

Tyrosine kinase phosphorylation sites.

amino acids 216-223, 773-780

N-myristoylation sites.

amino acids 2-7, 6-11, 27-32, 96-101, 137-142, 179-184, 247-252, 281-286, 334-339, 379-384, 491-496, 495-500, 509-514, 542-547, 547-552, 550-555, 553-558, 560-565, 611-616, 785-790, 834-839, 844-849

Prokaryotic membrane lipoprotein lipid attachment site.

amino acids 541-551

ATP/GTP-binding site motif A (P-loop).

amino acids 926-933

Growth factor and cytokines receptors family signature 2.

amino acids 306-312

FIGURE 47

GCTGACAATCCCCTTGACGTTCTATCCCGGAAGCTCCACCTGGGGCCCAATGTTGGGCGTG
ATGTTCCTCGCCTGTCTCTGCCTGGAAAACTGGTCTTCCCAAGCTCCACTGGCAGCCACTT
CTCCATGTTGGGCATCGGAGACATCGTTATGCCTGGTCTCCTACTATGCTTTGTCCTTCGC
TATGACAACTACAAAAAGCAAGCCAGTGGGGACTCCTGTGGGGCCCCTGGACCTGCCAACA
TCTCCGGGCGCATGCAGAAGGTCTCCTACTCTCACTGCACCCTCATCGGATACTTTGTAGG
CCTGCTCACTGCTACTGTGGCGTCTCGCATTCACCGGGCCGCCCAGCCCGCCCTTCTCTAT
TTGGTGCCATTTACTTTATTGCCACTCCTCACGATGGCCTATTTAAAGGGCGACCTCCGGC
GGATGTGGTCTGAGCCTTTCCACTCCAAGTCCAGCAGCTCCCGATTCCTGGAAGTATGATG
GATCACGTGGAAAGTGACCAGATGGCCGTCATAGTCCTTTTCTCTCAACTCATGGTTTGTT
TCCTCTTAGAGCTGGCCTGGTACTCAGAAATGTACCTGTGTTTAAGGAACTGCCGTGTGAC
TGGATTTGGCATTGAAAGGGAGCTCGTTTGCAGGAGAGAGGTGCTGGAGCCCTGTTTGGTT
CCTTCTCTTCCTGCGGATGTAGAGGTGGGGCCCCTTCCAAGAGGGACAGGCCTCTCCCCAG
CGCGCCTTCCTCCCACGTTTTTATGGATCTGCACCAGACTGTTACCTTCTGGGGGAGATGG
AGATTTGACTGTTTAAAAACTGAAAACAGCGAGGAGTCTTTCTAGAACTTTTGAACACTAA
AAGGATGAAAAAATTAGC

FIGURE 48

></usr/seqdb2/sst/DNA/Dnaseqs.min/ss.DNA100272

><subunit 1 of 1, 108 aa, 1 stop

><MW: 12055, pI: 4.69, NX(S/T): 0

MMDHVESDQMAVIVLFSQLMVCFLLELAWYSEMYLCLRNCRVTGFGIERELVCR

REVLEPCLVPSLPADVEVGPLPRGTGLSPARLPPTFLWICTRLLPSGGDGDLTV

FIGURE 49

CGGACGCGTGGGGGAAGATGGATAAATAATTCTGTCACACGTGCCCTGGCCTCTGGAGCTCAGCTGCCAGTCCA
CGTCTAGGGAATCTTAGCATCTGGGACCAAGACACTTTACAGCAATCATCACCCTTTGCAGAGGAGGTGAGCTC
ACCAGGACTCATCTGCCATTTCAGACCTTTTGCTGCTACCTGCCAGGTGGCCCCCACTGCTGACGAGAGATGGT
GGATCTCTCAGTCTCCCCGGACTCCTTGAAGCCAGTATCGCTGACCAGCAGTCTTGTCTTCCTCATGCACCTCC
TCCTCCTTCAGCCTGGGGAGCCGAGCTCAGAGGTCAAGGTGCTAGGCCCTGAGTATCCCATCCTGGCCCTCGTC
GGGGAGGAGGTGGAGTTCCCGTGCCACCTATGGCCACAGCTGGATGCCCAGCAAATGGAGATCCGCTGGTTCCG
GAGTCAGACCTTCAATGTGGTACACCTGTACCAGGAGCAGCAGGAGCTCCCTGGCAGGCAGATGCCGGCGTTCC
GGAACAGGACCAAGTTGGTCAAGGACGACATCGCCTATGGCAGCGTGGTCCTGCAGCTTCACAGCATCATCCCC
TCTGACAAGGGCACATATGGCTGCCGCTTCCACTCCGACAACTTCTCTGGCGAAGCTCTCTGGGAACTGGAGGT
AGCAGGGCTGGGCTCAGACCCTCACCTCTCCCTTGAGGGCTTCAAGGAAGGAGGCATTCAGCTGAGGCTCAGAT
CCAGTGGCTGGTACCCCAAGCCTAAGGTTCAGTGGAGAGACCACCAGGGACAGTGCCTGCCTCCAGAGTTTGAA
GCCATCGTCTGGGATGCCCAGGACCTGTTCAGTCTGGAAACATCTGTGGTTGTCCGAGCGGGAGCCCTCAGCAA
TGTGTCCGTCTCCATCCAGAATCTCCTCTTGAGCCAGAAGAAAGAGTTGGTGGTCCAGATAGCAGACGTGTTCG
TACCCGGAGCCTCTGCGTGGAAGAGCGCGTTCGTCGCGACCCTGCCGCTGCTGTTGGTCCTCGCGGCGCTGGCG
CTGGGCGTCCTCCGGAAGCAGCGGAGAAGCCGAGAAAAGCTGAGGAAGCAGGCGGAGAAGAGACAAGAGAAACT
CACTGCAGAGCTGGAAAAGCTTCAGACAGAGCTTGACTGGAGACGGGCTGAAGGCCAGGCTGAGTGGAGAGCAG
CCCAAAAATATGCAGTGGATGTGACGCTGGACCCGGCCTCGGCGCACCCCAGCCTGGAGGTGTCGGAGGATGGC
AAGAGCGTGTCTTCCCGCGGGGCGCCGCCAGGCCCGGCGCCTGGCCACCCGCAGCGGTTCTCGGAGCAGACGTG
CGCGCTGAGCCTGGAGCGGTTCTCCGCCGGCCGCCACTACTGGGAGGTGCACGTGGGCCGCCGCAGCCGCTGGT
TCCTGGGCGCCTGCCTGGCCGCGGTGCCGCGCGCGGGGCCTGCGCGCCTGAGCCCTGCGGCCGGCTACTGGGTG
CTGGGGCTGTGGAACGGCTGCGAGTACTTCGTCCTGGCCCCGCACCGCGTCGCGCTCACCCTGCGCGTGCCCCC
GCGGCGCCTGGGCGTCTTCCTGGACTACGAGGCCGGAGAGCTGTCCTTCTTCAACGTGTCCGACGGCTCCCACA
TCTTCACCTTCCACGACACCTTCTCGGGCGCGCTCTGTGCGTACTTCAGGCCCAGGGCCCACGACGGCGGCGAA
CATCCGGATCCCCTGACCATCTGCCCGCTGCCGGTTAGAGGGACGGGCGTCCCCGAAGAGAACGACAGTGACAC
CTGGCTACAGCCCTATGAGCCCGCGGACCCCGCCCTGGACTGGTGGTGAGGCGCCCTCGTGGCCGCGGGACTGG
CCCCGGGGGGCCCCCTGGATCCCAGGCCAGCGCTTTGCTCTCCTGCTCCGTCTGAAGGGAGCAGGTGCACCAGC
CAAAATGTCAGCGAGGGGGACAAAGAGAGGGACCTTTGCCTACGTAGATGTGTATGTGTAGTGCGATTTTCTTC
AAGGAAAGGAGACAAGTCCAAAGCTCGTTTGTGGATTGTGGGACTGAGCGAAGGAGTACAAATATATCCACGTC
GCTCAGAGCTGGGGTGCTCACGGTGGGCGGTGGGCAAGAAGCCAGCATGGAAGAAAGAAGGGAGAAAACTTTGG
TGACTGCCTTAGAGGGATCAGTTAATTTGTATAGTTTTATATTTTTTGTATATGTTTGCTAGCTCTAAAAAGGT
CGAGATGCAATAACACTTCGTAAGCAACGAGTTCACCTAAGTAAGGCTCAGATCCTAGTTTTAAAAACCATTTC
CCATTAAAATGAAGTTGGAGGAACAGCTGCTTCTGAGCCGGGGCAAAAATTTCAAGGTGAGCCTGGAGCATTGT
GTGTGGTGAAGTAAAATAAAGGCTCAAAACGTGACGGCAACCCGGCAAAAGGGTAGGGAGCCAGGCCGAAGGGG
CCTCACTGACCAATTGTGGGACAATTTGAACATCAGGATGAATAATGACAGGAGAGATTATAACACACTGAATA
AAAACATAATCCATGAGTTCATGCTGATACTCAAATTTCTTTTTAAAAAGGAGAAACAGGAAGGTTTCTTTTGG
AGGTGAAATCTAATTATTGGTGAGAGTCTTGGAGAACAGGCTGTTTCCAGTCTCAAAGCAGTAACCTTATACAC
TACTTATAAGTTTGAAAGGGGAAAGGTTACCTTTACAATGGAGACATCTACCAGATCATCCAAGTGATTAAATT
TAACATCATCAATGATGGGACCAAGGACATTATTAGTTTGACAACTGGGGAAAGAAGTGTTCTTCACCCCCTAC
CCCCAAGACATTCTCTCTGTCGGCCAGGCTGGAGTGCAGCCTCAACCTCCTGGGCCCAAGTGATCCTCCCACCT
CAGCACACAACACCATGCCCAATTTTAAGTGCGTTATAGAGACGGGGGTCTCACTTTGTTACCCAGGCTGGTCT
CAAACTCCTGCGCTCAAGCAATCCTCCCACCTGGGCCTCCCAAAATGCTGGGTGTACAGGCATGAGCCGCTGTG
CCTGGCTTCATTTTCAGAGTGAGACATTTGTACTGTGGCTATGTAGGAGAACATTCTTGTTCTTAGCAAACATA
CTGAAGTTTTTAGATATTAATTACCACAGTGTCTGCCACTGAATTTCCAGTGACTAAGTGGAAAAATATAAAAC
ATATGAATATAAAGAAAGAAAGAGACAAGTCAAATGTAGTAAAATGACAACACTTGGTGACTCTAGGTGACTGG
TCGACAGATGTTCATTGTACTATCAATGTGGCTTTGCTGTGGGTTTGAAATTTTGCAAACTAAGAGTTGGGTGG
CGGGGAGAAGGATACACCAAAAAACTAAGTGATTATCTTTGGATGGGAAAATGTTTGGTAATTGCATTCTTAAA
ATGTCTTCTTTGTATTTTTTAATGTTCAATAATGTATATGTATCAGTTCTGTAATAAAGGGGAAAACACTTTTCA

FIGURE 50

MVDLSVSPDSLKPVSLTSSLVFLMHLLLLQPGEPSSEVKVLGPEYPILALVGEEVEFPCHL
WPQLDAQQMEIRWFRSQTFNVVHLYQEQQELPGRQMPAFRNRTKLVKDDIAYGSVVLQLHS
IIPSDKGTYGCRFHSDNFSGEALWELEVAGLGSDPHLSLEGFKEGGIQLRLRSSGWYPKPK
VQWRDHQGQCLPPEFEAIVWDAQDLFSLETSVVVRAGALSNVSVSIQNLLLSQKKELVVQI
ADVFVPGASAWKSAFVATLPLLLVLAALALGVLRKQRRSREKLRKQAEKRQEKLTAELEKL
QTELDWRRAEGQAEWRAAQKYAVDVTLDPASAHPSLEVSEDGKSVSSRGAPPGPAPGHPQR
FSEQTCALSLERFSAGRHYWEVHVGRRSRWFLGACLAAVPRAGPARLSPAAGYWVLGLWNG
CEYFVLAPHRVALTLRVPPRRLGVFLDYEAGELSFFNVSDGSHIFTFHDTFSGALCAYFRP
RAHDGGEHPDPLTICPLPVRGTGVPEENDSDTWLQPYEPADPALDWW

Important features of the protein:

Signal peptide:

amino acids 1-34

Transmembrane domain:

amino acids 247-272

N-glycosylation sites.

amino acids 102-106, 139-143, 224-228, 464-468, 516-520

Tyrosine kinase phosphorylation site.

amino acids 105-114

N-myristoylation sites.

amino acids 129-135, 220-226, 399-405, 423-429, 480-486

Amidation site.

amino acids 390-394

FIGURE 51

GTGGGCCGCCCCTGCTGCTGCCGTCCATGCTGATGTTTGCGGTGATCGTGGCCTCCAGCGG
GCTGCTGCTCATGATCGAGCGGGGCATCCTGGCCGAGATGAAGCCCCTGCCCCTGCACCCG
CCCGGCCGCGAGGGCACAGCCTGGCGCGGGAAAGCCCCCAAGCCTGGGGGCCTGTCCCTCA
GGGCTGGGGACGCGGACTTGCAAGTGCGGCAGGACGTCCGGAACAGGACCCTGCGGGCGGT
GTGCGGACAGCCAGGCATGCCCCGGGACCCCTGGGACTTGCCGGTGGGGCAGCGGCGCACC
CTGCTGCGCCACATCCTCGTAAGTGACCGTTACCGCTTCCTCTACTGCTACGTCCCCAAGG
TGGCCTGCTCTAACTGGAAGCGGGTGATGAAGGTGCTGGCAGGCGTCCTGGACAGCGTGGA
CGTCCGCCTCAAGATGGACCACCGCAGTGACCTGGTGTTCCTGGCCGACCTGCGGCCTGAG
GAGATTCGCTACCGCCTGCAGCACTACTTTAAGTTCCTGTTTGTGCGGGAGCCCTTGGAAC
GCCTCCTCTCTGCCTACCGCAACAAGTTTGGCGAGATCCGAGAGTACCAGCAACGCTATGG
GGCTGAGATAGTGAGGCGGTACAGGGCTGGAGCGGGGCCCAGCCCTGCAGGCGACGATGTC
ACATTCCCCGAGTTCCTGAGATACCTGGTGGATGAGGACCCTGAGCGCATGAATGAGCATT
GGATGCCCGTGTACCACCTGTGCCAGCCTTGTGCCGTGCACTATGACTTTGTGGGCTCCTA
TGAGAGGCTGGAGGCTGATGCAAATCAGGTGCTGGAGTGGGTACGGGCACCACCTCACGTC
CGATTTCCAGCTCGCCAGGCCTGGTACCGGCCAGCCAGCCCCGAAAGCCTGCATTACCACT
TGTGCAGTGCCCCCCGGGCCCTGCTGCAGGATGTGCTGCCTAAGTATATCCTGGACTTCTC
CCTCTTTGCCTACCCACTGCCTAATGTCACCAAGGAGGCGTGTCAGCAGTGACCATGGGTG
TGGGGCCAGCAGCTGGTGGGGACTGGTTTCAACGCCAGCTTTCTGTGCTTCTGCCTGTCAT
TCGGAGAAACTCTGGCTCTGGGGCTTGGGGCTTCTCAGGATCCTGGATGGCAGAGACTGCC
CTCAGAAGTTCCTTGTCCAGGGTGGGCACCCACAGTGACTCAGAGGACAGGGCTAGGCAGG
AGACCTGCTGCTCCTCATTGGGGGGATCTCTTGGGGGGCAGACACCAGTTTGCCAATGAAG
CAACACATCTGATCTAAAGACTGGCTCCAGACCCCGGGCTGCCAGGATTATGCAGTCCACT
TGGTCTACCTTAATTTAACCTGTGGCCAAACTCAGAGATGGTACCAGCCAGGGGCAAGCAT
GACCAGAGCCAGGGACCCTGTGGCTCTGATCCCCCATTTATCCACCCCATGTGCCTCAGGA
CTAGAGTGAGCAATCATACCTTATAAATGACTTTTGTGCCTTTCTGCTCCAGTCTCAAAAT
TTCCTACACCTGCCAGTTCTTTACATTTTTCCAAGGAAAGGAAAACGGAAGCAGGGTTCTT
GCCTGGTAGCTCCAGGACCCAGCTCTGCAGGCACCCAAAGACCCTCTGTGCCCAGCCTCTT
CCTTGAGTTCTCGGAACCTCCTCCCTAATTCTCCCTTCCTTCCCCACAAGGCCTTTGAGGT
TGTGACTGTGGCTGGTATATCTGGCTGCCATTTTTCTGATGCATTTATTTAAAATTTGTAC
TTTTTGATAGAACCCTTGTAAGGGCTTTGTTTTCCTAATAGCTGACTTTTTAATAAAGCAG
TTTTATATAT

FIGURE 52

MLMFAVIVASSGLLLMIERGILAEMKPLPLHPPGREGTAWRGKAPKPGGLSLRAGDADLQV
RQDVRNRTLRAVCGQPGMPRDPWDLPVGQRRTLLRHILVSDRYRFLYCYVPKVACSNWKRV
MKVLAGVLDSVDVRLKMDHRSDLVFLADLRPEEIRYRLQHYFKFLFVREPLERLLSAYRNK
FGEIREYQQRYGAEIVRRYRAGAGPSPAGDDVTFPEFLRYLVDEDPERMNEHWMPVYHLCQ
PCAVHYDFVGSYERLEADANQVLEWVRAPPHVRFPARQAWYRPASPESLHYHLCSAPRALL
QDVLPKYILDFSLFAYPLPNVTKEACQQ

Important features of the protein:

Signal peptide:

amino acids 1-23

N-glycosylation sites.

amino acids 67-71, 325-329

Tyrosine kinase phosphorylation sites.

amino acids 152-159, 183-183

N-myristoylation sites.

amino acids 89-95, 128-134

FIGURE 53

GCCCTAACCTTCCCAGGGCTCAGCTCTTTGGAGCTGCCCATTCCTCCGGCTGCGAGAAAGGACGCGCGCCCTGC
GTCGGGCGAAGAAAAGAAGCAAAACTTGTCGGGAGGGTTTCGTCATCAACCTCCTTCCCGCAAACCTAAACCTC
CTGCCGGGGCCATCCCTAGACAGAGGAAAGTTCCTGCAGAGCCGACCAGCCCTAGTGGATCTGGGGCAGGCAGC
GGCGCTGGCTGTGGAATTAGATCTGTTTTGAACCCAGTGGAGCGCATCGCTGGGGCTCGGAAGTCACCGTCCGC
GGGCACCGGGTTGGCGCTGCCCGAGTGGAACCGACAGTTTGCGAGCCTCGGCTGCAAGTGGCCTCTCCTCCCCG
CGGTTGTTGTTCAGTGTCGGGTGAGGGCTGCGAGTGTGGCAAGTTGCAAAGAGAGCCTCAGAGGTCCGAAGAGC
GCTGCGCTCCTACTCGCGTTCGCTTCTTCCTCTTCTCGGTTCCCTACTGTGAAATCGCAGCGACATTTACAAAG
GCCTCCGGGTCCTACCGAGACCGATCCGCAGCGTTTGGCCCGGTCGTGCCTATTGCATCGGGAGCCCCCGAGCA
CCGGCGAAGGACTGGCGGGTGGGGTAGGGAGGTGGCGGCGGCGGCATGGCGAGGTTCCCGAAGGCCGACCTGGC
CGCTGCAGGAGTTATGTTACTTTGCCACTTCTTCACGGACCAGTTTCAGTTCGCCGATGGGAAACCCGGAGACC
AAATCCTTGATTGGCAGTATGGAGTTACTCAGGCCTTCCCTCACACAGAGGAGGAGGTGGAAGTTGATTCACAC
GCGTACAGCCACAGGTGGAAAAGAAACTTGGACTTTCTCAAGGCGGTAGACACGAACCGAGCAAGCGTCGGCCA
AGACTCTCCTGAGCCCAGAAGCTTCACAGACCTGCTGCTGGATGATGGGCAGGACAATAACACTCAGATCGAGG
AGGATACAGACCACAATTACTATATATCTCGAATATATGGTCCATCTGATTCTGCCAGCCGGGATTTATGGGTG
AACATAGACCAAATGGAAAAAGATAAAGTGAAGATTCATGGAATATTGTCCAATACTCATCGGCAAGCTGCAAG
AGTGAATCTGTCCTTCGATTTTCCATTTTATGGCCACTTCCTACGTGAAATCACTGTGGCAACCGGGGGTTTCA
TATACACTGGAGAAGTCGTACATCGAATGCTAACAGCCACACAGTACATAGCACCTTTAATGGCAAATTTCGAT
CCCAGTGTATCCAGAAATTCAACTGTCAGATATTTTGATAATGGCACAGCACTTGTGGTCCAGTGGGACCATGT
ACATCTCCAGGATAATTATAACCTGGGAAGCTTCACATTCCAGGCAACCCTGCTCATGGATGGACGAATCATCT
TTGGATACAAAGAAATTCCTGTCTTGGTCACACAGATAAGTTCAACCAATCATCCAGTGAAAGTCGGACTGTCC
GATGCATTTGTCGTTGTCCACAGGATCCAACAAATTCCCAATGTTCGAAGAAGAACAATTTATGAATACCACCG
AGTAGAGCTACAAATGTCAAAAATTACCAACATTTCGGCTGTGGAGATGACCCCATTACCCACATGCCTCCAGT
TTAACAGATGTGGCCCCTGTGTATCTTCTCAGATTGGCTTCAACTGCAGTTGGTGTAGTAAACTTCAAAGATGT
TCCAGTGGATTTGATCGTCATCGGCAGGACTGGGTGGACAGTGGATGCCCTGAAGAGTCAAAAGAGAAGATGTG
TGAGAATACAGAACCAGTGGAAACTTCTTCTCGAACCACCACAACCGTAGGAGCGACAACCACCCAGTTCAGGG
TCCTAACTACCACCAGAAGAGCAGTGACTTCTCAGTTTCCCACCAGCCTCCCTACAGAAGATGATACCAAGATA
GCACTACATCTAAAAGATAATGGAGCTTCTACAGATGACAGTGCAGCTGAGAAGAAAGGGGGAACCCTCCACGC
TGGCCTCATCATTGGAATCCTCATCCTGGTCCTCATTGTAGCCACAGCCATTCTTGTGACAGTCTATATGTATC
ACCACCCAACATCAGCAGCCAGCATCTTCTTTATTGAGAGACGCCCAAGCAGATGGCCTGCGATGAAGTTTAGA
AGAGGCTCTGGACATCCTGCCTATGCTGAAGTTGAACCAGTTGGAGAGAAAGAAGGCTTTATTGTATCAGAGCA
GTGCTAAAATTTCTAGGACAGAACAACACCAGTACTGGTTTACAGGTGTTAAGACTAAAATTTTGCCTATACCT
TTAAGACAAACAAACAAACACACACACAAACAAGCTCTAAGCTGCTGTAGCCTGAAGAAGACAAGATTTCTGGA
CAAGCTCAGCCCAGGAAACAAAGGGTAAACAAAAAACTAAAACTTATACAAGATACCATTTACACTGAACATAG
AATTCCCTAGTGGAATGTCATCTATAGTTCACTCGGAACATCTCCCGTGGACTTATCTGAAGTATGACAAGATT
ATAATGCTTTTGGCTTAGGTGCAGGGTTGCAAAGGGATCAGAAAAAAAAAATCATAATAAAGCTTTAGTTCATG
AGGG

FIGURE 54

MARFPKADLAAAGVMLLCHFFTDQFQFADGKPGDQILDWQYGVTQAFPHTEEEV
EVDSHAYSHRWKRNLDFLKAVDTNRASVGQDSPEPRSFTDLLLDDGQDNNTQIEE
DTDHNYYISRIYGPSDSASRDLWVNIDQMEKDKVKIHGILSNTHRQAARVNLSFDF
PFYGHFLREITVATGGFIYTGEVVHRMLTATQYIAPLMANFDPSVSRNSTVRYFDN
GTALVVQWDHVHLQDNYNLGSFTFQATLLMDGRIIFGYKEIPVLVTQISSTNHPVK
VGLSDAFVVVHRIQQIPNVRRRTIYEYHRVELQMSKITNISAVEMTPLPTCLQFNRC
GPCVSSQIGFNCSWCSKLQRCSSGFDRHRQDWVDSGCPEESKEKMCENTEPVETSS
RTTTTVGATTTQFRVLTTTRRAVTSQFPTSLPTEDDTKIALHLKDNGASTDDSAAE
KKGGTLHAGLIIGILILVLIVATAILVTVYMYHHPTSAASIFFIERRPSRWPAMKFRR
GSGHPAYAEVEPVGEKEGFIVSEQC

Important features of the protein:

Transmembrane domain:

amino acids 454-478

N-glycosylation sites.

amino acids 103-107, 160-164, 213-217, 221-225, 316-320, 345-349 cAMP- and cGMP-dependent protein kinase phosphorylation sites.

amino acids 297-301, 492-496, 503-507

N-myristoylation sites.

amino acids 42-48, 100-106, 147-153, 279-285, 397-403, 450-456, 455-461

FIGURE 55

GCGCCCGGCGCAGCTCGGCCAGAGCGACCGCGGGGCTGAGCGCGCGTCCGCCCAGGGGGCTCCGGAAGCTGCCC
CGGCCCGCGGCCTCCTCCCTCGCTCCCGCTTCCCCTTTCTCGCTCACCGCCGCCCTCCTTCCCCAGCTCCCTCG
CCGTCCGCCCGCCCCACAGCCAGCGGCTCCGCGCCCCCTGCAGCCACGATGCCCGCGGCCCGGCCGCCCGCCGC
GGGACTCCGCGGGATCTCGCTGTTCCTCGCTCTGCTCCTGGGGAGCCCGGCGGCAGCGCTGGAGCGAGATGCTC
TTCCCGAGGGAGATGCTAGCCCTTTGGGTCCTTACCTCCTGCCCTCAGGAGCCCCGGAGAGAGGCAGTCCTGGC
AAAGAGCACCCTGAAGAGAGAGTGGTAACAGCGCCCCCCAGTTCCTCACAGTCGGCGGAAGTGCTGGGCGAGCT
GGTGCTGGATGGGACCGCACCCTCTGCACATCACGACATCCCAGCCCTGTCACCGCTGCTTCCAGAGGAGGCCC
GCCCCAAGCACGCCTTGCCCCCCAAGAAGAAACTGCCTTCGCTCAAGCAGGTGAACTCTGCCAGGAAGCAGCTG
AGGCCCAAGGCCACCTCCGCAGCCACTGTCCAAAGGGCAGGGTCCCAGCCAGCGTCCCAGGGCCTAGATCTCCT
CTCCTCCTCCACGGAGAAGCCTGGCCCACCGGGGGACCCGGACCCCATCGTGGCCTCCGAGGAGGCATCAGAAG
TGCCCCTTTGGCTGGATCGAAAGGAGAGTGCGGTCCCTACAACACCCGCACCCCTGCAAATCTCCCCCTTCACT
TCGCAGCCCTATGTGGCCCACACACTCCCCCAGAGGCCAGAACCCGGGGAGCCTGGGCCTGACATGGCCCAGGA
GGCCCCCCAGGAGGACACCAGCCCCATGGCCCTGATGGACAAAGGTGAGAATGAGCTGACTGGGTCAGCCTCAG
AGGAGAGCCAGGAGACCACTACCTCCACCATTATCACCACCACGGTCATCACCACCGAGCAAGCACCAGCTCTC
TGCAGTGTGAGCTTCTCCAATCCTGAGGGGTACATTGACTCCAGCGACTACCCACTGCTGCCCCTCAACAACTT
TCTGGAGTGCACATACAACGTGACAGTCTACACTGGCTATGGGGTGGAGCTCCAGGTGAAGAGTGTGAACCTGT
CCGATGGGGAACTGCTCTCCATCCGCGGGGTGGACGGCCCTACCCTGACCGTCCTGGCCAACCAGACACTCCTG
GTGGAGGGGCAGGTAATCCGAAGCCCCACCAACACCATCTCCGTCTACTTCCGGACCTTCCAGGACGACGGCCT
TGGGACCTTCCAGCTTCACTACCAGGCCTTCATGCTGAGCTGCAACTTTCCCCGCCGGCCTGACTCTGGGGATG
TCACGGTGATGGACCTGCACTCAGGTGGGGTGGCCCACTTTCACTGCCACCTGGGCTATGAGCTCCAGGGCGCT
AAGATGCTGACATGCATCAATGCCTCCAAGCCGCACTGGAGCAGCCAGGAGCCCATCTGCTCAGCTCCTTGTGG
AGGGGCAGTGCACAATGCCACCATCGGCCGCGTCCTCTCCCCAAGTTACCCTGAAAACACAAATGGGAGCCAAT
TCTGCATCTGGACGATTGAAGCTCCAGAGGGCCAGAAGCTGCACCTGCACTTTGAGAGGCTGTTGCTGCATGAC
AAGGACAGGATGACGGTTCACAGCGGGCAGACCAACAAGTCAGCTCTTCTCTACGACTCCCTTCAAACCGAGAG
TGTCCCTTTTGAGGGCCTGCTGAGCGAAGGCAACACCATCCGCATCGAGTTCACGTCCGACCAGGCCCGGGCGG
CCTCCACCTTCAACATCCGATTTGAAGCGTTTGAGAAAGGCCACTGCTATGAGCCCTACATCCAGAATGGGAAC
TTCACTACATCCGACCCGACCTATAACATTGGGACTATAGTGGAGTTCACCTGCGACCCCGGCCACTCCCTGGA
GCAGGGCCCGGCCATCATCGAATGCATCAATGTGCGGGACCCATACTGGAATGACACAGAGCCCCTGTGCAGAG
CCATGTGTGGTGGGGAGCTCTCTGCTGTGGCTGGGGTGGTATTGTCCCCAAACTGGCCCGAGCCCTACGTGGAA
GGTGAAGATTGTATCTGGAAGATCCACGTGGGAGAAGAGAAACGGATCTTCTTAGATATCCAGTTCCTGAATCT
GAGCAACAGTGACATCTTGACCATCTACGATGGCGACGAGGTCATGCCCCACATCTTGGGGCAGTACCTTGGGA
ACAGTGGCCCCCAGAAACTGTACTCCTCCACGCCAGACTTAACCATCCAGTTCCATTCGGACCCTGCTGGCCTC
ATCTTTGGAAAGGGCCAGGGATTTATCATGAACTACATAGAGGTATCAAGGAATGACTCCTGCTCGGATTTACC
CGAGATCCAGAATGGCTGGAAAACCACTTCTCACACGGAGTTGGTGCGGGGAGCCAGAATCACCTACCAGTGTG
ACCCCGGCTATGACATCGTGGGGAGTGACACCCTCACCTGCCAGTGGGACCTCAGCTGGAGCAGCGACCCCCCA
TTTTGTGAGAAAATTATGTACTGCACCGACCCCGGAGAGGTGGATCACTCGACCCGCTTAATTTCGGATCCTGT
GCTGCTGGTGGGGACCACCATCCAATACACCTGCAACCCCGGTTTTGTGCTTGAAGGGAGTTCTCTTCTGACCT
GCTACAGCCGTGAAACAGGGACTCCCATCTGGACGTCTCGCCTGCCCCACTGCGTTTCGGAGGAGTCCCTGGCA
TGTGACAACCCAGGGCTGCCTGAAAATGGATACCAAATCCTGTACAAGCGACTCTACCTGCCAGGAGAGTCCCT
CACCTTCATGTGCTACGAAGGCTTTGAGCTCATGGGTGAAGTGACCATCCGCTGCATCCTGGGACAGCCATCCC
ACTGGAACGGGCCCCTGCCCGTGTGTAAAGTTAATCAAGACAGTTTTGAACATGCTTTAGAAGCAGAAGCGGCA
GCAGAGACGTCGCTGGAAGGGGGGAACATGGCCCTGGCTATCTTCATCCCGGTCCTCATCATCTCCTTACTGCT
GGGAGGAGCCTACATTTACATCACAAGATGTCGCTACTATTCCAACCTCCGCCTGCCTCTGATGTACTCCCACC
CCTACAGCCAGATCACCGTGGAAACCGAGTTTGACAACCCCATTTACGAGACAGGGGAAACCAGAGAGTATGAG
GTTTCTATCTAAAGAGAGCTACACTTGAGAAGGGGACTTGTGAACTCAACCACAATCTCCTCGAGACATTCATC
CAGAGACCATGTGGCACTTGATTGAAACCCCAGAATGTCGACTGTCTTTTGTTTAGACTCTTTATCAAAGGTTT
ACTGTTTTCTTCCCTGTATTTATTATATTTAAAAGTGAAAAAAAAAAAAAAAAAAAA

FIGURE 56

MPAARPPAAGLRGISLFLALLLGSPAAALERDALPEGDASPLGPYLLPSGAPERGSPGKEHPEERVVTAPPSSS
QSAEVLGELVLDGTAPSAHHDIPALSPLLPEEARPKHALPPKKKLPSLKQVNSARKQLRPKATSAATVQRAGSQ
PASQGLDLLSSSTEKPGPPGDPDPIVASEEASEVPLWLDRKESAVPTTPAPLQISPFTSQPYVAHTLPQRPEPG
EPGPDMAQEAPQEDTSPMALMDKGENELTGSASEESQETTTSTIITTTVITTEQAPALCSVSFSNPEGYIDSSD
YPLLPLNNFLECTYNVTVYTGYGVELQVKSVNLSDGELLSIRGVDGPTLTVLANQTLLVEGQVIRSPTNTISVY
FRTFQDDGLGTFQLHYQAFMLSCNFPRRPDSGDVTVMDLHSGGVAHFHCHLGYELQGAKMLTCINASKPHWSSQ
EPICSAPCGGAVHNATIGRVLSPSYPENTNGSQFCIWTIEAPEGQKLHLHFERLLLHDKDRMTVHSGQTNKSAL
LYDSLQTESVPFEGLLSEGNTIRIEFTSDQARAASTFNIRFEAFEKGHCYEPYIQNGNFTTSDPTYNIGTIVEF
TCDPGHSLEQGPAIIECINVRDPYWNDTEPLCRAMCGGELSAVAGVVLSPNWPEPYVEGEDCIWKIHVGEEKRI
FLDIQFLNLSNSDILTIYDGDEVMPHILGQYLGNSGPQKLYSSTPDLTIQFHSDPAGLIFGKGQGFIMNYIEVS
RNDSCSDLPEIQNGWKTTSHTELVRGARITYQCDPGYDIVGSDTLTCQWDLSWSSDPPFCEKIMYCTDPGEVDH
STRLISDPVLLVGTTIQYTCNPGFVLEGSSLLTCYSRETGTPIWTSRLPHCVSEESLACDNPGLPENGYQILYK
RLYLPGESLTFMCYEGFELMGEVTIRCILGQPSHWNGPLPVCKVNQDSFEHALEAEAAAETSLEGGNMALAIFI
PVLIISLLLGGAYIYITRCRYYSNLRLPLMYSHPYSQITVETEFDNPIYETGETREYEVSI

Signal peptide:

amino acids 1-28

Transmembrane domain:

amino acids 893-915

N-glycosylation sites.

amino acids 311-315, 328-332, 350-354, 435-439, 458-462, 474-478, 514-518, 576-580, 618-622, 674-678, 742-746 cAMP- and cGMP-dependent protein kinase phosphorylation site.

amino acids 188-192

N-myristoylation sites.

amino acids 23-29, 87-93, 146-152, 454-460, 475-481, 575-581, 629-635, 695-701, 723-729, 766-772, 877-883, 953-959

Prokaryotic membrane lipoprotein lipid attachment site.

amino acids 383-394

FIGURE 57

GCGAGCCGGGTCCCACCATGGCCGCGAATTATTCCAGTACCAGTACCCGGAGAGAACATGT
CAAAGTTAAAACCAGCTCCCAGCCAGGCTTCCTGGAACGGCTGAGCGAGACCTCGGGTGGG
ATGTTTGTGGGGCTCATGGCCTTCCTGCTCTCCTTCTACCTAATTTTCACCAATGAGGGCC
GCGCATTGAAGACGGCAACCTCATTGGCTGAGGGGCTCTCGCTTGTGGTGTCTCCCGACAG
CATCCACAGTGTGGCTCCGGAGAATGAAGGAAGGCTGGTGCACATCATTGGCGCCTTACGG
ACATCCAAGCTTTTGTCTGATCCAAACTATGGGGTCCATCTTCCGGCTGTGAAACTGCGGA
GGCACGTGGAGATGTACCAATGGGTAGAAACTGAGGAGTCCAGGGAGTACACCGAGGATGG
GCAGGTGAAGAAGGAGACGAGGTATTCCTACAACACTGAATGGAGGTCAGAAATCATCAAC
AGCAAAAACTTCGACCGAGAGATTGGCCACAAAAACCCCAGTGCCATGGCAGTGGAGTCAT
TCATGGCAACAGCCCCCTTTGTCCAAATTGGCAGGTTTTTCCTCTCGTCAGGCCTCATCGA
CAAAGTCGACAACTTCAAGTCCCTGAGCCTATCCAAGCTGGAGGACCCTCATGTGGACATC
ATTCGCCGTGGAGACTTTTTCTACCACAGCGAAAATCCCAAGTATCCAGAGGTGGGAGACT
TGCGTGTCTCCTTTTCCTATGCTGGACTGAGCGGCGATGACCCTGACCTGGGCCCAGCTCA
CGTGGTCACTGTGATTGCCCGGCAGCGGGGTGACCAGCTAGTCCCATTCTCCACCAAGTCT
GGGGATACCTTACTGCTCCTGCACCACGGGGACTTCTCAGCAGAGGAGGTGTTTCATAGAG
AACTAAGGAGCAACTCCATGAAGACCTGGGGCCTGCGGGCAGCTGGCTGGATGGCCATGTT
CATGGGCCTCAACCTTATGACACGGATCCTCTACACCTTGGTGGACTGGTTTCCTGTTTTC
CGAGACCTGGTCAACATTGGCCTGAAAGCCTTTGCCTTCTGTGTGGCCACCTCGCTGACCC
TGCTGACCGTGGCGGCTGGCTGGCTCTTCTACCGACCCCTGTGGGCCCTCCTCATTGCCGG
CCTGGCCCTTGTGCCCATCCTTGTTGCTCGGACACGGGTGCCAGCCAAAAAGTTGGAGTGA
AAAGACCCTGGCACCCGCCCGACACCTGCGTGAGCCCTGAGGCTGGTTGTACAATGCCCAC
GCCTGCCTGGCTGCTTTCACCTGGGAGTGCTTTCGATGTGGGCACCTGGGCTTCCTAGGGC
TGCTTCTGAGTGGTTCTTTCACGTGTTGTGTCCATAGCTTTAGTCTTCCTAAATAAGATCC
ACCCACACCTAAGTCACAGAATTTCTAAGTTCCCCAACTACTCTCACACCCTTTTAAAGAT
AAAGTATGTTGTAACCAGGACGTCTTAAATGATTCTTTGTGTACCTTTTCTGTCATATTCA
GAAACCGTTCTGTGCCTGCTGGGAGTAATTCCTTTAGCAATTAAGTATTTGGTAGCTGAAT
AAGGGGTCAGAACTTCTGAAACCAGAGATCTGTAATCATCTCTATTGGCCTGGGGTGCCTG
TGCTATAAATGAGTTTCTTCACATGAAAAACACAGCCAGCCCAAGATGACTTATCTGGGTT
TAGGATTCAATAGTATTCACTAACTGCTTATTACATGAGCAATTTCATCAAATCTCCAAAC
TCTTAAAGGATGCTTTCGGAAAACACGCTGTATACCTAGATGATGACTAAATGCAAAATCC
TTGGGCTTTGGTTTTTTTCTAGTAAGGATTTTAAATAACTGCCGACTTCAAAAGTGTTCTT
AAAACGAAAGATAATGTTAAGAAAAATTTGAAAGCTTTGGAAAACCAAATTTGTAATATCA
TTGTATTTTTTATTAAAAGTTTTGTAATAAATTTCTAAATTATCA

FIGURE 58

></usr/seqdb2/sst/DNA/Dnaseqs.min/ss.DNA108743
><subunit 1 of 1, 400 aa, 1 stop
><MW: 44876, pI: 8.32, NX(S/T): 2
MAANYSSTSTRREHVKVKTSSQPGFLERLSETSGGMFVGLMAFLLSFYLIFTNEGRALKT
ATSLAEGLSLVVSPDSIHSVAPENEGRLVHIIGALRTSKLLSDPNYGVHLPAVKLRRHVE
MYQWVETEESREYTEDGQVKKETRYSYNTEWRSEIINSKNFDREIGHKNPSAMAVESFMA
TAPFVQIGRFFLSSGLIDKVDNFKSLSLSKLEDPHVDIIRRGDFFYHSENPKYPEVGDLR
VSFSYAGLSGDDPDLGPAHVVTVIARQRGDQLVPFSTKSGDTLLLLHHGDFSAEEVFHRE
LRSNSMKTWGLRAAGWMAMFMGLNLMTRILYTLVDWFPVFRDLVNIGLKAFAFCVATSLT
LLTVAAGWLFYRPLWALLIAGLALVPILVARTRVPAKKLE

Important features of the protein:

Transmembrane domains:
Amino acids 34-53;365-388

N-glycosylation site:
Amino acids 4-8 cAMP- and cGMP-dependent protein kinase phosphorylation site:
Amino acids 140-144

Tyrosine kinase phosphorylation sites:
Amino acids 99-107;220-227

N-myristoylation sites:
Amino acids 35-41;93-99;310-316

Cell attachment sequences:
Amino acids 221-224;268-271

FIGURE 59

GATCAAGCGCCTTCCTTTCCCTTCCTCTCCCTACTTGGCCTTTGCCCTAAGCCAAGACCTGGCCATCAGCCTGG
CTGCAGGGGCCTGCAGAGCCAGCTGCACTTTTTCAGGTATGGGGGAGGGCCAGGCACCATGAAGCCAGTGTGGG
TCGCCACCCTTCTGTGGATGCTACTGCTGGTGCCCAGGCTGGGGGCCGCCCGGAAGGGGTCCCCAGAAGAGGCC
TCCTTCTACTATGGAACCTTCCCTCTTGGCTTCTCCTGGGGCGTGGGCAGTTCTGCCTACCAGACGGAGGGCGC
CTGGGACCAGGACGGGAAAGGGCCTAGCATCTGGGACGTCTTCACACACAGTGGGAAGGGGAAAGTGCTTGGGA
ATGAGACGGCAGATGTAGCCTGTGACGGCTACTACAAGGTCCAGGAGGACATCATTCTGCTGAGGGAACTGCAC
GTCAACCACTACCGATTCTCCCTGTCTTGGCCCCGGCTCCTGCCCACAGGCATCCGAGCCGAGCAGGTGAACAA
GAAGGGAATCGAATTCTACAGTGATCTTATCGATGCCCTTCTGAGCAGCAACATCACTCCCATCGTGACCTTGC
ACCACTGGGATCTGCCACAGCTGCTCCAGGTCAAATACGGTGGGTGGCAGAATGTGAGCATGGCCAACTACTTC
AGAGACTACGCCAACCTGTGCTTTGAGGCCTTTGGGGACCGTGTGAAGCACTGGATCACGTTCAGTGATCCTCG
GGCAATGGCAGAAAAAGGCTATGAGACGGGCCACCATGCGCCGGGCCTGAAGCTCCGCGGCACCGGCCTGTACA
AGGCAGCACACCACATCATTAAGGCCCACGCCAAAACCTGGCATTCTTATAACACCACGTGGCGCAGCAAGCAG
CAAGGTCTGGTGGGAATTTCACTGAACTGTGACTGGGGGGAACCTGTGGACATTAGTAACCCCAAGGACCTAGA
GGCTGCCGAGAGATACCTACAGTTCTGTCTGGGCTGGTTTGCCAACCCCATTTATGCCGGTGACTACCCCCAAG
TCATGAAGGACTACATTGGAAGAAAGAGTGCAGAGCAAGGCCTGGAGATGTCGAGGTTACCGGTGTTCTCACTC
CAGGAGAAGAGCTACATTAAAGGCACATCCGATTTCTTGGGATTAGGTCATTTTACTACTCGGTACATCACGGA
AAGGAACTACCCCTCCCGCCAGGGGCCCAGCTACCAGAACGATCGTGACTTGATAGAGCTGGTTGACCCAAACT
GGCCAGATCTGGGGTCTAAATGGCTATATTCTGTGCCATGGGGATTTAGGAGGCTCCTTAACTTTGCTCAGACT
CAATACGGTGATCCTCCCATATATGTGATGGAAAATGGAGCATCTCAAAAATTCCACTGTACTCAATTATGTGA
TGAGTGGAGAATTCAATACCTTAAAGGATACATAAATGAAATGCTAAAAGCTATAAAAGATGGTGCTAATATAA
AGGGGTATACTTCCTGGTCTCTGTTGGATAAGTTTGAATGGGAGAAAGGATACTCAGATAGATATGGATTCTAC
TATGTTGAATTTAACGACAGAAATAAGCCTCGCTATCCAAAGGCTTCAGTTCAATATTACAAGAAGATTATCAT
TGCCAATGGGTTTCCCAATCCAAGAGAGGTGGAAAGTTGGTACCTCAAAGCTTTGGAAACTTGCTCTATCAACA
ATCAGATGCTTGCTGCAGAGCCTTTGCTAAGTCACATGCAAATGGTTACGGAGATCGTGGTACCCACTGTCTGC
TCCCTCTGTGTCCTCATCACTGCTGTTCTACTAATGCTCCTCCTGAGGAGGCAGAGCTGAGACAGGATTATCAA
TTTTGGAGCTTCATAAGAGAATCTTCAGGATCTTCCTCCCTTTTCTGCTTTGAGGGTTTCCATACATTGCTGTT
TTCAGGTTCTACAATAATTACCTTTTTTTCTCTTTCTCTTTTTGGCTTGTGCTGGGATTTAAGAATTAGAAAAT
AAAAATAAGCAGAAATTA

FIGURE 60

MKPVWVATLLWMLLLVPRLGAARKGSPEEASFYYGTFPLGFSWGVGSSAYQTEGAWDQDGKGPSIWDVFTHSGK
GKVLGNETADVACDGYYKVQEDIILLRELHVNHYRFSLSWPRLLPTGIRAEQVNKKGIEFYSDLIDALLSSNIT
PIVTLHHWDLPQLLQVKYGGWQNVSMANYFRDYANLCFEAFGDRVKHWITFSDPRAMAEKGYETGHHAPGLKLR
GTGLYKAAHHIIKAHAKTWHSYNTTWRSKQQGLVGISLNCDWGEPVDISNPKDLEAAERYLQFCLGWFANPIYA
GDYPQVMKDYIGRKSAEQGLEMSRLPVFSLQEKSYIKGTSDFLGLGHFTTRYITERNYPSRQGPSYQNDRDLIE
LVDPNWPDLGSKWLYSVPWGFRRLLNFAQTQYGDPPIYVMENGASQKFHCTQLCDEWRIQYLKGYINEMLKAIK
DGANIKGYTSWSLLDKFEWEKGYSDRYGFYYVEFNDRNKPRYPKASVQYYKKIIIANGFPNPREVESWYLKALE
TCSINNQMLAAEPLLSHMQMVTEIVVPTVCSLCVLITAVLLMLLLRRQS

Important features:
Signal peptide:
amino acids 1-21

Transmembrane domain:
amino acids 541-558

N-glycosylation sites:
amino acids 80-84,171-175,245-249

Glycosaminoglycan attachment site:
amino acids 72-76 cAMP- and cGMP-dependent protein kinase phosphorylation sites:
amino acids 23-27,564-568

Tyrosine kinase phosphorylation sites:
amino acids 203-211,347-355,460-468,507-514

N-myristoylation sites:
amino acids 44-50,79-85,167-173,225-231,257-263,315-321

Amidation site:
amino acids 307-311

Glycosyl hydrolases family 1 active site:
amino acids 407-416

Glycosyl hydrolases family 1 N-terminal signature:
amino acids 41-56

Motif name Glycosyl hydrolases family:
amino acids 37- 67

FIGURE 61

CCCGTGCCAAGAGTGACGTAAGTACCGCCTATAGAGTCTATAGGCCCACTTGGCTTCGTTA
GAACGCGGCTACAATTAATACATAACCTTATGTATCATACACATACGATTTAGGTGACACT
ATAGAATAACATCCACTTTGCCTTTCTCTCCACAGGTGTCCACTCCCAGGTCCAACTGCAC
CTCGGTTCTATCGATAATCTCAGCACCAGCCACTCAGAGCAGGGCACGATGTTGGGGGCCC
GCCTCAGGCTCTGGGTCTGTGCCTTGTGCAGCGTCTGCAGCATGAGCGTCCTCAGAGCCTA
TCCCAATGCCTCCCCACTGCTCGGCTCCAGCTGGGGTGGCCTGATCCACCTGTACACAGCC
ACAGCCAGGAACAGCTACCACCTGCAGATCCACAAGAATGGCCATGTGGATGGCGCACCCC
ATCAGACCATCTACAGTGCCCTGATGATCAGATCAGAGGATGCTGGCTTTGTGGTGATTAC
AGGTGTGATGAGCAGAAGATACCTCTGCATGGATTTCAGAGGCAACATTTTTGGATCACAC
TATTTCGACCCGGAGAACTGCAGGTTCCAACACCAGACGCTGGAAAACGGGTACGACGTCT
ACCACTCTCCTCAGTATCACTTCCTGGTCAGTCTGGGCCGGGCGAAGAGAGCCTTCCTGCC
AGGCATGAACCCACCCCCGTACTCCCAGTTCCTGTCCCGGAGGAACGAGATCCCCCTAATT
CACTTCAACACCCCCATACCACGGCGGCACACCCGGAGCGCCGAGGACGACTCGGAGCGGG
ACCCCCTGAACGTGCTGAAGCCCCGGGCCCGGATGACCCCGGCCCCGGCCTCCTGTTCACA
GGAGCTCCCGAGCGCCGAGGACAACAGCCCGATGGCCAGTGACCCATTAGGGGTGGTCAGG
GGCGGTCGAGTGAACACGCACGCTGGGGGAACGGGCCCGGAAGGCTGCCGCCCCTTCGCCA
AGTTCATCTAGGGTCGCTGG

FIGURE 62

MLGARLRLWVCALCSVCSMSVLRAYPNASPLLGSSWGGLIHLYTATARNSYHLQIHKNGHV
DGAPHQTIYSALMIRSEDAGFVVITGVMSRRYLCMDFRGNIFGSHYFDPENCRFQHQTLEN
GYDVYHSPQYHFLVSLGRAKRAFLPGMNPPPYSQFLSRRNEIPLIHFNTPIPRRHTRSAED
DSERDPLNVLKPRARMTPAPASCSQELPSAEDNSPMASDPLGVVRGGRVNTHAGGTGPEGC
RPFAKFI

Important features:
Signal peptide:
amino acids 1-24 cAMP- and cGMP-dependent protein kinase phosphorylation site.
amino acids 175-179

N-myristoylation site.
amino acids 33-39, 100-106, 225-231, 229-235

HBGF/FGF family proteins
amino acids 73-124

FIGURE 63

CATGTCTAGACTGGGAGCCCTGGGTGGTGCCCGTGCCGGGCTGGGACTGTTGCTGGGTACCGCCGCCGGCCTTG
GATTCCTGTGCCTCCTTTACAGCCAGCGATGGAAACGGACCCAGCGTCATGGCCGCAGCCAGAGCCTGCCCAAC
TCCCTGGACTATACGCAGACTTCAGATCCCGGACGCCACGTGATGCTCCTGCGGGCTGTCCCAGGTGGGGCTGG
AGATGCCTCAGTGCTGCCCAGCCTTCCACGGGAAGGACAGGAGAAGGTGCTGGACCGCCTGGACTTTGTGCTGA
CCAGCCTTGTGGCGCTGCGGCGGGAGGTGGAGGAGCTGAGAAGCAGCCTGCGAGGGCTTGCGGGGGAGATTGTT
GGGGAGGTCCGATGCCACATGGAAGAGAACCAGAGAGTGGCTCGGCGGCGAAGGTTTCCGTTTGTCCGGGAGAG
GAGTGACTCCACTGGCTCCAGCTCTGTCTACTTCACGGCCTCCTCGGGAGCCACGTTCACAGATGCTGAGAGTG
AAGGGGGTTACACAACAGCCAATGCGGAGTCTGACAATGAGCGGGACTCTGACAAAGAAAGTGAGGACGGGGAA
GATGAAGTGAGCTGTGAGACTGTGAAGATGGGGAGAAAGGATTCTCTTGACTTGGAGGAAGAGGCAGCTTCAGG
TGCCTCCAGTGCCCTGGAGGCTGGAGGTTCCTCAGGCTTGGAGGATGTGCTGCCCCTCCTGCAGCAGGCCGACG
AGCTGCACAGGGGTGATGAGCAAGGCAAGCGGGAGGGCTTCCAGCTGCTGCTCAACAACAAGCTGGTGTATGGA
AGCCGGCAGGACTTTCTCTGGCGCCTGGCCCGAGCCTACAGTGACATGTGTGAGCTCACTGAGGAGGTGAGCGA
GAAGAAGTCATATGCCCTAGATGGAAAAGAAGAAGCAGAGGCTGCTCTGGAGAAGGGGGATGAGAGTGCTGACT
GTCACCTGTGGTATGCGGTGCTTTGTGGTCAGCTGGCTGAGCATGAGAGCATCCAGAGGCGCATCCAGAGTGGC
TTTAGCTTCAAGGAGCATGTGGACAAAGCCATTGCTCTCCAGCCAGAAAACCCCATGGCTCACTTTCTTCTTGG
CAGGTGGTGCTATCAGGTCTCTCACCTGAGCTGGCTAGAAAAAAAAACTGCTACAGCCTTGCTTGAAAGCCCTC
TCAGTGCCACTGTGGAAGATGCCCTCCAGAGCTTCCTAAAGGCTGAAGAACTACAGCCAGGATTTTCCAAAGCA
GGAAGGGTATATATTTCCAAGTGCTACAGAGAACTAGGGAAAAACTCTGAAGCTAGATGGTGGATGAAGTTGGC
CCTGGAGCTGCCAGATGTCACGAAGGAGGATTTGGCTATCCAGAAGGACCTGGAAGAACTGGAAGTCATTTTAC
GAGACTAACCACGTTTCACTGGCCTTCATGACTTGATGCCACTATTTAAGGTGGGGGGGCGGGGAGGCTTTTTT
CCTTAGACCTTGCTGAGATCAGGAAACCACACAAATCTGTCTCCTGGGTCTGACTGCTACCCACTACCACTCCC
CATTAGTTAATTTATTCTAACCTCTAACCTAATCTAGAATTGGGGCAGTACTCATGGCTTCCGTTTCTGTTGTT
CTCTCCCTTGAGTAATCTCTTAAAAAAATCAAGATTCACACCTGCCCCAGGATTACACATGGGTAGAGCCTGCA
AGACCTGAGACCTTCCAATTGCTGGTGAGGTGGATGAACTTCAAAGCTATAGGAACAAAGCACATAACTTGTCA
CTTTAATCTTTTTCACTGACTAATAGGACTCAGTACATATAGTCTTAAGATCATACCTTACCTACCAAGGTAAA
AAGAGGGATCAGAGTGGCCCACAGACATTGCTTTCTTATCACCTATCATGTGAATTCTACCTGTATTCCTGGGC
TGGACCACTTGATAACTTCCAGTGTCCTGGCAGCTTTTGGAATGACAGCAGTGGTATGGGGTTTATGATGCTAT
AAAACAATGTCTGAAAAGTTGCCTAGAATATATTTTGTTACAAACTTGAAATAAACCAAATTTGATGTT

FIGURE 64

> </usr/seqdb2/sst/DNA/Dnaseqs.min/ss.DNA139686
> <subunit 1 of 1, 470 aa, 1 stop
> <MW: 52118, pI: 5.06, NX(S/T): 0
MSRLGALGGARAGLGLLLGTAAGLGFLCLLYSQRWKRTQRHGRSQSLPNSLDYTQTSDPGRHVMLL
RAVPGGAGDASVLPSLPREGQEKVLDRLDFVLTSLVALRREVEELRSSLRGLAGEIVGEVRCHMEEN
QRVARRRRFPFVRERSDSTGSSSVYFTASSGATFTDAESEGGYTTANAESDNERDSDKESEDGEDEVS
CETVKMGRKDSLDLEEEAASGASSALEAGGSSGLEDVLPLLQQADELHRGDEQGKREGFQLLLNNK
LVYGSRQDFLWRLARAYSDMCELTEEVSEKKSYALDGKEEAEAALEKGDESADCHLWYAVLCGQL
AEHESIQRRIQSGFSFKEHVDKAIALQPENPMAHFLLGRWCYQVSHLSWLEKKTATALLESPLSATVE
DALQSFLKAEELQPGFSKAGRVYISKCYRELGKNSEARWWMKLALELPDVTKEDLAIQKDLEELEVILRD

Important features of the protein:
Signal peptide:
Amino acids 1-32 cAMP- and cGMP-dependent protein kinase phosphorylation site:
Amino acids 209-213

N-myristoylation sites:
Amino acids 5-11;8-14;9-15;15-21;19-25;72-78;164-170;
174-180;222-228;230-236

Amidation sites:
Amino acids 207-211;254-258

Cell attachment sequence:
Amino acids 250-253

FIGURE 65

TGAAGGCCTGTGAGTGAGGAATGCCTCTCACCAGCTGTGCCTGAGCTGCAGCACTCCAGCC
ACTGCTGTCTCCTTAGCTGCTCACATATGGATACTTTCACAGTTCAGGATTCCACTGCAAT
GAGCTGGTGGAGGAATAATTTCTGGATCATCTTAGCTGTGGCCATCATTGTTGTCTCTGTG
GGCCTGGGCCTCATCCTGTACTGTGTCTGTAAGTGGCAGCTTAGACGAGGCAAGAAATGGG
AAATTGCCAAGCCCCTGAAACACAAGCAAGTAGATGAAGAAAAGATGTATGAGAATGTTCT
TAATGAGTCGCCAGTTCAATTACCGCCTCTGCCACCGAGGAATTGGCCTTCTCTAGAAGAC
TCTTCCCCACAGGAAGCCCCAAGTCAGCCGCCCGCTACATACTCACTGGTAAATAAAGTTA
AAAATAAGAAGACTGTTTCCATCCCAAGCTACATTGAGCCTGAAGATGACTATGACGATGT
TGAAATCCCTGCAAATACTGAAAAAGCATCATTTTGAAACAGCCATTTCTTCTTTTTGGCA
AAACTGAAGAGGGTTCACACAACTTATTTTAAAACAATCAAGAATGGTTGAACTTCAGTAG
GTCTCTGGGCCCTGAAAGCCAGTGGTGATTTTATGAAGCTCTATAAGATAAAGCACTTCCC
AAACCTTAGATGAAGACACCCCTGCGATCGGATGACTGCAGCCAGAGGAGACACATGGGTG
CTCGGCTCTGAGGACTTAGAGGGGTCAGCCTTGTGCTGTTGAGGAAACTTTCCATGGGAAG
GACCACGGGGCTCCATGGCTCCCACCTGTGGGAAACTACTCATTTCTTGGCATTCTTTCCC
CCTTCATTCCCTTTGGTTTGCATGGTTCTGAGTGATATTAAATCTCAGCATTTGGTTGTGC
AAAAAAAAAA

FIGURE 66

></usr/seqdb2/sst/DNA/Dnaseqs.min/ss.DNA144844
><subunit 1 of 1, 145 aa, 1 stop
><MW: 16618, pI: 5.26, NX(S/T): 1
MDTFTVQDSTAMSWWRNNFWIILAVAIIVVSVGLGLILYCVCKWQLRRGKKWEIAKPLKH
KQVDEEKMYENVLNESPVQLPPLPPRNWPSLEDSSPQEAPSQPPATYSLVNKVKNKKTVS
IPSYIEPEDDYDDVEIPANTEKASF

Important features of the protein:
Signal peptide:
Amino acids 1-35

Tyrosine kinase phosphorylation site:
Amino acids 61-70

Amidation site:
Amino acids 48-52

FIGURE 67

CTCCAGTTCGCCGACTGTAACATGTTTCATCCAGTTCAGTATGTTTTGTATGCAAGTTGGAAATAAATAAACGT
CCTGAACTGGATGAAACATGTTACAGTCGGCCGAAACATGAGAGGCTGTGTGAGAAGCTGCAGCCGCCGGCAGA
GGAGACCTCAGCATCATCTAGAGCCCAGCGCTGGCCCTGCCTCCGCCTGCGCCGCCGCCGCCGTCGCCGTTTCT
GTTCCTGCTACTGTCCCACCTAAACAACTCCCGTTACACGGACAAGTGAACATCTGTGGCTGTCCTCTCCTTTT
CTTCCTCCTCTTCCAACTCCTTCTCCTCCTCCCACTTCCCAGCCGCAGCAGAAAGCCCCCAACCCAACTGACGC
TGGCACAACTGCAAACGGTGTCATCCGCACAACTTTATCTCGCTCCTCGGGCTCCCCTAAGGCATTGGACCCAT
CGCCGCGTCTTTTATTTTTGCAAAGTTGCATCGCTGTACATATTTTTGTCCCCGCCACCTCCCTCTGTCTCTGG
AGTGCCCTACAGCCCCGCAAACTCCTCCTGGAGCTGCGCCCTAGTGCCCCTGCTGGGCAGTGGCGTTCCCCCCC
ATCCTCCCGCGCCCAGCCCCTGCTGCTCTGGGCAGACGATGCTGAAGATGCTCTCCTTTAAGCTGCTGCTGCTG
GCCGTGGCTCTGGGCTTCTTTGAAGGAGATGCTAAGTTTGGGGAAAGAAACGAAGGGAGCGGAGCAAGGAGGAG
AAGGTGCCTGAATGGGAACCCCCCGAAGCGCCTGAAAAGGAGAGACAGGAGGATGATGTCCCAGCTGGAGCTGC
TGAGTGGGGGAGAGATGCTGTGCGGTGGCTTCTACCCTCGGCTGTCCTGCTGCCTGCGGAGTGACAGCCCGGGG
CTAGGGCGCCTGGAGAATAAGATATTTTCTGTTACCAACAACACAGAATGTGGGAAGTTACTGGAGGAAATCAA
ATGTGCACTTTGCTCTCCACATTCTCAAAGCCTGTTCCACTCACCTGAGAGAGAAGTCTTGGAAAGAGACCTAG
TACTTCCTCTGCTCTGCAAAGACTATTGCAAAGAATTCTTTTACACTTGCCGAGGCCATATTCCAGGTTTCCTT
CAAACAACTGCGGATGAGTTTTGCTTTTACTATGCAAGAAAAGATGGTGGGTTGTGCTTTCCAGATTTTCCAAG
AAAACAAGTCAGAGGACCAGCATCTAACTACTTGGACCAGATGGAAGAATATGACAAAGTGGAAGAGATCAGCA
GAAAGCACAAACACAACTGCTTCTGTATTCAGGAGGTTGTGAGTGGGCTGCGGCAGCCCGTTGGTGCCCTGCAT
AGTGGGGATGGCTCGCAACGTCTCTTCATTCTGGAAAAAGAAGGTTATGTGAAGATACTTACCCCTGAAGGAGA
AATTTTCAAGGAGCCTTATTTGGACATTCACAAACTTGTTCAAAGTGGAATAAAGGGAGGAGATGAAAGAGGAC
TGCTAAGCCTCGCATTCCATCCCAATTACAAGAAAAATGGAAAGTTGTATGTGTCCTATACCACCAACCAAGAA
CGGTGGGCTATCGGGCCTCATGACCACATTCTTAGGGTTGTGGAATACACAGTATCCAGAAAAAATCCACACCA
AGTTGATTTGAGAACAGCCAGAGTCTTTCTTGAAGTTGCAGAACTCCACAGAAAGCATCTGGGAGGACAACTGC
TCTTTGGCCCTGACGGCTTTTTGTACATCATTCTTGGTGATGGGATGATTACACTGGATGATATGGAAGAAATG
GATGGGTTAAGTGATTTCACAGGCTCAGTGCTACGGCTGGATGTGGACACAGACATGTGCAACGTGCCTTATTC
CATACCAAGGAGCAACCCACACTTCAACAGCACCAACCAGCCCCCCGAAGTGTTTGCTCATGGGCTCCACGATC
CAGGCAGATGTGCTGTGGATAGACATCCCACTGATATAAACATCAATTTAACGATACTGTGTTCAGACTCCAAT
GGAAAAAACAGATCATCAGCCAGAATTCTACAGATAATAAAGGGGAAAGATTATGAAAGTGAGCCATCACTTTT
AGAATTCAAGCCATTCAGTAATGGTCCTTTGGTTGGTGGATTTGTATACCGGGGCTGCCAGTCAGAAAGATTGT
ATGGAAGCTACGTGTTTGGAGATCGTAATGGGAATTTCCTAACTCTCCAGCAAAGTCCTGTGACAAAGCAGTGG
CAAGAAAAACCACTCTGTCTCGGCACTAGTGGGTCCTGTAGAGGCTACTTTTCCGGTCACATCTTGGGATTTGG
AGAAGATGAACTAGGTGAAGTTTACATTTTATCAAGCAGTAAAAGTATGACCCAGACTCACAATGGAAAACTCT
ACAAAATTGTAGATCCCAAAAGACCTTTAATGCCTGAGGAATGCAGAGCCACGGTACAACCTGCACAGACACTG
ACTTCAGAGTGCTCCAGGCTCTGTCGAAACGGCTACTGCACCCCCACGGGAAAGTGCTGCTGCAGTCCAGGCTG
GGAGGGGGACTTCTGCAGAACTGCAAAATGTGAGCCAGCATGTCGTCATGGAGGTGTCTGTGTTAGACCGAACA
AGTGCCTCTGTAAAAAAGGATATCTTGGTCCTCAATGTGAACAAGTGGACAGAAACATCCGCAGAGTGACCAGG
GCAGGTATTCTTGATCAGATCATTGACATGACATCTTACTTGCTGGATCTAACAAGTTACATTGTATAGTTTCT
GGGACTGTTTGAATATTCTATTCCAATGGGCATTTATTTTTTATCCTGTCATTAAAAAAAAAAAGACTGTTATC
CTGCTACACACTCCTGTGATTTCATTCTCTTTTATTAATTTAAAAATAATTTCCAGAAATGTGCAGATCCTCTG
TGTGTATGTCAGCATGTTTGTTCACATATGCACATACACATACTCATAACCCCTATATGCGTTGTTGCATAACA
GATG

FIGURE 67 CONTINUED

ATTTTTTAAAATATATACTTCCTTATGCAAAGTAATTTACACAGAAATTCCATTGTAAATTGATAATGGATTTT
TTATGTTACTAGAAGAGATTATTTGACTTCCCAGGAATTTTCTGTCTGTAATCACTAAAGTCAACTTTAATAGA
GTTTTGAAACAGTACTGTGCAATCCGATGGATCTAATTAAAAAAAAGGCAATATTTTTATATTAAAGTACTATA
CTAGGAGAGAATGTTTCAGAACTCCCTGATGAATTTCTAAGTGAGCAACTTGATATAAAATTGTAATCTTCATT
TTTGTCAGTGTATCCAGTTACAGAATGCTACACACTTACCTTTTTATTGGCTGAGAAATCTGGTTATTTCATCT
TAATCTCAAGATTGTTTTCAAGTGTTTTATAATTAAATCATAATAGCATATTTTAAAATCAAAAA

FIGURE 68

></usr/seqdb2/sst/DNA/Dnaseqs.min/ss.DNA139592
><subunit 1 of 1, 882 aa, 1 stop
><MW: 98428, pI: 8.89, NX(S/T): 5
MKHVTVGRNMRGCVRSCSRRQRRPQHHLEPSAGPASACAAAAVAVSVPATVPPKQLPLHG
QVNICGCPLLFFLLFQLLLLLPLPSRSRKPPTQLTLAQLQTVSSAQLYLAPRAPLRHWTH
RRVFYFCKVASLYIFLSPPPPSVSGVPYSPANSSWSCALVPLLGSGVPPHPPAPSPCCSG
QTMLKMLSFKLLLLAVALGFFEGDAKFGERNEGSGARRRRCLNGNPPKRLKRRDRRMMSQ
LELLSGGEMLCGGFYPRLSCCLRSDSPGLGRLENKIFSVTNNTECGKLLEEIKCALCSPH
SQSLFHSPEREVLERDLVLPLLCKDYCKEFFYTCRGHIPGFLQTTADEFCFYYARKDGGL
CFPDFPRKQVRGPASNYLDQMEEYDKVEEISRKHKHNCFCIQEVVSGLRQPVGALHSGDG
SQRLFILEKEGYVKILTPEGEIFKEPYLDIHKLVQSGIKGGDERGLLSLAFHPNYKKNGK
LYVSYTTNQERWAIGPHDHILRVVEYTVSRKNPHQVDLRTARVFLEVAELHRKHLGGQLL
FGPDGFLYIILGDGMITLDDMEEMDGLSDFTGSVLRLDVDTDMCNVPYSIPRSNPHFNST
NQPPEVFAHGLHDPGRCAVDRHPTDININLTILCSDSNGKNRSSARILQIIKGKDYESEP
SLLEFKPFSNGPLVGGFVYRGCQSERLYGSYVFGDRNGNFLTLQQSPVTKQWQEKPLCLG
TSGSCRGYFSGHILGFGEDELGEVYILSSSKSMTQTHNGKLYKIVDPKRPLMPEECRATV
QPAQTLTSECSRLCRNGYCTPTGKCCCSPGWEGDFCRTAKCEPACRHGGVCVRPNKCLCK
KGYLGPQCEQVDRNIRRVTRAGILDQIIDMTSYLLDLTSYIV

Important features of the protein:

Transmembrane domains:
Amino acids 63-80;186-201

N-glycosylation sites:
Amino acids 152-156;281-285;598-602;629-633;641-645

Glycosaminoglycan attachment site:
Amino acids 417-421 cAMP- and cGMP-dependent protein kinase phosphorylation site:
Amino acids 856-860

N-myristoylation sites:
Amino acids 12-18;413-419;457-463;698-695;720-726;723-729

EGF-like domain cysteine pattern signatures:
Amino acids 805-817;837-849

FIGURE 69

CCGGGGCCTCCGGAGAACGCTGTCCCATGAACGTGCGGGGAGCGGCCCCCGGCGTCCGCGCGTCCCCGCGTCCC
TGGCAATTCCCGACTTCCCAACGGCTTCCCGCTGGCAGCCCCGAAGCCGCACCATGTTCCGCCTCTGGTTGCTG
CTGGCCGGGCTCTGCGGCCTCCTGGCGTCAAGACCCGGTTTTCAAAATTCACTTCTACAGATCGTAATTCCAGA
GAAAATCCAAACAAATACAAATGACAGTTCAGAAATAGAATATGAACAAATATCCTATATTATTCCAATAGATG
AGAAACTGTACACTGTGCACCTTAAACAAAGATATTTTTTAGCAGATAATTTTATGATCTATTTGTACAATCAA
GGATCTATGAATACTTATTCTTCAGATATTCAGACTCAATGCTACTATCAAGGAAATATTGAAGGATATCCAGA
TTCCATGGTCACACTCAGCACGTGCTCTGGACTAAGAGGAATACTGCAATTTGAAAATGTTTCTTATGGAATTG
AGCCTCTGGAATCTGCAGTTGAATTTCAGCATGTTCTTTACAAATTAAAGAATGAAGACAATGATATTGCAATT
TTTATTGACAGAAGCCTGAAAGAACAACCAATGGATGACAACATTTTTATAAGTGAAAAATCAGAACCAGCTGT
TCCAGATTTATTTCCTCTTTATCTAGAAATGCATATTGTGGTGGACAAAACTTTGTATGATTACTGGGGCTCTG
ATAGCATGATAGTAACAAATAAAGTCATCGAAATTGTTGGCCTTGCAAATTCAATGTTCACCCAATTTAAAGTT
ACTATTGTGCTGTCATCATTGGAGTTATGGTCAGATGAAAATAAGATTTCTACAGTTGGTGAGGCAGATGAATT
ATTGCAAAAATTTTTAGAATGGAAACAATCTTATCTTAACCTAAGGCCTCATGATATTGCATATCTACTAATTT
ATATGGATTATCCTCGTTATTTGGGAGCAGTGTTTCCTGGAACAATGTGTATTACTCGTTATTCTGCAGGAGTT
GCATTGTACCCCAAGGAGATAACTCTGGAGGCATTTGCAGTTATTGTCACCCAGATGCTGGCACTCAGTCTGGG
AATATCATATGACGACCCAAAGAAATGTCAATGTTCAGAATCCACCTGTATAATGAATCCAGAAGTTGTGCAAT
CCAATGGTGTGAAGACTTTTAGCAGTTGCAGTTTGAGGAGCTTTCAAAATTTCATTTCAAATGTGGGTGTCAAA
TGTCTTCAGAATAAGCCACAAATGCAAAAAAAATCTCCGAAACCAGTCTGTGGCAATGGCAGATTGGAGGGAAA
TGAAATCTGTGATTGTGGTACTGAGGCTCAATGTGGACCTGCAAGCTGTTGTGATTTTCGAACTTGTGTACTGA
AAGACGGAGCAAAATGTTATAAAGGACTGTGCTGCAAAGACTGTCAAATTTTACAATCAGGCGTTGAATGTAGG
CCGAAAGCACATCCTGAATGTGACATCGCTGAAAATTGTAATGGAAGCTCACCAGAATGTGGTCCTGACATAAC
TTTAATCAATGGACTTTCATGCAAAAATAATAAGTTTATTTGTTATGACGGAGACTGCCATGATCTCGATGCAC
GTTGTGAGAGTGTATTTGGAAAAGGTTCAAGAAATGCTCCATTTGCCTGCTATGAAGAAATACAATCTCAATCA
GACAGATTTGGGAACTGTGGTAGGGATAGAAATAACAAATATGTGTTCTGTGGATGGAGGAATCTTATATGTGG
AAGATTAGTTTGTACCTACCCTACTCGAAAGCCTTTCCATCAAGAAAATGGTGATGTGATTTATGCTTTCGTAC
GAGATTCTGTATGCATAACTGTAGACTACAAATTGCCTCGAACAGTTCCAGATCCACTGGCTGTCAAAAATGGC
TCTCAGTGTGATATTGGGAGGGTTTGTGTAAATCGTGAATGTGTAGAATCAAGGATAATTAAGGCTTCAGCACA
TGTTTGTTCACAACAGTGTTCTGGACATGGAGTGTGTGATTCCAGAAACAAGTGCCATTGTTCGCCAGGCTATA
AGCCTCCAAACTGCCAAATACGTTCCAAAGGATTTTCCATATTTCCTGAGGAAGATATGGGTTCAATCATGGAA
AGAGCATCTGGGAAGACTGAAAACACCTGGCTTCTAGGTTTCCTCATTGCTCTTCCTATTCTCATTGTAACAAC
CGCAATAGTTTTGGCAAGGAAACAGTTGAAAAAGTGGTTCGCCAAGGAAGAGGAATTCCCAAGTAGCGAATCTA
AATCGGAAGGTAGCACACAGACATATGCCAGCCAATCCAGCTCAGAAGGCAGCACTCAGACATATGCCAGCCAA
ACCAGATCAGAAAGCAGCAGTCAAGCTGATACTAGCAAATCCAAATCAGAAGATAGTGCTGAAGCATATACTAG
CAGATCCAAATCACAGGACAGTACCCAAACACAAAGCAGTAGTAACTAGTGATTCCTTCAGAAGGCAACGGATA
ACATCGAGAGTCTCGCTAAGAAATGAAAATTCTGTCTTTCCTTCCGTGGTCACAGCTGAAAGAAACAATAAATT
GAGTGTGGATC

FIGURE 70

></usr/seqdb2/sst/DNA/Dnaseqs.min/ss.DNA176775
><subunit 1 of 1, 787 aa, 1 stop
><MW: 87934, pI: 5.49, NX(S/T): 4

MFRLWLLLAGLCGLLASRPGFQNSLLQIVIPEKIQTNTNDSSEIEYEQISYIIPIDEKLY
TVHLKQRYFLADNFMIYLYNQGSMNTYSSDIQTQCYYQGNIEGYPDSMVTLSTCSGLRGI
LQFENVSYGIEPLESAVEFQHVLYKLKNEDNDIAIFIDRSLKEQPMDDNIFISEKSEPAV
PDLFPLYLEMHIVVDKTLYDYWGSDSMIVTNKVIEIVGLANSMFTQFKVTIVLSSLELWS
DENKISTVGEADELLQKFLEWKQSYLNLRPHDIAYLLIYMDYPRYLGAVFPGTMCITRYS
AGVALYPKEITLEAFAVIVTQMLALSLGISYDDPKKCQCSESTCIMNPEVVQSNGVKTFS
SCSLRSFQNFISNVGVKCLQNKPQMQKKSPKPVCGNGRLEGNEICDCGTEAQCGPASCCD
FRTCVLKDGAKCYKGLCCKDCQILQSGVECRPKAHPECDIAENCNGSSPECGPDITLING
LSCKNNKFICYDGDCHDLDARCESVFGKGSRNAPFACYEEIQSQSDRFGNCGRDRNNKYV
FCGWRNLICGRLVCTYPTRKPFHQENGDVIYAFVRDSVCITVDYKLPRTVPDPLAVKNGS
QCDIGRVCVNRECVESRIIKASAHVCSQQCSGHGVCDSRNKCHCSPGYKPPNCQIRSKGF
SIFPEEDMGSIMERASGKTENTWLLGFLIALPILIVTTAIVLARKQLKKWFAKEEEFPSS
ESKSEGSTQTYASQSSSEGSTQTYASQTRSESSSQADTSKSKSEDSAEAYTSRSKSQDST
QTQSSSN

Important features of the protein:

Signal peptide:

Amino acids 1-16

Transmembrane domain:

Amino acids 309-326;681-705

N-glycosylation sites:

Amino acids 39-43;125-129;465-469;598-602

Glycosaminoglycan attachment site:

Amino acids 631-635

Tyrosine kinase phosphorylation site:

Amino acids 269-276

N-myristoylation sites:

Amino acids 13-19;82-88;99-105;218-224;401-407;634-640;
726-732;739-745

EGF-like domain proteins:

Amino acids 642-654

Disintegrins proteins:

Amino acids 400-407;422-472;403-453;467-517;634-684

Reprolysin (M12B) family zinc metalloprotease:

Amino acids 186-383

Reprolysin family propeptide:

Amino acids 63-176

FIGURE 71

1 ggcacgagag atctgtggtc catctgccct aaggacttga gctgcacctg tctcaaaggg 61 agctacttgc ctcgagtctc atgcctctgt gcttgctgct tctggtcttc gctcctgtcg 121 gagtccagtc cgactggttg agcatcagcc ttccacaccg ttcttatgaa ggagaccaag 181 tagttataag ctgcacaggg aaaaataatg gtgacataaa gagactgaag tacttcaagg 241 atggatatca catagaaact tacagcagtg cttcaagcta caccattagg aatgcaagac 301 gcggtgacag tggctcctat tcctgtaagg cagataggaa atttttccta tttatagaca 361 caacagaaga aacaggatct aagtggctga atgtccaaga gctgtttcca gcacctgggc 421 tgacagccag ccccctgcag cccgtagagg ggagttcagt gaccctgtcc tgcaacacct 481 ggctcccttc agatagggca acgacccagc tacgctattc cttcttcaaa gatggccaca 541 ctttgcaatc gggctggacc tcatcaaaat ttaccatctc agcaatatcg aaggaagact 601 caggaaatta ctggtgtgaa gcaatgactg cctctcgcag tgtctcaaag cagagtcacc 661 ggtcctacat agatgtagag aggatccctg tatctcaagt caccatggag atccagcctt 721 caagaggctg gggagttgaa ggggagccac tggtcgttga aggggagccc ctggtccttg 781 cttgttctgt ggctaaaggc actgggctaa tcacattctc ctggcatagg caggacacta 841 aggaaagtgt ggggaagaaa agtcagcgtt cccagagagt ggagctggag atccctacta 901 tcagggaaag ccatgctggg gggtactact gcacagcaga caacaactac ggcctgatcc 961 agagtgcaat cgtgaacatc accgtgaaaa ttccagtgtt gaacccgctc ctctccatca

FIGURE 71 CONTINUED 1021 gtgttcctgg ggtcttgccc ttcatcggag atgtggcgga gcttcactgt gaagacaaga
1081 gagcatctcc tccggttctc tactggtttt atcatgaaaa tatcactctg gctaacacct
1141 cggcaccttt tggaggaaag gcatccttta agctctctct gactgcaggg cattctggga
1201 actactcttg tgaggctgaa aacgcctggg gtaccaagcg cagtgaggtg gtaacgctca
1261 atgtcacaga gcccccaccc aaagtgcgtt tggtgaatgg cccccaccac tgtgaaggac
1321 gcgtagaggt tgaacaggaa ggtcgctggg gcactgtatg tgatgatggc tgggacatga
1381 gggatgtggc tgtggtgtgc cgagagctgg gctgtggagc agcccaacac acacctatag
1441 ccatgctgta tccaccagca gttgatgaag ctctgcctgt gctcattcag gtagccctgt
1501 gcaatggcac agaaaagacc ctggctgaat gtgaccaggt tgaggccttt gattgtggac
1561 atgatgagga tgctggagct gtgtgtgaag tcttacccag cactttc<u>tga</u> agatctagag
1621 accagagacc atcagacctc ctactttctg cactgggcct cacagccctc acggtctgca
1681 gctcccagtg gacttccaga cttcagctgt ggcttatcat tcaagaggac tcaaaactat
1741 attaatctgc tctgagataa tgttccaaaa gctccaaaga aagcccgagt cccttgcccc
1801 cagaggccaa gcttggaaaa attgttcccc tgtccaggtt ccctgccttt ctagctcctt
1861 cttgctatct ccttgggcag acgtgcgcag aggtggcgca agtgaggatc acatacatgt
1921 gcctgggctt ccatctggta gaatgtggtc ta

FIGURE 72

MPLCLLLLVFAPVGVQSDWLSISLPHRSYEGDQVVISCTGKNNGDIKRLKYFKDGYH
IETYSSASSYTIRNARRGDSGSYSCKADRKFFLFIDTTEETGSKWLNVQELFPAPGLT
ASPLQPVEGSSVTLSCNTWLPSDRATTQLRYSFFKDGHTLQSGWTSSKFTISAISKED
SGNYWCEAMTASRSVSKQSHRSYIDVERIPVSQVTMEIQPSRGWGVEGEPLVVEGE
PLVLACSVAKGTGLITFSWHRQDTKESVGKKSQRSQRVELEIPTIREGHAGGYYCTA
DNNYGLIQSAIVNITVKIPVLNPLLSISVPGVLPFIGDVAELHCEDKRASPPVLYWFYH
ENITLANTSAPFGGKASFKLSLTAGHSGNYSCEAENAWGTKRSEVVTLNVTEPPPKV
RLVNGPHHCEGRVEVEQEGRWGTVCDDGWDMRDVAVVCRELGCGAAQHTPIAM
LYPPAVDEALPVLIQVALCNGTEKTLAECDQVEAFDCGHDEDAEFGGGLNDIFEAQ
KIEWHEGRAHHHHHH

FIGURE 73

ATATATCGATATGCTGCCGAGGCTGTTGCTGTTGATCTGTGCTCCACTCTGTGAACCTGC

CGAGCTGTTTTTGATAGCCAGCCCCTCCCATCCCACAGAGGGGAGCCCAGTGACCCTGAC

GTGTAAGATGCCCTTTCTACAGAGTTCAGATGCCCAGTTCCAGTTCTGCTTTTTCAGAGA

CACCCGGGCCTTGGGCCCAGGCTGGAGCAGCTCCCCCAAGCTCCAGATCGCTGCCATGTG

GAAAGAAGACACAGGGTCATACTGGTGCGAGGCACAGACAATGGCGTCCAAAGTCTTGAG

GAGCAGGAGATCCCAGATAAATGTGCACAGGGTCCCTGTCGCTGATGTGAGCTTGGAGAC

TCAGCCCCCAGGAGGACAGGTGATGGAGGGAGACAGGCTGGTCCTCATCTGCTCAGTTGC

TATGGGCACAGGAGACATCACCTTCCTTTGGTACAAAGGGGCTGTAGGTTTAAACCTTCA

GTCAAAGACCCAGCGTTCACTGACAGCAGAGTATGAGATTCCTTCAGTGAGGGAGAGTGA

TGCTGAGCAATATTACTGTGTAGCTGAAAATGGCTATGGTCCCAGCCCCAGTGGGCTGGT

GAGCATCACTGTCAGAATCCCGGTGTCTCGCCCAATCCTCATGCTCAGGGCTCCCAGGGC

CCAGGCTGCAGTGGAGGATGTGCTGGAGCTTCACTGTGAGGCCCTGAGAGGCTCTCCTCC

GATCCTGTACTGGTTTTATCACGAGGATATCACCCTGGGGAGCAGGTCGGCCCCCTCTGG

AGGAGGAGCCTCCTTCAACCTTTCCCTGACTGAAGAACATTCTGGAAACTACTCCTGTGA

GGCCAACAATGGCCTGGGGGCCCAGCGCAGTGAGGCGGTGACACTCAACTTCACAGTGCC

TACTGGGGCCAGAAGCAATCATCTTACCTCAGGAGTCATTGAGGGGCTGCTCAGCACCCT

TGGTCCAGCCACCGTGGCCTTATTATTTTGCTACGGCCTCAAAAGAAAAATAGGAAGACG

TTCAGCCAGGGATCCACTCAGGAGCCTTCCCAGCCCTCTACCCCAAGAGTTCACGTACCT

CAACTCACCTACCCCAGGGCAGCTACAGCCTATATATGAAAATGTGAATGTTGTAAGTGG

GGATGAGGTTTATTCACTGGCGTACTATAACCAGCCGGAGCAGGAATCAGTAGCAGCAGA

AACCCTGGGGACACATATGGAGGACAAGGTTTCCTTAGACATCTATTCCAGGCTGAGGAA

FIGURE 73 CONTINUED

AGCAAACATTACAGATGTGGACTATGAAGATGCTATGTAAGGTTATGGAAGATTCTGCTC

PRO85143

></usr/seqdb2/sst/DNA/Dnaseqs.min/ss.DNA340394

><subunit 1 of 1, 429 aa, 1 stop

><MW: 46936, pI: 5.42, NX(S/T): 4

MLPRLLLLICAPLCEPAELFLIASPSHPTEGSPVTLTCKMPFLQSSDAQFQFCFFRDTRA

LGPGWSSSPKLQIAAMWKEDTGSYWCEAQTMASKVLRSRRSQINVHRVPVADVSLETQPP

GGQVMEGDRLVLICSVAMGTGDITFLWYKGAVGLNLQSKTQRSLTAEYEIPSVRESDAEQ

YYCVAENGYGPSPSGLVSITVRIPVSRPILMLRAPRAQAAVEDVLELHCEALRGSPPILY

WFYHEDITLGSRSAPSGGGASFNLSLTEEHSGNYSCEANNGLGAQRSEAVTLNFTVPTGA

RSNHLTSGVIEGLLSTLGPATVALLFCYGLKRKIGRRSARDPLRSLPSPLPQEFTYLNSP

TPGQLQPIYENVNVVSGDEVYSLAYYNQPEQESVAAETLGTHMEDKVSLDIYSRLRKANI

TDVDYEDAM

FIGURE 75

GCCAGGAATAACTAGAGAGGAACAATGGGGTTATTCAGAGGTTTTGTTTTCCTCTTAGTTC
TGTGCCTGCTGCACCAGTCAAATACTTCCTTCATTAAGCTGAATAATAATGGCTTTGAAGA
TATTGTCATTGTTATAGATCCTAGTGTGCCAGAAGATGAAAAAATAATTGAACAAATAGAG
GATATGGTGACTACAGCTTCTACGTACCTGTTTGAAGCCACAGAAAAAAGATTTTTTTCA
AAAATGTATCTATATTAATTCCTGAGAATTGGAAGGAAAATCCTCAGTACAAAAGGCCAAA
ACATGAAAACCATAAACATGCTGATGTTATAGTTGCACCACCTACACTCCCAGGTAGAGAT
GAACCATACACCAAGCAGTTCACAGAATGTGGAGAGAAAGGCGAATACATTCACTTCACCC
CTGACCTTCTACTTGGAAAAAAACAAAATGAATATGGACCACCAGGCAAACTGTTTGTCCA
TGAGTGGGCTCACCTCCGGTGGGGAGTGTTTGATGAGTACAATGAAGATCAGCCTTTCTAC
CGTGCTAAGTCAAAAAAAATCGAAGCAACAAGGTGTTCCGCAGGTATCTCTGGTAGAAATA
GAGTTTATAAGTGTCAAGGAGGCAGCTGTCTTAGTAGAGCATGCAGAATTGATTCTACAAC
AAAACTGTATGGAAAAGATTGTCAATTCTTTCCTGATAAAGTACAAACAGAAAAAGCATCC
ATAATGTTTATGCAAAGTATTGATTCTGTTGTTGAATTTTGTAACGAAAAAACCCATAATC
AAGAAGCTCCAAGCCTACAAAACATAAAGTGCAATTTTAGAAGTACATGGGAGGTGATTAG
CAATTCTGAGGATTTTAAAAACACCATACCCATGGTGACACCACCTCCTCCACCTGTCTTC
TCATTGCTGAAGATCAGTCAAAGAATTGTGTGCTTAGTTCTTGATAAGTCTGGAAGCATGG
GGGGTAAGGACCGCCTAAATCGAATGAATCAAGCAGCAAAACATTTCCTGCTGCAGACTGT
TGAAAATGGATCCTGGGTGGGGATGGTTCACTTTGATAGTACTGCCACTATTGTAAATAAG
CTAATCCAAATAAAAAGCAGTGATGAAAGAAACACACTCATGGCAGGATTACCTACATATC
CTCTGGGAGGAACTTCCATCTGCTCTGGAATTAAATATGCATTTCAGGTGATTGGAGAGCT
ACATTCCCAACTCGATGGATCCGAAGTACTGCTGCTGACTGATGGGGAGGATAACACTGCA
AGTTCTTGTATTGATGAAGTGAAACAAAGTGGGGCCATTGTTCATTTTATTGCTTTGGGAA
GAGCTGCTGATGAAGCAGTAATAGAGATGAGCAAGATAACAGGAGGAAGTCATTTTTATGT
TTCAGATGAAGCTCAGAACAATGGCCTCATTGATGCTTTTGGGGCTCTTACATCAGGAAAT
ACTGATCTCTCCCAGAAGTCCCTTCAGCTCGAAAGTAAGGGATTAACACTGAATAGTAATG
CCTGGATGAACGACACTGTCATAATTGATAGTACAGTGGGAAAGGACACGTTCTTTCTCAT
CACATGGAACAGTCTGCCTCCCAGTATTTCTCTCTGGGATCCCAGTGGAACAATAATGGAA
AATTTCACAGTGGATGCAACTTCCAAAATGGCCTATCTCAGTATTCCAGGAACTGCAAAGG
TGGGCACTTGGGCATACAATCTTCAAGCCAAAGCGAACCCAGAAACATTAACTATTACAGT
AACTTCTCGAGCAGCAAATTCTTCTGTGCCTCCAATCACAGTGAATGCTAAAATGAATAAG
GACGTAAACAGTTTCCCCAGCCCAATGATTGTTTACGCAGAAATTCTACAAGGATATGTAC
CTGTTCTTGGAGCCAATGTGACTGCTTTCATTGAATCACAGAATGGACATACAGAAGTTTT
GGAACTTTTGGATAATGGTGCAGGCGCTGATTCTTTCAAGAATGATGGAGTCTACTCCAGG
TATTTTACAGCATATACAGAAAATGGCAGATATAGCTTAAAAGTTCGGGCTCATGGAGGAG
CAAACACTGCCAGGCTAAAATTACGGCCTCCACTGAATAGAGCCGCGTACATACCAGGCTG
GGTAGTGAACGGGGAAATTGAAGCAAACCCGCCAAGACCTGAAATTGATGAGGATACTCAG
ACCACCTTGGAGGATTTCAGCCGAACAGCATCCGGAGGTGCATTTGTGGTATCACAAGTCC
CAAGCCTTCCCTTGCCTGACCAATACCCACCAAGTCAAATCACAGACCTTGATGCCACAGT
TCATGAGGATAAGATTATTCTTACATGGACAGCACCAGGAGATAATTTTGATGTTGGAAAA
GTTCAACGTTATATCATAAGAATAAGTGCAAGTATTCTTGATCTAAGAGACAGTTTTGATG
ATGCTCTTCAAGTAAATACTACTGATCTGTCACCAAAGGAGGCCAACTCCAAGGAAAGCTT
TGCATTTAAACCAGAAAATATCTCAGAAGAAAATGCAACCCACATATTTATTGCCATTAAA
AGTATAGATAAAAGCAATTTGACATCAAAAGTATCCAACATTGCACAAGTAACTTTGTTTA
TCCCTCAAGCAAATCCTGATGACATTGATCCTACACCTACTCCTACTCCTACTCCTACTCC
TGATAAAAGTCATAATTCTGGAGTTAATATTTCTACGCTGGTATTGTCTGTGATTGGGTCT
GTTGTAATTGTTAACTTTATTTTAAGTACCACCATTTGAACCTTAACGAAGAAAAAAATCT
TCAAGTAGACCTAGAAGAGAGTTTTAAAAAACAAAACAATGTAAGTAAAGGATATTTCTGA
ATCTTAAAATTCATCCCATGTGTGATCATAAACTCATAAAAATAATTTTAAGATGTCGGAA
AAGGATACTTTGATTAAATAAAAACACTCATGGATATGTAAAAACTGTCAAGATTAAAATT
TAATAGTTTCATTTATTTGTTATTTTATTTGTAAGAAATAGTGATGAACAAAGATCCTTTT
TCATACTGATACCTGGTTGTATATTATTTGATGCAACAGTTTTCTGAAATGATATTTCAAA
TTGCATCAAGAAATTAAAATCATCTATCTGAGTAGTCAAAATACAAGTAAAGGAGAGCAAA
TAAACAACATTTGGAAAAAAAAAAAAAAAAAAAAAAAAAAAAAAAAAAAAAAAAAAAAAAAA
AAAAAAAAAAAAAAAAAAAAAAAAAAAAAAAA

FIGURE 76

MGLFRGFVFLLVLCLLHQSNTSFIKLNNNGFEDIVIVIDPSVPEDEKIIEQIEDMVTTAST
YLFEATEKRFFFKNVSILIPENWKENPQYKRPKHENHKHADVIVAPPTLPGRDEPYTKQFT
ECGEKGEYIHFTPDLLLGKKQNEYGPPGKLFVHEWAHLRWGVFDEYNEDQPFYRAKSKKIE
ATRCSAGISGRNRVYKCQGGSCLSRACRIDSTTKLYGKDCQFFPDKVQTEKASIMFMQSID
SVVEFCNEKTHNQEAPSLQNIKCNFRSTWEVISNSEDFKNTIPMVTPPPPPVFSLLKISQR
IVCLVLDKSGSMGGKDRLNRMNQAAKHFLLQTVENGSWVGMVHFDSTATIVNKLIQIKSSD
ERNTLMAGLPTYPLGGTSICSGIKYAFQVIGELHSQLDGSEVLLLTDGEDNTASSCIDEVK
QSGAIVHFIALGRAADEAVIEMSKITGGSHFYVSDEAQNNGLIDAFGALTSGNTDLSQKSL
QLESKGLTLNSNAWMNDTVIIDSTVGKDTFFLITWNSLPPSISLWDPSGTIMENFTVDATS
KMAYLSIPGTAKVGTWAYNLQAKANPETLTITVTSRAANSSVPPITVNAKMNKDVNSFPSP
MIVYAEILQGYVPVLGANVTAFIESQNGHTEVLELLDNGAGADSFKNDGVYSRYFTAYTEN
GRYSLKVRAHGGANTARLKLRPPLNRAAYIPGWVVNGEIEANPPRPEIDEDTQTTLEDFSR
TASGGAFVVSQVPSLPLPDQYPPSQITDLDATVHEDKIILTWTAPGDNFDVGKVQRYIIRI
SASILDLRDSFDDALQVNTTDLSPKEANSKESFAFKPENISEENATHIFIAIKSIDKSNLT
SKVSNIAQVTLFIPQANPDDIDPTPTPTPTPTPDKSHNSGVNISTLVLSVIGSVVIVNFIL
STTI

Signal peptide:

amino acids 1-21

Putative transmembrane domains:

amino acids 284-300, 617-633

Leucine zipper pattern.

amino acids 469-491, 476-498

N-glycosylation site.

amino acids 20-24, 75-79, 340-344, 504-508, 542-546, 588-592, 628-632, 811-815, 832-836, 837-841, 852-856, 896-900

FIGURE 77

CTTCTGTAGGACAGTCACCAGGCCAGATCCAGAAGCCTCTCTAGGCTCCAGCTTTCTCTGT
GGAAGATGACAGCAATTATAGCAGGACCCTGCCAGGCTGTCGAAAAGATTCCGCAATAAAA
CTTTGCCAGTGGGAAGTACCTAGTGAAACGGCCTAAGATGCCACTTCTTCTCATGTCCCAG
GCTTGAGGCCCTGTGGTCCCCATCCTTGGGAGAAGTCAGCTCCAGCACCATGAAGGGCATC
CTCGTTGCTGGTATCACTGCAGTGCTTGTTGCAGCTGTAGAATCTCTGAGCTGCGTGCAGT
GTAATTCATGGGAAAAATCCTGTGTCAACAGCATTGCCTCTGAATGTCCCTCACATGCCAA
CACCAGCTGTATCAGCTCCTCAGCCAGCTCCTCTCTAGAGACACCAGTCAGATTATACCAG
AATATGTTCTGCTCAGCGGAGAACTGCAGTGAGGAGACACACATTACAGCCTTCACTGTCC
ACGTGTCTGCTGAAGAACACTTTCATTTTGTAAGCCAGTGCTGCCAAGGAAAGGAATGCAG
CAACACCAGCGATGCCCTGGACCCTCCCCTGAAGAACGTGTCCAGCAACGCAGAGTGCCCT
GCTTGTTATGAATCTAATGGAACTTCCTGTCGTGGGAAGCCCTGGAAATGCTATGAAGAAG
AACAGTGTGTCTTTCTAGTTGCAGAACTTAAGAATGACATTGAGTCTAAGAGTCTCGTGCT
GAAAGGCTGTTCCAACGTCAGTAACGCCACCTGTCAGTTCCTGTCTGGTGAAAACAAGACT
CTTGGAGGAGTCATCTTTCGAAAGTTTGAGTGTGCAAATGTAAACAGCTTAACCCCCACGT
CTGCACCAACCACTTCCCACAACGTGGGCTCCAAAGCTTCCCTCTACCTCTTGGCCCTTGC
CAGCCTCCTTCTTCGGGGACTGCTGCCCTGAGGTCCTGGGGCTGCACTTTGCCCAGCACCC
CATTTCTGCTTCTCTGAGGTCCAGAGCACCCCCTGCGGTGCTGACACCCTCTTTCCCTGCT
CTGCCCCGTTTAACTGCCCAGTAAGTGGGAGTCACAGGTCTCCAGGCAATGCCGACAGCTG
CCTTGTTCTTCATTATTAAAGCACTGGTTCATTCACTGCCAAAAAAAAAAAAAAAAAAAAA
AAAAA

FIGURE 78

MKGILVAGITAVLVAAVESLSCVQCNSWEKSCVNSIASECPSHANTSCISSSASSSLETPV
RLYQNMFCSAENCSEETHITAFTVHVSAEEHFHFVSQCCQGKECSNTSDALDPPLKNVSSN
AECPACYESNGTSCRGKPWKCYEEEQCVFLVAELKNDIESKSLVLKGCSNVSNATCQFLSG
ENKTLGGVIFRKFECANVNSLTPTSAPTTSHNVGSKASLYLLALASLLLRGLLP

FIGURE 79

GGAATTCCCTGATATACACCTGGACCACCACCAATGGATATACAAATGGCAAACAATTTT

ACTCCGCCCTCTGCAACTCCTCAGGGAAATGACTGTGACCTCTATGCACATCACAGCACG

GCCAGGATAGTAATGCCTCTGCATTACAGCCTCGTCTTCATCATTGGGCTCGTGGGAAAC

TTACTAGCCTTGGTCGTCATTGTTCAAAACAGGAAAAAAATCAACTCTACCACCCTCTAT

TCAACAAATTTGGTGATTTCTGATATACTTTTTACCACGGCTTTGCCTACACGAATAGCC

TACTATGCAATGGGCTTTGACTGGAGAATCGGAGATGCCTTGTGTAGGATAACTGCGCTA

GTGTTTTACATCAACACATATGCAGGTGTGAACTTTATGACCTGCCTGAGTATTGACCGC

TTCATTGCTGTGGTGCACCCTCTACGCTACAACAAGATAAAAAGGATTGAACATGCAAAA

GGCGTGTGCATATTTGTCTGGATTCTAGTATTTGCTCAGACACTCCCACTCCTCATCAAC

CCTATGTCAAAGCAGGAGGCTGAAAGGATTACATGCATGGAGTATCCAAACTTTGAAGAA

ACTAAATCTCTTCCCTGGATTCTGCTTGGGGCATGTTTCATAGGATATGTACTTCCACTT

ATAATCATTCTCATCTGCTATTCTCAGATCTGCTGCAAACTCTTCAGAACTGCCAAACAA

AACCCACTCACTGAGAAATCTGGTGTAAACAAAAAGGCTCTCAACACAATTATTCTTATT

ATTGTTGTGTTTGTTCTCTGTTTCACACCTTACCATGTTGCAATTATTCAACATATGATT

AAGAAGCTTCGTTTCTCTAATTTCCTGGAATGTAGCCAAAGACATTCGTTCCAGATTTCT

CTGCACTTTACAGTATGCCTGATGAACTTCAATTGCTGCATGGACCCTTTTATCTACTTC

TTTGCATGTAAAGGGTATAAGAGAAAGGTTATGAGGATGCTGAAACGGCAAGTCAGTGTA

TCGATTTCTAGTGCTGTGAAGTCAGCCCCTGAAGAAAATTCACGTGAAATGACAGAAACG

CAGATGATGATACATTCCAAGTCTTCAAATGGAAAGTGAAATGGATTGTATTTTGGTTTA

FIGURE 79 CONTINUED

TAGTGACGTAAACTGTATGACAAACTTTGCAGGACTTCCCTTATAAAGCAAAATAATTGT

TCAGCTTCCAATTAGTATTCTTTTATATTTCTTTCATTGGGCGCTTTCCCATCTCCAACT

CGGAAGTAAGCCCAAGAGAACAACATAAAGCAAACAACATAAAGCACAATAAAAATGCAA

ATAAATATTTTCATTTTTATTTGTAAACGAATACACCAAAAGGAGGCGCTCTTAATAACT

CCCAATGTAAAAAGTTTTGTTTTAATAAAAAATTAATTATTATTCTTGCCAACAAATGGC

TAGAAAGGACTGAATAGATTATATATTGCCAGATGTTAATACTGTAACATACTTTTTAAA

TAACATATTTCTTAAATCCAAATTTCTCTCAATGTTAGATTTAATTCCCTCAATAACACC

AATGTTTTGTTTTGTTTCGTTCTGGGTCATAAAACTTTGTTAAGGAACTCTTTTGGAATA

AAGAGCAGGATGCTGCGGAATTC

FIGURE 80

></usr/seqdb2/sst/DNA/Dnaseqs.min/ss.DNA193963

><subunit 1 of 1, 361 aa, 1 stop

><MW: 41224, pI: 9.44, NX(S/T): 2

MDIQMANNFTPPSATPQGNDCDLYAHHSTARIVMPLHYSLVFIIGLVGNLLALVVIVQNR

KKINSTTLYSTNLVISDILFTTALPTRIAYYAMGFDWRIGDALCRITALVFYINTYAGVN

FMTCLSIDRFIAVVHPLRYNKIKRIEHAKGVCIFVWILVFAQTLPLLINPMSKQEAERIT

CMEYPNFEETKSLPWILLGACFIGYVLPLIIILICYSQICCKLFRTAKQNPLTEKSGVNK

KALNTIILIIVVFVLCFTPYHVAIIQHMIKKLRFSNFLECSQRHSFQISLHFTVCLMNFN

CCMDPFIYFFACKGYKRKVMRMLKRQVSVSISSAVKSAPEENSREMTETQMMIHSKSSNG

K

GENE DISRUPTIONS, COMPOSITIONS AND METHODS RELATING THERETO

RELATED APPLICATIONS

This application is a US national stage continuation application claiming priority under 35 USC §371 of international application PCT/US2005/037291, filed Oct. 18, 2005, which claims priority under 35 USC §119 to U.S. Provisional Application 60/623,789 filed Oct. 29, 2004.

FIELD OF THE INVENTION

The present invention relates to compositions, including transgenic and knockout animals and methods of using such compositions for the diagnosis and treatment of diseases or disorders.

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.* 93:7108-7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesion molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immuno-adhesions, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

Given the importance of secreted and membrane-bound proteins in biological and disease processes, in vivo studies and characterizations may provide valuable identification and discovery of therapeutics and/or treatments useful in the prevention, amelioration or correction of diseases or dysfunctions. In this regard, genetically engineered mice have proven to be invaluable tools for the functional dissection of biological processes relevant to human disease, including immunology, cancer, neuro-biology, cardiovascular biology, obesity and many others. Gene knockouts can be viewed as modeling the biological mechanism of drug action by presaging the activity of highly specific antagonists in vivo. Knockout mice have been shown to model drug activity; phenotypes of mice deficient for specific pharmaceutical target proteins can resemble the human clinical phenotype caused by the corresponding antagonist drug. Gene knockouts enable the discovery of the mechanism of action of the target, the predominant physiological role of the target, and mechanism-based side-effects that might result from inhibition of the target in mammals. Examples of this type include mice deficient in the angiotensin converting enzyme (ACE) [Esther, C. R. et al., *Lab. Invest.,* 74:953-965 (1996)] and cyclooxygenase-1 (COX1) genes [Langenbach, R. et al., *Cell,* 83:483-492 (1995)]. Conversely, knocking the gene out in the mouse can have an opposite phenotypic effect to that observed in humans after administration of an agonist drug to the corresponding target. Examples include the erythropoietin knockout [Wu, C. S. et al., *Cell,* 83:59-67 (1996)], in which a consequence of the mutation is deficient red blood cell production, and the GABA(A)-R-β3 knockout [DeLorey, T. M., *J. Neurosci.,* 18:8505-8514 (1998)], in which the mutant mice show hyperactivity and hyper-responsiveness. Both these phenotypes are opposite to the effects of erythropoietin and benzodiazepine administration in humans. A striking example of a target validated using mouse genetics is the ACC2 gene. Although the human ACC2 gene had been identified several years ago, interest in ACC2 as a target for drug development was stimulated only recently after analysis of ACC2 function using a knockout mouse. ACC2 mutant mice eat more than their wild-type littermates, yet burn more fat and store less fat in their adipocytes, making this enzyme a probable target for chemical antagonism in the treatment of obesity [Abu-Elheiga, L. et al., *Science,* 291:2613-2616 (2001)].

In the instant application, mutated gene disruptions have resulted in phenotypic observations related to various disease conditions or dysfunctions including: CNS/neurological disturbances or disorders such as anxiety; eye abnormalities and associated diseases; cardiovascular, endothelial or angiogenic disorders including atherosclerosis; abnormal metabolic disorders including diabetes and dyslipidemias associated with elevated serum triglycerides and cholesterol levels;

immunological and inflammatory disorders; oncological disorders; bone metabolic abnormalities or disorders such as arthritis, osteoporosis and osteopetrosis; or a developmental disease such as embryonic lethality.

SUMMARY OF THE INVENTION

A. Embodiments

The invention provides an isolated nucleic acid molecule comprising a nucleotide sequence that encodes a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide cDNA as disclosed herein, the coding sequence of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide lacking the signal peptide as disclosed herein, the coding sequence of an extracellular domain of a transmembrane PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect of the invention provides an isolated nucleic acid molecule comprising a nucleotide sequence encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides are contemplated.

The invention also provides fragments of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide coding sequence, or the complement thereof, that may find use as, for example, hybridization probes, for encoding fragments of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide that may optionally encode a polypeptide comprising a binding site for an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody or as antisense oligonucleotide probes. Such nucleic acid fragments usually are or are at least about 10 nucleotides in length, alternatively are or are at least about 15 nucleotides in length, alternatively are or are at least about 20 nucleotides in length, alternatively are or are at least about 30 nucleotides in length, alternatively are or are at least about 40 nucleotides in length, alternatively are or are at least about 50 nucleotides in length, alternatively are or are at least about 60 nucleotides in length, alternatively are or are at least about 70 nucleotides in length, alternatively are or are at least about 80 nucleotides in length, alternatively are or are at least about 90 nucleotides in length, alternatively are or are at least about 100 nucleotides in length, alternatively are or are at least about 110 nucleotides in length, alternatively are or are at least about 120 nucleotides in length, alternatively are or are at least about 130 nucleotides in length, alternatively are or are at least about 140 nucleotides in length, alternatively are or are at least about 150 nucleotides in length, alternatively are or are at least about 160 nucleotides in length, alternatively are or are at least about 170 nucleotides in length, alternatively are or are at least about 180 nucleotides in length, alternatively are or are at least about 190 nucleotides in length, alternatively are or are at least about 200 nucleotides in length, alternatively are or are at least about 250 nucleotides in length, alternatively are or are at least about 300 nucleotides in length, alternatively are or are at least about 350 nucleotides in length, alternatively are or are at least about 400 nucleotides in length, alternatively are or are at least about 450 nucleotides in length, alternatively are or are at least about 500 nucleotides in length, alternatively are or are at least about 600 nucleotides in length, alternatively are or are at least about 700 nucleotides in length, alternatively are or are at least about 800 nucleotides in length, alternatively are or are at least about 900 nucleotides in length and alternatively are or are at least about 1000 nucleotides in length, wherein in this context the term “about” means the referenced nucleotide sequence length plus or minus 10% of that referenced length. It is noted that novel fragments of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding nucleotide sequence may be determined in a routine manner by aligning the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding nucleotide sequence with other known nucleotide sequences using any of a number of well known sequence alignment programs and determining which PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding nucleotide sequence fragment(s) are novel. All of such PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding nucleotide sequences are contemplated herein. Also contemplated are the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fragments encoded by these nucleotide molecule fragments, preferably those PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fragments that comprise a binding site for an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention provides isolated PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides encoded by any of the isolated nucleic acid sequences hereinabove identified.

In a certain aspect, the invention concerns an isolated PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In one aspect, the invention concerns PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polypeptides which are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polypeptides will have or have no more than one conservative amino acid substitution as compared to the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence, alternatively will have or will have no more than 2, 3, 4, 5, 6, 7, 8, 9, or 10 conservative amino acid substitution as compared to the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence.

In a specific aspect, the invention provides an isolated PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and recovering the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide from the cell culture.

Another aspect the invention provides an isolated PRO194, PRO220, PRO241, PRO284, PRO331, PRO354, PRO355, PRO533, PRO541, PRO725, PRO937, PRO1014, PRO120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and recovering the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide from the cell culture.

The invention provides agonists and antagonists of a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as defined herein. In particular, the agonist or antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody or a small molecule.

The invention provides a method of identifying agonists or antagonists to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which comprise contacting the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with a candidate molecule and monitoring a biological activity mediated by said PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Preferably, the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

The invention provides a composition of matter comprising a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, or an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as herein described, or an anti-4, anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, in combination with a carrier. Optionally, the carrier is a pharmaceutically acceptable carrier.

The invention provides the use of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, or an agonist or antagonist thereof as hereinbefore described, or an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, for the preparation of a medicament useful in the treatment of a condition which is responsive to the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO120, anti-PRO182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

The invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

The invention provides an antibody which binds, preferably specifically, to any of the above or below described polypeptides. Optionally, the antibody is a monoclonal antibody, humanized antibody, antibody fragment or single-chain antibody.

The invention provides oligonucleotide probes which may be useful for isolating genomic and cDNA nucleotide sequences, measuring or detecting expression of an associated gene or as antisense probes, wherein those probes may be derived from any of the above or below described nucleotide sequences. Preferred probe lengths are described above.

The invention also provides a method of identifying a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal. In one aspect, the non-human transgenic animal is a mammal. In another aspect, the mammal is a rodent. In still another aspect, the mammal is a rat or a mouse. In one aspect, the non-human transgenic animal is heterozygous for the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In another aspect, the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer’s disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histrionic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave’s disease), corneal and other tissue transplantation, retinal artery obstruction or occlusion; retinal degeneration causing secondary atrophy of the retinal vasculature, retinitis pigmentosa, macular dystrophies, Stargardt’s disease, congenital stationary night blindness, choroideremia, gyrate atrophy, Leber’s congenital amaurosis, retinoschisis disorders, Wagner’s syndrome, Usher syndromes, Zellweger syndrome, Saldino-Mainzer syndrome, Senior-Loken syndrome, Bardet-Biedl syndrome, Alport’s syndrome, Alstrom’s syndrome, Cockayne’s syndrome, dysplaisa spondyloepiphysaria congentia, Flynn-Aird syndrome, Friedreich ataxia, Hallgren syndrome, Marshall syndrome, Albers-Schnoberg disease, Refsum’s disease, Keams-Sayre syndrome, Waardenburg’s syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten’s disease, mucopolysaccharidoses, homocystinuria, or mannosidosis.

In still another aspect, the eye abnormality is a cataract. In still yet another aspect, the cataract is a systemic disease such as human Down’s syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In still yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud’s disease and Reynaud’s phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi’s sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies;

systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In still another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

The invention also provides an isolated cell derived from a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In one aspect, the isolated cell is a murine cell. In yet another aspect, the murine cell is an embryonic stem cell. In still another aspect, the isolated cell is derived from a non-human transgenic animal which exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality. The invention also provides a method of identifying an agent that modulates a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

In one aspect, the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In yet another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In still another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

The invention also provides an agent which modulates the phenotype associated with gene disruption. In one aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti- PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of identifying an agent that modulates a physiological characteristic associated with a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

In one aspect, the non-human transgenic animal exhibits at least one of the following physiological characteristics compared with gender matched wild-type littermates:

In another aspect, the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

The invention also provides an agent that modulates a physiological characteristic which is associated with gene disruption. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO120, anti-PRO182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of identifying an agent which modulates a behavior associated with a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

In one aspect, the observed behavior is an increased anxiety-like response during open field activity testing. In yet another aspect, the observed behavior is a decreased anxiety-like response during open field activity testing. In yet another aspect, the observed behavior is an abnormal circadian rhythm during home-cage activity testing. In yet another aspect, the observed behavior is an enhanced motor coordination during inverted screen testing. In yet another aspect, the observed behavior is impaired motor coordination during inverted screen testing. In yet another aspect, the observed behavior includes depression, generalized anxiety disorders, attention deficit disorder, sleep disorder, hyperactivity disorder, obsessive compulsive disorder, schizophrenia, cognitive disorders, hyperalgesia and sensory disorders. Such disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer’s disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The invention also provides an agent that modulates a behavior which is associated with gene disruption. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti- PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) administering a test agent to said non-human transgenic animal; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality associated with the gene disruption in the non-human transgenic animal.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism, or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect, the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a therapeutic agent for the treatment of a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a method of identifying an agent that modulates the expression of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) contacting a test agent with a host cell expressing a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide; and (b) determining whether the test agent modulates the expression of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by the host cell.

The invention also provides an agent that modulates the expression of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of evaluating a therapeutic agent capable of affecting a condition associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

In one aspect, the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

The invention also provides a therapeutic agent which is capable of affecting a condition associated with gene disruption. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a pharmaceutical composition comprising a therapeutic agent capable of affecting the condition associated with gene disruption.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject in need of such treatment whom may already have the disorder, or may be prone to have the disorder or may be in whom the disorder is to be prevented, a therapeutically effective amount of a therapeutic agent, or agonists or antagonists thereof, thereby effectively treating or preventing or ameliorating said disorder or disease.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

In another aspect the therapeutic agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti- PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal cell culture, each cell of said culture comprising a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) administering a test agent to said cell culture; and (c) determining whether the test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said culture.

In yet another aspect, the neurological disorder is an increased anxiety-like response during open field activity testing. In yet another aspect, the neurological disorder is a decreased anxiety-like response during open field activity testing. In yet another aspect, the neurological disorder is an abnormal circadian rhythm during home-cage activity testing. In yet another aspect, the neurological disorder is an enhanced motor coordination during inverted screen testing. In yet another aspect, the neurological disorder is impaired motor coordination during inverted screen testing. In yet another aspect, the neurological disorder includes depression, generalized anxiety disorders, attention deficit disorder, sleep disorder, hyperactivity disorder, obsessive compulsive disorder, schizophrenia, cognitive disorders, hyperalgesia and sensory disorders. Such neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

In another aspect, the eye abnormality is a retinal abnormality. In still another aspect, the eye abnormality is consistent with vision problems or blindness. In yet another aspect, the retinal abnormality is consistent with retinitis pigmentosa or is characterized by retinal degeneration or retinal dysplasia.

In still another aspect, the retinal abnormalities are consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis.

In still another aspect, the eye abnormality is a cataract. In still yet another aspect, the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

In still another aspect, the developmental abnormality comprises embryonic lethality or reduced viability.

In yet another aspect, the cardiovascular, endothelial or angiogenic disorders are arterial diseases, such as diabetes mellitus; papilledema; optic atrophy; atherosclerosis; angina;

myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

In still yet another aspect, the immunological disorders are consistent with systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

In yet another aspect, the bone metabolic abnormality or disorder is arthritis, osteoporosis, osteopenia or osteopetrosis.

The invention also provides an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality which is associated with gene disruption in said culture. In one aspect, the agent is an agonist or antagonist of the phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agent is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In yet another aspect, the agonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody. In still another aspect, the antagonist agent is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

The invention also provides a method of modulating a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already have the phenotype, or may be prone to have the phenotype or may be in whom the phenotype is to be prevented, an effective amount of an agent identified as modulating said phenotype, or agonists or antagonists thereof, thereby effectively modulating the phenotype.

The invention also provides a method of modulating a physiological characteristic associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already exhibit the physiological characteristic, or may be prone to exhibit the physiological characteristic or may be in whom the physiological characteristic is to be prevented, an effective amount of an agent identified as modulating said physiological characteristic, or agonists or antagonists thereof, thereby effectively modulating the physiological characteristic.

The invention also provides a method of modulating a behavior associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already exhibit the behavior, or may be prone to exhibit the behavior or may be in whom the exhibited behavior is to be prevented, an effective amount of an agent identified as modulating said behavior, or agonists or antagonists thereof, thereby effectively modulating the behavior.

The invention also provides a method of modulating the expression of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a host cell expressing said PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, an effective amount of an agent identified as modulating said expression, or agonists or antagonists thereof, thereby effectively modulating the expression of said polypeptide.

The invention also provides a method of modulating a condition associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may have the condition, or may be prone to have the condition or may be in whom the condition is to be prevented, a therapeutically effective amount of a therapeutic agent identified as modulating said condition, or agonists or antagonists thereof, thereby effectively modulating the condition.

The invention also provides a method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a non-human transgenic animal cell culture, each cell of said culture comprising a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, an effective amount of an agent identified as treating or preventing or ameliorating said disorder, or agonists or antagonists thereof, thereby effectively treating or preventing or ameliorating said disorder.

B. Further Embodiments

In yet further embodiments, the invention is directed to the following set of potential claims for this application:

1. A method of identifying a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal; and (c) comparing the measured physiological characteristic with that of a gender matched wild-type animal, wherein the physiological characteristic of the non-human transgenic animal that differs from the physiological characteristic of the wild-type animal is identified as a phenotype resulting from the gene disruption in the non-human transgenic animal.

2. The method of claim 1, wherein the non-human transgenic animal is heterozygous for the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

3. The method of claim 1, wherein the phenotype exhibited by the non-human transgenic animal as compared with gender matched wild-type littermates is at least one of the following: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

4. The method of claim 3, wherein the neurological disorder is an increased anxiety-like response during open field activity testing.

5. The method of claim 3, wherein the neurological disorder is a decreased anxiety-like response during open field activity testing.

6. The method of claim 3, wherein the neurological disorder is an abnormal circadian rhythm during home-cage activity testing.

7. The method of claim 3, wherein the neurological disorder is an enhanced motor coordination during inverted screen testing.

8. The method of claim 3, wherein the neurological disorder is an impaired motor coordination during inverted screen testing.

9. The method of claim 3, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

10. The method of claim 3, wherein the eye abnormality is a retinal abnormality.

11. The method of claim 3, wherein the eye abnormality is consistent with vision problems or blindness.

12. The method of claim 10, wherein the retinal abnormality is consistent with retinitis pigmentosa.

13. The method of claim 10, wherein the retinal abnormality is characterized by retinal degeneration or retinal dysplasia.

14. The method of claim 10, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

15. The method of claim 3, wherein the eye abnormality is a cataract.

16. The method of claim 15, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

17. The method of claim 3, wherein the developmental abnormality comprises embryonic lethality or reduced viability.

18. The method of claim 3, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

19. The method of claim 3, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

20. The method of claim 3, wherein the bone metabolic abnormality or disorder is arthritis, osteoporosis or osteopetrosis.

21. The method of claim 1, wherein the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing;

decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

22. An isolated cell derived from a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

23. The isolated cell of claim 22 which is a murine cell.

24. The isolated cell of claim 23, wherein the murine cell is an embryonic stem cell.

25. The isolated cell of claim 22, wherein the non-human transgenic animal exhibits at least one of the following phenotypes compared with gender matched wild-type littermates: a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

26. A method of identifying an agent that modulates a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a phenotype resulting from the gene disruption in the non-human transgenic animal;

(d) administering a test agent to the non-human transgenic animal of (a); and (e) determining whether the test agent modulates the identified phenotype associated with gene disruption in the non-human transgenic animal.

27. The method of claim 26, wherein the phenotype associated with the gene disruption comprises a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

28. The method of claim 27, wherein the neurological disorder is an increased anxiety-like response during open field activity testing.

29. The method of claim 27, wherein the neurological disorder is a decreased anxiety-like response during open field activity testing.

30. The method of claim 27, wherein the neurological disorder is an abnormal circadian rhythm during home-cage activity testing.

31. The method of claim 27, wherein the neurological disorder is an enhanced motor coordination during inverted screen testing.

32. The method of claim 27, wherein the neurological disorder is an impaired motor coordination during inverted screen testing.

33. The method of claim 27, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

34. The method of claim 27, wherein the eye abnormality is a retinal abnormality.

35. The method of claim 27, wherein the eye abnormality is consistent with vision problems or blindness.

36. The method of claim 34, wherein the retinal abnormality is consistent with retinitis pigmentosa.

37. The method of claim 34, wherein the retinal abnormality is characterized by retinal degeneration or retinal dysplasia.

38. The method of claim 34, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

39. The method of claim 27, wherein the eye abnormality is a cataract.

40. The method of claim 39, wherein the cataract is consistent with systemic diseases such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

41. The method of claim 27, wherein the developmental abnormality comprises embryonic lethality or reduced viability.

42. The method of claim 27, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

43. The method of claim 27, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation-associated diseases including graft rejection and graft-versus-host disease.

44. The method of claim 27, wherein said bone metabolic abnormality or disorder is arthritis, osteoporosis or osteopetrosis.

45. The method of claim 2, wherein the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing;

increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

46. An agent identified by the method of claim 26.

47. The agent of claim 46 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

48. The agent of claim 47, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

49. The agent of claim 47, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

50. A method of identifying an agent that modulates a physiological characteristic associated with a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic exhibited by the non-human transgenic animal of (a);

(c) comparing the measured physiological characteristic of (b) with that of a gender matched wild-type animal, wherein the physiological characteristic exhibited by the non-human transgenic animal that differs from the physiological characteristic exhibited by the wild-type animal is identified as a physiological characteristic associated with gene disruption;

(d) administering a test agent to the non-human transgenic animal of (a); and (e) determining whether the physiological characteristic associated with gene disruption is modulated.

51. The method of claim 50, wherein the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

52. An agent identified by the method of claim 50.

53. The agent of claim 52 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

54. The agent of claim 53, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

55. The agent of claim 53, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

56. A method of identifying an agent which modulates a behavior associated with a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) observing the behavior exhibited by the non-human transgenic animal of (a);

(c) comparing the observed behavior of (b) with that of a gender matched wild-type animal, wherein the observed behavior exhibited by the non-human transgenic animal that differs from the observed behavior exhibited by the wild-type animal is identified as a behavior associated with gene disruption;

(d) administering a test agent to the non-human transgenic animal of (a); and (e) determining whether the agent modulates the behavior associated with gene disruption.

57. The method of claim 56, wherein the behavior is an increased anxiety-like response during open field activity testing.

58. The method of claim 56, wherein the behavior is a decreased anxiety-like response during open field activity testing.

59. The method of claim 56, wherein the behavior is an abnormal circadian rhythm during home-cage activity testing.

60. The method of claim 56, wherein the behavior is an enhanced motor coordination during inverted screen testing.

61. The method of claim 56, wherein the behavior is an impaired motor coordination during inverted screen testing.

62. The method of claim 56, wherein the behavior is depression, generalized anxiety disorders, attention deficit disorder, sleep disorder, hyperactivity disorder, obsessive compulsive disorder, schizophrenia, cognitive disorders, hyperalgesia or sensory disorders.

63. An agent identified by the method of claim 56.

64. The agent of claim 63 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

65. The agent of claim 64, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

66. The agent of claim 64, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

67. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) administering a test agent to said non-human transgenic animal; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in the non-human transgenic animal.

68. The method of claim 67, wherein the neurological disorder is an increased anxiety-like response during open field activity testing.

69. The method of claim 67, wherein the neurological disorder is a decreased anxiety-like response during open field activity testing.

70. The method of claim 67, wherein the neurological disorder is an abnormal circadian rhythm during home-cage activity testing.

71. The method of claim 67, wherein the neurological disorder is an enhanced motor coordination during inverted screen testing.

72. The method of claim 67, wherein the neurological disorder is an impaired motor coordination during inverted screen testing.

73. The method of claim 73, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

74. The method of claim 67, wherein the eye abnormality is a retinal abnormality.

75. The method of claim 67, wherein the eye abnormality is consistent with vision problems or blindness.

76. The method of claim 74, wherein the retinal abnormality is consistent with retinitis pigmentosa.

77. The method of claim 74, wherein the retinal abnormality is characterized by retinal degeneration or retinal dysplasia.

78. The method of claim 74, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

79. The method of claim 67, wherein the eye abnormality is a cataract.

80. The method of claim 79, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

81. The method of claim 67, wherein the developmental abnormality comprises embryonic lethality or reduced viability.

82. The method of claim 67, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

83. The method of claim 67, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

84. The method of claim 67, wherein said bone metabolic abnormality or disorder is arthritis, osteoporosis or osteopetrosis.

85. The method of claim 67, wherein the non-human transgenic animal exhibits at least one of the following physiological characteristics compared with gender matched wild-type littermates: increased anxiety-like response during open field testing; decreased anxiety-like response during open field activity testing; hyperactivity during open field testing; hypoactivity during open field testing; increased exploratory activity during open-field testing; decreased exploratory activity during open-field testing; abnormal circadian rhythm during home-cage activity testing including decreased ambulatory counts; abnormal circadian rhythm during home-cage activity testing including increased ambulatory counts; increased habituation response to a novel environment; increased resistance to stress induced hyperthermia; impaired motor coordination during inverted screen testing; increased depressive-like response during tail suspension testing; decreased depressive-like response during tail suspension testing; decreased startle response during prepulse inhibition testing; enhanced sensor/motor gating/attention during prepulse inhibition testing; reduced latency to respond in hot plate testing; opthamological abnormalities; retinal depigmentation; cataracts; decreased heart rate; increased insulin sensitivity; increased mean fasting serum glucose levels; decreased mean serum glucose levels; increased mean serum cholesterol levels; increased mean serum triglyceride levels; decreased mean serum triglyceride levels; enhanced glucose tolerance; impaired glucose tolerance; decreased mean serum insulin levels; increased uric acid levels; decreased uric acid levels; decreased serum phosphate levels; increased serum phosphate levels; increased bilirubin levels; increased nitrituria; decreased mean serum albumin; liver disorders; decreased mean percentage of natural killer cells; increased mean percentage of CD4 cells; decreased mean percentage of CD4 cells; decreased mean percentage of CD8+ cells; decreased basophils; decreased lymphocytes; increased mean absolute monocyte count; macrocytic anemia; decreased red blood cell count, decreased hemoglobin and decreased hematocrit; increased mean platelet count; decreased mean serum IgG1 response to an ovalbumin challenge; increased mean serum IgG1 response to an ovalbumin challenge; decreased mean serum IgG2a response to an ovalbumin challenge; increased mean serum IgG2a response to an ovalbumin challenge; increased mean serum MCP-1 response to a LPS challenge; increased mean serum TNF-alpha response to a LPS challenge; increased mean serum IL-6 response to a LPS challenge; increased skin fibroblast proliferation; increased hemosiderin pigment in both spleen and bone marrow; increased mean percent of total body fat and total fat mass; increased mean body weight; increased total tissue mass (TTM); increased lean body mass (LBM); increased femoral bone mineral density (BMD); increased vertebral bone mineral density (BMD); increased BMC/LBM ratio; increased bone mineral density (BMD); increased bone mineral content (BMC); increased mean femoral midshaft cortical thickness and cross-sectional area; increased mean vertebral trabecular bone volume, number and connectivity density; decreased mean percent of total body fat and total fat mass; decreased mean body weight; decreased mean body length; decreased total tissue mass (TTM); decreased lean body mass (LBM); decreased femoral bone mineral density (BMD); decreased vertebral bone mineral density (BMD); decreased BMC/LBM ratio; decreased bone mineral density (BMD); decreased bone mineral content (BMC); decreased volumetric bone mineral density (vBMD); decreased mean femoral midshaft cortical thickness and cross-sectional area; decreased mean vertebral trabecular bone volume, number and connectivity density; osteodystrophy and metastatic calcification; decreased intra-abdominal fat; growth retardation; development abnormalities; multi focal acute and granulomatous inflammation; male infertility; female infertility; testicular degeneration; male hypogonadism; defective or arrested spermatogenesis; decreased testicular weight; inflammatory and degenerative myopathy; alterations in pancreatic acinar cells; enlarged kidneys; kidney disorders; muscle disorders; stunted growth with general reduction in all organ size; growth retardation with reduced viability; and embryonic lethality.

86. An agent identified by the method of claim 67.

87. The agent of claim 86 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

88. The agent of claim 87, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

89. The agent of claim 87, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

90. A therapeutic agent identified by the method of claim 67.

91. A method of identifying an agent that modulates the expression of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) contacting a test agent with a host cell expressing a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide; and (b) determining whether the test agent modulates the expression of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by the host cell.

92. An agent identified by the method of claim 91.

93. The agent of claim 92 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

94. The agent of claim 93, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

95. The agent of claim 93, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

96. A method of evaluating a therapeutic agent capable of affecting a condition associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal whose genome comprises a disruption of the gene which encodes for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) measuring a physiological characteristic of the non-human transgenic animal of (a);

(c) comparing the measured physiological characteristic of (b) with that of a gender matched wild-type animal, wherein the physiological characteristic of the non-human transgenic animal that differs from the physiological characteristic of the wild-type animal is identified as a condition resulting from the gene disruption in the non-human transgenic animal;

(d) administering a test agent to the non-human transgenic animal of (a); and (e) evaluating the effects of the test agent on the identified condition associated with gene disruption in the non-human transgenic animal.

97. The method of claim 96, wherein the condition is a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality.

98. A therapeutic agent identified by the method of claim 96.

99. The therapeutic agent of claim 98 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

100. The therapeutic agent of claim 99, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

101. The therapeutic agent of claim 99, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

102. A pharmaceutical composition comprising the therapeutic agent of claim 98.

103. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject in need of such treatment whom may already have the disorder, or may be prone to have the disorder or may be in whom the disorder is to be prevented, a therapeutically effective amount of the therapeutic agent of claim 94, or agonists or antagonists thereof, thereby effectively treating or preventing or ameliorating said disorder.

104. The method of claim 103, wherein the neurological disorder is an increased anxiety-like response during open field activity testing.

105. The method of claim 103, wherein the neurological disorder is a decreased anxiety-like response during open field activity testing.

106. The method of claim 103, wherein the neurological disorder is an abnormal circadian rhythm during home-cage activity testing.

107. The method of claim 103, wherein the neurological disorder is an enhanced motor coordination during inverted screen testing.

108. The method of claim 103, wherein the neurological disorder is an impaired motor coordination during inverted screen testing.

109. The method of claim 103, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

110. The method of claim 103, wherein the eye abnormality is a retinal abnormality.

111. The method of claim 103, wherein the eye abnormality is consistent with vision problems or blindness.

112. The method of claim 110, wherein the retinal abnormality is consistent with retinitis pigmentosa.

113. The method of claim 110, wherein the retinal abnormality is characterized by retinal degeneration or retinal dysplasia.

114. The method of claim 110, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

115. The method of claim 103, wherein the eye abnormality is a cataract.

116. The method of claim 115, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

117. The method of claim 103, wherein the developmental abnormality comprises embryonic lethality or reduced viability.

118. The method of claim 103, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

119. The method of claim 103, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

120. The method of claim 103, wherein said bone metabolic abnormality or disorder is arthritis, osteoporosis or osteopetrosis.

121. A method of identifying an agent that ameliorates or modulates a neurological disorder; a cardiovascular, endothelial or angiogenic disorder; an eye abnormality; an immunological disorder; an oncological disorder; a bone metabolic abnormality or disorder; a lipid metabolic disorder; or a developmental abnormality associated with a disruption in the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising:

(a) providing a non-human transgenic animal cell culture, each cell of said culture comprising a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide;

(b) administering a test agent to said cell culture; and (c) determining whether said test agent ameliorates or modulates the neurological disorder; cardiovascular, endothelial or angiogenic disorder; eye abnormality; immunological disorder; oncological disorder; bone metabolic abnormality or disorder; lipid metabolic disorder; or developmental abnormality in said cell culture.

122. The method of claim 121, wherein the neurological disorder is an increased anxiety-like response during open field activity testing.

123. The method of claim 121, wherein the neurological disorder is a decreased anxiety-like response during open field activity testing.

124. The method of claim 121, wherein the neurological disorder is an abnormal circadian rhythm during home-cage activity testing.

125. The method of claim 121, wherein the neurological disorder is an enhanced motor coordination during inverted screen testing.

126. The method of claim 121, wherein the neurological disorder is an impaired motor coordination during inverted screen testing.

127. The method of claim 121, wherein the neurological disorder is depression, generalized anxiety disorders, attention deficit disorder, sleep disorder, hyperactivity disorder, obsessive compulsive disorder, schizophrenia, cognitive disorders, hyperalgesia or sensory disorders.

128. The method of claim 121, wherein the eye abnormality is a retinal abnormality.

129. The method of claim 121, wherein the eye abnormality is consistent with vision problems or blindness.

130. The method of claim 128, wherein the retinal abnormality is consistent with retinitis pigmentosa.

131. The method of claim 128, wherein the retinal abnormality is characterized by retinal degeneration or retinal dysplasia.

132. The method of claim 128, wherein the retinal abnormality is consistent with retinal dysplasia, various retinopathies, including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

133. The method of claim 121, wherein the eye abnormality is a cataract.

134. The method of claim 133, wherein the cataract is a systemic disease such as human Down's syndrome, Hallerman-Streiff syndrome, Lowe syndrome, galactosemia, Marfan syndrome, Trismoy 13-15, Alport syndrome, myotonic dystrophy, Fabry disease, hypoparathroidism or Conradi syndrome.

135. The method of claim 121, wherein the developmental abnormality comprises embryonic lethality or reduced viability.

136. The method of claim 121, wherein the cardiovascular, endothelial or angiogenic disorders are arterial diseases, such as diabetes mellitus; papilledema; optic atrophy; atherosclerosis; angina; myocardial infarctions such as acute myocardial infarctions, cardiac hypertrophy, and heart failure such as congestive heart failure; hypertension; inflammatory vasculitides; Reynaud's disease and Reynaud's phenomenon; aneurysms and arterial restenosis; venous and lymphatic disorders such as thrombophlebitis, lymphangitis, and lymphedema; peripheral vascular disease; cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma; tumor angiogenesis; trauma such as wounds, burns, and other injured tissue, implant fixation, scarring; ischemia reperfusion injury; rheumatoid arthritis; cerebrovascular disease; renal diseases such as acute renal failure, or osteoporosis.

137. The method of claim 121, wherein the immunological disorders are systemic lupus erythematosis; rheumatoid arthritis; juvenile chronic arthritis; spondyloarthropathies; systemic sclerosis (scleroderma); idiopathic inflammatory myopathies (dermatomyositis, polymyositis); Sjögren's syndrome; systemic vasculitis; sarcoidosis; autoimmune hemolytic anemia (immune pancytopenia, paroxysmal nocturnal hemoglobinuria); autoimmune thrombocytopenia (idiopathic thrombocytopenic purpura, immune-mediated thrombocytopenia); thyroiditis (Grave's disease, Hashimoto's thyroiditis, juvenile lymphocytic thyroiditis, atrophic thyroiditis); diabetes mellitus; immune-mediated renal disease (glomerulonephritis, tubulointerstitial nephritis); demyelinating diseases of the central and peripheral nervous systems such as multiple sclerosis, idiopathic demyelinating polyneuropathy or Guillain-Barré syndrome, and chronic inflammatory demyelinating polyneuropathy; hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis; inflammatory bowel disease (ulcerative colitis: Crohn's disease); gluten-sensitive enteropathy, and Whipple's disease; autoimmune or immune-mediated skin diseases including bullous skin diseases, erythema multiforme and contact dermatitis, psoriasis; allergic diseases such as asthma, allergic rhinitis, atopic dermatitis, food hypersensitivity and urticaria; immunologic diseases of the lung such as eosinophilic pneumonia, idiopathic pulmonary fibrosis and hypersensitivity pneumonitis; or transplantation associated diseases including graft rejection and graft-versus-host disease.

138. The method of claim 121, wherein said bone metabolic abnormality or disorder is arthritis, osteoporosis or osteopetrosis.

139. An agent identified by the method of claim 121.

140. The agent of claim 139 which is an agonist or antagonist of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

141. The agent of claim 140, wherein the agonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

142. The agent of claim 140, wherein the antagonist is an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody.

143. A therapeutic agent identified by the method of claim 121.

144. A method of modulating a phenotype associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already have the phenotype, or may be prone to have the phenotype or may be in whom the phenotype is to be prevented, an effective amount of the agent of claim 46, or agonists or antagonists thereof, thereby effectively modulating the phenotype.

145. A method of modulating a physiological characteristic associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already exhibit the physiological characteristic, or may be prone to exhibit the physiological characteristic or may be in whom the physiological characteristic is to be prevented, an effective amount of the agent of claim 52, or agonists or antagonists thereof, thereby effectively modulating the physiological characteristic.

146. A method of modulating a behavior associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may already exhibit the behavior, or may be prone to exhibit the behavior or may be in whom the exhibited behavior is to be prevented, an effective amount of the agent of claim 63, or agonists or antagonists thereof, thereby effectively modulating the behavior.

147. A method of modulating the expression of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a host cell expressing said PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, an effective amount of the agent of claim 92, or agonists or antagonists thereof, thereby effectively modulating the expression of said polypeptide.

148. A method of modulating a condition associated with a disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a subject whom may have the condition, or may be prone to have the condition or may be in whom the condition is to be prevented, a therapeutically effective amount of the therapeutic agent of claim 98, or agonists or antagonists thereof, thereby effectively modulating the condition.

149. A method of treating or preventing or ameliorating a neurological disorder; cardiovascular, endothelial or angiogenic disorder; immunological disorder; oncological disorder; bone metabolic abnormality or disorder, or embryonic lethality associated with the disruption of a gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the method comprising administering to a non-human transgenic animal cell culture, each cell of said culture comprising a disruption of the gene which encodes for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, a therapeutically effective amount of the agent of claim 139, or agonists or antagonists thereof, thereby effectively treating or preventing or ameliorating said disorder.

BRIEF DESCRIPTION OF THE DRAWINGS

FIG. 1 shows a nucleotide sequence (SEQ ID NO:1) of a native sequence PRO194 cDNA, wherein SEQ ID NO:1 is a clone designated herein as “DNA26844-1394” (UNQ168).

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO220 cDNA, wherein SEQ ID NO:3 is a clone designated herein as “DNA32298-1132” (UNQ194).

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO241 cDNA, wherein SEQ ID NO:5 is a clone designated herein as “DNA34392-1170” (UNQ215).

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO284 cDNA, wherein SEQ ID NO:7 is a clone designated herein as “DNA23318-1211” (UNQ247).

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO331 cDNA, wherein SEQ ID NO:9 is a clone designated herein as “DNA40981-1234” (UNQ292).

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO354 cDNA, wherein SEQ ID NO:11 is a clone designated herein as “DNA44192-1246” (UNQ311).

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO355 cDNA, wherein SEQ ID NO:13 is a clone designated herein as “DNA39518-1247” (UNQ312).

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO533 cDNA, wherein SEQ ID NO:15 is a clone designated herein as “DNA49435-1219” (UNQ334).

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO541 cDNA, wherein SEQ ID NO:17 is a clone designated herein as “DNA45417-1432” (UNQ342).

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO725 cDNA, wherein SEQ ID NO:19 is a clone designated herein as “DNA52758-1399” (UNQ390).

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO937 cDNA, wherein SEQ ID NO:21 is a clone designated herein as “DNA56436-1448” (UNQ474).

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO1014 cDNA, wherein SEQ ID NO:23 is a clone designated herein as “DNA56409-1377” (UNQ497).

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO1120 cDNA, wherein SEQ ID NO:25 is a clone designated herein as “DNA48606-1479” (UNQ559).

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1182 cDNA, wherein SEQ ID NO:27 is a clone designated herein as “DNA59848-1512” (UNQ596).

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO1325 cDNA, wherein SEQ ID NO:29 is a clone designated herein as “DNA66659-1593” (UNQ685).

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1382 cDNA, wherein SEQ ID NO:31 is a clone designated herein as "DNA66526-1616" (UNQ718).

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1410 cDNA, wherein SEQ ID NO:33 is a clone designated herein as "DNA68874-1622" (UNQ728).

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1555 cDNA, wherein SEQ ID NO:35 is a clone designated herein as "DNA73744-1665" (UNQ763).

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO1556 cDNA, wherein SEQ ID NO:37 is a clone designated herein as "DNA76529-1666" (UNQ764).

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1760 cDNA, wherein SEQ ID NO:39 is a clone designated herein as "DNA76532-1702" (UNQ833).

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1787 cDNA, wherein SEQ ID NO:41 is a clone designated herein as "DNA76510-2504" (UNQ849).

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1868 cDNA, wherein SEQ ID NO:43 is a clone designated herein as "DNA77624-2515" (UNQ859).

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO4326 cDNA, wherein SEQ ID NO:45 is a clone designated herein as "DNA91779-2571" (UNQ1883).

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO4332 cDNA, wherein SEQ ID NO:47 is a clone designated herein as "DNA100272-2969" (UNQ1887).

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO4346 cDNA, wherein SEQ ID NO:49 is a clone designated herein as "DNA86594-2587" (UNQ1900).

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO4400 cDNA, wherein SEQ ID NO:51 is a clone designated herein as "DNA87974-2609" (UNQ1925).

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO6003 cDNA, wherein SEQ ID NO:53 is a clone designated herein as "DNA83568-2692" (UNQ2514).

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO6094 cDNA, wherein SEQ ID NO:55 is a clone designated herein as "DNA96995-2709" (UNQ2542).

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO6244 cDNA, wherein SEQ ID NO:57 is a clone designated herein as "DNA108743-2722" (UNQ2564).

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO9820 cDNA, wherein SEQ ID NO:59 is a clone designated herein as "DNA108769-2765" (UNQ3022).

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO9828 cDNA, wherein SEQ ID NO:61 is a clone designated herein as "DNA142238-2768" (UNQ3027).

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO10274 cDNA, wherein SEQ ID NO:63 is a clone designated herein as "DNA139686-2823" (UNQ3122).

FIG. 64 shows the amino acid sequence (SEQ ID NO:64) derived from the coding sequence of SEQ ID NO:63 shown in FIG. 63.

FIG. 65 shows a nucleotide sequence (SEQ ID NO: 65) of a native sequence PRO16090 cDNA, wherein SEQ ID NO:65 is a clone designated herein as "DNA144844-2843" (UNQ5783).

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO19644 cDNA, wherein SEQ ID NO:67 is a clone designated herein as "DNA139592-2866" (UNQ5825).

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO21340 cDNA, wherein SEQ ID NO:69 is a clone designated herein as "DNA176775-2957" (UNQ5982).

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO92165 cDNA, wherein SEQ ID NO:71 is a clone designated herein as "DNA340392" (UNQ17826).

FIG. 72 shows the amino acid sequence (SEQ ID NO:72) derived from the coding sequence of SEQ ID NO:71 shown in FIG. 71.

Figure 73:
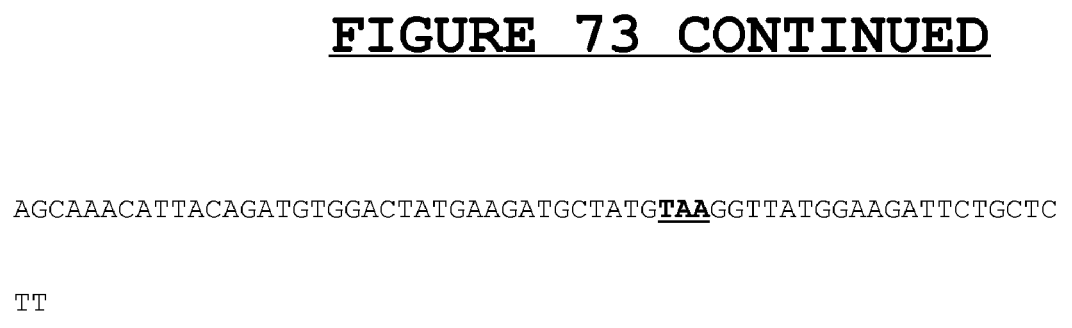

FIG. 73 shows a nucleotide sequence (SEQ ID NO:73) of a native sequence PRO85143 cDNA, wherein SEQ ID NO:73 is a clone designated herein as "DNA340394" (UNQ11831).

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO1124 cDNA, wherein SEQ ID NO:75 is a clone designated herein as "DNA60629-1481" (UNQ18919).

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO1026 cDNA, wherein SEQ ID NO:77 is a clone designated herein as "DNA59613-1417" (UNQ511).

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO23370 cDNA, wherein SEQ ID NO:79 is a clone designated herein as "DNA193963" (UNQ8344).

FIG. 80 shows the amino acid sequence (SEQ ID NO:80) derived from the coding sequence of SEQ ID NO:79 shown in FIG. 79.

DETAILED DESCRIPTION OF THE PREFERRED EMBODIMENTS

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide" comprises a polypeptide having the same amino acid sequence as the corresponding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide derived from nature. Such native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides can be isolated from nature or can be produced by recombinant or synthetic means. The term "native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide" specifically encompasses naturally-occurring truncated or secreted forms of the specific PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide (e.g., an extracellular domain sequence), naturally-occurring variant forms (e.g., alternatively spliced forms) and naturally-occurring allelic variants of the polypeptide. The invention provides native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides disclosed herein which are mature or full-length native sequence polypeptides comprising the full-length amino acids sequences shown in the accompanying figures. Start and stop codons are shown in bold font and underlined in the figures. However, while the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides.

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide "extracellular domain" or "ECD" refers to a form of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which is essentially free of the transmembrane and cytoplasmic domains. Ordinarily, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide ECD will have less than 1% of such transmembrane and/or cytoplasmic domains and preferably, will have less than 0.5% of such domains. It will be understood that any transmembrane domains identified for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

The approximate location of the "signal peptides" of the various PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., *Prot. Eng.* 10:1-6 (1997) and von Heinje et al., *Nucl. Acids. Res.* 14:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide variant" means a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, preferably an active PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, as defined herein having at least about 80% amino acid sequence identity with a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence lacking the signal peptide as disclosed herein, an extracellular domain of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, with or without the signal peptide, as disclosed herein or any other fragment of a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein (such as those encoded by a nucleic acid that represents only a portion of the complete coding sequence for a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide). Such PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide variants include, for instance, PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides wherein one or more amino acid residues are added, or deleted, at the N or C-terminus of the full-length native amino acid sequence. Ordinarily, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide variant will have or will have at least about 80% amino acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% amino acid sequence identity, to a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence lacking the signal peptide as disclosed herein, an extracellular domain of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, with or without the signal peptide, as disclosed herein or any other specifically defined fragment of a full-length PRO194, PRO220, PRO241, PRO284, PRO331, PRO354, PRO355, PRO533, PRO541, PRO725, PRO937, PRO1014, PRO1120, PRO182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein. Ordinarily, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polypeptides are or are at least about 10 amino acids in length, alternatively are or are at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polypeptides will have no more than one conservative amino acid substitution as compared to the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence, alternatively will have or will have no more than 2, 3, 4, 5, 6, 7, 8, 9, or 10 conservative amino acid substitution as compared to the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence.

"Percent (%) amino acid sequence identity" with respect to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequences identified herein is defined as the percentage of amino acid residues in a candidate sequence that are identical with the amino acid residues in the specific PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y" and "Z" each represent different hypothetical amino acid residues. Unless specifically stated otherwise, all % amino acid sequence identity values used herein are obtained as described in the immediately preceding paragraph using the ALIGN-2 computer program.

"PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polynucleotide" or "PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant nucleic acid sequence" means a nucleic acid molecule which encodes a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, preferably an active PRO194, PRO220, PRO241, PRO284, PRO331, PRO354, PRO355, PRO533, PRO541, PRO725, PRO937, PRO1014, PRO1120, PRO182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, as defined herein and which has at least about 80% nucleic acid sequence identity with a nucleotide acid sequence encoding a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein, a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence lacking the signal peptide as disclosed herein, an extracellular domain of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, with or without the signal peptide, as disclosed herein or any other fragment of a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein (such as those encoded by a nucleic acid that represents only a portion of the complete coding sequence for a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide). Ordinarily, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polynucleotide will have or will have at least about 80% nucleic acid sequence identity, alternatively will have or will have at least about 81%, 82%, 83%, 84%, 85%, 86%, 87%, 88%, 89%, 90%, 91%, 92%, 93%, 94%, 95%, 96%, 97%, 98%, or 99% nucleic acid sequence identity with a nucleic acid sequence encoding a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein, a full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence lacking the signal peptide as disclosed herein, an extracellular domain of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, with or without the signal sequence, as disclosed herein or any other fragment of a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide sequence as disclosed herein. Variants do not encompass the native nucleotide sequence.

Ordinarily, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polynucleotides are or are at least about 5 nucleotides in length, alternatively are or are at least about 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides in length, wherein in this context the term "about" means the referenced nucleotide sequence length plus or minus 10% of that referenced length.

"Percent (%) nucleic acid sequence identity" with respect to PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-encoding nucleic acid sequences identified herein is defined as the percentage of nucleotides in a candidate sequence that are identical with the nucleotides in the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction $W/Z$ where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides. Unless specifically stated otherwise, all % nucleic acid sequence identity values used herein are obtained as described in the immediately preceding paragraph using the ALIGN-2 computer program.

The invention also provides PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polynucleotides which are nucleic acid molecules that encode a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and which are capable of hybridizing, preferably under stringent hybridization and wash conditions, to nucleotide sequences encoding a full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as disclosed herein. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polypeptides may be those that are encoded by a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant polynucleotide.

The term "full-length coding region" when used in reference to a nucleic acid encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide refers to the sequence of nucleotides which encode the full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide of the invention (which is often shown between start and stop codons, inclusive thereof, in the accompanying figures). The term "full-length coding region" when used in reference to an ATCC deposited nucleic acid refers to the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding portion of the cDNA that is inserted into the vector deposited with the ATCC (which is often shown between start and stop codons, inclusive thereof, in the accompanying figures).

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. The invention provides that the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide natural environment will not be present. Ordinarily, however, isolated polypeptide will be prepared by at least one purification step.

An "isolated" PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" for the purposes herein refers to form(s) of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which retain a biological and/or an immunological activity of native or naturally-occurring PRO194, PRO220, PRO241, PRO284, PRO331, PRO354, PRO355, PRO533, PRO541, PRO725, PRO937, PRO1014, PRO120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, wherein "biological" activity refers to a biological function (either inhibitory or stimulatory) caused by a native or naturally-occurring PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide other than the ability to induce the production of an antibody against an antigenic epitope possessed by a native or naturally-occurring PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and an "immunological" activity refers to the ability to induce the production of an antibody against an antigenic epitope possessed by a native or naturally-occurring PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

The term "antagonist" is used in the broadest sense [unless otherwise qualified], and includes any molecule that partially or fully blocks, inhibits, or neutralizes a biological activity of a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide disclosed herein. In a similar manner, the term "agonist" is used in the broadest sense [unless otherwise qualified] and includes any molecule that mimics a biological activity of a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide disclosed herein. Suitable agonist or antagonist molecules specifically include agonist or antagonist antibodies or antibody fragments, fragments or amino acid sequence variants of native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides, peptides, antisense oligonucleotides, small organic molecules, etc. Methods for identifying agonists or antagonists of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may comprise contacting a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with a candidate agonist or antagonist molecule and measuring a detectable change in one or more biological activities normally associated with the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

"Treating" or "treatment" or "alleviation" refers to both therapeutic treatment and prophylactic or preventative measures, wherein the object is to prevent or slow down (lessen) the targeted pathologic condition or disorder. A subject in need of treatment may already have the disorder, or may be prone to have the disorder or may be in whom the disorder is to be prevented.

"Chronic" administration refers to administration of the agent(s) in a continuous mode as opposed to an acute mode, so as to maintain the initial therapeutic effect (activity) for an extended period of time. “Intermittent” administration is treatment that is not consecutively done without interruption, but rather is cyclic in nature.

“Mammal” for purposes of treatment refers to any animal classified as a mammal, including humans, rodents such as rats or mice, domestic and farm animals, and zoo, sports, or pet animals, such as dogs, cats, cattle, horses, sheep, pigs, goats, rabbits, etc. Preferably, the mammal is human.

Administration “in combination with” one or more further therapeutic agents includes simultaneous (concurrent) and consecutive administration in any order.

“Carriers” as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

By “solid phase” is meant anon-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. Depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A “liposome” is a small vesicle composed of various types of lipids, phospholipids and/or surfactant which is useful for delivery of a drug (such as a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or antibody thereto) to a mammal. The components of the liposome are commonly arranged in a bilayer formation, similar to the lipid arrangement of biological membranes.

A “small molecule” is defined herein to have a molecular weight below about 500 Daltons.

An “effective amount” of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule or an agonist or antagonist thereof as disclosed herein is an amount sufficient to carry out a specifically stated purpose. An “effective amount” may be determined empirically and in a routine manner, in relation to the stated purpose.

The term “therapeutically effective amount” refers to an amount of an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide, a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule or other drug effective to “treat” a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. See the definition herein of "treating". To the extent the drug may prevent growth and/or kill existing cancer cells, it may be cytostatic and/or cytotoxic.

The phrases "cardiovascular, endothelial and angiogenic disorder", "cardiovascular, endothelial and angiogenic dysfunction", "cardiovascular, endothelial or angiogenic disorder" and "cardiovascular, endothelial or angiogenic dysfunction" are used interchangeably and refer in part to systemic disorders that affect vessels, such as diabetes mellitus, as well as diseases of the vessels themselves, such as of the arteries, capillaries, veins, and/or lymphatics. This would include indications that stimulate angiogenesis and/or cardiovascularization, and those that inhibit angiogenesis and/or cardiovascularization. Such disorders include, for example, arterial disease, such as atherosclerosis, hypertension, inflammatory vasculitides, Reynaud's disease and Reynaud's phenomenon, aneurysms, and arterial restenosis; venous and lymphatic disorders such as thrombophlebitis, lymphangitis, and lymphedema; and other vascular disorders such as peripheral vascular disease, cancer such as vascular tumors, e.g., hemangioma (capillary and cavernous), glomus tumors, telangiectasia, bacillary angiomatosis, hemangioendothelioma, angiosarcoma, haemangiopericytoma, Kaposi's sarcoma, lymphangioma, and lymphangiosarcoma, tumor angiogenesis, trauma such as wounds, burns, and other injured tissue, implant fixation, scarring, ischemia reperfusion injury, rheumatoid arthritis, cerebrovascular disease, renal diseases such as acute renal failure, or osteoporosis. This would also include angina, myocardial infarctions such as acute myocardial infarctions, cardiac hypertrophy, and heart failure such as CHF.

"Hypertrophy", as used herein, is defined as an increase in mass of an organ or structure independent of natural growth that does not involve tumor formation. Hypertrophy of an organ or tissue is due either to an increase in the mass of the individual cells (true hypertrophy), or to an increase in the number of cells making up the tissue (hyperplasia), or both. Certain organs, such as the heart, lose the ability to divide shortly after birth. Accordingly, "cardiac hypertrophy" is defined as an increase in mass of the heart, which, in adults, is characterized by an increase in myocyte cell size and contractile protein content without concomitant cell division. The character of the stress responsible for inciting the hypertrophy, (e.g., increased preload, increased after load, loss of myocytes, as in myocardial infarction, or primary depression of contractility), appears to play a critical role in determining the nature of the response. The early stage of cardiac hypertrophy is usually characterized morphologically by increases in the size of myofibrils and mitochondria, as well as by enlargement of mitochondria and nuclei. At this stage, while muscle cells are larger than normal, cellular organization is largely preserved. At a more advanced stage of cardiac hypertrophy, there are preferential increases in the size or number of specific organelles, such as mitochondria, and new contractile elements are added in localized areas of the cells, in an irregular manner. Cells subjected to long-standing hypertrophy show more obvious disruptions in cellular organization, including markedly enlarged nuclei with highly lobulated membranes, which displace adjacent myofibrils and cause breakdown of normal Z-band registration. The phrase "cardiac hypertrophy" is used to include all stages of the progression of this condition, characterized by various degrees of structural damage of the heart muscle, regardless of the underlying cardiac disorder. Hence, the term also includes physiological conditions instrumental in the development of cardiac hypertrophy, such as elevated blood pressure, aortic stenosis, or myocardial infarction.

"Heart failure" refers to an abnormality of cardiac function where the heart does not pump blood at the rate needed for the requirements of metabolizing tissues. The heart failure can be caused by a number of factors, including ischemic, congenital, rheumatic, or idiopathic forms.

"Congestive heart failure" (CHF) is a progressive pathologic state where the heart is increasingly unable to supply adequate cardiac output (the volume of blood pumped by the heart over time) to deliver the oxygenated blood to peripheral tissues. As CHF progresses, structural and hemodynamic damages occur. While these damages have a variety of manifestations, one characteristic symptom is ventricular hypertrophy. CHF is a common end result of a number of various cardiac disorders.

"Myocardial infarction" generally results from atherosclerosis of the coronary arteries, often with superimposed coronary thrombosis. It may be divided into two major types: transmural infarcts, in which myocardial necrosis involves the full thickness of the ventricular wall, and subendocardial (nontransmural) infarcts, in which the necrosis involves the subendocardium, the intramural myocardium, or both, without extending all the way through the ventricular wall to the epicardium. Myocardial infarction is known to cause both a change in hemodynamic effects and an alteration in structure in the damaged and healthy zones of the heart. Thus, for example, myocardial infarction reduces the maximum cardiac output and the stroke volume of the heart. Also associated with myocardial infarction is a stimulation of the DNA synthesis occurring in the interstice as well as an increase in the formation of collagen in the areas of the heart not affected.

As a result of the increased stress or strain placed on the heart in prolonged hypertension due, for example, to the increased total peripheral resistance, cardiac hypertrophy has long been associated with "hypertension". A characteristic of the ventricle that becomes hypertrophic as a result of chronic pressure overload is an impaired diastolic performance. Fouad et al., *J. Am. Coll. Cardiol.,* 4: 1500-1506 (1984); Smith et al., *J. Am. Coll. Cardiol.,* 5: 869-874 (1985). A prolonged left ventricular relaxation has been detected in early essential hypertension, in spite of normal or supranormal systolic function. Hartford et al., *Hypertension,* 6: 329-338 (1984). However, there is no close parallelism between blood pressure levels and cardiac hypertrophy. Although improvement in left ventricular function in response to antihypertensive therapy has been reported in humans, patients variously treated with a diuretic (hydrochlorothiazide), a β-blocker (propranolol), or a calcium channel blocker (diltiazem), have shown reversal of left ventricular hypertrophy, without improvement in diastolic function. Inouye et al, *Am. J. Cardiol.,* 53: 1583-7 (1984).

Another complex cardiac disease associated with cardiac hypertrophy is "hypertrophic cardiomyopathy". This condition is characterized by a great diversity of morphologic, functional, and clinical features (Maron et al, *N. Engl. J. Med.,* 316: 780-789 (1987); Spirito et al, *N. Engl. J. Med.,* 320: 749-755 (1989); Louie and Edwards, *Prog. Cardiovasc. Dis.,* 36: 275-308 (1994); Wigle et al, *Circulation,* 92: 1680-1692 (1995)), the heterogeneity of which is accentuated by the fact that it afflicts patients of all ages. Spirito et al, *N. Engl. J. Med.,* 336: 775-785 (1997). The causative factors of hypertrophic cardiomyopathy are also diverse and little understood. In general, mutations in genes encoding sarcomeric proteins are associated with hypertrophic cardiomyopathy. Recent data suggest that β-myosin heavy chain mutations may account for approximately 30 to 40 percent of cases of familial hypertrophic cardiomyopathy. Watkins et al., *N. Engl. J. Med.,* 326: 1108-1114 (1992); Schwartz et al, *Circulation,* 91: 532-540 (1995); Marian and Roberts, *Circulation,* 92: 1336-1347 (1995); Thierfelder et al., *Cell,* 77: 701-712 (1994); Watkins et al, *Nat. Gen.,* 11: 434-437 (1995). Besides β-myosin heavy chain, other locations of genetic mutations include cardiac troponin T, alpha topomyosin, cardiac myosin binding protein C, essential myosin light chain, and regulatory myosin light chain. See, Malik and Watkins, *Curr. Opin. Cardiol.,* 12: 295-302 (1997).

Supravalvular "aortic stenosis" is an inherited vascular disorder characterized by narrowing of the ascending aorta, but other arteries, including the pulmonary arteries, may also be affected. Untreated aortic stenosis may lead to increased intracardiac pressure resulting in myocardial hypertrophy and eventually heart failure and death. The pathogenesis of this disorder is not fully understood, but hypertrophy and possibly hyperplasia of medial smooth muscle are prominent features of this disorder. It has been reported that molecular variants of the elastin gene are involved in the development and pathogenesis of aortic stenosis. U.S. Pat. No. 5,650,282 issued Jul. 22, 1997.

"Valvular regurgitation" occurs as a result of heart diseases resulting in disorders of the cardiac valves. Various diseases, like rheumatic fever, can cause the shrinking or pulling apart of the valve orifice, while other diseases may result in endocarditis, an inflammation of the endocardium or lining membrane of the atrioventricular orifices and operation of the heart. Defects such as the narrowing of the valve stenosis or the defective closing of the valve result in an accumulation of blood in the heart cavity or regurgitation of blood past the valve. If uncorrected, prolonged valvular stenosis or insufficiency may result in cardiac hypertrophy and associated damage to the heart muscle, which may eventually necessitate valve replacement.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, or transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases.

"Autoimmune disease" can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.). Preferred such diseases include autoimmune rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

Specific examples of other autoimmune diseases as defined herein, which in some cases encompass those listed above, include, but are not limited to, arthritis (acute and chronic, rheumatoid arthritis including juvenile-onset rheumatoid arthritis and stages such as rheumatoid synovitis, gout or gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, osteoarthritis, arthritis chronica progrediente, arthritis deformans, polyarthritis chronica primaria, reactive arthritis, menopausal arthritis, estrogen-depletion arthritis, and ankylosing spondylitis/rheumatoid spondylitis), autoimmune lymphoproliferative disease, inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, hives, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, gastrointestinal inflammation, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, graft-versus-host disease, angioedema such as hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN (RPGN), proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, food allergies, drug allergies, insect allergies, rare allergic disorders such as mastocytosis, allergic reaction, eczema including allergic or atopic eczema, asteatotic eczema, dyshidrotic eczema, and vesicular palmoplantar eczema, asthma such as asthma bronchiale, bronchial asthma, and auto-immune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, SLE, such as cutaneous SLE or subacute cutaneous SLE, neonatal lupus syndrome (NLE), and lupus erythematosus disseminatus, juvenile onset (Type I) diabetes mellitus, including pediatric IDDM, adult onset diabetes mellitus (Type II diabetes), autoimmune diabetes, idiopathic diabetes insipidus, diabetic retinopathy, diabetic nephropathy, diabetic colitis, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia(s), cytopenias such as pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, motoneuritis, allergic neuritis, Behcet's disease/syndrome, Castleman's syndrome, Goodpasture's syndrome, Reynaud's syndrome, Sjögren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, andpemphigus erythematosus), autoimmune polyendocrinopathies, Reiter's disease or syndrome, thermal injury due to an autoimmune condition, preeclampsia, an immune complex disorder such as immune complex nephritis, antibody-mediated nephritis, neuroinflammatory disorders, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia including, for example, idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes, for example, type I (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, pneumonitis such as lymphoid interstitial pneumonitis (LIP), bronchiolitis obliterans (non-transplant) vs NSIP, Guillain-Barré syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia such as mixed cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine opthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyl), and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, fibrosing mediastinitis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis (systemic inflammatory response syndrome (SIRS)), endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, conjunctivitis, such as vernal catarrh, keratoconjunctivitis sicca, and epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders (cerebral vascular insufficiency) such as arteriosclerotic encephalopathy and arteriosclerotic retinopathy, aspermiogenese, autoimmune hemolysis, Boeck's disease, cryoglobulinemia, Dupuytren's contracture, endophthalmia phacoanaphylactica, enteritis allergica, erythema nodo sum lepro sum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, lymphofollicular thymitis, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndromes, including polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, allergic sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, spondyloarthropathies, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism such as chronic arthrorheumatism, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

The phrase "anxiety related disorders" refers to disorders of anxiety, mood, and substance abuse, including but not limited to: depression, generalized anxiety disorders, attention deficit disorder, sleep disorder, hyperactivity disorder, obsessive compulsive disorder, schizophrenia, cognitive disorders, hyperalgesia and sensory disorders. Such disorders include the mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, social anxiety, autism, specific phobia, substance-induced anxiety disorder, acute alcohol withdrawal, obsessive compulsive disorder, agoraphobia, monopolar disorders, bipolar disorder I or II, bipolar disorder not otherwise specified, cyclothymic disorder, depressive disorder, major depressive disorder, mood disorder, substance-induced mood disorder, enhancement of cognitive function, loss of cognitive function associated with but not limited to Alzheimer's disease, stroke, or traumatic injury to the brain, seizures resulting from disease or injury including but not limited to epilepsy, learning disorders/disabilities, cerebral palsy. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

The term "lipid metabolic disorder" refers to abnormal clinical chemistry levels of cholesterol and triglycerides, wherein elevated levels of these lipids is an indication for atherosclerosis. Additionally, abnormal serum lipid levels may be an indication of various cardiovascular diseases including hypertension, stroke, coronary artery diseases, diabetes and/or obesity.

The phrase "eye abnormality" refers to such potential disorders of the eye as they may be related to atherosclerosis or various opthalmological abnormalities. Such disorders include but are not limited to the following: retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstrom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentiapigmenti, Batten's disease, mucopolysaccharidoses, homocystinuria, or mannosidosis. Cataracts are also considered an eye abnormality and are associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, or Conradi syndrome. Other ocular developmental anomalies include: Aniridia, anterior segment and dysgenesis syndrome. Cataracts may also occur as a result of an intraocular infection or inflammation (uveitis).

A "growth inhibitory amount" of an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule is an amount capable of inhibiting the growth of a cell, especially tumor, e.g., cancer cell, either in vitro or in vivo. A "growth inhibitory amount" of an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule for purposes of inhibiting neoplastic cell growth may be determined empirically and in a routine manner.

A "cytotoxic amount" of an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule is an amount capable of causing the destruction of a cell, especially tumor, e.g., cancer cell, either in vitro or in vivo. A "cytotoxic amount" of an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule for purposes of inhibiting neoplastic cell growth may be determined empirically and in a routine manner.

The term "antibody" is used in the broadest sense and specifically covers, for example, single anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody monoclonal antibodies (including agonist, antagonist, and neutralizing antibodies), anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody compositions with polyepitopic specificity, polyclonal antibodies, single chain anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies, and fragments of anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. The invention provides that the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ϵ isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology,* 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ϵ, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest,* 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H1$, $C_H2$ and $C_H3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large $F(ab')_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332: 323-329 (1988); and Presta, *Curr. Op. Struct. Biol.* 2:593-596 (1992).

A "species-dependent antibody," e.g., a mammalian anti-human IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1\times10^{-7}$ M, preferably no more than about $1\times10^{-8}$ and most preferably no more than about $1\times10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

A "PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptide" is an oligopeptide that binds, preferably specifically, to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as described herein. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptides may be chemically synthesized using known oligopeptide synthesis methodology or may be prepared and purified using recombinant technology. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptides usually are or are at least about 5 amino acids in length, alternatively are or are at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as described herein. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.,* 81:3998-4002 (1984); Geysen et al., *Proc. Natl. Acad. Sci. U.S.A.,* 82:178-182 (1985); Geysen et al., in *Synthetic Peptides as Antigens,* 130-149 (1986); Geysen et al., *J. Immunol. Meth.,* 102:259-274 (1987); Schoofs et al., *J. Immunol.,* 140:611-616 (1988), Cwirla, S. E. et al. (1990) *Proc. Natl. Acad. Sci. USA,* 87:6378; Lowman, H. B. et al. (1991) *Biochemistry,* 30:10832; Clackson, T. et al. (1991) *Nature,* 352: 624; Marks, J. D. et al. (1991), *J. Mol. Biol.,* 222:581; Kang, A. S. et al. (1991) *Proc. Natl. Acad. Sci. USA,* 88:8363, and Smith, G. P. (1991) *Current Opin. Biotechnol.,* 2:668).

A "PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecule" is an organic molecule other than an oligopeptide or antibody as defined herein that binds, preferably specifically, to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as described herein. PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecules may be identified and chemically synthesized using known methodology (see, e.g., PCT Publication Nos. WO00/00823 and WO00/39585). PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding organic molecules are usually less than about 2000 daltons in size, alternatively less than about 1500, 750, 500, 250 or 200 daltons in size, wherein such organic molecules that are capable of binding, preferably specifically, to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is preferably useful as a diagnostic and/or therapeutic agent in targeting a cell or tissue expressing the antigen, and does not significantly cross-react with other proteins. The extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. The term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits" the growth of tumor cells expressing a "PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370" or a "growth inhibitory" antibody, oligopeptide or other organic molecule is one which results in measurable growth inhibition of cancer cells expressing or overexpressing the appropriate PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be a transmembrane polypeptide expressed on the surface of a cancer cell or may be a polypeptide that is produced and secreted by a cancer cell. Preferred growth inhibitory anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies, oligopeptides or organic molecules inhibit growth of PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-expressing tumor cells by or by greater than 20%, preferably from about 20% to about 50%, and even more preferably, by or by greater than 50% (e.g., from about 50% to about 100%) as compared to the appropriate control, the control typically being tumor cells not treated with the antibody, oligopeptide or other organic molecule being tested. Growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO120, anti-PRO182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which over-expresses a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in or in about 2 to 50 fold, preferably in or in about 5 to 50 fold, and most preferably in or in about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif(ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia);

chronic lymphocytic leukemia (CLL); acute lymphoblastic leukemia (ALL); Hairy cell leukemia; chronic myeloblastic leukemia; and post-transplant lymphoproliferative disorder (PTLD). Preferably, the cancer comprises a tumor that expresses an IGF receptor, more preferably breast cancer, lung cancer, colorectal cancer, or prostate cancer, and most preferably breast or prostate cancer.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma II and calicheamicin omega II (see, e.g., *Agnew, Chem Intl. Ed. Engl.*, 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The terms "cell proliferative disorder" and "proliferative disorder" refer to disorders that are associated with some degree of abnormal cell proliferation. In one aspect of the invention, the cell proliferative disorder is cancer.

"Tumor", as used herein, refers to all neoplastic cell growth and proliferation, whether malignant or benign, and all pre-cancerous and cancerous cells and tissues.

An antibody, oligopeptide or other organic molecule which "induces cell death" is one which causes a viable cell to become nonviable. The cell is one which expresses a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, preferably a cell that overexpresses a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as compared to a normal cell of the same tissue type. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be a transmembrane polypeptide expressed on the surface of a cancer cell or may be a polypeptide that is produced and secreted by a cancer cell. Preferably, the cell is a cancer cell, e.g., a breast, ovarian, stomach, endometrial, salivary gland, lung, kidney, colon, thyroid, pancreatic or bladder cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated seru (i.e., in the absence of complement) and in the absence of immune effector cells. To determine whether the antibody, oligopeptide or other organic molecule is able to induce cell death, loss of membrane integrity as evaluated by uptake of propidium iodide (PI), trypan blue (see Moore et al. *Cytotechnology* 17:1-11 (1995)) or 7AAD can be assessed relative to untreated cells. Preferred cell death-inducing antibodies, oligopeptides or other organic molecules are those which induce PI uptake in the PI uptake assay in BT474 cells.

As used herein, the term “immunoadhesion” designates antibody-like molecules which combine the binding specificity of a heterologous protein (an “adhesion”) with the effector functions of immunoglobulin constant domains. Structurally, the immunoadhesions comprise a fusion of an amino acid sequence with the desired binding specificity which is other than the antigen recognition and binding site of an antibody (i.e., is “heterologous”), and an immunoglobulin constant domain sequence. The adhesion part of an immunoadhesion molecule typically is a contiguous amino acid sequence comprising at least the binding site of a receptor or a ligand. The immunoglobulin constant domain sequence in the immunoadhesion may be obtained from any immunoglobulin, such as IgG-1, IgG-2, IgG-3, or IgG-4 subtypes, IgA (including IgA-1 and IgA-2), IgE, IgD or IgM.

The word “label” when used herein refers to a detectable compound or composition which is conjugated directly or indirectly to the antibody so as to generate a “labeled” antibody. The label may be detectable by itself (e.g. radioisotope labels or fluorescent labels) or, in the case of an enzymatic label, may catalyze chemical alteration of a substrate compound or composition which is detectable.

“Replication-preventing agent” is an agent wherein replication, function, and/or growth of the cells is inhibited or prevented, or cells are destroyed, no matter what the mechanism, such as by apoptosis, angiostasis, cytosis, tumoricide, mytosis inhibition, blocking cell cycle progression, arresting cell growth, binding to tumors, acting as cellular mediators, etc. Such agents include a chemotherapeutic agent, cytotoxic agent, cytokine, growth-inhibitory agent, or anti-hormonal agent, e.g., an anti-estrogen compound such as tamoxifen, an anti-progesterone such as onapristone (see, EP 616 812); or an anti-androgen such as flutamide, as well as aromidase inhibitors, or a hormonal agent such as an androgen.

The term “cytotoxic agent” as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

Preferred cytotoxic agents herein for the specific tumor types to use in combination with the antagonists herein are as follows:

1. Prostate cancer: androgens, docetaxel, paclitaxel, estramustine, doxorubicin, mitoxantrone, antibodies to ErbB2 domain(s) such as 2C4 (WO 01/00245; hybridoma ATCC HB-12697), which binds to a region in the extracellular domain of ErbB2 (e.g., any one or more residues in the region from about residue 22 to about residue 584 of ErbB2, inclusive), AVASTIN™ anti-vascular endothelial growth factor (VEGF), TARCEVA™ OSI-774 (erlotinib) (Genenetech and OSI Pharmaceuticals), or other epidermal growth factor receptor tyrosine kinase inhibitors (EGFR TKI’s).
2. Stomach cancer: 5-fluorouracil (5FU), XELODA™ capecitabine, methotrexate, etoposide, cisplatin/carboplatin, paclitaxel, docetaxel, gemcitabine, doxorubicin, and CPT-11 (camptothcin-11; irinotecan, USA Brand Name: CAMPTOSAR®).
3. Pancreatic cancer: gemcitabine, 5FU, XELODA™ capecitabine, CPT-11, docetaxel, paclitaxel, cisplatin, carboplatin, TARCEVA™ erlotinib, and other EGFR TKI’s.
4. Colorectal cancer: 5FU, XELODA™ capecitabine, CPT-11, oxaliplatin, AVASTIN™ anti-VEGF, TARCEVA™ erlotinib and other EGFR TKI’s, and ERBITUX™ (formerly known as IMC-C225) human:murine-chimerized monoclonal antibody that binds to EGFR and blocks the ability of EGF to initiate receptor activation and signaling to the tumor.
5. Renal cancer: IL-2, interferon alpha, AVASTIN™ anti-VEGF, MEGACE™ (Megestrol acetate) progestin, vinblastine, TARCEVA™ erlotinib, and other EGFR TKI’s.

A “growth inhibitory agent” when used herein refers to a compound or composition which inhibits growth of a cell, especially a PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-expressing cancer cell, either in vitro or in vivo. Thus, the growth inhibitory agent may be one which significantly reduces the percentage of PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,1-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumornecrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "package insert" is used to refer to instructions customarily included in commercial packages of therapeutic products, that contain information about the indications, usage, dosage, administration, contraindications and/or warnings concerning the use of such therapeutic products.

The term "gene" refers to (a) a gene containing at least one of the DNA sequences disclosed herein; (b) any DNA sequence that encodes the amino acid sequence encoded by the DNA sequences disclosed herein and/or; (c) any DNA sequence that hybridizes to the complement of the coding sequences disclosed herein. Preferably, the term includes coding as well as noncoding regions, and preferably includes all sequences necessary for normal gene expression.

The term "gene targeting" refers to a type of homologous recombination that occurs when a fragment of genomic DNA is introduced into a mammalian cell and that fragment locates and recombines with endogenous homologous sequences. Gene targeting by homologous recombination employs recombinant DNA technologies to replace specific genomic sequences with exogenous DNA of particular design.

The term "homologous recombination" refers to the exchange of DNA fragments between two DNA molecules or chromatids at the site of homologous nucleotide sequences.

The term "target gene" (alternatively referred to as "target gene sequence" or "target DNA sequence") refers to any nucleic acid molecule, polynucleotide, or gene to be modified by homologous recombination. The target sequence includes an intact gene, an exon or intron, a regulatory sequence or any region between genes. The target gene my comprise a portion of a particular gene or genetic locus in the individual's genomic DNA.

"Disruption" of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene occurs when a fragment of genomic DNA locates and recombines with an endogenous homologous sequence wherein the disruption is a deletion of the native gene or a portion thereof, or a mutation in the native gene or wherein the disruption is the functional inactivation of the native gene. Alternatively, sequence disruptions may be generated by non-specific insertional inactivation using a gene trap vector (i.e. non-human transgenic animals containing and expressing a randomly inserted transgene; see for example U.S. Pat. No. 6,436,707 issued Aug. 20, 2002). These sequence disruptions or modifications may include insertions, missense, frameshift, deletion, or substitutions, or replacements of DNA sequence, or any combination thereof. Insertions include the insertion of entire genes, which may be of animal, plant, fungal, insect, prokaryotic, or viral origin. Disruption, for example, can alter the normal gene product by inhibiting its production partially or completely or by enhancing the normal gene product's activity. Preferably, the disruption is a null disruption, wherein there is no significant expression of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene. The term "native expression" refers to the expression of the full-length polypeptide encoded by the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene, at expression levels present in the wild-type mouse. Thus, a disruption in which there is "no native expression" of the endogenous PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene refers to a partial or complete reduction of the expression of at least a portion of a polypeptide encoded by an endogenous PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene of a single cell, selected cells, or all of the cells of a mammal.

The term "knockout" refers to the disruption of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene wherein the disruption results in: the functional inactivation of the native gene; the deletion of the native gene or a portion thereof; or a mutation in the native gene.

The term "knock-in" refers to the replacement of the mouse ortholog (or other mouse gene) with a human cDNA encoding any of the specific human PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-encoding genes or variants thereof (ie. the disruption results in a replacement of a native mouse gene with a native human gene).

The term "construct" or "targeting construct" refers to an artificially assembled DNA segment to be transferred into a target tissue, cell line or animal. Typically, the targeting construct will include a gene or a nucleic acid sequence of particular interest, a marker gene and appropriate control sequences. As provided herein, the targeting construct comprises a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 targeting construct. A "PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 targeting construct" includes a DNA sequence homologous to at least one portion of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene and is capable of producing a disruption in a PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene in a host cell.

The term "transgenic cell" refers to a cell containing within its genome a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene that has been disrupted, modified, altered, or replaced completely or partially by the method of gene targeting.

The term "transgenic animal" refers to an animal that contains within its genome a specific gene that has been disrupted or otherwise modified or mutated by the methods described herein or methods otherwise well known in the art. Preferably the non-human transgenic animal is a mammal. More preferably, the mammal is a rodent such as a rat or mouse. In addition, a "transgenic animal" may be a heterozygous animal (i.e., one defective allele and one wild-type allele) or a homozygous animal (i.e., two defective alleles). An embryo is considered to fall within the definition of an animal. The provision of an animal includes the provision of an embryo or foetus in utero, whether by mating or otherwise, and whether or not the embryo goes to term.

As used herein, the terms "selective marker" and "position selection marker" refer to a gene encoding a product that enables only the cells that carry the gene to survive and/or grow under certain conditions. For example, plant and animal cells that express the introduced neomycin resistance ($Neo^r$) gene are resistant to the compound G418. Cells that do not carry the $Neo^r$ gene marker are killed by G418. Other positive selection markers are known to, or are within the purview of, those of ordinary skill in the art.

The term "modulates" or "modulation" as used herein refers to the decrease, inhibition, reduction, amelioration, increase or enhancement of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene function, expression, activity, or alternatively a phenotype associated with PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene.

The term "ameliorates" or "amelioration" as used herein refers to a decrease, reduction or elimination of a condition, disease, disorder, or phenotype, including an abnormality or symptom.

The term "abnormality" refers to any disease, disorder, condition, or phenotype in which PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is implicated, including pathological conditions and behavioral observations.

TABLE 1

```
/*
 *
 * C-C increased from 12 to 15
 * Z is average of EQ
 * B is average of ND
 * match with stop is _M; stop-stop = 0; J (joker) match = 0
 */
#define    _M         -8        /* value of a match with a stop */
int        _day[26][26] = {
/*         A B C D E F G H I J K L M N O P Q R S T U V W X Y Z */
/* A */    { 2, 0,-2, 0, 0,-4, 1,-1,-1, 0,-1,-2,-1, 0,_M, 1, 0,-2, 1, 1, 0, 0,-6, 0,-3, 0},
/* B */    { 0, 3,-4, 3, 2,-5, 0, 1,-2, 0, 0,-3,-2, 2,_M,-1, 1, 0, 0, 0, 0,-2,-5, 0,-3, 1},
/* C */    {-2,-4,15,-5,-5,-4,-3,-3,-2, 0,-5,-6,-5,-4,_M,-3,-5,-4, 0,-2, 0,-2,-8, 0, 0,-5},
/* D */    { 0, 3,-5, 4, 3,-6, 1, 1,-2, 0, 0,-4,-3, 2,_M,-1, 2,-1, 0, 0, 0,-2,-7, 0,-4, 2},
/* E */    { 0, 2,-5, 3, 4,-5, 0, 1,-2, 0, 0,-3,-2, 1,_M,-1, 2,-1, 0, 0, 0,-2,-7, 0,-4, 3},
/* F */    {-4,-5,-4,-6,-5, 9,-5,-2, 1, 0,-5, 2, 0,-4,_M,-5,-5,-4,-3,-3, 0,-1, 0, 0, 7,-5},
/* G */    { 1, 0,-3, 1, 0,-5, 5,-2,-3, 0,-2,-4,-3, 0,_M,-1,-1,-3, 1, 0, 0,-1,-7, 0,-5, 0},
/* H */    {-1, 1,-3, 1, 1,-2,-2, 6,-2, 0, 0,-2,-2, 2,_M, 0, 3, 2,-1,-1, 0,-2,-3, 0, 0, 2},
/* I */    {-1,-2,-2,-2,-2, 1,-3,-2, 5, 0,-2, 2, 2,-2,_M,-2,-2,-2,-1, 0, 0, 4,-5, 0,-1,-2},
/* J */    { 0, 0, 0, 0, 0, 0, 0, 0, 0, 0, 0, 0, 0, 0,_M, 0, 0, 0, 0, 0, 0, 0, 0, 0, 0, 0},
/* K */    {-1, 0,-5, 0, 0,-5,-2, 0,-2, 0, 5,-3, 0, 1,_M,-1, 1, 3, 0, 0, 0,-2,-3, 0,-4, 0},
/* L */    {-2,-3,-6,-4,-3, 2,-4,-2, 2, 0,-3, 6, 4,-3,_M,-3,-2,-3,-3,-1, 0, 2,-2, 0,-1,-2},
/* M */    {-1,-2,-5,-3,-2, 0,-3,-2, 2, 0, 0, 4, 6,-2,_M,-2,-1, 0,-2,-1, 0, 2,-4, 0,-2,-1},
/* N */    { 0, 2,-4, 2, 1,-4, 0, 2,-2, 0, 1,-3,-2, 2,_M,-1, 1, 0, 1, 0, 0,-2,-4, 0,-2, 1},
/* O */    {_M,_M,_M,_M,_M,_M,_M,_M,_M,_M,_M,_M,_M,_M, 0,_M,_M,_M,_M,_M,_M,_M,_M,_M,_M,_M},
/* P */    { 1,-1,-3,-1,-1,-5,-1, 0,-2, 0,-1,-3,-2,-1,_M, 6, 0, 0, 1, 0, 0,-1,-6, 0,-5, 0},
/* Q */    { 0, 1,-5, 2, 2,-5,-1, 3,-2, 0, 1,-2,-1, 1,_M, 0, 4, 1,-1,-1, 0,-2,-5, 0,-4, 3},
/* R */    {-2, 0,-4,-1,-1,-4,-3, 2,-2, 0, 3,-3, 0, 0,_M, 0, 1, 6, 0,-1, 0,-2, 2, 0,-4, 0},
/* S */    { 1, 0, 0, 0, 0,-3, 1,-1,-1, 0, 0,-3,-2, 1,_M, 1,-1, 0, 2, 1, 0,-1,-2, 0,-3, 0},
/* T */    { 1, 0,-2, 0, 0,-3, 0,-1, 0, 0, 0,-1,-1, 0,_M, 0,-1,-1, 1, 3, 0, 0,-5, 0,-3, 0},
/* U */    { 0, 0, 0, 0, 0, 0, 0, 0, 0, 0, 0, 0, 0, 0,_M, 0, 0, 0, 0, 0, 0, 0, 0, 0, 0, 0},
/* V */    { 0,-2,-2,-2,-2,-1,-1,-2, 4, 0,-2, 2, 2,-2,_M,-1,-2,-2,-1, 0, 0, 4,-6, 0,-2,-2},
/* W */    {-6,-5,-8,-7,-7, 0,-7,-3,-5, 0,-3,-2,-4,-4,_M,-6,-5, 2,-2,-5, 0,-6,17, 0, 0,-6},
/* X */    { 0, 0, 0, 0, 0, 0, 0, 0, 0, 0, 0, 0, 0, 0,_M, 0, 0, 0, 0, 0, 0, 0, 0, 0, 0, 0},
/* Y */    {-3,-3, 0,-4,-4, 7,-5, 0,-1, 0,-4,-1,-2,-2,_M,-5,-4,-4,-3,-3, 0,-2, 0, 0,10,-4},
/* Z */    { 0, 1,-5, 2, 3,-5, 0, 2,-2, 0, 0,-2,-1, 1,_M, 0, 3, 0, 0, 0, 0,-2,-6, 0,-4, 4}
};
 /*
 */
#include <stdio.h>
#include <ctype.h>
#define    MAXJMP     16       /* max jumps in a diag */
#define    MAXGAP     24       /* don't continue to penalize gaps larger than this */
#define    JMPS       1024     /* max jmps in an path */
#define    MX         4        /* save if there's at least MX-1 bases since last jmp */
#define    DMAT       3        /* value of matching bases */
#define    DMIS       0        /* penalty for mismatched bases */
#define    DINS0      8        /* penalty for a gap */
#define    DINS1      1        /* penalty per base */
#define    PINS0      8        /* penalty for a gap */
#define    PINS1      4        /* penalty per residue */
struct jmp {
           short              n[MAXJMP];       /* size of jmp (neg for dely) */
           unsigned short     x[MAXJMP];       /* base no. of jmp in seq x */
};                                             /* limits seq to 2^16 -1 */
struct diag {
           int                score;           /* score at last jmp */
           long               offset;          /* offset of prev block */
           short              ijmp;            /* current jmp index */
           struct jmp         jp;              /* list of jmps */
};
struct path {
           int        spc;                     /* number of leading spaces */
           short      n[JMPS];/* size of jmp (gap) */
           int        x[JMPS];/* loc of jmp (last elem before gap) */
};
char                  *ofile;                  /* output file name */
```

TABLE 1-continued

```
char            *namex[2];              /* seq names: getseqs( ) */
char            *prog;                  /* prog name for err msgs */
char            *seqx[2];               /* seqs: getseqs( ) */
int             dmax;                   /* best diag: nw( ) */
int             dmax0;                  /* final diag */
int             dna;                    /* set if dna: main( ) */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw( ) */
int             *xbm;                   /* bitmap for matching */
long            offset;                 /* current offset in jmp file */
struct  diag    *dx;                    /* holds diagonals */
struct  path    pp[2];                  /* holds path for seqs */
char            *calloc( ), *malloc( ), *index( ), *strcpy( );
char            *getseq( ), *g_calloc( );
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
#include "nw.h"
#include "day.h"
static  _dbval[26] = {
        1,14,2,13,0,0,4,11,0,0,12,0,3,15,0,0,0,5,6,8,8,7,9,0,10,0
};
static  _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
};
main(ac, av)                                                            main
        int     ac;
        char    *av[ ];
{
        prog = av[0];
        if (ac != 3) {
                fprintf(stderr,"usage: %s file1 file2\n", prog);
                fprintf(stderr,"where file1 and file2 are two dna or two protein sequences.\n");
                fprintf(stderr,"The sequences can be in upper- or lower-case\n");
                fprintf(stderr,"Any lines beginning with ';' or '<' are ignored\n");
                fprintf(stderr,"Output is in the file \"align.out\"\n");
                exit(1);
        }
        namex[0] = av[1];
        namex[1] = av[2];
        seqx[0] = getseq(namex[0], &len0);
        seqx[1] = getseq(namex[1], &len1);
        xbm = (dna)? _dbval : _pbval;
        endgaps = 0;                    /* 1 to penalize endgaps */
        ofile = "align.out";            /* output file */
        nw( );                  /* fill in the matrix, get the possible jmps */
        readjmps( );            /* get the actual jmps */
        print( );               /* print stats, alignment */
        cleanup(0);             /* unlink any tmp files */}
/* do the alignment, return best score: main( )
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw( )                                                                   nw
{
        char    *px, *py;               /* seqs and ptrs */
        int     *ndely, *dely;          /* keep track of dely */
        int     ndelx, delx;            /* keep track of delx */
        int     *tmp;                   /* for swapping row0, row1 */
        int     mis;                    /* score for each type */
        int     ins0, ins1;             /* insertion penalties */
```

TABLE 1-continued

```
register    id;                         /* diagonal index */
register    ij;                         /* jmp index */
register    *col0, *col1;               /* score for curr, last row */
register    xx, yy;                     /* index into seqs */
dx = (struct diag *)g_calloc("to get diags", len0+len1+1, sizeof(struct diag));
ndely = (int *)g_calloc("to get ndely", len1+1, sizeof(int));
dely = (int *)g_calloc("to get dely", len1+1, sizeof(int));
col0 = (int *)g_calloc("to get col0", len1+1, sizeof(int));
col1 = (int *)g_calloc("to get col1", len1+1, sizeof(int));
ins0 = (dna)? DINS0 : PINS0;
ins1 = (dna)? DINS1 : PINS1;
smax = -10000;
if (endgaps) {
        for (col0[0] = dely[0] = -ins0, yy = 1; yy <= len1; yy++) {
                col0[yy] = dely[yy] = col0[yy-1] - ins1;
                ndely[yy] = yy;
        }
        col0[0] = 0;        /* Waterman Bull Math Biol 84 */
}
else
        for (yy = 1; yy <= len1; yy++)
                dely[yy] = -ins0;
/* fill in match matrix
 */
for (px = seqx[0], xx = 1; xx <= len0; px++, xx++) {
        /* initialize first entry in col
         */
        if (endgaps) {
                if (xx == 1)
                        col1[0] = delx = -(ins0+ins1);
                else
                        col1[0] = delx = col0[0] - ins1;
                ndelx = xx;
        }
        else {
                col1[0] = 0;
                delx = -ins0;
                ndelx = 0;
        }
                                                                        ...nw
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];
        /* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }
        /* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
```

TABLE 1-continued

```
                        } else
                                ndelx++;
                }
                /* pick the maximum score; we're favoring
                 * mis over any del and delx over dely
                 */
                                                                                                                          ...nw
                id = xx - yy + len1 - 1;
                if (mis >= delx && mis >= dely[yy])
                        col1[yy] = mis;
                        else if (delx >= dely[yy]) {
                                col1[yy] = delx;
                                ij = dx[id].ijmp;
                                if (dx[id].jp.n[0] && (!dna || (ndelx >= MAXJMP
                                && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                col1[yy] = dely[yy];
                                ij = dx[id].ijmp;
        if (dx[id].jp.n[0] && (!dna || (ndely[yy] >= MAXJMP
                                && xx > dx[id].jp.x[ij]+MX) || mis > dx[id].score+DINS0)) {
                                        dx[id].ijmp++;
                                                if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < len1) {
                                /* last col
                                 */
                                if (endgaps)
                                        col1[yy] -= ins0+ins1*(len1-yy);
                                if (col1[yy] > smax) {
                                        smax = col1[yy];
                                        dmax = id;
                                }
                        }
                }
                if (endgaps && xx < len0)
                        col1[yy-1] -= ins0+ins1*(len0-xx);
                if (col1[yy-1] > smax) {
                        smax = col1[yy-1];
                        dmax = id;
                }
                tmp = col0; col0 = col1; col1 = tmp;                    }
        (void) free((char *)ndely);
        (void) free((char *)dely);
        (void) free((char *)col0);
        (void) free((char *)col1);                              }
/*
 *
 * print( ) -- only routine visible outside this module
 *
 * static:
 * getmat( ) -- trace back best path, count matches: print( )
 * pr_align( ) -- print alignment of described in array p[ ]: print( )
 * dumpblock( ) -- dump a block of lines with numbers, stars: pr_align( )
 * nums( ) -- put out a number line: dumpblock( )
 * putline( ) -- put out a line (name, [num], seq, [num]): dumpblock( )
 * stars( ) - -put a line of stars: dumpblock( )
 * stripname( ) -- strip any path and prefix from a seqname
 */
#include "nw.h"
```

TABLE 1-continued

```
#define SPC        3
#define P_LINE     256        /* maximum output line */
#define P_SPC      3          /* space between name or num and seq */
extern     _day[26][26];
int        olen;              /* set output line length */
FILE       *fx;               /* output file */
print( )                                                                print
{
           int        lx, ly, firstgap, lastgap;        /* overlap */
           if ((fx = fopen(ofile, "w")) == 0) {
                      fprintf(stderr,"%s: can't write %s\n", prog, ofile);
                      cleanup(1);
           }
           fprintf(fx, "<first sequence: %s (length = %d)\n", namex[0], len0);
           fprintf(fx, "<second sequence: %s (length = %d)\n", namex[1], len1);
           olen = 60;
           lx = len0;
           ly = len1;
           firstgap = lastgap = 0;
           if (dmax < len1 - 1) {          /* leading gap in x */
                      pp[0].spc = firstgap = len1 - dmax - 1;
                      ly -= pp[0].spc;
           }
           else if (dmax > len1 - 1) {     /* leading gap in y */
                      pp[1].spc = firstgap = dmax - (len1 - 1);
                      lx -= pp[1].spc;
           }
           if (dmax0 < len0 - 1) {         /* trailing gap in x */
                      lastgap = len0 - dmax0 -1;
                      lx -= lastgap;
           }
           else if (dmax0 > len0 - 1) {  /* trailing gap in y */
                      lastgap = dmax0 - (len0 - 1);
                      ly -= lastgap;
           }
           getmat(lx, ly, firstgap, lastgap);
           pr_align( );       }
/*
 * trace back the best path, count matches
 */
static
getmat(lx, ly, firstgap, lastgap)                                       getmat
           int        lx, ly;                 /* "core" (minus endgaps) */
           int        firstgap, lastgap;      /* leading trailing overlap */
{
           int                   nm, i0, i1, siz0, siz1;
           char                  outx[32];
           double                pct;
           register              n0, n1;
           register char         *p0, *p1;
           /* get total matches, score
            */
           i0 = i1 = siz0 = siz1 = 0;
           p0 = seqx[0] + pp[1].spc;
           p1 = seqx[1] + pp[0].spc;
           n0 = pp[1].spc + 1;
           n1 = pp[0].spc + 1;
           nm = 0;
           while ( *p0 && *p1 ) {
                      if (siz0) {
                                 p1++;
                                 n1++;
                                 siz0--;
                      }
                      else if (siz1) {
                                 p0++;
                                 n0++;
                                 siz1--;
                      }
                      else {
                                 if (xbm[*p0-'A']&xbm[*p1-'A'])
                                            nm++;
                                 if (n0++ == pp[0].x[i0])
                                            siz0 = pp[0].n[i0++];
                                 if (n1++ == pp[1].x[i1])
                                            siz1 = pp[1].n[i]++];
                                 p0++;
                                 p1++;
                      }
           }
```

```
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                    ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
 * print alignment of described in struct path pp[ ]
 */
static
pr_align( )                                                                  pr_align
{
        int             nn;     /* char count */
        int             more;
        register        I;
        for (I = 0, lmax = 0; I < 2; I++) {
                nn = stripname(namex[i]);
                if (nn > lmax)
                        lmax = nn;
                nc[i] = 1;
                ni[i] = 1;
                siz[i] = ij[i] = 0;
                ps[i] = seqx[i];
                po[i] = out[i];                 }
        for (nn = nm = 0, more = 1; more; ) {                                ...pr_align
                for (I = more = 0; I < 2; I++) {
                        /*
                         * do we have more of this sequence?
                         */
                        if (!*ps[i])
                                continue;
                        more++;
                        if (pp[i].spc) {        /* leading space */
                                *po[i]++ = ' ';
                                pp[i].spc--;
                        }
                        else if (siz[i]) {      /* in a gap */
```

TABLE 1-continued

```
*po[i]++ = '-';
siz[i]--;
}
else {          /* we're putting a seq element
                 */
    *po[i] = *ps[i];
    if (islower(*ps[i]))
        *ps[i] = toupper(*ps[i]);
    po[i]++;
    ps[i]++;
    /*
     * are we at next gap for this seq?
     */
    if (ni[i] == pp[i].x[ij[i]]) {
        /*
         * we need to merge all gaps
         * at this location
         */
        siz[i] = pp[i].n[ij[i]++];
        while (ni[i] == pp[i].x[ij[i]])
            siz[i] += pp[i].n[ij[i]++];
    }
    ni[i]++;
}
}
if (++nn == olen || !more && nn) {
    dumpblock( );
    for (I = 0; I < 2; I++)
        po[i] = out[i];
    nn = 0;
}
}
}
/*
 * dump a block of lines, including numbers, stars: pr_align( )
 */
static
dumpblock( )                                            dumpblock
{
    register I;
    for (I = 0; I < 2; I++)
        *po[i]-- = '\0';
                                                        ...dumpblock
    (void) putc('\n', fx);
    for (I = 0; I < 2; I++) {
        if (*out[j] && (*out[i] != ' ' || *(po[i]) != ' ')) {
            if (I == 0)
                nums(I);
            if (I == 0 && *out[1])
                stars( );
            putline(I);
            if (I == 0 && *out[1])
                fprintf(fx, star);
            if (I == 1)
                nums(I);
        }
    }
}
/*
 * put out a number line: dumpblock( )
 */
static
nums(ix)                                                nums
    int     ix;     /* index in out[ ] holding seq line */
{
    char            nline[P_LINE];
    register        I, j;
    register char   *pn, *px, *py;
    for (pn = nline, I = 0; I < lmax+P_SPC; I++, pn++)
        *pn = ' ';
    for (I = nc[ix], py = out[ix]; *py; py++, pn++) {
        if (*py == ' ' || *py == '-')
            *pn = ' ';
        else {
            if (I%10 == 0 || (I == 1 && nc[ix] != 1)) {
                j = (I < 0)? -I : I;
                for (px = pn; j; j /= 10, px--)
                    *px = j%10 + '0';
                if (I < 0)
                    *px = '-';
```

TABLE 1-continued

```
                    }
                    else
                              *pn = ' ';
                    I++;
          }
     }
     *pn = '\0';
     nc[ix] = I;
     for (pn = nline; *pn; pn++)
          (void) putc(*pn, fx);
     (void) putc('\n', fx);
}
/*
 * put out a line (name, [num], seq, [num]): dumpblock( )
 */
static
putline(ix)                                                                    putline
     int       ix;                 {
                                                                            ...putline
     int                 I;
     register char       *px;
     for (px = namex[ix], I = 0; *px && *px != ':'; px++, I++)
          (void) putc(*px, fx);
     for (; I < lmax+P_SPC; I++)
          (void) putc(' ', fx);
     /* these count from 1:
      * ni[ ] is current element (from 1)
      * nc[ ] is number at start of current line
      */
     for (px = out[ix]; *px; px++)
          (void) putc(*px&0x7F, fx);
     (void) putc('\n', fx);
}
/*
 * put a line of stars (seqs always in out[0], out[1]): dumpblock( )
 */
static
stars( )                                                                         stars
{
     int                 I;
     register char       *p0, *p1, cx, *px;
     if (!*out[0] || (*out[0] == ' ' && *(po[0]) == ' ') ||
          !*out[1] || (*out[1] == ' ' && *(po[1]) == ' '))
          return;
     px = star;
     for (I = lmax+P_SPC; I; I--)
          *px++ = ' ';
     for (p0 = out[0], p1 = out[1]; *p0 && *p1; p0++, p1++) {
          if (isalpha(*p0) && isalpha(*p1)) {
               if (xbm[*p0-'A']&xbm[*p1-'A']) {
                    cx = '*';
                    nm++;
               }
               else if (!dna && _day[*p0-'A'][*p1-'A'] > 0)
                    cx = '.';
               else
                    cx = ' ';
          }
          else
               cx = ' ';
          *px++ = cx;
     }
     *px++ = '\n';
     *px = '\0';
}
/*
 * strip path or prefix from pn, return len: pr_align( )
 */
static
stripname(pn)                                                               stripname
     char      *pn;      /* file name (may be path) */
{
     register char       *px, *py;
     py = 0;
     for (px = pn; *px; px++)
          if (*px == '/')
               py = px + 1;
     if (py)
          (void) strcpy(pn, py);
     return(strlen(pn));
```

TABLE 1-continued

```
}
/*
 * cleanup( ) -- cleanup any tmp file
 * getseq( ) -- read in seq, set dna, len, maxlen
 * g_calloc( ) -- calloc( ) with error checkin
 * readjmps( ) -- get the good jmps, from tmp file if necessary
 * writejmps( ) -- write a filled array of jmps to a tmp file: nw( )
 */
#include “nw.h”
#include <sys/file.h>
char    *jname = “/tmp/homgXXXXXX”;          /* tmp file for jmps */
FILE    *fj;
int     cleanup( );                          /* cleanup tmp file */
long    lseek( );
/*
 * remove any tmp file if we blow
 */
cleanup(I)                                                          cleanup
        int     I;
{
        if (fj)
                (void) unlink(jname);
        exit(I);
}
/*
 * read, return.ptr to seq, set dna, len, maxlen
 * skip lines starting with ‘;’, ‘<’, or ‘>’
 * seq in upper or lower case
 */
char    *
getseq(file, len)                                                   getseq
        char    *file;  /* file name */
        int     *len;   /* seq len */
{
        char            line[1024], *pseq;
        register char   *px, *py;
        int             natgc, tlen;
        FILE            *fp;
        if ((fp = fopen(file,“r”)) == 0) {
                fprintf(stderr,“%s: can’t read %s\n”, prog, file);
                exit(1);
        }
        tlen = natgc = 0;
        while (fgets(line, 1024, fp)) {
                if (*line == ‘;’ || *line == ‘<’ || *line == ‘>’)
                        continue;
                for (px = line; *px != ‘\n’; px++)
                        if (isupper(*px) || islower(*px))
                                tlen++;
        }
        if ((pseq = malloc((unsigned)(tlen+6))) == 0) {
                fprintf(stderr,“%s: malloc( ) failed to get %d bytes for %s\n”, prog, tlen+6, file);
                exit(1);
        }
        pseq[0] = pseq[1] = pseq[2] = pseq[3] = ‘\0’;
                                                                    ...getseq
        py = pseq + 4;
        *len = tlen;
        rewind(fp);
        while (fgets(line, 1024, fp)) {
                if (*line == ‘;’ || *line == ‘<’ || *line == ‘>’)
                        continue;
                for (px = line; *px != ‘\n’; px++) {
                        if (isupper(*px))
                                *py++ = *px;
                        else if (islower(*px))
                                *py++ = toupper(*px);
                        if (index(“ATGCU”,*(py−1)))
                                natgc++;
                }
        }
        *py++ = ‘\0’;
        *py = ‘\0’;
        (void) fclose(fp);
        dna = natgc > (tlen/3);
        return(pseq+4);
}
char    *
g_calloc(msg, nx, sz)                                               g_calloc
        char    *msg;           /* program, calling routine */
```

TABLE 1-continued

```
        int     nx, sz;             /* number and size of elements */
{
        char            *px, *calloc( );
        if ((px = calloc((unsigned)nx, (unsigned)sz)) == 0) {
                if (*msg) {
                        fprintf(stderr, "%s: g_calloc( ) failed %s (n= %d, sz= %d)\n", prog, msg, nx, sz);
                        exit(1);
                }
        }
        return(px);
}
/*
 * get final jmps from dx[ ] or tmp file, set pp[ ], reset dmax: main( )
 */
readjmps( )                                                                     readjmps
{
        int             fd = -1;
        int             siz, i0, i1;
        register  I, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (I = i0 = i1 = 0, dmax0 = dmax, xx = len0; ; I++) {
                while (1) {
                        for (j = dx[dmax].ijmp; j >= 0 && dx[dmax].jp.x[j] >= xx; j--)
                                ;
                                                                                ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset, sizeof(dx[dmax].offset));
                                dx[dmax].ijmp = MAXJMP-1; }
                        else
                                break;          }
                if (I >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {          /* gap in second seq */
                                pp[1].n[i1] = -siz;
                                xx += siz;
                                /* id = xx - yy + len1 - 1                      */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) { /* gap in first seq */
                                pp[0].n[i0] = siz;
                                pp[0].x[i0] = xx;
                                gapx++;
                                ngapx += siz;
/* ignore MAXGAP when doing endgaps */
                                siz = (siz < MAXGAP || endgaps)? siz : MAXGAP;
                                i0++;
                        }
                }
                else
                        break;
        }
        /* reverse the order of jmps */
        for (j = 0, i0--; j < i0; j++, i0--) {
                I = pp[0].n[j]; pp[0].n[j] = pp[0].n[i0]; pp[0].n[i0] = I;
                I = pp[0].x[j]; pp[0].x[j] = pp[0].x[i0]; pp[0].x[i0] = I;
        }
        for (j = 0, i1--; j < i1; j++, i1--) {
                I = pp[1].n[j]; pp[1].n[j] = pp[1].n[i1]; pp[1].n[i1] = I;
                I = pp[1].x[j]; pp[1].x[j] = pp[1].x[i1]; pp[1].x[i1] = I;
        }
        if (fd >= 0)
```

TABLE 1-continued

```
                (void) close(fd);
        if (fj) {
                (void) unlink(jname);
                fj = 0;
                offset = 0;
        }                                   }
/*
 * write a filled jmp struct offset of the prev one (if any): nw( )
 */
writejmps(ix)                                                                   writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptides The present invention provides newly identified and isolated nucleotide sequences encoding polypeptides referred to in the present application as PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. In particular, cDNAs encoding various PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides and encoding nucleic acids described herein, Applicants have identified what is believed to be the reading frame best identifiable with the sequence information available at the time.

B. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptide Variants In addition to the full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides described herein, it is contemplated that PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variants can be prepared. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variants can be prepared by introducing appropriate nucleotide changes into the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA, and/or by synthesis of the desired PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Those skilled in the art will appreciate that amino acid changes may alter post-translational processes of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, such as changing the number or position of glycosylation sites or altering the membrane anchoring characteristics.

Variations in the native full-length sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or in various domains of the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO194, PRO220, PRO241, PRO284, PRO331, PRO354, PRO355, PRO533, PRO541, PRO725, PRO937, PRO1014, PRO1120, PRO182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide that results in a change in the amino acid sequence of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as compared with the native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Optionally the variation is by substitution of at least one amino acid with any other amino acid in one or more of the domains of the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Guidance in determining which amino acid residue may be inserted, substituted or deleted without adversely affecting the desired activity may be found by comparing the sequence of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 fragments may be prepared by any of a number of conventional techniques. Desired peptide fragments may be chemically synthesized. An alternative approach involves generating PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fragments share at least one biological and/or immunological activity with the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide disclosed herein.

Conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are preferably introduced and the products screened.

TABLE 6

| Original Residue | Exemplary Substitutions | Preferred Substitutions |
|---|---|---|
| Ala (A) | Val; Leu; Ile | Val |
| Arg ®) | Lys; Gln; Asn | Lys |
| Asn (N) | Gln; His; Asp, Lys; Arg | Gln |
| Asp (D) | Glu; Asn | Glu |
| Cys ©) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or ©) the bulk of the side chain. Naturally occurring residues are divided into groups based on common side-chain properties:

Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys ®), Tyr (Y), Asn (N), Gln (Q)
(3) acidic: Asp (D), Glu (E)
(4) basic: Lys (K), Arg ®), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370

Covalent modifications of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides are included within the scope of this invention. One type of covalent modification includes reacting targeted amino acid residues of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with an organic derivatizing agent that is capable of reacting with selected side chains or the or C-terminal residues of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Derivatization with bifunctional agents is useful, for instance, for crosslinking PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides to a water-insoluble support matrix or surface for use in the method for purifying anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties*, W.H. Freeman & Co., San Francisco, pp. 79-86 (1983)], acetylation of the N-terminal amine, and amidation of any C-terminal carboxyl group.

Another type of covalent modification of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide included within the scope of this invention comprises altering the native glycosylation pattern of the polypeptide. "Altering the native glycosylation pattern" is intended for purposes herein to mean deleting one or more carbohydrate moieties found in native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides (either by removing the underlying glycosylation site or by deleting the glycosylation by chemical and/or enzymatic means), and/or adding one or more glycosylation sites that are not present in the native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. In addition, the phrase includes qualitative changes in the glycosylation of the native proteins, involving a change in the nature and proportions of the various carbohydrate moieties present.

Addition of glycosylation sites to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be accomplished by altering the amino acid sequence. The alteration may be made, for example, by the addition of, or substitution by, one or more serine or threonine residues to the native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 (for O-linked glycosylation sites). The PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 amino acid sequence may optionally be altered through changes at the DNA level, particularly by mutating the DNA encoding the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide at preselected bases such that codons are generated that will translate into the desired amino acids.

Another means of increasing the number of carbohydrate moieties on the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem., pp.* 259-306 (1981).

Removal of carbohydrate moieties present on the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides comprises linking the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides of the present invention may also be modified in a way to form a chimeric molecule comprising the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide fused to another, heterologous polypeptide or amino acid sequence.

Such a chimeric molecule comprises a fusion of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with a tag polypeptide which provides an epitope to which an anti-tag antibody can selectively bind. The epitope tag is generally placed at the amino- or carboxyl-terminus of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. The presence of such epitope-tagged forms of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be detected using an antibody against the tag polypeptide. Also, provision of the epitope tag enables the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.,* 8:2159-2165 (1988)]; the c-myc tag and the 8F9, 3C7, 6E10, G4, B7 and 9E10 antibodies thereto [Evan et al., *Molecular and Cellular Biology,* 5:3610-3616 (1985)]; and the Herpes Simplex virus glycoprotein D (gD) tag and its antibody [Paborsky et al., *Protein Engineering,* 3(6):547-553 (1990)]. Other tag polypeptides include the Flag-peptide [Hopp et al., *BioTechnology,* 6:1204-1210 (1988)]; the KT3 epitope peptide [Martin et al., *Science,* 255:192-194 (1992)]; an α-tubulin epitope peptide [Skinner et al., *J. Biol. Chem.,* 266:15163-15166 (1991)]; and the T7 gene 10 protein peptide tag [Lutz-Freyermuth et al., *Proc. Natl. Acad. Sci. USA,* 87:6393-6397 (1990)].

The chimeric molecule may comprise a fusion of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide in place of at least one variable region within an Ig molecule. In a particularly preferred aspect of the invention, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptides The description below relates primarily to production of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides by culturing cells transformed or transfected with a vector containing PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acid. It is, of course, contemplated that alternative methods, which are well known in the art, may be employed to prepare PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. For instance, the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.,* 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be chemically synthesized separately and combined using chemical or enzymatic methods to produce the full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

1. Isolation of DNA Encoding PRO194, PRO220, PRO241, PRO284, PRO331, PRO354, PRO355 PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptides DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides may be obtained from a cDNA library prepared from tissue believed to possess the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 mRNA and to express it at a detectable level. Accordingly, human PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-DNA can be conveniently obtained from a cDNA library prepared from human tissue, such as described in the Examples. The PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-encoding gene may also be obtained from a genomic library or by known synthetic procedures (e.g., automated nucleic acid synthesis).

Libraries can be screened with probes (such as antibodies to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO194, PRO220, PRO241, PRO284, PRO331, PRO354, PRO355, PRO533, PRO541, PRO725, PRO937, PRO1014, PRO1120, PRO182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene,* 23:315 (1983) and WO 89/05859 published 29 Jun. 1989. For mammalian cells without such cell walls, the calcium phosphate precipitation method of Graham and van der Eb, *Virology,* 52:456-457 (1978) can be employed. General aspects of mammalian cell host system transfections have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527-537 (1990) and Mansour et al., *Nature,* 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5772 (ATCC 53,635). Other suitable prokaryotic host cells include Enterobacteriaceae such as *Escherichia*, e.g., *E. coli, Enterobacter, Erwinia, Klebsiella, Proteus, Salmonella,* e.g., *Salmonella typhimurium, Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3phoA E15 (argF-lac)169 degP ompT $kan^r$; *E. coli* W3110 strain 37D6, which has the complete genotype tonA ptr3phoA E15 (argF-lac)169 degP ompT rbs7 ilvG $kan^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, or PRO1026 or PRO23370-encoding vectors. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans*, and *K. marxianus; yarrowia* (EP 402,226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112:284-289 [1983]; Tilburn et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis*, and *Rhodotorula*. A list of specific species that are exemplary of this class of yeasts may be found in C. Anthony, *The Biochemistry of Methylotrophs,* 269 (1982).

Suitable host cells for the expression of glycosylated PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides are derived from multicellular organisms. Examples of invertebrate cells include insect cells such as *Drosophila* S2 and *Spodoptera*

Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/−DHFR (CHO, Urlaub and Chasin, *Proc. Natl. Acad. Sci. USA,* 77:4216 (1980)); mouse sertoli cells (TM4, Mather, *Biol. Reprod.,* 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026 or PRO23370-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli.*

An example of suitable selectable markers for mammalian cells are those that enable the identification of cells competent to take up the PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026 or PRO23370-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7[Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026 or PRO23370-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides.

Still other methods, vectors, and host cells suitable for adaptation to the synthesis of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides in recombinant vertebrate cell culture are described in Gething et al., *Nature*, 293:620-625 (1981); Mantei et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA*, 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or against a synthetic peptide based on the DNA sequences provided herein or against exogenous sequence fused to PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA and encoding a specific antibody epitope.

5. Purification of Polypeptide

Forms of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides may be recovered from culture medium or from host cell lysates. If membrane-bound, it can be released from the membrane using a suitable detergent solution (e.g. Triton-X 100) or by enzymatic cleavage. Cells employed in expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides can be disrupted by various physical or chemical means, such as freeze-thaw cycling, sonication, mechanical disruption, or cell lysing agents.

It may be desired to purify PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides from recombinant cell proteins or polypeptides. The following procedures are exemplary of suitable purification procedures: by fractionation on anion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide produced.

E. Uses for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptides Nucleotide sequences (or their complement) encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides have various applications in the art of molecular biology, including uses as hybridization probes, in chromosome and gene mapping and in the generation of anti-sense RNA and DNA. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acid will also be useful for the preparation of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides by the recombinant techniques described herein.

The full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene, or portions thereof, may be used as hybridization probes for a cDNA library to isolate the full-length PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 cDNA or to isolate still other cDNAs (for instance, those encoding naturally-occurring variants of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides from other species) which have a desired sequence identity to the native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370. By way of example, a screening method will comprise isolating the coding region of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acids include antisense or sense oligonucleotides comprising a singe-stranded nucleic acid sequence (either RNA or DNA) capable of binding to target PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 mRNA (sense) or PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA (antisense) sequences. Antisense or sense oligonucleotides, according to the present invention, comprise a fragment of the coding region of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 coding sequences.

Nucleotide sequences encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can also be used to construct hybridization probes for mapping the gene which encodes that PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 encode a protein which binds to another protein (for example, where the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is a receptor), the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can be used to isolate correlative ligand(s). Screening assays can be designed to find lead compounds that mimic the biological activity of a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or a receptor for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides or its modified forms can also be used to generate either transgenic animals or “knock out” animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. The invention provides cDNA encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide which can be used to clone genomic DNA encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide in accordance with established techniques and the genomic sequences used to generate transgenic animals that contain cells which express DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. Any technique known in the art may be used to introduce a target gene transgene into animals to produce the founder lines of transgenic animals. Such techniques include, but are not limited to pronuclear microinjection (U.S. Pat. Nos. 4,873,191, 4,736,866 and 4,870,009); retrovirus mediated gene transfer into germ lines (Van der Putten, et al., *Proc. Natl. Acad. Sci., USA,* 82:6148-6152 (1985)); gene targeting in embryonic stem cells (Thompson, et al., *Cell,* 56:313-321 (1989)); nonspecific insertional inactivation using a gene trap vector (U.S. Pat. No. 6,436,707); electroporation of embryos (Lo, *Mol. Cell. Biol.,* 3:1803-1814 (1983)); and sperm-mediated gene transfer (Lavitrano, et al., *Cell,* 57:717-723 (1989)); etc. Typically, particular cells would be targeted for a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 transgene incorporation with tissue-specific enhancers. Transgenic animals that include a copy of a transgene encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide introduced into the germ line of the animal at an embryonic stage can be used to examine the effect of increased expression of DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides can be used to construct a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370"knock out" animal which has a defective or altered gene encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 proteins as a result of homologous recombination between the endogenous gene encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides and altered genomic DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides introduced into an embryonic stem cell of the animal. Preferably the knock out animal is a mammal. More preferably, the mammal is a rodent such as a rat or mouse. For example, cDNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides can be used to clone genomic DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides in accordance with established techniques. A portion of the genomic DNA encoding the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the gene encoding the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

In addition, knockout mice can be highly informative in the discovery of gene function and pharmaceutical utility for a drug target, as well as in the determination of the potential on-target side effects associated with a given target. Gene function and physiology are so well conserved between mice and humans, since they are both mammals and contain similar numbers of genes, which are highly conserved between the species. It has recently been well documented, for example, that 98% of genes on mouse chromosome 16 have a human ortholog (Mural et al., *Science* 296:1661-71 (2002)).

Although gene targeting in embryonic stem (ES) cells has enabled the construction of mice with null mutations in many genes associated with human disease, not all genetic diseases are attributable to null mutations. One can design valuable mouse models of human diseases by establishing a method for gene replacement (knock-in) which will disrupt the mouse locus and introduce a human counterpart with mutation, Subsequently one can conduct in vivo drug studies targeting the human protein (Kitamoto et. Al., *Biochemical and Biophysical Res. Commun.,* 222:742-47 (1996)).

Nucleic acid encoding the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO124, PRO1026 or PRO23370 polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83:4143-4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.* 262, 4429-4432 (1987); and Wagner et al., *Proc. Natl. Acad. Sci. USA* 87, 3410-3414 (1990). For review of gene marking and gene therapy protocols see Anderson et al., *Science* 256, 808-813 (1992).

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides described herein may also be employed as molecular weight markers for protein electrophoresis purposes and the isolated nucleic acid sequences may be used for recombinantly expressing those markers.

The nucleic acid molecules encoding the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides or fragments thereof described herein are useful for chromosome identification. In this regard, there exists an ongoing need to identify new chromosome markers, since relatively few chromosome marking reagents, based upon actual sequence data are presently available. Each PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acid molecule of the present invention can be used as a chromosome marker.

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides and nucleic acid molecules of the present invention may also be used diagnostically for tissue typing, wherein the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides of the present invention may be differentially expressed in one tissue as compared to another, preferably in a diseased tissue as compared to a normal tissue of the same tissue type. PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 nucleic acid molecules will find use for generating probes for PCR, Northern analysis, Southern analysis and Western analysis.

The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides described herein may also be employed as therapeutic agents. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides of the present invention can be formulated according to known methods to prepare pharmaceutically useful compositions, whereby the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or agonist or antagonist thereof is employed, normal dosage amounts may vary from about 10 ng/kg to up to 100 mg/kg of mammal body weight or more per day, preferably about 1 μg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is desired in a formulation with release characteristics suitable for the treatment of any disease or disorder requiring administration of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, microencapsulation of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide (agonists) or prevent the effect of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide (antagonists). Agonists that mimic a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide would be especially valuable therapeutically in those instances where a negative phenotype is observed based on findings with the non-human transgenic animal whose genome comprises a disruption of the gene which encodes for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Antagonists that prevent the effects of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide would be especially valuable therapeutically in those instances where a positive phenotype is observed based upon observations with the non-human transgenic knockout animal. Screening assays for antagonist drug candidates are designed to identify compounds that bind or complex with the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide encoded by the genes identified herein, or otherwise interfere with the interaction of the encoded polypeptide with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide encoded by a nucleic acid identified herein under conditions and for a time sufficient to allow these two components to interact.

In binding assays, the interaction is binding and the complex formed can be isolated or detected in the reaction mixture. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and drying. Alternatively, an immobilized antibody, e.g., a monoclonal antibody, specific for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature* (London), 340:245-246 (1989); Chien et al., *Proc. Natl. Acad. Sci. USA,* 88:9578-9582 (1991)) as disclosed by Chevray and Nathans, *Proc. Natl. Acad. Sci. USA,* 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be added to a cell along with the compound to be screened for a particular activity and the ability of the compound to inhibit the activity of interest in the presence of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide indicates that the compound is an antagonist to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Alternatively, antagonists may be detected by combining the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and a potential antagonist with membrane-bound PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide receptors or recombinant receptors under appropriate conditions for a competitive inhibition assay. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be labeled, such as by radioactivity, such that the number of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and a cDNA library created from this RNA is divided into pools and used to transfect COS cells or other cells that are not responsive to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Transfected cells that are grown on glass slides are exposed to labeled PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, the labeled PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

Another approach in assessing the effect of an antagonist to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, would be administering a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 antagonist to a wild-type mouse in order to mimic a known knockout phenotype. Thus, one would initially knockout the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene of interest and observe the resultant phenotype as a consequence of knocking out or disrupting the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene. Subsequently, one could then assess the effectiveness of an antagonist to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by administering an antagonist to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to a wild-type mouse. An effective antagonist would be expected to mimic the phenotypic effect that was initially observed in the knockout animal. Likewise, one could assess the effect of an agonist to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, by administering a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 agonist to a non-human transgenic mouse in order to ameliorate a known negative knockout phenotype. Thus, one would initially knockout the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene of interest and observe the resultant phenotype as a consequence of knocking out or disrupting the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 gene. Subsequently, one could then assess the effectiveness of an agonist to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by administering an agonist to the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to a the non-human transgenic mouse. An effective agonist would be expected to ameliorate the negative phenotypic effect that was initially observed in the knockout animal.

In another assay for antagonists, mammalian cells or a membrane preparation expressing the receptor would be incubated with a labeled PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide in the presence of the candidate compound. The ability of the compound to enhance or block this interaction could then be measured.

More specific examples of potential antagonists include an oligonucleotide that binds to the fusions of immunoglobulin with the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide that recognizes the receptor but imparts no effect, thereby competitively inhibiting the action of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

Another potential PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241: 456 (1988); Dervan et al., *Science,* 251:1360 (1991)), thereby preventing transcription and the production of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. The antisense RNA oligonucleotide hybridizes to the mRNA in vivo and blocks translation of the mRNA molecule into the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide (antisense-Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, thereby blocking the normal biological activity of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by anyone or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO194, Anti-PRO220, Anti-PRO241, Anti-PRO284, Anti-PRO331, Anti-PRO354, Anti-PRO355, Anti-PRO533, Anti-PRO541, Anti-PRO725, Anti-PRO937, Anti-PRO1014, Anti-PRO1120, Anti-PRO1182, Anti-PRO1325, Anti-PRO1382, Anti-PRO1410, Anti-PRO1555, Anti-PRO1556, Anti-PRO1760, Anti-PRO1787, Anti-PRO1868, Anti-PRO4326, Anti-PRO4332, Anti-PRO4346, Anti-PRO4400, Anti-PRO6003, Anti-PRO6094, Anti-PRO6244, Anti-PRO9820, Anti-PRO9828, Anti-PRO10274, Anti-PRO16090, Anti-PRO19644, Anti-PRO21340, Anti-PRO92165, Anti-PRO85143, Anti-PRO1124, Anti-PRO1026 or Anti-PRO23370 Antibodies The present invention provides anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.,* 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130: 151-188 (1992).

Monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl. Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature,* 321:522-525 (1986); Riechmann et al., *Nature,* 332:323-329 (1988); and Presta, *Curr. Op. Struct. Biol.,* 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature,* 321:522-525 (1986); Riechmann et al., *Nature,* 332:323-327 (1988); Verhoeyen et al., *Science,* 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.,* 196:901 (1987)). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggemann et al., *Year in Immuno.* 7:33 (1993); U.S. Pat. Nos. 5,545,806, 5,569,825, 5,591,669 (all of GenPharm); 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S, and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10: 163-167 (1992)). According to another approach, $F(ab')_2$ fragments can be isolated directly from recombinant host cell culture. Fab and $F(ab')_2$ fragment with increased in vivo half-life comprising a salvage receptor binding epitope residues are described in U.S. Pat. No. 5,869,046. Other techniques for the production of antibody fragments will be apparent to the skilled practitioner. The antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 protein as described herein. Other such antibodies may combine a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 binding site with a binding site for another protein. Alternatively, an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CD16), so as to focus and localize cellular defense mechanisms to the PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143, PRO1124-, PRO1026- or PRO23370-expressing cell. Bispecific antibodies may also be used to localize cytotoxic agents to cells which express a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide. These antibodies possess a PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026 or PRO23370-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., $F(ab')_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificity (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region (CHI) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

The invention provides bispecific antibodies which are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-$(X1)_n$-VD2-$(X2)_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise alight chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced antitumor activity may also be prepared using heterobifunctional cross-linkers as described in Wolff et al., *Cancer Research*

53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{186}Re$. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

The invention provides an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody (full length or fragments) which is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA. 1 that binds the HER-2/neu oncogene. The cytotoxicity of the TA. 1-maytansonoid conjugate was tested in vitro on the human breast cancer cell line SK-BR-3, which expresses $3\times10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-PRO194, Anti-PRO220, Anti-PRO241, Anti-PRO284, Anti-PRO331, Anti-PRO354, Anti-PRO355, Anti-PRO533, Anti-PRO541, Anti-PRO725, Anti-PRO937, Anti-PRO1014, Anti-PRO1120, Anti-PRO1182, Anti-PRO1325, Anti-PRO1382, Anti-PRO1410, Anti-PRO1555, Anti-PRO1556, Anti-PRO1760, Anti-PRO1787, Anti-PRO1868, Anti-PRO4326, Anti-PRO4332, Anti-PRO4346, Anti-PRO4400, Anti-PRO6003, Anti-PRO6094, Anti-PRO6244, Anti-PRO9820, Anti-PRO9828, Anti-PRO10274, Anti-PRO16090, Anti-PRO19644, Anti-PRO21340, Anti-PRO92165, Anti-PRO85143, Anti-PRO1124, Anti-PRO1026 or Anti-PRO23370Antibody-Maytansinoid Conjugates (Immunoconjugates)

Anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody-maytansinoid conjugates are prepared by chemically linking an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. The linkage is formed at the C-3 position of maytansinol or a maytansinol analogue.

Calicheamicin

Another immunoconjugate of interest comprises an anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO124, anti-PRO1026 or anti-PRO23370 antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

The invention provides that the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl. Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257: 286-288 (1982) via a disulfide interchange reaction. A chemotherapeutic agent is optionally contained within the liposome. See Gabizon et al., *J. National Cancer Inst.* 81(19): 1484 (1989).

11. Pharmaceutical Compositions of Antibodies

Antibodies specifically binding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide identified herein, as well as other molecules identified by the screening assays disclosed hereinbefore, can be administered for the treatment of various disorders in the form of pharmaceutical compositions.

If the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA,* 90: 7889-7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

G. Uses for Anti-PRO194, Anti-PRO220, Anti-PRO241, Anti-PRO284, Anti-PRO331, Anti-PRO354, Anti-PRO355, Anti-PRO533, Anti-PRO541, Anti-PRO725, Anti-PRO937, Anti-PRO1014, Anti-PRO1120, Anti-PRO1182, Anti-PRO1325, Anti-PRO1382, Anti-PRO1410, Anti-PRO1555, Anti-PRO1556, Anti-PRO1760, Anti-PRO1787, Anti-PRO1868, Anti-PRO4326, Anti-PRO4332, Anti-PRO4346, Anti-PRO4400, Anti-PRO6003, Anti-PRO6094, Anti-PRO6244, Anti-PRO9820, Anti-PRO9828, Anti-PRO10274, Anti-PRO16090, Anti-PRO19644, Anti-PRO21340, Anti-PRO92165, Anti-PRO85143, Anti-PRO1124, Anti-PRO1026 or Anti-PRO23370 Antibodies The anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies of the invention have various therapeutic and/or diagnostic utilities for a neurological disorder; a cardiovascular, endothelial or angiogenic disorder; an immunological disorder; an oncological disorder; an embryonic developmental disorder or lethality, or a metabolic abnormality. For example, anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies may be used in diagnostic assays for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147-158]. The antibodies used in the diagnostic assays can be labeled with a detectable moiety. The detectable moiety should be capable of producing, either directly or indirectly, a detectable signal. For example, the detectable moiety may be a radioisotope, such as $^{3}H$, $^{14}C$, $^{32}P$, $^{35}S$, or $^{125}I$, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:

1014 (1974); Pain et al., *J. Immunol. Meth.,* 40:219 (1981); and Nygren, *J. Histochem. and Cytochem.,* 30:407 (1982).

Anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies also are useful for the affinity purification of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides from recombinant cell culture or natural sources. In this process, the antibodies against PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides are immobilized on a suitable support, such a Sephadex resin or filter paper, using methods well known in the art. The immobilized antibody then is contacted with a sample containing the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide to be purified, and thereafter the support is washed with a suitable solvent that will remove substantially all the material in the sample except the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, which is bound to the immobilized antibody. Finally, the support is washed with another suitable solvent that will release the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding Therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., *Methods in Enzymology,* 266:460-480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253: 1278-1280 (1991)) in the unique XhoI and NotI sites.

Example 2

Isolation of cDNA clones by Amylase Screening

1. Preparation of Oligo dT Primed cDNA Library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500-1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, $MAL^+$, $SUC^+$, $GAL^+$. Preferably, yeast mutants can be employed that have deficient post-translational pathways. Such mutants may have translocation deficient alleles in sec71, sec72, sec62, with truncated sec71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p-4-p) or the complex formation of these proteins may also be preferably employed in combination with the amylase-expressing yeast.

Transformation was performed based on the protocol outlined by Gietz et al., *Nucl. Acid. Res.,* 20:1425 (1992). Transformed cells were then inoculated from agar into YEPD complex media broth (100 ml) and grown overnight at 30° C. The YEPD broth was prepared as described in Kaiser et al., *Methods in Yeast Genetics*, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{60}$=0.4-0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 μl) with freshly denatured single stranded salmon testes DNA (Lofstrand Labs, Gaithersburg, Md.) and transforming DNA (1 μg, vol.<10 μl) in microfuge tubes. The mixture was mixed briefly by vortexing, then 40% PEG/TE (600 μl, 40% polyethylene glycol-4000, mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5-10 seconds, decanted and resuspended into TE (500 μl, 10 mM Tris-HCl, 1 mM EDTA pH 7.5) followed by recentrifugation. The cells were then diluted into TE (1 ml) and aliquots (200 μl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., *Methods in Yeast Genetics*, Cold Spring Harbor Press, Cold Spring Harbor, N.Y., p. 208-210 (1994). Transformants were grown at 30° C. for 2-3 days.

The detection of colonies secreting amylase was performed by including red starch in the selective growth media. Starch was coupled to the red dye (Reactive Red-120, Sigma) as per the procedure described by Biely et al., *Anal. Biochem.,* 172:176-179 (1988). The coupled starch was incorporated into the SCD-Ura agar plates at a final concentration of 0.15% (w/v), and was buffered with potassium phosphate to a pH of 7.0 (50-100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 μl) in a 96 well plate. At this time, the positive colonies were either frozen and stored for subsequent analysis or immediately amplified. An aliquot of cells (5 μl) was used as a template for the PCR reaction in a 25 μl volume containing: 0.5 μl Klentaq (Clontech, Palo Alto, Calif.); 4.0 μl 10 mM dNTP's (Perkin Elmer-Cetus); 2.5 μl Kentaq buffer (Clontech); 0.25 μl forward oligo 1; 0.25 μl reverse oligo 2; 12.5 μl distilled water. The sequence of the forward oligonucleotide 1 was:

```
                                       (SEQ ID NO: 81)
5'-TGTAAAACGACGGCCAGTTAAATAGACCTGCAATTATTAATCT-3'
```

The sequence of reverse oligonucleotide 2 was:

```
                                       (SEQ ID NO: 82)
5'-CAGGAAACAGCTATGACCACCTGCACACCTGCAAATCCATT-3'
```

PCR was then performed as follows:

| | | | | |
|---|---|---|---|---|
| a. | | Denature | 92° C., | 5 minutes |
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 bp. However, signal sequence-fused cDNA resulted in considerably longer nucleotide sequences.

Following the PCR, an aliquot of the reaction (5 μl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 Qiaquick PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Using the techniques described in Examples 1 to 3 above, numerous full-length cDNA clones were identified as encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO1124 or PRO1026 polypeptides as disclosed herein. These cDNAs were then deposited under the terms of the Budapest Treaty with the American Type Culture Collection, 10801 University Blvd., Manassas, Va. 20110-2209, USA (ATCC) as shown in Table 7 below. In addition, the sequence of DNA340392 encoding PRO92165 polypeptides was identified from GenBank accession no.: AB028714; the sequence of DNA340394 encoding PRO85143 polypeptides was identified from GenBank accession no.: AF329488; and the sequence of DNA193963 encoding PRO23370 polypeptides was identified from GenBank accession no.: L08177.

TABLE 7

| Material | ATCC Dep. No. | Deposit Date |
|---|---|---|
| DNA26844-1394 | 209926 | Jun. 2, 1998 |
| DNA32298-1132 | 209257 | Sep. 16, 1997 |
| DNA34392-1170 | 209526 | Dec. 10, 1997 |
| DNA23318-1211 | 209787 | Apr. 21, 1998 |
| DNA40981-1234 | 209439 | Nov. 7, 1997 |
| DNA44192-1246 | 209531 | Dec. 10, 1997 |
| DNA39518-1247 | 209529 | Dec. 10, 1997 |
| DNA49435-1219 | 209480 | Nov. 21, 1997 |
| DNA45417-1432 | 209910 | May 27, 1998 |
| DNA52758-1399 | 209773 | Apr. 14, 1998 |
| DNA56436-1448 | 209902 | May 27, 1998 |
| DNA56409-1377 | 209882 | May 20, 1998 |
| DNA48606-1479 | 203040 | Jul. 1, 1998 |
| DNA59848-1512 | 203088 | Aug. 4, 1998 |
| DNA66659-1593 | 203269 | Sep. 22, 1998 |
| DNA66526-1616 | 203246 | Sep. 9, 1998 |
| DNA68874-1622 | 203277 | Sep. 22, 1998 |
| DNA73744-1665 | 203322 | Oct. 6, 1998 |
| DNA76529-1666 | 203315 | Oct. 6, 1998 |
| DNA76532-1702 | 203473 | Nov. 17, 1998 |
| DNA76510-2504 | 203477 | Nov. 17, 1998 |
| DNA77624-2515 | 203553 | Dec. 22, 1998 |
| DNA91779-2571 | 203844 | Mar. 16, 1999 |
| DNA100272-2969 | PTA-2299 | Jul. 25, 2000 |
| DNA86594-2587 | 203894 | Mar. 30, 1999 |
| DNA87974-2609 | 203963 | Apr. 27, 1999 |
| DNA83568-2692 | PTA-386 | Jul. 20, 1999 |
| DNA96995-2709 | PTA-475 | Aug. 3, 1999 |
| DNA108743-2722 | PTA-508 | Aug. 10, 1999 |
| DNA108769-2765 | PTA-861 | Oct. 19, 1999 |
| DNA142238-2768 | PTA-819 | Oct. 5, 1999 |
| DNA139686-2823 | PTA-1264 | Feb. 2, 2000 |
| DNA144844-2843 | PTA-1536 | Mar. 21, 2000 |
| DNA139592-2866 | PTA-1587 | Mar. 28, 2000 |
| DNA176775-2957 | PTA-2303 | Jul. 25, 2000 |
| DNA60629-1481 | 209979 | Jun. 16, 1998 |
| DNA59613-1417 | 203007 | Jun. 23, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 4

Isolation of cDNA clones Encoding Human PRO194 Polypeptides [UNQ168]

A consensus DNA sequence was assembled relative to other EST sequences using phrap as described in Example 1 above. This consensus sequence is herein DNA19464. Based on the DNA19464 consensus sequence, oligonucleotides were synthesized: 1) to identify by PCR a cDNA library that contained the sequence of interest, and 2) for use as probes to isolate a clone of the full-length coding sequence for PRO194. PCR primers (forward and reverse) were synthesized based upon the DNA19464 sequence. Additionally, a synthetic oligonucleotide hybridization probe was constructed from the consensus DNA19464 sequence.

In order to screen several libraries for a source of a full-length clone, DNA from the libraries was screened by PCR amplification with the PCR primer pair identified above. A positive library was then used to isolate clones encoding the PRO194 gene using the probe oligonucleotide and one of the PCR primers. RNA for construction of the cDNA libraries was isolated from human fetal lung tissue (LIB25).

DNA sequencing of the clones isolated as described above gave the full-length DNA sequence for PRO194 [herein designated as DNA26844-1394] (SEQ ID NO:1) and the derived protein sequence for PRO194.

The entire nucleotide sequence of DNA26844-1394 is shown in FIG. 1 (SEQ ID NO:1). Clone DNA26844-1394 contains a single open reading frame with an apparent translational initiation site at nucleotide positions 81-83 and ending at the stop codon at nucleotide positions 873-875 (FIG. 1). The predicted polypeptide precursor is 264 amino acids long (FIG. 2). The full-length PRO194 protein shown in FIG. 2 has an estimated molecular weight of about 29,665 daltons and a pI of about 9.34. Analysis of the full-length PRO194 sequence shown in FIG. 2 (SEQ ID NO:2) evidences the presence of various important polypeptides domains as shown in FIG. 2. Clone DNA26844-1394 has been deposited with ATCC on Jun. 2, 1998 and is assigned ATCC deposit no. 209926.

Analysis of the amino acid sequence of the full-length PRO194 polypeptide suggests that it does not exhibit significant sequence similarity to any known human protein. However, an analysis of the Dayhoff database (version 35.45 SwissProt 35) evidenced some homology between the PRO194 amino acid sequence and the following Dayhoff sequences, HUMORFT_1, CET07F10_5, ATFCA9_12, F64934, YDJX_ECOLI, ATAF00065719F29G20.19, H70002, S76980, H64934 and S76385.

Example 5

Isolation of cDNA clones Encoding Human PRO220 Polypeptides [UNQ194]

A consensus DNA sequence was assembled relative to the other identified EST sequences as described in Example 1 above, wherein the consensus sequence is designated herein as DNA28749. Based on the DNA28749 consensus sequence, oligonucleotides were synthesized to identify by PCR a cDNA library that contained the sequence of interest and for use as probes to isolate a clone of the full-length coding sequence for PRO220.

A pair of PCR primers (forward and reverse) were synthesized:

```
                                           (SEQ ID NO:83)
forward PCR primer 5'-TCACCTGGAGCCTTTATTGGCC-3'
                                           (SEQ ID NO:84)
reverse PCR primer 5'-ATACCAGCTATAACCAGGCTGCG-3'
```

Additionally, a synthetic oligonucleotide hybridization probe was constructed from the consensus DNA28749 sequence which had the following nucleotide sequence:
hybridization probe

```
                                           (SEQ ID NO:85)
5'-CAACAGTAAGTGGTTTGATGCTCTTCCAAATCTAGAGATTCTGATGA

TTGGG-3'.
```

In order to screen several libraries for a source of a full-length clone, DNA from the libraries was screened by PCR amplification with the PCR primer pair identified above. A positive library was then used to isolate clones encoding the PRO220 gene using the probe oligonucleotide and one of the PCR primers.

RNA for construction of the cDNA libraries was isolated from human fetal lung tissue. DNA sequencing of the clones isolated as described above gave the full-length DNA sequence for PRO220 [herein designated as DNA32298-1132 and the derived protein sequence for PRO220].

The entire nucleotide sequence of DNA32298-1132 is shown in FIG. 3 (SEQ ID NO:3). Clone DNA32298-1132 contains a single open reading frame with an apparent translational initiation site at nucleotide positions 480-482 and ending at the stop codon at nucleotide positions 2604-2606 (FIG. 3). The predicted polypeptide precursor is 708 amino acids long (FIG. 4; SEQ ID NO:4). Clone DNA32298-1132 has been deposited with ATCC on Sep. 16, 1997 and is assigned ATCC deposit no. ATCC 209257.

Analysis of the amino acid sequence of the full-length PRO220 shows it has homology to member of the leucine rich repeat protein superfamily, including the leucine rich repeat protein and the neuronal leucine-rich repeat protein 1.

Example 6

Isolation of cDNA clones Encoding Human PRO241 Polypeptides [UNQ215]

A consensus DNA sequence was assembled relative to other EST sequences as described in Example 1 above. This consensus sequence is herein designated DNA30876. Based on the DNA30876 consensus sequence, oligonucleotides were synthesized: 1) to identify by PCR a cDNA library that contained the sequence of interest, and 2) for use as probes to isolate a clone of the full-length coding sequence for PRO241.

PCR primers (forward and reverse) were synthesized:

```
forward PCR primer
5'-GGAAATGAGTGCAAACCCTC-3'          (SEQ ID NO:86)

reverse PCR primer
5'-TCCCAAGCTGAACACTCATTCTGC-3'      (SEQ ID NO:87)
```

Additionally, a synthetic oligonucleotide hybridization probe was constructed from the consensus DNA30876 sequence which had the following nucleotide sequence hybridization probe

```
                                          (SEQ ID NO:88)
5'-GGGTGACGGTGTTCCATATCAGAATTGCAGAAGCAAAACTGACCTCA

GTT-3'
```

In order to screen several libraries for a source of a full-length clone, DNA from the libraries was screened by PCR amplification with the PCR primer pair identified above. A positive library was then used to isolate clones encoding the PRO241 gene using the probe oligonucleotide and one of the PCR primers. RNA for construction of the cDNA libraries was isolated from human fetal kidney tissue (LIB29).

DNA sequencing of the clones isolated as described above gave the full-length DNA sequence for PRO241 [herein designated as DNA34392-1170] (SEQ ID NO:5) and the derived protein sequence for PRO241.

The entire nucleotide sequence of DNA34392-1170 is shown in FIG. 5 (SEQ ID NO:5). Clone DNA34392-1170 contains a single open reading frame with an apparent translational initiation site at nucleotide positions 234-236 and ending at the stop codon at nucleotide positions 1371-1373 (FIG. 5). The predicted polypeptide precursor is 379 amino acids long (FIG. 6). The full-length PRO241 protein shown in FIG. 6 has an estimated molecular weight of about 43,302 daltons and a pI of about 7.30. Clone DNA34392-1170 has been deposited with ATCC on Dec. 10, 1997 and is assigned ATCC deposit no. ATCC 209526.

Analysis of the amino acid sequence of the full-length PRO241 polypeptide suggests that it possess significant homology to the various biglycan proteoglycan proteins, thereby indicating that PRO241 is a novel biglycan homolog polypeptide.

Example 7

Isolation of cDNA clones Encoding Human PRO284 Polypeptides [UNQ247]

Two cDNA sequences were isolated in the amylase screen described in Example 2 and those cDNA sequences are herein designated DNA12982 and DNA15886. The DNA12982 and DNA15886 sequences were then clustered and aligned, giving rise to a consensus nucleotide sequence herein designated DNA18832.

Based on the DNA18832 consensus sequence, oligonucleotide probes were generated and used to screen a human placenta library (LIB89) prepared as described in paragraph 1 of Example 2 above. The cloning vector was pRK5B (pRK5B is a precursor of pRK5D that does not contain the SfiI site; see, Holmes et al., *Science,* 253:1278-1280 (1991)), and the cDNA size cut was less than 2800 bp.

PCR primers (forward and reverse) were synthesized:

```
forward PCR primer 1 (18832.est.f)
5'-TCGTACAGTTACGCTCTCCC-3'      (SEQ ID NO:89)

forward PCR primer 2 (18832.f)
5'-CTTGAGGAGCGTCAGAAGCG-3'      (SEQ ID NO:90)

reverse PCR primer (18832.r)
5'-ATAACGAATGAAGCCTCGTG-3'      (SEQ ID NO:91)
```

Additionally, a synthetic oligonucleotide hybridization probe was constructed from the DNA 18832 sequence which had the following nucleotide sequence
hybridization probe (18832.p)

```
                                     (SEQ ID NO:92)
5'-GCTAATATCTGTAAGACGGCAGCTACAGCAGGCATCATTG-3'
```

In order to screen several libraries for a source of a full-length clone, DNA from the libraries was screened by PCR amplification with the PCR primer pairs identified above. A positive library was then used to isolate clones encoding the PRO284 gene using the probe oligonucleotide and one of the PCR primers.

A full length clone was identified that contained a single open reading frame with an apparent translational initiation site at nucleotide positions 167-169 and ending at the stop codon found at nucleotide positions 1022-1024 (FIG. 7; SEQ ID NO:7). The predicted polypeptide precursor is 285 amino acids long, has a calculated molecular weight of approximately 32,190 daltons and an estimated pI of approximately 9.03. Analysis of the full-length PRO284 sequence shown in FIG. 8 (SEQ ID NO:8) evidences the presence of the following: a signal peptide from about amino acid 1 to about amino acid 24, transmembrane domains from about amino acid 76 to about amino acid 96 and from about amino acid 171 to about amino acid 195 and a potential N-glycosylation site from about amino acid 153 to about amino acid 156. Clone UNQ247 (DNA23318-1211) has been deposited with ATCC on Apr. 21, 1998 and is assigned ATCC deposit no. 209787.

Analysis of the amino acid sequence of the full-length PRO284 polypeptide suggests that it possesses no significant sequence similarity to any known protein. However, an analysis of the Dayhoff database (version 35.45 SwissProt 35) evidenced some degree of homology between the PRO284 amino acid sequence and the following Dayhoff sequences, JQ0124, CELE04A4_5, AB006451_1, AF030162_1, IM23_YEAST, S71194, NIA_CUCMA, IM17_YEAST, I50479 and HUMZFHP_1.

Example 8

Isolation of cDNA Clones Encoding Human PRO331 Polypeptides [UNQ292]

A consensus DNA sequence was assembled relative to other EST sequences using phrap as described in Example 1 above. This consensus sequence is herein designated DNA36685. Based on the DNA36685 consensus sequence, and Incyte EST sequence no. 2228990, oligonucleotides were synthesized: 1) to identify by PCR a cDNA library that contained the sequence of interest, and 2) for use as probes to isolate a clone of the full-length coding sequence for PRO331.

Forward and reverse PCR primers were synthesized for the determination of PRO331:

```
forward PCR primer
5'-GCCTTTGACAACCTTCAGTCACTAGTGG-3'   (SEQ ID NO:93)

reverse PCR primer
5'-CCCCATGTGTCCATGACTGTTCCC-3'       (SEQ ID NO:94)
```

Additionally, a synthetic oligonucleotide hybridization probe was constructed for the determination of PRO331 which had the following nucleotide sequence
hybridization probe

```
                                              (SEQ ID NO:95)
5'-TACTGCCTCATGACCTCTTCACTCCCTTGCATCATCTTAGAGCG

G-3'
```

In order to screen several libraries for a source of a full-length clone, DNA from the libraries was screened by PCR amplification with the PCR primer pairs identified above. A positive library was then used to isolate clones encoding the PRO331 gene using the probe oligonucleotide and one of the PCR primers.

RNA for construction of the cDNA libraries was isolated from human fetal brain (PRO331).

DNA sequencing of the clones isolated as described above gave the full-length DNA sequence for PRO331 [herein designated as DNA40981-1234; SEQ ID NO:9; see FIG. 9], and the derived protein sequence for PRO331 (see FIG. 10; SEQ ID NO:10).

The entire nucleotide sequence is shown in FIG. 9, deposited with the ATCC on Nov. 7, 1997 and is assigned ATCC deposit no. 209439.

Analysis of the amino acid sequence of the full-length PRO331 polypeptide suggests that portions of it possess significant homology to the LIG-1 protein, thereby indicating that PRO331 may be a novel LIG-1-related protein.

Example 9

Isolation of cDNA clones Encoding Human PRO354 Polypeptides [UNQ311]

An expressed sequence tag (EST) DNA database (LIFESEQ™, Incyte Pharmaceuticals, Palo Alto, Calif.) was searched and various EST sequences were identified which possessed certain degrees of homology with the inter-alpha-trypsin inhibitor heavy chain and with one another. Those homologous EST sequences were then aligned and a consensus sequence was obtained. The obtained consensus DNA sequence was then extended using repeated cycles of BLAST and phrap to extend the consensus sequence as far as possible using homologous EST sequences derived from both public EST databases (e.g., GenBank) and a proprietary EST DNA database (LIFESEQ™, Incyte Pharmaceuticals, Palo Alto, Calif.). The extended assembly sequence is herein designated DNA39633. The above searches were performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

Based on the DNA39633 consensus sequence, oligonucleotides were synthesized: 1) to identify by PCR a cDNA library that contained the sequence of interest, and 2) for use as probes to isolate a clone of the full-length coding sequence for PRO354. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers were synthesized as follows:

```
forward PCR primer 1 (39633.f1)
5'-GTGGGAACCAAACTCCGGCAGACC-3'   (SEQ ID NO:96)

forward PCR primer 2 (39633.f2)
5'-CACATCGAGCGTCTCTGG-3'         (SEQ ID NO:97)

reverse PCR primer (39633.r1)
5'-AGCCGCTCCTTCTCCGGTTCATCG-3'   (SEQ ID NO:98)
```

Additionally, a synthetic oligonucleotide hybridization probe was constructed from the consensus DNA39633 sequence which had the following nucleotide sequence
hybridization probe

```
                                              (SEQ ID NO:99)
5'-TGGAAGGACCACTTGATATCAGTCACTCCAGACAGCATCAGGGATGG

G-3'
```

In order to screen several libraries for a source of a full-length clone, DNA from the libraries was screened by PCR amplification with the PCR primer pairs identified above. A positive library was then used to isolate clones encoding the PRO354 gene using the probe oligonucleotide and one of the PCR primers.

RNA for construction of the cDNA libraries was isolated from human fetal kidney tissue (LIB227). The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO354 [herein designated as DNA44192-1246] (SEQ ID NO:11) and the derived protein sequence for PRO354.

The entire nucleotide sequence of DNA44192-1246 is shown in FIG. 11 (SEQ ID NO:11). Clone DNA44192-1246 contains a single open reading frame with an apparent translational initiation site at nucleotide positions 72-74 and ending at the stop codon at nucleotide positions 2154-2156 (FIG. 11). The predicted polypeptide precursor is 694 amino acids long (FIG. 12; SEQ ID NO:12). The full-length PRO354 protein shown in FIG. 12 has an estimated molecular weight of about 77,400 daltons and a pI of about 9.54. Clone DNA44192-1246 has been deposited with ATCC on Dec. 10, 1997 and is assigned ATCC deposit no. ATCC 209531.

Analysis of the amino acid sequence of the full-length PRO354 polypeptide suggests that it possess significant homology to the inter-alpha-trypsin inhibitor heavy chain protein, thereby indicating that PRO354 may be a novel inter-alpha-trypsin inhibitor heavy chain protein homolog.

Example 10

Isolation of cDNA clones Encoding Human PRO355 Polypeptides [UNQ312]

A consensus DNA sequence was assembled relative to other EST sequences using BLAST and phrap as described in Example 1 above. This consensus sequence is herein designated DNA35702. Based on the DNA35702 consensus sequence, oligonucleotides were synthesized: 1) to identify by PCR a cDNA library that contained the sequence of interest, and 2) for use as probes to isolate a clone of the full-length coding sequence for PRO355.

Forward and reverse PCR primers were synthesized as follows:

```
forward PCR primer
5'-GGCTTCTGCTGTTGCTCTTCTCCG-3'    (SEQ ID NO:100)

forward PCR primer
5'-GTACACTGTGACCAGTCAGC-3'        (SEQ ID NO:101)

forward PCR primer
5'-ATCATCACAGATTCCCGAGC-3'        (SEQ ID NO:102)

reverse PCR primer
5'-TTCAATCTCCTCACCTTCCACCGC-3'    (SEQ ID NO:103)

reverse PCR primer
5'-ATAGCTGTGTCTGCGTCTGCTGCG-3'    (SEQ ID NO:104)
```

Additionally, a synthetic oligonucleotide hybridization probe was constructed from the consensus DNA35702 sequence which had the following nucleotide sequence:
hybridization probe

```
                                          (SEQ ID NO:105)
5'-CGCGGCACTGATCCCCACAGGTGATGGGCAGAATCTGTTTACGAAAG

ACG-3'
```

In order to screen several libraries for a source of a full-length clone, DNA from the libraries was screened by PCR amplification with one of the PCR primer pairs identified above. A positive library was then used to isolate clones encoding the PRO355 gene using the probe oligonucleotide. RNA for construction of the cDNA libraries was isolated from human fetal liver tissue.

DNA sequencing of the clones isolated as described above gave the full-length DNA sequence for PRO355 [herein designated as DNA39518-1247] (SEQ ID NO:13) and the derived protein sequence for PRO355.

The entire nucleotide sequence of DNA39518-1247 is shown in FIG. 13 (SEQ ID NO:13). Clone DNA39518-1247 contains a single open reading frame with an apparent translational initiation site at nucleotide positions 22-24 and ending at the stop codon at nucleotide positions 1342-1344 (FIG. 13). The predicted polypeptide precursor is 440 amino acids long (FIG. 14; SEQ ID NO:14). The full-length PRO355 protein shown in FIG. 14 has an estimated molecular weight of about 48,240 daltons and a pI of about 4.93. In addition, regions of interest including the signal peptide, Ig repeats in the extracellular domain, potential N-glycosylation sites, and the potential transmembrane domain, are designated in FIG. 14. Clone DNA39518-1247 has been deposited with ATCC on Dec. 10, 1997 and is assigned ATCC deposit no. ATCC 209529.

Analysis of the amino acid sequence of the full-length PRO355 polypeptide suggests that portions of it possess significant homology to the CRTAM protein, thereby indicating that PRO355 may be CRTAM protein.

Example 11

Isolation of cDNA Clones Encoding Human PRO533 Polypeptides [UNQ334]

The EST sequence accession number AF007268, a murine fibroblast growth factor (FGF-15) was used to search various public EST databases (e.g., GenBank, Dayhoff, etc.). The search was performed using the computer program BLAST or BLAST2 [Altschul et al., *Methods in Enzymology,* 266: 460-480 (1996); as a comparison of the ECD protein sequences to a 6 frame translation of the EST sequences. The search resulted in a hit with GenBank EST AA220994, which has been identified as stratagene NT2 neuronal precursor 937230.

Based on the Genbank EST AA220994 sequence, oligonucleotides were synthesized: 1) to identify by PCR a cDNA library that contained the sequence of interest, and 2) for use as probes to isolate a clone of the full-length coding sequence. Forward and reverse PCR primers may range from 20 to 30 nucleotides (typically about 24), and are designed to give a PCR product of 100-1000 bp in length. The probe sequences are typically 40-55 bp (typically about 50) in length. In order to screen several libraries for a source of a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the PCR primers.

In order to screen several libraries for a source of a full-length clone, DNA from the libraries was screened by PCR amplification with the PCR primer pair identified below. A positive library was then used to isolate clones encoding the PRO533 gene using the probe oligonucleotide and one of the PCR primers.

RNA for construction of the cDNA libraries was isolated from human fetal retina. The cDNA libraries used to isolated the cDNA clones were constructed by standard methods using commercially available reagents (e.g., Invitrogen, San Diego, Calif.; Clontech, etc.) The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

A cDNA clone was sequenced in its entirety. The full length nucleotide sequence of PRO533 is shown in FIG. 15 (SEQ ID NO:15). Clone DNA49435-1219 contains a single open reading frame with an apparent translational initiation site at nucleotide positions 459-461 (FIG. 15; SEQ ID NO:15). The predicted polypeptide precursor is 216 amino acids long (FIG. 16; SEQ ID NO:16). Clone DNA49435-1219 has been deposited with ATCC on Nov. 21, 1997 and is assigned ATCC deposit no. ATCC 209480.

Based on a BLAST-2 and FastA sequence alignment analysis of the full-length sequence, PRO533 shows amino acid sequence identity to fibroblast growth factor (53%).

The oligonucleotide sequences used in the above procedure were the following:

```
FGF15.forward:
                                        (SEQ ID NO:106)
5'-ATCCGCCCAGATGGCTACAATGTGTA-3';

FGF15.probe:
                                        (SEQ ID NO:107)
5'-GCCTCCCGGTCTCCCTGAGCAGTGCCAAACAGCGGCAGTGTA-3';

FGF15.reverse:
                                        (SEQ ID NO:108)
5'-CCAGTCCGGTGACAAGCCCAAA-3'.
```

Example 12

Isolation of cDNA clones Encoding Human PRO541 Polypeptides [UNQ342]

A consensus sequence was obtained relative to a variety of EST sequences as described in Example 1 above, wherein the consensus sequence obtained is herein designated DNA42259. Based on the DNA42259 consensus sequence, oligonucleotides were synthesized: 1) to identify by PCR a cDNA library that contained the sequence of interest, and 2) for use as probes to isolate a clone of the full-length coding sequence for PRO541.

PCR primers (forward and reverse) were synthesized:

```
forward PCR primer
5'-GGACAGAATTTGGGAGCACACTGG-3'    (SEQ ID NO:109)

forward PCR primer
5'-CCAAGAGTATACTGTCCTCG-3'        (SEQ ID NO:110)

reverse PCR primer
5'-AGCACAGATTTTCTCTACAGCCCCC-3'   (SEQ ID NO:111)

reverse PCR primer
5'-AACCACTCCAGCATGTACTGCTGC-3'    (SEQ ID NO:112)
```

Additionally, a synthetic oligonucleotide hybridization probe was constructed from the consensus DNA42259 sequence which had the following nucleotide sequence hybridization probe

```
                                        (SEQ ID NO:113)
5'-CCATTCAGGTGTTCTGGCCCTGTATGTACACATTATACACAGGTCGT

GTG-3'
```

In order to screen several libraries for a source of a full-length clone, DNA from the libraries was screened by PCR amplification with one of the PCR primer pairs identified above. A positive library was then used to isolate clones encoding the PRO541 gene using the probe oligonucleotide and one of the PCR primers. RNA for construction of the cDNA libraries was isolated from human fetal kidney tissue (LIB227).

DNA sequencing of the clones isolated as described above gave the full-length DNA sequence for PRO541 [herein designated as UNQ342 (DNA45417-1432)] (SEQ ID NO:17) and the derived protein sequence for PRO541.

The entire nucleotide sequence of UNQ342 (DNA45417-1432) is shown in FIG. 17 (SEQ ID NO:17). Clone UNQ342 (DNA45417-1432) contains a single open reading frame with an apparent translational initiation site at nucleotide positions 469-471 and ending at the stop codon at nucleotide positions 1969-1971 (FIG. 17). The predicted polypeptide precursor is 500 amino acids long (FIG. 18). The full-length PRO541 protein shown in FIG. 18 has an estimated molecular weight of about 56,888 daltons and a pI of about 8.53. Analysis of the full-length PRO541 sequence shown in FIG. 18 (SEQ ID NO:18) evidences the presence of the following: a signal peptide from about amino acid 1 to about amino acid 20, amino acid sequence blocks having homology to extracellular proteins SCP/Tpx-1/Ag5/PR-1/Sc7 from about amino acid 165 to about amino acid 186, from about amino acid 196 to about amino acid 218, from about amino acid 134 to about amino acid 146, from about amino acid 96 to about amino acid 108 and from about amino acid 58 to about amino acid 77 and a potential N-glycosylation site from about amino acid 28 to about amino acid 31. Clone UNQ342 (DNA45417-1432) has been deposited with ATCC on May 27, 1998 and is assigned ATCC deposit no. 209910.

Analysis of the amino acid sequence of the full-length PRO541 polypeptide suggests that it possesses significant sequence similarity to a trypsin inhibitor protein, thereby indicating that PRO541 may be a novel trypsin inhibitor. More specifically, an analysis of the Dayhoff database (version 35.45 SwissProt 35) evidenced significant homology between the PRO541 amino acid sequence and the following Dayhoff sequences, D45027_1, AB009609_1, JC5308, CRS3_HORSE, TPX1_HUMAN, HELO_HELHO, GEN14351, A28112_1, CET05A10_4 and P_W11485.

Example 13

Isolation of cDNA clones Encoding Human PRO725 Polypeptides [UNQ390]

A consensus sequence was obtained relative to a variety of EST sequences as described in Example 1 above. Based upon an observed homology between this consensus sequence and an EST sequence contained within Incyte EST clone No. 4242090, Incyte EST clone No. 4242090 was purchased and its insert was obtained and sequenced.

A cDNA sequence isolated in the amylase screen described in Example 2 above is herein designated DNA43301. The DNA43301 sequence was then compared to a variety of expressed sequence tag (EST) databases which included public EST databases (e.g., GenBank) and a proprietary EST DNA database (LIFESEQ™, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into consensus DNA sequences with the program "phrap" (Phil Green, University of Washington, Seattle, Wash.). The consensus sequence obtained therefrom is herein designated DNA45458. Based on the DNA45458 consensus sequence, oligonucleotide probes were generated and used to screen a human fetal brain (LIB153) library prepared as described in paragraph 1 of Example 2 above. The cloning vector was pRK5B (pRK5B is a precursor of pRK5D that does not contain the SfiI site; see, Holmes et al., *Science,* 253:1278-1280 (1991)), and the cDNA size cut was less than 2800 bp.

PCR primers (forward and reverse) were synthesized:

```
forward PCR primer (45458.f1)
5'-CCAAACTCACCCAGTGAGTGTGAGC-3'   (SEQ ID NO: 114)

reverse PCR primer (45458.r1)
5'-TGGGAAATCAGGAATGGTGTTCTCC-3'   (SEQ ID NO: 115)
```

Additionally, a synthetic oligonucleotide hybridization probe was constructed from the consensus DNA45458 sequence which had the following nucleotide sequence
hybridization probe (45458.p1)

```
                                        (SEQ ID NO: 116)
5'-CTTGTTTTCACCATTGGGCTAACTTTGCTGCTAGGAGTTCAAGCCAT

GCC-3'
```

In order to screen several libraries for a source of a full-length clone, DNA from the libraries was screened by PCR amplification with the PCR primer pair identified above. A positive library was then used to isolate clones encoding the PRO725 gene using the probe oligonucleotide and one of the PCR primers.

A full length clone (herein identified as DNA52758-1399) was identified that contained a single open reading frame with an apparent translational initiation site at nucleotide positions 161-163 and ending at the stop codon found at nucleotide positions 455-457 (FIG. 19; SEQ ID NO:19). The predicted polypeptide precursor is 98 amino acids long, has a calculated molecular weight of approximately 11,081 daltons and an estimated pI of approximately 6.68 (FIG. 20; SEQ ID NO:20). Analysis of the full-length PRO725 sequence shown in FIG. 20 (SEQ ID NO:20) evidences the presence of the following: a signal peptide from about amino acid 1 to about amino acid 20, a potential N-glycosylation site from about amino acid 72 to about amino acid 75 and a tyrosine kinase phosphorylation site from about amino acid 63 to about amino acid 70. Clone DNA52758-1399 has been deposited with ATCC on Apr. 14, 1998 and is assigned ATCC deposit no. 209773.

Analysis of the amino acid sequence of the full-length PRO725 polypeptide suggests that it possesses no significant sequence similarity to any known protein. However, an analysis of the Dayhoff database (version 35.45 SwissProt 35) evidenced some degree of homology between the PRO725 amino acid sequence and the following Dayhoff sequences, POL_BLVAU, PSSP_RAT, CELC36C5__7, AF019234__1, I48862, P_R12498, P_P10125, P_R26861, A64527 and P_W20495.

Example 14

Isolation of cDNA clones Encoding Human PRO937 Polypeptides [UNQ474]

The extracellular domain (ECD) sequences (including the secretion signal, if any) of from about 950 known secreted proteins from the Swiss-Prot public protein database were used to search expressed sequence tag (EST) databases. The EST databases included public EST databases (e.g., GenBank) and a proprietary EST DNA database (LIFESEQ™, Incyte Pharmaceuticals, Palo Alto, Calif.). The search was performed using the computer program BLAST or BLAST2 (Altshul et al., *Methods in Enzymology* 266:460-480 (1996)) as a comparison of the ECD protein sequences to a 6 frame translation of the EST sequence. Those comparisons resulting in a BLAST score of 70 (or in some cases 90) or greater that did not encode known proteins were clustered and assembled into consensus DNA sequences with the program "phrap" (Phil Green, University of Washington, Seattle, Wash.).

A consensus DNA sequence was identified using the above described analysis as encoding a potential secreted protein. This sequence is herein designated DNA49651.init. In addition, the DNA46951.init sequence was then extended using repeated cycles of BLAST and phrap to extend the sequence as far as possible using the sources of EST sequences discussed above. The extended assembly sequence is referred to herein as "DNA49651".

Based on the DNA49651 consensus sequence oligonucleotides were synthesized: 1) to identify by PCR a cDNA library that contained the sequence of interest, and 2) for use as probes to isolate a clone of the full-length coding sequence for PRO937. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, with the PCR primer pair. A positive library was then used to isolate clones encoding the gene of interest using the probe oligonucleotide and one of the primer pairs.

PCR primers (forward and reverse) were synthesized:

```
forward PCR primer (49651.f1)
5'- CTCCGTGGTAAACCCCACAGCCC -3';   (SEQ ID NO: 117)
and

reverse PCR primer (49651.r1).
5'- TCACATCGATGGGATCCATGACCG -3'.  (SEQ ID NO: 118)
```

Additionally, a synthetic oligonucleotide hybridization probe was constructed from the DNA48651 sequence which had the following nucleotide sequence:
hybridization probe (49651.p1)

```
                                        (SEQ ID NO: 119)
5'-GGTCTCGTGACTGTGAAGCCATGTTACAACTACTGCTCAAACATCAT

GAG-3'.
```

In order to screen several libraries for a source of a full-length clone, DNA from the libraries was screened by PCR amplification with the PCR primer pair identified above. A positive library was then used to isolate clones encoding the PRO937 gene using the probe oligonucleotide and one of the PCR primers.

RNA for construction of the cDNA libraries was isolated from human fetal kidney tissue (LIB227). The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al, *Science,* 253:1278-1280 (1991)) in the unique XhoI and NotI sites.

DNA sequencing of the clones isolated as described above gave the full-length DNA sequence for PRO937 [herein designated as UNQ474 (DNA56436-1448)] (SEQ ID NO:21) and the derived protein sequence for PRO937.

The entire nucleotide sequence of UNQ474 (DNA56436-1448) is shown in FIG. 21 (SEQ ID NO:21). It contains a single open reading frame having an apparent translational initiation site at nucleotide positions 499-501 and ending at the stop codon found at nucleotide positions 2167-2169 (FIG. 21, SEQ ID NO:21). The predicted polypeptide precursor is 556 amino acids long, has a calculated molecular weight of approximately 62,412 daltons and an estimated pI of approximately 6.62. Analysis of the full-length PRO937 sequence shown in FIG. 22 (SEQ ID NO:22) evidences the presence of the following features: signal peptide at about amino acids 1-22; ATP/GTP-binding site motif A (P-loop) at about amino acids 515-523; a potential N-glycosylation site at about amino acids 514-517; and sites of glypican homology at about amino acids 54-74, 106-156, 238-279, 309-345, 423-459, and 468-505.

Clone UNQ474 (DNA56436-1448) has been deposited with ATCC on May 27, 1998, and is assigned ATCC deposit no. 209902.

Analysis of the amino acid sequence of the full-length PRO937 polypeptide suggests that it possesses significant sequence similarity to glypican proteins, thereby indicating that PRO937 may be a novel glypican protein. More specifically, an analysis of the Dayhoff database (version 35.45 SwissProt 35) evidenced significant homology between the PRO937 amino acid sequence and the following Dayhoff sequences: GPCK_MOUSE, GPC2_RAT, GPC5_HUMAN, GPC3_HUMAN, P_R30168, CEC03H12__2, GEN13820, HS119E23__1, HDAC_DROME, and AF017637__1.

Example 15

Isolation of cDNA clones Encoding Human PRO1014 Polypeptides [UNQ497]

A consensus DNA sequence was assembled relative to other EST sequences using phrap as described in Example 1 above, wherein the consensus sequence obtained is herein designated DNA49811. Based upon an observed homology between the DNA49811 sequence and Incyte EST clone no. 2612207, Incyte EST clone no. 2612207 was purchased and its insert was obtained and sequenced, wherein the sequence obtained is shown in FIG. 23 (SEQ OD NO:23).

DNA sequencing gave the full-length DNA sequence for PRO1014 [herein designated as UNQ497 (DNA56409-1377)] (SEQ ID NO:23) and the derived protein sequence for PRO1014.

The entire nucleotide sequence of UNQ497 (DNA56409-1377) is shown in FIG. 23 (SEQ ID NO:23). Clone UNQ497 (DNA56409-1377) contains a single open reading frame with an apparent translational initiation site at nucleotide positions 66-68 and ending at the stop codon at nucleotide positions 966-968 (FIG. 23). The predicted polypeptide precursor is 300 amino acids long (FIG. 24; SEQ ID NO:24). The full-length PRO1014 protein shown in FIG. 24 has an estimated molecular weight of about 33,655 daltons and a pI of about 9.31. Clone UNQ497 (DNA56409-1377) has been deposited with the ATCC on May 20, 1998 and has the accession number 209882. Regarding the sequence, it is understood that the deposited clone contains the correct sequence, and the sequences provided herein are based on known sequencing techniques.

Analysis of the amino acid sequence of the full-length PRO1014 polypeptide suggests that portions of it possess sequence identity with reductase, thereby indicating that PRO1014 may be a novel member of the reductase family.

Still analyzing the amino acid sequence of SEQ ID NO:24, the putative signal peptide is at about amino acids 1-19 of SEQ ID NO:24. The cAMP and cGMP dependent protein kinase phosphorylation sites are at about amino acids 30-33 and 58-61 of SEQ ID NO:24. Short chain alcohol dehydrogenase family proteins are at about amino acids 165-202, 37-49, 112-122 and 210-219 of SEQ ID NO:24. The corresponding nucleotides of these domains and any other amino acids provided herein can be routinely determined given the sequences provided herein.

Example 16

Isolation of cDNA clones Encoding Human PRO1120 Polypeptides [UNQ559]

A consensus DNA sequence was assembled relative to other EST sequences using phrap as described in Example 1 above. This consensus sequence is designated herein consen0352. The consen0352 sequence was then extended using repeated cycles of BLAST and phrap to extend the consensus sequence as far as possible using the sources of EST sequences discussed above. The extended consensus sequence is designated herein as DNA34365. Based on the DNA34365 consensus sequence, oligonucleotides were synthesized: 1) to identify by PCR a cDNA library that contained the sequence of interest, and 2) for use as probes to isolate a clone of the full-length coding sequence for PRO1120.

PCR primers (forward and reverse) were synthesized:

forward PCR primers:

| | |
|---|---|
| 5'-GAAGCCGGCTGTCTGAATC-3', | (SEQ ID NO: 120) |
| 5'-GGCCAGCTATCTCCGCAG-3', | (SEQ ID NO: 121) |
| 5'-AAGGGCCTGCAAGAGAAG-3', | (SEQ ID NO: 122) |
| 5'-CACTGGGACAACTGTGGG-3', | (SEQ ID NO: 123) |
| 5'-CAGAGGCAACGTGGAGAG-3', and | (SEQ ID NO: 124) |
| 5'-AAGTATTGTCATACAGTGTTC-3'; | (SEQ ID NO: 125) |

reverse PCR primers:

| | |
|---|---|
| 5'-TAGTACTTGGGCACGAGGTTGGAG-3', and | (SEQ ID NO: 126) |
| 5'-TCATACCAACTGCTGGTCATTGGC-3'. | (SEQ ID NO: 127) |

Additionally, a synthetic oligonucleotide hybridization probe was constructed from the DNA34365 consensus sequence which had the following nucleotide sequence: hybridization probe:

(SEQ ID NO: 128)
5'-CTCAAGCTGCTGGACACGGAGCGGCCGGTGAATCGGTTTCACTTG-3'.

In order to screen several libraries for a source of a full-length clone, DNA from the libraries was screened by PCR amplification with the PCR primer pairs identified above. A positive library was then used to isolate clones encoding the PRO1120 gene using the probe oligonucleotide and one of the PCR primers. RNA for construction of the cDNA libraries was isolated from human fetal kidney tissue.

DNA sequencing of the clones isolated as described above gave the full-length DNA sequence for PRO1120 (designated herein as DNA48606-1479 [FIG. 25, SEQ ID NO:25]; and the derived protein sequence for PRO1120.

The entire coding sequence of PRO1120 is shown in FIG. 25 (SEQ ID NO:25). Clone DNA48606-1479 contains a single open reading frame with an apparent translational initiation site at nucleotide positions 608-610 and an apparent stop codon at nucleotide positions 3209-3211. The predicted polypeptide precursor is 867 amino acids long. The full-length PRO1120 protein shown in FIG. 26 (SEQ ID NO:26) has an estimated molecular weight of about 100,156 Daltons and a pI of about 9.44. Additional features of the PRO1120 polypeptide include a signal peptide at about amino acids 1-17; a sulfatase signature at about amino acids 86-98; regions of homology to sulfatases at about amino acids 87-106, 133-146, 216-229, 291-320, and 365-375; and potential N-glycosylation sites at about amino acids 65-68, 112-115, 132-135, 149-152, 171-174, 198-201, 241-245, 561-564, 608-611, 717-720, 754-757, and 764-767.

An analysis of the Dayhoff database (version 35.45 SwissProt 35), using a WU-BLAST-2 sequence alignment analysis of the full-length sequence shown in FIG. 26 (SEQ ID NO:26), revealed significant homology between the PRO1120 amino acid sequence and the following Dayhoff sequences: CELK09C4_1, GL6S_HUMAN, G65169, NCU89492_1, BCU44852_1, E64903, P_R51355, STS_HUMAN, GA6S_HUMAN, and IDS_MOUSE. Clone DNA48606-1479 was deposited with the ATCC on Jul. 1, 1998, and is assigned ATCC deposit no. 203040.

Example 17

Isolation of cDNA clones Encoding Human PRO182 Polypeptides [UNQ596]

Use of the signal sequence algorithm described in Example 3 above allowed identification of a single EST cluster sequence from the Incyte database, designated herein as 146647. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., Methods in Enzymology 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56033.

In light of an observed sequence homology between the DNA56033 consensus sequence and an EST sequence encompassed within the Incyte EST clone no. 2595195, the Incyte EST clone 2595195 was purchased and the cDNA insert was obtained and sequenced. It was found that this insert encoded a full-length protein. The sequence of this cDNA insert is shown in FIG. 27 and is herein designated as DNA59848-1512.

Clone DNA59848-1512 contains a single open reading frame with an apparent translational initiation site at nucleotide positions 67-69 and ending at the stop codon at nucleotide positions 880-882 (FIG. 27; SEQ ID NO:27). The predicted polypeptide precursor is 271 amino acids long (FIG. 28; SEQ ID NO:28). The full-length PRO1182 protein shown in FIG. 28 has an estimated molecular weight of about 28,665 daltons and a pI of about 5.33. Analysis of the full-length PRO1182 sequence shown in FIG. 28 (SEQ ID NO:28) evidences the presence of the following: a signal peptide from about amino acid 1 to about amino acid 25, an amino acid block having homology to C-type lectin domain proteins from about amino acid 247 to about amino acid 256 and an amino acid sequence block having homology to C1q domain proteins from about amino acid 44 to about amino acid 77. Clone DNA59848-1512 has been deposited with ATCC on Aug. 4, 1998 and is assigned ATCC deposit no. 203088.

An analysis of the Dayhoff database (version 35.45 SwissProt 35), using a WU-BLAST2 sequence alignment analysis of the full-length sequence shown in FIG. 28 (SEQ ID NO:28), evidenced significant homology between the PRO1182 amino acid sequence and the following Dayhoff sequences: PSPD_BOVIN, CL43_BOVIN, CONG_BOVIN, P_W18780, P_R45005, P_R53257 and CELEGAP7_1.

Example 18

Isolation of cDNA clones Encoding Human PRO1325 Polypeptides [UNQ685]

Use of the signal sequence algorithm described in Example 3 above allowed identification of an EST cluster sequence from the Incyte database, designated Incyte EST cluster sequence no. 139524. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56115.

In light of the sequence homology between the DNA56115 sequence and an EST sequence contained within the Incyte EST clone no. 3744079, the Incyte EST clone no. 3744079 was purchased and the cDNA insert was obtained and sequenced. The sequence of this cDNA insert is shown in FIG. 29 and is herein designated as DNA66659-1593.

Clone DNA66659-1593 contains a single open reading frame with an apparent translational initiation site at nucleotide positions 51-53 and ending at the stop codon at nucleotide positions 2547-2549 (FIG. 29; SEQ ID NO:29). The predicted polypeptide precursor is 832 amino acids long (FIG. 30). The full-length PRO1325 protein shown in FIG. 30 has an estimated molecular weight of about 94,454 daltons and a pI of about 6.94. Analysis of the full-length PRO1325 sequence shown in FIG. 30 (SEQ ID NO:30) evidences the presence of the following: a signal peptide from about amino acid 1 to about amino acid 18, transmembrane domains from about amino acid 292 to about amino acid 317, from about amino acid 451 to about amino acid 470, from about amino acid 501 to about amino acid 520, from about amino acid 607 to about amino acid 627 from about amino acid 751 to about amino acid 770, a leucine zipper pattern sequence from about amino acid 497 to about amino acid 518 and potential N-glycosylation sites from about amino acid 27 to about amino acid 30, from about amino acid 54 to about amino acid 57, from about amino acid 60 to about amino acid 63, from about amino acid position 123 to about amino acid position 126, from about amino acid position 141 to about amino acid position 144, from about amino acid position 165 to about amino acid position 168, from about amino acid position 364 to about amino acid position 367, from about amino acid position 476 to about amino acid position 479, from about amino acid position 496 to about amino acid position 499, from about amino acid position 572 to about amino acid position 575, from about amino acid position 603 to about amino acid position 606 and from about amino acid position 699 to about amino acid position 702. Clone DNA66659-1593 has been deposited with ATCC on Sep. 22, 1998 and is assigned ATCC deposit no. 203269.

An analysis of the Dayhoff database (version 35.45 SwissProt 35), using a WU-BLAST2 sequence alignment analysis of the full-length sequence shown in FIG. 30 (SEQ ID NO:30), evidenced significant homology between the PRO1325 amino acid sequence and the following Dayhoff sequences: CELR04E5_1, CELZK721_5, CELC30 μl_5, CELC30 μl_6, CELC30 μl_2, CEY37H2C_1, CELC30 μl_7, CELT07H8_7 and E64006.

Example 19

Isolation of cDNA clones Encoding Human PRO1382 Polypeptides [UNQ718]

Using the method described in Example 1 above, Incyte EST no. 2719 was identified as a sequence of interest having a BLAST score of 70 or greater that does not encode a known protein. The nucleotide sequence of EST no. 2719 is designated herein "DNA42842". Based on the DNA42842 sequence, oligonucleotides were synthesized: 1) to identify by PCR a cDNA library that contained the sequence of interest, and 2) for use as probes to isolate a clone of the full-length coding sequence for PRO1382.

PCR primers (forward and reverse) were synthesized:

```
forward PCR primer
ACGGCTCACCATGGGCTCCG      (42842.f1; SEQ ID NO: 129)

reverse PCR primer
AGGAAGAGGAGCCCTTGGAGTCCG (42842.r1; SEQ ID NO: 130)
```

Additionally, a synthetic oligonucleotide hybridization probe was constructed from the consensus DNA42842 sequence which had the following nucleotide sequence: hybridization probe CGTGCTGGAGGGCAAGTGTCTG-GTGGTGTGCGACTCGAAC (42842.p1; SEQ ID NO:131).

In order to screen several libraries for a source of a full-length clone, DNA from the libraries was screened by PCR amplification with the PCR primer pair identified above. A positive library was then used to isolate clones encoding the PRO1382 gene using the probe oligonucleotide and one of the PCR primers. RNA for construction of the cDNA libraries was isolated from a human breast carcinoma.

DNA sequencing of the clones isolated as described above gave the full-length DNA sequence for PRO1382 (designated herein as DNA66526-1616 [FIG. 31, SEQ ID NO:31]; and the derived protein sequence for PRO1382.

The entire coding sequence of PRO1382 is shown in FIG. 31 (SEQ ID NO:31). Clone DNA66526-1616 contains a single open reading frame with an apparent translational initiation site at nucleotide positions 337-339 and an apparent stop codon at nucleotide positions 940-942. The predicted polypeptide precursor is 201 amino acids long. The full-length PRO1382 protein shown in FIG. 32 (SEQ ID NO:32) has an estimated molecular weight of about 21,808 daltons and a pI of about 9.04. Additional features include a signal peptide at about amino acids 1-27; potential N-glycosylation sites at about amino acids 29-32 and 88-91; and regions of homology with C1q proteins at about amino acids 92-126, 159-178, and 191-200.

An analysis of the Dayhoff database (version 35.45 SwissProt 35), using a WU-BLAST2 sequence alignment analysis of the full-length sequence shown in FIG. 32 (SEQ ID NO:32), revealed significant homology between the PRO1382 amino acid sequence Dayhoff sequence no. CERL_RAT. Homology was also revealed between the PRO1382 amino acid sequence and the following Dayhoff sequences: CERB_HUMAN, S76975_1, A41752, HUMC1QB2_1, A57131, CALA_HUMAN, ACR3_MOUSE, and COLE_LEPMA.

Clone DNA66526-1616 has been deposited with ATCC on Sep. 9, 1998 and is assigned ATCC deposit no. 203246.

Example 20

Isolation of cDNA clones Encoding Human PRO1410 Polypeptides [UNQ728]

Use of the signal sequence algorithm described in Example 3 above allowed identification of an EST cluster sequence from the Incyte database, designated Incyte EST cluster sequence no. 98502. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56451.

In light of the sequence homology between the DNA56451 sequence and an EST sequence contained within the Incyte EST clone no. 1257046, the Incyte EST clone 125046 was purchased and the cDNA insert was obtained and sequenced. The sequence of this cDNA insert is shown in FIG. 33 and is herein designated as DNA68874-1622.

Clone DNA68874-1622 contains a single open reading frame with an apparent translational initiation site at nucleotide positions 152-154 and ending at the stop codon at nucleotide positions 866-868 (FIG. 33; SEQ ID NO:33). The predicted polypeptide precursor is 238 amino acids long (FIG. 34). The full-length PRO1410 protein shown in FIG. 34 has an estimated molecular weight of about 25,262 daltons and a pI of about 6.44. Analysis of the full-length PRO1410 sequence shown in FIG. 34 (SEQ ID NO:34) evidences the presence of the following: a signal peptide from about amino acid 1 to about amino acid 20, a transmembrane domain from about amino acid 194 to about amino acid 220 and a potential N-glycosylation site from about amino acid 132 to about amino acid 135. Clone DNA68874-1622 has been deposited with ATCC on Sep. 22, 1998 and is assigned ATCC deposit no. 203277.

An analysis of the Dayhoff database (version 35.45 SwissProt 35), using a WU-BLAST2 sequence alignment analysis of the full-length sequence shown in FIG. 34 (SEQ ID NO:34), evidenced significant homology between the PRO1410 amino acid sequence and the following Dayhoff sequences: I48652, P_R76466, HSMHC3W36A__2, EPB4_HUMAN, P_R14256, EPA8_MOUSE, P_R77285, P_W13569, AF000560__1, and ASF1_HELAN.

Example 21

Isolation of cDNA clones Encoding Human PRO1555 Polypeptides [UNQ763]

Use of the signal sequence algorithm described in Example 3 above allowed identification of an EST cluster sequence from the LIFESEQ® database, designated EST cluster no. 521, and also referred to herein as "DNA10316". This EST cluster sequence was then compared to a variety of expressed sequence tag (EST) databases which included public EST databases (e.g., GenBank) and the LIFESEQ® database to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated "DNA56374".

In light of the sequence homology between the DNA56374 sequence and an EST sequence contained within Incyte EST no. 2855769, EST no. 2855769 was purchased and the cDNA insert was obtained and sequenced. EST no. 2855769 was derived from a library constructed from female breast fat tissue. The sequence of this cDNA insert is shown in FIG. 35 and is herein designated as DNA73744-1665.

The full length clone shown in FIG. 35 contained a single open reading frame with an apparent translational initiation site at nucleotide positions 90 to 92 and ending at the stop codon found at nucleotide positions 828 to 830 (FIG. 35; SEQ ID NO:35). The predicted polypeptide precursor (FIG. 36, SEQ ID NO:36) is 246 amino acids long. PRO1555 has a calculated molecular weight of approximately 26,261 daltons and an estimated p1 of approximately 5.65. Additional features include: a signal peptide at about amino acids 1-31; transmembrane domains at about amino acids 11-31 and 195-217; a potential N-glycosylation site at about amino acids 111-114; potential casein kinase II phosphorylation sites at about amino acids 2-5, 98-101, and 191-194; and potential N-myristoylation sites at about amino acids 146-151, and 192-197.

An analysis of the Dayhoff database (version 35.45 SwissProt 35), using a WU-BLAST2 sequence alignment analysis of the full-length sequence shown in FIG. 36 (SEQ ID NO:36), revealed some homology between the PRO1555 amino acid sequence and the following Dayhoff sequences: YKA4_CAEEL, AB014541__1, HVSX99518__2, SSU63019__1, GEN14286, MMU68267__1, XP2_XENLA, ICP4_HSV11, P_W40200, and AE001360__1.

Clone DNA73744-1665 was deposited with the ATCC on Oct. 6, 1998, and is assigned ATCC deposit no. 203322.

Example 22

Isolation of cDNA Clones Encoding Human PRO1556 Polypeptides [UNQ764]

Use of the signal sequence algorithm described in Example 3 above allowed identification of an EST cluster sequence from the LIFESEQ® database, designated EST Cluster No. 103158, and also referred to herein as "DNA10398". This EST cluster sequence was then compared to a variety of expressed sequence tag (EST) databases which included public EST databases (e.g., GenBank) and the LIFESEQ® database, to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56417.

In light of the sequence homology between the DNA56417 sequence and a sequence contained within Incyte EST no. 959332, EST no. 959332 was purchased and the cDNA insert was obtained and sequenced. The sequence of this cDNA insert is shown in FIG. 37 and is herein designated as DNA76529-1666.

The full length clone shown in FIG. 37 contained a single open reading frame with an apparent translational initiation site at nucleotide positions 85 to 87 and ending at the stop codon found at nucleotide positions 892 to 894 (FIG. 37; SEQ ID NO:37). The predicted polypeptide precursor (FIG. 38, SEQ ID NO:38) is 269 amino acids long. PRO1556 has a calculated molecular weight of approximately 28,004 daltons and an estimated pI of approximately 5.80. Additional features include: a signal peptide sequence at about amino acids 1-24; transmembrane domains at about amino acids 11-25 and 226-243; a potential N-glycosylation site at about amino acids 182-185, potential cAMP- and cGMP-dependent protein kinase phosphorylation site at about amino acids 70-73; and potential N-myristoylation sites at about amino acids 29-34, 35-39, 117-122, 121-126, 125-130, 154-159, 166-171, 241-246, 246-251, 247-252, 249-254, 250-255, 251-256, 252-257, 253-258, 254-259, 255-260, 256-261, 257-262, and 259-264.

An analysis of the Dayhoff database (version 35.45 SwissProt 35), using a WU-BLAST2 sequence alignment analysis of the full-length sequence shown in FIG. 38 (SEQ ID NO:38), revealed some homology between the PRO1556 amino acid sequence and the following Dayhoff sequences: T8F5__4, R23B_MOUSE, CANS_HUMAN, P_W41640, DSU51091__1, TP2B_CHICK, DVU20660__1, S43296, P_R23962, and BRN1_HUMAN.

Clone DNA76529-1666 was deposited with the ATCC on Oct. 6, 1998, and is assigned ATCC deposit no. 203315.

Example 23

Isolation of cDNA clones Encoding Human PRO1760 Polypeptides [UNQ833]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. One or more of the ESTs was derived from a prostate tumor library. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA58798.

In light of the sequence homology between DNA58798 sequence and the Incyte EST 3358745, the clone including this EST was purchased and the cDNA insert was obtained and sequenced. The sequence of this cDNA insert is shown in FIG. 39 and is herein designated as DNA76532-1702.

The full length clone shown in FIG. 39 contained a single open reading frame with an apparent translational initiation site at nucleotide positions 60-62 and ending at the stop codon found at nucleotide positions 624-626 (FIG. 39; SEQ ID NO:39). The predicted polypeptide precursor (FIG. 40, SEQ ID NO:40) is 188 amino acids long. Motifs are further indicated in FIG. 40. PRO1760 has a calculated molecular weight of approximately 21,042 daltons and an estimated pI of approximately 5.36. Clone DNA76532-1702 was deposited with the ATCC on Nov. 17, 1998 and is assigned ATCC deposit no. 203473.

An analysis of the Dayhoff database (version 35.45 SwissProt 35), using a WU-BLAST2 sequence alignment analysis of the full-length sequence shown in FIG. 40 (SEQ ID NO:40), revealed sequence identity between the PRO1760 amino acid sequence and the following Dayhoff sequences: CELT07F12_2, T22J18_16, ATF1C12_3, APE3_YEAST, P_W22471, SAU56908_1, SCPA_STRPY, ATAC00423817, SAPURCLUS_2 and AF041468_9.

Example 24

Isolation of cDNA clones Encoding Human PRO1787 Polypeptides [UNQ849]

A consensus DNA sequence was assembled relative to other EST sequences using phrap to form an assembly as described in Example 1 above. This consensus sequence is designated herein "DNA45123". Based on homology of DNA45123 to Incyte EST 3618549 identified in the assembly, as well as other discoveries and information provided herein, the clone including this EST was purchased and sequenced. DNA sequencing of the clone gave the full-length DNA sequence for PRO1787 (herein designated as DNA76510-2504) and the derived protein sequence for PRO1787.

The entire coding sequence of DNA76510-2504 is included in FIG. 41 (SEQ ID NO:41). Clone DNA76510-2504 contains a single open reading frame with an apparent translational initiation site at nucleotide positions 163-165 and an apparent stop codon at nucleotide positions 970-972 of SEQ ID NO:41. The approximate locations of the signal peptide, transmembrane domain, N-glycosylation sites, N-myristoylation sites and a kinase phosphorylation site are indicated in FIG. 42 (SEQ ID NO:42). The predicted polypeptide precursor is 269 amino acids long. Clone DNA76510-2504 has been deposited with the ATCC on Nov. 17, 1998 and is assigned ATCC deposit no. 203477. The full-length PRO1787 protein shown in FIG. 42 has an estimated molecular weight of about 29,082 daltons and a pI of about 9.02.

An analysis of the Dayhoff database (version 35.45 SwissProt 35), using a WU-BLAST2 sequence alignment analysis of the full-length sequence shown in FIG. 42 (SEQ ID NO:42), revealed sequence identity between the PRO1787 amino acid sequence and the following Dayhoff sequences: MYP0_RAT, MYP0_HUMAN, MYP0_BOVIN, GEN12838, HSSCN2B2_1, AF007783_1, HSU90716_1, P_W42015, XLU43330_1 and AF060231_1.

Example 25

Isolation of cDNA clones Encoding Human PRO1868 Polypeptides [UNQ859]

A consensus DNA sequence was assembled relative to other EST sequences using phrap as described in Example 1 above. This consensus sequence is herein designated DNA49803. Based up an observed homology between the DNA49803 consensus sequence and an EST sequence contained within the Incyte EST clone no. 2994689, Incyte EST clone no. 2994689 was purchased and its insert obtained and sequenced. The sequence of that insert is shown in FIG. 43 and is herein designated DNA77624-2515.

The entire nucleotide sequence of DNA77624-2515 is shown in FIG. 43 (SEQ ID NO:43). Clone DNA77624-2515 contains a single open reading frame with an apparent translational initiation site at nucleotide positions 51-53 and ending at the stop codon at nucleotide positions 981-983 (FIG. 43). The predicted polypeptide precursor is 310 amino acids long (FIG. 44). The full-length PRO1868 protein shown in FIG. 44 has an estimated molecular weight of about 35,020 daltons and a pI of about 7.90. Analysis of the full-length PRO1868 sequence shown in FIG. 44 (SEQ ID NO:44) evidences the presence of the following: a signal peptide from about amino acid 1 to about amino acid 30, a transmembrane domain from about amino acid 243 to about amino acid 263, potential N-glycosylation sites from about amino acid 104 to about amino acid 107 and from about amino acid 192 to about amino acid 195, a cAMP- and cGMP-dependent protein kinase phosphorylation site from about amino acid 107 to about amino acid 110, casein kinase II phosphorylation sites from about amino acid 106 to about amino acid 109 and from about amino acid 296 to about amino acid 299, a tyrosine kinase phosphorylation site from about amino acid 69 to about amino acid 77 and potential N-myristolation sites from about amino acid 26 to about amino acid 31, from about amino acid 215 to about amino acid 220, from about amino acid 226 to about amino acid 231, from about amino acid 243 to about amino acid 248, from about amino acid 244 to about amino acid 249 and from about amino acid 262 to about amino acid 267. Clone DNA77624-2515 has been deposited with ATCC on Dec. 22, 1998 and is assigned ATCC deposit no. 203553.

An analysis of the Dayhoff database (version 35.45 SwissProt 35), using a WU-BLAST2 sequence alignment analysis of the full-length sequence shown in FIG. 44 (SEQ ID NO:44), evidenced significant homology between the PRO1868 amino acid sequence and the following Dayhoff sequences: HGS_RC75, P_W61379, A33_HUMAN, P_W14146, P_W14158, AMAL_DROME, P_R77437, I38346, NCM2_HUMAN and PTPD_HUMAN.

Example 26

Isolation of cDNA clones Encoding Human PRO4326 Polypeptides [UNQ1883]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap. This consensus sequence is herein designated DNA85767. Based on the DNA85767 consensus sequence oligonucleotides were synthesized: 1) to identify by PCR a cDNA library that contained the sequence of interest, and 2) for use as probes to isolate a clone of the full-length coding sequence for PRO4326. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'-CGAGGTGCAGATCGAGGTGTCGC-3'     (SEQ ID NO: 132)

reverse PCR primer
5'-GGCACTGCAGGAGAACCTCATGGTC-3'   (SEQ ID NO: 133)
```

Additionally, a synthetic oligonucleotide hybridization probe was constructed from the consensus DNA85767 sequence which had the following nucleotide sequence
hybridization probe

```
                                          (SEQ ID NO: 134)
5'-CAGCAGGTGGAGGAGCTCTTTGGGCTGGAGGATTACTGGTGC-3'
```

RNA for construction of the cDNA libraries was isolated from human bone marrow tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO4326 (designated herein as DNA91779-2571 [FIG. 45, SEQ ID NO: 45]; (UNQ1883) and the derived protein sequence for PRO4326.

The entire nucleotide sequence of UNQ1883 (DNA91779-2571) is shown in FIG. 45 (SEQ ID NO:45). Clone UNQ1883 (DNA91779-2571) contains a single open reading frame with an apparent translational initiation site at nucleotide positions 398-400 and ending at the stop codon at nucleotide positions 3233-3235 (FIG. 45). The predicted polypeptide precursor is 945 amino acids long (FIG. 46). The full-length PRO4326 protein shown in FIG. 46 has an estimated molecular weight of about 103,638 daltons and a pI of about 5.94. Analysis of the full-length PRO4326 sequence shown in FIG. 46 (SEQ ID NO:46) evidences the presence of a variety of important polypeptide domains as shown in FIG. 46. Clone UNQ1883 (DNA91779-2571) has been deposited with ATCC on Mar. 16, 1999 and is assigned ATCC deposit no. 203844.

An analysis of the Dayhoff database (version 35.45 Swiss-Prot 35), using a WU-BLAST2 sequence alignment analysis of the full-length sequence shown in FIG. 46 (SEQ ID NO:46), evidenced significant homology between the PRO4326 amino acid sequence and the following Dayhoff sequences: RNU87306_1, P_W78900, MMU72634_1, AF055634_1, P_W78899, P_W78901, AB005297_1, TSP1_CHICK, SSPO_BOVIN and CFU55935_1.

Example 27

Isolation of cDNA clones Encoding Human PRO4332 Polypeptides [UNQ1887]

A cDNA clone (DNA100272-2969) encoding a native human PRO4332 polypeptide was identified using a yeast screen, in a human breast carcinoma cDNA library that preferentially represents the 5' ends of the primary cDNA clones.

Clone DNA100272-2969 contains a single open reading frame with an apparent translational initiation site at nucleotide positions 483-485 and ending at the stop codon at nucleotide positions 807-809 (FIG. 47; SEQ ID NO:47). The predicted polypeptide precursor is 108 amino acids long (FIG. 48; SEQ ID NO:48). The full-length PRO4332 protein shown in FIG. 48 has an estimated molecular weight of about 12055 daltons and a pI of about 4.69. Analysis of the full-length PRO4332 sequence shown in FIG. 48 (SEQ ID NO:48) evidences the presence of a variety of important polypeptide domains as shown in FIG. 48, wherein the locations given for those important polypeptide domains are approximate as described above. Clone DNA100272-2969 has been deposited with ATCC on Jul. 25, 2000 and is assigned ATCC deposit no. PTA-2299.

An analysis of the Dayhoff database (version 35.45 Swiss-Prot 35), using the ALIGN-2 sequence alignment analysis of the full-length sequence shown in FIG. 48 (SEQ ID NO:48), did not evidence sequence identity between the PRO4332 amino acid sequence and sequences in the Dayhoff database.

Example 28

Isolation of cDNA clones Encoding Human PRO4346 Polypeptides [UNQ1900]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.). The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO4346 was assembled relative to other EST sequences using phrap. This consensus sequence is designated herein "DNA81243".

Based on the DNA81243 consensus sequence oligonucleotides were synthesized: 1) to identify by PCR a cDNA library that contained the sequence of interest, and 2) for use as probes to isolate a clone of the full-length coding sequence for PRO4346. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'GACATATGCTGCCGCTTCCACTCC3'      (SEQ ID NO: 135)
and

reverse PCR primer
5'TCTCTTCTCCGCCTGCTTCCTCAGC3'.    (SEQ ID NO: 136)
```

Additionally, a synthetic oligonucleotide hybridization probe was constructed from the consensus DNA81243 sequence which had the following nucleotide sequence: hybridization probe 5' GACAACTTCTCTGGCGAAGCTCTCTGGGAACTGGAGGTAGCAGG3' (SEQ ID NO:137).

In order to screen several libraries for a source of a full-length clone, DNA from the libraries was screened by PCR amplification with the PCR primer pair identified above. A positive library was then used to isolate clones encoding the PRO4346 gene using the probe oligonucleotide and one of the PCR primers.

RNA for construction of the cDNA libraries was isolated from human bone marrow. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO4346 (designated herein as DNA86594-2587 [FIG. 49, SEQ ID NO:49]; and the derived protein sequence for PRO4346.

The entire coding sequence of PRO4346 is shown in FIG. 49 (SEQ ID NO:49). Clone DNA86594-2587 contains a single open reading frame with an apparent translational initiation site at nucleotide positions 218-220, and an apparent stop codon at nucleotide positions 1823-1825. The predicted polypeptide precursor is 535 amino acids long (FIG. 50; SEQ ID NO:50). Clone DNA86594-2587 (UNQ1900), designated as DNA86594-2587 has been deposited with ATCC on Mar. 30, 1999 and is assigned ATCC deposit no. 203894. The full-length PRO4346 protein shown in FIG. 50 has an estimated molecular weight of about 59716 daltons and a pI of about 6.36.

An analysis of the Dayhoff database (version 35.45 SwissProt 35), using a WU-BLAST2 sequence alignment analysis of the full-length sequence shown in FIG. 50 (SEQ ID NO: 50), revealed homology between the PRO4346 amino acid sequence and the following Dayhoff sequences (sequences and related text incorporated herein): P_W78916, HS45P21__1, HS45P21__3, HSU90552__1, HS45P21__4, P_W71592, S37583, HSAJ03147__4, MOG_HUMAN and AF096870__1.

Example 29

Isolation of cDNA Clones Encoding Human PRO4400 Polypeptides [UNQ1925]

The extracellular domain (ECD) sequences (including the secretion signal sequence, if any) from about 950 known secreted proteins from the Swiss-Prot public database were used to search EST databases. The EST databases included public EST databases (e.g., GenBank), and a proprietary EST database (LIFESEQ®, Incyte Pharmaceuticals, Palo Alto, Calif.) and proprietary ESTs from Genentech. The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence encoding PRO4400 was assembled relative to other EST sequences using repeated cycles of phrap. This consensus sequence is designated herein "DNA77634".

Based on the 77634 consensus sequence oligonucleotides were synthesized: 1) to identify by PCR a cDNA library that contained the sequence of interest, and 2) for use as probes to isolate a clone of the full-length coding sequence for PRO4400. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'GCTGCTGCCGTCCATGCTGATG3'        (SEQ ID NO: 138)
and

reverse PCR primer
5'CTCGGGGAATGTGACATCGTCGC3'..     (SEQ ID NO 139)
```

Additionally, a synthetic oligonucleotide hybridization probe was constructed from the consensus DNA77634 sequence which had the following nucleotide sequence: hybridization probe 5' GCTGCCGTCCATGCTGATGTTTGCGGTGATCGTGG3' (SEQ ID NO:140).

In order to screen several libraries for a source of a full-length clone, DNA from the libraries was screened by PCR amplification with the PCR primer pair identified above. A positive library was then used to isolate clones encoding the PRO4400 gene using the probe oligonucleotide and one of the PCR primers.

RNA for construction of the cDNA libraries was isolated from human adenocarcinoma cell line. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for PRO4400 (designated herein as DNA87974-2609 [FIG. 51, SEQ ID NO:51]; and the derived protein sequence for PRO4400.

The entire coding sequence of PRO4400 is shown in FIG. 51 (SEQ ID NO:51). Clone DNA87974-2609 contains a single open reading frame with an apparent translational initiation site at nucleotide positions 27-29, and an apparent stop codon at nucleotide positions 1026-1028. The predicted polypeptide precursor is 333 amino acids long (FIG. 52; SEQ ID NO:52). Clone DNA87974-2609 (UNQ1925), designated as DNA87974-2609 has been deposited with ATCC on Apr. 27, 1999 and is assigned ATCC deposit no. 203963. The full-length PRO4400 protein shown in FIG. 52 has an estimated molecular weight of about 38618 daltons and a pI of about 9.27.

An analysis of the Dayhoff database (version 35.45 SwissProt 35), using a WU-BLAST2 sequence alignment analysis of the full-length sequence shown in FIG. 52 (SEQ ID NO:52), revealed homology between the PRO4400 amino acid sequence and the following Dayhoff sequences: AF033827_1, AF070594_1, AF022729_1, CEC34F6_4, SYFB_THETH, G70405, SD_DROME, S64023, ALK11YEAST and VG04_HSVII.

Example 30

Isolation of cDNA clones Encoding Human PRO6003 Polypeptides [UNQ2514]

A cDNA clone (DNA83568-2692) encoding a native human PRO6003 polypeptide was identified using a yeast screen, in a human fetal kidney cDNA library that preferentially represents the 5' ends of the primary cDNA clones.

Clone DNA83568-2692 contains a single open reading frame with an apparent translational initiation site at nucleotide positions 638-640 and ending at the stop codon at nucleotide positions 2225-2227 (FIG. 53; SEQ ID NO:53). The predicted polypeptide precursor is 529 amino acids long (FIG. 54; SEQ ID NO:54). The full-length PRO6003 protein shown in FIG. 54 has an estimated molecular weight of about 59,583 daltons and a pI of about 6.36. Analysis of the full-length PRO6003 sequence shown in FIG. 54 (SEQ ID NO:54) evidences the presence of a variety of important polypeptide domains as shown in FIG. 54, wherein the locations given for those important polypeptide domains are approximate as described above. Clone DNA83568-2692 has been deposited with ATCC on Jul. 20, 1999 and is assigned ATCC Deposit No. PTA-386.

An analysis of the Dayhoff database (version 35.45 SwissProt 35), using the ALIGN-2 sequence alignment analysis of the full-length sequence shown in FIG. 54 (SEQ ID NO:54), evidenced sequence identity between the PRO6003 amino acid sequence and the following Dayhoff sequences: P_W58986, PTND7_1, YKZ3_YEAST, CEK04B12_1, AB014464_1, PCU07059_1, S31213, CELF25E2_2, AF036408_1, and AB007932_1.

Example 31

Isolation of cDNA clones Encoding Human PRO6094 Polypeptides [UNQ2542]

The extracellular domain (ECD) sequences (including the secretion signal sequence, if any) from about 950 known secreted proteins from the Swiss-Prot public database were used to search EST databases. The EST databases included a proprietary EST database (LIFESEQ®, Incyte Pharmaceuticals, Palo Alto, Calif.). The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program "phrap" (Phil Green, University of Washington, Seattle, Wash.).

A consensus DNA sequence was assembled relative to other EST sequences using phrap as described above. This consensus sequence is herein designated DNA94621. In some cases, the DNA94621 consensus sequence derives from an intermediate consensus DNA sequence which was extended using repeated cycles of BLAST and phrap to extend that intermediate consensus sequence as far as possible using the sources of EST sequences discussed above.

Based on the DNA94621 consensus sequence, oligonucleotides were synthesized: 1) to identify by PCR a cDNA library that contained the sequence of interest, and 2) for use as probes to isolate a clone of the full-length coding sequence for PRO6094. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., Current Protocols in Molecular Biology, supra, with the PCR primer pair. A positive library was then used to isolate clones encoding the gene of interest using the probe oligonucleotide and one of the primer pairs.

PCR primers (forward and reverse) were synthesized:

```
forward PCR primer
5'GGAGAGGTGGATCACTCGACCCG'        (SEQ ID NO: 141)
and
reverse PCR primer
5'ACATGCCAGGGACTCCTCCGAAAC3'..    (SEQ ID NO: 142)
```

Additionally, a synthetic oligonucleotide hybridization probe was constructed from the consensus DNA94621 sequence which had the following nucleotide sequence: hybridization probe 5' GTGGATCACTCGACCCGCT-TAATTTCGGATCCTGTGCTGCTG' (SEQ ID NO:143).

In order to screen several libraries for a source of a full-length clone, DNA from the libraries was screened by PCR amplification with the PCR primer pair identified above. A positive library was then used to isolate clones encoding the PRO6094 gene using the probe oligonucleotide and one of the PCR primers.

RNA for construction of the cDNA libraries was isolated from human adrenal gland tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for a full-length PRO6094 polypeptide (designated herein as DNA96995-2709 (FIG. 55; SEQ ID NO:55) and the derived protein sequence for that PRO6094 polypeptide.

The full length clone identified above contained a single open reading frame with an apparent translational initiation site at nucleotide positions 197-199 and a stop signal at nucleotide positions 3,266-3,268 (FIG. 55, SEQ ID NO: 55). The predicted polypeptide precursor is 1,023 amino acids long, has a calculated molecular weight of approximately 111,682 daltons and an estimated pI of approximately 4.72. Analysis of the full-length PRO6094 sequence shown in FIG. 56 (SEQ ID NO: 56) evidences the presence of a variety of important polypeptide domains as shown in FIG. 56, wherein the locations given for those important polypeptide domains are approximate as described above. Clone DNA96995-2709 has been deposited with ATCC on Aug. 3, 1999 and is assigned ATCC Deposit No. PTA-475

An analysis of the Dayhoff database (version 35.45 SwissProt 35), using the ALIGN-2 sequence alignment analysis of the full-length sequence shown in FIG. 56 (SEQ ID NO: 56), evidenced sequence identity between the PRO6094 amino acid sequence and the following Dayhoff sequences: AB023144_1, I52657, XLXOLL_1, P_W40224, DAF_CAVPO, HSBMP16_1, P_P80618, GEN10655, P_P94774, and P_R66683.

Example 32

Isolation of cDNA clones Encoding Human PRO6244 Polypeptides [UNQ2564]

A cDNA clone (DNA108743-2722) encoding a native human PRO6244 polypeptide was identified using a yeast screen, in a human cDNA library that preferentially represents the 5' ends of the primary cDNA clones.

Clone DNA108743-2722 contains a single open reading frame with an apparent translational initiation site at nucleotide positions 18-20 and ending at the stop codon at nucleotide positions 1218-1220 (FIG. 57; SEQ ID NO:57). The predicted polypeptide precursor is 400 amino acids long (FIG. 58; SEQ ID NO:58). The full-length PRO6244 protein shown in FIG. 58 has an estimated molecular weight of about 44,876 daltons and a pI of about 8.32. Analysis of the full-length PRO6244 sequence shown in FIG. 58 (SEQ ID NO: 58) evidences the presence of a variety of important polypeptide domains as shown in FIG. 58, wherein the locations given for those important polypeptide domains are approximate as described above. Clone DNA108743-2722 has been deposited with ATCC on Aug. 10, 1999 and is assigned ATCC Deposit No. PTA-508.

An analysis of the Dayhoff database (version 35.45 SwissProt 35), using the ALIGN-2 sequence alignment analysis of the full-length sequence shown in FIG. 58 (SEQ ID NO: 58), evidenced sequence identity between the PRO6244 amino acid sequence and the following Dayhoff sequences: P_W29676; I45887; YN99_YEAST; S63403; S75481; RS2_SPICI; HGS_RK142; A44811; and STRGTFJA_1.

Example 33

Isolation of cDNA clones Encoding Human PRO9820 Polypeptides [UNQ3022]

DNA108769-2765 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST sequence from the Incyte database, designated herein as DNA20895 also designated herein as DNA85061.

Based on the DNA85061 sequence, clone no. 3110062H1 was purchased from Incyte and the cDNA insert from human exocrine gland tissue was obtained and sequenced. It was found herein that cDNA insert encoded a full-length protein. The sequence of this cDNA insert is herein designated as DNA108769-2765.

Clone DNA108769-2765 contains a single open reading frame with an apparent translational initiation site at nucleotide positions 133-135 and ending at the stop codon at nucleotide positions 1834-1836 (FIG. 59; SEQ ID NO:59). The predicted polypeptide precursor is 567 amino acids long (FIG. 60; SEQ ID NO:60). The full-length PRO9820 protein shown in FIG. 60 has an estimated molecular weight of about 65118 daltons and a pI of about 8.33. Analysis of the full-length PRO9820 sequence shown in FIG. 60 (SEQ ID NO:60) evidences the presence of a variety of important polypeptide domains as shown in FIG. 60, wherein the locations given for those important polypeptide domains are approximate as described above. Clone DNA108769-2765 has been deposited with the ATCC on Oct. 19, 1999 and is assigned ATCC deposit no. PTA-861.

An analysis of the Dayhoff database (version 35.45 SwissProt 35), using the ALIGN-2 sequence alignment analysis of the full-length sequence shown in FIG. 60 (SEQ ID NO:60), evidenced sequence identity between the PRO9820 amino acid sequence and the following Dayhoff sequences: S43720; LPH_HUMAN; P_W93002; AB010089S3__1; AB009666S2__1; JC5925; PSU26025__1; S50756; P_W56024; and P_W53469.

Example 34

Isolation of cDNA clones Encoding Human PRO9828 Polypeptides [UNQ3027]

A consensus DNA sequence was assembled relative to other nucleic sequences using phrap as described in Example 1 above. This consensus sequence is herein designated DNA139814. Based on the DNA139814 consensus sequence, oligonucleotides were synthesized: 1) to identify by PCR a cDNA library that contained the sequence of interest, and 2) for use as probes to isolate a clone of the full-length coding sequence for PRO9828. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology*, supra, with the PCR primer pair. A positive library was then used to isolate clones encoding the gene of interest using the probe oligonucleotide and one of the primer pairs.

PCR primers (forward and reverse) were synthesized:

```
5'-AATCTCAGCACCAGCCACTCAGAGCA-3'  (SEQ ID NO: 144)

5'-GTTAAAGAGGGTGCCCTTCCAGCGA-3'   (SEQ ID NO: 145)

5'-TATCCCAATGCCTCCCCACTGCTC-3'    (SEQ ID NO: 146)

5'-GATGAACTTGGCGAAGGGGCGGCA-3'    (SEQ ID NO: 147)
```

RNA for construction of the cDNA libraries was isolated from human fetal liver tissue. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science,* 253:1278-1280 (1991)) in the unique XhoI and NotI sites.

DNA sequencing of the clones isolated as described above gave the full-length DNA sequence for a full-length PRO9828 polypeptide (designated herein as DNA142238-2768 [FIG. 61, SEQ ID NO:61]) and the derived protein sequence for that PRO9828 polypeptide.

The full length clone identified above contained a single open reading frame with an apparent translational initiation site at nucleotide positions 232-234 and a stop signal at nucleotide positions 985-987 (FIG. 61, SEQ ID NO:61). The predicted polypeptide precursor is 251 amino acids long, has a calculated molecular weight of approximately 27,954 daltons and an estimated pI of approximately 9.22. Analysis of the full-length PRO9828 sequence shown in FIG. 62 (SEQ ID NO:62) evidences the presence of a variety of important polypeptide domains as shown in FIG. 62, wherein the locations given for those important polypeptide domains are approximate as described above. Chromosome mapping evidences that the PRO9828-encoding nucleic acid maps to chromosome 12p13 in humans. Clone DNA142238-2768 has been deposited with ATCC on Oct. 5, 1999 and is assigned ATCC deposit no. PTA-819.

An analysis of the Dayhoff database (version 35.45 SwissProt 35), using the ALIGN-2 sequence alignment analysis of the full-length sequence shown in FIG. 62 (SEQ ID NO: 62), evidenced sequence identity between the PRO9828 amino acid sequence and the following Dayhoff sequences: P_Y08581, AB018122__1, FGF3_HUMAN, P_R70824, S54407, P_R80780, P_Y23761, P_W92312, OMFGF6__1 and P_R80871.

Example 35

Isolation of cDNA clones Encoding Human PRO10274 Polypeptides [UNQ3122]

The extracellular domain (ECD) sequences (including the secretion signal sequence, if any) from about 950 known secreted proteins from the Swiss-Prot public database were used to search EST databases. The EST databases included (1) public EST databases (e.g., GenBank and Merck/Washington Univ.), (2) a proprietary EST database (LIFESEQ®, Incyte Pharmaceuticals, Palo Alto, Calif.), and (3) a proprietary EST database from Genentech]. The search was performed using the computer program BLAST or BLAST2 [Altschul et al., *Methods in Enzymology,* 266:460-480 (1996)] as a comparison of the ECD protein sequences to a 6 frame translation of the EST sequences. Those comparisons resulting in a BLAST score of 70 (or in some cases, 90) or greater that did not encode known proteins were clustered and assembled into consensus DNA sequences with the program “phrap” (Phil Green, University of Washington, Seattle, Wash.).

A consensus DNA sequence was assembled relative to other EST sequences using phrap as described above. This consensus sequence is herein designated DNA 120444. In some cases, the consensus sequence derives from an intermediate consensus DNA sequence which was extended using repeated cycles of BLAST and phrap to extend that intermediate consensus sequence as far as possible using the sources of EST sequences discussed above.

EST clone no. 4522347 was then purchased from LIFESEQ®, Incyte Pharmaceuticals, Palo Alto, Calif. and the cDNA insert of that clone was obtained and sequenced in entirety.

DNA sequencing of the insert obtained from the above mentioned clone gave the full-length DNA sequence for a full-length PRO10274 polypeptide (designated herein as DNA139686-2823 [FIG. 63, SEQ ID NO: 63]) and the derived protein sequence for that PRO10274 polypeptide.

The full length clone identified above contained a single open reading frame with an apparent translational initiation site at nucleotide positions 2-4 and a stop signal at nucleotide positions 1412-1414 (FIG. 63, SEQ ID NO:63). The predicted polypeptide precursor is 470 amino acids long, has a calculated molecular weight of approximately 52118 daltons and an estimated pI of approximately 5.06. Analysis of the full-length PRO10274 sequence shown in FIG. 64 (SEQ ID NO:64) evidences the presence of a variety of important polypeptide domains as shown in FIG. 64, wherein the locations given for those important polypeptide domains are approximate as described above. Clone DNA139686-2823 has been deposited with ATCC on Feb. 2, 2000 and is assigned ATCC deposit no. PTA-1264.

An analysis of the Dayhoff database (version 35.45 SwissProt 35), using the ALIGN-2 sequence alignment analysis of the full-length sequence shown in FIG. 64 (SEQ ID NO:64), evidenced sequence identity between the PRO10274 amino acid sequence and the following Dayhoff sequences: af151848_1, cec27h6_4, ceb0491_2, celf36h12_2, cet05g5_10, ynp7_caeel, celc16c8_17, p_w61533, rdaxx_1 AND hsf0811_1.

Example 36

Isolation of cDNA clones Encoding Human PRO16090 Polypeptides [UNQ5783]

DNA144844-2843 was identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally the second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals.

Use of the above described signal sequence algorithm allowed identification of an EST cluster sequence from the Incyte database, designated herein as 1607358. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program “phrap” (Phil Green, University of Washington, Seattle, Wash.). The consensus sequence obtained therefrom is herein designated DNA87966.

In light of an observed sequence homology between the DNA87966 sequence and an EST sequence encompassed within clone no. 1607358 from the Incyte database, clone no. 1607358 was purchased and the cDNA insert was obtained and sequenced. It was found herein that that cDNA insert encoded a full-length protein. The sequence of this cDNA insert is shown in FIG. 65 and is herein designated as DNA144844-2843.

Clone DNA144844-2843 contains a single open reading frame with an apparent translational initiation site at nucleotide positions 88-90 and ending at the stop codon at nucleotide positions 523-525 (FIG. 65; SEQ ID NO:65). The predicted polypeptide precursor is 145 amino acids long (FIG. 66; SEQ ID NO:66). The full-length PRO16090 protein shown in FIG. 66 has an estimated molecular weight of about 16,618 daltons and a pI of about 5.26. Analysis of the full-length PRO16090 sequence shown in FIG. 66 (SEQ ID NO:66) evidences the presence of a variety of important polypeptide domains as shown in FIG. 66, wherein the locations given for those important polypeptide domains are approximate as described above. Clone DNA144844-2843 has been deposited with ATCC on Mar. 21, 2000 and is assigned ATCC deposit no. PTA-1536.

An analysis of the Dayhoff database (version 35.45 SwissProt 35), using the ALIGN-2 sequence alignment analysis of the full-length sequence shown in FIG. 66 (SEQ ID NO:66), evidenced sequence identity between the PRO16090 amino acid sequence and the following Dayhoff sequences: P_W62772, AF161080_1, T04798, D84131_1, D88358_1, GUNA_MICBI, T16251, AF001628_1, AF176784_1, and T26081.

Example 37

Isolation of cDNA clones Encoding Human PRO19644 Polypeptides [UNQ5825]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program “phrap” (Phil Green, University of Washington, Seattle, Wash.). The consensus sequence obtained therefrom is herein designated DNA60765. In light of DNA60765, DNA139592-2866 was identified.

The full length clone (designated herein as DNA139592-2866) shown in FIG. 67 contained a single open reading frame with an apparent translational initiation site at nucleotide positions 192-194 and ending at the stop codon found at nucleotide positions 1122-1124 (FIG. 67; SEQ ID NO:67). The predicted PRO19644 polypeptide precursor (FIG. 68, SEQ ID NO:68) is 882 amino acids long. PRO19644 has a calculated molecular weight of approximately 98428 daltons and an estimated pI of approximately 8.89.

An analysis of the Dayhoff database (version 35.45 SwissProt 35), using a WU-BLAST2 sequence alignment analysis of the full-length sequence shown in FIG. 68 (SEQ ID NO:68), revealed homology between the PRO19644 amino acid sequence and the following Dayhoff sequences (sequences and related text incorporated herein): P_W56538.

Clone DNA139592-2866 was deposited with the ATCC on Mar. 28, 2000 and is assigned ATCC deposit no. PTA-1587.

Example 38

Isolation of cDNA clones Encoding Human PRO21340 Polypeptides [UNQ5982]

A cDNA clone (DNA 176775-2957) encoding a native human PRO21340 polypeptide was identified using a yeast screen, in a cDNA library derived from a mixture of human tissues that preferentially represents the 5' ends of the primary cDNA clones.

Clone DNA176775-2957 contains a single open reading frame with an apparent translational initiation site at nucleotide positions 128-130 and ending at the stop codon at nucleotide positions 2489-2491 (FIG. 69; SEQ ID NO: 69). The predicted polypeptide precursor is 787 amino acids long (FIG. 70; SEQ ID NO:70). The full-length PRO21340 protein shown in FIG. 70 has an estimated molecular weight of about 87934 daltons and a pI of about 5.49. Analysis of the full-length PRO21340 sequence shown in FIG. 70 (SEQ ID NO:70) evidences the presence of a variety of important polypeptide domains as shown in FIG. 70, wherein the locations given for those important polypeptide domains are approximate as described above. Clone DNA176775-2957 has been deposited with ATCC on Jul. 25, 2000 and is assigned ATCC deposit no. PTA-2303.

An analysis of the Dayhoff database (version 35.45 SwissProt 35), using the ALIGN-2 sequence alignment analysis of the full-length sequence shown in FIG. 70 (SEQ ID NO:70), evidenced sequence identity between the PRO21340 amino acid sequence and the following Dayhoff sequences: MFTMDCIII_1, HSA133005_1, ADO2_HUMAN, P_R87036, S18968, P_W44120, AF167403_1, AF171931_1, AF029899_1 and AF029900_1.

Example 39

Isolation of cDNA Clones Encoding Human PRO1026 Polypeptides [UNQ511]

Use of the signal sequence algorithm described in Example 3 above allowed identification of an EST cluster sequence from the Incyte database. This EST cluster sequence was then compared to a variety of expressed sequence tag (EST) databases which included public EST databases (e.g., GenBank) and a proprietary EST DNA database (Lifeseq®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56434.

In light of an observed sequence homology between the DNA56434 sequence and an EST sequence encompassed within the Incyte EST clone no. 1227491, the Incyte EST clone 1227491 was purchased and the cDNA insert was obtained and sequenced. It was found that this insert encoded a full-length protein. The sequence of this cDNA insert is shown in FIG. 77 and is herein designated as DNA59613-1417.

The entire nucleotide sequence of DNA59613-1417 is shown in FIG. 77 (SEQ ID NO:77). Clone DNA59613-1417 contains a single open reading frame with an apparent translational initiation site at nucleotide positions 233-235 and ending at the stop codon at nucleotide positions 944-946 (FIG. 77). The predicted polypeptide precursor is 237 amino acids long (FIG. 78). The full-length PRO1026 protein shown in FIG. 78 has an estimated molecular weight of about 25,284 daltons and a pI of about 5.74. Clone DNA59613-1417 has been deposited with the ATCC. Regarding the sequence, it is understood that the deposited clone contains the correct sequence, and the sequences provided herein are based on known sequencing techniques.

Analyzing the amino acid sequence of SEQ ID NO:78, the putative signal peptide is at about amino acids 1-25 of SEQ ID NO:78. The N-glycosylation sites are at about amino acids 45-48, 73-76, 107-110, 118-121, 132-135, 172-175, 175-178 and 185-188 of SEQ ID NO:78. An arthropod defensins conserved region is at about amino acids 176-182 of SEQ ID NO:78. A kringle domain begins at about amino acid 128 of SEQ ID NO:78 and a ly-6/u-PAR domain begins at about amino acid 6 of SEQ ID NO:78. The corresponding nucleotides of these amino acid sequences and others can be routinely determined given the sequences provided herein.

The designations appearing in a Dayhoff database with which PRO1026 has some sequence identity are as follows: SSC20F10_1; SF041083; P_W26579; S44208; JC2394; PSTA_DICDI; A27020; S59310; RAG11_RABIT; and MUSBALBC1_1.

Example 40

Isolation of cDNA clones Encoding Human PRO1124 Polypeptides (UNQ18919)

Use of the signal sequence algorithm described in Example 3 above allowed identification of a single EST cluster sequence from the Incyte database. This EST cluster sequence was then compared to a variety of expressed sequence tag (EST) databases which included public EST databases (e.g., GenBank) and a proprietary EST DNA database (LIFESEQ®, Incyte Pharmaceuticals, Palo Alto, Calif.) to identify existing homologies. The homology search was performed using the computer program BLAST or BLAST2 (Altshul et al., *Methods in Enzymology* 266:460-480 (1996)). Those comparisons resulting in a BLAST score of 70 (or in some cases 90) or greater that did not encode known proteins were clustered and assembled into a consensus DNA sequence with the program "phrap" (Phil Green, University of Washington, Seattle, Wash.). The consensus sequence obtained therefrom is herein designated DNA56035.

In light of an observed sequence homology between the DNA56035 consensus sequence and an EST sequence encompassed within the Incyte EST clone no. 2767646, the Incyte EST clone 2767646 was purchased and the cDNA insert was obtained and sequenced. It was found that this insert encoded a full-length protein. The sequence of this cDNA insert is shown in FIG. 75 and is herein designated as DNA60629-1481.

The full length clone shown in FIG. 75 contained a single open reading frame with an apparent translational initiation site at nucleotide positions 25-27 and ending at the stop codon found at nucleotide positions 2782-2784 (FIG. 75; SEQ ID NO:75). The predicted polypeptide precursor (FIG. 76, SEQ ID NO:76) is 919 amino acids long. PRO1124 has a calculated molecular weight of approximately 101,282 daltons and an estimated pI of approximately 5.37. Clone DNA60629-1481 has been deposited with the ATCC on Jun. 16, 1998 and is assigned ATCC deposit no. 209979. It is understood that the deposited clone has the actual sequence, whereas only representations based on current sequencing techniques which may include normal and minor errors, are provided herein.

Based on a WU-BLAST2 sequence alignment analysis of the full-length sequence, PRO1124 shows significant amino acid sequence identity to a chloride channel protein and to ECAM-1. Specifically, the following Dayhoff designations were identified as having sequence identity with PRO1124: ECLC_BOVIN, AF001261_1, P_W06548, SSC6A10_1, AF004355_1, S76691, AF017642, BYU06866_2, CSA_DICDI and SAU47139_2.

Example 41

Generation and Analysis of Mice Comprising PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Gene Disruptions To investigate the role of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides, disruptions in PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 genes were produced by homologous recombination or retroviral insertion techniques. Specifically, transgenic mice comprising disruptions in PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 genes (i.e., knockout mice) were created by either gene targeting or gene trapping. Mutations were confirmed by southern blot analysis to confirm correct targeting on both the 5' and 3' ends. Gene-specific genotyping was also performed by genomic PCR to confirm the loss of the endogenous native transcript as demonstrated by RT-PCR using primers that anneal to exons flanking the site of insertion. Targeting vectors were electroporated into 129 strain ES cells and targeted clones were identified. Targeted clones were microinjected into host blastocysts to produce chimeras. Chimeras were bred with C57 animals to produce F1 heterozygotes. Heterozygotes were intercrossed to produce F2 wildtype, heterozygote and homozygote cohorts which were used for phenotypic analysis. Rarely, if not enough F1 heterozygotes were produced, the F1 hets were bred to wildtype C57 mice to produce sufficient heterozygotes to breed for cohorts to be analyzed for a phenotype. All phenotypic analysis was performed from 12-16 weeks after birth.

Summary of Results 41.1. Generation and Analysis of Mice Comprising DNA26844-1394 (UNQ168) Gene Disruptions In these knockout experiments, the gene encoding PRO194 polypeptides (designated as DNA26844-1394) (UNQ168) was disrupted. The gene specific information for these studies is as follows: the mutated mouse gene corresponds to nucleotide reference: NM_025693 or ACCESSION: NM_025693 NID: gi 21313375 ref NM_025693.1 *Mus musculus* RIKEN cDNA 5730578N08 gene (5730578N08Rik); protein reference: Q9D8U2 or ACCESSION: Q9D8U2 NID: *Mus musculus* (Mouse). 5730578N08Rik protein (RIKEN cDNA 5730578N08 gene). MOUSESPTRNRDB; the human gene sequence reference: NM_080652 or ACCESSION: NM_080652 NID: gi 18087812 ref NM_080652.1 *Homo sapiens* similar to RIKEN cDNA 5730578N08 gene (MGC15397); the human protein sequence corresponds to reference: Q96HV5 or ACCESSION: Q96HV5 NID: *Homo sapiens* (Human). Hypothetical protein. HUMANSPTRNRDB.

The mouse gene of interest is RIKEN cDNA 5730578N08 gene, ortholog of human MGC15397 (similar to RIKEN cDNA 5730578N08 gene). Aliases include 2900010K02Rik. MGC15397 is a hypothetical plasma membrane protein, consisting of a signal peptide and six transmembrane segments.

| | wt | het | hom | Total |
|---|---|---|---|---|
| Observed | 17 | 37 | 16 | 70 |
| Expected | 17.5 | 35 | 17.5 | 70 |

Chi-Sq. = 0.26
Significance = 0.87935
(hom/n) = 0.23
Avg. Litter Size = 7
Mutation Type: Retroviral Insertion (OST)

Retroviral insertion occurred in the intron between coding exons 1 and 2 (NCBI accession NM_025693.1).

Wild-type Expression Panel: Expression of the target gene was detected in all 13 adult tissue samples tested by RT-PCR, except skeletal muscle, bone, and adipose. This gene is elevated in normal small intestine.

RT-PCR analysis revealed that the transcript was absent in the (−/−) mouse analyzed (F-97). Disruption of the target gene was confirmed by Inverse PCR.

41.1.1. Phenotypic Analysis (for Disrupted Gene: DNA26844-1394 (UNQ168)

(a) Overall Phenotypic Summary:

Mutation of the gene encoding the ortholog of a human hypothetical membrane protein resulted in immunological abnormalities marked by an increased mean serum TNF-alpha, MCP 1 and IL-6 response to a LPS challenge. In addition, male knockouts exhibited a significant increase in triglyceride levels as well as an increased total body fat. Both male homozygous (−/−) and heterozygous (+/−) mice showed increased bone mineral density measurements. Female (−/−) mice also showed increased bone-related measurements. Transcript was absent by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACS Calibur instrument.

Results:

The (−/−) mice exhibited an increased mean serum IL-6, MCP-1 and TNF-alpha response to LPS challenge when compared with their (+/+) littermates and the historical mean.

Analyzed wt/het/hom: 6/4/8

In summary, the LPS endotoxin challenge demonstrated that knockout mice deficient in the gene encoding PRO194 polypeptides exhibit immunological abnormalities when compared with their wild-type littermates. In particular, the mutant mice exhibited an increased ability to elicit an immunological response (TNF-alpha, MCP 1 and IL-6 production) when challenged with the LPS endotoxin indicating a pronounced proinflammatory response. IL-6 contributes to the later stages of B cell activation. In addition, IL-6 plays a critical role in inducing the acute phase response and systemic inflammation. This suggests that antagonists (inhibitors) of PRO194 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO194 polypeptides or agonists thereof, would be useful in inhibiting the immune response and would be useful candidates for suppressing harmful immune responses, e.g. in the case of graft rejection or graft-versus-host diseases.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

The male (−/−) knockout mice showed a significant increase in triglyceride levels when compared to their wild-type littermate controls.

As summarized above, the male (−/−) mice exhibited notably increased triglyceride levels when compared with their gender-matched (+/+) littermates and the historical means. However, both insulin levels and glucose tolerance testing showed no abnormalities. Because the triglyceride levels were significantly elevated, mutant mice deficient in the PRO194 gene can serve as a model for cardiovascular disease. PRO194 polypeptides or its encoding gene would be useful in regulating blood lipids such as triglycerides. Thus, PRO194 polypeptides or agonists thereof would be useful in the treatment of such cardiovascular diseases as hypertension, atherosclerosis, heart failure, stroke, various coronary diseases, or hypertriglyceridemia, and/or obesity.

(d) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited increased mean percent total body fat when compared with their gender-matched (+/+) littermates. In addition, an increased mean bone mineral density was exhibited in both male homozygous (−/−) and heterozygous (+/−) mice. The female (−/−) mice exhibited increased mean bone mineral content (BMC), BMC/LBM ratio, total body bone mineral density (BMD), femoral bone mineral density, and vertebrae bone mineral density when compared with their (+/+) littermates and the historical means.

Analyzed wt/het/hom: 4/4/8

Summary:

The (−/−) mice exhibited increased mean total body fat, bone mineral density, bone mineral content, BMC/LBM, and total body and femoral bone mineral density when compared with their gender-matched (+/+) littermates. These results indicate that the knockout mutant phenotype is associated with such bone abnormalities as osteopetrosis. Osteopetrosis is a condition characterized by abnormal thickening and hardening of bone and abnormal fragility of the bones. As such, PRO194 polypeptides or agonists thereof would be beneficial for the treatment of osteopetrosis. A phenotype associated with an increased bone mineral content, and total body and femoral bone mineral density suggests that agents which mimic these effects (e.g. antagonists of PRO194 polypeptides) would be useful in bone healing.

(e) Expression Profiles

Expression profile analysis indicates that UNQ168 is elevated in normal small intestine. Thus, this gene is likely involved in innate immunity in the intestine.

41.2. Generation and Analysis of Mice Comprising DNA32298-1132 (UNQ194) Gene Disruptions In these knockout experiments, the gene encoding PRO220 polypeptides (designated as DNA32298-1132) (UNQ194) was disrupted. The gene specific information for these studies is as follows: the mutated mouse gene corresponds to nucleotide reference: D49802 or ACCESSION: D49802 NID: 1369905 *Mus musculus Mus musculus* mRNA for leucine-rich repeat protein; protein reference: P97860 or ACCESSION: P97860 NID: *Mus musculus* (Mouse). LEUCINE-RICH REPEAT PROTEIN PRECURSOR (FRAGMENT). MOUSE SPTRNRDB; the human gene sequence reference: NM 018334 or *Homo sapiens* leucine rich repeat neuronal 3 (LRRN3); the human protein sequence corresponds to reference: Q9H3W5 or ACCESSION: Q9H3W5 NID: *Homo sapiens* (Human). HYPOTHETICAL 79.4 KDA PROTEIN (NEURONAL LEUCINE-RICH REPEAT PROTEIN-3). HUMANSPTRNRDB.

The mouse gene of interest is Lrrn3 (leucine rich repeat protein 3, neuronal), ortholog of human LRRN3 (leucine rich repeat neuronal 3). Aliases include NLRR-3; NLRR3; FLJ1129; and leucine-rich repeat protein, neuronal 3.

LRRN3 is a type I plasma membrane protein, consisting of an extracellular segment, a transmembrane segment, and a short cytoplasmic C terminus. The extracellular segment is composed of a signal peptide, several leucine-rich repeats, an immunoglobulin-like domain, and a fibronectin type III domain; the cytoplasmic domain contains clathrin-mediated endocytosis motifs. Since immunoglobulin-like domains and fibronectin type III domains are typically involved in protein-protein interactions, LRRN3 may function as a cell adhesion or signal transduction molecule (Taniguchi et al, *Brain Res Mol Brain Res;* 36(1):45-52 (1996); Fukamachi et al, *J Biol Chem;* 277(46):43549-52 (2002)). In fibroblasts transfected with LRRN3 expression plasmid, LRRN3 is likely to facilitate internalization of EGF in clathrin-coated vesicles, potentiating Ras-MAPK signaling (Fukamachi et al, *J Biol Chem;* 277(46):43549-52 (2002)). Expression of LRRN3 is highest in the developing brain and is upregulated in injured brain, suggesting that the protein may play a role in development and maintenance of the nervous system (Taniguchi et al, *Brain Res Mol Brain Res;* 36(1):45-52 (1996); Ishii et al, *Brain Res Mol Brain Res;* 40(1):148-52 (1996); Fukamachi et al, *J Biol Chem;* 277(46):43549-52 (2002)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 18 | 31 | 23 | 72 |
| Expected | 18 | 36 | 18 | 72 |

Chi-Sq. = 2.08
Significance = 0.35287
(hom/n) = 0.32
Avg. Litter Size = 8
Mutation Type: Homologous Recombination (standard)
Coding exon 1 was targeted (NCBI accession D49802.1).

Wild-type Expression Panel: Expression of the target gene was detected, among 13 adult tissue samples tested by RT-PCR, in brain, spinal cord, eye, spleen, liver, and adipose.

Disruption of the target gene was confirmed by Southern hybridization analysis.

41.2.1. Phenotypic Analysis (for Disrupted Gene: DNA32298-1132 (UNQ194)

(a) Overall Phenotypic Summary:

The homozygous mutant mice exhibited increased mean percent body fat and fat mass as well as abnormal bone-related measurements when compared with their gender-matched wild-type littermates and the historical means. In addition, the homozygous mutant mice exhibited enhanced glucose tolerance with increased insulin sensitivity when compared with their gender-matched wild-type littermates. The mutant mice also exhibited decreased activity in open field testing suggestive of depressive disorders. Hotplate results suggest an enhanced nociception response or increased sensitivity. Disruption of the target gene was confirmed by Southern hybridization analysis.

(b) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited increased mean percent total body fat when compared with their gender-matched (+/+) littermates and the historical means. The female (−/−) mice also exhibited increased mean total fat mass.

Micro-CT: The male (−/−) mice exhibited decreased mean femoral mid-shaft cortical thickness and cross-sectional area when compared with their gender-matched (+/+) littermates and the historical means.

Analyzed wt/het/hom: 4/4/8

Summary:

The (−/−) mice analyzed by DEXA exhibited decreased bone measurements when compared with their (+/+) littermates, suggestive of abnormal bone disorders. In addition, both male and female mutant (−/−) mice also exhibited an increased mean percentage of body fat suggestive of an obesity phenotype. These observations suggest that mutant mice deficient in the gene which encodes PRO220 polypeptides leads to metabolic disorders associated with accumulation of fat but also abnormal bone measurements reflective of general metabolic disorders which can be associated with obesity. This in combination with Blood Chemistry analysis (showing an enhanced glucose tolerance) suggest that the mutant mice exhibit complex metabolic effects including an abnormal glucose metabolism. In addition, the mutant mice exhibited increased insulin sensitivity as demonstrated by no change in insulin levels, yet an enhanced glucose tolerance. Thus, PRO220 polypeptides or agonists thereof would be useful in the treatment or prevention of such disorders as obesity or other metabolic diseases.

(c) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

Glucose Tolerance Test: The mutant (−/−) mice tested exhibited enhanced glucose tolerance when compared with their gender-matched (+/+) littermates.

Analyzed wt/het/hom: 4/4/8

Summary:

In these studies the mutant (−/−) mice showed an increased or enhanced glucose tolerance in the presence of normal fasting glucose at all 3 intervals tested when compared with their gender-matched (+/+) littermates and the historical means. In addition, hyperinsulinemia was not apparent in the (−/−) mice. Thus, knockout mice exhibited an increased insulin sensitivity or the opposite phenotypic pattern of an impaired glucose homeostasis, and as such antagonists (inhibitors) to PRO220 polypeptides or its encoding gene would be useful in the treatment of impaired glucose homeostasis.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 5/4/8

Results:

A notable difference was observed during open field activity testing. The male (−/−) mice exhibited an increased median sum time in the center area when compared with their gender-matched (+/+) littermates, which is indicative of a decreased anxiety-like response in the mutants. Thus, knockout mice demonstrated a phenotype consistent with depressive disorders, schizophrenia and/or bipolar disorders. Thus, PRO220 polypeptides and agonists thereof would be useful for the treatment or amelioration of the symptoms associated with depressive disorders.

Hot Plate Testing

Test Description: The hot plate test for nociception is carried out by placing each mouse on a small enclosed 55° C. hot plate. Latency to a hind limb response (lick, shake, or jump) is recorded, with a maximum time on the hot plate of 30 sec. Each animal is tested once.

Results:

The mutant (−/−) mice exhibited a reduced latency to respond (for example an increased sensitivity-difference) when compared with their gender-matched (+/+) littermate controls. These results suggest an enhanced nociception response.

41.3. Generation and Analysis of Mice Comprising DNA34392-1170 (UNQ215) Gene Disruptions In these knockout experiments, the gene encoding PRO241 polypeptides (designated as DNA34392-1170) (UNQ215) was disrupted. The gene specific information for these studies is as follows: the mutated mouse gene corresponds to nucleotide reference: NM_025711 or ACCESSION: NM_025711 NID: gi 13385169 ref NM_025711.1 *Mus musculus* asporin (Aspn); protein reference: Q99MQ4 or ACCESSION: Q99MQ4 NID: *Mus musculus* (Mouse). ASPORIN PRECURSOR. MOUSESPTRNRDB; the human gene sequence reference: NM_017680 or ACCESSION: NM_017680 NID: gi 16596677 ref NM_017680.2 *Homo sapiens* asporin (LRR class 1) (ASPN); the human protein sequence corresponds to reference: Q9BXN1 or ACCESSION: Q9BXN1 NID: *Homo sapiens* (Human). ASPORIN PRECURSOR. HUMANSPTRNRDB.

The mouse gene of interest is Aspn (asporin), ortholog of human ASPN (asporin [LRR class 1]). Aliases include PLAP1, SLRR1C, 4631401G09Rik, FLJ20129, small leucine-rich protein 1C, and periodontal ligament associated protein 1.

ASPN is a secreted leucine-rich repeat-containing protein that binds with collagen and associates with extracellular matrix. ASPN consists of a signal peptide, a putative propeptide, 4 amino-terminal cysteines, 10 leucine-rich repeats, and 2 C-terminal cysteines. The N terminus also contains a unique aspartate-rich region. ASPN is expressed primarily in developing skeleton, cartilage, and connective tissue. Relatively high levels of ASPN are found in osteoarthritic articular cartilage, aorta, uterus, heart, and liver. ASPN may play a role in modulating the organization or stabilization of collagen fibrils and in formation of mineralized matrix in periodontal ligament tissues (Lorenzo et al, *J Biol Chem;* 276(15):12201-11 (2001); Henry et al, *J Biol Chem;* 276(15):12212-21 (2001); Yamada et al, *Gene;* 275(2):279-86 (2001)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 19 | 37 | 17 | 73 |
| Expected | 18.25 | 36.5 | 18.25 | 73 |

Chi-Sq. = 0.12
Significance = 0.94022
(hom/n) = 0.23
Avg. Litter Size = 7
Mutation Type: Homologous Recombination (standard)
Coding exon 1 was targeted (NCBI accession AF316825.1).

Wild-type Expression Panel: Expression of the target gene was detected in all 13 adult tissue samples tested by RT-PCR, except liver and bone.

Disruption of the target gene was confirmed by Southern hybridization analysis.

41.3.1. Phenotypic Analysis (for Disrupted Gene: DNA34392-1170 (UNQ215)

(a) Overall Phenotypic Summary:

Mutation of the gene encoding the ortholog of human asporin (LRR class 1) (ASPN) resulted in enhanced glucose tolerance with possibly increased insulin sensitivity in mutant (−/−) mice. Both male and female (−/−) mice exhibited decreased bone-related measurements. Gene disruption was confirmed by Southern blot.

(b) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

Glucose Tolerance Test: The male mutant (−/−) mice tested exhibited an enhanced glucose tolerance when compared with their gender-matched (+/+) littermates.

Analyzed wt/het/hom: 4/4/8

Summary:

In these studies, the male mutant (−/−) mice showed an increased or enhanced glucose tolerance in the presence of normal fasting glucose at all 3 intervals tested when compared with their gender-matched (+/+) littermates and the historical means. In addition, hyperinsulinemia was not apparent in the (−/−) mice. Thus, knockout mice exhibited the opposite phenotypic pattern of an impaired glucose homeostasis, and as such antagonists (inhibitors) to PRO241 polypeptides or its encoding gene would be useful in the treatment of impaired glucose homeostasis and/or various cardiovascular diseases.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Female (−/−) mice exhibited a lower total body volume bone mineral density (vBMD>1 standard deviation), total body bone mineral density (1 standard deviation), and femoral bone mineral density (1 standard deviation) compared with their gender-matched littermate controls. Male (−/−) mice exhibited decreased trabecular bone volume, number, and connectivity density as well as midshaft femoral total area compared to wild-type littermates.

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO241 polypeptides or agonists thereof would be useful in maintaining bone homeostasis. In addition, PRO241 polypeptides or its encoding gene would be important in bone healing or for the treatment of arthritis or osteoporosis; whereas antagonists to PRO241 polypeptides or its encoding gene would lead to abnormal or pathological bone disorders including inflammatory diseases associated with abnormal bone metabolism including arthritis, osteoporosis, and osteopenia.

41.4. Generation and Analysis of Mice Comprising DNA23318-1211 (UNQ247) Gene Disruptions In these knockout experiments, the gene encoding PRO284 polypeptides (designated as DNA23318-1211) (UNQ247) was disrupted. The gene specific information for these studies is as follows: the mutated mouse gene corresponds to nucleotide reference: NM_024273 or ACCESSION: NM_024273 NID: gi 13357215 ref NM_024273.1 *Mus musculus* RIKEN cDNA 4930455C21 gene (4930455C21Rik); protein reference: Q99LS9 or ACCESSION: Q99LS9 NID: *Mus musculus* (Mouse). Similar to M5-14 protein. MOUSESPTRNRDB; the human gene sequence reference: NM_016589 or ACCESSION: NM_016589 NID: gi 7706124 ref NM_016589.1 *Homo sapiens* chromosome 3 open reading frame 1 (C3orf1); the human protein sequence corresponds to reference: Q9NPL8 or ACCESSION: Q9NPL8 NID: *Homo sapiens* (Human). C3orf1 hypothetical protein. HUMANSPTRNRDB.

The mouse gene of interest is RIKEN cDNA 4930455C21 gene, ortholog of human C3orf1 (chromosome 3 open reading frame 1). Aliases include 2810021C21Rik and M5-14 protein.

C3orf1 is a hypothetical protein translocase subunit, consisting of a Tim17/Tim22/Tim23 family domain. This domain is found in inner mitochondrial proteins Tim17, Tim22, and Tim23. These proteins, along with the pre-protein translocase of the mitochondrial outer membrane (Tom), form a translocase channel through which proteins from the cytoplasm enter the mitochondrial matrix. A mitochondrial matrix protein provides the ATPase associated with this complex (Pfam accession PF02466). C3orf1 expression is widespread but particularly high in skeletal and heart muscle (Escarceller et al, *DNA Seq;* 11(3-4):335-8 (2000)).

| | wt | het | hom | Total |
|---|---|---|---|---|
| Observed | 22 | 40 | 0 | 62 |
| Expected | 15.5 | 31 | 15.5 | 62 |

Chi-Sq. = 20.84
Significance = 0.00003
(hom/n) = 0.00
Avg. Litter Size = 6
Mutation Type: Retroviral Insertion (OST)

Retroviral insertion occurred in the intron between coding exons 5 and 6 (NCBI accession NM_024273.1).

Wild-type Expression Panel: Expression of the target gene was detected in all 13 adult tissue samples tested by RT-PCR, except bone.

Due to lethality, transcript expression analysis was not performed. Disruption of the target gene was confirmed by Inverse PCR.

UNQ247 is expressed ubiquitously during early development.

41.4.1. Phenotypic Analysis (for Disrupted Gene: DNA23318-1211 (UNQ247)

(a) Overall Phenotypic Summary:

Mutation of the gene encoding the ortholog of human chromosome 3 open reading frame 1 (C3orf1) resulted in lethality of (−/−) mutants. The (+/−) mice exhibited decreased bone-related measurements.

Discussion Related to Embryonic Developmental Abnormality of Lethality:

Embryonic lethality in knockout mice usually results from various serious developmental problems including but not limited to neurodegenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Pathology

Microscopic Observations: Not tested due to embryonic lethality. At day 12.5, there were 54 embryos observed: 30 (+/−) embryos, 13 (+/+) embryos, 10 resorption moles, and 1 inconclusive. Lethality occurs before embryonic day 12.5d.

Gene Expression: LacZ activity was not detected in the panel of tissues by immunohistochemical analysis.

Analyzed wt/het/hom: 1/2/0

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type and 4 heterozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 heterozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Male heterozygous (+/−) mice had decreased bone mineral content (1 standard deviation) and bone mineral density (1 standard deviation) measurements when compared to wild-type littermates. Female heterozygotes (+/−) also showed decreased bone mineral content, BMC/LBM, total body bone mineral density (1 standard deviation), femoral bone mineral density (1 standard deviation) and vertebrae bone mineral density (1 standard deviation) compared to wild-type littermates. Male heterozygotes (+/−) showed decreased trabecular bone volume, number, thickness, and connectivity density compared to gender-matched (+/+) littermates. Midshaft femoral cortical thickness also was decreased compared to the wild-type littermates. Thus, the gene encoding PRO284 polypeptides must be essential for normal bone development.

41.5. Generation and Analysis of Mice Comprising DNA40981-1234 (UNQ292) Gene Disruptions In these knockout experiments, the gene encoding PRO331 polypeptides (designated as DNA40981-1234) (UNQ292) was disrupted. The gene specific information for these studies is as follows: the mutated mouse gene corresponds to nucleotide reference: NM_178725 or *Mus musculus* RIKEN cDNA 6430556C10 gene (6430556C10Rik); protein reference: Q8BGH8 or ACCESSION: Q8BGH8 NID: *Mus musculus* (Mouse). Weakly similar to brain tumor associated protein NAG14; the human gene sequence reference: XM_045271 or *Homo sapiens* KIAA1580 protein (KIAA1580); the human protein sequence corresponds to reference: Q9HCJ2 or ACCESSION: Q9HCJ2 NID: *Homo sapiens* (Human). KIAA1580 PROTEIN (FRAGMENT). HUMANSPTRNRDB.

The mouse gene of interest is RIKEN cDNA 6430556C10 gene, ortholog of human NGL-1 (netrin-G1 ligand). Aliases include NGL-1, mKIAA1580, netrin-G1 ligand, and KIAA1580.

NGL-1 is a type I plasma membrane protein expressed on striatal and cortical neurons that functions as a ligand for axon guidance co-receptor netrin-G1, a lipid anchored protein expressed on thalamocortical axons. NGL-1 consists of a signal peptide, leucine-rich repeats, an immunoglobulin-like domain, a transmembrane segment, and a short cytoplasmic C terminus. NGL-1 interacts with netrin-G1 via its leucine-rich repeat. Moreover, the C-terminal cytoplasmic segment may interact with intracellular signal transduction proteins. NGL-1 plays a role in promoting the growth of thalamocortical axons to the striatum and cerebral cortex during development (Lin et al, *Nat Neurosci;* 6(12): 1270-6 (2003)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 24 | 43 | 26 | 93 |
| Expected | 23.25 | 46.5 | 23.25 | 93 |

Chi-Sq. = 0.61
Significance = 0.73605
(hom/n) = 0.28
Avg. Litter Size = 9
Mutation Type: Homologous Recombination (standard)

Coding exon 1 was targeted (NCBI accession AK048322.1).

Wild-type Expression Panel: Expression of the target gene was detected in all 13 adult tissue samples tested by RT-PCR, except lung, skeletal muscle, and bone.

Disruption of the target gene was confirmed by Southern hybridization analysis.

41.5.1. Phenotypic Analysis (for Disrupted Gene: DNA40981-1234 (UNQ292)

(a) Overall Phenotypic Summary:

Mutation of the gene encoding the ortholog of human netrin-G1 ligand (NGL-1) resulted in an increased IL-6 and mean serum TNF-alpha response to a LPS challenge. In addition, the mutant (−/−) mice exhibited a decrease in learned helplessness. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders. In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFa, MCP-1, and IL-6 on the FACSCalibur instrument.

Results:

The (−/−) mice exhibited an increased mean serum IL-6 and TNF-alpha response to a LPS challenge when compared with their (+/+) littermates and the historical mean.

Analyzed wt/het/hom: 6/4/8

In summary, the LPS endotoxin challenge demonstrated that knockout mice deficient in the gene encoding PRO331 polypeptides exhibit immunological abnormalities when compared with their wild-type littermates. In particular, the mutant mice exhibited an increased ability to elicit an immunological response (TNF-alpha and IL-6 production) when challenged with the LPS endotoxin indicating a pronounced proinflammatory response. IL-6 contributes to the later stages of B cell activation. In addition, IL-6 plays a critical role in inducing the acute phase response and systemic inflammation. This suggests that antagonists (inhibitors) of PRO331 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO331 polypeptides or agonists thereof, would be useful in inhibiting the immune response and would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Tail Suspension Testing:

The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

The (−/−) mice showed an increased response time during the tail suspension testing. These results are indicative of a decrease in learned helplessness. Thus, the mutant mice showed a phenotype relevant to depression.

41.6. Generation and Analysis of Mice Comprising DNA44192-1246 (UNQ311) Gene Disruptions In these knockout experiments, the gene encoding PRO354 polypeptides (designated as DNA44192-1246) (UNQ311) was disrupted. The gene specific information for these studies is as follows: the mutated mouse gene corresponds to nucleotide reference: NM_172471 or *Mus musculus* inter-alpha (globulin) inhibitor H5 (Itih5); protein reference: Q80VG0 or ACCESSION: Q80VG0 NID: *Mus musculus* (Mouse). Inter-alpha trypsin inhibitor heavy chain 5; the human gene sequence reference: NM_030569 or *Homo sapiens* inter-alpha (globulin) inhibitor H5 (ITIH5); the human protein sequence corresponds to reference: Q86UX2 or ACCESSION: Q86UX2 NID: *Homo sapiens* (Human). Inter-alpha trypsin inhibitor heavy chain 5.

The mouse gene of interest is Itih5 (inter-alpha (globulin) inhibitor H5), ortholog of human ITIH5. Aliases include E130106B02, 5430408M01Rik, and inter-alpha trypsin inhibitor heavy chain precursor 5.

ITIH5 is a heavy chain subunit of a secreted protease inhibitor of the inter-alpha-trypsin inhibitor (ITI) family. The ITI holoprotein typically consists of a light chain and a variable set of heavy chains. ITIH5 consists of a signal peptide, a von Willebrand factor type A domain, and an ITI heavy chain C-terminus. Von Willebrand factor type A domains are typically found in extracellular proteins and mediate adhesion to extracellular matrix via metal-dependent adhesion sites (SMART accession SM00327). ITI heavy chain C-terminus domains are found in heavy chain subunits of ITIs. The heavy chain subunits do not have trypsin protease inhibitory activity per se. Rather, they interact with hyaluronic acid, promoting the stability of extracellular matrix (Salier et al, *Biochem J;* 315 (Pt 1): 1-9 (1996)). Loss of ITIH5 may play a role in breast cancer development (Himmelfarb et al, *Cancer Lett;* 204(1):69-77 (2004)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 22 | 32 | 22 | 76 |
| Expected | 19 | 38 | 19 | 76 |

Chi-Sq. = 1.89
Significance = 0.38776
(hom/n) = 0.29
Avg. Litter Size = 8
Mutation Type: Homologous Recombination (standard)

Coding exon 1 was targeted (NCBI accession NM_172471.1).

Wild-type Expression Panel: Expression of the target gene was detected in all 13 adult tissue samples tested by RT-PCR, except bone.

Disruption of the target gene was confirmed by Southern hybridization analysis.

41.6.1. Phenotypic Analysis (for Disrupted Gene: DNA44192-1246 (UNQ311)

(a) Overall Phenotypic Summary:

Mutation of the gene encoding the ortholog of human inter-alpha (globulin) inhibitor H5 (ITIH5) resulted in an increased mean percentage of CD4 cells in the peripheral blood of (−/−) mice. Male (−/−) mice also exhibited testicular degeneration but there was no indication of male infertility. Female (−/−) mice showed significantly increased uric acid levels. Knockout mice also showed increased quantities of hemosiderin pigment in both the spleen and bone marrow. This gene is interesting from the standpoint that expression is consistently decreased in invasive mammary ductal carcinoma as determined by microarray analysis (data not shown). Testicular degeneration suggests a role in tumor development. Gene disruption was confirmed by Southern blot.

(b) Pathology

Microscopic Observations: The 3 male (−/−) mice exhibited mild focal lesions characteristic of testicular degeneration. Of the 6 (−/−) mice available for analysis, 2 (−/−) mice (M-109 and F-134) exhibited increased quantities of hemosiderin pigment in both the spleen and bone marrow and an additional 2 (−/−) mice (F-74 and F-111) exhibited increased hemosiderin in the spleen only. One knockout mouse (M-113) exhibited multifocal acute and granulomatous inflammation.

Gene Expression: LacZ activity was not detected in the panel of tissues by immunohistochemical analysis.

Analyzed wt/het/hom: 0/1/6

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node. In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACS Calibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRbAPC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS: The (−/−) mice exhibited an increased mean percentage of CD4 cells when compared with their (+/+) littermates and the historical mean. Thus, knocking out the gene which encodes PRO354 polypeptides causes an increase in the T cell population. From these observations, PRO354 polypeptides or the gene encoding PRO354 appears to act as a negative regulator of T cell proliferation. Thus, PRO354 polypeptides or agonists thereof would be beneficial as a negative regulator of T cell proliferation in those instances wherein a pronounced T-cell proliferation is present such as occurs in autoimmune diseases (for example rheumatoid arthritis patients). In addition, PRO354 polypeptides would be especially useful in preventing skin graft rejections.

(d) Blood Chemistry

Test Description: Lexicon Genetics uses the COBAS Integra 400 (mfr: Roche) in its clinical settings for running blood chemistry tests on mice.

Results:

The female (−/−) mice showed a significant decrease in uric acid levels compared to wild-type littermates. No other indications of renal impairment were observed.

41.7. Generation and Analysis of Mice Comprising DNA39518-1247 (UNQ312) Gene Disruptions In these knockout experiments, the gene encoding PRO355 polypeptides (designated as DNA39518-1247) (UNQ312) was disrupted. The gene specific information for these studies is as follows: the mutated mouse gene corresponds to nucleotide reference: NM_018770 or ACCESSION: NM_018770 NID: gi 9055173 ref NM_018770.1 *Mus musculus* immunoglobulin superfamily, member 4 (Igsf4); protein reference: Q9CRY3 or ACCESSION: Q9CRY3 NID: *Mus musculus* (Mouse). 3100001108RIK PROTEIN (FRAGMENT). MOUSESPTRNRDB; the human gene sequence reference: NM_014333 or ACCESSION: NM_014333 NID: gi 22095346 ref NM_014333.2 *Homo sapiens* immunoglobulin superfamily, member 4 (IGSF4); the human protein sequence corresponds to reference: Q9BY67 or ACCESSION: Q9BY67 NID: *Homo sapiens* (Human). NECTIN-LIKE PROTEIN 2. HUMANSPTRNRDB.

The mouse gene of interest is Igsf4 (immunoglobulin superfamily, member 4), ortholog of human IGSF4. Aliases include RA175A, RA175B, RA175C, RA175N, SgIGSF, SynCam, BL2, ST17, NECL2, TSLC1, SYNCAM, nectin-like protein 2, 2900073G06Rik; 3100001108Rik, immunosuperfamily protein B12, and tumor suppressor in lung cancer 1.

IGSF4 is a membrane glycoprotein belonging to the immunoglobulin superfamily that is localized at cell-cell boundaries in lung epithelial cells (Ito et al, *Cancer Res;* 63(19): 6320-6 (2003)). IGSF4 participates in cell adhesion and acts as a tumor suppressor in non-small cell lung and esophageal squamous cell carcinoma (Fukuhara et al, *Oncogene;* 22(40): 6160-5 (2003); Watabe et al, *Histol Histopathol;* 18(4):1321-9 (2003)). The cytoplasmic region of IGSF4 contains protein motifs thought critical to its tumor suppressor activity (Mao et al, *Cancer Res;* 63(22):7979-85 (2003)). IGSF4 associates with MPP3, a human homologue of *Drosophila* tumor suppressor Discs large (Dlg), possibly IGSF4 and MMP3 are involved in identical cell-cell interactions, disruption of which may lead to malignancy (Fukuhara et al, *Oncogene;* 23(2):629 (2004), Fukuhara et al, *Oncogene;* 22(40): 6160-5 (2003)).

| | wt | het | hom | Total |
|---|---|---|---|---|
| Observed | 22 | 41 | 15 | 78 |
| Expected | 19.5 | 39 | 19.5 | 78 |

Chi-Sq. = 1.46
Significance = 0.48154
(hom/n) = 0.19
Avg. Litter Size = 8
Mutation Type: Retroviral Insertion (OST)

Retroviral insertion occurred between coding exons 1 and 2 (Accession: AF434663).

Wild-type Expression Panel: Expression of the target gene was detected in embryonic stem (ES) cells and in all 13 adult tissue samples tested by RT-PCR.

RT-PCR analysis revealed that the transcript was absent in heart and reduced in brain in the (−/−) mouse analyzed (M-179).

41.7.1. Phenotypic Analysis (for Disrupted Gene: DNA39518-1247 (UNQ312)

(a) Overall Phenotypic Summary:

Mutation of the gene encoding the ortholog of human immunoglobulin superfamily, member 4 (IGSF4) resulted in an increased exploratory response in (−/−) mice. The (−/−) mice also exhibited an increased TNF-alpha response to LPS challenge. The mutant (−/−) mice also showed signs of growth retardation and abnormal bone measurements. The male (−/−) mice exhibited an increased mean serum triglyceride level. Transcript was absent in heart and reduced in brain as determined by RT-PCR.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc. Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 μL sterile saline using a 26 gauge needle. The doses were based on the average weight of the mice tested at 1 μg/g body weight 3 hours after injection; a 100 ul blood sample was then taken and analyzed for the presence of TNFα, MCP-1, and IL-6 on the FACS Calibur instrument.

Results:

The (−/−) mice exhibited an increased mean serum TNF-alpha response to a LPS challenge when compared with their (+/+) littermates and the historical mean.

Analyzed wt/het/hom: 8/4/8

In summary, the LPS endotoxin challenge demonstrated that knockout mice deficient in the gene encoding PRO355 polypeptides exhibit immunological abnormalities when compared with their wild-type littermates. In particular, the mutant mice exhibited an increased ability to elicit an immunological response (TNF-alpha production) when challenged with the LPS endotoxin indicating a pronounced proinflammatory response. This suggests that antagonists (inhibitors) of PRO355 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO355 polypeptides or agonists thereof, would be useful in inhibiting the immune response and would be useful candidates for suppressing harmful immune responses, e.g. in the case of graft rejection or graft-versus-host diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 5/4/8

Results:

A notable difference was observed during open field activity testing. The (−/−) mice exhibited an increased sum total distance traveled and rearing activity when compared with their gender-matched (+/+) littermates, which is indicative of an increased exploratory response to a novel environment in the mutants. Thus, knockout mice demonstrated a phenotype consistent with hyperactivity. Thus, PRO355 polypeptides and agonists thereof would be useful for the treatment or amelioration of the symptoms associated with hyperactivity.

Inverted Screen Testing:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Inverted Screen Test Data:

The Inverted Screen is used to measure motor strength/coordination. Untrained mice were placed individually on top of a square (7.5 cm×7.5 cm) wire screen which was mounted horizontally on a metal rod. The rod was then rotated 180 degrees so that the mice were on the bottom of the screens. The following behavioral responses were recorded over a 1 min testing session: fell off, did not climb, and climbed up.

| Genotype | Ratio Fell Down % | | Ratio Climbed up % | |
|---|---|---|---|---|
| +/+ (n = 4) | 0/4 | 0 | 3/4 | 75 |
| +/− (n = 4) | 0/4 | 0 | 2/4 | 50 |
| −/− (n = 8) | 8/8 | 100 | 0/8 | 0 |

* coding indicates a notable difference.

A motor strength deficit is apparent when there is a 50% point difference between (−/−) or (+/−) mice and (+/+) mice for the fell down response. 0/8 or 1/8 (−/−) or (+/−) mice not climbing indicates impaired motor coordination. 7/8 or 8/8(−/−) or (+/−) mice climbing up indicates enhanced motor coordination.

Results:

The Inverted Screen Test is designed to measure basic sensory & motor observations: A notable difference was observed during inverted screen testing when all 8 (−/−) mice fell off the screen, whereas 0/4 (+/+) mice fell off. However, the hyperactivity observed in these mutants should be considered when interpreting motor coordination results.

(d) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and decreased mean body length when compared with their gender-matched (+/+) littermates and the historical means. The organ weights were also decreased which is consistent with decreased mean body weight and length measurements. Analyzed wt/het/hom: 17/38/14

(2) Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited decreased mean lean body mass, bone mineral content, and bone mineral density in total body and vertebrae when compared with their gender-matched (+/+) littermates and the historical means. The bone mineral content index (BMC/LBM) for the mutants was also decreased, the difference being more notable in the males.

Micro-CT: The male (−/−) mice exhibited decreased mean vertebral trabecular bone volume, number and connectivity density and decreased mean femoral midshaft cross-sectional area when compared with their gender-matched (+/+) littermates and the historical means. Analyzed wt/het/hom: 4/4/7

Summary

These results demonstrate that knockout mutant mice exhibit abnormal bone metabolism with significant bone loss similar to osteoporosis characterized by decrease in bone mass with decreased density and possibly fragility leading to bone fractures or to osteo-related diseases. Thus, it appears that PRO355 polypeptides or agonists thereof would be useful in maintaining bone homeostasis. In addition, PRO355 polypeptides or its encoding gene would be important in bone healing or for the treatment of arthritis or osteoporosis; whereas antagonists (inhibitors) to PRO355 polypeptides would lead to abnormal or pathological bone disorders including inflammatory diseases associated with abnormal bone metabolism including arthritis, osteoporosis, and osteopenia. In addition, the (–/–) mice analyzed by DEXA exhibited notably decreased lean body mass when compared with their (+/+) littermates, suggestive of growth retardation in these mutants. This in conjunction with the observations of decreased body weight and length (and decreased organ weights) suggest a tissue wasting condition such as cachexia or other growth disorder. Thus, PRO355 polypeptides or agonists thereof would be useful in the treatment or prevention of growth disorders such as cachexia and/or other tissue wasting diseases.

(e) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results: As summarized above, the (–/–) mice exhibited notably increased triglyceride levels when compared with their gender-matched (+/+) littermates and the historical means. Thus, mutant mice deficient in the PRO355 gene can serve as a model for cardiovascular disease. PRO355 polypeptides or its encoding gene would be useful in regulating blood lipids such as triglycerides. Thus, PRO355 polypeptides or agonists thereof would be useful in the treatment of such cardiovascular diseases as hypertension, atherosclerosis, heart failure, stroke, various coronary diseases, hypercholesterolemia, hypertriglyceridemia, diabetes and/or obesity.

41.8. Generation and Analysis of Mice Comprising DNA49435-1219 (UNQ334) Gene Disruptions In these knockout experiments, the gene encoding PRO533 polypeptides (designated as DNA49435-1219) (UNQ334) was disrupted. The gene specific information for these studies is as follows: the mutated mouse gene corresponds to nucleotide reference: NM_008003 or ACCESSION: NM_008003 NID: 6679776 *Mus musculus Mus musculus* fibroblast growth factor 15 (Fgf15); protein reference: 035622 or ACCESSION: O35622 NID: *Mus musculus* (Mouse). FIBROBLAST GROWTH FACTOR-15 PRECURSOR (FGF-15). MOUSESPTRNRDB; the human gene sequence reference: NM_005117 or ACCESSION: NM_005117 NID: 15011922 *Homo sapiens Homo sapiens* fibroblast growth factor 19 (FGF19); the human protein sequence corresponds to reference: 095750 or ACCESSION: O95750 NID: *Homo sapiens* (Human). FIBROBLAST GROWTH FACTOR-19 PRECURSOR (FGF-19). HUMANSPTRNRDB.

The mouse gene of interest is Fgf15 (fibroblast growth factor 15), ortholog of human FGF19 (fibroblast growth factor 19).

FGF19, a member of the fibroblast growth factor family, is a secreted protein that functions as a ligand for fibroblast growth factor receptor 4 (FGFR4) (Xie et al, *Cytokine;* 11(10):729-35 (1999); Harmer et al, *Biochemistry;* 43(3): 629-40 (2004)). FGF19 is expressed strongly in fetal brain and is likely to be involved in development of the brain and the inner ear (Nishimura et al, *Biochim Biophys Acta;* 1444 (1):148-51 (1999); Ladher et al, *Science;* 290(5498):1965-7 (2000)). FGF19 suppresses expression of liver cholesterol 7 alpha-hydroxylase (CYP7A1), the first and rate-limiting step in bile acid biosynthesis, and consequently regulates liver cholesterol catabolism and elimination (Holt et al, *Genes Dev;* 17(13):1581-91 (2003)).

Transgenic mice expressing FGF19 display increased energy expenditure and brown fat mass but decreased overall fat mass, liver triglycerides, and liver acetyl CoA carboxylase 2, suggesting that FGF19 plays a role in energy metabolism (Tomlinson et al, *Endocrinology;* 143(5): 1741-7 (2002)). However, ectopic expression of FGF19 in transgenic mice results in development of liver tumors, suggesting that FGF19 may play a role in hepatocellular carcinomas (Nicholes et al, *Am J Pathol;* 160(6):2295-307 (2002)).

Wright and coworkers (*Dev Biol;* 269(1):264-75 (2004)) investigated the role of mouse Fgf15 in inner ear development using Fgf15-deficient mice. They found that although mouse Fgf15 or human FGF19 are sufficient to induce expression of otic markers in a chick explant assay, mouse embryos lacking Fgf15 do not have otic abnormalities. They concluded that mouse Fgf15 is the ortholog of human FGF19 but is not uniquely required for otic induction or patterning in mice.

Fu and coworkers (Endocrinology 145(6):2594-603 (2004) reported that FGF19 increases metabolic rate and reverses dietary and leptin-deficient diabetes.

| | wt | het | hom | Total |
|---|---|---|---|---|
| Observed | 23 | 44 | 10 | 77 |
| Expected | 19.25 | 38.5 | 19.25 | 77 |

Chi-Sq. = 5.96
Significance = 0.05077
(hom/n) = 0.13
Avg. Litter Size = 8
Mutation Type: Homologous Recombination (standard)

Coding exons 1 and 2 were targeted (NCBI accession NM_008003.1).

Wild-type Expression Panel: Expression of the target gene was detected in brain; spinal cord; eye; thymus; kidney; and stomach, small intestine, and colon among the 13 adult tissue samples tested by RT-PCR.

Disruption of the target gene was confirmed by Southern hybridization analysis.

41.8.1. Phenotypic Analysis (for Disrupted Gene: DNA49435-1219 (UNQ334)

(a) Overall Phenotypic Summary:

Mutation of the gene encoding the ortholog of human fibroblast growth factor 19 (FGF19) resulted in growth retardation and decreased bone measurements in (–/–) mice. The (–/–) mice also exhibited a decreased serum IgG2a response to ovalbumin challenge. In addition, the mutant (–/–) mice exhibited a decreased mean serum insulin level. Decreased viability was also present in the homozygous (–/–) mice (10 observed when 19.25 were expected). By genotyping (at postnatal day 10-12) half the homozygotes were dead. Disruption of the target gene was confirmed by Southern hybridization analysis.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 4 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

Both the male and female (−/−) mice exhibited decreased mean body weight and decreased mean body length when compared with their gender-matched (+/+) littermates and the historical means the difference being more notable in male (−/−) mice.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 4 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 4 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean total tissue mass and lean body mass when compared with their gender-matched (+/+) littermates and the historical means. However, wild-type total tissue mass and lean body mass were higher than the historical control. The male mutant mice also exhibited decreased mean bone mineral content and bone mineral density related measurements. In addition, the female knockouts (−/−) showed lower femur bone mineral density, although the wild-type was higher than the historical control.

Micro-CT: The male (−/−) mice exhibited decreased mean vertebral trabecular bone volume, number, thickness, and connectivity density and decreased mean femoral mid-shaft cortical thickness and cross-sectional area when compared with their gender-matched (+/+) littermates and the historical means. These changes may be due to the reduced body size of the male (−/−) mice.

Summary

These results demonstrate that knockout mutant mice exhibit abnormal bone metabolism with bone loss similar to osteoporosis characterized by decrease in bone mass with decreased density and possibly fragility leading to bone fractures, indicative of osteo-related diseases. Thus, it appears that PRO533 polypeptides or agonists thereof would be useful in maintaining bone homeostasis. In addition, PRO533 polypeptides or its encoding gene would be important in bone healing or for the treatment of arthritis or osteoporosis; whereas antagonists to PRO533 polypeptides would lead to abnormal or pathological bone disorders including inflammatory diseases associated with abnormal bone metabolism including arthritis, osteoporosis, and osteopenia. In addition, the (−/−) mice analyzed by DEXA exhibited notably decreased total tissue mass and lean body mass when compared with their (+/+) littermates, suggestive of growth retardation in these mutants. This in conjunction with the observations of decreased body weight and length suggest a tissue wasting condition such as cachexia or other growth disorder.

Thus, PRO533 polypeptides or agonists thereof would be useful in the treatment or prevention of growth disorders such as cachexia and/or other tissue wasting diseases. Phenotypic analysis also indicated reduced viability of homozygotes. By the time of genotyping (at post-natal day 10-12) half the homozygotes were dead.

(c) Blood Chemistry

Blood chemistry analysis was performed using the COBAS Integra 400 (mfr: Roche) in its clinical settings for running blood chemistry tests on mice.

Insulin Data:

Test Description: Lexicon Genetics uses the Cobra II Series Auto-Gamma Counting System in its clinical settings for running quantitative Insulin assays on mice.

Results:

The male (−/−) mice exhibited a decreased mean serum insulin level when compared with their gender-matched (+/+) littermates and the historical mean.

Summary

Mutant (−/−) mice deficient in the gene encoding PRO533 polypeptides show a phenotype consistent with growth retardation, reduced viability and tissue wasting diseases. Insulin levels are abnormally low which can be indicative of diabetes. Thus, antagonists or inhibitors of PRO533 polypeptides or its encoding gene would mimic these metabolic and growth related effects. On the other hand, PRO533 polypeptides or agonists thereof would be useful in the prevention and/or treatment of such metabolic disorders as diabetes or other tissue wasting diseases.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Ovalbumin Challenge

Procedure: This assay was carried out on wild types and homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this challenge:

The (−/−) mice exhibited a decreased mean serum IgG2a response to ovalbumin challenge when compared with their (+/+) littermates and the historical means. Thus, these knockout mice exhibited a decreased ability to elicit an OVA specific antibody response to the T-cell dependent OVA antigen.

In summary, the ovalbumin challenge studies indicate that knockout mice deficient in the gene encoding PRO533 polypeptides exhibit immunological abnormalities when compared with their wild-type littermates. In particular, the mutant mice exhibited a decreased ability to elicit an immunological response when challenged with the T-cell dependent OVA antigen. Thus, PRO533 polypeptides or agonists thereof, would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO533 polypeptides would be useful for inhibiting the immune response and thus would be useful candidates for suppressing harmful immune responses, e.g. in the case of graft rejection or graft-versus-host diseases.

41.9. Generation and Analysis of Mice Comprising DNA45417-1432 (UNQ342) Gene Disruptions In these knockout experiments, the gene encoding PRO541 polypeptides (designated as DNA45417-1432) (UNQ342) was disrupted. The gene specific information for these studies is as follows: the mutated mouse gene corresponds to nucleotide reference: NM_031402 or ACCESSION: NM_031402 NID: 13878236 *Mus musculus Mus musculus* Cocoacrisp (Cocoacrisp-pending); protein reference: Q99MM6 or ACCESSION: Q99MM6 NID: *Mus musculus* (Mouse). COCOACRISP. MOUSESPTRNRDB; the human gene sequence reference: NM_031461 or ACCESSION: NM_031461 NID: 21314740 *Homo sapiens Homo sapiens* CocoaCrisp (LOC83690); the human protein sequence corresponds to reference: Q9H33 or ACCESSION: Q9H336 NID: *Homo sapiens* (Human). PUTATIVE SECRETORY PROTEIN PRECURSOR (COCOACRISP). HUMANSPTRNRDB.

The mouse gene of interest is Cocoacrisp (Cocoacrisp protein), ortholog of human CocoaCrisp.

CocoaCrisp is a hypothetical secreted protein, consisting of a signal peptide, an SCP-like extracellular protein domain, and an LCCL domain. The SCP-like extracellular protein domain is found in a wide variety of eukaryotic extracellular proteins, such as sperm-coating glycoprotein, which is thought to be involved in sperm maturation, and venom allergens from insects (Pfam accession PF00188). The LCCL domain is likely to be involved in lipopolysaccharide binding as well as other functions, such as cell signaling (Pfam accession PF03815).

Targeted or gene trap mutations are generated in strain $129SvEv^{Brd}$-derived embryonic stem (ES) cells.

The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 12 | 41 | 15 | 68 |
| Expected | 17 | 34 | 17 | 68 |

Chi-Sq. = 3.15
Significance = 0.20731
(hom/n) = 0.22
Avg. Litter Size = 7
Mutation Type: Homologous Recombination (standard)

Coding exon 1 was targeted (NCBI accession BC040768.1).

Wild-type Expression Panel: Expression of the target gene was detected in embryonic stem (ES) cells and in all 13 adult tissue samples tested by RT-PCR.

Disruption of the target gene was confirmed by Southern hybridization analysis.

41.9.1. Phenotypic Analysis (for Disrupted Gene: DNA45417-1432 (UNQ342)

(a) Overall Phenotypic Summary:

Mutation of the gene encoding the ortholog of human CocoaCrisp resulted in a growth retardation and abnormal bone measurements in the mutant (−/−) mice. In addition, the (−/−) mice exhibited an increased skin fibroblast proliferation. Microarray analysis shows UNQ342 to be up-regulated in breast tumors and prostate cancers. UNQ342 has a region of high similarity to protease inhibitor 15 (human P115), which is a trypsin inhibitor that helps to regulate extracellular proteolysis aiding tumor invasion. Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and decreased mean body length when compared with their gender-matched (+/+) littermates and the historical means. Analyzed wt/het/hom: 15/39/21

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The (−/−) mice exhibited decreased mean total tissue mass and lean body mass when compared with their gender-matched (+/+) littermates and the historical means. These mutant mice also exhibited decreased mean bone mineral content compared with their gender-matched littermates and the historical means. Analyzed wt/het/hom: 4/4/8

Summary

These results demonstrate that knockout mutant mice exhibit abnormal bone metabolism with bone loss similar to osteoporosis characterized by decrease in bone mass with decreased density and possibly fragility leading to bone fractures or osteo-related diseases. Thus, it appears that PRO541 polypeptides or agonists thereof would be useful in maintaining bone homeostasis. In addition, PRO541 polypeptides or its encoding gene would be important in bone healing or for the treatment of arthritis or osteoporosis; whereas antagonists to PRO544 polypeptides would lead to abnormal or pathological bone disorders including inflammatory diseases associated with abnormal bone metabolism including arthritis, osteoporosis, and osteopenia. In addition, the (−/−) mice analyzed by DEXA exhibited decreased total tissue mass and lean body mass when compared with their (+/+) littermates, suggestive of growth retardation in these mutants. This in conjunction with the observations of decreased body weight and length suggest a tissue wasting condition such as cachexia or other growth disorder. Thus, PRO541 polypeptides or agonists thereof would be useful in the treatment or prevention of growth disorders such as cachexia and/or other tissue wasting diseases.

(c) Adult Skin Cell Proliferation:

Procedure: Skin cells were isolated from 16 week old animals (2 wild type and 4 homozygotes). These were developed into primary fibroblast cultures and the fibroblast proliferation rates were measured in a strictly controlled protocol. The ability of this assay to detect hyper-proliferative and hypo-proliferative phenotypes has been demonstrated with p53 and Ku80. Proliferation was measured using Brdu incorporation.

Specifically, in these studies the skin fibroblast proliferation assay was used. An increase in the number of cells in a standardized culture was used as a measure of relative proliferative capacity. Primary fibroblasts were established from skin biopsies taken from wild type and mutant mice. Duplicate or triplicate cultures of 0.05 million cells were plated and allowed to grow for six days. At the end of the culture period, the number of cells present in the culture was determined using a electronic particle counter.

Results: The (−/−) mice exhibited an increased skin fibroblast proliferation rate when compared with their gender-matched (+/+) littermates and the historical mean. [Analyzed wt/het/hom: 2/0/4]

Thus, homozygous mutant mice demonstrated a hyper-proliferative phenotype. As suggested by these observations, PRO541 polypeptides or agonists thereof could function as tumor suppressors and would be useful in decreasing abnormal cell proliferation.

41.10. Generation and Analysis of Mice Comprising DNA52758-1399 (UNQ390) Gene Disruptions In these knockout experiments, the gene encoding PRO725 polypeptides (designated as DNA52758-1399) (UNQ390) was disrupted. The gene specific information for these studies is as follows: the mutated mouse gene corresponds to nucleotide reference: NM_009136 or ACCESSION: NM_009136 NID: gi 6677876 ref NM_009136.1 *Mus musculus* scrapie responsive gene 1 (Scrg1); protein reference: 088745 or ACCESSION: 088745 NID: *Mus musculus* (Mouse). SCRAPIE-RESPONSIVE PROTEIN 1 PRECURSOR (SCRG-1). MOUSESPTRNRDB; the human gene sequence reference: NM_007281 or ACCESSION: NM_007281 NID: gi 6005869 ref NM_007281.1 *Homo sapiens* scrapie responsive protein 1 (SCRG1); the human protein sequence corresponds to reference: O75711 or ACCESSION: O75711 NID: *Homo sapiens* (Human). SCRAPIE-RESPONSIVE PROTEIN 1 PRECURSOR (SCRG-1). HUMANSPTRNRDB.

The mouse gene of interest is Scrg1 (scrapie responsive gene 1), ortholog of human SCRG1. Aliases include SCRG-1.

SCRG1 is a putative secreted protein expressed primarily in the central nervous system. The 98-amino-acid protein consists of a signal peptide, a characteristic cysteine distribution pattern, and a 35-amino-acid segment that is highly conserved between mouse, rat, and human species. SCRG1 expression occurs in glial cells and neurons (Dandoy-Dron et al, *J Biol Chem;* 273(13):7691-7 (1998); Dron et al, *J Biol Chem;* 273(29): 18015-8 (1998); Dron et al, *Genomics;* 70(1): 140-9 (2000)). Moreover, SCRG1 appears to be associated with dense-core vesicles in vitro and in vivo, suggesting that SCRG1 is associated with the secretory pathway of neuronal cells (Dandoy-Dron et al, *Eur J Neurosci;* 18(9): 2449-59 (2003)).

SCRG1 may play a role in glial cell activation in response to brain injury or infectious agents. Moreover, SCRG1 has been proposed to be involved in prolonged and widespread glial cell activation in response to transmissible progressive neuro-degenerative diseases, such as Creutzfeldt-Jakob disease, German-Straussler-Scheinker syndrome, Kuru, scrapie, and bovine spongiform encephalopathy. Because prolonged and widespread glial cell activation is likely to be detrimental to brain function, SCRG1 may play a role in the neurodegenerative process (Dandoy-Dron et al, *J Biol Chem;* 273(13):7691-7 (1998); Dron et al, *J Biol Chem;* 273(29):18015-8 (1998)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 21 | 38 | 23 | 82 |
| Expected | 20.5 | 41 | 20.5 | 82 |

Chi-Sq. = 0.54
Significance = 0.76468
(hom/n) = 0.28
Avg. Litter Size = 8
Mutation Type: Homologous Recombination (standard)

Coding exon 1 was targeted (NCBI accession NM_009136.2).

Wild-type Expression Panel: Expression of the target gene was detected in all 13 adult tissue samples tested by RT-PCR, except liver, skeletal muscle, heart, and adipose.

Disruption of the target gene was confirmed by Southern hybridization analysis.

41.10.1. Phenotypic Analysis (for Disrupted Gene: DNA52758-1399 (UNQ390)

(a) Overall Phenotypic Summary:

Mutation of the gene encoding the ortholog of human scrapie responsive protein 1 (SCRG1) resulted in an increased mean percent total body fat and total fat mass. Gene disruption was confirmed by Southern blot.

(b) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

DEXA Results: The female mutant (−/−) mice exhibited increased mean percent total body fat and total fat mass when compared with their gender-matched (+/+) littermates and the historical means. This phenotype is associated with obesity or metabolic disorders marked by dyslipidemia. Thus, antagonists (or inhibitors) of PRO725 polypeptides or its encoding gene would be expected to mimic this negative phenotype. On the other hand, PRO725 polypeptides or agonists thereof would be useful in the prevention and/or treatment of these metabolic disorders.

41.11. Generation and Analysis of Mice Comprising DNA56436-1448 (UNQ474) Gene Disruptions In these knockout experiments, the gene encoding PRO937 polypeptides (designated as DNA56436-1448) (UNQ474) was disrupted. The gene specific information for these studies is as follows: the mutated mouse gene corresponds to nucleotide reference: NM_008150 or ACCESSION: NM_008150 NID: na *Mus musculus Mus musculus* glypican 4 (Gpc4); protein reference: P51655 or GPC4_MOUSE P51655 GLYPICAN-4 PRECURSOR K-GLYPICAN; the human gene sequence reference: NM_001448 or ACCESSION: NM_001448 NID: na *Homo sapiens Homo sapiens* glypican 4 (GPC4); the human protein sequence corresponds to reference: 075487 or GPC4_HUMAN 075487 GLYPICAN-4 PRECURSOR K-GLYPICAN.

The mouse gene of interest is Gpc4 (glypican 4), ortholog of human GPC4. Aliases include K-glypican.

GPC4 is a glycosylphosphatidylinositol (GPI)-anchored extracellular heparan sulfate proteoglycan that binds and modulates polycationic hormones, such as fibroblast growth factor and endostatin (Fransson, *Int J Biochem Cell Biol;* 35(2):125-9 (2003); Galli et al, *Development;* 130(20):4919-29 (2003); Karumanchi et al, *Mol Cell;* 7(4):811-22 (2001)). GPC4 is likely to participate in brain development, kidney development, and bone remodeling (Watanabe et al, *J Cell Biol;* 130(5): 1207-18 (1995); Karumanchi et al, *Mol Cell;* 7(4):811-22 (2001); Galli et al, *Development;* 130(20):4919-29 (2003); Sheu et al, *J Bone Miner Res;* 17(5):915-22 (2002).

Deletions in the glypican 3 (GPC3) and GPC4 genes on chromosome X are likely to explain the variability in phenotype of Simpson-Golabi-Behmel syndrome, which is characterized by pre- and postnatal overgrowth, visceral and skeletal abnormalities, and embryonal tumor development (Veugelers et al, *Genomics;* 53(1): 1-11 (1998); Huber et al, *Gene;* 225 (1-2):9-16 (1998)).

This project is X-linked:

Summary of X-linked Gene Distribution by Sex and Genotype (Only the agouti pups from the male chimeras are included.)

Summary of X-linked Gene Distributions for Sex by Genotype

| Progeny | Agouti F1 (M chimera × wt) | | Progeny | F1a (F het × wt) | | |
|---|---|---|---|---|---|---|
| Sex | wt | het | Sex | wt | het | hemi |
| M | 4 | 0 | M | 20 | n/a | 19 |
| F | 0 | 19 | F | 22 | 22 | n/a |

Targeted or gene trap mutations are generated in strain $129SvEv^{Brd}$-derived embryonic stem (ES) cells.

The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 22 | 20 | 41 | 83 |
| Expected | 20.75 | 41.5 | 20.75 | 83 |

Chi-Sq. = 30.98
Significance = 0.00000
(hom/n) = 0.49
Avg. Litter Size = 8
Mutation Type: Homologous Recombination (standard)

Coding exon 3 was targeted (NCBI accession NM_008150.1).

Wild-type Expression Panel: Expression of the target gene was detected in eye; spleen; kidney; liver; stomach, small intestine, and colon; heart; and adipose among the 13 adult tissue samples tested by RT-PCR.

Disruption of the target gene was confirmed by Southern hybridization analysis.

41.11.1. Phenotypic Analysis (for Disrupted Gene: DNA56436-1448 (UNQ474)

(a) Overall Phenotypic Summary:

Mutation of the gene encoding the ortholog of human glypican 4 (GPC4) resulted in anemia in male (−/−) mice. This mutation is in an X-linked gene. Both male and female wild-type mice were analyzed, whereas only male hemizygous mutant mice were analyzed. The male hemizygous (wild-type) and hemizygous mutant mice are designated as (0/+) and (0/−), respectively.

The male hemizygous mutant mice exhibited signs of anemia when compared with their gender-matched wild-type littermates and the historical means. In addition, the (−/−) mice showed a decreased in IgG2a response to ovalbumin challenge. UNQ474 is specifically upregulated on T7 monocytes only (data not shown). The (−/−) mice exhibited a decreased mean serum glucose level however, there was normal growth and insulin and glucose tolerance testing was normal. In addition, the hemizygous (0/−) mutant mice exhibited a decreased mean percent of total body fat and abnormal bone related measurements. Disruption of the target gene was confirmed by Southern hybridization analysis.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

The male (0/−) mice exhibited a decreased mean red blood cell count and decreased mean hemoglobin and hematocrit levels when compared with their gender-matched wild-type (0/+) littermates and the historical means.

Analyzed wt/het/hom: 6/4/12

These results are related to a phenotype associated with anemia. Thus, PRO937 polypeptides, agonists thereof or the encoding gene for PRO937 polypeptides must be essential for normal red blood cell production and as such would be useful in the treatment of blood disorders associated with anemia or a low hematocrit.

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Results of this challenge: The (−/−) mice exhibited a decreased mean serum IgG2a response to the ovalbumin challenge when compared with their (+/+) littermates. Thus, these knockout mice exhibited a decreased ability to elicit an OVA specific antibody response to the T-cell dependent OVA antigen.

In summary, the ovalbumin challenge studies indicate that knockout mice deficient in the gene encoding PRO937 polypeptides exhibit immunological abnormalities when compared with their wild-type littermates. The mutant mice exhibited a decreased ability to elicit an immunological response when challenged with the T-cell dependent OVA antigen. This suggests that PRO937 polypeptides or their agonists would be important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO937 polypeptides would be useful in inhibiting the immune response and would be useful candidates for suppressing harmful immune responses, e.g. in the case of graft rejection or graft-versus-host diseases.

(c) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan.

Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (0/−) mice exhibited a decreased mean percent total body fat when compared with their gender-matched (0/+) littermates and the historical mean.

Micro-CT: The male (0/−) mice exhibited an increased mean femoral midshaft cortical thickness and a decreased mean femoral midshaft cross-sectional area when compared with their gender-matched (0/+) littermates and the historical means. Analyzed wt/het/hom: 4/4/8

These results suggest that the hemizygotes exhibit a negative phenotype which is associated with abnormal bone measurements or osteo-related diseases. The decrease in total body fat is suggestive of a tissue wasting condition or phenotype.

(d) Phenotypic Analysis: Metabolism-Blood Chemistry

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes.

Results:

The (−/−) mice exhibited a decrease in mean serum glucose when compared with their gender-matched (+/+) littermates and the historical means. However, the mutant mice (−/−) showed normal weight gain, growth, insulin and glucose tolerance.

41.12. Generation and Analysis of Mice Comprising DNA56409-1377 (UNQ497) Gene Disruptions In these knockout experiments, the gene encoding PRO1014 polypeptides (designated as DNA56409-1377) (UNQ497) was disrupted. The gene specific information for these studies is as follows: the mutated mouse gene corresponds to nucleotide reference: NM_198030 or *Mus musculus* expressed sequence A1047820 (AI047820); protein reference: Q8VCR2 or ACCESSION: Q8VCR2 NID: *Mus musculus* (Mouse). Similar to hydroxysteroid 17-beta dehydrogenase 11; the human gene sequence reference: NM_178135 or *Homo sapiens* short-chain dehydrogenase/reductase 9 (SCDR9); the human protein sequence corresponds to reference: Q7Z5P4 or ACCESSION: Q7Z5P4 NID: *Homo sapiens* (Human). Short-chain dehydrogenase/reductase 9.

The mouse gene of interest is A1047820 (expressed sequence A1047820), ortholog of human SCDR9 (short-chain dehydrogenase/reductase 9). Aliases include PAN1B-like and alcohol dehydrogenase PAN1B-like. SCDR9 is a hypothetical oxidoreductase that catalyzes the NAD(P)H-dependent reduction of short chain alcohols. The protein contains a signal peptide and a short-chain dehydrogenase domain, which consists of an NAD(P)H-binding segment and an alcohol co-substrate binding segment (Pfam accession PF00106). The cell location of SCDR9 is ambiguous; bioinformatic analyses suggest that SCDR9 is located in the endoplasmic reticulum or plasma membrane.

Targeted or gene trap mutations are generated in strain 129SvEv$^{Brd}$-derived embryonic stem (ES) cells. The chimeric mice were bred to C57BL/6J albino mice to generate F 1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 15 | 48 | 12 | 75 |
| Expected | 18.75 | 37.5 | 18.75 | 75 |

Chi-Sq. = 6.12
Significance = 0.04689
(hom/n) = 0.16
Avg. Litter Size = 8
Mutation Type: Homologous Recombination (standard)

Coding exons 1 and 2 were targeted (NCBI accession BC019427.1).

Wild-type Expression Panel: Expression of the target gene was detected in embryonic stem (ES) cells and in all 13 adult tissue samples tested by RT-PCR, except skeletal muscle and bone.

Disruption of the target gene was confirmed by Southern hybridization analysis.

41.12.1. Phenotypic Analysis (for Disrupted Gene: DNA56409-1377 (UNQ497)

(a) Overall Phenotypic Summary:

Mutation of the gene encoding the ortholog of human short-chain dehydrogenase/reductase 9 (SCDR9) resulted in the observation that male mutant (−/−) mice showed an increased trabecular number and connectivity density and a decreased midshaft femoral cross-sectional area. Gene disruption was confirmed by Southern blot.

(b) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

The male mutant (−/−) mice exhibited an increased trabecular number and connectivity density compared to wild-type littermates. In addition, midshaft femoral total area seemed to be decreased relative to wild-type littermates. These results indicate that the knockout mutant phenotype may be associated with such bone abnormalities as osteopetrosis. Osteopetrosis is a condition characterized by abnormal thickening and hardening of bone and abnormal fragility of the bones. As such, PRO1014 polypeptides or agonists thereof would be beneficial for the treatment of osteopetrosis. A phenotype associated with an increased trabecular number and connectivity density suggests that agents which mimic these effects (e.g. antagonists of PRO1014 polypeptides) would play a role in bone healing.

41.13. Generation and Analysis of Mice Comprising DNA48606-1479 (UNQ559) Gene Disruptions In these knockout experiments, the gene encoding PRO1120 polypeptides (designated as DNA48606-1479) (UNQ559) was disrupted. The gene specific information for these studies is as follows: the mutated mouse gene corresponds to nucleotide reference: BC062900 or *Mus musculus* RIKEN cDNA 2010004N24 gene, mRNA (cDNA clone MGC: 86096 IMAGE: 6810085); protein reference: Q8CFG0 or ACCESSION: Q8CFG0 NID: *Mus musculus* (Mouse). Extracellular sulfatase Sulf-2 precursor (EC 3.1.6.-) (MSulf-2). MOUSESPTRNRDB; the human gene sequence reference: NM 018837 or similar to glucosamine-6-sulfatases (SULF2); the human protein sequence corresponds to reference: Q81WU5 or ACCESSION: Q81WU5 NID: *Homo sapiens* (Human). Extracellular sulfatase Sulf-2 precursor (EC 3.1.6.-) (HSulf-2). HUMANSPTRNRDB.

The mouse gene of interest is Sulf2 (sulfatase 2), ortholog of human SULF2. Aliases include mKIAA1247, 2010004N24Rik, HSULF-2, KIAA1247, and extracellular sulfatase SULF-2.

SULF2 is an extracellular endosulfatase with high selectivity for glucosamine 6-sulfate in the appropriate context within heparin (Morimoto-Tomita et al, *J Biol Chem;* 277 (51):49175-85 (2002)). The enzyme precursor is predicted to be a protein of about 890 amino acids, consisting of overlapping signal peptide and transmembrane segments and a sulfatase domain (Pfam accession number PF00884). SULF2 is endoproteolytically processed and secreted. SULF2 may modulate heparan sulfate proteoglycan interactions in processes such as cell adhesion, basement membrane and extracellular matrix barrier function, cell growth, and cell differentiation (Morimoto-Tomita et al, *J Biol Chem;* 277(51): 49175-85 (2002).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 17 | 36 | 16 | 69 |
| Expected | 17.25 | 34.5 | 17.25 | 69 |

Chi-Sq. = 0.16
Significance = 0.92338
(hom/n) = 0.23
Avg. Litter Size = 7
Mutation Type: Retroviral Insertion (OST)

Retroviral insertion occurred in the intron between coding exons 2 and 3 (NCBI accession AK034712.1).

Wild-type Expression Panel: Expression of the target gene was detected in embryonic stem (ES) cells and in all 13 adult tissue samples tested by RT-PCR, except skeletal muscle and bone.

RT-PCR analysis revealed that the transcript was absent in the (−/−) mouse analyzed (M-166). Disruption of the target gene was confirmed by Inverse PCR.

41.13.1. Phenotypic Analysis (for Disrupted Gene: DNA48606-1479 (UNQ559)

(a) Overall Phenotypic Summary:

Mutation of the gene encoding the ortholog of human sulfatase 2 (SULF2) resulted in an increased anxiety-related response in male (−/−) mice. In addition, the mutant (−/−) mice exhibited decreased tissue mass and decreased body weight as well as decreased bone related measurements. The female knockouts (−/−) showed a significant decrease in triglyceride levels yet the cholesterol levels showed an increasing trend. Transcript was absent by RT-PCR.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The female (−/−) mice exhibited a decreased mean total tissue mass and lean body mass and bone mineral content when compared with their gender-matched (+/+) littermates and the historical means. The male mutant (−/−) mice also exhibited a decreased lean body mass when compared with their gender-matched littermates and the historical means.

Micro-CT: The male (−/−) mice exhibited a decreased mean femoral mid-shaft cross-sectional area when compared with their gender-matched (+/+) littermates and the historical means.

These results demonstrate that knockout mutant mice exhibit abnormal bone metabolism with bone loss similar to osteoporosis characterized by decrease in bone mass with decreased density and possibly fragility leading to bone fractures or other osteo-related diseases. Thus, it appears that PRO1120 polypeptides or agonists thereof would be useful in maintaining bone homeostasis. In addition, PRO1120 polypeptides or its encoding gene would be useful in bone healing or for the treatment of arthritis or osteoporosis; whereas antagonists to PRO1120 polypeptides would lead to abnormal or pathological bone disorders including inflammatory diseases associated with abnormal bone metabolism including arthritis, osteoporosis, and osteopenia. In addition, the (−/−) mice analyzed by DEXA exhibited notably decreased total tissue mass and lean body mass when compared with their (+/+) littermates, suggestive of growth retardation in these mutants. Male (−/−) mice also showed decreased weights compared to the historical means. This suggests a tissue wasting condition such as cachexia or other growth disorder. Thus, PRO1120 polypeptides or agonists thereof would be useful in the treatment or prevention of growth disorders such as cachexia and/or other tissue wasting diseases.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), cancer and/or obesity.

The phenotypic tests included the measurement of serum cholesterol and triglycerides. In addition, inflammation assays were performed to identify potential targets for the inflammatory component of atherosclerosis.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results: As summarized above, the female (−/−) mice exhibited a significant decrease in triglyceride levels (p=0.04488) and a trend in increasing cholesterol levels (p=0.05857) when compared with their gender-matched (+/+) littermates and the historical means. Thus, mutant mice deficient in the PRO1120 gene can serve as a model for studying metabolic disorders. PRO1120 polypeptides or its encoding gene would be useful in regulating blood lipids.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 5/4/8

Results:

A notable difference was observed during open field activity testing. The male mutant (−/−) mice exhibited a decreased median sum time in the center area when compared with their gender-matched (+/+) littermates. This type of behavior is consistent with an increased anxiety like response. Knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO1120 polypeptides or agonists thereof would be useful in the treatment of such neurological disorders or the amelioration of the symptoms associated with anxiety disorders.

41.14. Generation and Analysis of Mice Comprising DNA59848-1512 (UNQ596) Gene Disruptions In these knockout experiments, the gene encoding PRO1182 polypeptides (designated as DNA59848-1512) (UNQ596) was disrupted. The gene specific information for these studies is as follows: the mutated mouse gene corresponds to nucleotide reference: AK003121 or ACCESSION: AK003121 NID: 12833583 *Mus musculus Mus musculus* adult male heart cDNA, RIKEN full-length enriched library, clone: 1010001H16:homolog to COLLECTIN 34, full insert sequence; protein reference: Q9DC75 or ACCESSION: Q9DC75 NID: *Mus musculus* (Mouse). 1010001H16RIK PROTEIN. MOUSESPTRNRDB; the human gene sequence reference: NM_024027 or *Homo sapiens* collectin sub-family member 11 (COLEC11), transcript variant 1; the human protein sequence corresponds to reference: Q9BWP8 or ACCESSION: Q9BWP8 NID: *Homo sapiens* (Human). Hypothetical protein.

The mouse gene of interest is Colec11 (collectin sub-family member 11), ortholog of human COLEC11. Aliases include 1010001H16Rik and MGC3279.

COLEC11 is a putative secreted protein of the collectin family that likely functions as a binding protein. COLEC11 consists of a signal peptide, a collagen triple helix repeat (Pfam accession PF01391), and a lectin C-type domain (Pfam accession PF00059). Collectins, which display the general domain organization of COLEC11, play an important role in innate immunity. They recognize and bind with microorganisms, enhancing adhesion and phagocytosis of microorganisms by agglutination and opsonization. Collectins also function as components of lung surfactant or protect against respiratory infections (Hickling et al, *J Leukoc Biol;* 75(1): 27-33 (2004)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 24 | 31 | 24 | 79 |
| Expected | 19.75 | 39.5 | 19.75 | 79 |

Chi-Sq. = 3.66
Significance = 0.16056
(hom/n) = 0.30
Avg. Litter Size = 8
Mutation Type: Homologous Recombination (standard)

Coding exon 1 was targeted (NCBI accession AK003121.1).

Wild-type Expression Panel: Expression of the target gene was detected in brain, spleen, kidney, liver, heart, and adipose among the 13 adult tissue samples tested by RT-PCR.

Disruption of the target gene was confirmed by Southern hybridization analysis.

41.14.1. Phenotypic Analysis (for Disrupted Gene: DNA59848-1512 (UNQ596)

(a) Overall Phenotypic Summary:

Mutation of the gene encoding the ortholog of human collectin sub-family member 11 (COLEC11) resulted in growth retardation in mutant (−/−) mice. Abnormal bone-related measurements were also exhibited by the (−/−) mice. The (−/−) mice also exhibited decreased serum triglycerides and increased serum glucose-associated with decreased growth/weight gain. Both male and female (−/−) mice showed a decreased heart rate (<2 standard deviation) compared to the historical means. Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The male (−/−) mice exhibited decreased mean body weight, length and growth when compared with their gender-matched (+/+) littermates and the historical means.

Heart Rate:

The male and female mutant (−/−) mice exhibited a significant decrease (<2 standard deviations) in mean heart rate when compared with their gender-matched (+/+) littermates and the historical means.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean total tissue mass, lean body mass, fat (%) and fat (gram) when compared with their gender-matched (+/+) littermates and the historical means. However, the (+/+) mice had weights which were higher than the historical means. In addition to these noted changes, the male mutant (−/−) mice also exhibited decreased bone mineral density and related measurements. Analyzed wt/het/hom: 4/4/8

Micro-CT: The male (−/−) mice exhibited decreased mean femoral mid-shaft cross-sectional area when compared with their gender-matched (+/+) littermates and the historical means.

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO1182 polypeptides or agonists thereof would be useful in maintaining bone homeostasis. In addition, PRO1182 polypeptides or its encoding gene would be useful in bone healing or for the treatment of arthritis or osteoporosis; whereas antagonists to PRO1182 polypeptides or its encoding gene would lead to abnormal or pathological bone disorders including inflammatory diseases associated with abnormal bone metabolism including arthritis, osteoporosis, and osteopenia.

In summary, the (−/−) mice analyzed by DEXA exhibited a notable decrease in body weight, decrease in total tissue mass, lean body mass and decreased bone mineral content and density suggestive of growth retardation in these mutants. Thus, PRO1182 polypeptides or agonists thereof must be essential for normal growth and/or growth metabolism and therefore would be useful in the treatment or prevention of growth disorders, cachexia or other tissue wasting diseases.

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche).

Results:

The male mutant (−/−) mice exhibited a decreased mean serum triglyceride level and an increased mean serum glucose level (although normal insulin levels and glucose tolerance testing) when compared with their gender-matched (+/+) littermates and the historical means. In summary, these knockout mutant mice exhibited a lipid related phenotype consistent with the observed decreased weight, growth and length measurements.

41.15. Generation and Analysis of Mice Comprising DNA66659-1593 (UNQ685) Gene Disruptions In these knockout experiments, the gene encoding PRO1325 polypeptides (designated as DNA66659-1593) (UNQ685) was disrupted. The gene specific information for these studies is as follows: the mutated mouse gene corresponds to nucleotide reference: NM_172257 or ACCESSION: NM_172257 NID: gi 26986550 ref NM_172257.1 *Mus musculus* hypothetical protein LOC214597 (LOC214597); protein reference: Q922R2 or ACCESSION: Q922R2NID: *Mus musculus* (Mouse). Similar to hypothetical protein FLJ20174 (Fragment).

MOUSESPTRNRDB; the human gene sequence reference: NM 015996 or ACCESSION: NM_015996 NID: gi 7705756 ref NM_015996.1 *Homo sapiens* CGI-40 protein (CGI-40); the human protein sequence corresponds to reference: Q9Y357 or ACCESSION: Q9Y357 NID: *Homo sapiens* (Human). CGI-40 protein. HUMANSPTRNRDB.

The mouse gene of interest is BC023957 (cDNA sequence BC023957), ortholog of human CGI-40 (CGI-40 protein). Aliases include MGC36407, MGC58967, B930096019.

CGI-40 is a hypothetical multispan transmembrane protein located in the plasma membrane. It consists of a signal peptide, a relatively large extracellular domain, and nine transmembrane domains. The molecular function of CGI-40 is not known; however, it is structurally similar to *C. elegans* sid-1 (systemic RNA Interference Defective SID-1, putative transmembrane protein, systemic RNAi enabling [87.9 kD] [sid-1]) (Lai et al, *Genome Res;* 10(5):703-13 (2000)). Sid-1 transports double-stranded RNA into cells, enabling systemic RNA interference-mediated gene silencing in *C. elegans* (Winston et al, *Science;* 295(5564):2456-9 (2002); Feinberg and Hunter, *Science;* 301(5639):1545-7 (2003)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 24 | 35 | 26 | 85 |
| Expected | 21.25 | 42.5 | 21.25 | 85 |

Chi-Sq. = 2.74
Significance = 0.25396
(hom/n) = 0.31
Avg. Litter Size = 8
Mutation Type: Homologous Recombination (standard)

Coding exons 1 and 2 were targeted (NCBI accession NM_172257.1).

Wild-type Expression Panel: Expression of the target gene was detected only in spinal cord and eye among the 13 adult tissue samples tested by RT-PCR.

Disruption of the target gene was confirmed by Southern hybridization analysis.

41.15.1. Phenotypic Analysis (for disrupted gene: DNA66659-1593 (UNQ685)

(a) Overall Phenotypic Summary:

Mutation of the gene encoding the ortholog of human CGI-40 protein (CGI-40) resulted in multifocal degenerative myopathy and alterations in pancreatic acinar cells in (−/−) mice. The mutant (−/−) mice also exhibited decreased mean total tissue mass, lean body mass and fat mass (%&g) as well as decreased bone-related measurements. The (−/−) mice also exhibited a decreased serum IgG1 response to ovalbumin challenge and an increased mean platelet count. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample.

Analyzed wt/het/hom: 7/4/8

Results of this Challenge:

The mutant (−/−) mice exhibited a decreased mean serum IgG1 response to the ovalbumin challenge when compared with their (+/+) littermates. Thus, these knockout mice exhibited a decreased ability to elicit an OVA specific antibody response to the T-cell dependent OVA antigen. In summary, ovalbumin challenge studies indicate that knockout mice deficient in the gene encoding PRO1325 polypeptides exhibit immunological abnormalities when compared with their wild-type littermates. The mutant mice exhibited a decreased ability to elicit an immunological response when challenged with the T-cell dependent OVA antigen. This suggests that PRO1325 polypeptides or their agonists would be useful agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, inhibitors (antagonists) of PRO1325 polypeptides would be useful in inhibiting the immune response and would be useful candidates for suppressing harmful immune responses, e.g. in the case of graft rejection or graft-versus-host diseases.

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

The (−/−) mice exhibited an increased mean platelet count when compared with their (+/+) littermates and the historical mean. Analyzed wt/het/hom: 8/4/9

Thus, mutant mice deficient in the DNA66659-1593 gene resulted in a phenotype related to coagulation disorders. In this regard, inhibitors or antagonists of PRO1325 polypeptides would be useful intreating disorders related to abnormal blood coagulation such as hemophilia.

(c) Pathology

Microscopic Observations: The 6 (−/−) mice available for analysis exhibited mild-to-moderate multifocal degenerative myopathy, characterized in the skeletal muscle by eosinophilia, loss of striations, vacuolization, shrunken fibers, and centralization of nuclei (basophilia and increased nuclei). The changes were present within individual fibers and were scattered widely in the muscles. There was an inflammatory component in some areas, with infiltrating granulocytes and macrophages associated with coagulative necrosis of individual myofibers. These findings confirm the diagnosis of an inflammatory and degenerative myopathy. In addition, 3/3 female (−/−) mice exhibited a change in the cytoplasm of pancreatic acinar cells, reflecting a reduction in rough endoplasmic reticulum in the basilar area of these cells. Alterations were observed in the pancreatic acinar cells.

Gene Expression: LacZ activity was not detected in the panel of tissues by immunohistochemical analysis.

Analyzed wt/het/hom: 2/1/6

(d) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited decreased mean total tissue mass and mean lean tissue mass (1 standard deviation for males) when compared with their gender-matched littermates and the historical means. Both male and female (−/−) mice showed decreased fat (%) and fat (gram) compared with their gender-matched (+/+) littermates and the historical means. The female (−/−) mice also showed an increased BMC/LBM ratio.

Micro-CT: The male (−/−) mice exhibited a notably decreased mean vertebral trabecular bone volume, number, thickness, connectivity density when compared with their gender-matched (+/+) littermates and the historical means. The reduced body size of the mutant mice must be considered when interpreting these results.

Analyzed wt/het/hom: 4/4/8

Summary:

These results demonstrate that knockout mutant mice exhibit abnormal bone metabolism with significant decreased bone measurements similar to osteoporosis characterized by decrease in bone mass with decreased density and possibly fragility leading to bone fractures. Thus, it appears that PRO1325 polypeptides or agonists thereof would be useful in maintaining bone homeostasis. In addition, PRO1325 polypeptides or its encoding gene would be useful in bone healing or for the treatment of arthritis or osteoporosis;

whereas antagonists to PRO1325 polypeptides or its encoding gene would lead to abnormal or pathological bone disorders including arthritis, osteoporosis, and osteopenia.

In summary, the (–/–) mice analyzed by DEXA exhibited a notable decrease in body weight, decrease in total tissue, lean body mass, decreased fat content and decreased bone mineral content and density suggestive of growth retardation in these mutants. Thus, PRO1325 polypeptides or agonists thereof must be essential for normal growth and/or growth metabolism and therefore would be useful in the treatment or prevention of growth disorders, cachexia or other tissue wasting diseases. The pathological findings (as shown above) confirm the fact that these mutant (–/–) mice exhibit muscle mass depletion (specifically multifocal degenerative myopathy).

41.16. Generation and Analysis of Mice Comprising DNA66526-1616 (UNQ718) Gene Disruptions In these knockout experiments, the gene encoding PRO1382 polypeptides (designated as DNA66526-1616) (UNQ718) was disrupted. The gene specific information for these studies is as follows: the mutated mouse gene corresponds to nucleotide reference: NM_175631 or ACCESSION: NM_175631 NID: gi 28274689 ref NM_175631.1 *Mus musculus* cerebellin 4 precursor protein (Cbln4); protein reference: Q8BME9 or ACCESSION: Q8BME9 NID: *Mus musculus* (Mouse). Cerebellin-like glycoprotein 1 precursor (Cerebellin 4); the human gene sequence reference: NM_080617 or ACCESSION: NM_080617 NID: 21313626 *Homo sapiens Homo sapiens* cerebellin precursor-like 1 (CBLNL1); the human protein sequence corresponds to reference: Q9NTU7 or ACCESSION: Q9NTU7 NID: *Homo sapiens* (Human). CEREBELLIN-LIKE GLYCOPROTEIN PRECURSOR (DJ885A10.1). HUMANSPTRNRDB.

The mouse gene of interest is Cbln4 (cerebellin 4 precursor protein), ortholog of human CBLNL1 (cerebellin precursor-like 1). Aliases include cerebellin-like glycoprotein 1 and dJ885A10.1.

CBLNL1 is a likely secreted protein, consisting of a signal peptide and a complement component C1q domain. The C1q fold is similar to that of tumor necrosis factor (SMART accession SM00110). Although the function of CBLNL1 is not currently known, it is structurally similar to family member precerebellin (CBLN1), which functions as a neuromodulator in both brain and adrenal gland (Mazzocchi et al, *J Clin Endocrinol Metab;* 84(2):632-5 (1999); Pang et al, *J Neurosci;* 20(17):6333-9 (2000)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 18 | 42 | 13 | 73 |
| Expected | 18.25 | 36.5 | 18.25 | 73 |

Chi-Sq. = 2.34
Significance = 0.30998
(hom/n) = 0.18
Avg. Litter Size = 7
Mutation Type: Homologous Recombination (standard)

Coding exon 1 was targeted (NCBI accession NM_175631.1).

Wild-type Expression Panel: Expression of the target gene was detected in brain; spinal cord; eye; thymus; and stomach, small intestine, and colon among the 13 adult tissue samples tested by RT-PCR.

Disruption of the target gene was confirmed by Southern hybridization analysis.

41.16.1. Phenotypic Analysis (for Disrupted Gene: DNA66526-1616 (UNQ718)

(a) Overall Phenotypic Summary:

Mutation of the gene encoding the ortholog of human cerebellin precursor-like 1 (CBLNL1) resulted in the observation that female mutant (–/–) mice exhibited decreased ambulatory counts during home-cage activity testing. However, male (–/–) mice exhibited increased anxiety during open field testing. Both male and female (–/–) mice showed significant increase in uric acid levels. In addition, the male (–/–) mice exhibited decreased bone-related measurements. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal’s movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period. Analyzed wt/het/hom: 8/0/8

Results:

The female (–/–) mice exhibited mild hypoactivity during home-cage activity testing when compared with their gender-matched (+/+) littermates and the historical means.

As summarized above, differences were observed during home-cage activity testing. The (−/−) mice exhibited decreased ambulatory counts during the observed time periods when compared with their (+/+) littermates suggesting an abnormal circadian rhythm response in the mutants. These results are consistent with lethargy.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 4/4/8

Results:

A difference was observed during open field activity testing. The male (−/−) mice exhibited a decreased median sum time in the center area when compared with their gender-matched (+/+) littermates. This type of behavior is consistent with an increased anxiety like response. Knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO1382 polypeptides or agonists thereof would be useful in the treatment of such neurological disorders or the amelioration of the symptoms associated with anxiety disorders.

(c) Blood Chemistry

Test Description: Lexicon Genetics uses the COBAS Integra 400 (mfr: Roche) in its clinical settings for running blood chemistry tests on mice.

Results:

The (−/−) mice showed a significant increase in uric acid levels (female p=0.04156; male p=0.01383) compared to wild-type littermates. No other indications of renal impairment were observed.

(d) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Male knockouts (−/−) showed a decrease in bone mineral content and bone mineral density measurements. Female heterozygotes (+/−) and homozygotes (−/−) showed an increase in total tissue mass, lean body mass and bone mineral content compared to wild-type littermates.

MicroCT: Male knockouts showed decreased trabecular bone volume (1 standard deviation) and thickness (1 standard deviation) than the historical means. Midshaft femoral total area was also decreased in the male knockouts. However, wild-type measurements were higher than the historical means.

These results demonstrate that knockout mutant mice exhibit abnormal bone metabolism. Thus, PRO1382 polypeptides would be useful for maintaining bone homeostasis and in the treatment of osteo-related disorders, whereas antagonists or inhibitors of PRO1382 polypeptides or its encoding DNA would lead to abnormal or pathological bone disorders.

41.17. Generation and Analysis of Mice Comprising DNA68874-1622 (UNQ728) Gene Disruptions In these knockout experiments, the gene encoding PRO1410 polypeptides (designated as DNA68874-1622) (UNQ728) was disrupted. The gene specific information for these studies is as follows: the mutated mouse gene corresponds to nucleotide reference: AK087615 or *Mus musculus* 2 days pregnant adult female oviduct cDNA, RIKEN full-length enriched library, clone: E230025L24 product: hypothetical protein, full insert sequence; protein reference: Q8C2Z8 or ACCESSION: Q8C2Z8NID: *Mus musculus* (Mouse). Hypothetical protein; the human gene sequence reference: NM_203422 or *Homo sapiens* similar to hypothetical protein (LOC221091); the human protein sequence corresponds to reference: Q8ND94 or ACCESSION: Q8ND94 NID: *Homo sapiens* (Human). Hypothetical protein. HUMANSPTRNRDB.

The mouse gene of interest and human ortholog encode a hypothetical protein. Aliases include MGC61707.

The hypothetical protein is a likely type I plasma membrane protein, containing a signal peptide, a fibronectin type 3 domain, and a C-terminal transmembrane segment. Fibronectin type 3 domains are found in a wide variety of intracellular and extracellular proteins and are involved in protein-protein interactions (SMART accession SM00060).

Targeted or gene trap mutations are generated in strain 129SvEv$^{Brd}$-derived embryonic stem (ES) cells.

The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 22 | 46 | 24 | 92 |
| Expected | 23 | 46 | 23 | 92 |

Chi-Sq. = 0.09
Significance = 0.95745
(hom/n) = 0.26
Avg. Litter Size = 9
Mutation Type: Homologous Recombination (standard)

Coding exon 1 was targeted (NCBI accession AK087615.1).

Wild-type Expression Panel: Expression of the target gene was detected in all 13 adult tissue samples tested by RT-PCR, except bone.

Disruption of the target gene was confirmed by Southern hybridization analysis.

41.17.1. Phenotypic Analysis (for Disrupted Gene: DNA68874-1622 (UNQ728)

(a) Overall Phenotypic Summary:

Mutation of the gene encoding the ortholog of a human hypothetical membrane protein resulted in the observation that female mutant (−/−) mice exhibited elevated levels of serum glucose with decreased insulin levels. In addition, male knockouts showed decreased total tissue mass and bone-mineral density measurements. Gene disruption was confirmed by Southern blot.

(b) Phenotypic Analysis: Metabolism-Blood Chemistry/ Serum Glucose Levels

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Abnormal glucose test results may indicate but may not be limited to the following disorders or conditions: Diabetes Type 1 and Type 2, Syndrome X, various cardiovascular diseases and/or obesity.

Procedure: A cohort of 4 wild type and 8 homozygous mice were used in this assay.

Results:

Blood Chemistry: The female (−/−) mice exhibited an increased mean serum glucose level when compared with their gender-matched (+/+) littermates and the historical mean. In addition, the (−/−) mice showed decreased levels of insulin. Thus, knockout mice exhibited the phenotypic pattern of an impaired glucose homeostasis with abnormal insulin levels (low) and elevated levels of fasting serum glucose indicative of diabetes or a pre-diabetic condition. Based on these results, PRO1410 polypeptides (or agonists thereof) would be useful in the treatment of an impaired glucose metabolism and/or diabetes.

(c) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Male knockouts (−/−) showed a decrease in total tissue mass and bone mineral density measurements compared to gender-matched (+/+) littermates and the historical means.

MicroCT: Male knockouts showed decreased trabecular bone volume and thickness as well as midshaft femoral total area.

These results demonstrate that male knockout mutant mice exhibit abnormal bone metabolism with bone loss similar to osteoporosis characterized by decrease in bone mass with decreased density and possibly fragility leading to bone fractures. Thus, PRO1410 polypeptides would be useful in maintaining bone homeostasis and would be useful for bone healing or for the treatment of arthritis or osteoporosis, whereas antagonists or inhibitors of PRO1410 polypeptides or its encoding DNA would lead to abnormal or pathological bone disorders similar to osteoporosis.

41.18. Generation and Analysis of Mice Comprising DNA73744-1665 (UNQ763) Gene Disruptions In these knockout experiments, the gene encoding PRO1555 polypeptides (designated as DNA73744-1665) (UNQ763) was disrupted. The gene specific information for these studies is as follows: the mutated mouse gene corresponds to nucleotide reference: NM_022418 or ACCESSION: NM_022418 NID: na *Mus musculus Mus musculus* hypothetical protein, clone 1-2 (AB030183); protein reference: Q9JMG3 or Q9JMG3 Q9JMG3 mRNA, COMPLETE CDS, CLONE: 1-22010004020R1; the human gene sequence reference: NM_031434 or ACCESSION: NM_031434 NID: na *Homo sapiens Homo sapiens* hypothetical protein MGC5442 (MGC5442); the human protein sequence corresponds to reference: Q9BVT8 or Q9BVT8 Q9BVT8 SIMILAR TO HYPOTHETICAL PROTEIN, CLONE 1-2.

The mouse gene of interest is RIKEN cDNA 2010004O20 gene, ortholog of human C7orf21 (chromosome 7 open reading frame 21). Aliases include SB144 and MGC5442.

C7orf21 is a hypothetical protein, consisting of a signal peptide, a ubiquitin family domain (Pfam accession PF00240), and two C-terminal transmembrane segments. The cell location of this protein is not clear; however, bioinformatic analysis suggests that C7orf21 may be secreted. Ubiquitin family domains are found in ubiquitin-like proteins, such as SUMO, NEDD8, and Apg12. Ubiquitin-like proteins undergo ligation with target proteins and thereby mediate biological processes such as proteasome degradation, cell cycle progression, cell signaling, and immune recognition (Yeh et al, *Gene;* 248(1-2):1-14 (2000); Hochstrasser, *Nat Cell Biol;* 2(8): E153-7 (2000); Hochstrasser, *Cell;* 107(1):5-8 (2001)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 26 | 37 | 22 | 85 |
| Expected | 21.25 | 42.5 | 21.25 | 85 |

Chi-Sq. = 1.80
Significance = 0.40657
(hom/n) = 0.26
Avg. Litter Size = 9
Mutation Type: Homologous Recombination (standard)

Coding exons 1 and 2 were targeted (NCBI accession NM_022418.1).

Wild-type Expression Panel: Expression of the target gene was detected in all 13 adult tissue samples tested by RT-PCR, except lung, skeletal muscle, and bone.

Disruption of the target gene was confirmed by Southern hybridization analysis.

41.18.1. Phenotypic Analysis (for Disrupted Gene: DNA73744-1665 (UNQ763)

(a) Overall Phenotypic Summary:

Mutation of the gene encoding the ortholog of human chromosome 7 open reading frame 21 (C7orf21) resulted in an increased mean absolute monocyte count in (−/−) mice. The (−/−) mice exhibited decreased total body fat with abnormal bone measurements. In addition, the (−/−) mice also exhibited increased locomotor activity during circadian rhythm testing. The male (−/−) mice showed an impaired glucose tolerance although insulin levels were normal. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal’s movements, with beam breaks automatically divided into ambulations.

Activity is recorded in 60, one-hour intervals during the three-day test. Data generated are displayed by median activity levels recorded for each hour (circadian rhythm) and median total activity during each light/dark cycle (locomotor activity) over the three-day testing period. Thus, the mutant (−/−) mice exhibited severe hypoactivity. Analyzed wt/het/hom: 4/4/8

Results:

The (−/−) mice exhibited increased median ambulatory counts during both dark phases of the habituation period when compared with their gender-matched (+/+) littermates and the historical means.

Analyzed wt/het/hom: 8/0/8

As summarized above, notable differences were observed during home-cage activity testing. These results are consistent with increased locomotor activity during the dark periods. These finding suggest that the mutant (−/−) mice are hyperactive suggestive of neurological disorders associated with abnormal circadian rhythm patterns. Antagonists or inhibitors of PRO1555 polypeptides would be expected to mimic this neurological phenotype. Whereas PRO1555 polypeptides or agonists thereof would be useful in the treatment of such neurological disorders.

(c) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 heterozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for 10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

DEXA: Both the male and female (−/−) mice exhibited decreased mean percent total body fat and mean total fat mass when compared with their gender-matched (+/+) littermates and the historical means. The male mutants also exhibited an increased lean body mass and mean femoral bone mineral density. The female (−/−) mice showed a decreased total tissue mass compared to their gender-matched wild-type littermates although the wild-type mice were higher than the historical controls.

Micro-CT: The male mutant (−/−) mice exhibited an increased mean femoral midshaft cortical thickness when compared with their gender-matched (+/+) littermates and the historical means, though wild-type were higher than historical means. In addition, the male (−/−) mice trabecular bone volume, number, and connectivity density was increased though wild-type measurements were lower than the historical means.

CAT-Scan: The 2 (−/−) mice tested exhibited a decreased intra-abdominal fat and possibly enlarged kidneys.

In summary, the (−/−) mice exhibited a decreased mean total body fat and fat mass when compared with their gender-matched (+/+) littermates. These observations suggest a tissue wasting disorder associated with dyslipidemia or fat storage depletion or other metabolic disorder. The CAT scan results show that the kidneys are enlarged as well. In addition, the mutant (−/−) mice exhibited an abnormal bone development. Thus, antagonists or inhibitors of PRO1555 polypeptides or the PRO1555 encoding gene would be expected to mimic this negative metabolic phenotype. Likewise, PRO1555 polypeptides or agonists thereof would be essential for normal metabolic and or growth development and would be useful in the treatment of related growth or metabolic disorders associated with this observed negative phenotype.

(d) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following test was performed:

(1) Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

The (−/−) mice exhibited an increased mean absolute monocyte count when compared with their (+/+) littermates and the historical means. Analyzed wt/het/hom: 7/4/8

In summary, the hematology results indicate that the homozygous mutant mice exhibited an increased monocyte count compared to their littermate controls indicating elevated levels of precursors of macrophages. These results indicate that the homozygous (−/−) knockout mice exhibit a positive immunological phenotype. These immunological findings suggest that inhibitors (antagonists) of PRO1555 polypeptides would be important agents which could stimulate the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO1555 polypeptides or agonists thereof would play a role in inhibiting the immune response and would be useful candidates for suppressing harmful immune responses, e.g. in the case of graft rejection or graft-versus-host diseases.

(e) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 4 wild type and 8 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

These studies indicated that male (−/−) mice exhibit impaired glucose tolerance in the presence of normal fasting glucose at all 3 intervals tested when compared with their gender-matched (+/+) littermates and the historical means. In addition, hyperinsulinemia was not apparent in the (−/−) mice. No abnormality was seen in the remaining clinical chemistry data. Thus, knockout mice exhibited the phenotypic pattern of an impaired glucose homeostasis, and as such antagonists to PRO1555 polypeptides would be expected to mimic these metabolic effects. Likewise, PRO1555 polypeptides or agonists thereof would be useful in the treatment of impaired glucose homeostasis.

41.19. Generation and Analysis of Mice Comprising DNA76529-1666 (UNQ764) Gene Disruptions In these knockout experiments, the gene encoding PRO1556 polypeptides (designated as DNA76529-1666) (UNQ764) was disrupted. The gene specific information for these studies is as follows: the mutated mouse gene corresponds to nucleotide reference: NM_197991 or *Mus musculus* RIKEN cDNA 2310044H10 gene (2310044H10Rik); protein reference: Q8VCD8 or ACCESSION: Q8VCD8 NID: *Mus musculus* (Mouse). Hypothetical 27.0 kDa protein. MOUSESPTRNRDB; the human gene sequence reference: NM_206538 or *Homo sapiens* hypothetical protein LOC284361 (LOC284361), transcript variant 2; the human protein sequence corresponds to reference: Q8N541 or ACCESSION: Q8N541 NID: *Homo sapiens* (Human). LOC126122 (Hypothetical protein). HUMANSPTRNRDB.

The mouse gene of interest is RIKEN cDNA 2310044H10 gene, ortholog of human hypothetical protein LOC284361. Aliases include INM02, AAAS764, MGC33203, and 2310044H10Rik.

The hypothetical protein consists of a signal peptide and a C-terminal transmembrane segment, suggesting that the protein is a type I plasma membrane protein. The orthologous human gene encodes a second variant, consisting of a signal peptide and a divergent C-terminus that lacks the transmembrane segment. This variant is predicted to be secreted.

| | wt | het | hom | Total |
|---|---|---|---|---|
| Observed | 12 | 43 | 19 | 74 |
| Expected | 18.5 | 37 | 18.5 | 74 |

Chi-Sq. = 3.27
Significance = 0.19493
(hom/n) = 0.26
Avg. Litter Size = 7
Mutation Type: Retroviral Insertion (OST)

Retroviral insertion occurred in the intron between coding exons 1 and 2 (NCBI accession NM_197991.1).

Wild-type Expression Panel: Expression of the target gene was detected in all 13 adult tissue samples tested by RT-PCR, except skeletal muscle, bone, and adipose.

RT-PCR analysis revealed that the transcript was absent in the (−/−) mouse analyzed (M-184). Disruption of the target gene was confirmed by Inverse PCR.

41.19.1. Phenotypic Analysis (for Disrupted Gene: DNA76529-1666 (UNQ764)

(a) Overall Phenotypic Summary:

Mutation of the gene encoding the ortholog of a human hypothetical membrane protein resulted in enhanced glucose tolerance and decreased fertility in male (−/−) mice. Female knockouts showed significantly increased bilirubin levels and decreased phosphorous levels. Male knockouts showed decreased trabecular bone measurements. Female (−/−) mice exhibited an increased anxiety-related response. Transcript was absent by RT-PCR.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value. Analyzed wt/het/hom: 4/4/8

Results:

A notable difference was observed during open field activity testing. The female (−/−) mice exhibited a decreased median sum time in the center area when compared with their gender-matched (+/+) littermates. This type of behavior is consistent with an increased anxiety like response. Knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO1556 polypeptides or agonists thereof would be useful in the treatment of such neurological disorders or the amelioration of the symptoms associated with anxiety disorders.

(c) Phenotypic Analysis: Metabolism-Blood Chemistry (1) Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 4 wild type and 8 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

These studies indicated that male (−/−) mice exhibit enhanced glucose tolerance in the presence of normal fasting glucose at all 3 intervals tested when compared with their gender-matched (+/+) littermates and the historical means. Male (−/−) mice also showed decreased serum glucose levels. In addition, hyperinsulinemia was not apparent in the (−/−) mice. No abnormality was seen in the remaining clinical chemistry data. Thus, knockout mice exhibited the opposite phenotypic pattern of an impaired glucose homeostasis, and as such antagonists to PRO1556 polypeptides or its encoding gene would be useful in the treatment of impaired glucose homeostasis.

(2) Bilirubin/Phosphorous

The female knockout mice (−/−) showed significantly elevated levels of serum bilirubin (p=0.04399). Phosphorous levels were significantly decreased (p=0.046203) in male mice.

(d) Body Diagnostics

Fertility

Results:

The single male (−/−) mouse available for analysis was infertile. No pups were produced after 60 days of breeding and 4 matings. The male mutant appeared healthy, a penile erection could be induced by abdominal pressure, and vaginal plugs were observed in the female mates, suggesting that the infertility is most likely due to a sperm defect.

(c) Bone Metabolism & Body Diagnostics: Bone Metabolism: Radiology Phenotypic Analysis In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 heterozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

MicroCT: The male knockouts (−/−) showed a decrease in trabecular connectivity density and midshaft femoral thickness and total area when compared to wild-type littermates. These results demonstrate that knockout mutant mice exhibit abnormal bone metabolism with bone loss similar to osteoporosis characterized by decrease in bone mass with decreased density and possibly fragility leading to bone fractures. Thus, it appears that PRO1556 polypeptides or agonists thereof would be useful in maintaining bone homeostasis. In addition, PRO1556 polypeptides or its encoding gene would be important in bone healing or for the treatment of arthritis or osteoporosis; whereas antagonists to PRO1556 polypeptides or its encoding gene would lead to abnormal or pathological bone disorders including inflammatory diseases associated with abnormal bone metabolism including arthritis, osteoporosis, and osteopenia.

41.20. Generation and Analysis of Mice Comprising DNA76532-1702 (UNQ833) Gene Disruptions In these knockout experiments, the gene encoding PRO1760 polypeptides (designated as DNA76532-1702) (UNQ833) was disrupted. The gene specific information for these studies is as follows: the mutated mouse gene corresponds to nucleotide reference: AK006658 or ACCESSION: AK006658 NID: na *Mus musculus* adult male testis cDNA, product: hypothetical Protease associated (PA) domain containing protein, full insert sequence; protein reference: BAB24693 or unnamed protein product [*Mus musculus*]; the human gene sequence reference: NM_032319 or *Homo sapiens* chromosome 2 open reading frame 7 (C2orf7); the human protein sequence corresponds to reference: NP_115695 or chromosome 2 open reading frame 7.

The mouse gene of interest is a hypothetical protein, ortholog of human C2orf7 (chromosome 2 open reading frame 7).

C2orf7 is predicted to have a signal peptide, a protease-associated (PA) domain or an N-terminal transmembrane region. PA domains have been observed in the plant vacuolar sorting receptor and in various protease and RING-type zinc finger families (InterPro IPR003137). Although containing a PA-type region, nothing else suggests that C2orf7 is a protease.

| | wt | het | hom | Total |
|---|---|---|---|---|
| Observed | 26 | 34 | 17 | 77 |
| Expected | 19.25 | 38.5 | 19.25 | 77 |

Chi-Sq. = 3.16
Significance = 0.20640
(hom/n) = 0.22
Avg. Litter Size = 8
Mutation Type: Retroviral Insertion (OST)

Retroviral insertion occurred in the intron between coding exons 1 and 2 (NCBI Accession AK006658).

Wild-type Expression Panel: Expression of the target gene was detected in embryonic stem (ES) cells and in all 13 adult tissue samples tested by RT-PCR, except skeletal muscle and stomach, small intestine, and colon.

RT-PCR analysis revealed that the transcript was reduced in kidney and absent in spleen in the (−/−) mouse analyzed (F-70).

41.20.1. Phenotypic Analysis (for Disrupted Gene: DNA76523-1702 (UNQ833)

(a) Overall Phenotypic Summary:

Mutation of the gene encoding the ortholog of human chromosome 2 open reading frame 7 (C2orf7) resulted in increased lumbar vertebrae measurements in (−/−) mice. Transcript was absent in spleen and reduced in kidney as determined by RT-PCR.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

The knockout (−/−) mice exhibited increased lumbar 5 vertebrae measurements compared to their wild-type littermates. Thus, knocking out the gene encoding PRO1760 polypeptides results in a phenotype suggestive of osteo-related diseases. Thus, PRO1760 polypeptides or agonists thereof would be useful for treating conditions associated with abnormal bone development such as osteopetrosis.

41.21. Generation and Analysis of Mice Comprising DNA76510-2504 (UNQ849) Gene Disruptions In these knockout experiments, the gene encoding PRO1787 polypeptides (designated as DNA76510-2504) (UNQ849) was disrupted. The gene specific information for these studies is as follows: the mutated mouse gene corresponds to nucleotide reference: AK090278 or *Mus musculus* 16 days neonate male medulla oblongata cDNA, RIKEN full-length enriched library, clone: G630033K19 product: similar to PROTEIN ZERO RELATED PROTEIN (MYELIN PROTEIN ZERO-LIKE 1) [*Homo sapiens*], full insert sequence; protein reference: XP_129565 or RIKEN cDNA 1110007A10 [*Mus musculus*]; the human gene sequence reference: NM_003953 or *Homo sapiens* myelin protein zero-like 1 (MPZL1); the human protein sequence corresponds to reference: NP_003944 or myelin protein zero-like 1; protein zero related [*Homo sapiens]*.

The mouse gene of interest is Mpzl1 (myelin protein zero-like 1, 1110007A10Rik), which is the ortholog of human MPZL1. Aliases include PZR and protein zero related.

MPZL1 is a type I membrane protein that likely functions as a receptor for extracellular matrix protein fibronectin (Zannettino et al, *Biochem J;* 370(Pt 2):537-49 (2003)). MPZL1 contains a signal peptide, an immunoglobulin type V domain, a transmembrane domain, and two tandem immunoreceptor tyrosine-based inhibitory motifs (ITIMs). Upon activation of MPZL1, the ITIMs become tyrosine phosphorylated, resulting in recruitment and activation of SHP-2 (Src homology phosphatase type-2) (Zhao et al, *J Biol Chem;* 277(10):7882-8 (2002); Zhao and Zhao, *J Biol Chem;* 275 (8):5453-9 (2000)). MPZL1 is widely expressed but is particularly abundant in heart, placenta, kidney, and pancreas (Zhao and Zhao, *J Biol Chem;* 273(45):29367-72 (1998)). In addition to MPZL1, two other isoforms lacking the ITIMs occur by alternative splicing. MPZL1 is likely to be involved in cell motility and development (Zannettino et al, *Biochem J;* 370(Pt 2):537-49 (2003)).

| | wt | het | hom | Total |
|---|---|---|---|---|
| Observed | 12 | 49 | 21 | 82 |
| Expected | 20.5 | 41 | 20.5 | 82 |

Chi-Sq. = 5.10
Significance = 0.07818
(hom/n) = 0.26
Avg. Litter Size = 8
Mutation Type: Retroviral Insertion (OST)

Retroviral insertion occurred between coding exons 1 and 2 (Accession AK090278).

Wild-type Expression Panel: Expression of the target gene was detected in embryonic stem (ES) cells and in all 13 adult tissue samples tested by RT-PCR.

RT-PCR analysis revealed that the transcript was absent in spleen and greatly reduced in heart at 30 PCR cycles in the (−/−) mouse analyzed (M-126).

41.21.1. Phenotypic Analysis (for Disrupted Gene: DNA76510-2504 (UNQ849)

(a) Overall Phenotypic Summary:

Mutation of the gene encoding the ortholog of human myelin protein zero-like 1 (MPZL1) resulted in the observation that mutant (−/−) mice exhibited increased lumbar vertebral measurements. Transcript was absent in spleen and greatly reduced in heart as determined by RT-PCR.

(b) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

The knockout (−/−) mice exhibited increased lumbar 5 vertebrae measurements with increased trabecular number compared to their wild-type littermates. Thus, knocking out the gene encoding PRO1787 polypeptides results in a phenotype suggestive of osteo-related diseases. Thus, PRO1787 polypeptides or agonists thereof would be useful for treating conditions associated with abnormal bone development.

41.22. Generation and Analysis of Mice Comprising DNA77624-2515 (UNQ859) Gene Disruptions In these knockout experiments, the gene encoding PRO1868 polypeptides (designated as DNA77624-2515) (UNQ859) was disrupted. The gene specific information for these studies is as follows: the mutated mouse gene corresponds to nucleotide reference: NM_023277 or ACCESSION: NM_023277 NID: 12963612 *Mus musculus Mus musculus* junction cell adhesion molecule 3 (Jcam3); protein reference: Q9EPK4 or ACCESSION: Q9EPK4 NID: *Mus musculus* (Mouse). JUNCTIONAL ADHESION MOLECULE-2, JAM-2 (1110002N23RIK PROTEIN). MOUSESPTRNRDB; the human gene sequence reference: NM_032801 or ACCESSION: NM_032801 NID: 21704285 *Homo sapiens Homo sapiens* junctional adhesion molecule 3 (JAM3); the human protein sequence corresponds to reference: Q8WWL8 or ACCESSION: Q8WWL8 NID: *Homo sapiens* (Human). Junction adhesion molecule 3.

The mouse gene of interest is Jam3 (junction adhesion molecule 3), ortholog of human JAM3. Aliases include JAM-3, Jcam3, 1110002N23Rik, FLJ14529, and junction cell adhesion molecule 3.

JAM3 is a type I plasma membrane protein that functions as a cell adhesion molecule and counter-receptor for the beta2-integrin Mac-I, which is expressed on leukocytes, and the junctional adhesion molecule JAM2, which is expressed at the tight junctions of epithelial and endothelial cells. The protein consists of a signal peptide, two immunoglobulin-like folds, a transmembrane segment, and a 46-amino acid cytoplasmic segment (Arrate et al, *J Biol Chem;* 276(49):45826-32 (2001); Santoso et al, *J Exp Med;* 196(5):679-91 (2002); Cunningham et al, *J Biol Chem;* 277(31):27589-92 (2002); Palmeri et al, *J Biol Chem;* 275(25):19139-45 (2000)). JAM3 expression has been detected on platelets, T cells, natural killer cells, and dendritic cells (Liang et al, *J Immunol;* 168 (4):1618-26 (2002)).

JAM3 likely mediates the migration of immune cells into secondary lymphoid organs and sites of inflammation via the tight junctions of endothelial cells, which express JAM2 (Arrate et al, *J Biol Chem;* 276(49):45826-32 (2001); Liang et al, *J Immunol;* 168(4):1618-26 (2002)). Moreover, JAM3 likely facilitates the migration of immune cells expressing Mac-1 through injured vasculature denuded of endothelium via deposited platelets, which express JAM3 (Santoso et al, *J Exp Med;* 196(5):679-91 (2002)). These biological roles suggest that JAM3 may be a novel target for therapeutic intervention of inflammatory diseases, including atherothrombosis (Chavakis et al, *Thromb Haemost;* 89(1): 13-7 (2003)). JAM3 may also be involved in cardiogenesis and the severe human congenital heart defect hypoplastic left heart (Phillips et al, *Genomics;* 79(4):475-8 (2002)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 18 | 42 | 12 | 72 |
| Expected | 18 | 36 | 18 | 72 |

Chi-Sq. = 3.00
Significance = 0.22313
(hom/n) = 0.17
Avg. Litter Size = 8
Mutation Type: Homologous Recombination (standard)

Coding exon 1 was targeted (NCBI accession NM_023277.1).

Wild-type Expression Panel: Expression of the target gene was detected only in brain, spinal cord, and eye among the 13 adult tissue samples tested by RT-PCR.

Disruption of the target gene was confirmed by Southern hybridization analysis.

41.22.1. Phenotypic Analysis (for Disrupted Gene: DNA77624-2515 (UNQ859)

(a) Overall Phenotypic Summary:

Mutation of the gene encoding the ortholog of human junctional adhesion molecule 3 (JAM3) resulted in mature congenital nuclear lenticular cataracts in (−/−) mice. The (−/−) mice also exhibited increased locomotor activity (hyperactivity in open field testing). The mutant (−/−) mice exhibited a marked growth retardation being smaller in size, decreased body weight, and decreased mean total tissue mass, lean body mass and total fat mass. Male (−/−) mice were infertile and exhibited hypogonadism with defective spermatogenesis. In addition, in Genentech's breeding colony knockout animals are not represented at Mendelian frequencies-about 50% of UNQ859 (−/−) mice die after birth. Gene disruption was confirmed by Southern blot.

(b) Bone Metabolism & Body Diagnostics (1) Tissue Mass & Lean Body Mass Measurements—Dexa Dexa Analysis—Test Description:

Procedure: Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

General Observations:

The 4 albino (−/−) mice analyzed exhibited cataracts. Cataracts were also observed in the black and agouti (−/−) mice upon further examination, the phenotype being more pronounced in the albino mutants.

Body Measurements (Body Length & Weight):

Body Measurements: A measurement of body length and weight was performed at approximately 16 weeks of age.

Results:

The (−/−) mice exhibited decreased mean body weight and decreased mean body length when compared with their gender-matched (+/+) littermates and the historical means.

Fertility:

The male (−/−) mouse available for analysis produced no pups after 4 matings and 40 days of breeding.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

CAT-Scan Protocol:

Mice were injected with a CT contrast agent, Omnipaque 300 (Nycomed Amershan, 300 mg of iodine per ml, 0.25 ml per animal, or 2.50-3.75 g iodine/kg of body weight) intraperitoneally. After resting in the cage for 10 minutes, the mouse was then sedated by intraperitoneal injection of Avertin (1.25% 2,2,2,-tribromoethanol, 20 ml/kg body weight). A CAT-scan was performed using a MicroCAT scanner (ImTek, Inc.) with the anesthetized animal lying prone on the test bed. Three dimensional images were reconstructed by the Feldkamp algorithm in a cluster of workstations using an ImTek 3D RECON software.

Results:

DEXA: The male (−/−) mice exhibited decreased mean total tissue mass, lean body mass, and total fat mass when compared with their gender-matched (+/+) littermates and the historical means. In addition, male knockout (−/−) mice showed an increased BMC/LBM ratio compared with wild-type littermates.

CAT-Scan: Both of the male (−/−) mice available for analysis (M-147 and M-186) exhibited moderately smaller testes, suggesting hypogonadism. The male (−/−) mice exhibited a decreased testicular weight (mean of 0.137 g) compared to a wild-type sibling (0.214 g) and historical data (0.216 g with a standard deviation of 0.058 g). A single (+/−) male mouse exhibited a markedly enlarged left testis (M-148), which might be due to an acquired lesion such as inflammation. Analyzed wt/het/hom: 4/5/9

Pathology

Gross Observations Cataracts were noted in all of the (−/−) mice.

Microscopic Observations: The (−/−) mice exhibited congenital nuclear lenticular cataracts, which were the only major ocular lesion seen in these mutant mice. In addition, the male (−/−) mice available for analysis exhibited small testes and epididymides. Defective or arrested spermatogenesis was noted in all seminiferous tubules with profound alterations in the number and proportion of germ cells; a few tubules were lined exclusively with Sertoli cells. There were numerous giant cells and apopotic germ cells but very few mature spermatids present in the epididymus and seminiferous tubules.

Gene Expression: LacZ activity was not detected in the panel of tissues by immunohistochemical analysis.

Analyzed wt/het/hom: 2/1/10

Summary:

The diagnostic/radiology and pathological studies indicate that the mutant (−/−) mice exhibit pronounced growth retardation marked by low body weight and decreased mean total tissue mass, lean body mass and total body fat. The male mice also show severe reproductive disorders with defective spermatogenesis, infertility and hypogonadism. Heterozygous male (+/−) mice also showed signs of reproductive disorders linked to inflammatory conditions. In addition, the pathology report indicates that mutant (−/−) mice have severe congenital nuclear lenticular cataracts. Thus, knocking out the gene that encodes PRO1868 polypeptides causes severe growth, reproductive and opthalmological disorders. Antagonists or inhibitors of PRO1868 polypeptides or the gene encoding PRO1868 polypeptides would be expected to mimic these negative phenotypic conditions. Thus, the gene that encodes PRO1868 polypeptides appears to be essential for normal growth and reproductive development especially in males.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet- Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Keams-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

All 8 (−/−) mice exhibited differing degrees of mature cataracts. The retinal artery-to-vein ratio (A/V) could not be measured for the (−/−) mice due to blockage from the cataracts. Analyzed wt/het/hom: 4/5/8

In summary, by knocking out the gene identified as DNA77624-2515 (UNQ859) which encodes PRO1868 polypeptides, the homozygous mutant progeny exhibit phenotypes which are associated with cataract formation and/or other opthalmological disorders. Such detected opthalmology changes are most commonly associated with cardiovascular systemic diseases. In particular, cataract formation may be indicative of a cardiovascular complication related to disturbances in the blood coagulation cascade. Cataracts are also associated with such systemic diseases as: Human Down's syndrome, Hallerman-Streiff syndrome, Lowe syndrome, galactosemia, Marfan syndrome, Trismoy 13-15 condition, Alport syndrome, myotonic dystrophy, Fabry disease, hypothroidisms, Conradi syndrome. Thus, antagonists of PRO1868 encoding genes would lead to similar pathological changes, whereas agonists would be useful as therapeutic agents in the prevention of cataract formation and/or the underlying cardiovascular disease or opthalmological disorders.

(d) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15;94 (8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

A notable difference was observed during open field activity testing. The (−/−) mice exhibited an increased sum total distance traveled and rearing activity when compared with their gender-matched (+/+) littermates, which is indicative of an increased exploratory response to a novel environment in the mutants. Thus, knockout mice demonstrated a phenotype consistent with hyperactivity. In light of these observations, PRO1868 polypeptides and agonists thereof would be useful for the treatment or amelioration of the symptoms associated with hyperactivity.

41.23. Generation and Analysis of Mice Comprising DNA91779-2571 (UNQ1883) Gene Disruptions In these knockout experiments, the gene encoding PRO4326 polypeptides (designated as DNA91779-2571) (UNQ1883) was disrupted. The gene specific information for these studies is as follows: the mutated mouse gene corresponds to nucleotide reference: NM_029770 or *Mus musculus* unc-5 homolog B (*C. elegans*) (Unc5b); protein reference: Q8K1S3 or ACCESSION: Q8K1S3 NID: *Mus musculus* (Mouse). Netrin receptor Unc5h2. MOUSESPTRNRDB; the human gene sequence reference: NM_170744 or ACCESSION: NM_170744 NID: gi 25014104 ref NM_170744.1 *Homo sapiens* transmembrane receptor Unc5H2 (UNC5H2); the human protein sequence corresponds to reference: Q81ZJ1 or ACCESSION: Q81ZJ1 NID: *Homo sapiens* (Human). Transmembrane receptor UNC5H2.

The mouse gene of interest is Unc5b (unc-5 homolog B [*C. elegans*]), ortholog of human UNC5B. Aliases include Unc5h2, 6330415E02Rik, unc5 homolog (*C. elegans*) 2, p53RDL1, transmembrane receptor Unc5H2, and p53-regulated receptor for death and life.

UNC5B is a type I plasma membrane protein and receptor for the chemorepulsive axonal guidance ligand netrin-1 (Leonardo et al, *Nature;* 386(6627):833-8 (1997)). The protein consists of a signal peptide, two immunoglobulin domains, two thrombospondin type-1 motifs, a transmembrane segment, a ZU-5 domain, a DCC-binding domain, and a C-terminal death domain. UNC5B may stimulate cAMP synthesis by interacting with G protein subunit G1-alpha2 in its active, GTP-bound form, relieving adenylyl cyclase from inhibition by G1-alpha2. UNC5B plays a role in axonal guidance and is likely to participate in immune cell chemotaxis (Komatsuzaki et al, *Biochem Biophys Res Commun;* 297(4):898-905 (2002)). In the absence of netrin-1, UNC5B may function as a tumor suppressor by inducing apoptosis (Thiebault et al, *Proc Natl Acad Sci USA;* 100(7):4173-8 (2003); Llambi et al, *EMBO J;* 20(11):2715-22 (2001); Tanikawa et al, *Nat Cell Biol;* 5(3):216-23 (2003)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 22 | 44 | 0 | 66 |
| Expected | 16.5 | 33 | 16.5 | 66 |

Chi-Sq. = 22.00
Significance = 0.00002
(hom/n) = 0.00
Avg. Litter Size = 7
Mutation Type: Retroviral Insertion (OST)

Retroviral insertion occurred in the intron between coding exons 1 and 2 (NCBI accession NM_029770.1).

Wild-type Expression Panel: Expression of the target gene was detected in all 13 adult tissue samples tested by RT-PCR, except thymus, skeletal muscle, bone, and adipose.

Due to lethality, transcript expression analysis was not performed. Disruption of the target gene was confirmed by Inverse PCR.

41.23.1. Phenotypic Analysis (for Disrupted Gene: DNA91779-2571 (UNQ1883)

(a) Overall Phenotypic Summary:

Mutation of the gene encoding the ortholog of human unc-5 homolog B (*C. elegans*) (UNC5B) resulted in lethality of (−/−) mutants. Nitrituria was observed in the (+/−) mice. In addition, female (+/−) mice showed increased total body fat content.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Pathology

Gross Observations: The 12.5 day (−/−) embryos exhibited moderately stunted growth.

Microscopic Observations: At 12.5 days, 63 embryos were observed: 14 (−/−) embryos, 28 (+/−) embryos, 12 (+/+) embryos, and 9 resorption moles. Normal organogenesis was observed in the 12.5 day (−/−) embryos, although there was a general reduction in size of all organs except for the brain and spinal cord.

Gene Expression: LacZ activity was detected in the brain among the panel of tissues analyzed by immunohistochemistry.

(c) Blood Chemistry—Urinalysis

Of the eight (8) heterozygous (+/−) mice analyzed, seven exhibited nitrituria.

(d) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type and 4 heterozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

Female heterozygotes (+/−) showed an increased total body fat content compared to the gender-matched littermates and the historical means, however there were no changes in blood triglycerides to suggest abnormal lipid metabolism.

41.24. Generation and Analysis of Mice Comprising DNA100272-2969 (UNQ1887) Gene Disruptions In these knockout experiments, the gene encoding PRO4332 polypeptides (designated as DNA100272-2969) (UNQ1887) was disrupted. The gene specific information for these studies is as follows: the mutated mouse gene corresponds to nucleotide reference: AK014709 or ACCESSION: AK014709 NID: 12852724 *Mus musculus Mus musculus* 0 day neonate head cDNA, RIKEN full-length enriched library, clone: 4833416109: related to CG5901 PROTEIN, full insert sequence; protein reference: Q9CUS9 or Signal peptide peptidase-like 3 (SPP-like 3 protein) (Intramembrane protease 2) (IMP2) (Presenilin-like protein 4); the human gene sequence reference: NM__139015 or *Homo sapiens* signal peptide peptidase 3 (SPPL3); the human protein sequence corresponds to reference: Q8TCT6 or ACCESSION: Q8TCT6 NID: *Homo sapiens* (Human). Presenilin-like protein 4 (EC 3.4.99.-) (SPPL3 protein). HUMANSPTRNRDB.

The mouse gene of interest is presenilin-like protein 4, ortholog of human SPPL3 (signal peptide peptidase 3). Aliases include 4833416109Rik, IMP2, PSL4, DKFZP586C1324, intramembrane protease, and presenilin-like protein 4.

SPPL3 is a putative presenilin-type aspartic protease located in the membrane of the endoplasmic reticulum that catalyzes the intramembrane proteolysis of signal peptides cleaved from preproteins. Signal protein peptidases, such as SPPL3, are involved in cell signaling, cell regulation, and protein processing (Weihofen et al, *Science;* 296(5576):2215-8 (2002); Grigorenko et al, *Biochemistry* (*Mosc*); 67(7):826-35 (2002); Xia and Wolfe, *J Cell Sci;* 116(Pt 14):2839-44 (2003); Urny et al, *Gene Expr Patterns;* 3(5):685-91 (2003)).

| | wt | het | hom | Total |
|---|---|---|---|---|
| Observed | 14 | 40 | 14 | 68 |
| Expected | 17 | 34 | 17 | 68 |

Chi-Sq. = 2.12
Significance = 0.34686
(hom/n) = 0.21
Avg. Litter Size = 7
Mutation Type: Retroviral Insertion (OST)

Retroviral insertion occurred between coding exons 6 and 7 (NCBI accession AK014709.1).

Wild-type Expression Panel: Expression of the target gene was detected in brain, spinal cord, kidney, and heart among the 13 adult tissue samples tested by RT-PCR.

RT-PCR analysis revealed that the transcript was absent in the (−/−) mouse analyzed (M-185). Larger transcripts were also detected in both tissues in the (−/−) mouse due to the splicing of a fragment from the retroviral vector into the target transcript, as determined by nucleotide sequence analysis. However, the in-frame stop codon in the retroviral vector sequence was predicted to disrupt translation of this transcript. Disruption of the target gene was confirmed by Inverse PCR.

41.24.1. Phenotypic Analysis (for Disrupted Gene: DNA100272-2969 (UNQ1887)

(a) Overall Phenotypic Summary:

Mutation of the gene encoding the ortholog of human signal peptide peptidase 3 (SPPL3) resulted in growth retardation and decreased fertility in (−/−) mice. The (−/−) mice also exhibited numerous neurological abnormalities. In addition, the mutant (−/−) mice exhibited decreased triglyceride and mean fasting serum glucose levels. Expression of LacZ was observed in seminiferous tubules including sperm. Transcript was absent by RT-PCR.

(b) Body Diagnostics—Tissue Mass & Leas Body Mass Measurements—Dexa (1) Dexa Analysis—Test Description:

Procedure: Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

General Observations:

The (−/−) mice were smaller than their (+/+) littermates and exhibited an agitated behavior.

Body Measurements (Body Length & Weight):

Body Measurements: A measurement of body length and weight was performed at approximately 16 weeks of age.

Results:

Both the male and female (−/−) mice exhibited decreased mean body weight and decreased mean body length when compared with their gender-matched (+/+) littermates and the historical means.

Fertility:

Both the male and female (−/−) mice exhibited impaired fertility. The single male (−/−) mouse available for analysis was infertile. No pups were produced after 60 days of breeding and 4 matings, although the mutant appeared healthy but small. A penile erection could be induced by abdominal pressure, and vaginal plugs were observed in the female mates. However, the plugs were soft, malformed, and did not tightly fill the vagina, indicating a possible accessory sex gland or sperm defect in the mutant. The 3 female (−/−) mice available for analysis produced small litters, further suggesting decreased fertility in the mutants.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: Both the male and female (−/−) mice exhibited notably decreased mean total tissue mass and lean body mass when compared with their gender-matched (+/+) littermates and the historical means. The male (−/−) mutants also exhibited decreased mean bone mineral content and bone mineral density-related measurements.

Micro-CT: The male (−/−) mice exhibited decreased mean vertebral trabecular bone volume and thickness and notably decreased mean femoral mid-shaft cross-sectional area and cortical thickness when compared with their gender-matched (+/+) littermates and the historical means. Analyzed wt/het/hom: 5/4/8

Summary:

The (−/−) mice were quite small in size and showed a notable decrease in body weight suggestive of growth retardation in these mutants. Although pathology observations failed to reveal any histopathological lesions, the negative phenotype is indicative of a tissue wasting condition with growth retardation. The mutant male (−/−) mice also exhibited decreased bone-related measurements. Thus, PRO4332 polypeptides or agonists thereof must be essential for normal growth and/or growth metabolism and therefore would be useful in the treatment or prevention of growth disorders such as cachexia or other tissue wasting diseases.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Functional Observational Battery

Test Description: The FOB is a series of situations applied to the animal to determine gross sensory and motor deficits. A subset of tests from the Irwin neurological screen that evaluates gross neurological function is used. In general, short-duration, tactile, olfactory, and visual stimuli are applied to the animal to determine their ability to detect and respond normally. These simple tests take approximately 10 minutes and the mouse is returned to its home cage at the end of testing.

Tail Suspension Analysis:

Test Description: The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm.

Results:

Basic Sensory & Motor Observations:

Numerous abnormalities were noted during the functional observational battery. Among the 8 (−/−) mice tested, 5 exhibited an abnormal response to the 20-second tail suspension test, 3 exhibited shaking behavior, and 2 exhibited circling behavior. With regard to the response to helplessness: The (−/−) mice exhibited a decreased median immobility time during tail suspension testing when compared with their (+/+) littermates and the historical mean.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm)

was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The (−/−) mice exhibited a decreased median sum time-in-center during open field testing when compared with their gender-matched (+/+) littermates and the historical mean, suggesting an increased anxiety-like response in the mutants. The (−/−) mice also exhibited a decreased normalized slope during open field testing when compared with their (+/+) littermates, suggesting an accelerated habituation response to novelty.

In summary, the open field testing as well as the functional observational battery testing revealed a phenotype associated with pronounced increased anxiety with associated agitated behavior which could be associated with severe to moderate anxiety, hyperactivity; sensory disorders; obsessive-compulsive disorders, schizophrenia or a paranoid personality. Antagonists or inhibitors of PRO4332 polypeptides or the encoding gene would be expected to mimic these neurological abnormalities. On the other hand, PRO4332 polypeptides or agonists thereof would be useful in the prevention or treatment of such neurological disorders.

Analyzed wt/het/hom: 8/0/8

Prepulse inhibition of the acoustic startle reflex

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

The mutant (−/−) mice exhibited a trend towards a decreased startle response indicative of a decreased ability to respond to an external auditory stimuli.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, measurements were recorded using the COBAS Integra 400 (mfr: Roche). Analyzed wt/het/hom: 4/4/8

Results:

The male mutant (−/−) mice exhibited a decreased mean serum triglyceride level ($p=0.014$) when compared with their gender-matched (+/+) littermates and the historical mean.

As summarized above, the homozygous (−/−) mutant mice exhibited a decreased mean serum triglyceride level (compared to normal levels) when compared with their gender-matched (+/+) littermates and the historical mean. (Analyzed wt/het/hom: 4/4/8)

Thus, mutant mice deficient in the PRO4332 can serve as a model for cardiovascular disease especially for those diseases which are associated with an abnormal lipid metabolism. Antagonists or inhibitors of PRO4332 polypeptides would be useful in regulating blood lipids and in particular maintaining normal triglyceride levels and fat metabolism and would be useful in the treatment of such cardiovascular diseases as: hypertension, atherosclerosis, heart failure, stroke, various coronary artery diseases, and/or obesity or diabetes.

Serum Glucose Levels

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Abnormal glucose test results may indicate but may not be limited to the following disorders or conditions: Diabetes Type 1 and Type 2, Syndrome X, various cardiovascular diseases and/or obesity.

Procedure: A cohort of 4 wild type and 8 homozygous mice were used in this assay.

Results:

Blood Chemistry: The male (−/−) mice exhibited a decreased mean fasting serum glucose level when compared with their gender-matched (+/+) littermates and the historical mean. Thus, knockout mice exhibited the phenotypic pattern opposite of an impaired glucose homeostasis which would occur in diabetes or a pre-diabetic condition. The blood chemistry levels shown above are consistent with these findings. Based on these results, antagonists or inhibitors of PRO4332 polypeptides would be useful in the treatment of an impaired glucose metabolism and/or diabetes.

41.25. Generation and Analysis of Mice Comprising DNA86594-2587 (UNQ1900) Gene Disruptions In these knockout experiments, the gene encoding PRO4346 polypeptides (designated as DNA86594-2587) (UNQ1900) was disrupted. The gene specific information for these studies is as follows: the mutated mouse gene corresponds to nucleotide reference: NM_172793 or *Mus musculus* RIKEN cDNA D330012D11 gene (D330012D11Rik); protein reference: Q8BJE2 or ACCESSION: Q8BJE2 NID: *Mus musculus* (Mouse). Weakly similar to cDNA FLJ32535 FIS; the human gene sequence reference: AY358358 or *Homo sapiens* clone DNA86594 VDLS1900 (UNQ1900); the human protein sequence corresponds to reference: AAQ88724 or VDLS1900 [*Homo sapiens]*.

The mouse gene of interest is RIKEN cDNA D330012D11 gene, ortholog of human butyrophilin 3. Aliases include Btn3, B430208101, and butyrophilin 3.

Butyrophilin 3 is a type I plasma membrane protein that likely functions as a receptor. The 536-amino acid protein consists of a signal peptide, two immunoglobulin domains (Pfam accession PF00047), a transmembrane segment, and a SPRY domain (Pfam accession PF000622). Immunoglobulin domains are usually involved in protein-protein interactions. SPRY domains are found in ryanodine receptors and IP3 receptors, which gate release of calcium from the lumen of the endoplasmic reticulum. Butyrophilin 3 is similar to butyrophilin subfamily 1 member A1 (BTN1A1), which is thought to play a role in mediating secretion of milk-fat droplets in mammary gland (Jack and Mather, *J Biol Chem;* 265(24):14481-6 (1990); Ishii et al, *Biochim Biophys Acta;* 1245(3):285-92 (1995)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 13 | 36 | 17 | 66 |
| Expected | 16.5 | 33 | 16.5 | 66 |

Chi-Sq. = 1.03
Significance = 0.59741
(hom/n) = 0.26
Avg. Litter Size = 7
Mutation Type: Homologous Recombination (standard)

Coding exons 1 and 2 were targeted (the signal sequence and the IgV domain were removed in the knockout) (NCBI accession NM_172793.1).

Wild-type Expression Panel: Expression of the target gene was detected in all 13 adult tissue samples tested by RT-PCR, except lung and bone.

Disruption of the target gene was confirmed by Southern hybridization analysis.

41.25.1. Phenotypic Analysis (for Disrupted Gene: DNA86594-2587 (UNQ1900)

(a) Overall Phenotypic Summary:

Mutation of the gene encoding the ortholog of human butyrophilin 3 resulted in an increased IgG1 and IgG2a response to ovalbumin. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc.

In the area of immunology, targets were identified herein for the treatment of inflammation and inflammatory disorders. Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Ovalbumin Challenge

Procedure: This assay was carried out on 7 wild types and 8 homozygotes. Chicken ovalbumin (OVA) is a T-cell dependent antigen, which is commonly used as a model protein for studying antigen-specific immune responses in mice. OVA is non-toxic and inert and therefore will not cause harm to the animals even if no immune response is induced. The murine immune response to OVA has been well characterized, to the extent that the immunodominant peptides for eliciting T cell responses have been identified. Anti-OVA antibodies are detectable 8 to 10 days after immunization using enzyme-linked immunosorbent assay (ELIZA), and determination of different isotypes of antibodies gives further information on the complex processes that may lead to a deficient response in genetically engineered mice.

As noted above, this protocol assesses the ability of mice to raise an antigen-specific immune response. Animals were injected IP with 50 mg of chicken ovalbumin emulsified in Complete Freund's Adjuvant and 14 days later the serum titer of anti-ovalbumin antibodies (IgM, IgG1 and IgG2 subclasses) was measured. The amount of OVA-specific antibody in the serum sample is proportional to the Optical Density (OD) value generated by an instrument that scans a 96-well sample plate. Data was collected for a set of serial dilutions of each serum sample. Analyzed wt/het/hom: 8/4/9

Results of this Challenge:

The (−/−) mice exhibited an increased mean serum IgG1 and IgG2a response to ovalbumin challenge when compared with their (+/+) littermates and the historical means. Thus, these knockout mice exhibited an increased ability to elicit an OVA specific antibody response to the T-cell dependent OVA antigen.

In summary, the ovalbumin challenge studies indicate that knockout mice deficient in the gene encoding PRO4346 polypeptides exhibit immunological abnormalities when compared with their wild-type littermates. In particular, the mutant mice exhibited an increased ability to elicit an immunological response when challenged with the T-cell dependent OVA antigen. Thus, inhibitors or antagonists of PRO4346 polypeptides would be useful for stimulating the immune system (such as T cell proliferation) and would find utility in the cases wherein this effect would be beneficial to the individual such as in the case of leukemia, and other types of cancer, and in immunocompromised patients, such as AIDS sufferers. Accordingly, PRO4346 polypeptides or agonists thereof would be useful for inhibiting the immune response and thus would be useful candidates for suppressing harmful immune responses, e.g. in the case of graft rejection or graft-versus-host diseases.

FACS and BiaCore Binding Studies Binding assays were performed both by FACS and BiaCore binding assays. UNQ1900-ECD-Fc was coated on a chip and the BiaCore assay tested 275 proteins to determine binding to the UNQ1900-ECD-Fc coated chip. The following proteins bound to UNQ1900: EGFL8 (also called NG3), NT3, NT4, BDNF, FGF8 and INF-gamma. Binding between UNQ1900 and EGFL8 (NG3) was also seen by FACSUNQ1900 FACS analysis showed EGFL8 (NG3) binding with UNQ1900. BDNF has been shown to regulate glucose metabolism and energy expenditure (Chaldakov et al., *Med Sci Monit.* 9(10): HY19-21 (2003); Kuroda et al. *Metabolism* 52(2); 203-8 (2003); Nonomura et al., *Int J Exp Diabetes Res.* 2(3):201-9 (2001)). BDNF, NT3 and NT4 are trophic factors for sensory neurons (Anand P., *Prog Brain Res.* 146:477-92 (204); Fritzsch et al. *Prog Brain Res.* 146:265-78 (2004); Erickson et al. *J. Neurosci.* 21(2):581-9 (2001)). UNQ1900 is strongly expressed in sensory neurons.

In Situ Hybridization Studies

In situ hybridization was determined in E13.5 mouse embryos. EGFL8 (NG3) and UNQ1900 were found to be both expressed in the nervous system and in a subset of blood vessels. UNQ1900 was also expressed ubiquitously at a low level. E13.5 mouse limbs showed UNQ1900 expression as well as EGFL8 expression, however, UNQ1900 expression was not as restricted as EGFL8 but the strongest UNQ1900 signals was found in the same tissues as was the case for EGFL8. In situ hybridization studies were also conducted on murine MCH66 kidney tumor sections, which also showed that UNQ1900 was expressed in these tumor cells. Immunofluorescent staining of rhabdomyosarcoma A676 xenograft tumor sections showed that EGFL8 (NG3) was expressed in this subset of tumor blood vessels.

41.26. Generation and Analysis of Mice Comprising DNA87974-2609 (UNQ1925) Gene Disruptions In these knockout experiments, the gene encoding PRO4400 polypeptides (designated as DNA87974-2609) (UNQ1925) was disrupted. The gene specific information for these studies is as follows: the mutated mouse gene corresponds to nucleotide reference: NM_028117 or ACCESSION: NM_028117 NID: gi 21312415 ref NM_028117.1 *Mus musculus* RIKEN cDNA 2600016L03 gene (2600016L03Rik); protein reference: Q9DOP2 or ACCESSION: Q9DOP2 NID: *Mus musculus* (Mouse). 2600016L03Rik protein. MOUSESPTRNRDB; the human gene sequence reference: NM 130468 or *Homo sapiens* dermatan 4 sulfotransferase 1 (D4ST1); the human protein sequence corresponds to reference: Q96P94 or ACCESSION: Q96P94 NID: *Homo sapiens* (Human). Dermatan-4-sulfotransferase-1 (Dermatan 4-sulfotransferase). HUMANSPTRNRDB.

The mouse gene of interest is D4st1 (dermatan 4 sulfotransferase 1), ortholog of human D4ST1. Aliases include 2600016L03Rik, dermatan-4-sulfotransferase-1, HD4ST, D4ST-1, and HNK1 ST.

D4ST1 is a type II membrane protein and enzyme that catalyzes the 4-O-sulfation of GalNAc substituted at C-3 with alpha-linked iduronic acid (i.e., IdoUA-GalNAc) during biosynthesis of dermatan sulfate. The protein consists of a short cytoplasmic N terminus, a signal anchor, and a catalytic domain located in the lumen of the endoplasmic reticulum. Most tissues express D4ST1, but it is particularly high in pituitary, placenta, uterus, and thyroid. D4ST1 is an important enzyme for the synthesis of dermatan sulfate proteoglycans, which play a role in extracellular matrix assembly, cell adhesion, cell migration, cell proliferation, neurite outgrowth, wound repair, and anticoagulant processes (Mikami et al, *J Biol Chem;* 278(38):36115-27 (2003); Evers et al, *J Biol Chem;* 276(39):36344-53 (2001)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 23 | 36 | 19 | 78 |
| Expected | 19.5 | 39 | 19.5 | 78 |

Chi-Sq. = 0.87
Significance = 0.64668
(hom/n) = 0.24
Avg. Litter Size = 8
Mutation Type: Homologous Recombination (standard)

Coding exon 1 was targeted (NCBI accession NM_028117.2).

Wild-type Expression Panel: Expression of the target gene was detected in embryonic stem (ES) cells and in all 13 adult tissue samples tested by RT-PCR, except skeletal muscle and adipose.

Disruption of the target gene was confirmed by Southern hybridization analysis.

41.26.1. Phenotypic Analysis (for Disrupted Gene: DNA87974-2609 (UNQ1925)

(a) Overall Phenotypic Summary:

Mutation of the gene encoding the ortholog of human dermatan 4 sulfotransferase 1 (D4ST1) resulted in decreased mean body weight and length, decreased total tissue mass, lean body mass and decreased total body fat suggestive of growth retardation in (−/−) mice. The (−/−) mice also exhibited enhanced sensor/motor gating/attention, and the (−/−) mice also exhibited a decreased anxiety-related response. Opthamalogical abnormalities were noted in (−/−) mice consistent with early signs of retinal degeneration. The (−/−) mice also showed an enhanced glucose tolerance with decreased fasting mean serum glucose levels. Similarly, the (−/−) mice showed a decrease in triglyceride blood levels. Gene disruption was confirmed by Southern blot.

(b) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygous mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

The (−/−) mice exhibited a decreased mean fasting serum glucose and an enhanced glucose tolerance when compared with their gender-matched (+/+) littermates and the historical means. Similarly, as shown below, the mutant (−/−) mice exhibited decreased triglyceride blood levels (especially in the female (−/−) mice). Thus, knockout mice exhibited the opposite phenotypic pattern of an impaired glucose homeostasis, and as such antagonists to PRO4400 polypeptides or its encoding gene would be useful in the treatment of impaired glucose homeostasis and diseases associated with abnormal glucose metabolism such as found in diabetes.

(c) Cardiovascular Phenotypic Analysis:

In the area of cardiovascular biology, phenotypic testing was performed to identify potential targets for the treatment of cardiovascular, endothelial or angiogenic disorders. One such phenotypic test included optic fundus photography and angiography to determine the retinal arteriovenous ratio (A/V ratio) in order to flag various eye abnormalities. An abnormal A/V ratio signals such systemic diseases or disorders that may be related to the vascular disease of hypertension (and any disease that causes hypertension, e.g. atherosclerosis), diabetes or other ocular diseases corresponding to opthalmological disorders. Such eye abnormalities may include but are not limited to the following: retinal abnormality is retinal dysplasia, various retinopathies, restenosis, retinal artery obstruction or occlusion; retinal degeneration causing secondary atrophy of the retinal vasculature, retinitis pigmentosa, macular dystrophies, Stargardt's disease, congenital stationary night blindness, choroideremia, gyrate atrophy, Leber's congenital amaurosis, retinoschisis disorders, Wagner's syndrome, Usher syndromes, Zellweger syndrome, Saldino-Mainzer syndrome, Senior-Loken syndrome, Bardet-Biedl syndrome, Alport's syndrome, Alstom's syndrome, Cockayne's syndrome, dysplaisa spondyloepiphysaria congentia, Flynn-Aird syndrome, Friedreich ataxia, Hallgren syndrome, Marshall syndrome, Albers-Schnoberg disease, Refsum's disease, Kearns-Sayre syndrome, Waardenburg's syndrome, Alagile syndrome, myotonic dystrophy, olivopontocerebellar atrophy, Pierre-Marie dunsdrome, Stickler syndrome, carotinemeia, cystinosis, Wolfram syndrome, Bassen-Kornzweig syndrome, abetalipoproteinemia, incontinentia pigmenti, Batten's disease, mucopolysaccharidoses, homocystinuria, or mannosidosis.

Procedure: A cohort of 4 wild type, 4 heterozygotes and 8 homozygotes were tested in this assay. Optic fundus photography was performed on conscious animals using a Kowa Genesis small animal fundus camera modified according to Hawes and coauthors (Hawes et al., 1999 Molecular Vision 1999; 5:22). Intra-peritoneal injection of fluorescein permitted the acquisition of direct light fundus images and fluorescent angiograms for each examination. In addition to direct opthalmological changes, this test can detect retinal changes associated with systemic diseases such as diabetes and atherosclerosis or other retinal abnormalities. Pictures were provided of the optic fundus under normal light. The angiographic pictures allowed examination of the arteries and veins of the eye. In addition an artery to vein (A/V) ratio was determined for the eye.

Opthalmology analysis was performed on generated F2 wild type, heterozygous, and homozygous mutant progeny using the protocol described above. Specifically, the A/V ratio was measured and calculated according to the fundus images with Kowa COMIT+software. This test takes color photographs through a dilated pupil: the images help in detecting and classifying many diseases. The artery to vein ratio (A/V) is the ratio of the artery diameter to the vein diameter (measured before the bifurcation of the vessels). Many diseases will influence the ratio, i.e., diabetes, cardiovascular disorders, papilledema, optic atrophy or other eye abnormalities such as retinal degeneration (known as retinitis pigmentosa) or retinal dysplasia, vision problems or blindness. Thus, phenotypic observations which result in an increased artery-to-vein ratio in homozygous (−/−) and heterozygous (+/−) mutant progeny compared to wildtype (+/+) littermates would be indicative of such pathological conditions.

Results:

Fundus: Sporadic depigmentation spots were noted in the retinas of the (−/−) mice. One (−/−) mouse (F-131) exhibited projected optic disc vessels, suggesting increased intra-cranial pressure.

Analyzed wt/het/hom: 4/4/8

In this study, homozygous (−/−) mice exhibited heterogeneous retinal backgrounds with mild depigmentation spots, which indicates early signs of retinal degeneration. In addition, the homozygous mice exhibited projected optic disc vessels when compared with their (+/+) littermates indicative of increased intra-cranial pressure. In summary, by knocking out the gene identified as DNA87974-2609 encoding PRO4400 polypeptides, the homozygous mutant progeny exhibit phenotypes which are associated with retinal degeneration. Such detected retinal changes are most commonly associated with cardiovascular systemic diseases or disorders that are related to the vascular disease of hypertension (and/or any disease that causes hypertension, e.g. atherosclerosis), diabetes or other ocular diseases corresponding to opthalmological disorders such as retinal degeneration. Thus, antagonists of PRO4400 encoding genes would lead to similar pathological retinal changes, whereas agonists would be useful as therapeutic agents in the treatment atherosclerosis or other opthamological disorders including retinal degeneration and diseases associated with this condition (as indicated above).

(d) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The (−/−) mice exhibited decreased mean body weight and decreased mean body length when compared with their gender-matched (+/+) littermates and the historical mean. Analyzed wt/het/hom: 29/53/22

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male and female (−/−) mice both exhibited a decreased total body fat content and the male mice exhibited a decreased total tissue mass and lean body mass.

Micro-CT: The male (−/−) mice exhibited decreased mean vertebral trabecular bone volume, number, thickness, and connectivity density when compared with their gender-matched (+/+) littermates and the historical means.

Analyzed wt/het/hom: 4/4/9

In summary, the (−/−) mice exhibited decreased body weight and length, decreased mean total tissue mass and lean body mass, decreased total body fat and fat mass and decreased trabecular bone measurements when compared with their gender-matched (+/+) littermates. These observations suggest a growth retardation phenotype. In addition, the mutant (−/−) mice exhibited abnormal bone measurements. Thus, PRO4400 polypeptides or agonists thereof, would be useful for normal growth and bone development and would be useful in the treatment of related growth or metabolic disorders such as osteopetrosis and/or tissue wasting conditions.

(e) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Stress-Induced Hyperthermia:

Test Description: Stress-induced hyperthermia (SIH) is a measurement of autonomic hyperactivity induced by anxiety-provoking stimuli. The method involves taking two rectal body temperature measurements 10 minutes apart. SIH is determined by subtracting the basal body temperature (T1) from the stress-enhanced temperature (T2). The difference in delta values (T2−T1=deltaT) indicates the severity of autonomic hyperactivity or SIH. The rise in body temperature associated with SIH is a sign of anticipatory anxiety to the second rectal body temperature measurement. Lower deltaT values suggest decreased anxiety-like responses.

Results:

Anxiety: The (−/−) mice exhibited resistance to stress-induced hyperthermia when compared with their gender-matched (+/+) littermates and the historical mean, suggesting a decreased anxiety-like response.

Summary

The mutant (−/−) mice exhibited resistance to stress-induced hyperthermia when compared with their gender-matched (+/+) littermates, which is indicative of a decreased anxiety-like response in the mutants. Thus, knockout mice demonstrated a phenotype consistent with depressive disorders, schizophrenia and/or bipolar disorders. Thus, PRO4400 polypeptides and agonists thereof would be useful for the treatment or amelioration of the symptoms associated with depressive disorders.

Prepulse Inhibition Testing (PPI):

Prepulse inhibition of the acoustic startle reflex occurs when a loud 120 decibel (dB) startle-inducing tone is preceded by a softer (prepulse) tone. The PPI paradigm consists of six different trial types (70 dB background noise, 120 dB alone, 74 dB+120 dB−pp4, 78 dB+120 dB−pp8, 82 dB+120 dB−pp12, and 90 dB+120 dB−pp20) each repeated in pseudo random order six times for a total of 36 trials. The max response to the stimulus (V max) is averaged for each trial type. Animals with a 120 dB average value equal to or below 100 are excluded from analysis. The percent that the prepulse inhibits the animal's response to the startle stimulus is calculated and graphed.

Results:

Sensorimotor Gating/Attention: During prepulse inhibition testing, the (−/−) mice exhibited increased inhibition at pp4, pp8, and pp12 when compared with their (+/+) littermates and the historical means, suggesting enhanced sensor/motor gating/attention in the mutants.

Analyzed wt/het/hom: 8/0/8

41.27. Generation and Analysis of Mice Comprising DNA83568-2692 (UNQ2514) Gene Disruptions In these knockout experiments, the gene encoding PRO6003 polypeptides (designated as DNA8368-2692) (UNQ2514) was disrupted. The gene specific information for these studies is as follows: the mutated mouse gene corresponds to nucleotide reference: NM_026162 or ACCESSION: NM_026162 NID: 16757971 *Mus musculus Mus musculus* RIKEN cDNA 1200007L24 gene (1200007L24Rik); protein reference: Q9DC11 or ACCESSION: Q9DC11 NID: *Mus musculus* (Mouse). 1200007L24RIK PROTEIN; the human gene sequence reference: NM_032812 or ACCESSION: NM_032812 NID: 17511212 *Homo sapiens Homo sapiens* tumor endothelial marker 7-related precursor (TEM7R); the human protein sequence corresponds to reference: Q96PD9 or ACCESSION: Q96PD9 NID: *Homo sapiens* (Human). TUMOR ENDOTHELIAL MARKER 7-RELATED PRECURSOR.

The mouse gene of interest is Plxdc2 (plexin domain containing 2), ortholog of human PLXDC2. Aliases include Tem7r, 1200007L24Rik, FLJ14623, tumor endothelial marker 7-related, and tumor endothelial marker 7 related precursor.

PLXDC2 is a type I plasma membrane protein, consisting of a relatively large extracellular domain, a transmembrane segment, and a phylogenetically conserved cytoplasmic domain. The extracellular domain of PLXDC2 contains a signal peptide and a plexin/semaphorin/integrin domain, which is found in plexins, semaphorins, and integrins. Plexins regulate development of neural and epithelial tissue, semaphorins mediate the collapse of neural growth cones, and integrins mediate migration and adhesion of epithelial cells (SMART accession SM00423). In humans, PLXCD2 is highly expressed in endothelium from tumors. However, in mice, PLXCD2 is expressed not only in endothelium from tumors but also in endothelium from normal lung and skeletal muscle. PLXDC2 may be a target for treatment of cancer by anti-angiogenic therapies (Carson-Walter et al, *Cancer Res;* 61(18):6649-55 (2001); St. Croix et al, *Science;* 289(5482): 1197-202 (2000)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 14 | 40 | 22 | 76 |
| Expected | 19 | 38 | 19 | 76 |

Chi-Sq. = 1.89
Significance = 0.38776
(hom/n) = 0.29
Avg. Litter Size = 8
Mutation Type: Homologous Recombination (standard)

Coding exon 2 was targeted (NCBI accession NM_026162.2).

Wild-type Expression Panel: Expression of the target gene was detected in all 13 adult tissue samples tested by RT-PCR, except skeletal muscle; stomach, small intestine, and colon; and adipose.

Disruption of the target gene was confirmed by Southern hybridization analysis.

41.27.1. Phenotypic Analysis (for Disrupted Gene: DNA83568-2692 (UNQ2514)

(a) Overall Phenotypic Summary:

Mutation of the gene encoding the ortholog of human plexin domain containing 2 (PLXDC2) resulted in an increased depressive-like response in (−/−) mice. The mutant mice also exhibited growth retardation and abnormal bone-related measurements. Gene disruption was confirmed by Southern blot.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing.

Tail Suspension Analysis

Test Description: The tail suspension test is a procedure that has been developed as a model for depressive-like behavior in rodents. In this particular setup, a mouse is suspended by its tail for 6 minutes, and in response the mouse will struggle to escape from this position. After a certain period of time the struggling of the mouse decreases and this is interpreted as a type of learned helplessness paradigm. Animals with invalid data (i.e. climbed their tail during the testing period) are excluded from analysis.

Results:

Response to Helplessness: The (−/−) mice exhibited an increased median immobility time during tail suspension testing when compared with their (+/+) littermates and the historical mean, suggesting an increased depressive-like response in the mutants. Thus, knockout mice demonstrated a phenotype consistent with depressive disorders, schizophrenia and/or bipolar disorders. Thus, PRO6003 polypeptides and agonists thereof would be useful for the treatment or amelioration of the symptoms associated with depressive disorders.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The male mutant (−/−) mice exhibited a decreased mean body weight and mean body length when compared with their gender-matched (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and mid-shaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased mean body mass-related measurements (total tissue mass and lean body mass) and decreased mean bone mineral-related measurements (bone mineral content, and bone mineral density in total body, vertebrae, and femur) when compared with their gender-matched (+/+) littermates and the historical means, suggesting growth retardation and bone abnormalities in the male mutants.

Micro-CT: The male (−/−) mice exhibited a notably decreased mean vertebral trabecular bone volume, number, thickness, and connective density and decreased mean femoral mid-shaft cortical thickness and cross-sectional area when compared with their gender-matched (+/+) littermates and the historical means.

These results demonstrate that knockout mutant mice exhibit decreased mean body weight and length as well as abnormal bone metabolism with significant bone loss similar to osteoporosis characterized by decrease in bone mass with decreased density and possibly fragility leading to bone fractures. Thus, it appears that PRO6003 or agonists thereof would be useful in maintaining bone homeostasis. In addition, PRO6003 or its encoding gene would be useful in bone healing or for the treatment of arthritis or osteoporosis; whereas antagonists to PRO6003 or its encoding gene would lead to abnormal or pathological bone disorders including inflammatory diseases associated with abnormal bone metabolism.

Thus in summary, the (−/−) mice analyzed by DEXA were quite small in size and exhibited a notable decrease in body weight and length as well as a decrease in total tissue, lean body mass and decreased bone mineral content and density suggestive of growth retardation in these mutants. These observations are consistent with a tissue wasting condition and/or growth retardation. Thus, PRO6003 polypeptides or agonists thereof must be essential for normal growth and/or growth metabolism and therefore would be useful in the treatment or prevention of growth disorders, cachexia or other tissue wasting diseases.

41.28. Generation and Analysis of Mice Comprising DNA96995-2709 (UNQ2542) Gene Disruptions In these knockout experiments, the gene encoding PRO6094 polypeptides (designated as DNA96995-6094) (UNQ2542) was disrupted. The gene specific information for these studies is as follows: the mutated mouse gene corresponds to nucleotide reference: BC065129 or *Mus musculus* expressed sequence A1843918, mRNA (cDNA clone MGC: 86028 IMAGE: 30362651), complete cds; protein reference: Q8C420 or ACCESSION: Q8C420 NID: *Mus musculus* (Mouse). Acupuncture induced gene 1; the human gene sequence reference: NM_021115 or ACCESSION: NM_021115 NID: 10863914 *Homo sapiens Homo sapiens* seizure related 6 homolog (mouse)-like (SEZ6L); the human protein sequence corresponds to reference: Q9BYH1 or Seizure 6-like protein precursor gi/13603398|dbj|BAB40970.1|SEZ6L [*Homo sapiens].*

The mouse gene of interest is expressed sequence AI843918, ortholog of human SEZ6L (seizure related 6 homolog (mouse)-like). Aliases include AIG1, Acigl, mKIAA0927, KIAA0927, acupuncture induced gene 1, and seizure related gene 6 (mouse)-like.

SEZ6L is a hypothetical type I plasma membrane protein, consisting of a signal peptide, alternating CUB (Pfam accession PF00431) and Sushi (Pfam accession PF00084) domains, a transmembrane segment, and a short cytoplasmic segment. CUB and Sushi domains are generally involved in protein-protein interactions. SEZ6L is a candidate tumor suppressor gene involved in certain types of small cell lung cancer (Nishioka et al, *Oncogene;* 19(54):6251-60 (2000)). However, the function of this protein has not been determined.

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 21 | 43 | 12 | 76 |
| Expected | 19 | 38 | 19 | 76 |

Chi-Sq. = 3.45
Significance = 0.17841
(hom/n) = 0.16
Avg. Litter Size = 8
Mutation Type: Homologous Recombination (standard)

Coding exons 2 and 3 were targeted (NCBI accession AK083229.1).

Wild-type Expression Panel: Expression of the target gene was detected in embryonic stem (ES) cells and in all 13 adult tissue samples tested by RT-PCR, except lung, kidney, liver, skeletal muscle, and bone.

Disruption of the target gene was confirmed by Southern hybridization analysis.

41.28.1. Phenotypic Analysis (for Disrupted Gene: DNA96995-2709 (UNQ2542)

(a) Overall Phenotypic Summary:

Mutation of the gene encoding the ortholog of human seizure related 6 homolog (mouse)-like (SEZ6L) resulted in decreased locomotor activity in (−/−) mice. In addition, the mutant (−/−) mice exhibited a decreased mean absolute lymphocyte count. Female mutant (−/−) mice showed decreased bone mineral content and density as well as a decreased BMC/LBM ratio. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited a decreased mean total white blood cell count when compared with their (+/+) littermates and the historical mean. The decrease was due to a decreased mean absolute lymphocyte count in the (−/−) mice.

(c) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

General & Exploratory Activity: The (−/−) mice exhibited decreased median sum total distance traveled during open field testing when compared with their (+/+) littermates and the historical mean. Rearing behavior was absent in 7 of 8 (−/−) mice and 1 of 8 (+/+) mice. These results are consistent with decreased locomotor activity in the (−/−) mice.

Circadian Test Description:

Female mice are individually housed at 4 pm on the first day of testing in 48.2 cm×26.5 cm home cages and administered food and water ad libitum. Animals are exposed to a 12-hour light/dark cycle with lights turning on at 7 am and turning off at 7 pm. The system software records the number of beam interruptions caused by the animal's movements, with beam breaks automatically divided into ambulations. Activity is recorded in 60, one-hour intervals during the three-day test. Data generated are displayed by median activity levels recorded for each hour (circadian rhythm) and median total activity during each light/dark cycle (locomotor activity) over the three-day testing period.

Results:

The mutant (−/−) mice exhibited a marked decrease in ambulatory counts during the 1-hour and 12-hour habituation periods and during all light/dark periods of home-cage activity testing when compared with their gender-matched (+/+) littermates and the historical means. Analyzed wt/het/hom: 8/0/8

These results are indicative of a suppression of circadian rhythm and coupled with the results observed during open field testing suggest a marked hypo-locomotor activity in the (−/−) mice. These results are consistent with lethargy or depressive disorders. Antagonists or inhibitors of PRO6094 polypeptides or the PRO6094 encoding gene would be expected to mimic this behavior. Likewise, PRO6094 polypeptides or agonists thereof, would be useful in the treatment of such neurological disorders including depressive disorders or other decreased anxiety-like symptoms.

(d) Bone Metabolism—Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited decreased bone mineral content and density-related measurements when compared with their gender-matched littermates and the historical means. The mean bone mineral content index (BMC/LBM) for the female (−/−) mice was also decreased. Analyzed wt/het/hom: 4/4/8

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO6094 or agonists thereof would be useful in maintaining bone homeostasis. In addition, PRO6094 or its encoding gene would be useful in bone healing or for the treatment of arthritis or osteoporosis; whereas antagonists to PRO6094 or its encoding gene would lead to abnormal or pathological bone disorders including inflammatory diseases associated with abnormal bone metabolism including arthritis, osteoporosis, and osteopenia.

41.29. Generation and Analysis of Mice Comprising DNA108743-2722 (UNQ2564) Gene Disruptions In these knockout experiments, the gene encoding PRO6244 polypeptides (designated as DNA108743-2722) (UNQ2564) was disrupted. The gene specific information for these studies is as follows: the mutated mouse gene corresponds to nucleotide reference: NM_028766 or ACCESSION: NM_028766 NID: gi 21311890 ref NM_028766.1 *Mus musculus* RIKEN cDNA 1200015A22 gene (1200015A22Rik); protein reference: Q9 DBS1 or ACCESSION: Q9 DBS1 NID: *Mus musculus* (Mouse). 1200015A22Rik protein (RIKEN cDNA 1200015A22 gene); the human gene sequence reference: NM_024334 or ACCESSION: NM_024334 NID: gi 13236586 ref NM_024334.1 *Homo sapiens* hypothetical protein MGC3222 (MGC3222); the human protein sequence corresponds to reference: Q9BTV4 or ACCESSION: Q9BTV4NID: *Homo sapiens* (Human). Hypothetical protein FLJ14971 (Hypothetical protein FLJ14851).

The mouse gene of interest is RIKEN cDNA 1200015A22 gene, ortholog of human hypothetical protein MGC3222. Aliases include DKFZp586G1919.

MGC3222 is a hypothetical integral membrane protein. The protein consists of four transmembrane segments and no other identifiable domains. MGC3222 is predicted to be located on the endoplasmic reticulum.

| | wt | het | hom | Total |
|---|---|---|---|---|
| Observed | 20 | 25 | 17 | 62 |
| Expected | 15.5 | 31 | 15.5 | 62 |

Chi-Sq. = 2.61
Significance = 0.27078
(hom/n) = 0.27
Avg. Litter Size = 7
Mutation Type: Retroviral Insertion (OST)

Retroviral insertion occurred in the intron between coding exons 1 and 2(NCBI accession NM_028766.1).

Wild-type Expression Panel: Expression of the target gene was detected in all 13 adult tissue samples tested by RT-PCR, except skeletal muscle and bone.

RT-PCR analysis revealed that the transcript was absent in the (−/−) mouse analyzed (M-207). Disruption of the target gene was confirmed by Inverse PCR.

41.29.1. Phenotypic Analysis (for Disrupted Gene: DNA108743 (UNQ2564)

(a) Overall Phenotypic Summary:

Mutation of the gene encoding the ortholog of a human hypothetical integral membrane protein resulted in an increased anxiety-related response in mutant (−/−) mice. Transcript was absent by RT-PCR.

(b) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as "anxiety disorders" which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

General Observations:

The mutant (−/−) mice exhibited a decreased hyperthermic response to stress but baseline temperature tended towards elevation.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The mutant (−/−) mice exhibited a decreased median sum time in the center area when compared with their gender-matched (+/+) littermates. In addition, the (−/−) mice showed a decreased hyperthermic response to stress, but baseline temperature showed a trend towards elevation. The open field behavior is consistent with an increased anxiety like response. Knockout mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO6244 polypeptides or agonists thereof would be useful in the treatment of such neurological disorders or the amelioration of the symptoms associated with anxiety disorders.

41.30. Generation and Analysis of Mice Comprising DNA108769-2765 (UNQ3022) Gene Disruptions In these knockout experiments, the gene encoding PRO9820 polypeptides (designated as DNA108769-2765) (UNQ3022) was disrupted. The gene specific information for these studies is as follows: the mutated mouse gene corresponds to nucleotide reference: NM_145835 or ACCESSION: NM_145835 NID: 22003881 *Mus musculus Mus musculus* lactase-like (Lctl-pending); protein reference: Q8K1F9 or ACCESSION: Q8K1F9 NID: *Mus musculus* (Mouse). Klotho-LPH related protein; the human gene sequence reference: NM_207338 or *Homo sapiens* likely ortholog of mouse klotho lactase-phlorizin hydrolase related protein (KLPH); the human protein sequence corresponds to reference: NP_997221 or likely ortholog of mouse klotho lactase-phlorizin hydrolase related protein [*Homo sapiens*] gi/37182579|gb|AAQ89091.1|KPVW3022 [*Homo sapiens]*.

The mouse gene of interest is Lctl (lactase-like), ortholog of human KLPH (ortholog of mouse klotho lactase-phlorizin hydrolase-related protein). Aliases include KLPH, E1130104105Rik, and klotho-LPH related.

KLPH is a type I membrane protein that is likely to function as a family 1 glycosidase. The protein consists of a signal peptide, a glycosidase hydrolase (family 1) domain, and a C-terminal transmembrane segment. Proteins with this domain catalyze the hydrolysis of glycosidic bonds between two or more carbohydrates or between a carbohydrate and a non-carbohydrate moiety (InterPro accession IPR001360). KLPH is located on the endoplasmic reticulum and is expressed primarily in kidney and skin (Ito et al, *Biochim Biophys Acta;* 1576(3):341-5 (2002)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 16 | 30 | 19 | 65 |
| Expected | 16.25 | 32.5 | 16.25 | 65 |

Chi-Sq. = 0.66
Significance = 0.71837
(hom/n) = 0.29
Avg. Litter Size = 6
Mutation Type: Homologous Recombination (standard)

Coding exons 1 through 4 were targeted (NCBI accession NM_145835.1).

Wild-type Expression Panel: Expression of the target gene was detected only in eye; thymus; and stomach, small intestine, and colon among the 13 adult tissue samples tested by RT-PCR.

Disruption of the target gene was confirmed by Southern hybridization analysis.

41.30.1. Phenotypic Analysis (for Disrupted Gene: DNA108769-2765 (UNQ3022)

(a) Overall Phenotypic Summary:

Mutation of the gene encoding the ortholog of human likely ortholog of mouse klotho lactase-phlorizin hydrolase related protein (KLPH) resulted in higher monocyte counts in heterozygotes (+/−) and homozygotes (−/−). Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

Monocytes counts appeared to be higher in heterozygotes (+/−) and homozygotes (−/−) compared to their gender-matched wild-type littermates and the historical means. Thus, both homozygotes and heterozygotes appear to have higher levels of monocytes which are the precursors of macrophages. These immunological findings suggest a role for inhibitors or antagonists of PRO9820 polypeptides for stimulating the immune response.

41.31. Generation and Analysis of Mice Comprising DNA142238-2768 (UNQ3027) Gene Disruptions In these knockout experiments, the gene encoding PRO9828 polypeptides (designated as DNA142238-2768) (UNQ3027) was disrupted. The gene specific information for these studies is as follows: the mutated mouse gene corresponds to nucleotide reference: NM_022657 or ACCESSION: NM_022657 NID: 12083588 *Mus musculus Mus musculus* fibroblast growth factor 23 (Fgf23); protein reference: Q9EPC2 or ACCESSION: Q9EPC2 NID: *Mus musculus* (Mouse). FIBROBLAST GROWTH FACTOR-23 PRECURSOR (FGF-23); the human gene sequence reference: NM_020638 or ACCESSION: NM_020638 NID: 15055547 *Homo sapiens Homo sapiens* fibroblast growth factor 23 (FGF23); the human protein sequence corresponds to reference: Q9GZV9 or ACCESSION: Q9GZV9 NID: *Homo sapiens* (Human). FIBROBLAST GROWTH FACTOR-23 PRECURSOR (FGF-23) (TUMOR-DERIVED HYPOPHOSPHATEMIA INDUCING FACTOR).

The mouse gene of interest is Fgf23 (fibroblast growth factor 23), ortholog of human FGF23. Aliases include ADHR, HYPF, HPDR2, tumor-derived hypophosphatemia inducing factor, and hypophosphatemia vitamin D-resistant rickets-2 (autosomal dominant).

FGF23 is a secreted peptide of the fibroblast growth factor family that is primarily expressed in the ventrolateral thalamic nucleus of the brain. The protein functions as a ligand for receptors that regulate phosphate and vitamin D metabolism (Yamashita et al, *Biochem Biophys Res Commun;* 277 (2):494-8 (2000); Saito et al, *J Biol Chem;* 278(4):2206-11 (2003)). FGF23 inhibits reabsorption of phosphate in the renal distal tubule (Bowe et al, *Biochem Biophys Res Commun;* 284(4):977-81 (2001)). Moreover, FGF23 decreases expression of 1-alpha-hydroxylase in the kidney, lowering 1,25-dihydroxy vitamin D(3) in the circulation (Shimada et al, *J Clin Invest;* 113(4):561-8 (2004)).

Shimada and colleagues (*J Clin Invest;* 1134:561-8 (2004)) investigated the physiological role of FGF23 using FGF23-deficient mice. They found that renal phosphate reabsorption and serum 1,25-dihydroxy vitamin D(3) were higher in FGF23 homozygous null mice than in wild-type mice. Moreover, the resulting hyperphosphatemia was independent of the actions of parathyroid hormone, suggesting that FGF23 is the principal hormone regulating phosphate homeostasis.

Mutations in the FGF23 gene that result in resistance to proteolysis, prolonging the activity of the hormone, are likely to be the underlying cause of autosomal dominant hypophosphatemic rickets (ADHR) phenotype (The ADHR Consortium, *Nat Genet;* 26(3):345-8 (2000); Shimada et al, *J Clin Invest;* 113(4):561-8 (2004)). Moreover, over-expression of FGF23 likely causes tumor-induced rickets/osteomalacia (Shimada et al, *Proc Natl Acad Sci USA;* 98(11):6500-5 (2001)) and X-linked hypophosphatemic rickets/osteomalacia (Yamazaki et al, *J Clin Endocrinol Metab;* 87(11):4957-60 (2002); Jonsson et al, *N Engl J Med;* 348(17):1656-63 (2003)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 17 | 30 | 25 | 72 |
| Expected | 18 | 36 | 18 | 72 |

Chi-Sq. = 3.78
Significance = 0.15124
(hom/n) = 0.35
Avg. Litter Size = 8
Mutation Type: Homologous Recombination (standard)

Coding exon 1 was targeted (NCBI accession NM_022657.2).

Wild-type Expression Panel: Expression of the target gene was detected in embryonic stem (ES) cells and in all 13 adult tissue samples tested by RT-PCR, except kidney; skeletal muscle; stomach, small intestine, and colon; and adipose.

Disruption of the target gene was confirmed by Southern hybridization analysis.

RT-PCR analysis revealed 41.31.1. Phenotypic Analysis (for Disrupted Gene: DNA142238-2768 (UNQ3027)

(a) Overall Phenotypic Summary:

Mutation of the gene encoding the ortholog of human fibroblast growth factor 23 (FGF23) resulted in small (−/−) mice that failed to thrive. The homozygous mutant mice were smaller than their wild-type littermates, exhibiting notably decreased body weight and length. Due to their failure to thrive, the mutants were euthanized or transferred to necropsy by 6 weeks of age. Microscopic analysis revealed diffuse osteodystrophy and metastatic calcification in the homozygous mutants available for analysis. The heterozygotes showed decreased levels of triglycerides and increased phosphates compared to their wild-type littermates. The heterozygotes (+/−) also showed an increase in B cells as well as decreased basophils, CD4 and NK cells. In addition, the male heterozygous mice exhibited an increased anxiety-like response during open field activity testing when compared with their gender-matched wild-type littermates and the historical mean. No other notable phenotype was observed for the heterozygous mice.

Disruption of the target gene was confirmed by Southern hybridization analysis.

(b) Bone Metabolism & Body Diagnostics

Tissue Mass & Lean Body Mass Measurements—Dexa

Dexa Analysis—Test Description:

Procedure: A cohort of wild type, heterozygotes and homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

General Observations: The (−/−) mice were smaller than their (+/+) littermates and gained little or no weight after birth, exhibiting ruffled fur and eye drainage. At 4 weeks of age, 6 (−/−) mice were transferred to pathology for analysis. The remaining (−/−) mice were euthanized at 6 weeks of age due to their ill health.

Both the male and female (−/−) mice exhibited notably decreased mean body weight when compared with their (+/+) littermates and the historical means.

Length: No (−/−) mice were available for analysis.

(c) Pathology

Microscopic Observations: The (−/−) mice exhibited marked diffuse osteodystrophy and moderate metastatic calcification. Metatstatic calcification was well documented in the trachea, small intestine and aorta. Defective mineralization of bone was observed, characterized by retention of cartilage cores in cortical and trabecular bone and thickening of turbinate and calvarial bones, as well as apposition of woven bone on the endosteal surfaces of the diaphysis. Although osteoblasts in regions with normally high bone turnover had a normal appearance, the overwhelming majority of osteoblasts in other areas were abnormal. The abnormal osteoblasts were up to 5 times normal size and frequently filled the intertrabecular marrow spaces. The cytoplasm of affected osteoblasts and osteocytes was distended by abundant basophilic material, presumably matrix proteins. The calcium x phosphate product was found to be well above the level at which metastatic calcification of tissues is expected to occur. Mineralization was consistently present at regions of calcium absorption in the kidney and duodenum and regions in the aorta, trachea, and stomach submucosa that have connective tissue elements particularly prone to calcification. The renal changes were relatively mild and limited in distribution to proximal tubules located near arcuate vessels. Lymphocyte depletion in the thymus and spleen was also observed.

In summary, the knockout mice exhibit focally enlarged osteoblasts and abnormalities in bone mineralization, consistent with osteodystrophy. In humans, dialysis is a common cause of osteodystrophy (renal osteodystrophy). Less common causes in humans are genetic mutations associated with autosomal dominant hypophosphatemic rickets and oncogenic osteomalacia. Thus, this knockout could be a good model of osteodystrophy in humans.

Gene Expression LacZ activity was not detected in the panel of tissues by immunohistochemical analysis.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The female heterozygous (+/−) mice exhibited a decreased mean serum triglyceride level when compared with their gender-matched (+/+) littermates and the historical means.

Thus, mutant mice deficient in the PRO9828 encoding gene can serve as a model for treatment of cardiovascular disease especially those diseases which are associated with dyslipidemia.

(e) Blood Chemistry

Blood chemistry analysis was performed using the COBAS Integra 400 (mfr: Roche) in its clinical settings for running blood chemistry tests on mice.

Results:

Male heterozygotes (+/−) showed an increased phosphate level compared to their wildtype gender-matched littermates (p=0.02636). This observation indicates that the bone-related abnormalities found in the pathology report could be due to dysregulation of $Ca^{++}/PO_4^{-2}$ metabolism.

(f) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests was performed:

Flourescence-activated cell-sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

The heterozygous (+/−) mice exhibited decreased mean percentages of CD4 cells, basophils and natural killer cells and an increased mean percentage of B cells in the peripheral blood when compared with their (+/+) littermates and the historical means. Analyzed wt/het/hom: 6/9/0

In summary, the FACS results indicate that the heterozygous mutant mice demonstrate immunological abnormalities marked by decreased T cell populations as well as decreased mean percentages of natural killer cells (which is an indicator of a negative phenotype associated with knocking out the PRO9828 gene). Natural killer cells are the first line of defense to viral infection since these cells have been implicated in viral immunity and in defense against tumors. Natural killer cells or NK cells act as effectors in antibody-dependent cell-mediated cytotoxicity and have been identified by their ability to kill certain lymphoid tumor cell lines in vitro without the need for prior immunization or activation. However, their known function in host defense is in the early phases of infection with several intracellular pathogens, particularly herpes viruses. Thus, PRO9828 polypeptides and agonists thereof would be important for a healthy immune system and would be useful in stimulating the immune system particularly during viral infections.

(g) Phenotypic Analysis: CNS/Neurology

In the area of neurology, analysis focused herein on identifying in vivo validated targets for the treatment of neurological and psychiatric disorders including depression, generalized anxiety disorders, attention deficit hyperactivity disorder, obsessive compulsive disorder, schizophrenia, cognitive disorders, hyperalgesia and sensory disorders. Neurological disorders include the category defined as “anxiety disorders” which include but are not limited to: mild to moderate anxiety, anxiety disorder due to a general medical condition, anxiety disorder not otherwise specified, generalized anxiety disorder, panic attack, panic disorder with agoraphobia, panic disorder without agoraphobia, posttraumatic stress disorder, social phobia, specific phobia, substance-induced anxiety disorder, acute alcohol withdrawal, obsessive compulsive disorder, agoraphobia, bipolar disorder I or II, bipolar disorder not otherwise specified, cyclothymic disorder, depressive disorder, major depressive disorder, mood disorder, substance-induced mood disorder. In addition, anxiety disorders may apply to personality disorders including but not limited to the following types: paranoid, antisocial, avoidant behavior, borderline personality disorders, dependent, histronic, narcissistic, obsessive-compulsive, schizoid, and schizotypal.

Procedure:

Behavioral screens were performed on a cohort of 4 wild type, 4 heterozygous and 8 homozygous mutant mice. All behavioral tests were done between 12 and 16 weeks of age unless reduced viability necessitates earlier testing. These tests included open field to measure anxiety, activity levels and exploration.

Open Field Test:

Several targets of known drugs have exhibited phenotypes in the open field test. These include knockouts of the seratonin transporter, the dopamine transporter (Giros et al., Nature. 1996 Feb. 15; 379(6566):606-12), and the GABA receptor (Homanics et al., Proc Natl Acad Sci USA. 1997 Apr. 15; 94(8):4143-8). An automated open-field assay was customized to address changes related to affective state and exploratory patterns related to learning. First, the field (40×40 cm) was selected to be relatively large for a mouse, thus designed to pick up changes in locomotor activity associated with exploration. In addition, there were 4 holes in the floor to allow for nose-poking, an activity specifically related to exploration. Several factors were also designed to heighten the affective state associated with this test. The open-field test is the first experimental procedure in which the mice are tested, and the measurements that were taken were the subjects' first experience with the chamber. In addition, the open-field was brightly lit. All these factors will heighten the natural anxiety associated with novel and open spaces. The pattern and extent of exploratory activity, and especially the center-to-total distance traveled ratio, may then be able to discern changes related to susceptibility to anxiety or depression. A large arena (40 cm×40 cm, VersaMax animal activity monitoring system from AccuScan Instruments) with infrared beams at three different levels was used to record rearing, hole poke, and locomotor activity. The animal was placed in the center and its activity was measured for 20 minutes. Data from this test was analyzed in five, 4-minute intervals. The total distance traveled (cm), vertical movement number (rearing), number of hole pokes, and the center to total distance ratio were recorded.

The propensity for mice to exhibit normal habituation responses to a novel environment is assessed by determining the overall change in their horizontal locomotor activity across the 5 time intervals. This calculated slope of the change in activity over time is determined using normalized, rather than absolute, total distance traveled. The slope is determined from the regression line through the normalized activity at each of the 5 time intervals. Normal habituation is represented by a negative slope value.

Results:

The male (+/−) mice exhibited a decreased median sum time-in-center during open field testing when compared with their gender-matched (+/+) littermates and the historical mean, suggesting an increased anxiety-like response. The heterozygous (+/−) mice demonstrated a phenotype consistent with anxiety related disorders which are associated with mild to moderate anxiety, anxiety due to a general medical condition, and/or bipolar disorders; hyperactivity; sensory disorders; obsessive-compulsive disorders, schizophrenia or a paranoid personality. Thus, PRO9828 polypeptides or agonists thereof would be useful in the treatment of such neurological disorders or the amelioration of the symptoms associated with anxiety disorders.

41.32. Generation and Analysis of Mice Comprising DNA139686-2823 (UNQ3122) Gene Disruptions In these knockout experiments, the gene encoding PRO10274 polypeptides (designated as DNA139686-2823) (UNQ3122) was disrupted. The gene specific information for these studies is as follows: the mutated mouse gene corresponds to nucleotide reference: XM_203936 or *Mus musculus* RIKEN cDNA 1200015F23 gene (1200015F23Rik); protein reference: Q7TNF2 or ACCESSION: Q7TNF2 NID: *Mus musculus* (Mouse). Hypothetical protein (Fragment); the human gene sequence reference: NM_018145 or ACCESSION: NM_018145

NID: gi 8922531 ref NM_018145.1 *Homo sapiens* hypothetical protein FLJ10579 (FLJ10579); the human protein sequence corresponds to reference: Q96TC7 or ACCESSION: Q96TC7 NID: *Homo sapiens* (Human). Cerebral protein-10.

The mouse gene of interest is RIKEN cDNA 1200015F23 gene, ortholog of human hypothetical protein FLJ10579 (FLJ10579).

FLJ10579 is a hypothetical secreted protein of about 470 amino acids, containing a signal peptide. The function of this protein is not known; however, it may be related to DNA photolyases, which play a role in DNA repair. Moreover, the protein has been defined as "putative T-cell protein tyrosine phosphatase-interacting protein" (NCBI accession CAC39480). Bioinformatic analyses suggest that the hypothetical protein may be located in the endoplasmic reticulum.

| | wt | het | hom | Total |
|---|---|---|---|---|
| Observed | 15 | 32 | 24 | 71 |
| Expected | 17.75 | 35.5 | 17.75 | 71 |

Chi-Sq. = 2.97
Significance = 0.22630
(hom/n) = 0.34
Avg. Litter Size = 8
Mutation Type: Retroviral Insertion (OST)

Retroviral insertion occurred in the intron between coding exons 5 and 6 (NCBI accession BC055754.1).

Wild-type Expression Panel: Expression of the target gene was detected in all 13 adult tissue samples tested by RT-PCR, except bone.

RT-PCR analysis revealed that the transcript was absent in the (−/−) mouse analyzed (M-156). Disruption of the target gene was confirmed by Inverse PCR.

41.32.1. Phenotypic Analysis (for Disrupted Gene: DNA139686-2823 (UNQ3122)

(a) Overall Phenotypic Summary:

Mutation of the gene encoding the ortholog of a human hypothetical protein (FLJ10579) resulted in the observation that mutant (−/−) mice exhibit signs of abnormal bone metabolism with decreased bone-related measurements as well as signs of growth retardation (mice were smaller and showed decreased body length). Transcript was absent by RT-PCR.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results: The mutant (−/−) mice exhibited a decreased mean body length when compared with their (+/+) littermates and the historical mean.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: Female (−/−) mice exhibited a decreased mean bone mineral content and bone mineral density in total body and femur when compared with their gender-matched (+/+) littermates and the historical means. The female (−/−) mice also exhibited a decreased mean bone mineral content index. Male knockouts showed decreased total body volumetric bone mineral density and femur bone mineral density. Analyzed wt/het/hom: 4/4/8

Summary

These results demonstrate that knockout mutant mice exhibit abnormal bone metabolism with significant bone loss similar to osteoporosis characterized by decrease in bone mass with decreased density and possibly fragility leading to bone fractures. Thus, it appears that PRO10274 polypeptides or agonists thereof would be useful in maintaining bone homeostasis. In addition, PRO10274 polypeptides or its encoding gene would be useful in bone healing or for the treatment of arthritis or osteoporosis; whereas antagonists (inhibitors) of PRO10274 polypeptides would lead to abnormal or pathological bone disorders including inflammatory diseases associated with abnormal bone metabolism such as arthritis or osteoporosis. The observation that the (−/−) mice showed decreased body length was also indicative of growth retardation.

41.33. Generation and Analysis of Mice Comprising DNA144844-2843 (UNQ5783) Gene Disruptions In these knockout experiments, the gene encoding PRO16090 polypeptides (designated as DNA144844-2843) (UNQ5783) was disrupted. The gene specific information for these studies is as follows: the mutated mouse gene corresponds to nucleotide reference: XM_282993 or *Mus musculus* similar to DTFT5783 (LOC327957); protein reference: XP_282993 or similar to DTFT5783 [*Mus musculus*]; the human gene sequence reference: NM_207103 or *Homo sapiens* DTFT5783 (UNQ5783); the human protein sequence corresponds to reference: Q96MD0 or ACCESSION: Q96MD0 NID: *Homo sapiens* (Human). Hypothetical protein FLJ32580.

The mouse gene of interest is LOC327957 (similar to DTFT5783), ortholog of human UNQ5783 (DTFT5783). Aliases include FLJ32580.

UNQ5783 is a hypothetical protein of about 130 amino acids (Clark et al, *Genome Res;* 13(10):2265-70 (PMID 12975309) (2003); Ota et al, *Nat Genet;* 36(1):40-5 (PMID 14702039) (2004)) that is likely to be a type II plasma membrane protein or a secreted protein. Both mouse and human orthologs contain an N-terminal peptide that functions as either a signal anchor or signal peptide; no other domains were detected.

| | wt | het | hom | Total |
|---|---|---|---|---|
| Observed | 20 | 40 | 20 | 80 |
| Expected | 20 | 40 | 20 | 80 |

Chi-Sq. = 0.00
Significance = 1.00000
(hom/n) = 0.25
Avg. Litter Size = 8
Mutation Type: Homologous Recombination (standard)

Coding exons 1 and 2 were targeted (NCBI accession XM_282993.1).

Wild-type Expression Panel: Expression of the target gene was detected in all 13 adult tissue samples tested by RT-PCR, except eye, skeletal muscle, bone, and heart.

Disruption of the target gene was confirmed by Southern hybridization analysis.

41.33.1. Phenotypic Analysis (for Disrupted Gene: DNA144844-2843 (UNQ5783)

(a) Overall Phenotypic Summary:

Mutation of the gene encoding the ortholog of a human hypothetical membrane protein resulted in anemia. The (−/−) mice exhibited a decreased mean serum albumin level, an increased mean serum cholesterol level and an increased serum glucose level. The male mutant (−/−) mice also exhibited increased body weight. The male (−/−) mice also exhibited an increased mean total tissue mass and lean body mass. The female (−/−) mice showed increased fat percentages and total fat mass (g). Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Hematology Analysis:

Test Description: Blood tests are carried out by Abbott's Cell-Dyn 3500R, an automated hematology analyzer. Some of its features include a five-part WBC differential. 'Patient' reports can cover over 22 parameters in all.

Results:

Hematology: The (−/−) mice exhibited a decreased mean total red blood cell count, hemoglobin level, and hematocrit level when compared with their (+/+) littermates and the historical means. The anemia is macrocytic (elevated MCV) and normochromic (normal MCHC) suggestive of a regenerative anemia although there is no notation of reticulocytes. As shown below, serum levels of albumin are decreased-protein loss and anemia are suggestive of chronic hemorrhage.

Analyzed wt/het/hom: 6/4/8

These results are related to a phenotype associated with anemia. Thus, PRO16090 polypeptides, agonists thereof or the encoding gene for PRO16090 polypeptides must be essential for normal red blood cell production and as such would be useful in the treatment of blood disorders associated with anemia or a low hematocrit.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The male mutant (−/−) mice exhibited an increased mean body weight when compared with their gender-matched (+/+) littermates.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The male (−/−) mice exhibited increased mean total tissue mass and lean body mass when compared with their gender-matched (+/+) littermates and the historical means. Female (−/−) mice showed increased fat (%) and fat (g).

Analyzed wt/het/hom: 4/4/8

Summary

These results demonstrate that knockout mutant mice exhibit abnormal body measurements. Specifically, the (−/−) mice analyzed by DEXA exhibited notably increased total tissue mass and lean body mass and increased body weight and fat (%) and (g) when compared with their (+/+) littermates, suggestive of obesity in these mutants. These results are consistent with blood tests wherein elevated cholesterol levels were detected. Thus, PRO16090 polypeptides and/or its encoding gene are essential for normal fat and/or lipid metabolism.

(d) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type, 4 heterozygotes and 8 homozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche). Analyzed wt/het/hom: 4/4/8

Results:

The (−/−) mice exhibited a decreased mean serum albumin level when compared with their (+/+) littermates and the historical mean. In addition, the (−/−) mice also exhibited an increased mean serum cholesterol level when compared with their gender-matched (+/+) littermates and the historical mean.

Analyzed wt/het/hom: 4/5/8

As summarized above, the homozygous (−/−) mutant mice exhibited an increased mean serum cholesterol level when compared with their gender-matched (+/+) littermates and the historical mean. No change in triglycerides was observed.

Thus, mutant mice deficient in the PRO16090 can serve as a model for cardiovascular disease especially for those diseases which are associated with an abnormal cholesterol metabolism. PRO16090 polypeptides or its encoding gene would be useful in regulating blood lipids and in particular maintaining normal cholesterol. Thus, PRO16090 polypeptides would be useful in the treatment of such cardiovascular diseases as: hypertension, atherosclerosis, heart failure, stroke, various coronary artery diseases, and/or obesity or diabetes.

41.34. Generation and Analysis of Mice Comprising DNA139592-2866 (UNQ5825) Gene Disruptions In these knockout experiments, the gene encoding PRO19644 polypeptides (designated as DNA139592-2866) (UNQ5825) was disrupted. The gene specific information for these studies is as follows: the mutated mouse gene corresponds to nucleotide reference: NM_020259 or ACCESSION: NM_020259 NID: 9938019 *Mus musculus Mus musculus* Hedgehog-interacting protein (Hhip); protein reference: Q9WU59 or Q9WU59 Q9WU59 HEDGEHOG-INTERACTING PROTEIN; the human gene sequence reference: NM_022475 or ACCESSION: NM_022475 NID: 20143972 *Homo sapiens Homo sapiens* hedgehog interacting protein (HHIP); the human protein sequence corresponds to reference: Q96QV1 or Q96QV1HEDGEHOG-INTERACTING PROTEIN.

The mouse gene of interest is Hhip (Hedgehog-interacting protein), ortholog of human HHIP. Aliases include Hip, Hip1, hedgehog-interacting, FLJ20992, and hedgehog-interacting protein.

HHIP is a type I plasma membrane protein that binds with hedgehog proteins, which are membrane-anchored extracellular signaling proteins that regulate morphogenesis during embryonic development. HHIP functions as a negative regulator of hedgehog protein signaling. Hedgehog proteins induce HHIP expression in adjacent cells, attenuating further hedgehog signaling by binding with hedgehog proteins and thereby inhibiting activation of its cognate receptors. A soluble form of HHIP has been detected in brain (Chuang and McMahon, *Nature;* 397(6720):617-21 (1999); Coulombe et al, *Mol Cell Neurosci;* 25(2):323-33 (2004)).

The biological role of HHIP has been investigated with HHIP knockout mice. Chuang and colleagues; *Genes Dev;* 17(3):342-7 (2003) showed that in HHIP homozygous null mice, HHIP signaling was upregulated and lung and skeletal development was defective. Moreover, they showed that HHIP modulates early lung branching by a mechanism involving interaction between hedgehog and fibroblast growth factor signaling. They concluded that HHIP is likely involved in modulating hedgehog and fibroblast growth factor signal transduction. Kawahira and colleagues; *Development;* 130(20):4871-9 (2003)) showed that in HHIP homozygous null mice, pancreas morphogenesis, islet formation, and endocrine cell proliferation was impaired and fibroblast growth factor 10 expression was reduced. They concluded that loss of HHIP function increases hedgehog signaling within the pancreas enlarge and decreases fibroblast growth factor signaling at early stages of pancreas development, causing at least part of the observed pancreatic development phenotype.

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 15 | 19 | 4 | 38 |
| Expected | 9.5 | 19 | 9.5 | 38 |

Chi-Sq. = 6.37
Significance = 0.04141
(hom/n) = 0.11
Avg. Litter Size = 4
Mutation Type: Retroviral Insertion (OST)

Retroviral insertion occurred in the intron between coding exons 4 and 5 (NCBI accession NM_020259.3).

Wild-type Expression Panel: Expression of the target gene was detected in embryonic stem (ES) cells and in all 13 adult tissue samples tested by RT-PCR, except skeletal muscle, bone, and adipose.

Due to lethality, transcript expression analysis was not performed. Disruption of the target gene was confirmed by Inverse PCR.

41.34.1. Phenotypic Analysis (for Disrupted Gene: DNA139592-2866 (UNQ5825)

(a) Overall Phenotypic Summary:

Mutation of the gene encoding the ortholog of human hedgehog-interacting protein (HHIP) resulted in lethality of (−/−) mutants. The (−/−) mutants were dead at the time of genotyping. The heterozygous (+/−) mice showed a significant increase in mean serum cholesterol. Both female and male (+/−) mice showed increased weight.

Discussion Related to Embryonic Developmental Abnormality of Lethality:

Embryonic lethality in knockout mice usually results from various serious developmental problems including but not limited to neuro-degenerative diseases, angiogenic disorders, inflammatory diseases, or where the gene/protein has an important role in basic cell signaling processes in many cell types. In addition, embryonic lethals are useful as potential cancer models. Likewise, the corresponding heterozygous (+/−) mutant animals are particularly useful when they exhibit a phenotype and/or a pathology report which reveals highly informative clues as to the function of the knocked-out gene. For instance, EPO knockout animals were embryonic lethals, but the pathology reports on the embryos showed a profound lack of RBCs.

(b) Pathology

Microscopic Observations: At 12.5 days, there were 44 embryos observed: 5 (−/−) embryos, 18 (+/−) embryos, 9 (+/+) embryos, 11 resorption moles, and 1 inconclusive.

Gene Expression: LacZ activity was not detected in the panel of tissues by immunohistochemical analysis.

Analyzed wt/het/hom: 2/1/4

(c) Phenotypic Analysis: Cardiology

In the area of cardiovascular biology, targets were identified herein for the treatment of hypertension, atherosclerosis, heart failure, stroke, various coronary artery diseases, dyslipidemias such as high cholesterol (hypercholesterolemia) and elevated serum triglycerides (hypertriglyceridemia), diabetes and/or obesity. The phenotypic tests included the measurement of serum cholesterol and triglycerides.

Blood Lipids

Procedure: A cohort of 4 wild type and 4 heterozygotes were tested in this assay. High cholesterol levels and increased triglyceride blood levels are recognized risk factors in the development of cardiovascular disease and/or diabetes. Measuring blood lipids facilitates the finding of biological switches that regulate blood lipid levels. Inhibition of factors which elevate blood lipid levels may be useful for reducing the risk for cardiovascular disease. In these blood chemistry tests, cholesterol measurements were recorded using the COBAS Integra 400 (mfr: Roche).

Results:

The male heterozygous (+/−) mice exhibited a significant increase in mean serum cholesterol (p=0.01). In addition, both male and female heterozygous (+/−) mice showed increased body weights compared to their wild-type littermates and the historical means.

Thus, mutant mice deficient in the PRO19644 polypeptide encoding gene can serve as a model for cardiovascular disease. PRO19644 polypeptides or its encoding gene would be useful in regulating blood lipids and in particular maintaining normal cholesterol metabolism. Thus PRO19644 polypeptides would be important for the treatment of such cardiovascular diseases as: hypertension, atherosclerosis, heart failure, stroke, various coronary artery diseases or diabetes.

41.35. Generation and Analysis of Mice Comprising DNA176775-2957 (UNQ5982) Gene Disruptions In these knockout experiments, the gene encoding PRO21340 polypeptides (designated as DNA176775-2957) (UNQ5982) was disrupted. The gene specific information for these studies is as follows: the mutated mouse gene corresponds to nucleotide reference: NM_153397 or *Mus musculus* a disintegrin and metalloprotease domain 32 (Adam32); protein reference: Q8K410 or ACCESSION: Q8K410NID: *Mus musculus* (Mouse). ADAM32; the human gene sequence reference: NM_145004. ACCESSION: NM_145004 NID: 21450712 *Homo sapiens Homo sapiens* hypothetical protein MGC26899 (MGC26899); the human protein sequence corresponds to reference: Q8TC27 or ACCESSION: Q8TC27 NID: *Homo sapiens* (Human). Similar to a disintegrin and metalloproteinase domain 18 (Hypothetical protein MGC26899).

The mouse gene of interest is Adam32 (a disintegrin and metalloprotease domain 32), ortholog of human ADAM32. Aliases include hypothetical protein MGC26899 and "a disintegrin and metalloprotease domain 32."

ADAM32 is a type I plasma membrane protein expressed primarily in testis, possessing disintegrin and metalloprotease domains on the extracellular segment of the molecule (Choi et al, *Gene;* 304:151-62 (2003)). In general, ADAM family proteins interact with cell surface or extracellular matrix proteins via their disintegrin domain and catalyze the proteolysis and release of proteins, such as growth factors, cytokines, cell adhesion molecules, and receptors (White et al, *Curr Opin Cell Biol;* 15(5):598-606 (2003); Duffy et al, *Thromb Haemost;* 89(4):622-31 (2003)). ADAM32 mRNA is first observed in pachytene spermatocytes during meiotic prophase, suggesting that ADAM32 is involved in sperm development or fertilization (Choi et al, *Gene;* 304:151-62 (2003); Talbot et al, *Biol Reprod;* 68(1):1-9 (2003)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 17 | 35 | 15 | 67 |
| Expected | 16.75 | 33.5 | 16.75 | 67 |

Chi-Sq. = 0.25
Significance = 0.88085
(hom/n) = 0.22
Avg. Litter Size = 7
Mutation Type: Homologous Recombination (standard)

Coding exons 3 through 5 were targeted (NCBI accession NM_153397.1).

Wild-type Expression Panel: Expression of the target gene was detected in all 13 adult tissue samples tested by RT-PCR, except liver, skeletal muscle, and bone.

Disruption of the target gene was confirmed by Southern hybridization analysis.

41.35.1. Phenotypic Analysis (for Disrupted Gene: DNA176775-2957 (UNQ5982)

(a) Overall Phenotypic Summary:

Mutation of the gene encoding the ortholog of human "a disintegrin and metalloproteinase domain 32" (ADAM32) resulted in increased total body fat in female homozygous (−/−) and heterozygous (+/−) mice. Gene disruption was confirmed by Southern blot.

(b) Bone Metabolism & Body Diagnostics

Tissue Mass & Lean Body Mass Measurements—Dexa

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Results:

DEXA: The female homozygous (−/−) and heterozygous (+/−) mice exhibited notably increased mean percent total body fat and total fat mass when compared with their gender-matched (+/+) littermates and the historical means. Analyzed wt/het/hom: 4/4/8

These results indicate that both the homozygous (−/−) and heterozygous (+/−) mice exhibit an obesity type phenotype. These data suggest that the PRO21340 polypeptide encoding gene serves to negatively regulate fat metabolism. Thus, PRO21340 polypeptides and/or its encoding gene are essential for normal fat metabolism and for the prevention of disorders associated with abnormal fat metabolism such as obesity and/or Type II diabetes.

41.36. Generation and Analysis of Mice Comprising DNA340392 (UNQ17826) Gene Disruptions In these knockout experiments, the gene encoding PRO92165 polypeptides (designated as DNA340392 (UNQ17826) was disrupted. The gene specific information for these studies is as follows: the mutated mouse gene corresponds to nucleotide reference: NM_030707 or ACCESSION: NM_030707 NID: gi 13540504 ref NM_030707.1 *Mus musculus* macrophage scavenger receptor 2 (Msr2); protein reference: Q9EQY5 or ACCESSION: Q9EQY5 NID: *Mus musculus* (Mouse). MMAN-G PROTEIN PRECURSOR (IFGP2); the human gene sequence reference: NM_052939 or ACCESSION: NM_052939 NID: gi 21314763 ref NM_052939.2 *Homo sapiens* Fc receptor-like protein 3 (FCRH3); the human protein sequence corresponds to reference: Q96P31 or ACCESSION: Q96P31 NID: *Homo sapiens* (Human). SH2 DOMAIN-CONTAINING PHOSPHATASE ANCHOR PROTEIN 2A.

The mouse gene of interest is Msr2 (macrophage scavenger receptor 2), ortholog of human FCRH3 (Fc receptor-like protein 3). Aliases include IgSR, IFGP2, MMAN-g, 9330158F12,2810439C17Rik, immunoglobulin scavenger receptor, SPAP2, and SH2 domain-containing phosphatase anchor protein 2.

FCRH3 and mouse ortholog Msr2 are members of a family of proteins structurally related to leukocyte Fc receptors. Whereas mouse ortholog Msr2 is a hypothetical secreted protein expressed primarily in brain, human ortholog FCRH3 is a type I plasma membrane protein expressed primarily in B cells (Guselnikov et al, *Immunogenetics;* 54(2):87-95 (2002)).

Mouse ortholog Msr2 is composed of a signal peptide, several immunoglobulin-like domains, and a C-terminal scavenger receptor superfamily-related domain (Guselnikov et al, *Immunogenetics;* 54(2):87-95 (2002)). The function of Msr2 is not known; however, immunoglobulin-like domains (SMART accession SM00410) and scavenger receptor domains (Pfam accession PF00530) are likely to be involved in protein-protein interactions. Msr2 does not appear to compensate for loss-of-function of scavenger receptors Msr1 and CD36, which mediate uptake of modified LDL by macrophages and contribute to atherosclerotic plaque formation (Kunjathoor et al, *J Biol Chem;* 277(51):49982-8 (2002)).

Human ortholog FCRH3 is composed of a signal peptide, several immunoglobulin-like domains, a transmembrane segment, and a cytoplasmic C-terminus that contains consensus immunoreceptor tyrosine-based activating or inhibitory signaling motifs. Tyrosine-phosphorylated FCRH3 associates with protein tyrosine kinases Syk and Zap70 and with protein tyrosine phosphatases SHP-1 and SHP-2. Moreover, interaction of SHP-1 with tyrosine phosphorylated FCRH3 stimulates SHP-1 activity. Thus, FCRH3 is likely to function as a receptor, playing a role in B cell function or development (Davis et al, *Proc Natl Acad Sci USA;* 98(17):9772-7 (2001); Xu et al, *Biochem Biophys Res Commun;* 293(3):1037-46 (2002).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 17 | 47 | 26 | 90 |
| Expected | 22.5 | 45 | 22.5 | 90 |

Chi-Sq. = 1.98
Significance = 0.37199
(hom/n) = 0.29
Avg. Litter Size = 9
Mutation Type: Homologous Recombination (standard)

Coding exons 3 through 6 were targeted (NCBI accession NM_030707.1).

Wild-type Expression Panel: Expression of the target gene was detected in embryonic stem (ES) cells and in all 13 adult tissue samples tested by RT-PCR, except liver and bone.

Disruption of the target gene was confirmed by Southern hybridization analysis.

41.36.1. Phenotypic Analysis (for Disrupted Gene: DNA340392 (UNQ17826)

(a) Overall Phenotypic Summary:

Mutation of the gene encoding macrophage scavenger receptor 2 (Msr2) resulted in larger (−/−) mice with increased mean body weight, mean total tissue mass, lean body mass, percent body fat and total body fat. The (−/−) mice also exhibited a decreased percentage of CD8 cells in the peripheral blood. Gene disruption was confirmed by Southern blot.

(b) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The female mutant (−/−) mice exhibited an increased mean body weight compared with their gender-matched littermates.

(2) Bone Metabolism: Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

DEXA: The female (−/−) mice exhibited increased mean total tissue mass, lean body mass, fat (%) and fat (g) when compared with their gender-matched (+/+) littermates and the historical means.

Analyzed wt/het/hom: 4/4/8

Summary

These results demonstrate that female knockout mutant mice exhibit abnormal body measurements. Specifically, the (−/−) mice analyzed by DEXA exhibited notably increased total tissue mass, lean body mass, percent body fat, and total fat mass and increased body weight when compared with their (+/+) littermates, suggestive of obesity and/or growth related disorders in these mutants. These data suggest that the DNA340392 gene encoding PRO92165 polypeptides serves to regulate growth metabolism. Thus, PRO92165 polypeptides and/or its encoding gene are essential for normal fat and/or lipid metabolism as well as important in maintaining normal growth patterns. In addition, PRO92165 polypeptides or agonists thereof would be useful in the treatment or prevention of growth disorders and/or obesity.

(c) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

The following tests were performed:

Flourescence-Activated Cell-Sorting (FACS) Analysis

Procedure:

FACS analysis of immune cell composition from peripheral blood was performed including CD4, CD8 and T cell receptor to evaluate T lymphocytes, CD19 for B lymphocytes, CD45 as a leukocyte marker and pan NK for natural killer cells. The FACS analysis was carried out on 2 wild type and 6 homozygous mice and included cells derived from thymus, spleen, bone marrow and lymph node.

In these studies, analyzed cells were isolated from thymus, peripheral blood, spleen, bone marrow and lymph nodes. Flow cytometry was designed to determine the relative proportions of CD4 and CD8 positive T cells, B cells, NK cells and monocytes in the mononuclear cell population. A Becton-Dickinson FACSCalibur 3-laser FACS machine was used to assess immune status. For Phenotypic Assays and Screening, this machine records CD4+/CD8−, CD8+/CD4−, NK, B cell and monocyte numbers in addition to the CD4+/CD8+ ratio.

The mononuclear cell profile was derived by staining a single sample of lysed peripheral blood from each mouse with a panel of six lineage-specific antibodies: CD45 PerCP, anti-TCRb APC, CD4 PE, CD8 FITC, pan-NK PE, and CD19 FITC. The two FITC and PE labeled antibodies stain mutually exclusive cell types. The samples were analyzed using a Becton Dickinson FACS Calibur flow cytometer with CellQuest software.

Results:

FACS: The mutant (−/−) mice exhibited a decreased mean percentage of CD8 cells when compared with their (+/+) littermates and the historical mean. Females (but not males) had fewer CD8+ cells in the thymus. Analyzed wt/het/hom: 7/4/8

These results indicate that the homozygous (−/−) knockout mice exhibit a negative immunological phenotype. CD8+ molecules are the co-receptor molecules which cooperate with the T-cell receptor in antigen recognition and in particular specifically bind only to the invariant parts of the MHC class I molecule. During antigen recognition, the CD8+ molecules associate on the T-cell surface with components of the T-cell receptor to form the cytotoxic CD8+ T-cell. Thus, PRO92165 polypeptides or agonists thereof would be important in the T-cell mediated response involving the MHC class I pathway and would be beneficial in those instances wherein cytotoxic T cells are required in host defense against cytosolic pathogens. In contrast, antagonists or inhibitors of PRO92165 polypeptides, would be expected to mimic a negative phenotype resulting in a deficiency in the mean percentage of CD8+ cells and therefore an MHC class I deficiency would result. One such disease model occurs when there is an almost complete absence of cell-surface MHC class 1 molecules. Patients with this condition have normal levels of mRNA encoding MHC class 1 molecules and normal levels of production of MHC class I proteins. However, these individuals are immunodeficient, specifically owing to the lack of CD8+ T cells. This results in a severe immunodeficiency disease wherein the response to nearly all pathogens is critically suppressed.

41.37. Generation and Analysis of Mice Comprising DNA340394 (UNQ11831) Gene Disruptions In these knockout experiments, the gene encoding PRO85143 polypeptides (designated as DNA340394) (UNQ11831) was disrupted. The gene specific information for these studies is as follows: the mutated mouse gene corresponds to nucleotide reference: NM_153090 or ACCESSION: NM_153090 NID: gi 23346512 ref NM_153090.1 *Mus musculus* IFGP1 (IFGP1); protein reference: Q8R4Y0 or ACCESSION: Q8R4Y0 NID: *Mus musculus* (Mouse). IFGP1; the human gene sequence reference: NM_052938 or ACCESSION: NM_052938 NID: gi 21361835 ref NM_052938.2 *Homo sapiens* Fc receptor-like protein 1 (FCRH1); the human protein sequence corresponds to reference: Q96LA6 or ACCESSION: Q96LA6 NID: *Homo sapiens* (Human). Fc receptor-like protein 1.

The mouse gene of interest is RIKEN cDNA A230020G22 gene, ortholog of human FCRH1 (Fc receptor-like protein 1). Aliases include Fcrh1, IFGP1, BXMAS1, IRTA5, BXMAS1-like protein 1, and Fc receptor-like protein 1.

FCRH1 is a type I plasma membrane protein that likely functions as a receptor for the Fc region of immunoglobulins. The protein consists of a signal peptide, three immunoglobulin-like domains, a transmembrane segment, and a 99-amino acid cytoplasmic C terminus, containing immunoreceptor tyrosine-based activation motifs (ITAMS). FCRH1 is expressed primarily in resting and germinal center B cells and various lymphoid malignancies and is likely to play a role in regulating immune responses (Davis et al, *Proc Natl Acad Sci USA;* 98(17):9772-7 (2001); Miller et al, *Blood;* 99(8):2662-9 (2002); Guselnikov et al, *Immunogenetics;* 54(2):87-95 (2002)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 21 | 38 | 16 | 75 |
| Expected | 18.75 | 37.5 | 18.75 | 75 |

Chi-Sq. = 0.68
Significance = 0.71177
(hom/n) = 0.21
Avg. Litter Size = 8
Mutation Type: Homologous Recombination (standard)

Coding exons 2 through 6 were targeted (NCBI accession NM_153090.1).

Wild-type Expression Panel: Expression of the target gene was detected in all 13 adult tissue samples tested by RT-PCR, except skeletal muscle, bone, and adipose.

Disruption of the target gene was confirmed by Southern hybridization analysis.

41.37.1. Phenotypic Analysis (for Disrupted Gene: DNA340394 (UNQ11831)

(a) Overall Phenotypic Summary:

Mutation of the gene encoding the ortholog of human Fc receptor-like protein 1 (FCRH1) resulted in abnormal bone-related measurements. Gene disruption was confirmed by Southern blot.

(b) Bone Metabolism & Diagnostics/Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

Micro-CT: The male mutant (−/−) mice exhibited a decreased mean vertebral trabecular bone volume, number, and thickness when compared with their gender-matched (+/+) littermates and the historical means. The knockout mice also showed a decrease in midshaft femur cortical thickness compared to wild-type littermates.

Analyzed wt/het/hom: 4/4/8

These results indicate that the mutant (−/−) mice showed signs of abnormal bone-related measurements or a negative phenotype related to abnormal bone metabolism with bone loss (decreased volume and thickness in vertebral trabecular) similar to osteoporosis which is characterized by decrease in bone mass and possibly fragility leading to bone fractures. Thus, it appears that PRO85143 polypeptides or agonists thereof would be useful in maintaining bone homeostasis. In addition, PRO85143 polypeptides or its encoding gene would be useful for maintaining bone homeostasis and would be important in bone healing or for the treatment of arthritis or osteoporosis; whereas antagonists to PRO85143 polypeptides or its encoding gene would lead to abnormal or pathological bone disorders including inflammatory diseases associated with abnormal bone metabolism such as arthritis or osteoporosis.

41.38. Generation and Analysis of Mice Comprising DNA60629-1481 (UNQ18919) Gene Disruptions In these knockout experiments, the gene encoding PRO1124 polypeptides (designated as DNA60629-1481) (UNQ18919) was disrupted. The gene specific information for these studies is as follows: the mutated mouse gene corresponds to nucleotide reference: AK033591 or *Mus musculus* adult male cecum cDNA, RIKEN full-length enriched library, clone: 9130020L07 product: weakly similar to CALCIUM-ACTIVATED CHLORIDE CHANNEL PROTEIN 2 [*Homo sapiens*], full insert sequence; protein reference: XP_131262 or expressed sequence A1504701 [*Mus musculus*]; the human gene sequence reference: NM_012128 or ACCESSION: NM_012128 NID: gi 12025666 ref NM_012128.2 *Homo sapiens* chloride channel, calcium activated, family member 4 (CLCA4); the human protein sequence corresponds to reference: Q9UNF7 or ACCESSION: Q9UNF7 NID: *Homo sapiens* (Human). Calcium-activated chloride channel protein 2.

The mouse gene of interest is RIKEN cDNA 9130020L07 gene, ortholog of human CLCA4 (chloride channel, calcium activated, family member 4). Aliases include CLCA6, CaCC, CaCC2, hCLCA4, calcium activated chloride channel, and chloride channel calcium activated.

CLCA4 is a chloride channel expressed primarily in epithelia of lung and digestive tract. The protein of about 900 amino acids consists of a signal peptide, a von Willebrand factor domain (located near the middle of the polypeptide), a fibronectin domain (located near the C terminus of the polypeptide), and four hydrophobic segments that are likely to function as transmembrane domains. The CLCA4 polypeptide may undergo proteolytic processing to form subunits of a functional chloride channel. CLCA4 chloride channel activity is stimulated by phosphorylation catalyzed by calcium/calmodulin-dependent protein kinase II (Cunningham et al, *J Biol Chem;* 270(52):31016-26 (1995); Agnel et al,

*FEBS Lett;* 455(3):295-301 (1999); Pauli et al, *Clin Exp Pharmacol Physiol;* 27(11):901-5 (2000)).

Targeted or gene trap mutations are generated in strain 129SvEv$^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to 129SvEv$^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 18 | 55 | 21 | 94 |
| Expected | 23.5 | 47 | 23.5 | 94 |

Chi-Sq. = 2.91
Significance = 0.23283
(hom/n) = 0.22
Avg. Litter Size = 9
Mutation Type: Homologous Recombination (standard)

Coding exon 1 was targeted (NCBI accession AK033591.1).

Wild-type Expression Panel: Expression of the target gene was detected in embryonic stem (ES) cells and, among the 13 adult tissue samples tested by RT-PCR, in brain; eye; thymus; liver; and stomach, small intestine, and colon.

Disruption of the target gene was confirmed by Southern hybridization analysis.

41.38.1. Phenotypic Analysis (for Disrupted Gene: DNA60629-1481 (UNQ18919)

(a) Overall Phenotypic Summary:

Mutation of the gene encoding the ortholog of human chloride channel, calcium activated, family member 4 (CLCA4) resulted in an increased TNF-alpha response to LPS challenge. The mutant (−/−) mice also showed growth abnormalities with decreased mean body weight and length and abnormal bone-related measurements. The homozygous (−/−) mice also showed an enhanced or improved glucose tolerance. Gene disruption was confirmed by Southern blot.

(b) Immunology Phenotypic Analysis

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multistep pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

In many immune responses, inflammatory cells infiltrate the site of injury or infection. The migrating cells may be neutrophilic, eosinophilic, monocytic or lymphocytic as can be determined by histological examination of the affected tissues. Current Protocols in Immunology, ed. John E. Coligan, 1994, John Wiley & Sons, Inc.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, and graft rejection, etc. In the area of immunology, targets were identified for the treatment of inflammation and inflammatory disorders.

In the area of immunology, targets have been identified herein for the treatment of inflammation and inflammatory disorders. Immune related diseases, in one instance, could be treated by suppressing the immune response. Using neutralizing antibodies that inhibit molecules having immune stimulatory activity would be beneficial in the treatment of immune-mediated and inflammatory diseases. Molecules which inhibit the immune response can be utilized proteins directly or via the use of antibody agonists) to inhibit the immune response and thus ameliorate immune related disease.

The following tests were performed:

Acute Phase Response:

Test Description: Bacterial lipopolysaccharide (LPS) is an endotoxin, and as such is a potent inducer of an acute phase response and systemic inflammation. The Level I LPS mice were injected intraperitoneally (i.p.) with a sublethal dose of LPS in 200 L sterile saline using a 26 gauge needle. The doses were based on the average weight of the mice tested at 1 g/g body weight 3 hours after injection; a 100 ul blood sample was then taken and analyzed for the presence of TNFa, MCP-1, and IL-6 on the FACS Calibur instrument.

Results:

The (−/−) mice exhibited an increased mean serum TNF-alpha response to LPS challenge when compared with their (+/+) littermates and the historical mean.

Analyzed wt/het/hom: 7/4/8

In summary, the LPS endotoxin challenge demonstrated that knockout mice deficient in the gene encoding PRO1124 polypeptides exhibit immunological abnormalities when compared with their wild-type littermates. In particular, the mutant mice exhibited an increased ability to elicit an immunological response (TNF-alpha production) when challenged with the LPS endotoxin indicating a pronounced proinflammatory response. This suggests that antagonists (inhibitors) of PRO1124 polypeptides would stimulate the immune system and would find utility in the cases wherein this effect would be beneficial to the individual such as in the case of leukemia, and other types of cancer, and in immunocompromised patients, such as AIDS sufferers. Accordingly, PRO1124 polypeptides or agonists thereof, would be useful in inhibiting the immune response and would be useful candidates for suppressing harmful immune responses, e.g. in the case of graft rejection or graft-versus-host diseases.

(c) Bone Metabolism & Body Diagnostics (1) Tissue Mass & Lean Body Mass Measurements—Dexa Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in total tissue mass (TTM).

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI, i.e., whole body, vertebrae, and both femurs).

Body Measurements (Body Length & Weight):

Body Measurements: A measurement of body length and weight was performed at approximately 16 weeks of age.

Results:

The female (−/−) mice exhibited a decreased mean body weight and mean body length when compared with their gender-matched (+/+) littermates and the historical mean which indicates that the knockout mice show signs of growth retardation. Thus, PRO1124 polypeptides or agonists thereof would be useful in maintaining normal growth and development.

(2) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

- DEXA for measurement of bone mineral density on femur and vertebra
- MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: There is a clear difference in total body fat content between control wild-type and homozygous knockout female (−/−) mice but knockout mice are showing normal values and control mice are showing elevated levels (more than normal values). Similar situation is observed in blood triglyceride levels.

MicroCT: The male knockouts (−/−) show decreased trabecular bone volume, number and connectivity density compared to wild-type littermates, though wild-type mice were higher than the historical means.

(d) Phenotypic Analysis: Metabolism-Blood Chemistry/Glucose Tolerance

In the area of metabolism, targets may be identified for the treatment of diabetes. Blood chemistry phenotypic analysis includes blood glucose measurements. The COBAS Integra 400 (mfr: Roche) was used for running blood chemistry tests on the mice. In the area of metabolism, targets may be identified for the treatment of diabetes. Blood chemistry phenotypic analysis includes glucose tolerance tests to measure insulin sensitivity and changes in glucose metabolism. Abnormal glucose tolerance test results may indicate but may not be limited to the following disorders or conditions: Diabetes Type 1 and Type 2, Syndrome X, various cardiovascular diseases and/or obesity.

Procedure: A cohort of 2 wild type and 4 homozygote mice were used in this assay. The glucose tolerance test is the standard for defining impaired glucose homeostasis in mammals. Glucose tolerance tests were performed using a Lifescan glucometer. Animals were injected IP at 2 g/kg with D-glucose delivered as a 20% solution and blood glucose levels were measured at 0, 30, 60 and 90 minutes after injection. Analyzed wt/het/hom: 4/4/8

Results:

Glucose Tolerance Test: The mutant (−/−) mice tested exhibited enhanced glucose tolerance when compared with their gender-matched (+/+) littermates.

Analyzed wt/het/hom: 4/4/8

Summary:

In these studies the mutant (−/−) mice showed an increased or enhanced glucose tolerance in the presence of normal fasting glucose at all 3 intervals tested when compared with their gender-matched (+/+) littermates and the historical means. In addition, hyperinsulinemia was not apparent in the (−/−) mice. Thus, knockout mice exhibited the opposite phenotypic pattern of an impaired glucose homeostasis, with an increased insulin sensitivity and as such antagonists to PRO1124 polypeptides or its encoding gene would be useful in the treatment of impaired glucose homeostasis and/or various cardiovascular diseases.

41.39. Generation and Analysis of Mice Comprising DNA59613-1417 (UNQ511) Gene Disruptions In these knockout experiments, the gene encoding PRO1026 polypeptides (designated as DNA59613-1417) (UNQ511) was disrupted. The gene specific information for these studies is as follows: the mutated mouse gene corresponds to nucleotide reference: BC026828 or ACCESSION: BC026828 NID: 20072424 *Mus musculus Mus musculus*, similar to RIKEN cDNA 2210415F13 gene, clone MGC: 25895 IMAGE: 4218333; protein reference: Q9D7S0 or ACCESSION: Q9D7S0 NID: *Mus musculus* (Mouse). 2210415F13RIK PROTEIN. MOUSESPTRNRDB; the human gene sequence reference: AY358469 or *Homo sapiens* clone DNA59613 phospholipase inhibitor (UNQ511); the human protein sequence corresponds to reference: AAQ88833 ACCESSION: AAQ88833 NID: *Homo sapiens* (Human). Phospholipase inhibitor.

The mouse gene of interest is RIKEN cDNA 2210415F13 gene, ortholog of human "clone DNA59613 phospholipase inhibitor (UNQ511) mRNA." The gene of interest encodes a putative secreted protein containing a phospholipase A2 inhibitor domain (Pfam accession PF02988) and an overlapping CD59 antigen domain (InterPro accession IPR001526). Proteins with phospholipase A2 inhibitor and CD59 antigen domains are present in habu snake (*Trimeresurus flavoviridis*) serum and inhibit habu snake venom phospholipase A2 isozymes (Nobuhisa et al, *Eur J Biochem;* 249(3):838-45 (1997)). The biological role of this protein in mouse and human is not known.

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 20 | 33 | 20 | 73 |
| Expected | 18.25 | 36.5 | 18.25 | 73 |

Chi-Sq. = 0.67
Significance = 0.71490
(hom/n) = 0.27
Avg. Litter Size = 7
Mutation Type: Homologous Recombination (standard)

Coding exons 1 and 2 were targeted (NCBI accession AK008940.1).

Wild-type Expression Panel: Expression of the target gene was detected in all 13 adult tissue samples tested by RT-PCR, except spleen, lung, and skeletal muscle.

QC Expression: Disruption of the target gene was confirmed by Southern hybridization analysis.

41.39.1. Phenotypic Analysis (for Disrupted Gene: DNA59613-1417 (UNQ511)

(a) Overall Phenotypic Summary:

Mutation of the gene encoding the ortholog of human "clone DNA59613 phospholipase inhibitor (UNQ511) mRNA" resulted in a decrease in bone mineral content. Gene disruption was confirmed by Southern blot.

(b) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Results:

The female (−/−) mice exhibited a decreased bone mineral content. These results demonstrate that female knockout mutant mice exhibit abnormal bone metabolism with decreased bone mineral content (loss) similar to osteoporosis characterized by decrease in bone mass and possibly fragility leading to bone fractures. Thus, PRO1026 polypeptides would be useful in maintaining bone homeostasis and would be useful for bone healing or for the treatment of arthritis or osteoporosis, whereas antagonists or inhibitors of PRO1026 polypeptides or its encoding DNA would lead to abnormal or pathological bone disorders similar to osteoporosis.

41.40. Generation and Analysis of Mice Comprising DNA193963 (UNQ8344) Gene Disruptions In these knockout experiments, the gene encoding PRO23370 polypeptides (designated as DNA193963) (UNQ8344) was disrupted. The gene specific information for these studies is as follows: the mutated mouse gene corresponds to nucleotide reference: NM_183031 or *Mus musculus* Epstein-Barr virus induced gene 2 (Ebi2); protein reference: Q7TMV7 or ACCESSION: Q7TMV7 NID: *Mus musculus* (Mouse). Hypothetical protein; the human gene sequence reference: NM_004951 or ACCESSION: NM_004951 NID: 14577915 *Homo sapiens Homo sapiens* Epstein-Barr virus induced gene 2 (lymphocyte-specific G protein-coupled receptor) (EBI2); the human protein sequence corresponds to reference: P32249 or EBI2_HUMAN P32249 EBV-INDUCED G PROTEIN-COUPLED RECEPTOR.

The mouse gene of interest is Ebi2 (Epstein-Barr virus induced gene 2), ortholog of human EBI2 (Epstein-Barr virus induced gene 2 [lymphocyte-specific G protein-coupled receptor]).

EBI2 is a G protein-coupled receptor of the rhodopsin family that is expressed in B lymphocytes in response to Epstein-Barr virus infection. Expression of EBI2 is also detected in promyelocytic cell lines, monocytic cell lines, pokeweed mitogen-stimulated B cells, spleen, tonsil, peripheral blood mononuclear cells, and lung. The ligand and downstream signaling pathways for this receptor are not known; however, EBI2 is most similar structurally to F2R (coagulation factor II [thrombin] receptor) (Birkenbach et al, *J Virol;* 67(4):2209-20 (1993)). EBI2 may be involved in cell migration (Cahir-McFarland et al, *J Virol;* 78(8):4108-19 (2004)).

Targeted or gene trap mutations are generated in strain $129SvEv^{Brd}$-derived embryonic stem (ES) cells. The chimeric mice were bred to C57BL/6J albino mice to generate F1 heterozygous animals. These progeny were intercrossed to generate F2 wild type, heterozygous, and homozygous mutant progeny. On rare occasions, for example when very few F1 mice are obtained from the chimera, F1 heterozygous mice are crossed to $129SvEv^{Brd}$/C57 hybrid mice to yield additional heterozygous animals for the intercross to generate the F2 mice. Level I phenotypic analysis was performed on mice from this generation

| | wt | het | hom | Total |
|---|---|---|---|---|
| Observed | 15 | 46 | 15 | 76 |
| Expected | 19 | 38 | 19 | 76 |

Chi-Sq. = 3.37
Significance = 0.18559
(hom/n) = 0.20
Avg. Litter Size = 8
Mutation Type: Homologous Recombination (standard)

Coding exon 1 was targeted (NCBI accession AK087951.1).
Wild-type Expression Panel: Expression of the target gene was detected in embryonic stem (ES) cells and in all 13 adult tissue samples tested by RT-PCR, except skeletal muscle and bone.
QC Expression: Disruption of the target gene was confirmed by Southern hybridization analysis.

41.40.1. Phenotypic Analysis (for Disrupted Gene: DNA193963 (UNQ8344)

(a) Overall Phenotypic Summary:

Mutation of the gene encoding the ortholog of human Epstein-Barr virus induced gene 2 (lymphocyte-specific G protein-coupled receptor) (EBI2) resulted in abnormal bone-related measurements. Gene disruption was confirmed by Southern blot.

(b) Bone Metabolism & Radiology Phenotypic Analysis

In the area of bone metabolism, targets were identified herein for the treatment of arthritis, osteoporosis, osteopenia and osteopetrosis as well as identifying targets that promote bone healing. Tests included:

DEXA for measurement of bone mineral density on femur and vertebra

MicroCT for very high resolution and very high sensitivity measurements of bone mineral density for both trabecular and cortical bone.

Dexa Analysis—Test Description:

Procedure: A cohort of 4 wild type, 4 heterozygotes and 8 homozygotes were tested in this assay. Dual Energy X-ray Absorptiometry (DEXA) has been used successfully to identify changes in bone. Anesthetized animals were examined and bone mineral content (BMC), BMC/LBM ratios, volumetric bone mineral density (vBMD), total body BMD, femur BMD and vertebra BMD were measured.

The mouse was anesthetized by intraperitoneal injection of Avertin (1.25% 2,2,2,-tribromoethanol, 20 ml/kg body weight), body length and weight were measured, and then the mouse was placed in a prone position on the platform of the PIXImus™ Densitometer (Lunar Inc.) for a DEXA scan. Using Lunar PIXImus software, the bone mineral density (BMD) and fat composition (% fat) and total tissue mass (TTM) were determined in the regions of interest (ROI) [i.e., whole body, vertebrae, and both femurs].

Bone microCT Analysis:

Procedure: MicroCT was also used to get very sensitive measurements of BMD. One vertebra and 1 femur were taken from a cohort of 4 wild type and 8 homozygous mice. Measurements were taken of lumbar 5 vertebra trabecular bone volume, trabecular thickness, connectivity density and midshaft femur total bone area and cortical thickness. The μCT40 scans provided detailed information on bone mass and architecture. Multiple bones were placed into sample holders and scanned automatically. Instrument software was used to select regions of interest for analysis. Trabecular bone parameters were analyzed in the fifth lumbar vertebrae (LV5) at 16 micrometer resolution and cortical bone parameters were analyzed in the femur midshaft at a resolution of 20 micrometers.

Results:

DEXA: The male (−/−) mice exhibited decreased bone mineral density measurements when compared with their gender-matched (+/+) littermates and the historical means.

Micro-CT: The male (−/−) mice exhibited decreased trabecular bone volume (1 standard deviation), number and connectivity density when compared with their gender-matched (+/+) littermates and the historical means.

Summary

The male (−/−) mice analyzed by DEXA exhibited decreased bone measurements when compared with their (+/+) littermates, suggestive of abnormal bone disorders. These observations suggest that male mutant mice deficient in the gene which encodes PRO23370 polypeptides leads to metabolic disorders associated with abnormal bone measurements. Thus, PRO23370 polypeptides or agonists thereof would be useful in the treatment or prevention of bone-related disorders.

Example 42

Use of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 as a Hybridization Probe The following method describes use of a nucleotide sequence encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide as a hybridization probe.

DNA comprising the coding sequence of full-length or mature PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides as disclosed herein is employed as a probe to screen for homologous DNAs (such as those encoding naturally-occurring variants of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides) in human tissue cDNA libraries or human tissue genomic libraries.

Hybridization and washing of filters containing either library DNAs is performed under the following high stringency conditions. Hybridization of radiolabeled PRO194-, PRO220-, PRO241-, PRO284-, PRO331-, PRO354-, PRO355-, PRO533-, PRO541-, PRO725-, PRO937-, PRO1014-, PRO1120-, PRO1182-, PRO1325-, PRO1382-, PRO1410-, PRO1555-, PRO1556-, PRO1760-, PRO1787-, PRO1868-, PRO4326-, PRO4332-, PRO4346-, PRO4400-, PRO6003-, PRO6094-, PRO6244-, PRO9820-, PRO9828-, PRO10274-, PRO16090-, PRO19644-, PRO21340-, PRO92165-, PRO85143-, PRO1124-, PRO1026- or PRO23370-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides can then be identified using standard techniques known in the art.

Example 43

Expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in *E. coli*

This example illustrates preparation of an unglycosylated form of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides by recombinant expression in *E. coli.*

The DNA sequence encoding a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 protein can then be purified using a metal chelating column under conditions that allow tight binding of the protein.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may be expressed in *E. coli* in a poly-His tagged form, using the following procedure. The DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) Ion galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate. 2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 44

Expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in Mammalian Cells This example illustrates preparation of a potentially glycosylated form of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by recombinant expression in mammalian cells.

The vector, pRK5 (see EP 307,247, published Mar. 15, 1989), is employed as the expression vector. Optionally, the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA is ligated into pRK5 with selected restriction enzymes to allow insertion of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 DNA using ligation methods such as described in Sambrook et al., supra. The resulting vector is called pRK5-PRO194, pRK5-PRO220, pRK5-PRO241, pRK5-PRO284, pRK5-PRO331, pRK5-PRO354, pRK5-PRO355, pRK5-PRO533, pRK5-PRO541, pRK5-PRO725, pRK5-PRO937, pRK5-PRO1014, pRK5-PRO1120, pRK5-PRO1182, pRK5-PRO1325, pRK5-PRO1382, pRK5-PRO1410, pRK5-PRO1555, pRK5-PRO1556, pRK5-PRO1760, pRK5-PRO1787, pRK5-PRO1868, pRK5-PRO4326, pRK5-PRO4332, pRK5-PRO4346, pRK5-PRO4400, pRK5-PRO6003, pRK5-PRO6094, pRK5-PRO6244, pRK5-PRO9820, pRK5-PRO9828, pRK5-PRO10274, pRK5-PRO16090, pRK5-PRO19644, pRK5-PRO21340, pRK5-PRO92165, pRK5-PRO85143, pRK5-PRO1124, pRK5-PRO1026 or pRK5-23370.

The selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO194, pRK5-PRO220, pRK5-PRO241, pRK5-PRO284, pRK5-PRO331, pRK5-PRO354, pRK5-PRO355, pRK5-PRO533, pRK5-PRO541, pRK5-PRO725, pRK5-PRO937, pRK5-PRO1014, pRK5-PRO1120, pRK5-PRO1182, pRK5-PRO1325, pRK5-PRO1382, pRK5-PRO1410, pRK5-PRO1555, pRK5-PRO1556, pRK5-PRO1760, pRK5-PRO1787, pRK5-PRO1868, pRK5-PRO4326, pRK5-PRO4332, pRK5-PRO4346, pRK5-PRO4400, pRK5-PRO6003, pRK5-PRO6094, pRK5-PRO6244, pRK5-PRO9820, pRK5-PRO9828, pRK5-PRO10274, pRK5-PRO16090, pRK5-PRO19644, pRK5-PRO21340, pRK5-PRO92165, pRK5-PRO85143, pRK5-PRO1124, pRK5-PRO1026 or pRK5-23370 DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides. The cultures containing transfected cells may undergo further incubation (in serum free medium) and the medium is tested in selected bioassays.

In an alternative technique, PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may be introduced into 293 cells transiently using the dextran sulfate method described by Somparyrac et al., *Proc. Natl. Acad. Sci.,* 12:7575 (1981). 293 cells are grown to maximal density in a spinner flask and 700 μg pRK5-PRO194, pRK5-PRO220, pRK5-PRO241, pRK5-PRO284, pRK5-PRO331, pRK5-PRO354, pRK5-PRO355, pRK5-PRO533, pRK5-PRO541, pRK5-PRO725, pRK5-PRO937, pRK5-PRO1014, pRK5-PRO1120, pRK5-PRO1182, pRK5-PRO1325, pRK5-PRO1382, pRK5-PRO1410, pRK5-PRO1555, pRK5-PRO1556, pRK5-PRO1760, pRK5-PRO1787, pRK5-PRO1868, pRK5-PRO4326, pRK5-PRO4332, pRK5-PRO4346, pRK5-PRO4400, pRK5-PRO6003, pRK5-PRO6094, pRK5-PRO6244, pRK5-PRO9820, pRK5-PRO9828, pRK5-PRO10274, pRK5-PRO16090, pRK5-PRO19644, pRK5-PRO21340, pRK5-PRO92165, pRK5-PRO85143, pRK5-PRO1124, pRK5-PRO1026 or pRK5-PRO23370 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can then be concentrated and purified by any selected method, such as dialysis and/or column chromatography.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can be expressed in CHO cells. The pRK5-PRO194, pRK5-PRO220, pRK5-PRO241, pRK5-PRO284, pRK5-PRO331, pRK5-PRO354, pRK5-PRO355, pRK5-PRO533, pRK5-PRO541, pRK5-PRO725, pRK5-PRO937, pRK5-PRO1014, pRK5-PRO1120, pRK5-PRO1182, pRK5-PRO1325, pRK5-PRO1382, pRK5-PRO1410, pRK5-PRO1555, pRK5-PRO1556, pRK5-PRO1760, pRK5-PRO1787, pRK5-PRO1868, pRK5-PRO4326, pRK5-PRO4332, pRK5-PRO4346, pRK5-PRO4400, pRK5-PRO6003, pRK5-PRO6094, pRK5-PRO6244, pRK5-PRO9820, pRK5-PRO9828, pRK5-PRO10274, pRK5-PRO16090, pRK5-PRO19644, pRK5-PRO21340, pRK5-PRO92165, pRK5-PRO85143, pRK5-PRO1124, pRK5-PRO1026 or pRK5-PRO23370 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the culture medium may be replaced with serum free medium. Preferably, the cultures are incubated for about 6 days, and then the conditioned medium is harvested. The medium containing the expressed PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can then be concentrated and purified by any selected method.

Epitope-tagged PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may also be expressed in host CHO cells. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may be subcloned out of the pRK5 vector. The subclone insert can undergo PCR to fuse in frame with a selected epitope tag such as a poly-his tag into a Baculovirus expression vector. The poly-his tagged PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can then be concentrated and purified by any selected method, such as by $Ni^{2+}$-chelate affinity chromatography.

PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., *Nucl. Acids Res.* 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 μm filtered PS20 with 5% 0.2 μm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 μm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 μL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 45

Expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in Yeast The following method describes recombinant expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in yeast.

First, yeast expression vectors are constructed for intracellular production or secretion of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 from the ADH2/GAPDH promoter. DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 and the promoter is inserted into suitable restriction enzyme sites in the selected plasmid to direct intracellular expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370. For secretion, DNA encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can be cloned into the selected plasmid, together with DNA encoding the ADH2/GAPDH promoter, a native PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 signal peptide or other mammalian signal peptide, or, for example, a yeast alpha-factor or invertase secretory signal/leader sequence, and linker sequences (if needed) for expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can subsequently be isolated and purified by removing the yeast cells from the fermentation medium by centrifugation and then concentrating the medium using selected cartridge filters. The concentrate containing PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 may further be purified using selected column chromatography resins.

Example 46

Expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in Baculovirus-Infected Insect Cells The following method describes recombinant expression of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 in Baculovirus-infected insect cells.

The sequence coding for PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 or the desired portion of the coding sequence of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can then be purified, for example, by $Ni^{2+}$-chelate affinity chromatography as follows. Extracts are prepared from recombinant virus-infected Sf9 cells as described by Rupert et al., *Nature,* 362:175-179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 are pooled and dialyzed against loading buffer.

Alternatively, purification of the IgG tagged (or Fc tagged) PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 can be performed using known chromatography techniques, including for instance, Protein A or protein G column chromatography.

Example 47

Tissue Expression Profiling Using GeneExpress®

A proprietary database containing gene expression information (GeneExpress®, Gene Logic Inc., Gaithersburg, Md.) was analyzed in an attempt to identify polypeptides (and their encoding nucleic acids) whose expression is significantly upregulated in a particular tumor tissue(s) of interest as compared to other tumor(s) and/or normal tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The following is a list of molecules whose tissue expression profile as determined from an analysis of the GeneExpress® database evidences high tissue expression and significant upregulation of expression in a specific tumor or tumors as compared to other tumor(s) and/or normal tissues and optionally relatively low expression in normal essential and/or normal proliferating tissues. Tissue expression profiling was performed on several UNQ genes the results of which are disclosed in Example 41.

Example 48

Microarray Analysis to Detect Upregulation of UNQ Genes in Cancerous Tumors

Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (disease tissue) sample is greater than hybridization signal of a probe from a control (normal tissue) sample, the gene or genes overexpressed in the disease tissue are identified. The implication of this result is that an overexpressed protein in a diseased tissue is useful not only as a diagnostic marker for the presence of the disease condition, but also as a therapeutic target for treatment of the disease condition.

The methodology of hybridization of nucleic acids and microarray technology is well known in the art. In one example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In the present example, cancerous tumors derived from various human tissues were studied for upregulated gene expression relative to cancerous tumors from different tissue types and/or non-cancerous human tissues in an attempt to identify those polypeptides which are overexpressed in a particular cancerous tumor(s). In certain experiments, cancerous human tumor tissue and non-cancerous human tumor tissue of the same tissue type (often from the same patient) were obtained and analyzed for UNQ polypeptide expression. Additionally, cancerous human tumor tissue from any of a variety of different human tumors was obtained and compared to a "universal" epithelial control sample which was prepared by pooling non-cancerous human tissues of epithelial origin, including liver, kidney, and lung. mRNA isolated from the pooled tissues represents a mixture of expressed gene products from these different tissues. Microarray hybridization experiments using the pooled control samples generated a linear plot in a 2-color analysis. The slope of the line generated in a 2-color analysis was then used to normalize the ratios of (test:control detection) within each experiment. The normalized ratios from various experiments were then compared and used to identify clustering of gene expression. Thus, the pooled "universal control" sample not only allowed effective relative gene expression determinations in a simple 2-sample comparison, it also allowed multi-sample comparisons across several experiments.

In the present experiments, nucleic acid probes derived from the herein described UNQ polypeptide-encoding nucleic acid sequences were used in the creation of the microarray and RNA from various tumor tissues were used for the hybridization thereto. Below is shown the results of these experiments, demonstrating that various UNQ polypeptides of the present invention are significantly overexpressed in various human tumor tissues as compared to their normal counterpart tissue(s). Moreover, all of the molecules shown below are significantly overexpressed in their specific tumor tissue(s) as compared to in the "universal" epithelial control. As described above, these data demonstrate that the UNQ polypeptides of the present invention are useful not only as diagnostic markers for the presence of one or more cancerous tumors, but also serve as therapeutic targets for the treatment of those tumors. Microarray analysis was performed on several UNQ genes the results of which are disclosed in Example 41.

Example 49

Quantitative Analysis of UNQ mRNA Expression

In this assay, a 5' nuclease assay (for example, TaqMan®) and real-time quantitative PCR (for example, ABI Prizm 7700 Sequence Detection System® (Perkin Elmer, Applied Biosystems Division, Foster City, Calif.)), were used to find genes that are significantly overexpressed in a cancerous tumor or tumors as compared to other cancerous tumors or normal non-cancerous tissue. The 5' nuclease assay reaction is a fluorescent PCR-based technique which makes use of the 5' exonuclease activity of Taq DNA polymerase enzyme to monitor gene expression in real time. Two oligonucleotide primers (whose sequences are based upon the gene or EST sequence of interest) are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the PCR amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

The starting material for the screen was mRNA isolated from a variety of different cancerous tissues. The mRNA is quantitated precisely, e.g., fluorometrically. As a negative control, RNA was isolated from various normal tissues of the same tissue type as the cancerous tissues being tested.

5' nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer mRNA results to normal human mRNA results. As one Ct unit corresponds to 1 PCR cycle or approximately a 2-fold relative increase relative to normal, two units corresponds to a 4-fold relative increase, 3 units corresponds to an 8-fold relative increase and so on, one can quantitatively measure the relative fold increase in mRNA expression between two or more different tissues. Using this technique, the molecules have been identified as being significantly overexpressed in a particular tumor(s) as compared to their normal non-cancerous counterpart tissue(s) (from both the same and different tissue donors) and thus, represent excellent polypeptide targets for the diagnosis and therapy of cancer in mammals. Specific results for a UNQ gene are disclosed in Example 41.

Example 50

In Situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

In situ hybridization was performed following an optimized version of the protocol by Lu and Gillett, *Cell Vision* 1:169-176 (1994), using PCR-generated $^{33}$P-labeled riboprobes. Briefly, formalin-fixed, paraffin-embedded human tissues were sectioned, deparaffinized, deproteinated in proteinase K (20 g/ml) for 15 minutes at 37° C., and further processed for in situ hybridization as described by Lu and Gillett, supra. A [33-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 μl (125 mCi) of $^{33}$P-UTP (Amersham BF 1002, SA<2000 Ci/mmol) were speed vac dried. To each tube containing dried $^{33}$P-UTP, the following ingredients were added:

2.0 μl 5× transcription buffer 1.0 μl DTT (100 mM)

2.0 μl NTP mix (2.5 mM: 101; each of 10 mM GTP, CTP & ATP+10 μl $H_2O$)

1.0 μl UTP (50 μM)

1.0 μl Rnasin 1.0 μl DNA template (1 μg)

1.0 μl $H_2O$ 1.0 μl RNA polymerase (for PCR products T3=AS, T7=S, usually)

The tubes were incubated at 37° C. for one hour. 1.0 μl RQ1 DNase were added, followed by incubation at 37° C. for 15 minutes. 90 μl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 μl TE were added. 1 μl of the final product was pipetted on DE81 paper and counted in 6 ml of Biofluor II.

The probe was run on a TBE/urea gel. 1-3 μl of the probe or 5 μl of RNA Mrk III were added to 3 μl of loading buffer. After heating on a 95° C. heat block for three minutes, the probe was immediately placed on ice. The wells of gel were flushed, the sample loaded, and run at 180-250 volts for 45 minutes. The gel was wrapped in saran wrap and exposed to XAR film with an intensifying screen in −70° C. freezer one hour to overnight.

$^{33}$P-Hybridization

A. Pretreatment of Frozen Sections

The slides were removed from the freezer, placed on aluminium trays and thawed at room temperature for 5 minutes. The trays were placed in 55° C. incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ $H_2O$). After deproteination in 0.5 μg/ml proteinase K for 10 minutes at 37° C. (12.5 μl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

B. Pretreatment of Paraffin-Embedded Sections

The slides were deparaffinized, placed in SQ $H_2O$, and rinsed twice in 2×SSC at room temperature, for 5 minutes each time. The sections were deproteinated in 20 μg/ml proteinase K (500 μl of 10 mg/ml in 250 ml RNase-free RNase buffer; 37° C., 15 minutes)—human embryo, or 8× proteinase K (100 μl in 250 ml Rnase buffer, 37° C., 30 minutes)—formalin tissues. Subsequent rinsing in 0.5×SSC and dehydration were performed as described above.

C. Prehybridization

The slides were laid out in a plastic box lined with Box buffer (4×SSC, 50% formamide)—saturated filter paper.

D. Hybridization 1.0×10$^6$ cpm probe and 1.0 μl tRNA (50 mg/ml stock) per slide were heated at 95° C. for 3 minutes. The slides were cooled on ice, and 48 μl hybridization buffer were added per slide. After vortexing, 50 μl $^{33}$P mix were added to 50 μl prehybridization on slide. The slides were incubated overnight at 55° C.

E. Washes

Washing was done 2×10 minutes with 2×SSC, EDTA at room temperature (400 ml 20×SSC+16 ml 0.25M EDTA, $V_f$=4L), followed by RNaseA treatment at 37° C. for 30 minutes (500 μl of 10 mg/ml in 250 ml Rnase buffer=20 μg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, $V_f$=4L).

F. Oligonucleotides

In situ analysis was performed on a variety of DNA sequences disclosed herein. The oligonucleotides employed for these analyses were obtained so as to be complementary to the nucleic acids (or the complements thereof) as shown in the accompanying figures.

G. Results

In situ analysis was performed on a variety of DNA sequences disclosed herein the results of which are disclosed in Example 41.

Example 51

Preparation of Antibodies that Bind PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370

This example illustrates preparation of monoclonal antibodies which can specifically bind PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370.

Techniques for producing the monoclonal antibodies are known in the art and are described, for instance, in Goding, supra. Immunogens that may be employed include purified PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides, fusion proteins containing PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides, and cells expressing recombinant PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides on the cell surface. Selection of the immunogen can be made by the skilled artisan without undue experimentation.

Mice, such as Balb/c, are immunized with the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 antibodies.

After a suitable antibody titer has been detected, the animals "positive" for antibodies can be injected with a final intravenous injection of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370. Determination of "positive" hybridoma cells secreting the desired monoclonal antibodies against PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 is within the skill in the art.

The positive hybridoma cells can be injected intraperitoneally into syngeneic Balb/c mice to produce ascites containing the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 52

Purification of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 Polypeptides Using Specific Antibodies Native or recombinant PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides may be purified by a variety of standard techniques in the art of protein purification. For example, pro-PRO194, pro-PRO220, pro-PRO241, pro-PRO284, pro-PRO331, pro-PRO354, pro-PRO355, pro-PRO533, pro-PRO541, pro-PRO725, pro-PRO937, pro-PRO1014, pro-PRO1120, pro-PRO1182, pro-PRO1325, pro-PRO1382, pro-PRO1410, pro-PRO1555, pro-PRO1556, pro-PRO1760, pro-PRO1787, pro-PRO1868, pro-PRO4326, pro-PRO4332, pro-PRO4346, pro-PRO4400, pro-PRO6003, pro-PRO6094, pro-PRO6244, pro-PRO9820, pro-PRO9828, pro-PRO10274, pro-PRO16090, pro-PRO19644, pro-PRO21340, pro-PRO92165, pro-PRO85143, pro-PRO1124, pro-PRO1026 or pro-PRO23370 polypeptide, mature PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, or pre-PRO194, pre-PRO220, pre-PRO241, pre-PRO284, pre-PRO331, pre-PRO354, pre-PRO355, pre-PRO533, pre-PRO541, pre-PRO725, pre-PRO937, pre-PRO1014, pre-PRO1120, pre-PRO1182, pre-PRO1325, pre-PRO1382, pre-PRO1410, pre-PRO1555, pre-PRO1556, pre-PRO1760, pre-PRO1787, pre-PRO1868, pre-PRO4326, pre-PRO4332, pre-PRO4346, pre-PRO4400, pre-PRO6003, pre-PRO6094, pre-PRO6244, pre-PRO9820, pre-PRO9828, pre-PRO10274, pre-PRO16090, pre-PRO19644, pre-PRO21340, pre-PRO92165, pre-PRO85143, pre-PRO1124, pre-PRO1026 or pre-PRO23370 polypeptide is purified by immunoaffinity chromatography using antibodies specific for the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide of interest. In general, an immunoaffinity column is constructed by covalently coupling the anti-PRO194, anti-PRO220, anti-PRO241, anti-PRO284, anti-PRO331, anti-PRO354, anti-PRO355, anti-PRO533, anti-PRO541, anti-PRO725, anti-PRO937, anti-PRO1014, anti-PRO1120, anti-PRO1182, anti-PRO1325, anti-PRO1382, anti-PRO1410, anti-PRO1555, anti-PRO1556, anti-PRO1760, anti-PRO1787, anti-PRO1868, anti-PRO4326, anti-PRO4332, anti-PRO4346, anti-PRO4400, anti-PRO6003, anti-PRO6094, anti-PRO6244, anti-PRO9820, anti-PRO9828, anti-PRO10274, anti-PRO16090, anti-PRO19644, anti-PRO21340, anti-PRO92165, anti-PRO85143, anti-PRO1124, anti-PRO1026 or anti-PRO23370 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide by preparing a fraction from cells containing PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide in a soluble form. This preparation is derived by solubilization of the whole cell or of a subcellular fraction obtained via differential centrifugation by the addition of detergent or by other methods well known in the art. Alternatively, soluble polypeptide containing a signal sequence may be secreted in useful quantity into the medium in which the cells are grown.

A soluble PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-containing preparation is passed over the immunoaffinity column, and the column is washed under conditions that allow the preferential absorbance of PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide (e.g., high ionic strength buffers in the presence of detergent). Then, the column is eluted under conditions that disrupt antibody/PRO194, antibody/PRO220, antibody/PRO241, antibody/PRO284, antibody/PRO331, antibody/PRO354, antibody/PRO355, antibody/PRO533, antibody/PRO541, antibody/PRO725, antibody/PRO937, antibody/PRO1014, antibody/PRO1120, antibody/PRO1182, antibody/PRO1325, antibody/PRO1382, antibody/PRO1410, antibody/PRO1555, antibody/PRO1556, antibody/PRO1760, antibody/PRO1787, antibody/PRO1868, antibody/PRO4326, antibody/PRO4332, antibody/PRO4346, antibody/PRO4400, antibody/PRO6003, antibody/PRO6094, antibody/PRO6244, antibody/PRO9820, antibody/PRO9828, antibody/PRO10274, antibody/PRO16090, antibody/PRO19644, antibody/PRO21340, antibody/PRO92165, antibody/PRO85143, antibody/PRO1124, antibody/PRO1026 or antibody/PRO23370 polypeptide binding (e.g., a low pH buffer such as approximately pH 2-3, or a high concentration of a chaotrope such as urea or thiocyanate ion), and PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is collected.

Example 53

Drug Screening

This invention is particularly useful for screening compounds by using PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptides or binding fragment thereof in any of a variety of drug screening techniques. The PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment. Drugs are screened against such transformed cells in competitive binding assays. Such cells, either in viable or fixed form, can be used for standard binding assays. One may measure, for example, the formation of complexes between PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or a fragment and the agent being tested. Alternatively, one can examine the diminution in complex formation between the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and its target cell or target receptors caused by the agent being tested.

Thus, the present invention provides methods of screening for drugs or any other agents which can affect a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-associated disease or disorder. These methods comprise contacting such an agent with an PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment thereof and assaying (I) for the presence of a complex between the agent and the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment, or (ii) for the presence of a complex between the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment and the cell, by methods well known in the art. In such competitive binding assays, the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment is typically labeled. After suitable incubation, free PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragment is separated from that present in bound form, and the amount of free or uncomplexed label is a measure of the ability of the particular agent to bind to PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or to interfere with the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, the peptide test compounds are reacted with PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide and washed. Bound PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide is detected by methods well known in the art. Purified PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide specifically compete with a test compound for binding to PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or fragments thereof. In this manner, the antibodies can be used to detect the presence of any peptide which shares one or more antigenic determinants with PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide.

Example 54

Rational Drug Design

The goal of rational drug design is to produce structural analogs of biologically active polypeptide of interest (i.e., a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide) or of small molecules with which they interact, e.g., agonists, antagonists, or inhibitors. Any of these examples can be used to fashion drugs which are more active or stable forms of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide or which enhance or interfere with the function of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide in vivo (cf., Hodgson, *Bio/Technology*, 9: 19-21 (1991)).

In one approach, the three-dimensional structure of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide, or of a PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-inhibitor complex, is determined by x-ray crystallography, by computer modeling or, most typically, by a combination of the two approaches. Both the shape and charges of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide must be ascertained to elucidate the structure and to determine active site(s) of the molecule. Less often, useful information regarding the structure of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be gained by modeling based on the structure of homologous proteins. In both cases, relevant structural information is used to design analogous PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al., *J. Biochem.,* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO194, PRO220, PRO241, PRO284, PRO331, PRO354, PRO355, PRO533, PRO541, PRO725, PRO937, PRO1014, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide may be made available to perform such analytical studies as X-ray crystallography. In addition, knowledge of the PRO194, PRO220, PRO241, PRO284, PRO331, PRO354, PRO355, PRO533, PRO541, PRO725, PRO937, PRO114, PRO1120, PRO1182, PRO1325, PRO1382, PRO1410, PRO1555, PRO1556, PRO1760, PRO1787, PRO1868, PRO4326, PRO4332, PRO4346, PRO4400, PRO6003, PRO6094, PRO6244, PRO9820, PRO9828, PRO10274, PRO16090, PRO19644, PRO21340, PRO92165, PRO85143, PRO1124, PRO1026 or PRO23370 polypeptide amino acid sequence provided herein will provide guidance to those employing computer modeling techniques in place of or in addition to x-ray crystallography.

What is claimed is:

1. A method of identifying a test agent that modulates a lipid metabolic disorder associated with a disruption of an immunoglobulin superfamily, member 4 (Igsf4), the method comprising:

(a) providing a knockout mouse whose genome comprises a homozygous disruption of a nucleic acid sequence which is an ortholog of a human nucleic acid sequence that encodes for the polypeptide of SEQ ID NO:14, wherein said mouse lacks functional Igsf4 and exhibits as compared to the wild type mouse, at least one of: increased mean serum triglyceride level and increased mean serum tumor necrosis factor-α (TNF-α) response to a lipopolysaccharide (LPS) challenge, (b) administering a test agent to the knockout mouse of (a), (c) determining the knockout mouse's susceptibility to at least one of: increased mean serum triglyceride level and increased mean serum TNF-α response to a LPS challenge, and (d) identifying whether a test agent modulates a lipid metabolic disorder associated with a disruption of an Igsf4, wherein decreasing at least one of: the knockout mouse' mean serum triglyceride level and the knockout mouse' mean serum TNF-α response to a LPS challenge is indicative of an agonist of the Igsf4, and wherein increasing at least one of: the knockout mouse' mean serum triglyceride level and the knockout mouse' mean serum TNF-α response to a LPS challenge is indicative of an antagonist of the Igsf4.

2. The test agent of claim 1, wherein the agonist is an anti-Igsf4 antibody.

3. The test agent of claim 1, wherein the antagonist is an anti-Igsf4 antibody.

* * * * *

UNITED STATES PATENT AND TRADEMARK OFFICE

CERTIFICATE OF CORRECTION

PATENT NO. : 7,947,866 B2
APPLICATION NO. : 11/577547
DATED : May 24, 2011
INVENTOR(S) : Mary Jean Sparks It is certified that error appears in the above-identified patent and that said Letters Patent is hereby corrected as shown below:

On the Claim page Col. 618, Line 20 Claim 1(d) should read,

--wherein decreasing at least one of: the knockout mouse's--

Col. 618, line 21 Claim 1(d) should read,

--mean serum triglyceride level and the knockout mouse's--

Col. 618, line 24 Claim 1(d) should read,

--increasing at least one of: the knockout mouse's mean--

Col. 618, line 25 Claim 1(d) should read,

--serum triglyceride level and the knockout mouse's mean--

Signed and Sealed this
Twenty-second Day of November, 2011

David J. Kappos
*Director of the United States Patent and Trademark Office*

SEQUENCE LISTING

```
<160> NUMBER OF SEQ ID NOS: 147

<210> SEQ ID NO 1
<211> LENGTH: 1399
<212> TYPE: DNA
<213> ORGANISM: Homo sapiens

<400> SEQUENCE: 1

cccacgcgtc cgcccgccgc tgcgtcccgg agtgcaagtg agcttctcgg           50

ctgccccgcg ggccggggtg cggagccgac atgcgcccgc ttctcggcct          100

ccttctggtc ttcgccggct gcaccttcgc cttgtacttg ctgtcgacgc          150

gactgccccg cgggcggaga ctgggctcca ccgaggaggc tggaggcagg          200

tcgctgtggt tcccctccga cctggcagag ctgcgggagc tctctgaggt          250
```

-continued

```
ccttcgagag taccggaagg agcaccaggc ctacgtgttc ctgctcttct        300
gcggcgccta cctctacaaa cagggctttg ccatccccgg ctccagcttc        350
ctgaatgttt tagctggtgc cttgtttggg ccatggctgg ggcttctgct        400
gtgctgtgtg ttgacctcgg tgggtgccac atgctgctac ctgctctcca        450
gtatttttgg caaacagttg gtggtgtcct actttcctga taaagtggcc        500
ctgctgcaga gaaaggtgga ggagaacaga aacagcttgt ttttttcctt        550
attgtttttg agacttttcc ccatgacacc aaactggttc ttgaacctct        600
cggccccaat tctgaacatt cccatcgtgc agttcttctt ctcagttctt        650
atcggtttga tcccatataa tttcatctgt gtgcagacag ggtccatcct        700
gtcaacccta acctctctgg atgctctttt ctcctgggac actgtcttta        750
agctgttggc cattgccatg gtggcattaa ttcctggaac cctcattaaa        800
aaatttagtc agaaacatct gcaattgaat gaaacaagta ctgctaatca        850
tatacacagt agaaaagaca catgatctgg attttctgtt tgccacatcc        900
ctggactcag ttgcttattt gtgtaatgga tgtggtcctc taaagcccct        950
cattgttttt gattgccttc tataggtgat gtggacactg tgcatcaatg       1000
tgcagtgtct tttcagaaag gacactctgc tcttgaaggt gtattacatc       1050
aggttttcaa accagccctg gtgtagcaga cactgcaaca gatgcctcct       1100
agaaaatgct gtttgtggcc gggcgcggtg gctcacgcct gtaatcccag       1150
cactttggga ggccgaggcc ggtgattcac aaggtcagga gttcaagacc       1200
agcctggcca agatggtgaa atcctgtctc taataaaaat acaaaaatta       1250
gccaggcgtg gtggcaggca cctgtaatcc cagctactcg ggaggctgag       1300
gcaggagaat tgcttgaacc aaggtggcag aggttgcagt aagccaagat       1350
cacaccactg cactccagcc tgggtgatag agtgagacac  tgtcttgac       1399
```

```
<210> SEQ ID NO 2
<211> LENGTH: 264
<212> TYPE: PRT
<213> ORGANISM: Homo sapiens

<400> SEQUENCE: 2

Met Arg Pro Leu Leu Gly Leu Leu Leu Val Phe Ala Gly Cys Thr
  1               5                  10                  15

Phe Ala Leu Tyr Leu Leu Ser Thr Arg Leu Pro Arg Gly Arg Arg
             20                  25                  30

Leu Gly Ser Thr Glu Glu Ala Gly Gly Arg Ser Leu Trp Phe Pro
             35                  40                  45

Ser Asp Leu Ala Glu Leu Arg Glu Leu Ser Glu Val Leu Arg Glu
             50                  55                  60

Tyr Arg Lys Glu His Gln Ala Tyr Val Phe Leu Leu Phe Cys Gly
             65                  70                  75

Ala Tyr Leu Tyr Lys Gln Gly Phe Ala Ile Pro Gly Ser Ser Phe
             80                  85                  90

Leu Asn Val Leu Ala Gly Ala Leu Phe Gly Pro Trp Leu Gly Leu
             95                 100                 105

Leu Leu Cys Cys Val Leu Thr Ser Val Gly Ala Thr Cys Cys Tyr
            110                 115                 120

Leu Leu Ser Ser Ile Phe Gly Lys Gln Leu Val Val Ser Tyr Phe
            125                 130                 135
```

Pro Asp Lys Val Ala Leu Leu Gln Arg Lys Val Glu Glu Asn Arg
140 145 150

Asn Ser Leu Phe Phe Phe Leu Leu Phe Leu Arg Leu Phe Pro Met
155 160 165

Thr Pro Asn Trp Phe Leu Asn Leu Ser Ala Pro Ile Leu Asn Ile
170 175 180

Pro Ile Val Gln Phe Phe Phe Ser Val Leu Ile Gly Leu Ile Pro
185 190 195

Tyr Asn Phe Ile Cys Val Gln Thr Gly Ser Ile Leu Ser Thr Leu
200 205 210

Thr Ser Leu Asp Ala Leu Phe Ser Trp Asp Thr Val Phe Lys Leu
215 220 225

Leu Ala Ile Ala Met Val Ala Leu Ile Pro Gly Thr Leu Ile Lys
230 235 240

Lys Phe Ser Gln Lys His Leu Gln Leu Asn Glu Thr Ser Thr Ala
245 250 255

Asn His Ile His Ser Arg Lys Asp Thr
260

<210> SEQ ID NO 3
<211> LENGTH: 2639
<212> TYPE: DNA
<213> ORGANISM: Homo sapiens

<400> SEQUENCE: 3
gacatcggag gtgggctagc actgaaactg cttttcaaga cgaggaagag 50
gaggagaaag agaaagaaga ggaagatgtt gggcaacatt tatttaacat 100
gctccacagc ccggaccctg gcatcatgct gctattcctg caaatactga 150
agaagcatgg gatttaaata ttttacttct aaataaatga attactcaat 200
ctcctatgac catctataca tactccacct tcaaaaagta catcaatatt 250
atatcattaa ggaaatagta accttctctt ctccaatatg catgacattt 300
ttggacaatg caattgtggc actggcactt atttcagtga agaaaaactt 350
tgtggttcta tggcattcat catttgacaa atgcaagcat cttccttatc 400
aatcagctcc tattgaactt actagcactg actgtggaat ccttaagggc 450
ccattacatt tctgaagaag aaagctaaga tgaaggacat gccactccga 500
attcatgtgc tacttggcct agctatcact acactagtac aagctgtaga 550
taaaaaagtg gattgtccac ggttatgtac gtgtgaaatc aggccttggt 600
ttacacccag atccatttat atggaagcat ctacagtgga ttgtaatgat 650
ttaggtcttt taactttccc agccagattg ccagctaaca cacagattct 700
tctcctacag actaacaata ttgcaaaaat tgaatactcc acagactttc 750
cagtaaacct tactggcctg gatttatctc aaaacaattt atcttcagtc 800
accaatatta atgtaaaaaa gatgcctcag ctcctttctg tgtacctaga 850
ggaaaacaaa cttactgaac tgcctgaaaa atgtctgtcc gaactgagca 900
acttacaaga actctatatt aatcacaact tgctttctac aatttcacct 950
ggagccttta ttggcctaca taatcttctt cgacttcatc tcaattcaaa 1000
tagattgcag atgatcaaca gtaagtggtt tgatgctctt ccaaatctag 1050
agattctgat gattggggaa aatccaatta tcagaatcaa agacatgaac 1100

-continued

```
tttaagcctc ttatcaatct tcgcagcctg gttatagctg gtataaacct          1150

cacagaaata ccagataacg ccttggttgg actggaaaac ttagaaagca          1200

tctcttttta cgataacagg cttattaaag taccccatgt tgctcttcaa          1250

aaagttgtaa atctcaaatt tttggatcta aataaaaatc ctattaatag          1300

aatacgaagg ggtgatttta gcaatatgct acacttaaaa gagttgggga          1350

taaataatat gcctgagctg atttccatcg atagtcttgc tgtggataac          1400

ctgccagatt taagaaaaat agaagctact aacaacccta gattgtctta          1450

cattcacccc aatgcatttt tcagactccc caagctggaa tcactcatgc          1500

tgaacagcaa tgctctcagt gccctgtacc atggtaccat tgagtctctg          1550

ccaaacctca aggaaatcag catacacagt aaccccatca ggtgtgactg          1600

tgtcatccgt tggatgaaca tgaacaaaac caacattcga ttcatggagc          1650

cagattcact gttttgcgtg gacccacctg aattccaagg tcagaatgtt          1700

cggcaagtgc atttcaggga catgatggaa atttgtctcc ctcttatagc          1750

tcctgagagc tttccttcta atctaaatgt agaagctggg agctatgttt          1800

cctttcactg tagagctact gcagaaccac agcctgaaat ctactggata          1850

acaccttctg gtcaaaaact cttgcctaat accctgacag acaagttcta          1900

tgtccattct gagggaacac tagatataaa tggcgtaact cccaaagaag          1950

ggggtttata tacttgtata gcaactaacc tagttggcgc tgacttgaag          2000

tctgttatga tcaaagtgga tggatctttt ccacaagata acaatggctc          2050

tttgaatatt aaaataagag atattcaggc caattcagtt ttggtgtcct          2100

ggaaagcaag ttctaaaatt ctcaaatcta gtgttaaatg gacagccttt          2150

gtcaagactg aaaattctca tgctgcgcaa agtgctcgaa taccatctga          2200

tgtcaaggta tataatctta ctcatctgaa tccatcaact gagtataaaa          2250

tttgtattga tattcccacc atctatcaga aaaacagaaa aaaatgtgta          2300

aatgtcacca ccaaaggttt gcaccctgat caaaaaagagt atgaaaagaa          2350

taataccaca acacttatgg cctgtcttgg aggccttctg ggattattgg          2400

gtgtgatatg tcttatcagc tgcctctctc cagaaatgaa ctgtgatggt          2450

ggacacagct atgtgaggaa ttacttacag aaaccaacct ttgcattagg          2500

tgagctttat cctcctctga taaatctctg ggaagcagga aaagaaaaaa          2550

gtacatcact gaaagtaaaa gcaactgtta taggtttacc aacaaatatg          2600

tcctaaaaac caccaaggaa acctactcca  aaaatgaac                     2639
```

<210> SEQ ID NO 4
<211> LENGTH: 708
<212> TYPE: PRT
<213> ORGANISM: Homo sapiens

<400> SEQUENCE: 4

```
Met Lys Asp Met Pro Leu Arg Ile His Val Leu Leu Gly Leu Ala
  1               5                  10                  15

Ile Thr Thr Leu Val Gln Ala Val Asp Lys Lys Val Asp Cys Pro
                 20                  25                  30

Arg Leu Cys Thr Cys Glu Ile Arg Pro Trp Phe Thr Pro Arg Ser
                 35                  40                  45

Ile Tyr Met Glu Ala Ser Thr Val Asp Cys Asn Asp Leu Gly Leu
```

-continued 50 55 60

Leu Thr Phe Pro Ala Arg Leu Pro Ala Asn Thr Gln Ile Leu Leu
65 70 75

Leu Gln Thr Asn Asn Ile Ala Lys Ile Glu Tyr Ser Thr Asp Phe
80 85 90

Pro Val Asn Leu Thr Gly Leu Asp Leu Ser Gln Asn Asn Leu Ser
95 100 105

Ser Val Thr Asn Ile Asn Val Lys Lys Met Pro Gln Leu Leu Ser
110 115 120

Val Tyr Leu Glu Glu Asn Lys Leu Thr Glu Leu Pro Glu Lys Cys
125 130 135

Leu Ser Glu Leu Ser Asn Leu Gln Glu Leu Tyr Ile Asn His Asn
140 145 150

Leu Leu Ser Thr Ile Ser Pro Gly Ala Phe Ile Gly Leu His Asn
155 160 165

Leu Leu Arg Leu His Leu Asn Ser Asn Arg Leu Gln Met Ile Asn
170 175 180

Ser Lys Trp Phe Asp Ala Leu Pro Asn Leu Glu Ile Leu Met Ile
185 190 195

Gly Glu Asn Pro Ile Ile Arg Ile Lys Asp Met Asn Phe Lys Pro
200 205 210

Leu Ile Asn Leu Arg Ser Leu Val Ile Ala Gly Ile Asn Leu Thr
215 220 225

Glu Ile Pro Asp Asn Ala Leu Val Gly Leu Glu Asn Leu Glu Ser
230 235 240

Ile Ser Phe Tyr Asp Asn Arg Leu Ile Lys Val Pro His Val Ala
245 250 255

Leu Gln Lys Val Val Asn Leu Lys Phe Leu Asp Leu Asn Lys Asn
260 265 270

Pro Ile Asn Arg Ile Arg Arg Gly Asp Phe Ser Asn Met Leu His
275 280 285

Leu Lys Glu Leu Gly Ile Asn Asn Met Pro Glu Leu Ile Ser Ile
290 295 300

Asp Ser Leu Ala Val Asp Asn Leu Pro Asp Leu Arg Lys Ile Glu
305 310 315

Ala Thr Asn Asn Pro Arg Leu Ser Tyr Ile His Pro Asn Ala Phe
320 325 330

Phe Arg Leu Pro Lys Leu Glu Ser Leu Met Leu Asn Ser Asn Ala
335 340 345

Leu Ser Ala Leu Tyr His Gly Thr Ile Glu Ser Leu Pro Asn Leu
350 355 360

Lys Glu Ile Ser Ile His Ser Asn Pro Ile Arg Cys Asp Cys Val
365 370 375

Ile Arg Trp Met Asn Met Asn Lys Thr Asn Ile Arg Phe Met Glu
380 385 390

Pro Asp Ser Leu Phe Cys Val Asp Pro Pro Glu Phe Gln Gly Gln
395 400 405

Asn Val Arg Gln Val His Phe Arg Asp Met Met Glu Ile Cys Leu
410 415 420

Pro Leu Ile Ala Pro Glu Ser Phe Pro Ser Asn Leu Asn Val Glu
425 430 435

Ala Gly Ser Tyr Val Ser Phe His Cys Arg Ala Thr Ala Glu Pro
440 445 450

Gln Pro Glu Ile Tyr Trp Ile Thr Pro Ser Gly Gln Lys Leu Leu
455 460 465

Pro Asn Thr Leu Thr Asp Lys Phe Tyr Val His Ser Glu Gly Thr
470 475 480

Leu Asp Ile Asn Gly Val Thr Pro Lys Glu Gly Gly Leu Tyr Thr
485 490 495

Cys Ile Ala Thr Asn Leu Val Gly Ala Asp Leu Lys Ser Val Met
500 505 510

Ile Lys Val Asp Gly Ser Phe Pro Gln Asp Asn Asn Gly Ser Leu
515 520 525

Asn Ile Lys Ile Arg Asp Ile Gln Ala Asn Ser Val Leu Val Ser
530 535 540

Trp Lys Ala Ser Ser Lys Ile Leu Lys Ser Ser Val Lys Trp Thr
545 550 555

Ala Phe Val Lys Thr Glu Asn Ser His Ala Ala Gln Ser Ala Arg
560 565 570

Ile Pro Ser Asp Val Lys Val Tyr Asn Leu Thr His Leu Asn Pro
575 580 585

Ser Thr Glu Tyr Lys Ile Cys Ile Asp Ile Pro Thr Ile Tyr Gln
590 595 600

Lys Asn Arg Lys Lys Cys Val Asn Val Thr Thr Lys Gly Leu His
605 610 615

Pro Asp Gln Lys Glu Tyr Glu Lys Asn Asn Thr Thr Thr Leu Met
620 625 630

Ala Cys Leu Gly Gly Leu Leu Gly Ile Ile Gly Val Ile Cys Leu
635 640 645

Ile Ser Cys Leu Ser Pro Glu Met Asn Cys Asp Gly Gly His Ser
650 655 660

Tyr Val Arg Asn Tyr Leu Gln Lys Pro Thr Phe Ala Leu Gly Glu
665 670 675

Leu Tyr Pro Pro Leu Ile Asn Leu Trp Glu Ala Gly Lys Glu Lys
680 685 690

Ser Thr Ser Leu Lys Val Lys Ala Thr Val Ile Gly Leu Pro Thr
695 700 705

Asn Met Ser

<210> SEQ ID NO 5
<211> LENGTH: 2454
<212> TYPE: DNA
<213> ORGANISM: Homo sapiens

<400> SEQUENCE: 5
ggactaatct gtgggagcag tttattccag tatcacccag ggtgcagcca 50
caccaggact gtgttgaagg gtgttttttt tcttttaaat gtaatacctc 100
ctcatctttt cttcttacac agtgtctgag aacatttaca ttatagataa 150
gtagtacatg gtggataact tctactttta ggaggactac tctcttctga 200
cagtcctaga ctggtcttct acactaagac accatgaagg agtatgtgct 250
cctattattc ctggctttgt gctctgccaa acccttcttt agcccttcac 300
acatcgcact gaagaatatg atgctgaagg atatggaaga cacagatgat 350
gatgatgatg atgatgatga tgatgatgat gatgaggaca actctctttt 400
tccaacaaga gagccaagaa gccatttttt tccatttgat ctgtttccaa 450
tgtgtccatt tggatgtcag tgctattcac gagttgtaca ttgctcagat 500

-continued

```
ttaggtttga cctcagtccc aaccaacatt ccatttgata ctcgaatgct     550
tgatcttcaa aacaataaaa ttaaggaaat caaagaaaat gattttaaag     600
gactcacttc actttatggt ctgatcctga acaacaacaa gctaacgaag     650
attcacccaa aagcctttct aaccacaaag aagttgcgaa ggctgtatct     700
gtcccacaat caactaagtg aaataccact taatcttccc aaatcattag     750
cagaactcag aattcatgaa aataaagtta agaaaataca aaaggacaca     800
ttcaaaggaa tgaatgcttt acacgttttg gaaatgagtg caaaccctct     850
tgataataat gggatagagc caggggcatt tgaaggggtg acggtgttcc     900
atatcagaat tgcagaagca aaactgacct cagttcctaa aggcttacca     950
ccaactttat tggagcttca cttagattat aataaaattt caacagtgga    1000
acttgaggat tttaaacgat acaaagaact acaaaggctg ggcctaggaa    1050
acaacaaaat cacagatatc gaaaatggga gtcttgctaa cataccacgt    1100
gtgagagaaa tacatttgga aaacaataaa ctaaaaaaaa tcccttcagg    1150
attaccagag ttgaaatacc tccagataat cttccttcat tctaattcaa    1200
ttgcaagagt gggagtaaat gacttctgtc caacagtgcc aaagatgaag    1250
aaatctttat acagtgcaat aagtttattc aacaacccgg tgaaatactg    1300
ggaaatgcaa cctgcaacat ttcgttgtgt tttgagcaga atgagtgttc    1350
agcttgggaa ctttggaatg taataattag taattggtaa tgtccattta    1400
atataagatt caaaaatccc tacatttgga atacttgaac tctattaata    1450
atggtagtat tatatataca agcaaatatc tattctcaag tggtaagtcc    1500
actgacttat tttatgacaa gaaatttcaa cggaattttg ccaaactatt    1550
gatacataag ggttgagag aaacaagcat ctattgcagt ttcctttttg     1600
cgtacaaatg atcttacata aatctcatgc ttgaccattc ctttcttcat    1650
aacaaaaaag taagatattc ggtatttaac actttgttat caagcacatt    1700
ttaaaaagaa ctgtactgta aatggaatgc ttgacttagc aaaatttgtg    1750
ctctttcatt tgctgttaga aaaacagaat taacaaagac agtaatgtga    1800
agagtgcatt acactattct tattctttag taacttgggt agtactgtaa    1850
tatttttaat catcttaaag tatgatttga tataatctta ttgaaattac    1900
cttatcatgt cttagagccc gtctttatgt ttaaaactaa tttcttaaaa    1950
taaagccttc agtaaatgtt cattaccaac ttgataaatg ctactcataa    2000
gagctggttt ggggctatag catatgcttt ttttttttta attattacct    2050
gatttaaaaa tctctgtaaa aacgtgtagt gtttcataaa atctgtaact    2100
cgcattttaa tgatccgcta ttataagctt ttaatagcat gaaaattgtt    2150
aggctatata acattgccac ttcaactcta aggaatattt ttgagatatc    2200
cctttggaag accttgcttg gaagagcctg gacactaaca attctacacc    2250
aaattgtctc ttcaaatacg tatggactgg ataactctga gaaacacatc    2300
tagtataact gaataagcag agcatcaaat taaacagaca gaaaccgaaa    2350
gctctatata aatgctcaga gttctttatg tatttcttat tggcattcaa    2400
catatgtaaa atcagaaaac agggaaattt tcattaaaaa tattggtttg    2450
aaat                                                      2454
```

<210> SEQ ID NO 6
<211> LENGTH: 379
<212> TYPE: PRT
<213> ORGANISM: Homo sapiens

<400> SEQUENCE: 6

```
Met Lys Glu Tyr Val Leu Leu Leu Phe Leu Ala Leu Cys Ser Ala
  1               5                  10                  15

Lys Pro Phe Phe Ser Pro Ser His Ile Ala Leu Lys Asn Met Met
                 20                  25                  30

Leu Lys Asp Met Glu Asp Thr Asp Asp Asp Asp Asp Asp Asp Asp
                 35                  40                  45

Asp Asp Asp Asp Asp Glu Asp Asn Ser Leu Phe Pro Thr Arg Glu
                 50                  55                  60

Pro Arg Ser His Phe Phe Pro Phe Asp Leu Phe Pro Met Cys Pro
                 65                  70                  75

Phe Gly Cys Gln Cys Tyr Ser Arg Val Val His Cys Ser Asp Leu
                 80                  85                  90

Gly Leu Thr Ser Val Pro Thr Asn Ile Pro Phe Asp Thr Arg Met
                 95                 100                 105

Leu Asp Leu Gln Asn Asn Lys Ile Lys Glu Ile Lys Glu Asn Asp
                110                 115                 120

Phe Lys Gly Leu Thr Ser Leu Tyr Gly Leu Ile Leu Asn Asn Asn
                125                 130                 135

Lys Leu Thr Lys Ile His Pro Lys Ala Phe Leu Thr Thr Lys Lys
                140                 145                 150

Leu Arg Arg Leu Tyr Leu Ser His Asn Gln Leu Ser Glu Ile Pro
                155                 160                 165

Leu Asn Leu Pro Lys Ser Leu Ala Glu Leu Arg Ile His Glu Asn
                170                 175                 180

Lys Val Lys Lys Ile Gln Lys Asp Thr Phe Lys Gly Met Asn Ala
                185                 190                 195

Leu His Val Leu Glu Met Ser Ala Asn Pro Leu Asp Asn Asn Gly
                200                 205                 210

Ile Glu Pro Gly Ala Phe Glu Gly Val Thr Val Phe His Ile Arg
                215                 220                 225

Ile Ala Glu Ala Lys Leu Thr Ser Val Pro Lys Gly Leu Pro Pro
                230                 235                 240

Thr Leu Leu Glu Leu His Leu Asp Tyr Asn Lys Ile Ser Thr Val
                245                 250                 255

Glu Leu Glu Asp Phe Lys Arg Tyr Lys Glu Leu Gln Arg Leu Gly
                260                 265                 270

Leu Gly Asn Asn Lys Ile Thr Asp Ile Glu Asn Gly Ser Leu Ala
                275                 280                 285

Asn Ile Pro Arg Val Arg Glu Ile His Leu Glu Asn Asn Lys Leu
                290                 295                 300

Lys Lys Ile Pro Ser Gly Leu Pro Glu Leu Lys Tyr Leu Gln Ile
                305                 310                 315

Ile Phe Leu His Ser Asn Ser Ile Ala Arg Val Gly Val Asn Asp
                320                 325                 330

Phe Cys Pro Thr Val Pro Lys Met Lys Lys Ser Leu Tyr Ser Ala
                335                 340                 345

Ile Ser Leu Phe Asn Asn Pro Val Lys Tyr Trp Glu Met Gln Pro
                350                 355                 360
```

```
Ala Thr Phe Arg Cys Val Leu Ser Arg Met Ser Val Gln Leu Gly
                365                 370                 375

Asn Phe Gly Met


<210> SEQ ID NO 7
<211> LENGTH: 1351
<212> TYPE: DNA
<213> ORGANISM: Homo sapiens

<400> SEQUENCE: 7

gagcgaggcc ggggactgaa ggtgtgggtg tcgagccctc tggcagaggg           50

ttaacctggg tcaaatgcac ggattctcac ctcgtacagt tacgctctcc          100

cgcggcacgt ccgcgaggac ttgaagtcct gagcgctcaa gtttgtccgt          150

aggtcgagag aaggccatgg aggtgccgcc accggcaccg cggagctttc          200

tctgtagagc attgtgccta tttccccgag tctttgctgc cgaagctgtg          250

actgccgatt cggaagtcct tgaggagcgt cagaagcggc ttccctacgt          300

cccagagccc tattacccgg aatctggatg ggaccgcctc cgggagctgt          350

ttggcaaaga tgaacagcag agaatttcaa aggaccttgc taatatctgt          400

aagacggcag ctacagcagg catcattggc tgggtgtatg gggaatacc           450

agcttttatt catgctaaac aacaatacat tgagcagagc caggcagaaa          500

tttatcataa ccggtttgat gctgtgcaat ctgcacatcg tgctgccaca          550

cgaggcttca ttcgttatgg ctggcgctgg ggttggagaa ctgcagtgtt          600

tgtgactata ttcaacacag tgaacactag tctgaatgta taccgaaata          650

aagatgcctt aagccatttt gtaattgcag gagctgtcac gggaagtctt          700

tttaggataa acgtaggcct gcgtggcctg gtggctggtg gcataattgg          750

agccttgctg ggcactcctg taggaggcct gctgatggca tttcagaagt          800

acgctggtga gactgttcag gaaagaaaac agaaggatcg aaaggcactc          850

catgagctaa aactggaaga gtggaaaggc agactacaag ttactgagca          900

cctccctgag aaaattgaaa gtagtttacg ggaagatgaa cctgagaatg          950

atgctaagaa aattgaagca ctgctaaacc ttcctagaaa cccttcagta         1000

atagataaac aagacaagga ctgaaagtgc tctgaacttg aaactcactg         1050

gagagctgaa gggagctgcc atgtccgatg aatgccaaca gacaggccac         1100

tctttggtca gcctgctgac aaatttaagt gctggtacct gtggtggcag         1150

tggcttgctc ttgtcttttt cttttctttt taactaagaa tggggctgtt         1200

gtactctcac tttacttatc cttaaattta aatacatact tatgtttgta         1250

ttaatctatc aatatatgca tacatggata tatccaccca cctagatttt         1300

aagcagtaaa taaaacattt cgcaaaagat taaagttgaa ttttacagtt         1350

t                                                                1351


<210> SEQ ID NO 8
<211> LENGTH: 285
<212> TYPE: PRT
<213> ORGANISM: Homo sapiens

<400> SEQUENCE: 8

Met Glu Val Pro Pro Pro Ala Pro Arg Ser Phe Leu Cys Arg Ala
  1               5                  10                  15
```

Leu Cys Leu Phe Pro Arg Val Phe Ala Ala Glu Ala Val Thr Ala
20 25 30

Asp Ser Glu Val Leu Glu Glu Arg Gln Lys Arg Leu Pro Tyr Val
35 40 45

Pro Glu Pro Tyr Tyr Pro Glu Ser Gly Trp Asp Arg Leu Arg Glu
50 55 60

Leu Phe Gly Lys Asp Glu Gln Gln Arg Ile Ser Lys Asp Leu Ala
65 70 75

Asn Ile Cys Lys Thr Ala Ala Thr Ala Gly Ile Ile Gly Trp Val
80 85 90

Tyr Gly Gly Ile Pro Ala Phe Ile His Ala Lys Gln Gln Tyr Ile
95 100 105

Glu Gln Ser Gln Ala Glu Ile Tyr His Asn Arg Phe Asp Ala Val
110 115 120

Gln Ser Ala His Arg Ala Ala Thr Arg Gly Phe Ile Arg Tyr Gly
125 130 135

Trp Arg Trp Gly Trp Arg Thr Ala Val Phe Val Thr Ile Phe Asn
140 145 150

Thr Val Asn Thr Ser Leu Asn Val Tyr Arg Asn Lys Asp Ala Leu
155 160 165

Ser His Phe Val Ile Ala Gly Ala Val Thr Gly Ser Leu Phe Arg
170 175 180

Ile Asn Val Gly Leu Arg Gly Leu Val Ala Gly Gly Ile Ile Gly
185 190 195

Ala Leu Leu Gly Thr Pro Val Gly Gly Leu Leu Met Ala Phe Gln
200 205 210

Lys Tyr Ala Gly Glu Thr Val Gln Glu Arg Lys Gln Lys Asp Arg
215 220 225

Lys Ala Leu His Glu Leu Lys Leu Glu Glu Trp Lys Gly Arg Leu
230 235 240

Gln Val Thr Glu His Leu Pro Glu Lys Ile Glu Ser Ser Leu Arg
245 250 255

Glu Asp Glu Pro Glu Asn Asp Ala Lys Lys Ile Glu Ala Leu Leu
260 265 270

Asn Leu Pro Arg Asn Pro Ser Val Ile Asp Lys Gln Asp Lys Asp
275 280 285

<210> SEQ ID NO 9
<211> LENGTH: 2906
<212> TYPE: DNA
<213> ORGANISM: Homo sapiens

<400> SEQUENCE: 9
ggggagagga attgaccatg taaaaggaga cttttttttt tggtggtggt 50
ggctgttggg tgccttgcaa aaatgaagga tgcaggacgc agctttctcc 100
tggaaccgaa cgcaatggat aaactgattg tgcaagagag aaggaagaac 150
gaagcttttt cttgtgagcc ctggatctta acacaaatgt gtatatgtgc 200
acacagggag cattcaagaa tgaaataaac cagagttaga cccgcggggg 250
ttggtgtgtt ctgacataaa taaataatct taaagcagct gttcccctcc 300 ccaccccccaa aaaaaaggat gattggaaat gaagaaccga ggattcacaa 350
agaaaaaagt atgttcattt ttctctataa aggagaaagt gagccaagga 400
gatatttttg gaatgaaaag tttggggctt ttttagtaaa gtaaagaact 450

```
ggtgtggtgg tgttttcctt tctttttgaa tttcccacaa gaggagagga      500
aattaataat acatctgcaa agaaatttca gagaagaaaa gttgaccgcg      550
gcagattgag gcattgattg ggggagagaa accagcagag cacagttgga      600
tttgtgccta tgttgactaa aattgacgga taattgcagt tggatttttc      650
ttcatcaacc tcctttttt taaattttta ttccttttgg tatcaagatc       700
atgcgttttc tcttgttctt aaccacctgg atttccatct ggatgttgct      750
gtgatcagtc tgaaatacaa ctgtttgaat tccagaagga ccaacaccag      800
ataaattatg aatgttgaac aagatgacct tacatccaca gcagataatg      850
ataggtccta ggtttaacag ggccctattt gaccccctgc ttgtggtgct      900
gctggctctt caacttcttg tggtggctgg tctggtgcgg gctcagacct      950
gcccttctgt gtgctcctgc agcaaccagt tcagcaaggt gatttgtgtt     1000
cggaaaaacc tgcgtgaggt tccggatggc atctccacca acacacggct     1050
gctgaacctc catgagaacc aaatccagat catcaaagtg aacagcttca     1100
agcacttgag gcacttggaa atcctacagt tgagtaggaa ccatatcaga     1150
accattgaaa ttggggcttt caatggtctg gcgaacctca acactctgga     1200
actctttgac aatcgtctta ctaccatccc gaatggagct tttgtatact     1250
tgtctaaact gaaggagctc tggttgcgaa acaaccccat tgaaagcatc     1300
ccttcttatg cttttaacag aattccttct ttgcgccgac tagacttagg     1350
ggaattgaaa agactttcat acatctcaga aggtgccttt gaaggtctgt     1400
ccaacttgag gtatttgaac cttgccatgt gcaaccttcg ggaaatccct     1450
aacctcacac cgctcataaa actagatgag ctggatcttt ctgggaatca     1500
tttatctgcc atcaggcctg gctctttcca gggtttgatg caccttcaaa     1550
aactgtggat gatacagtcc cagattcaag tgattgaacg gaatgccttt     1600
gacaaccttc agtcactagt ggagatcaac ctggcacaca ataatctaac     1650
attactgcct catgacctct tcactccctt gcatcatcta gagcggatac     1700
atttacatca caacccttgg aactgtaact gtgacatact gtggctcagc     1750
tggtggataa aagacatggc cccctcgaac acagcttgtt gtgcccggtg     1800
taacactcct cccaatctaa aggggaggta cattggagag ctcgaccaga     1850
attacttcac atgctatgct ccggtgattg tggagccccc tgcagacctc     1900
aatgtcactg aaggcatggc agctgagctg aaatgtcggg cctccacatc     1950
cctgacatct gtatcttgga ttactccaaa tggaacagtc atgacacatg     2000
gggcgtacaa agtgcggata gctgtgctca gtgatggtac gttaaatttc     2050
acaaatgtaa ctgtgcaaga tacaggcatg tacacatgta tggtgagtaa     2100
ttccgttggg aatactactg cttcagccac cctgaatgtt actgcagcaa     2150
ccactactcc tttctcttac ttttcaaccg tcacagtaga gactatggaa     2200
ccgtctcagg atgaggcacg gaccacagat aacaatgtgg gtcccactcc     2250
agtggtcgac tgggagacca ccaatgtgac cacctctctc acaccacaga     2300
gcacaaggtc gacagagaaa accttcacca tcccagtgac tgatataaac     2350
agtgggatcc caggaattga tgaggtcatg aagactacca aaatcatcat     2400
tgggtgtttt gtggccatca cactcatggc tgcagtgatg ctggtcattt     2450
```

-continued

```
tctacaagat gaggaagcag caccatcggc aaaaccatca cgccccaaca          2500

aggactgttg aaattattaa tgtggatgat gagattacgg gagacacacc          2550

catggaaagc cacctgccca tgcctgctat cgagcatgag cacctaaatc          2600

actataactc atacaaatct cccttcaacc acacaacaac agttaacaca          2650

ataaattcaa tacacagttc agtgcatgaa ccgttattga tccgaatgaa          2700

ctctaaagac aatgtacaag agactcaaat ctaaaacatt tacagagtta          2750

caaaaaacaa acaatcaaaa aaaaagacag tttattaaaa atgacacaaa          2800

tgactgggct aaatctactg tttcaaaaaa gtgtctttac aaaaaaacaa          2850

aaaagaaaag aaatttattt attaaaaatt ctattgtgat ctaaagcaga          2900

caaaaa                                                          2906
```

<210> SEQ ID NO 10
<211> LENGTH: 640
<212> TYPE: PRT
<213> ORGANISM: Homo sapiens

<400> SEQUENCE: 10

```
Met Leu Asn Lys Met Thr Leu His Pro Gln Gln Ile Met Ile Gly
  1               5                  10                  15

Pro Arg Phe Asn Arg Ala Leu Phe Asp Pro Leu Leu Val Val Leu
                 20                  25                  30

Leu Ala Leu Gln Leu Leu Val Val Ala Gly Leu Val Arg Ala Gln
                 35                  40                  45

Thr Cys Pro Ser Val Cys Ser Cys Ser Asn Gln Phe Ser Lys Val
                 50                  55                  60

Ile Cys Val Arg Lys Asn Leu Arg Glu Val Pro Asp Gly Ile Ser
                 65                  70                  75

Thr Asn Thr Arg Leu Leu Asn Leu His Glu Asn Gln Ile Gln Ile
                 80                  85                  90

Ile Lys Val Asn Ser Phe Lys His Leu Arg His Leu Glu Ile Leu
                 95                 100                 105

Gln Leu Ser Arg Asn His Ile Arg Thr Ile Glu Ile Gly Ala Phe
                110                 115                 120

Asn Gly Leu Ala Asn Leu Asn Thr Leu Glu Leu Phe Asp Asn Arg
                125                 130                 135

Leu Thr Thr Ile Pro Asn Gly Ala Phe Val Tyr Leu Ser Lys Leu
                140                 145                 150

Lys Glu Leu Trp Leu Arg Asn Asn Pro Ile Glu Ser Ile Pro Ser
                155                 160                 165

Tyr Ala Phe Asn Arg Ile Pro Ser Leu Arg Arg Leu Asp Leu Gly
                170                 175                 180

Glu Leu Lys Arg Leu Ser Tyr Ile Ser Glu Gly Ala Phe Glu Gly
                185                 190                 195

Leu Ser Asn Leu Arg Tyr Leu Asn Leu Ala Met Cys Asn Leu Arg
                200                 205                 210

Glu Ile Pro Asn Leu Thr Pro Leu Ile Lys Leu Asp Glu Leu Asp
                215                 220                 225

Leu Ser Gly Asn His Leu Ser Ala Ile Arg Pro Gly Ser Phe Gln
                230                 235                 240

Gly Leu Met His Leu Gln Lys Leu Trp Met Ile Gln Ser Gln Ile
                245                 250                 255
```

```
Gln Val Ile Glu Arg Asn Ala Phe Asp Asn Leu Gln Ser Leu Val
                260                 265                 270

Glu Ile Asn Leu Ala His Asn Asn Leu Thr Leu Leu Pro His Asp
                275                 280                 285

Leu Phe Thr Pro Leu His His Leu Glu Arg Ile His Leu His His
                290                 295                 300

Asn Pro Trp Asn Cys Asn Cys Asp Ile Leu Trp Leu Ser Trp Trp
                305                 310                 315

Ile Lys Asp Met Ala Pro Ser Asn Thr Ala Cys Cys Ala Arg Cys
                320                 325                 330

Asn Thr Pro Pro Asn Leu Lys Gly Arg Tyr Ile Gly Glu Leu Asp
                335                 340                 345

Gln Asn Tyr Phe Thr Cys Tyr Ala Pro Val Ile Val Glu Pro Pro
                350                 355                 360

Ala Asp Leu Asn Val Thr Glu Gly Met Ala Ala Glu Leu Lys Cys
                365                 370                 375

Arg Ala Ser Thr Ser Leu Thr Ser Val Ser Trp Ile Thr Pro Asn
                380                 385                 390

Gly Thr Val Met Thr His Gly Ala Tyr Lys Val Arg Ile Ala Val
                395                 400                 405

Leu Ser Asp Gly Thr Leu Asn Phe Thr Asn Val Thr Val Gln Asp
                410                 415                 420

Thr Gly Met Tyr Thr Cys Met Val Ser Asn Ser Val Gly Asn Thr
                425                 430                 435

Thr Ala Ser Ala Thr Leu Asn Val Thr Ala Ala Thr Thr Thr Pro
                440                 445                 450

Phe Ser Tyr Phe Ser Thr Val Thr Val Glu Thr Met Glu Pro Ser
                455                 460                 465

Gln Asp Glu Ala Arg Thr Thr Asp Asn Asn Val Gly Pro Thr Pro
                470                 475                 480

Val Val Asp Trp Glu Thr Thr Asn Val Thr Thr Ser Leu Thr Pro
                485                 490                 495

Gln Ser Thr Arg Ser Thr Glu Lys Thr Phe Thr Ile Pro Val Thr
                500                 505                 510

Asp Ile Asn Ser Gly Ile Pro Gly Ile Asp Glu Val Met Lys Thr
                515                 520                 525

Thr Lys Ile Ile Ile Gly Cys Phe Val Ala Ile Thr Leu Met Ala
                530                 535                 540

Ala Val Met Leu Val Ile Phe Tyr Lys Met Arg Lys Gln His His
                545                 550                 555

Arg Gln Asn His His Ala Pro Thr Arg Thr Val Glu Ile Ile Asn
                560                 565                 570

Val Asp Asp Glu Ile Thr Gly Asp Thr Pro Met Glu Ser His Leu
                575                 580                 585

Pro Met Pro Ala Ile Glu His Glu His Leu Asn His Tyr Asn Ser
                590                 595                 600

Tyr Lys Ser Pro Phe Asn His Thr Thr Thr Val Asn Thr Ile Asn
                605                 610                 615

Ser Ile His Ser Ser Val His Glu Pro Leu Leu Ile Arg Met Asn
                620                 625                 630

Ser Lys Asp Asn Val Gln Glu Thr Gln Ile
                635                 640
```

<210> SEQ ID NO 11

<211> LENGTH: 2331
<212> TYPE: DNA
<213> ORGANISM: Homo sapiens

<400> SEQUENCE: 11

```
cggacgcgtg ggctgggcgc tgcaaagcgt gtcccgccgg gtccccgagc      50

gtcccgcgcc ctcgccccgc catgctcctg ctgctggggc tgtgcctggg     100

gctgtccctg tgtgtggggt cgcaggaaga ggcgcagagc tggggccact     150

cttcggagca ggatggactc agggtcccga ggcaagtcag actgttgcag     200

aggctgaaaa ccaaaccttt gatgacagaa ttctcagtga agtctaccat     250

catttcccgt tatgccttca ctacggtttc ctgcagaatg ctgaacagag     300

cttctgaaga ccaggacatt gagttccaga tgcagattcc agctgcagct     350

ttcatcacca acttcactat gcttattgga gacaaggtgt atcagggcga     400

aattacagag agagaaaaga agagtggtga tagggtaaaa gagaaaagga     450

ataaaaccac agaagaaaat ggagagaagg ggactgaaat attcagagct     500

tctgcagtga ttcccagcaa ggacaaagcc gcctttttcc tgagttatga     550

ggagcttctg cagaggcgcc tgggcaagta cgagcacagc atcagcgtgc     600

ggccccagca gctgtccggg aggctgagcg tggacgtgaa tatcctggag     650

agcgcgggca tcgcatccct ggaggtgctg ccgcttcaca acagcaggca     700

gaggggcagt gggcgcgggg aagatgattc tgggcctccc ccatctactg     750

tcattaacca aaatgaaaca tttgccaaca taatttttaa acctactgta     800

gtacaacaag ccaggattgc ccagaatgga attttgggag actttatcat     850

tagatatgac gtcaatagag aacagagcat tggggacatc caggttctaa     900

atggctattt tgtgcactac tttgctccta aagaccttcc tcctttaccc     950

aagaatgtgg tattcgtgct tgacagcagt gcttctatgg tgggaaccaa    1000

actccggcag accaaggatg ccctcttcac aattctccat gacctccgac    1050

cccaggaccg tttcagtatc attggatttt ccaaccggat caaagtatgg    1100

aaggaccact tgatatcagt cactccagac agcatcaggg atgggaaagt    1150

gtacattcac catatgtcac ccactggagg cacagacatc aacggggccc    1200

tgcagagggc catcaggctc ctcaacaagt acgtggccca cagtggcatt    1250

ggagaccgga gcgtgtccct catcgtcttc ctgacggatg ggaagcccac    1300

ggtcggggag acgcacaccc tcaagatcct caacaacacc cgagaggccg    1350

cccgaggcca agtctgcatc ttcaccattg gcatcggcaa cgacgtggac    1400

ttcaggctgc tggagaaact gtcgctggag aactgtggcc tcacacggcg    1450

cgtgcacgag gaggaggacg caggctcgca gctcatcggg ttctacgatg    1500

aaatcaggac cccgctcctc tctgacatcc gcatcgatta tccccccagc    1550

tcagtggtgc aggccaccaa gaccctgttc cccaactact tcaacggctc    1600

ggagatcatc attgcgggga agctggtgga caggaagctg gatcacctgc    1650

acgtggaggt caccgccagc aacagtaaga aattcatcat cctgaagaca    1700

gatgtgcctg tgcggcctca gaaggcaggg aaagatgtca caggaagccc    1750

caggcctgga ggcgatggag agggggacac caaccacatc gagcgtctct    1800

ggagctacct caccacaaag gagctgctga gctcctggct gcaaagtgac    1850
```

```
gatgaaccgg agaaggagcg gctgcggcag cgggcccagg ccctggctgt      1900

gagctaccgc ttcctcactc ccttcacctc catgaagctg agggggccgg      1950

tcccacgcat ggatggcctg gaggaggccc acggcatgtc ggctgccatg      2000

ggacccgaac cggtggtgca gagcgtgcga ggagctggca cgcagccagg      2050

acctttgctc aagaagccaa actccgtcaa aaaaaaacaa aacaaaacaa      2100

aaaaaagaca tgggagagat ggtgtttttc ctctccacca cctggggata      2150

cgatgagaag atggccacct gcaagccagg aagacggccc tcaccagaca      2200

ccatgtctgc tggcaccttg atcttggacc tcccagcctc cagaactgtg      2250

agaaataaat gtgttttgtt taagctaaaa aaaaaaaaaa aaaaaaaaaa      2300

aaaaaaaaaa aaaaaaaaaa aaaaaaaaaa  a                         2331


<210> SEQ ID NO 12
<211> LENGTH: 694
<212> TYPE: PRT
<213> ORGANISM: Homo sapiens

<400> SEQUENCE: 12

Met Leu Leu Leu Leu Gly Leu Cys Leu Gly Leu Ser Leu Cys Val
  1               5                  10                  15

Gly Ser Gln Glu Glu Ala Gln Ser Trp Gly His Ser Ser Glu Gln
                 20                  25                  30

Asp Gly Leu Arg Val Pro Arg Gln Val Arg Leu Leu Gln Arg Leu
                 35                  40                  45

Lys Thr Lys Pro Leu Met Thr Glu Phe Ser Val Lys Ser Thr Ile
                 50                  55                  60

Ile Ser Arg Tyr Ala Phe Thr Thr Val Ser Cys Arg Met Leu Asn
                 65                  70                  75

Arg Ala Ser Glu Asp Gln Asp Ile Glu Phe Gln Met Gln Ile Pro
                 80                  85                  90

Ala Ala Ala Phe Ile Thr Asn Phe Thr Met Leu Ile Gly Asp Lys
                 95                 100                 105

Val Tyr Gln Gly Glu Ile Thr Glu Arg Glu Lys Lys Ser Gly Asp
                110                 115                 120

Arg Val Lys Glu Lys Arg Asn Lys Thr Thr Glu Glu Asn Gly Glu
                125                 130                 135

Lys Gly Thr Glu Ile Phe Arg Ala Ser Ala Val Ile Pro Ser Lys
                140                 145                 150

Asp Lys Ala Ala Phe Phe Leu Ser Tyr Glu Glu Leu Leu Gln Arg
                155                 160                 165

Arg Leu Gly Lys Tyr Glu His Ser Ile Ser Val Arg Pro Gln Gln
                170                 175                 180

Leu Ser Gly Arg Leu Ser Val Asp Val Asn Ile Leu Glu Ser Ala
                185                 190                 195

Gly Ile Ala Ser Leu Glu Val Leu Pro Leu His Asn Ser Arg Gln
                200                 205                 210

Arg Gly Ser Gly Arg Gly Glu Asp Asp Ser Gly Pro Pro Pro Ser
                215                 220                 225

Thr Val Ile Asn Gln Asn Glu Thr Phe Ala Asn Ile Ile Phe Lys
                230                 235                 240

Pro Thr Val Val Gln Gln Ala Arg Ile Ala Gln Asn Gly Ile Leu
                245                 250                 255

Gly Asp Phe Ile Ile Arg Tyr Asp Val Asn Arg Glu Gln Ser Ile
```

-continued

```
                260                 265                 270

Gly Asp Ile Gln Val Leu Asn Gly Tyr Phe Val His Tyr Phe Ala
                275                 280                 285

Pro Lys Asp Leu Pro Pro Leu Pro Lys Asn Val Val Phe Val Leu
                290                 295                 300

Asp Ser Ser Ala Ser Met Val Gly Thr Lys Leu Arg Gln Thr Lys
                305                 310                 315

Asp Ala Leu Phe Thr Ile Leu His Asp Leu Arg Pro Gln Asp Arg
                320                 325                 330

Phe Ser Ile Ile Gly Phe Ser Asn Arg Ile Lys Val Trp Lys Asp
                335                 340                 345

His Leu Ile Ser Val Thr Pro Asp Ser Ile Arg Asp Gly Lys Val
                350                 355                 360

Tyr Ile His His Met Ser Pro Thr Gly Gly Thr Asp Ile Asn Gly
                365                 370                 375

Ala Leu Gln Arg Ala Ile Arg Leu Leu Asn Lys Tyr Val Ala His
                380                 385                 390

Ser Gly Ile Gly Asp Arg Ser Val Ser Leu Ile Val Phe Leu Thr
                395                 400                 405

Asp Gly Lys Pro Thr Val Gly Glu Thr His Thr Leu Lys Ile Leu
                410                 415                 420

Asn Asn Thr Arg Glu Ala Ala Arg Gly Gln Val Cys Ile Phe Thr
                425                 430                 435

Ile Gly Ile Gly Asn Asp Val Asp Phe Arg Leu Leu Glu Lys Leu
                440                 445                 450

Ser Leu Glu Asn Cys Gly Leu Thr Arg Arg Val His Glu Glu Glu
                455                 460                 465

Asp Ala Gly Ser Gln Leu Ile Gly Phe Tyr Asp Glu Ile Arg Thr
                470                 475                 480

Pro Leu Leu Ser Asp Ile Arg Ile Asp Tyr Pro Pro Ser Ser Val
                485                 490                 495

Val Gln Ala Thr Lys Thr Leu Phe Pro Asn Tyr Phe Asn Gly Ser
                500                 505                 510

Glu Ile Ile Ile Ala Gly Lys Leu Val Asp Arg Lys Leu Asp His
                515                 520                 525

Leu His Val Glu Val Thr Ala Ser Asn Ser Lys Lys Phe Ile Ile
                530                 535                 540

Leu Lys Thr Asp Val Pro Val Arg Pro Gln Lys Ala Gly Lys Asp
                545                 550                 555

Val Thr Gly Ser Pro Arg Pro Gly Gly Asp Gly Glu Gly Asp Thr
                560                 565                 570

Asn His Ile Glu Arg Leu Trp Ser Tyr Leu Thr Thr Lys Glu Leu
                575                 580                 585

Leu Ser Ser Trp Leu Gln Ser Asp Asp Glu Pro Glu Lys Glu Arg
                590                 595                 600

Leu Arg Gln Arg Ala Gln Ala Leu Ala Val Ser Tyr Arg Phe Leu
                605                 610                 615

Thr Pro Phe Thr Ser Met Lys Leu Arg Gly Pro Val Pro Arg Met
                620                 625                 630

Asp Gly Leu Glu Glu Ala His Gly Met Ser Ala Ala Met Gly Pro
                635                 640                 645

Glu Pro Val Val Gln Ser Val Arg Gly Ala Gly Thr Gln Pro Gly
                650                 655                 660
```

```
Pro Leu Leu Lys Lys Pro Asn Ser Val Lys Lys Lys Gln Asn Lys
                665                 670                 675

Thr Lys Lys Arg His Gly Arg Asp Gly Val Phe Pro Leu His His
                680                 685                 690

Leu Gly Ile Arg


<210> SEQ ID NO 13
<211> LENGTH: 1413
<212> TYPE: DNA
<213> ORGANISM: Homo sapiens

<400> SEQUENCE: 13

cggacgcgtg gggtgcccga catggcgagt gtagtgctgc cgagcggatc              50

ccagtgtgcg gcggcagcgg cggcggcggc gcctcccggg ctccggcttc             100

tgctgttgct cttctccgcc gcggcactga tccccacagg tgatgggcag             150

aatctgttta cgaaagacgt gacagtgatc gagggagagg ttgcgaccat             200

cagttgccaa gtcaataaga gtgacgactc tgtgattcag ctactgaatc             250

ccaacaggca gaccatttat ttcagggact tcaggccttt gaaggacagc             300

aggtttcagt tgctgaattt ttctagcagt gaactcaaag tatcattgac             350

aaacgtctca atttctgatg aaggaagata cttttgccag ctctataccg             400

atcccccaca ggaaagttac accaccatca cagtcctggt cccaccacgt             450

aatctgatga tcgatatcca gaaagacact gcggtggaag gtgaggagat             500

tgaagtcaac tgcactgcta tggccagcaa gccagccacg actatcaggt             550

ggttcaaagg gaacacagag ctaaaaggca aatcggaggt ggaagagtgg             600

tcagacatgt acactgtgac cagtcagctg atgctgaagg tgcacaagga             650

ggacgatggg gtcccagtga tctgccaggt ggagcaccct gcggtcactg             700

gaaacctgca gacccagcgg tatctagaag tacagtataa gcctcaagtg             750

cacattcaga tgacttatcc tctacaaggc ttaacccggg aaggggacgc             800

gcttgagtta acatgtgaag ccatcgggaa gccccagcct gtgatggtaa             850

cttgggtgag agtcgatgat gaaatgcctc aacacgccgt actgtctggg             900

cccaacctgt tcatcaataa cctaaacaaa acagataatg gtacataccg             950

ctgtgaagct tcaaacatag tggggaaagc tcactcggat tatatgctgt            1000

atgtatacga tccccccaca actatccctc ctcccacaac aaccaccacc            1050

accaccacca ccaccaccac caccatcctt accatcatca cagattcccg            1100

agcaggtgaa gaaggctcga tcagggcagt ggatcatgcc gtgatcggtg            1150

gcgtcgtggc ggtggtggtg ttcgccatgc tgtgcttgct catcattctg            1200

gggcgctatt ttgccagaca taaaggtaca tacttcactc atgaagccaa            1250

aggagccgat gacgcagcag acgcagacac agctataatc aatgcagaag            1300

gaggacagaa caactccgaa gaaaagaaag agtacttcat ctagatcagc            1350

ctttttgttt caatgaggtg tccaactggc cctatttaga tgataaagag            1400

acagtgatat  tgg                                                   1413


<210> SEQ ID NO 14
<211> LENGTH: 440
<212> TYPE: PRT
<213> ORGANISM: Homo sapiens
```

-continued

<400> SEQUENCE: 14

```
Met Ala Ser Val Val Leu Pro Ser Gly Ser Gln Cys Ala Ala Ala
  1               5                  10                  15

Ala Ala Ala Ala Ala Pro Pro Gly Leu Arg Leu Leu Leu Leu Leu
                 20                  25                  30

Phe Ser Ala Ala Ala Leu Ile Pro Thr Gly Asp Gly Gln Asn Leu
                 35                  40                  45

Phe Thr Lys Asp Val Thr Val Ile Glu Gly Glu Val Ala Thr Ile
                 50                  55                  60

Ser Cys Gln Val Asn Lys Ser Asp Asp Ser Val Ile Gln Leu Leu
                 65                  70                  75

Asn Pro Asn Arg Gln Thr Ile Tyr Phe Arg Asp Phe Arg Pro Leu
                 80                  85                  90

Lys Asp Ser Arg Phe Gln Leu Leu Asn Phe Ser Ser Ser Glu Leu
                 95                 100                 105

Lys Val Ser Leu Thr Asn Val Ser Ile Ser Asp Glu Gly Arg Tyr
                110                 115                 120

Phe Cys Gln Leu Tyr Thr Asp Pro Pro Gln Glu Ser Tyr Thr Thr
                125                 130                 135

Ile Thr Val Leu Val Pro Pro Arg Asn Leu Met Ile Asp Ile Gln
                140                 145                 150

Lys Asp Thr Ala Val Glu Gly Glu Glu Ile Glu Val Asn Cys Thr
                155                 160                 165

Ala Met Ala Ser Lys Pro Ala Thr Thr Ile Arg Trp Phe Lys Gly
                170                 175                 180

Asn Thr Glu Leu Lys Gly Lys Ser Glu Val Glu Glu Trp Ser Asp
                185                 190                 195

Met Tyr Thr Val Thr Ser Gln Leu Met Leu Lys Val His Lys Glu
                200                 205                 210

Asp Asp Gly Val Pro Val Ile Cys Gln Val Glu His Pro Ala Val
                215                 220                 225

Thr Gly Asn Leu Gln Thr Gln Arg Tyr Leu Glu Val Gln Tyr Lys
                230                 235                 240

Pro Gln Val His Ile Gln Met Thr Tyr Pro Leu Gln Gly Leu Thr
                245                 250                 255

Arg Glu Gly Asp Ala Leu Glu Leu Thr Cys Glu Ala Ile Gly Lys
                260                 265                 270

Pro Gln Pro Val Met Val Thr Trp Val Arg Val Asp Asp Glu Met
                275                 280                 285

Pro Gln His Ala Val Leu Ser Gly Pro Asn Leu Phe Ile Asn Asn
                290                 295                 300

Leu Asn Lys Thr Asp Asn Gly Thr Tyr Arg Cys Glu Ala Ser Asn
                305                 310                 315

Ile Val Gly Lys Ala His Ser Asp Tyr Met Leu Tyr Val Tyr Asp
                320                 325                 330

Pro Pro Thr Thr Ile Pro Pro Pro Thr Thr Thr Thr Thr Thr Thr
                335                 340                 345

Thr Thr Thr Thr Thr Thr Ile Leu Thr Ile Ile Thr Asp Ser Arg
                350                 355                 360

Ala Gly Glu Glu Gly Ser Ile Arg Ala Val Asp His Ala Val Ile
                365                 370                 375

Gly Gly Val Val Ala Val Val Val Phe Ala Met Leu Cys Leu Leu
                380                 385                 390
```

-continued

```
Ile Ile Leu Gly Arg Tyr Phe Ala Arg His Lys Gly Thr Tyr Phe
                395                 400                 405

Thr His Glu Ala Lys Gly Ala Asp Asp Ala Ala Asp Ala Asp Thr
                410                 415                 420

Ala Ile Ile Asn Ala Glu Gly Gly Gln Asn Asn Ser Glu Glu Lys
                425                 430                 435

Lys Glu Tyr Phe Ile
                440


<210> SEQ ID NO 15
<211> LENGTH: 2137
<212> TYPE: DNA
<213> ORGANISM: Homo sapiens

<400> SEQUENCE: 15

gctcccagcc aagaacctcg gggccgctgc gcggtgggga ggagttcccc            50

gaaacccggc cgctaagcga ggcctcctcc tcccgcagat ccgaacggcc           100

tgggcggggt caccccggct gggacaagaa gccgccgcct gcctgcccgg           150

gcccggggag ggggctgggg ctggggccgg aggcggggtg tgagtgggtg           200

tgtgcggggg gcggaggctt gatgcaatcc cgataagaaa tgctcgggtg           250

tcttgggcac ctacccgtgg ggcccgtaag gcgctactat ataaggctgc           300

cggcccggag ccgccgcgcc gtcagagcag gagcgctgcg tccaggatct           350

agggccacga ccatcccaac ccggcactca cagccccgca gcgcatcccg           400

gtcgccgccc agcctcccgc acccccatcg ccggagctgc gccgagagcc           450

ccagggaggt gccatgcgga gcgggtgtgt ggtggtccac gtatggatcc           500

tggccggcct ctggctggcc gtggccgggc gcccccctcgc cttctcggac           550

gcggggcccc acgtgcacta cggctggggc gaccccatcc gcctgcggca           600

cctgtacacc tccggccccc acgggctctc cagctgcttc ctgcgcatcc           650

gtgccgacgg cgtcgtggac tgcgcgcggg gccagagcgc gcacagtttg           700

ctggagatca aggcagtcgc tctgcggacc gtggccatca agggcgtgca           750

cagcgtgcgg tacctctgca tgggcgccga cggcaagatg caggggctgc           800

ttcagtactc ggaggaagac tgtgctttcg aggaggagat ccgcccagat           850

ggctacaatg tgtaccgatc cgagaagcac cgcctcccgg tctccctgag           900

cagtgccaaa cagcggcagc tgtacaagaa cagaggcttt cttccactct           950

ctcatttcct gcccatgctg cccatggtcc cagaggagcc tgaggacctc          1000

aggggccact tggaatctga catgttctct tcgcccctgg agaccgacag          1050

catggaccca tttgggcttg tcaccggact ggaggccgtg aggagtccca          1100

gctttgagaa gtaactgaga ccatgcccgg gcctcttcac tgctgccagg          1150

ggctgtggta cctgcagcgt gggggacgtg cttctacaag aacagtcctg          1200

agtccacgtt ctgtttagct ttaggaagaa acatctagaa gttgtacata          1250

ttcagagttt tccattggca gtgccagttt ctagccaata gacttgtctg          1300

atcataacat tgtaagcctg tagcttgccc agctgctgcc tgggccccca          1350

ttctgctccc tcgaggttgc tggacaagct gctgcactgt ctcagttctg          1400

cttgaatacc tccatcgatg gggaactcac ttcctttgga aaaattctta          1450

tgtcaagctg aaattctcta attttttctc atcacttccc caggagcagc          1500
```

```
cagaagacag gcagtagttt taatttcagg aacaggtgat ccactctgta           1550

aaacagcagg taaatttcac tcaaccccat gtgggaattg atctatatct           1600

ctacttccag ggaccatttg cccttcccaa atccctccag gccagaactg           1650

actggagcag gcatggccca ccaggcttca ggagtagggg aagcctggag           1700

ccccactcca gccctgggac aacttgagaa ttccccctga ggccagttct           1750

gtcatggatg ctgtcctgag aataacttgc tgtcccggtg tcacctgctt           1800

ccatctccca gcccaccagc cctctgccca cctcacatgc ctccccatgg           1850

attggggcct cccaggcccc ccaccttatg tcaacctgca cttcttgttc           1900

aaaaatcagg aaaagaaaag atttgaagac cccaagtctt gtcaataact           1950

tgctgtgtgg aagcagcggg ggaagaccta gaaccctttc cccagcactt           2000

ggttttccaa catgatattt atgagtaatt tattttgata tgtacatctc           2050

ttattttctt acattattta tgcccccaaa ttatatttat gtatgtaagt           2100

gaggtttgtt ttgtatatta aaatggagtt  tgtttgt                        2137
```

<210> SEQ ID NO 16
<211> LENGTH: 216
<212> TYPE: PRT
<213> ORGANISM: Homo sapiens

<400> SEQUENCE: 16

```
Met Arg Ser Gly Cys Val Val Val His Val Trp Ile Leu Ala Gly
  1               5                  10                  15

Leu Trp Leu Ala Val Ala Gly Arg Pro Leu Ala Phe Ser Asp Ala
                 20                  25                  30

Gly Pro His Val His Tyr Gly Trp Gly Asp Pro Ile Arg Leu Arg
                 35                  40                  45

His Leu Tyr Thr Ser Gly Pro His Gly Leu Ser Ser Cys Phe Leu
                 50                  55                  60

Arg Ile Arg Ala Asp Gly Val Val Asp Cys Ala Arg Gly Gln Ser
                 65                  70                  75

Ala His Ser Leu Leu Glu Ile Lys Ala Val Ala Leu Arg Thr Val
                 80                  85                  90

Ala Ile Lys Gly Val His Ser Val Arg Tyr Leu Cys Met Gly Ala
                 95                 100                 105

Asp Gly Lys Met Gln Gly Leu Leu Gln Tyr Ser Glu Glu Asp Cys
                110                 115                 120

Ala Phe Glu Glu Glu Ile Arg Pro Asp Gly Tyr Asn Val Tyr Arg
                125                 130                 135

Ser Glu Lys His Arg Leu Pro Val Ser Leu Ser Ser Ala Lys Gln
                140                 145                 150

Arg Gln Leu Tyr Lys Asn Arg Gly Phe Leu Pro Leu Ser His Phe
                155                 160                 165

Leu Pro Met Leu Pro Met Val Pro Glu Glu Pro Glu Asp Leu Arg
                170                 175                 180

Gly His Leu Glu Ser Asp Met Phe Ser Ser Pro Leu Glu Thr Asp
                185                 190                 195

Ser Met Asp Pro Phe Gly Leu Val Thr Gly Leu Glu Ala Val Arg
                200                 205                 210

Ser Pro Ser Phe Glu Lys
                215
```

<210> SEQ ID NO 17
<211> LENGTH: 3038
<212> TYPE: DNA
<213> ORGANISM: Homo sapiens

<400> SEQUENCE: 17
ggcgcctggt tctgcgcgta ctggctgtac ggagcaggag caagaggtcg 50
ccgccagcct ccgccgccga gcctcgttcg tgtccccgcc cctcgctcct 100
gcagctactg ctcagaaacg ctggggcgcc caccctggca gactaacgaa 150
gcagctccct tcccacccca actgcaggtc taattttgga cgctttgcct 200
gccatttctt ccaggttgag ggagccgcag aggcggaggc tcgcgtattc 250
ctgcagtcag cacccacgtc gcccccggac gctcggtgct caggcccttc 300
gcgagcgggg ctctccgtct gcggtccctt gtgaaggctc tgggcggctg 350
cagaggccgg ccgtccggtt tggctcacct ctcccaggaa acttcacact 400
ggagagccaa aaggagtgga agagcctgtc ttggagattt tcctggggaa 450
atcctgaggt cattcattat gaagtgtacc gcgcgggagt ggctcagagt 500
aaccacagtg ctgttcatgg ctagagcaat tccagccatg gtggttccca 550
atgccacttt attggagaaa cttttggaaa aatacatgga tgaggatggt 600
gagtggtgga tagccaaaca acgagggaaa agggccatca cagacaatga 650
catgcagagt attttggacc ttcataataa attacgaagt caggtgtatc 700
caacagcctc taatatggag tatatgacat gggatgtaga gctggaaaga 750
tctgcagaat cctgggctga aagttgcttg tgggaacatg gacctgcaag 800
cttgcttcca tcaattggac agaatttggg agcacactgg ggaagatata 850
ggcccccgac gtttcatgta caatcgtggt atgatgaagt gaaagacttt 900
agctacccat atgaacatga atgcaaccca tattgtccat tcaggtgttc 950
tggccctgta tgtacacatt atacacaggt cgtgtgggca actagtaaca 1000
gaatcggttg tgccattaat ttgtgtcata acatgaacat ctgggggcag 1050
atatggccca aagctgtcta cctggtgtgc aattactccc caaagggaaa 1100
ctggtggggc catgcccctt acaaacatgg gcggccctgt tctgcttgcc 1150
cacctagttt tggagggggc tgtagagaaa atctgtgcta caaagaaggg 1200
tcagacaggt attatccccc tcgagaagag gaaacaaatg aaatagaacg 1250
acagcagtca caagtccatg acacccatgt ccggacaaga tcagatgata 1300
gtagcagaaa tgaagtcata agcgcacagc aaatgtccca aattgtttct 1350
tgtgaagtaa gattaagaga tcagtgcaaa ggaacaacct gcaataggta 1400
cgaatgtcct gctggctgtt tggatagtaa agctaaagtt attggcagtg 1450
tacattatga aatgcaatcc agcatctgta gagctgcaat tcattatggt 1500
ataatagaca atgatggtgg ctgggtagat atcactagac aaggaagaaa 1550
gcattatttc atcaagtcca atagaaatgg tattcaaaca attggcaaat 1600
atcagtctgc taattccttc acagtctcta aagtaacagt tcaggctgtg 1650
acttgtgaaa caactgtgga acagctctgt ccatttcata agcctgcttc 1700
acattgccca agagtatact gtcctcgtaa ctgtatgcaa gcaaatccac 1750
attatgctcg tgtaattgga actcgagttt attctgatct gtccagtatc 1800
tgcagagcag cagtacatgc tggagtggtt cgaaatcacg gtggttatgt 1850
tgatgtaatg cctgtggaca aaagaaagac ctacattgct tcttttcaga 1900
atggaatctt ctcagaaagt ttacagaatc ctccaggagg aaaggcattc 1950
agagtgtttg ctgttgtgtg aaactgaata cttggaagag gaccataaag 2000
actattccaa atgcaatatt tctgaatttt gtataaaact gtaacattac 2050
tgtacagagt acatcaacta ttttcagccc aaaaaggtgc caaatgcata 2100
taaatcttga taaacaaagt ctataaaata aaacatggga cattagcttt 2150
gggaaaagta atgaaaatat aatggtttta gaaatcctgt gttaaatatt 2200
gctatatttt cttagcagtt atttctacag ttaattacat agtcatgatt 2250
gttctacgtt tcatatatta tatggtgctt tgtatatgcc actaataaaa 2300
tgaatctaaa cattgaatgt gaatggccct cagaaaatca tctagtgcat 2350
ttaaaaataa tcgactctaa aactgaaaga aaccttatca cattttcccc 2400
agttcaatgc tatgccatta ccaactccaa ataatctcaa ataattttcc 2450
acttaataac tgtaaagttt ttttctgtta atttaggcat atagaatatt 2500
aaattctgat attgcacttc ttattttata taaaataatc ctttaatatc 2550
caaatgaatc tgttaaaatg tttgattcct tgggaatggc cttaaaaata 2600
aatgtaataa agtcagagtg gtggtatgaa aacattccta gtgatcatgt 2650
agtaaatgta gggttaagca tggacagcca gagctttcta tgtactgtta 2700
aaattgaggt cacatatttt cttttgtatc ctggcaaata ctcctgcagg 2750
ccaggaagta taatagcaaa aagttgaaca aagatgaact aatgtattac 2800
attaccattg ccactgattt tttttaaatg gtaaatgacc ttgtatataa 2850
atattgccat atcatggtac ctataatggt gatatatttg tttctatgaa 2900
aaatgtattg tgctttgata ctaaaaatct gtaaaatgtt agttttggta 2950 atttttttc tgctggtgga tttacatatt aaattttttc tgctggtgga 3000
taaacattaa aattaatcat gtttcaaaaa aaaaaaaa 3038

<210> SEQ ID NO 18
<211> LENGTH: 500
<212> TYPE: PRT
<213> ORGANISM: Homo sapiens

<400> SEQUENCE: 18

Met Lys Cys Thr Ala Arg Glu Trp Leu Arg Val Thr Thr Val Leu
1 5 10 15

Phe Met Ala Arg Ala Ile Pro Ala Met Val Val Pro Asn Ala Thr
20 25 30

Leu Leu Glu Lys Leu Leu Glu Lys Tyr Met Asp Glu Asp Gly Glu
35 40 45

Trp Trp Ile Ala Lys Gln Arg Gly Lys Arg Ala Ile Thr Asp Asn
50 55 60

Asp Met Gln Ser Ile Leu Asp Leu His Asn Lys Leu Arg Ser Gln
65 70 75

Val Tyr Pro Thr Ala Ser Asn Met Glu Tyr Met Thr Trp Asp Val
80 85 90

Glu Leu Glu Arg Ser Ala Glu Ser Trp Ala Glu Ser Cys Leu Trp
95 100 105

Glu His Gly Pro Ala Ser Leu Leu Pro Ser Ile Gly Gln Asn Leu
110 115 120

-continued

```
Gly Ala His Trp Gly Arg Tyr Arg Pro Pro Thr Phe His Val Gln
                125                 130                 135

Ser Trp Tyr Asp Glu Val Lys Asp Phe Ser Tyr Pro Tyr Glu His
                140                 145                 150

Glu Cys Asn Pro Tyr Cys Pro Phe Arg Cys Ser Gly Pro Val Cys
                155                 160                 165

Thr His Tyr Thr Gln Val Val Trp Ala Thr Ser Asn Arg Ile Gly
                170                 175                 180

Cys Ala Ile Asn Leu Cys His Asn Met Asn Ile Trp Gly Gln Ile
                185                 190                 195

Trp Pro Lys Ala Val Tyr Leu Val Cys Asn Tyr Ser Pro Lys Gly
                200                 205                 210

Asn Trp Trp Gly His Ala Pro Tyr Lys His Gly Arg Pro Cys Ser
                215                 220                 225

Ala Cys Pro Pro Ser Phe Gly Gly Gly Cys Arg Glu Asn Leu Cys
                230                 235                 240

Tyr Lys Glu Gly Ser Asp Arg Tyr Tyr Pro Pro Arg Glu Glu Glu
                245                 250                 255

Thr Asn Glu Ile Glu Arg Gln Gln Ser Gln Val His Asp Thr His
                260                 265                 270

Val Arg Thr Arg Ser Asp Asp Ser Ser Arg Asn Glu Val Ile Ser
                275                 280                 285

Ala Gln Gln Met Ser Gln Ile Val Ser Cys Glu Val Arg Leu Arg
                290                 295                 300

Asp Gln Cys Lys Gly Thr Thr Cys Asn Arg Tyr Glu Cys Pro Ala
                305                 310                 315

Gly Cys Leu Asp Ser Lys Ala Lys Val Ile Gly Ser Val His Tyr
                320                 325                 330

Glu Met Gln Ser Ser Ile Cys Arg Ala Ala Ile His Tyr Gly Ile
                335                 340                 345

Ile Asp Asn Asp Gly Gly Trp Val Asp Ile Thr Arg Gln Gly Arg
                350                 355                 360

Lys His Tyr Phe Ile Lys Ser Asn Arg Asn Gly Ile Gln Thr Ile
                365                 370                 375

Gly Lys Tyr Gln Ser Ala Asn Ser Phe Thr Val Ser Lys Val Thr
                380                 385                 390

Val Gln Ala Val Thr Cys Glu Thr Thr Val Glu Gln Leu Cys Pro
                395                 400                 405

Phe His Lys Pro Ala Ser His Cys Pro Arg Val Tyr Cys Pro Arg
                410                 415                 420

Asn Cys Met Gln Ala Asn Pro His Tyr Ala Arg Val Ile Gly Thr
                425                 430                 435

Arg Val Tyr Ser Asp Leu Ser Ser Ile Cys Arg Ala Ala Val His
                440                 445                 450

Ala Gly Val Val Arg Asn His Gly Gly Tyr Val Asp Val Met Pro
                455                 460                 465

Val Asp Lys Arg Lys Thr Tyr Ile Ala Ser Phe Gln Asn Gly Ile
                470                 475                 480

Phe Ser Glu Ser Leu Gln Asn Pro Pro Gly Gly Lys Ala Phe Arg
                485                 490                 495

Val Phe Ala Val Val
                500
```

<210> SEQ ID NO 19
<211> LENGTH: 647
<212> TYPE: DNA
<213> ORGANISM: Homo sapiens

<400> SEQUENCE: 19
cccacgcgtc cgaaggcaga caaaggttca tttgtaaaga agctccttcc 50
agcacctcct ctcttctcct tttgcccaaa ctcacccagt gagtgtgagc 100
atttaagaag catcctctgc caagaccaaa aggaaagaag aaaaagggcc 150
aaaagccaaa atgaaactga tggtacttgt tttcaccatt gggctaactt 200
tgctgctagg agttcaagcc atgcctgcaa atcgcctctc ttgctacaga 250
aagatactaa aagatcacaa ctgtcacaac cttccggaag gagtagctga 300
cctgacacag attgatgtca atgtccagga tcatttctgg gatgggaagg 350
gatgtgagat gatctgttac tgcaacttca gcgaattgct ctgctgccca 400
aaagacgttt tctttggacc aaagatctct ttcgtgattc cttgcaacaa 450
tcaatgagaa tcttcatgta ttctggagaa caccattcct gatttcccac 500
aaactgcact acatcagtat aactgcattt ctagtttcta tatagtgcaa 550
tagagcatag attctataaa ttcttacttg tctaagacaa gtaaatctgt 600
gttaaacaag tagtaataaa agttaattca atctaaaaaa aaaaaaa 647

<210> SEQ ID NO 20
<211> LENGTH: 98
<212> TYPE: PRT
<213> ORGANISM: Homo sapiens

<400> SEQUENCE: 20

Met Lys Leu Met Val Leu Val Phe Thr Ile Gly Leu Thr Leu Leu
1               5                   10                  15

Leu Gly Val Gln Ala Met Pro Ala Asn Arg Leu Ser Cys Tyr Arg
                20                  25                  30

Lys Ile Leu Lys Asp His Asn Cys His Asn Leu Pro Glu Gly Val
                35                  40                  45

Ala Asp Leu Thr Gln Ile Asp Val Asn Val Gln Asp His Phe Trp
                50                  55                  60

Asp Gly Lys Gly Cys Glu Met Ile Cys Tyr Cys Asn Phe Ser Glu
                65                  70                  75

Leu Leu Cys Cys Pro Lys Asp Val Phe Phe Gly Pro Lys Ile Ser
                80                  85                  90

Phe Val Ile Pro Cys Asn Asn Gln
                95

<210> SEQ ID NO 21
<211> LENGTH: 2651
<212> TYPE: DNA
<213> ORGANISM: Homo sapiens

<400> SEQUENCE: 21
ggcacagccg cgcggcggag ggcagagtca gccgagccga gtccagccgg 50
acgagcggac cagcgcaggg cagcccaagc agcgcgcagc gaacgcccgc 100
cgccgcccac accctctgcg gtccccgcgg cgcctgccac ccttccctcc 150
ttccccgcgt ccccgcctcg ccggccagtc agcttgccgg gttcgctgcc 200
ccgcgaaacc ccgaggtcac cagcccgcgc ctctgcttcc ctgggccgcg 250

-continued

```
cgccgcctcc acgccctcct tctcccctgg cccggcgcct ggcaccgggg 300
accgttgcct gacgcgaggc ccagctctac ttttcgcccc gcgtctcctc 350
cgcctgctcg cctcttccac caactccaac tccttctccc tccagctcca 400
ctcgctagtc cccgactccg ccagccctcg gcccgctgcc gtagcgccgc 450
ttcccgtccg gtcccaaagg tgggaacgcg tccgccccgg cccgcaccat 500
ggcacggttc ggcttgcccg cgcttctctg caccctggca gtgctcagcg 550
ccgcgctgct ggctgccgag ctcaagtcga aaagttgctc ggaagtgcga 600
cgtctttacg tgtccaaagg cttcaacaag aacgatgccc ccctccacga 650
gatcaacggt gatcatttga agatctgtcc ccagggttct acctgctgct 700
ctcaagagat ggaggagaag tacagcctgc aaagtaaaga tgatttcaaa 750
agtgtggtca gcgaacagtg caatcatttg caagctgtct ttgcttcacg 800
ttacaagaag tttgatgaat tcttcaaaga actacttgaa aatgcagaga 850
aatccctgaa tgatatgttt gtgaagacat atggccattt atacatgcaa 900
aattctgagc tatttaaaga tctcttcgta gagttgaaac gttactacgt 950
ggtgggaaat gtgaacctgg aagaaatgct aaatgacttc tgggctcgcc 1000
tcctggagcg gatgttccgc ctggtgaact cccagtacca ctttacagat 1050
gagtatctgg aatgtgtgag caagtatacg gagcagctga agcccttcgg 1100
agatgtccct cgcaaattga agctccaggt tactcgtgct tttgtagcag 1150
cccgtacttt cgctcaaggc ttagcggttg cgggagatgt cgtgagcaag 1200
gtctccgtgg taaaccccac agcccagtgt acccatgccc tgttgaagat 1250
gatctactgc tcccactgcc ggggtctcgt gactgtgaag ccatgttaca 1300
actactgctc aaacatcatg agaggctgtt tggccaacca aggggatctc 1350
gattttgaat ggaacaattt catagatgct atgctgatgg tggcagagag 1400
gctagagggt cctttcaaca ttgaatcggt catggatccc atcgatgtga 1450
agatttctga tgctattatg aacatgcagg ataatagtgt tcaagtgtct 1500
cagaaggttt tccagggatg tggacccccc aagcccctcc cagctggacg 1550
aatttctcgt tccatctctg aaagtgcctt cagtgctcgc ttcagaccac 1600
atcaccccga ggaacgccca accacagcag ctggcactag tttggaccga 1650
ctggttactg atgtcaagga gaaactgaaa caggccaaga aattctggtc 1700
ctcccttccg agcaacgttt gcaacgatga gaggatggct gcaggaaacg 1750
gcaatgagga tgactgttgg aatgggaaag gcaaaagcag gtacctgttt 1800
gcagtgacag gaaatggatt agccaaccag ggcaacaacc cagaggtcca 1850
ggttgacacc agcaaaccag acatactgat ccttcgtcaa atcatggctc 1900
ttcgagtgat gaccagcaag atgaagaatg catacaatgg gaacgacgtg 1950
gacttctttg atatcagtga tgaaagtagt ggagaaggaa gtggaagtgg 2000
ctgtgagtat cagcagtgcc cttcagagtt tgactacaat gccactgacc 2050
atgctgggaa gagtgccaat gagaaagccg acagtgctgg tgtccgtcct 2100
ggggcacagg cctacctcct cactgtcttc tgcatcttgt tcctggttat 2150
gcagagagag tggagataat tctcaaactc tgagaaaaag tgttcatcaa 2200
aaagttaaaa ggcaccagtt atcacttttc taccatccta gtgactttgc 2250
```

-continued

```
tttttaaatg aatggacaac aatgtacagt ttttactatg tggccactgg              2300

tttaagaagt gctgactttg ttttctcatt cagttttggg aggaaaaggg              2350

actgtgcatt gagttggttc ctgctccccc aaaccatgtt aaacgtggct              2400

aacagtgtag gtacagaact atagttagtt gtgcatttgt gattttatca              2450

ctctattatt tgtttgtatg tttttttctc atttcgtttg tgggtttttt              2500

tttccaactg tgatctcgcc ttgtttctta caagcaaacc agggtccctt              2550

cttggcacgt aacatgtacg tatttctgaa atattaaata gctgtacaga              2600

agcaggtttt atttatcatg ttatcttatt aaaagaaaaa gcccaaaaag              2650

c                                                                   2651
```

<210> SEQ ID NO 22
<211> LENGTH: 556
<212> TYPE: PRT
<213> ORGANISM: Homo sapiens

<400> SEQUENCE: 22

```
Met Ala Arg Phe Gly Leu Pro Ala Leu Leu Cys Thr Leu Ala Val
 1               5                  10                  15

Leu Ser Ala Ala Leu Leu Ala Ala Glu Leu Lys Ser Lys Ser Cys
                20                  25                  30

Ser Glu Val Arg Arg Leu Tyr Val Ser Lys Gly Phe Asn Lys Asn
                35                  40                  45

Asp Ala Pro Leu His Glu Ile Asn Gly Asp His Leu Lys Ile Cys
                50                  55                  60

Pro Gln Gly Ser Thr Cys Cys Ser Gln Glu Met Glu Glu Lys Tyr
                65                  70                  75

Ser Leu Gln Ser Lys Asp Asp Phe Lys Ser Val Val Ser Glu Gln
                80                  85                  90

Cys Asn His Leu Gln Ala Val Phe Ala Ser Arg Tyr Lys Lys Phe
                95                 100                 105

Asp Glu Phe Phe Lys Glu Leu Leu Glu Asn Ala Glu Lys Ser Leu
               110                 115                 120

Asn Asp Met Phe Val Lys Thr Tyr Gly His Leu Tyr Met Gln Asn
               125                 130                 135

Ser Glu Leu Phe Lys Asp Leu Phe Val Glu Leu Lys Arg Tyr Tyr
               140                 145                 150

Val Val Gly Asn Val Asn Leu Glu Glu Met Leu Asn Asp Phe Trp
               155                 160                 165

Ala Arg Leu Leu Glu Arg Met Phe Arg Leu Val Asn Ser Gln Tyr
               170                 175                 180

His Phe Thr Asp Glu Tyr Leu Glu Cys Val Ser Lys Tyr Thr Glu
               185                 190                 195

Gln Leu Lys Pro Phe Gly Asp Val Pro Arg Lys Leu Lys Leu Gln
               200                 205                 210

Val Thr Arg Ala Phe Val Ala Ala Arg Thr Phe Ala Gln Gly Leu
               215                 220                 225

Ala Val Ala Gly Asp Val Val Ser Lys Val Ser Val Val Asn Pro
               230                 235                 240

Thr Ala Gln Cys Thr His Ala Leu Leu Lys Met Ile Tyr Cys Ser
               245                 250                 255

His Cys Arg Gly Leu Val Thr Val Lys Pro Cys Tyr Asn Tyr Cys
               260                 265                 270
```

-continued

Ser Asn Ile Met Arg Gly Cys Leu Ala Asn Gln Gly Asp Leu Asp
275 280 285

Phe Glu Trp Asn Asn Phe Ile Asp Ala Met Leu Met Val Ala Glu
290 295 300

Arg Leu Glu Gly Pro Phe Asn Ile Glu Ser Val Met Asp Pro Ile
305 310 315

Asp Val Lys Ile Ser Asp Ala Ile Met Asn Met Gln Asp Asn Ser
320 325 330

Val Gln Val Ser Gln Lys Val Phe Gln Gly Cys Gly Pro Pro Lys
335 340 345

Pro Leu Pro Ala Gly Arg Ile Ser Arg Ser Ile Ser Glu Ser Ala
350 355 360

Phe Ser Ala Arg Phe Arg Pro His His Pro Glu Glu Arg Pro Thr
365 370 375

Thr Ala Ala Gly Thr Ser Leu Asp Arg Leu Val Thr Asp Val Lys
380 385 390

Glu Lys Leu Lys Gln Ala Lys Lys Phe Trp Ser Ser Leu Pro Ser
395 400 405

Asn Val Cys Asn Asp Glu Arg Met Ala Ala Gly Asn Gly Asn Glu
410 415 420

Asp Asp Cys Trp Asn Gly Lys Gly Lys Ser Arg Tyr Leu Phe Ala
425 430 435

Val Thr Gly Asn Gly Leu Ala Asn Gln Gly Asn Asn Pro Glu Val
440 445 450

Gln Val Asp Thr Ser Lys Pro Asp Ile Leu Ile Leu Arg Gln Ile
455 460 465

Met Ala Leu Arg Val Met Thr Ser Lys Met Lys Asn Ala Tyr Asn
470 475 480

Gly Asn Asp Val Asp Phe Phe Asp Ile Ser Asp Glu Ser Ser Gly
485 490 495

Glu Gly Ser Gly Ser Gly Cys Glu Tyr Gln Gln Cys Pro Ser Glu
500 505 510

Phe Asp Tyr Asn Ala Thr Asp His Ala Gly Lys Ser Ala Asn Glu
515 520 525

Lys Ala Asp Ser Ala Gly Val Arg Pro Gly Ala Gln Ala Tyr Leu
530 535 540

Leu Thr Val Phe Cys Ile Leu Phe Leu Val Met Gln Arg Glu Trp
545 550 555

Arg

<210> SEQ ID NO 23
<211> LENGTH: 1818
<212> TYPE: DNA
<213> ORGANISM: Homo sapiens

<400> SEQUENCE: 23
agacagtacc tcctccctag gactacacaa ggactgaacc agaaggaaga 50
ggacagagca aagccatgaa catcatccta gaaatccttc tgcttctgat 100
caccatcatc tactcctact tggagtcgtt ggtgaagttt ttcattcctc 150
agaggagaaa atctgtggct ggggagattg ttctcattac tggagctggg 200
catggaatag gcaggcagac tacttatgaa tttgcaaaac gacagagcat 250
attggttctg tgggatatta ataagcgcgg tgtggaggaa actgcagctg 300
agtgccgaaa actaggcgtc actgcgcatg cgtatgtggt agactgcagc 350

```
aacagagaag agatctatcg ctctctaaat caggtgaaga aagaagtggg      400
tgatgtaaca atcgtggtga ataatgctgg gacagtatat ccagccgatc      450
ttctcagcac caaggatgaa gagattacca agacatttga ggtcaacatc      500
ctaggacatt tttggatcac aaaagcactt cttccatcga tgatggagag      550
aaatcatggc cacatcgtca cagtggcttc agtgtgcggc cacgaaggga      600
ttccttacct catcccatat tgttccagca aatttgccgc tgttggcttt      650
cacagaggtc tgacatcaga acttcaggcc ttgggaaaaa ctggtatcaa      700
aacctcatgt ctctgcccag tttttgtgaa tactgggttc accaaaaatc      750
caagcacaag attatggcct gtattggaga cagatgaagt cgtaagaagt      800
ctgatagatg gaatacttac caataagaaa atgatttttg ttccatcgta      850
tatcaatatc tttctgagac tacagaagtt tcttcctgaa cgcgcctcag      900
cgattttaaa tcgtatgcag aatattcaat ttgaagcagt ggttggccac      950
aaaatcaaaa tgaaatgaat aaataagctc cagccagaga tgtatgcatg     1000
ataatgatat gaatagtttc gaatcaatgc tgcaaagctt tatttcacat     1050
tttttcagtc ctgataatat taaaaacatt ggtttggcac tagcagcagt     1100
caaacgaaca agattaatta cctgtcttcc tgtttctcaa gaatatttac     1150
gtagtttttc ataggtctgt ttttcctttc atgcctctta aaaacttctg     1200
tgcttacata aacatactta aaaggttttc tttaagatat tttatttttc     1250
catttaaagg tggacaaaag ctacctccct aaaagtaaat acaaagagaa     1300
cttatttaca cagggaaggt ttaagactgt tcaagtagca ttccaatctg     1350
tagccatgcc acagaatatc aacaagaaca cagaatgagt gcacagctaa     1400
gagatcaagt ttcagcaggc agctttatct caacctggac atattttaag     1450
attcagcatt tgaaagattt ccctagcctc ttcctttttc attagcccaa     1500
aacggtgcaa ctctattctg gactttatta cttgattctg tcttctgtat     1550
aactctgaag tccaccaaaa gtggaccctc tatatttcct cccttttat      1600
agtcttataa gatacattat gaaaggtgac cgactctatt ttaaatctca     1650
gaattttaag ttctagcccc atgataacct ttttctttgt aatttatgct     1700
ttcatatatc cttggtccca gagatgttta gacaatttta ggctcaaaaa     1750
ttaaagctaa cacaggaaaa ggaactgtac tggctattac ataagaaaca     1800
atggacccaa  gagaagaa                                       1818
```

<210> SEQ ID NO 24
<211> LENGTH: 300
<212> TYPE: PRT
<213> ORGANISM: Homo sapiens

<400> SEQUENCE: 24

```
Met Asn Ile Ile Leu Glu Ile Leu Leu Leu Leu Ile Thr Ile Ile
  1               5                  10                  15

Tyr Ser Tyr Leu Glu Ser Leu Val Lys Phe Phe Ile Pro Gln Arg
                 20                  25                  30

Arg Lys Ser Val Ala Gly Glu Ile Val Leu Ile Thr Gly Ala Gly
                 35                  40                  45

His Gly Ile Gly Arg Gln Thr Thr Tyr Glu Phe Ala Lys Arg Gln
                 50                  55                  60
```

```
Ser Ile Leu Val Leu Trp Asp Ile Asn Lys Arg Gly Val Glu Glu
                65                  70                  75

Thr Ala Ala Glu Cys Arg Lys Leu Gly Val Thr Ala His Ala Tyr
                80                  85                  90

Val Val Asp Cys Ser Asn Arg Glu Glu Ile Tyr Arg Ser Leu Asn
                95                  100                 105

Gln Val Lys Lys Glu Val Gly Asp Val Thr Ile Val Val Asn Asn
                110                 115                 120

Ala Gly Thr Val Tyr Pro Ala Asp Leu Leu Ser Thr Lys Asp Glu
                125                 130                 135

Glu Ile Thr Lys Thr Phe Glu Val Asn Ile Leu Gly His Phe Trp
                140                 145                 150

Ile Thr Lys Ala Leu Leu Pro Ser Met Met Glu Arg Asn His Gly
                155                 160                 165

His Ile Val Thr Val Ala Ser Val Cys Gly His Glu Gly Ile Pro
                170                 175                 180

Tyr Leu Ile Pro Tyr Cys Ser Ser Lys Phe Ala Ala Val Gly Phe
                185                 190                 195

His Arg Gly Leu Thr Ser Glu Leu Gln Ala Leu Gly Lys Thr Gly
                200                 205                 210

Ile Lys Thr Ser Cys Leu Cys Pro Val Phe Val Asn Thr Gly Phe
                215                 220                 225

Thr Lys Asn Pro Ser Thr Arg Leu Trp Pro Val Leu Glu Thr Asp
                230                 235                 240

Glu Val Val Arg Ser Leu Ile Asp Gly Ile Leu Thr Asn Lys Lys
                245                 250                 255

Met Ile Phe Val Pro Ser Tyr Ile Asn Ile Phe Leu Arg Leu Gln
                260                 265                 270

Lys Phe Leu Pro Glu Arg Ala Ser Ala Ile Leu Asn Arg Met Gln
                275                 280                 285

Asn Ile Gln Phe Glu Ala Val Val Gly His Lys Ile Lys Met Lys
                290                 295                 300
```

<210> SEQ ID NO 25
<211> LENGTH: 3906
<212> TYPE: DNA
<213> ORGANISM: Homo sapiens

<400> SEQUENCE: 25

```
ctcgggcgcg cacaggcagc tcggtttgcc ctgcgattga gctgcgggtc      50

gcggccggcg ccggcctctc caatggcaaa tgtgtgtggc tggaggcgag     100

cgcgaggctt tcggcaaagg cagtcgagtg tttgcagacc ggggcgagtc     150

ctgtgaaagc agataaaaga aaacatttat taacgtgtca ttacgagggg     200

agcgcccggc cggggctgtc gcactccccg cggaacattt ggctccctcc     250

agctccgaga gaggagaaga agaaagcgga aaagaggcag attcacgtcg     300

tttccagcca agtggacctg atcgatggcc ctcctgaatt tatcacgata     350

tttgatttat tagcgatgcc ccctggtttg tgtgttacgc acacacacgt     400

gcacacaagg ctctggctcg cttccctccc tcgtttccag ctcctgggcg     450

aatcccacat ctgtttcaac tctccgccga gggcgagcag gagcgagagt     500

gtgtcgaatc tgcgagtgaa gagggacgag ggaaaagaaa caaagccaca     550

gacgcaactt gagactcccg catcccaaaa gaagcaccag atcagcaaaa     600
```

-continued

```
aaagaagatg ggccccccga gcctcgtgct gtgcttgctg tccgcaactg       650
tgttctccct gctgggtgga agctcggcct tcctgtcgca ccaccgcctg       700
aaaggcaggt ttcagaggga ccgcaggaac atccgcccca acatcatcct       750
ggtgctgacg gacgaccagg atgtggagct gggttccatg caggtgatga       800
acaagacccg gcgcatcatg gagcagggcg gggcgcactt catcaacgcc       850
ttcgtgacca cacccatgtg ctgcccctca cgctcctcca tcctcactgg       900
caagtacgtc cacaaccaca acacctacac caacaatgag aactgctcct       950
cgccctcctg gcaggcacag cacgagagcc gcacctttgc cgtgtacctc      1000
aatagcactg gctaccggac agctttcttc gggaagtatc ttaatgaata      1050
caacggctcc tacgtgccac ccggctggaa ggagtgggtc ggactcctta      1100
aaaactcccg cttttataac tacacgctgt gtcggaacgg ggtgaaagag      1150
aagcacggct ccgactactc caaggattac ctcacagacc tcatcaccaa      1200
tgacagcgtg agcttcttcc gcacgtccaa gaagatgtac ccgcacaggc      1250
cagtcctcat ggtcatcagc catgcagccc cccacggccc tgaggattca      1300
gccccacaat attcacgcct cttcccaaac gcatctcagc acatcacgcc      1350
gagctacaac tacgcgccca acccggacaa acactggatc atgcgctaca      1400
cggggcccat gaagcccatc cacatggaat tcaccaacat gctccagcgg      1450
aagcgcttgc agaccctcat gtcggtggac gactccatgg agacgattta      1500
caacatgctg gttgagacgg gcgagctgga caacacgtac atcgtataca      1550
ccgccgacca cggttaccac atcggccagt ttggcctggt gaaagggaaa      1600
tccatgccat atgagtttga catcagggtc ccgttctacg tgaggggccc      1650
caacgtggaa gccggctgtc tgaatcccca catcgtcctc aacattgacc      1700
tggcccccac catcctggac attgcaggcc tggacatacc tgcggatatg      1750
gacgggaaat ccatcctcaa gctgctggac acggagcggc cggtgaatcg      1800
gtttcacttg aaaaagaaga tgagggtctg gcgggactcc ttcttggtgg      1850
agagaggcaa gctgctacac aagagagaca atgacaaggt ggacgcccag      1900
gaggagaact ttctgcccaa gtaccagcgt gtgaaggacc tgtgtcagcg      1950
tgctgagtac cagacggcgt gtgagcagct gggacagaag tggcagtgtg      2000
tggaggacgc cacggggaag ctgaagctgc ataagtgcaa gggccccatg      2050
cggctgggcg gcagcagagc cctctccaac ctcgtgccca agtactacgg      2100
gcagggcagc gaggcctgca cctgtgacag cggggactac aagctcagcc      2150
tggccggacg ccggaaaaaa ctcttcaaga agaagtacaa ggccagctat      2200
gtccgcagtc gctccatccg ctcagtggcc atcgaggtgg acggcagggt      2250
gtaccacgta ggcctgggtg atgccgccca gccccgaaac ctcaccaagc      2300
ggcactggcc aggggcccct gaggaccaag atgacaagga tggtggggac      2350
ttcagtggca ctggaggcct tcccgactac tcagccgcca accccattaa      2400
agtgacacat cggtgctaca tcctagagaa cgacacagtc cagtgtgacc      2450
tggacctgta caagtccctg caggcctgga aagaccacaa gctgcacatc      2500
gaccacgaga ttgaaaccct gcagaacaaa attaagaacc tgagggaagt      2550
ccgaggtcac ctgaagaaaa agcggccaga agaatgtgac tgtcacaaaa      2600
```

tcagctacca cacccagcac aaaggccgcc tcaagcacag aggctccagt 2650
ctgcatcctt tcaggaaggg cctgcaagag aaggacaagg tgtggctgtt 2700
gcgggagcag aagcgcaaga agaaactccg caagctgctc aagcgcctgc 2750
agaacaacga cacgtgcagc atgccaggcc tcacgtgctt cacccacgac 2800
aaccagcact ggcagacggc gcctttctgg acactggggc ctttctgtgc 2850
ctgcaccagc gccaacaata acacgtactg gtgcatgagg accatcaatg 2900
agactcacaa tttcctcttc tgtgaatttg caactggctt cctagagtac 2950
tttgatctca acacagaccc ctaccagctg atgaatgcag tgaacacact 3000
ggacagggat gtcctcaacc agctacacgt acagctcatg gagctgagga 3050
gctgcaaggg ttacaagcag tgtaaccccc ggactcgaaa catggacctg 3100
gatggaggaa gctatgagca atacaggcag tttcagcgtc gaaagtggcc 3150
agaaatgaag agaccttctt ccaaatcact gggacaactg tgggaaggct 3200
gggaaggtta agaaacaaca gaggtggacc tccaaaaaca tagaggcatc 3250
acctgactgc acaggcaatg aaaaaccatg tgggtgattt ccagcagacc 3300
tgtgctattg gccaggaggc ctgagaaagc aagcacgcac tctcagtcaa 3350
catgacagat tctggaggat aaccagcagg agcagagata acttcaggaa 3400
gtccattttt gcccctgctt ttgctttgga ttatacctca ccagctgcac 3450
aaaatgcatt ttttcgtatc aaaaagtcac cactaaccct cccccagaag 3500
ctcacaaagg aaaacggaga gagcgagcga gagagatttc cttggaaatt 3550
tctcccaagg gcgaaagtca ttggaatttt taaatcatag gggaaaagca 3600
gtcctgttct aaatcctctt attcttttgg tttgtcacaa agaaggaact 3650
aagaagcagg acagaggcaa cgtggagagg ctgaaaacag tgcagagacg 3700
tttgacaatg agtcagtagc acaaaagaga tgacatttac ctagcactat 3750
aaaccctggt tgcctctgaa gaaactgcct tcattgtata tatgtgacta 3800
tttacatgta atcaacatgg gaacttttag gggaacctaa taagaaatcc 3850
caattttcag gagtggtggt gtcaataaac gctctgtggc cagtgtaaaa 3900
gaaaaa 3906

<210> SEQ ID NO 26
<211> LENGTH: 867
<212> TYPE: PRT
<213> ORGANISM: Homo sapiens

<400> SEQUENCE: 26

Met Gly Pro Pro Ser Leu Val Leu Cys Leu Leu Ser Ala Thr Val
1 5 10 15

Phe Ser Leu Leu Gly Gly Ser Ser Ala Phe Leu Ser His His Arg
20 25 30

Leu Lys Gly Arg Phe Gln Arg Asp Arg Arg Asn Ile Arg Pro Asn
35 40 45

Ile Ile Leu Val Leu Thr Asp Asp Gln Asp Val Glu Leu Gly Ser
50 55 60

Met Gln Val Met Asn Lys Thr Arg Arg Ile Met Glu Gln Gly Gly
65 70 75

Ala His Phe Ile Asn Ala Phe Val Thr Thr Pro Met Cys Cys Pro
80 85 90

```
Ser Arg Ser Ser Ile Leu Thr Gly Lys Tyr Val His Asn His Asn
                95                  100                 105

Thr Tyr Thr Asn Asn Glu Asn Cys Ser Ser Pro Ser Trp Gln Ala
                110                 115                 120

Gln His Glu Ser Arg Thr Phe Ala Val Tyr Leu Asn Ser Thr Gly
                125                 130                 135

Tyr Arg Thr Ala Phe Phe Gly Lys Tyr Leu Asn Glu Tyr Asn Gly
                140                 145                 150

Ser Tyr Val Pro Pro Gly Trp Lys Glu Trp Val Gly Leu Leu Lys
                155                 160                 165

Asn Ser Arg Phe Tyr Asn Tyr Thr Leu Cys Arg Asn Gly Val Lys
                170                 175                 180

Glu Lys His Gly Ser Asp Tyr Ser Lys Asp Tyr Leu Thr Asp Leu
                185                 190                 195

Ile Thr Asn Asp Ser Val Ser Phe Phe Arg Thr Ser Lys Lys Met
                200                 205                 210

Tyr Pro His Arg Pro Val Leu Met Val Ile Ser His Ala Ala Pro
                215                 220                 225

His Gly Pro Glu Asp Ser Ala Pro Gln Tyr Ser Arg Leu Phe Pro
                230                 235                 240

Asn Ala Ser Gln His Ile Thr Pro Ser Tyr Asn Tyr Ala Pro Asn
                245                 250                 255

Pro Asp Lys His Trp Ile Met Arg Tyr Thr Gly Pro Met Lys Pro
                260                 265                 270

Ile His Met Glu Phe Thr Asn Met Leu Gln Arg Lys Arg Leu Gln
                275                 280                 285

Thr Leu Met Ser Val Asp Asp Ser Met Glu Thr Ile Tyr Asn Met
                290                 295                 300

Leu Val Glu Thr Gly Glu Leu Asp Asn Thr Tyr Ile Val Tyr Thr
                305                 310                 315

Ala Asp His Gly Tyr His Ile Gly Gln Phe Gly Leu Val Lys Gly
                320                 325                 330

Lys Ser Met Pro Tyr Glu Phe Asp Ile Arg Val Pro Phe Tyr Val
                335                 340                 345

Arg Gly Pro Asn Val Glu Ala Gly Cys Leu Asn Pro His Ile Val
                350                 355                 360

Leu Asn Ile Asp Leu Ala Pro Thr Ile Leu Asp Ile Ala Gly Leu
                365                 370                 375

Asp Ile Pro Ala Asp Met Asp Gly Lys Ser Ile Leu Lys Leu Leu
                380                 385                 390

Asp Thr Glu Arg Pro Val Asn Arg Phe His Leu Lys Lys Lys Met
                395                 400                 405

Arg Val Trp Arg Asp Ser Phe Leu Val Glu Arg Gly Lys Leu Leu
                410                 415                 420

His Lys Arg Asp Asn Asp Lys Val Asp Ala Gln Glu Glu Asn Phe
                425                 430                 435

Leu Pro Lys Tyr Gln Arg Val Lys Asp Leu Cys Gln Arg Ala Glu
                440                 445                 450

Tyr Gln Thr Ala Cys Glu Gln Leu Gly Gln Lys Trp Gln Cys Val
                455                 460                 465

Glu Asp Ala Thr Gly Lys Leu Lys Leu His Lys Cys Lys Gly Pro
                470                 475                 480

Met Arg Leu Gly Gly Ser Arg Ala Leu Ser Asn Leu Val Pro Lys
```

-continued

```
                485                 490                 495

Tyr Tyr Gly Gln Gly Ser Glu Ala Cys Thr Cys Asp Ser Gly Asp
                500                 505                 510

Tyr Lys Leu Ser Leu Ala Gly Arg Arg Lys Lys Leu Phe Lys Lys
                515                 520                 525

Lys Tyr Lys Ala Ser Tyr Val Arg Ser Arg Ser Ile Arg Ser Val
                530                 535                 540

Ala Ile Glu Val Asp Gly Arg Val Tyr His Val Gly Leu Gly Asp
                545                 550                 555

Ala Ala Gln Pro Arg Asn Leu Thr Lys Arg His Trp Pro Gly Ala
                560                 565                 570

Pro Glu Asp Gln Asp Asp Lys Asp Gly Gly Asp Phe Ser Gly Thr
                575                 580                 585

Gly Gly Leu Pro Asp Tyr Ser Ala Ala Asn Pro Ile Lys Val Thr
                590                 595                 600

His Arg Cys Tyr Ile Leu Glu Asn Asp Thr Val Gln Cys Asp Leu
                605                 610                 615

Asp Leu Tyr Lys Ser Leu Gln Ala Trp Lys Asp His Lys Leu His
                620                 625                 630

Ile Asp His Glu Ile Glu Thr Leu Gln Asn Lys Ile Lys Asn Leu
                635                 640                 645

Arg Glu Val Arg Gly His Leu Lys Lys Lys Arg Pro Glu Glu Cys
                650                 655                 660

Asp Cys His Lys Ile Ser Tyr His Thr Gln His Lys Gly Arg Leu
                665                 670                 675

Lys His Arg Gly Ser Ser Leu His Pro Phe Arg Lys Gly Leu Gln
                680                 685                 690

Glu Lys Asp Lys Val Trp Leu Leu Arg Glu Gln Lys Arg Lys Lys
                695                 700                 705

Lys Leu Arg Lys Leu Leu Lys Arg Leu Gln Asn Asn Asp Thr Cys
                710                 715                 720

Ser Met Pro Gly Leu Thr Cys Phe Thr His Asp Asn Gln His Trp
                725                 730                 735

Gln Thr Ala Pro Phe Trp Thr Leu Gly Pro Phe Cys Ala Cys Thr
                740                 745                 750

Ser Ala Asn Asn Asn Thr Tyr Trp Cys Met Arg Thr Ile Asn Glu
                755                 760                 765

Thr His Asn Phe Leu Phe Cys Glu Phe Ala Thr Gly Phe Leu Glu
                770                 775                 780

Tyr Phe Asp Leu Asn Thr Asp Pro Tyr Gln Leu Met Asn Ala Val
                785                 790                 795

Asn Thr Leu Asp Arg Asp Val Leu Asn Gln Leu His Val Gln Leu
                800                 805                 810

Met Glu Leu Arg Ser Cys Lys Gly Tyr Lys Gln Cys Asn Pro Arg
                815                 820                 825

Thr Arg Asn Met Asp Leu Asp Gly Gly Ser Tyr Glu Gln Tyr Arg
                830                 835                 840

Gln Phe Gln Arg Arg Lys Trp Pro Glu Met Lys Arg Pro Ser Ser
                845                 850                 855

Lys Ser Leu Gly Gln Leu Trp Glu Gly Trp Glu Gly
                860                 865
```

<210> SEQ ID NO 27
<211> LENGTH: 1238

<212> TYPE: DNA
<213> ORGANISM: Homo sapiens

<400> SEQUENCE: 27

```
gcgacgggca ggacgccccg ttcgcctagc gcgtgctcag gagttggtgt          50
cctgcctgcg ctcaggatga gggggaatct ggccctggtg ggcgttctaa         100
tcagcctggc cttcctgtca ctgctgccat ctggacatcc tcagccggct         150
ggcgatgacg cctgctctgt gcagatcctc gtccctggcc tcaaagggga         200
tgcgggagag aagggagaca aaggcgcccc cggacggcct ggaagagtcg         250
gccccacggg agaaaaagga gacatggggg acaaaggaca gaaaggcagt         300
gtgggtcgtc atggaaaaat tggtcccatt ggctctaaag gtgagaaagg         350
agattccggt gacataggac cccctggtcc taatggagaa ccaggcctcc         400
catgtgagtg cagccagctg cgcaaggcca tcggggagat ggacaaccag         450
gtctctcagc tgaccagcga gctcaagttc atcaagaatg ctgtcgccgg         500
tgtgcgcgag acggagagca agatctacct gctggtgaag gaggagaagc         550
gctacgcgga cgcccagctg tcctgccagg gccgcggggg cacgctgagc         600
atgcccaagg acgaggctgc caatggcctg atggccgcat acctggcgca         650
agccggcctg gcccgtgtct tcatcggcat caacgacctg gagaaggagg         700
gcgccttcgt gtactctgac cactccccca tgcggacctt caacaagtgg         750
cgcagcggtg agcccaacaa tgcctacgac gaggaggact gcgtggagat         800
ggtggcctcg ggcggctgga acgacgtggc ctgccacacc accatgtact         850
tcatgtgtga gtttgacaag gagaacatgt gagcctcagg ctggggctgc         900
ccattggggg ccccacatgt ccctgcaggg ttggcaggga cagagcccag         950
accatggtgc cagccaggga gctgtccctc tgtgaagggt ggaggctcac        1000
tgagtagagg gctgttgtct aaactgagaa aatggcctat gcttaagagg        1050
aaaatgaaag tgttcctggg gtgctgtctc tgaagaagca gagtttcatt        1100
acctgtattg tagccccaat gtcattatgt aattattacc cagaattgct        1150
cttccataaa gcttgtgcct ttgtccaagc tatacaataa aatctttaag        1200
tagtgcagta gttaagtcca aaaaaaaaaa  aaaaaaaa                    1238
```

<210> SEQ ID NO 28
<211> LENGTH: 271
<212> TYPE: PRT
<213> ORGANISM: Homo sapiens

<400> SEQUENCE: 28

```
Met Arg Gly Asn Leu Ala Leu Val Gly Val Leu Ile Ser Leu Ala
  1               5                  10                  15

Phe Leu Ser Leu Leu Pro Ser Gly His Pro Gln Pro Ala Gly Asp
                 20                  25                  30

Asp Ala Cys Ser Val Gln Ile Leu Val Pro Gly Leu Lys Gly Asp
                 35                  40                  45

Ala Gly Glu Lys Gly Asp Lys Gly Ala Pro Gly Arg Pro Gly Arg
                 50                  55                  60

Val Gly Pro Thr Gly Glu Lys Gly Asp Met Gly Asp Lys Gly Gln
                 65                  70                  75

Lys Gly Ser Val Gly Arg His Gly Lys Ile Gly Pro Ile Gly Ser
                 80                  85                  90
```

```
Lys Gly Glu Lys Gly Asp Ser Gly Asp Ile Gly Pro Pro Gly Pro
                95                  100                 105

Asn Gly Glu Pro Gly Leu Pro Cys Glu Cys Ser Gln Leu Arg Lys
                110                 115                 120

Ala Ile Gly Glu Met Asp Asn Gln Val Ser Gln Leu Thr Ser Glu
                125                 130                 135

Leu Lys Phe Ile Lys Asn Ala Val Ala Gly Val Arg Glu Thr Glu
                140                 145                 150

Ser Lys Ile Tyr Leu Leu Val Lys Glu Glu Lys Arg Tyr Ala Asp
                155                 160                 165

Ala Gln Leu Ser Cys Gln Gly Arg Gly Gly Thr Leu Ser Met Pro
                170                 175                 180

Lys Asp Glu Ala Ala Asn Gly Leu Met Ala Ala Tyr Leu Ala Gln
                185                 190                 195

Ala Gly Leu Ala Arg Val Phe Ile Gly Ile Asn Asp Leu Glu Lys
                200                 205                 210

Glu Gly Ala Phe Val Tyr Ser Asp His Ser Pro Met Arg Thr Phe
                215                 220                 225

Asn Lys Trp Arg Ser Gly Glu Pro Asn Asn Ala Tyr Asp Glu Glu
                230                 235                 240

Asp Cys Val Glu Met Val Ala Ser Gly Gly Trp Asn Asp Val Ala
                245                 250                 255

Cys His Thr Thr Met Tyr Phe Met Cys Glu Phe Asp Lys Glu Asn
                260                 265                 270

Met
```

<210> SEQ ID NO 29
<211> LENGTH: 3939
<212> TYPE: DNA
<213> ORGANISM: Homo sapiens

<400> SEQUENCE: 29

```
cggcaaccag ccgccgccac caccgctgcc actgccgccc tgccggggcc     50

atgttcgctc tgggcttgcc cttcttggtg ctcttggtgg cctcggtcga    100

gagccatctg gggttctgg ggcccaagaa cgtctcgcag aaagacgccg    150

agtttgagcg cacctacgtg gacgaggtca acagcgagct ggtcaacatc    200

tacaccttca accatactgt gacccgcaac aggacagagg gcgtgcgtgt    250

gtctgtgaac gtcctgaaca agcagaaggg ggcgccgttg ctgtttgtgg    300

tccgccagaa ggaggctgtg gtgtccttcc aggtgcccct aatcctgcga    350

gggatgtttc agcgcaagta cctctaccaa aaagtggaac gaaccctgtg    400

tcagcccccc accaagaatg agtcggagat tcagttcttc tacgtggatg    450

tgtccaccct gtcaccagtc aacaccacat accagctccg ggtcagccgc    500

atggacgatt ttgtgctcag gactggggag cagttcagct tcaataccac    550

agcagcacag ccccagtact tcaagtatga gttccctgaa ggcgtggact    600

cggtaattgt caaggtgacc tccaacaagg ccttcccctg ctcagtcatc    650

tccattcagg atgtgctgtg tcctgtctat gacctggaca acaacgtagc    700

cttcatcggc atgtaccaga cgatgaccaa gaaggcggcc atcaccgtac    750

agcgcaaaga cttccccagc aacagctttt atgtggtggt ggtggtgaag    800

accgaagacc aagcctgcgg gggctccctg cctttctacc ccttcgcaga    850
```

```
agatgaaccg gtcgatcaag ggcaccgcca gaaaaccctg tcagtgctgg          900
tgtctcaagc agtcacgtct gaggcatacg tcagtgggat gctcttttgc          950
ctgggtatat ttctctcctt ttacctgctg accgtcctcc tggcctgctg         1000
ggagaactgg aggcagaaga agaagaccct gctggtggcc attgaccgag         1050
cctgcccaga aagcggtcac cctcgagtcc tggctgattc ttttcctggc         1100
agttcccctt atgagggtta caactatggc tcctttgaga atgtttctgg         1150
atctaccgat ggtctggttg acagcgctgg cactggggac ctctcttacg         1200
gttaccaggg ccgctccttt gaacctgtag gtactcggcc ccgagtggac         1250
tccatgagct ctgtggagga ggatgactac gacacattga ccgacatcga         1300
ttccgacaag aatgtcattc gcaccaagca atacctctat gtggctgacc         1350
tggcacggaa ggacaagcgt gttctgcgga aaaagtacca gatctacttc         1400
tggaacattg ccaccattgc tgtcttctat gcccttcctg tggtgcagct         1450
ggtgatcacc taccagacgg tggtgaatgt cacagggaat caggacatct         1500
gctactacaa cttcctctgc gcccacccac tgggcaatct cagcgccttc         1550
aacaacatcc tcagcaacct ggggtacatc ctgctggggc tgcttttcct         1600
gctcatcatc ctgcaacggg agatcaacca caaccgggcc ctgctgcgca         1650
atgacctctg tgccctggaa tgtgggatcc ccaaacactt tgggcttttc         1700
tacgccatgg gcacagccct gatgatggag gggctgctca gtgcttgcta         1750
tcatgtgtgc cccaactata ccaatttcca gtttgacaca tcgttcatgt         1800
acatgatcgc cggactctgc atgctgaagc tctaccagaa gcggcacccg         1850
gacatcaacg ccagcgccta cagtgcctac gcctgcctgg ccattgtcat         1900
cttcttctct gtgctgggcg tggtctttgg caaagggaac acggcgttct         1950
ggatcgtctt ctccatcatt cacatcatcg ccaccctgct cctcagcacg         2000
cagctctatt acatgggccg gtggaaactg gactcgggga tcttccgccg         2050
catcctccac gtgctctaca cagactgcat ccggcagtgc agcgggccgc         2100
tctacgtgga ccgcatggtg ctgctggtca tgggcaacgt catcaactgg         2150
tcgctggctg cctatgggct tatcatgcgc cccaatgatt tcgcttccta         2200
cttgttggcc attggcatct gcaacctgct cctttacttc gccttctaca         2250
tcatcatgaa gctccggagt ggggagagga tcaagctcat ccccctgctc         2300
tgcatcgttt gcacctccgt ggtctggggc ttcgcgctct tcttcttctt         2350
ccagggactc agcacctggc agaaaacccc tgcagagtcg agggagcaca         2400
accgggactg catcctcctc gacttctttg acgaccacga catctggcac         2450
ttcctctcct ccatcgccat gttcgggtcc ttcctggtgt tgctgacact         2500
ggatgacgac ctggatactg tgcagcggga caagatctat gtcttctagc         2550
aggagctggg cccttcgctt cacctcaagg ggccctgagc tcctttgtgt         2600
catagaccgg tcactctgtc gtgctgtggg gatgagtccc agcaccgctg         2650
cccagcactg gatggcagca ggacagccag gtctagctta ggcttggcct         2700
gggacagcca tggggtggca tggaaccttg cagctgccct ctgccgagga         2750
gcaggcctgc tcccctggaa cccccagatg ttggccaaat tgctgctttc         2800
ttctcagtgt tggggccttc catgggcccc tgtcctttgg ctctccattt         2850
```

```
gtccctttgc aagaggaagg atggaaggga caccctcccc atttcatgcc            2900

ttgcattttg cccgtcctcc tccccacaat gccccagcct gggacctaag            2950

gcctcttttt cctcccatac tcccactcca gggcctagtc tggggcctga            3000

atctctgtcc tgtatcaggg ccccagttct ctttgggctg tccctggctg            3050

ccatcactgc ccattccagt cagccaggat ggatgggggt atgagatttt            3100

gggggttggc cagctggtgc cagacttttg gtgctaaggc ctgcaagggg            3150

cctggggcag tgcgtattct cttccctctg acctgtgctc agggctggct            3200

ctttagcaat gcgctcagcc caatttgaga accgccttct gattcaagag            3250

gctgaattca gaggtcacct cttcatccca tcagctccca gactgatgcc            3300

agcaccagga ctggagggag aagcgcctca ccccttccct tccttctttc            3350

caggccctta gtcttgccaa accccagctg gtggcctttc agtgccattg            3400

acactgccca agaatgtcca ggggcaaagg agggatgata cagagttcag            3450

cccgttctgc ctccacagct gtgggcaccc cagtgcctac cttagaaagg            3500

ggcttcagga agggatgtgc tgtttccctc tacgtgccca gtcctagcct            3550

cgctctagga cccagggctg gcttctaagt ttccgtccag tcttcaggca            3600

agttctgtgt tagtcatgca cacacatacc tatgaaacct tggagtttac            3650

aaagaattgc cccagctctg ggcaccctgg ccaccctggt ccttggatcc            3700

ccttcgtccc acctggtcca ccccagatgc tgaggatggg ggagctcagg            3750

cggggcctct gctttgggga tgggaatgtg tttttctccc aaacttgttt            3800

ttatagctct gcttgaaggg ctgggagatg aggtgggtct ggatcttttc            3850

tcagagcgtc tccatgctat ggttgcattt ccgttttcta tgaatgaatt            3900

tgcattcaat aaacaaccag actcaaaaaa  aaaaaaaaa                       3939
```

<210> SEQ ID NO 30
<211> LENGTH: 832
<212> TYPE: PRT
<213> ORGANISM: Homo sapiens

<400> SEQUENCE: 30

```
Met Phe Ala Leu Gly Leu Pro Phe Leu Val Leu Leu Val Ala Ser
  1               5                  10                  15

Val Glu Ser His Leu Gly Val Leu Gly Pro Lys Asn Val Ser Gln
                 20                  25                  30

Lys Asp Ala Glu Phe Glu Arg Thr Tyr Val Asp Glu Val Asn Ser
                 35                  40                  45

Glu Leu Val Asn Ile Tyr Thr Phe Asn His Thr Val Thr Arg Asn
                 50                  55                  60

Arg Thr Glu Gly Val Arg Val Ser Val Asn Val Leu Asn Lys Gln
                 65                  70                  75

Lys Gly Ala Pro Leu Leu Phe Val Val Arg Gln Lys Glu Ala Val
                 80                  85                  90

Val Ser Phe Gln Val Pro Leu Ile Leu Arg Gly Met Phe Gln Arg
                 95                 100                 105

Lys Tyr Leu Tyr Gln Lys Val Glu Arg Thr Leu Cys Gln Pro Pro
                110                 115                 120

Thr Lys Asn Glu Ser Glu Ile Gln Phe Phe Tyr Val Asp Val Ser
                125                 130                 135
```

-continued

```
Thr Leu Ser Pro Val Asn Thr Thr Tyr Gln Leu Arg Val Ser Arg
                140                 145                 150

Met Asp Asp Phe Val Leu Arg Thr Gly Glu Gln Phe Ser Phe Asn
                155                 160                 165

Thr Thr Ala Ala Gln Pro Gln Tyr Phe Lys Tyr Glu Phe Pro Glu
                170                 175                 180

Gly Val Asp Ser Val Ile Val Lys Val Thr Ser Asn Lys Ala Phe
                185                 190                 195

Pro Cys Ser Val Ile Ser Ile Gln Asp Val Leu Cys Pro Val Tyr
                200                 205                 210

Asp Leu Asp Asn Asn Val Ala Phe Ile Gly Met Tyr Gln Thr Met
                215                 220                 225

Thr Lys Lys Ala Ala Ile Thr Val Gln Arg Lys Asp Phe Pro Ser
                230                 235                 240

Asn Ser Phe Tyr Val Val Val Val Val Lys Thr Glu Asp Gln Ala
                245                 250                 255

Cys Gly Gly Ser Leu Pro Phe Tyr Pro Phe Ala Glu Asp Glu Pro
                260                 265                 270

Val Asp Gln Gly His Arg Gln Lys Thr Leu Ser Val Leu Val Ser
                275                 280                 285

Gln Ala Val Thr Ser Glu Ala Tyr Val Ser Gly Met Leu Phe Cys
                290                 295                 300

Leu Gly Ile Phe Leu Ser Phe Tyr Leu Leu Thr Val Leu Leu Ala
                305                 310                 315

Cys Trp Glu Asn Trp Arg Gln Lys Lys Lys Thr Leu Leu Val Ala
                320                 325                 330

Ile Asp Arg Ala Cys Pro Glu Ser Gly His Pro Arg Val Leu Ala
                335                 340                 345

Asp Ser Phe Pro Gly Ser Ser Pro Tyr Glu Gly Tyr Asn Tyr Gly
                350                 355                 360

Ser Phe Glu Asn Val Ser Gly Ser Thr Asp Gly Leu Val Asp Ser
                365                 370                 375

Ala Gly Thr Gly Asp Leu Ser Tyr Gly Tyr Gln Gly Arg Ser Phe
                380                 385                 390

Glu Pro Val Gly Thr Arg Pro Arg Val Asp Ser Met Ser Ser Val
                395                 400                 405

Glu Glu Asp Asp Tyr Asp Thr Leu Thr Asp Ile Asp Ser Asp Lys
                410                 415                 420

Asn Val Ile Arg Thr Lys Gln Tyr Leu Tyr Val Ala Asp Leu Ala
                425                 430                 435

Arg Lys Asp Lys Arg Val Leu Arg Lys Lys Tyr Gln Ile Tyr Phe
                440                 445                 450

Trp Asn Ile Ala Thr Ile Ala Val Phe Tyr Ala Leu Pro Val Val
                455                 460                 465

Gln Leu Val Ile Thr Tyr Gln Thr Val Val Asn Val Thr Gly Asn
                470                 475                 480

Gln Asp Ile Cys Tyr Tyr Asn Phe Leu Cys Ala His Pro Leu Gly
                485                 490                 495

Asn Leu Ser Ala Phe Asn Asn Ile Leu Ser Asn Leu Gly Tyr Ile
                500                 505                 510

Leu Leu Gly Leu Leu Phe Leu Leu Ile Ile Leu Gln Arg Glu Ile
                515                 520                 525

Asn His Asn Arg Ala Leu Leu Arg Asn Asp Leu Cys Ala Leu Glu
                530                 535                 540
```

```
Cys Gly Ile Pro Lys His Phe Gly Leu Phe Tyr Ala Met Gly Thr
                545                 550                 555

Ala Leu Met Met Glu Gly Leu Leu Ser Ala Cys Tyr His Val Cys
                560                 565                 570

Pro Asn Tyr Thr Asn Phe Gln Phe Asp Thr Ser Phe Met Tyr Met
                575                 580                 585

Ile Ala Gly Leu Cys Met Leu Lys Leu Tyr Gln Lys Arg His Pro
                590                 595                 600

Asp Ile Asn Ala Ser Ala Tyr Ser Ala Tyr Ala Cys Leu Ala Ile
                605                 610                 615

Val Ile Phe Phe Ser Val Leu Gly Val Val Phe Gly Lys Gly Asn
                620                 625                 630

Thr Ala Phe Trp Ile Val Phe Ser Ile Ile His Ile Ile Ala Thr
                635                 640                 645

Leu Leu Leu Ser Thr Gln Leu Tyr Tyr Met Gly Arg Trp Lys Leu
                650                 655                 660

Asp Ser Gly Ile Phe Arg Arg Ile Leu His Val Leu Tyr Thr Asp
                665                 670                 675

Cys Ile Arg Gln Cys Ser Gly Pro Leu Tyr Val Asp Arg Met Val
                680                 685                 690

Leu Leu Val Met Gly Asn Val Ile Asn Trp Ser Leu Ala Ala Tyr
                695                 700                 705

Gly Leu Ile Met Arg Pro Asn Asp Phe Ala Ser Tyr Leu Leu Ala
                710                 715                 720

Ile Gly Ile Cys Asn Leu Leu Leu Tyr Phe Ala Phe Tyr Ile Ile
                725                 730                 735

Met Lys Leu Arg Ser Gly Glu Arg Ile Lys Leu Ile Pro Leu Leu
                740                 745                 750

Cys Ile Val Cys Thr Ser Val Val Trp Gly Phe Ala Leu Phe Phe
                755                 760                 765

Phe Phe Gln Gly Leu Ser Thr Trp Gln Lys Thr Pro Ala Glu Ser
                770                 775                 780

Arg Glu His Asn Arg Asp Cys Ile Leu Leu Asp Phe Phe Asp Asp
                785                 790                 795

His Asp Ile Trp His Phe Leu Ser Ser Ile Ala Met Phe Gly Ser
                800                 805                 810

Phe Leu Val Leu Leu Thr Leu Asp Asp Asp Leu Asp Thr Val Gln
                815                 820                 825

Arg Asp Lys Ile Tyr Val Phe
                830
```

<210> SEQ ID NO 31
<211> LENGTH: 2065
<212> TYPE: DNA
<213> ORGANISM: Homo sapiens

<400> SEQUENCE: 31

```
gtgaatgtga gggtttgatg actttcagat gtctaggaac cagagtgggt      50

gcaggggccc caggcagggc tgattcttgg gcggaggaga gtagggtaaa     100

gggttctgca tgagctcctt aaaggacaaa ggtaacagag ccagcgagag     150

agctcgaggg gagactttga cttcaagcca cagaattggt ggaagtgtgc     200

gcgccgccgc cgccgtcgct cctgcagcgc tgtcgaccta gccgctagca     250

tcttcccgag caccgggatc ccggggtagg aggcgacgcg ggcgagcacc     300
```

```
agcgccagcc ggctgcggct gcccacacgg ctcaccatgg gctccgggcg        350

ccgggcgctg tccgcggtgc cggccgtgct gctggtcctc acgctgccgg        400

ggctgcccgt ctgggcacag aacgacacgg agcccatcgt gctggagggc        450

aagtgtctgg tggtgtgcga ctcgaacccg gccacggact ccaagggctc        500

ctcttcctcc ccgctgggga tatcggtccg ggcggccaac tccaaggtcg        550

ccttctcggc ggtgcggagc accaaccacg agccatccga gatgagcaac        600

aagacgcgca tcatttactt cgatcagatc ctggtgaatg tgggtaattt        650

tttcacattg gagtctgtct ttgtagcacc aagaaaagga atttacagtt        700

tcagttttca cgtgattaaa gtctaccaga gccaaactat ccaggttaac        750

ttgatgttaa atggaaaacc agtaatatct gcctttgcgg gggacaaaga        800

tgttactcgt gaagctgcca cgaatggtgt cctgctctac ctagataaag        850

aggataaggt ttacctaaaa ctggagaaag gtaatttggt tggaggctgg        900

cagtattcca cgttttctgg ctttctggtg ttcccccctat aggattcaat        950

ttctccatga tgttcatcca ggtgagggat gacccactcc tgagttattg       1000

gaagatcatt ttttcatcat tggattgatg tcttttattg gtttctcatg       1050

ggtggatatg gattctaagg attctagcct gtctgaacca atacaaaatt       1100

tcacagatta tttgtgtgtg tctgtttcag tatatttgga ttgggactct       1150

aagcagataa tacctatgct taaatgtaac agtcaaaagc tgtctgcaag       1200

acttattctg aatttcattt cctgggatta ctgaattagt tacagatgtg       1250

gaattttatt tgtttagttt taaaagactg gcaaccaggt ctaaggatta       1300

gaaaactcta aagttctgac ttcaatcaac ggttagtgtg atactgccaa       1350

agaactgtat actgtgttaa tatattgatt atatttgttt ttattccttt       1400

ggaattagtt tgtttggttc ttgtaaaaaa cttggatttt tttttcagt        1450

aactggtatt atgttttctc ttaaaataag gtaatgaatg gcttgcccac       1500

aaatttacct tgactacgat atcatcgaca tgacttctct caaaaaaaaa       1550

gaatgcttca tagttgtatt ttaattgtat atgtgaaaga gtcatatttt       1600

ccaagttata ttttctaaga agaagaatag atcataaatc tgacaaggaa       1650

aaagttgctt acccaaaatc taagtgctca atccctgagc ctcagcaaaa       1700

cagctcccct ccgagggaaa tcttatactt tattgctcaa ctttaattaa       1750

aatgattgat aataaccact ttattaaaaa cctaaggttt ttttttttc        1800

cgtagacatg accactttat taactggtgg tgggatgctg ttgtttctaa       1850

ttatacctat ttttcaaggc ttctgttgta tttgaagtat catctggttt       1900

tgccttaact ctttaaattg tatatattta tctgtttagc taatattaaa       1950

ttcaaatatc ccatatctaa atttagtgca atatcttgtc ttttgtatag       2000

gtcatatgaa ttcataaaat tatttatgtc tgttatagaa taaagattaa       2050

tatatgttaa  aaaaa                                            2065
```

<210> SEQ ID NO 32
<211> LENGTH: 201
<212> TYPE: PRT
<213> ORGANISM: Homo sapiens

<400> SEQUENCE: 32

```
Met Gly Ser Gly Arg Arg Ala Leu Ser Ala Val Pro Ala Val Leu
  1               5                  10                  15

Leu Val Leu Thr Leu Pro Gly Leu Pro Val Trp Ala Gln Asn Asp
                 20                  25                  30

Thr Glu Pro Ile Val Leu Glu Gly Lys Cys Leu Val Val Cys Asp
                 35                  40                  45

Ser Asn Pro Ala Thr Asp Ser Lys Gly Ser Ser Ser Ser Pro Leu
                 50                  55                  60

Gly Ile Ser Val Arg Ala Ala Asn Ser Lys Val Ala Phe Ser Ala
                 65                  70                  75

Val Arg Ser Thr Asn His Glu Pro Ser Glu Met Ser Asn Lys Thr
                 80                  85                  90

Arg Ile Ile Tyr Phe Asp Gln Ile Leu Val Asn Val Gly Asn Phe
                 95                 100                 105

Phe Thr Leu Glu Ser Val Phe Val Ala Pro Arg Lys Gly Ile Tyr
                110                 115                 120

Ser Phe Ser Phe His Val Ile Lys Val Tyr Gln Ser Gln Thr Ile
                125                 130                 135

Gln Val Asn Leu Met Leu Asn Gly Lys Pro Val Ile Ser Ala Phe
                140                 145                 150

Ala Gly Asp Lys Asp Val Thr Arg Glu Ala Ala Thr Asn Gly Val
                155                 160                 165

Leu Leu Tyr Leu Asp Lys Glu Asp Lys Val Tyr Leu Lys Leu Glu
                170                 175                 180

Lys Gly Asn Leu Val Gly Gly Trp Gln Tyr Ser Thr Phe Ser Gly
                185                 190                 195

Phe Leu Val Phe Pro Leu
                200
```

<210> SEQ ID NO 33
<211> LENGTH: 1170
<212> TYPE: DNA
<213> ORGANISM: Homo sapiens

<400> SEQUENCE: 33

```
gtcgaaggtt ataaaagctt ccagccaaac ggcattgaag ttgaagatac      50

aacctgacag cacagcctga gatcttgggg atccctcagc ctaacaccca     100

cagacgtcag ctggtggatt cccgctgcat caaggcctac ccactgtctc     150

catgctgggc tctccctgcc ttctgtggct cctggccgtg accttcttgg     200

ttcccagagc tcagcccttg gcccctcaag actttgaaga agaggaggca     250

gatgagactg agacggcgtg gccgcctttg ccggctgtcc cctgcgacta     300

cgaccactgc cgacacctgc aggtgccctg caaggagcta cagagggtcg     350

ggccggcggc ctgcctgtgc ccaggactct ccagccccgc ccagccgccc     400

gacccgccgc gcatgggaga agtgcgcatt gcggccgaag agggccgcgc     450

agtggtccac tggtgtgccc ccttctcccc ggtcctccac tactggctgc     500

tgctttggga cggcagcgag gctgcgcaga aggggccccc gctgaacgct     550

acggtccgca gagccgaact gaaggggctg aagccagggg gcatttatgt     600

cgtttgcgta gtggccgcta acgaggccgg ggcaagccgc gtgccccagg     650

ctggaggaga gggcctcgag gggccgaca tccctgcctt cgggccttgc      700

agccgccttg cggtgccgcc caacccccgc actctggtcc acgcggccgt     750
```

```
cggggtgggc acggccctgg ccctgctaag ctgtgccgcc ctggtgtggc        800

acttctgcct gcgcgatcgc tggggctgcc cgcgccgagc cgccgcccga        850

gccgcagggg cgctctgaaa ggggcctggg ggcatctcgg gcacagacag        900

ccccacctgg ggcgctcagc ctggcccccg ggaaagagga aaacccgctg        950

cctccaggga gggctggacg gcgagctggg agccagcccc aggctccagg       1000

gccacggcgg agtcatggtt ctcaggactg agcgcttgtt taggtccggt       1050

acttggcgct ttgtttcctg gctgaggtct gggaaggaat agaaaggggc       1100

ccccaatttt tttttaagcg gccagataat aaataatgta acctttgcgg       1150

ttaaaaaaaa aaaaaaaaaa                                         1170
```

<210> SEQ ID NO 34
<211> LENGTH: 238
<212> TYPE: PRT
<213> ORGANISM: Homo sapiens

<400> SEQUENCE: 34

```
Met Leu Gly Ser Pro Cys Leu Leu Trp Leu Leu Ala Val Thr Phe
  1               5                  10                  15

Leu Val Pro Arg Ala Gln Pro Leu Ala Pro Gln Asp Phe Glu Glu
                 20                  25                  30

Glu Glu Ala Asp Glu Thr Glu Thr Ala Trp Pro Pro Leu Pro Ala
                 35                  40                  45

Val Pro Cys Asp Tyr Asp His Cys Arg His Leu Gln Val Pro Cys
                 50                  55                  60

Lys Glu Leu Gln Arg Val Gly Pro Ala Ala Cys Leu Cys Pro Gly
                 65                  70                  75

Leu Ser Ser Pro Ala Gln Pro Pro Asp Pro Pro Arg Met Gly Glu
                 80                  85                  90

Val Arg Ile Ala Ala Glu Glu Gly Arg Ala Val Val His Trp Cys
                 95                 100                 105

Ala Pro Phe Ser Pro Val Leu His Tyr Trp Leu Leu Leu Trp Asp
                110                 115                 120

Gly Ser Glu Ala Ala Gln Lys Gly Pro Pro Leu Asn Ala Thr Val
                125                 130                 135

Arg Arg Ala Glu Leu Lys Gly Leu Lys Pro Gly Gly Ile Tyr Val
                140                 145                 150

Val Cys Val Val Ala Ala Asn Glu Ala Gly Ala Ser Arg Val Pro
                155                 160                 165

Gln Ala Gly Gly Glu Gly Leu Glu Gly Ala Asp Ile Pro Ala Phe
                170                 175                 180

Gly Pro Cys Ser Arg Leu Ala Val Pro Pro Asn Pro Arg Thr Leu
                185                 190                 195

Val His Ala Ala Val Gly Val Gly Thr Ala Leu Ala Leu Leu Ser
                200                 205                 210

Cys Ala Ala Leu Val Trp His Phe Cys Leu Arg Asp Arg Trp Gly
                215                 220                 225

Cys Pro Arg Arg Ala Ala Ala Arg Ala Ala Gly Ala Leu
                230                 235
```

<210> SEQ ID NO 35
<211> LENGTH: 1310
<212> TYPE: DNA
<213> ORGANISM: Homo sapiens

<400> SEQUENCE: 35

```
cggctcgagc ccgcccggaa gtgcccgagg ggccgcgatg gagctggggg      50
agccgggcgc tcggtagcgc ggcgggcaag gcaggcgcca tgaccctgat     100
tgaaggggtg ggtgatgagg tgaccgtcct tttctcggtg cttgcctgcc     150
ttctggtgct ggcccttgcc tgggtctcaa cgcacaccgc tgagggcggg     200
gacccactgc cccagccgtc agggacccca acgccatccc agcccagcgc     250
agccatggca gctaccgaca gcatgagagg ggaggcccca ggggcagaga     300
cccccagcct gagacacaga ggtcaagctg cacagccaga gcccagcacg     350
gggttcacag caacaccgcc agccccggac tccccgcagg agcccctcgt     400
gctacggctg aaattcctca atgattcaga gcaggtggcc agggcctggc     450
cccacgacac cattggctcc ttgaaaagga cccagtttcc cggccgggaa     500
cagcaggtgc gactcatcta ccaagggcag ctgctaggcg acgacaccca     550
gaccctgggc agccttcacc tccctcccaa ctgcgttctc cactgccacg     600
tgtccacgag agtcggtccc ccaaatcccc cctgcccgcc ggggtccgag     650
cccggcccct ccgggctgga aatcggcagc ctgctgctgc ccctgctgct     700
cctgctgttg ctgctgctct ggtactgcca gatccagtac cggcccttct     750
ttcccctgac cgccactctg ggcctggccg gcttcaccct gctcctcagt     800
ctcctggcct ttgccatgta ccgcccgtag tgcctccgcg ggcgcttggc     850
agcgtcgccg gcccctccgg accttgctcc ccgcgccgcg gcgggagctg     900
ctgcctgccc aggcccgcct ctccggcctg cctcttcccg ctgccctgga     950
gcccagccct gcgccgcaga ggactcccgg gactggcgga ggccccgccc    1000
tgcgaccgcc ggggctcggg gccacctccc ggggctgctg aacctcagcc    1050
cgcactggga gtgggctcct cggggtcggg catctgctgt cgctgcctcg    1100
gccccgggca gagccgggcc gccccggggg cccgtcttag tgttctgccg    1150
gaggacccag ccgcctccaa tccctgacag ctccttgggc tgagttgggg    1200
acgccaggtc ggtgggaggc tggtgaaggg gagcggggag gggcagagga    1250
gttccccgga acccgtgcag attaaagtaa ctgtgaagtt ttaaaaaaaa    1300
aaaaaaaaaa                                                1310
```

<210> SEQ ID NO 36
<211> LENGTH: 246
<212> TYPE: PRT
<213> ORGANISM: Homo sapiens

<400> SEQUENCE: 36

```
Met Thr Leu Ile Glu Gly Val Gly Asp Glu Val Thr Val Leu Phe
  1               5                  10                  15

Ser Val Leu Ala Cys Leu Leu Val Leu Ala Leu Ala Trp Val Ser
                 20                  25                  30

Thr His Thr Ala Glu Gly Gly Asp Pro Leu Pro Gln Pro Ser Gly
                 35                  40                  45

Thr Pro Thr Pro Ser Gln Pro Ser Ala Ala Met Ala Ala Thr Asp
                 50                  55                  60

Ser Met Arg Gly Glu Ala Pro Gly Ala Glu Thr Pro Ser Leu Arg
                 65                  70                  75
```

```
His Arg Gly Gln Ala Ala Gln Pro Glu Pro Ser Thr Gly Phe Thr
                 80                  85                  90

Ala Thr Pro Pro Ala Pro Asp Ser Pro Gln Glu Pro Leu Val Leu
                 95                 100                 105

Arg Leu Lys Phe Leu Asn Asp Ser Glu Gln Val Ala Arg Ala Trp
                110                 115                 120

Pro His Asp Thr Ile Gly Ser Leu Lys Arg Thr Gln Phe Pro Gly
                125                 130                 135

Arg Glu Gln Gln Val Arg Leu Ile Tyr Gln Gly Gln Leu Leu Gly
                140                 145                 150

Asp Asp Thr Gln Thr Leu Gly Ser Leu His Leu Pro Pro Asn Cys
                155                 160                 165

Val Leu His Cys His Val Ser Thr Arg Val Gly Pro Pro Asn Pro
                170                 175                 180

Pro Cys Pro Pro Gly Ser Glu Pro Gly Pro Ser Gly Leu Glu Ile
                185                 190                 195

Gly Ser Leu Leu Leu Pro Leu Leu Leu Leu Leu Leu Leu Leu Leu
                200                 205                 210

Trp Tyr Cys Gln Ile Gln Tyr Arg Pro Phe Phe Pro Leu Thr Ala
                215                 220                 225

Thr Leu Gly Leu Ala Gly Phe Thr Leu Leu Leu Ser Leu Leu Ala
                230                 235                 240

Phe Ala Met Tyr Arg Pro
                245
```

<210> SEQ ID NO 37
<211> LENGTH: 1150
<212> TYPE: DNA
<213> ORGANISM: Homo sapiens

<400> SEQUENCE: 37

```
gtgacactat agaagagcta tgacgtcgca tgcacgcgta cgtaagctcg        50

gaattcggct cgaggctggt gggaagaagc cgagatggcg gcagccagcg       100

ctggggcaac ccggctgctc ctgctcttgc tgatggcggt agcagcgccc       150

agtcgagccc ggggcagcgg ctgccgggcc gggactggtg cgcgaggggc       200

tggggcggaa ggtcgagagg gcgaggcctg tggcacggtg gggctgctgc       250

tggagcactc atttgagatc gatgacagtg ccaacttccg gaagcggggc       300

tcactgctct ggaaccagca ggatggtacc ttgtccctgt cacagcggca       350

gctcagcgag gaggagcggg gccgactccg ggatgtggca gccctgaatg       400

gcctgtaccg ggtccggatc ccaaggcgac ccggggccct ggatggcctg       450

gaagctggtg gctatgtctc ctcctttgtc cctgcgtgct ccctggtgga       500

gtcgcacctg tcggaccagc tgaccctgca cgtggatgtg gccggcaacg       550

tggtgggcgt gtcggtggtg acgcaccccg gggctgccg gggccatgag        600

gtggaggacg tggacctgga gctgttcaac acctcggtgc agctgcagcc       650

gcccaccaca gccccaggcc ctgagacggc ggccttcatt gagcgcctgg       700

agatggaaca ggcccagaag gccaagaacc cccaggagca gaagtccttc       750

ttcgccaaat actggatgta catcattccc gtcgtcctgt tcctcatgat       800

gtcaggagcg ccagacaccg ggggccaggg tgggggtggg ggtgggggtg       850

gtggtggggg tagtggcctt tgctgtgtgc caccctccct gtaagtctat       900
```

```
ttaaaaacat cgacgataca ttgaaatgtg tgaacgtttt gaaaagctac              950

agcttccagc agccaaaagc aactgttgtt ttggcaagac ggtcctgatg             1000

tacaagcttg attgaaattc actgctcact tgatacgtta ttcagaaacc             1050

caaggaatgg ctgtccccat cctcatgtgg ctgtgtggag ctcagctgtg             1100

ttgtgtggca gtttattaaa ctgtccccca gatcgacacg caaaaaaaaa             1150
```

<210> SEQ ID NO 38
<211> LENGTH: 269
<212> TYPE: PRT
<213> ORGANISM: Homo sapiens

<400> SEQUENCE: 38

```
Met Ala Ala Ala Ser Ala Gly Ala Thr Arg Leu Leu Leu Leu Leu
  1               5                  10                  15

Leu Met Ala Val Ala Ala Pro Ser Arg Ala Arg Gly Ser Gly Cys
                 20                  25                  30

Arg Ala Gly Thr Gly Ala Arg Gly Ala Gly Ala Glu Gly Arg Glu
                 35                  40                  45

Gly Glu Ala Cys Gly Thr Val Gly Leu Leu Leu Glu His Ser Phe
                 50                  55                  60

Glu Ile Asp Asp Ser Ala Asn Phe Arg Lys Arg Gly Ser Leu Leu
                 65                  70                  75

Trp Asn Gln Gln Asp Gly Thr Leu Ser Leu Ser Gln Arg Gln Leu
                 80                  85                  90

Ser Glu Glu Glu Arg Gly Arg Leu Arg Asp Val Ala Ala Leu Asn
                 95                 100                 105

Gly Leu Tyr Arg Val Arg Ile Pro Arg Arg Pro Gly Ala Leu Asp
                110                 115                 120

Gly Leu Glu Ala Gly Gly Tyr Val Ser Ser Phe Val Pro Ala Cys
                125                 130                 135

Ser Leu Val Glu Ser His Leu Ser Asp Gln Leu Thr Leu His Val
                140                 145                 150

Asp Val Ala Gly Asn Val Val Gly Val Ser Val Val Thr His Pro
                155                 160                 165

Gly Gly Cys Arg Gly His Glu Val Glu Asp Val Asp Leu Glu Leu
                170                 175                 180

Phe Asn Thr Ser Val Gln Leu Gln Pro Pro Thr Thr Ala Pro Gly
                185                 190                 195

Pro Glu Thr Ala Ala Phe Ile Glu Arg Leu Glu Met Glu Gln Ala
                200                 205                 210

Gln Lys Ala Lys Asn Pro Gln Glu Gln Lys Ser Phe Phe Ala Lys
                215                 220                 225

Tyr Trp Met Tyr Ile Ile Pro Val Val Leu Phe Leu Met Met Ser
                230                 235                 240

Gly Ala Pro Asp Thr Gly Gly Gln Gly Gly Gly Gly Gly Gly Gly
                245                 250                 255

Gly Gly Gly Gly Ser Gly Leu Cys Cys Val Pro Pro Ser Leu
                260                 265
```

<210> SEQ ID NO 39
<211> LENGTH: 1098
<212> TYPE: DNA
<213> ORGANISM: Homo sapiens

<400> SEQUENCE: 39

```
gcgacgcgcg gcggggcggc gagaggaaac gcggcgccgg gccgggcccg          50
gccctggaga tggtccccgg cgccgcgggc tggtgttgtc tcgtgctctg         100
gctccccgcg tgcgtcgcgg cccacggctt ccgtatccat gattatttgt         150
actttcaagt gctgagtcct ggggacattc gatacatctt cacagccaca         200
cctgccaagg actttggtgg tatctttcac acaaggtatg agcagattca         250
ccttgtcccc gctgaacctc cagaggcctg cggggaactc agcaacggtt         300
tcttcatcca ggaccagatt gctctggtgg agagggggg ctgctccttc          350
ctctccaaga ctcgggtggt ccaggagcac ggcgggcggg cggtgatcat         400
ctctgacaac gcagttgaca atgacagctt ctacgtggag atgatccagg         450
acagtaccca gcgcacagct gacatccccg ccctcttcct gctcggccga         500
gacggctaca tgatccgccg ctctctggaa cagcatgggc tgccatgggc         550
catcatttcc atcccagtca atgtcaccag catccccacc tttgagctgc         600
tgcaaccgcc ctggaccttc tggtagaaga gtttgtccca cattccagcc         650
ataagtgact ctgagctggg aaggggaaac ccaggaattt tgctacttgg         700
aatttggaga tagcatctgg ggacaagtgg agccaggtag aggaaaaggg         750
tttgggcgtt gctaggctga aagggaagcc acaccactgg ccttcccttc         800
cccagggccc ccaagggtgt ctcatgctac aagaagaggc aagagacagg         850
ccccagggct tctggctaga acccgaaaca aaaggagctg aaggcaggtg         900
gcctgagagc catctgtgac ctgtcacact cacctggctc cagcctcccc         950
tacccagggt ctctgcacag tgaccttcac agcagttgtt ggagtggttt        1000
aaagagctgg tgtttgggga ctcaataaac cctcactgac tttttagcaa        1050
taaagcttct catcagggtt gcaaaaaaaa aaaaaaaaaa  aaaaaaaa         1098
```

```
<210> SEQ ID NO 40
<211> LENGTH: 188
<212> TYPE: PRT
<213> ORGANISM: Homo sapiens

<400> SEQUENCE: 40

Met Val Pro Gly Ala Ala Gly Trp Cys Cys Leu Val Leu Trp Leu
  1               5                  10                  15

Pro Ala Cys Val Ala Ala His Gly Phe Arg Ile His Asp Tyr Leu
                 20                  25                  30

Tyr Phe Gln Val Leu Ser Pro Gly Asp Ile Arg Tyr Ile Phe Thr
                 35                  40                  45

Ala Thr Pro Ala Lys Asp Phe Gly Gly Ile Phe His Thr Arg Tyr
                 50                  55                  60

Glu Gln Ile His Leu Val Pro Ala Glu Pro Pro Glu Ala Cys Gly
                 65                  70                  75

Glu Leu Ser Asn Gly Phe Phe Ile Gln Asp Gln Ile Ala Leu Val
                 80                  85                  90

Glu Arg Gly Gly Cys Ser Phe Leu Ser Lys Thr Arg Val Val Gln
                 95                 100                 105

Glu His Gly Gly Arg Ala Val Ile Ile Ser Asp Asn Ala Val Asp
                110                 115                 120

Asn Asp Ser Phe Tyr Val Glu Met Ile Gln Asp Ser Thr Gln Arg
                125                 130                 135

Thr Ala Asp Ile Pro Ala Leu Phe Leu Leu Gly Arg Asp Gly Tyr
```

```
                140                 145                 150

Met Ile Arg Arg Ser Leu Glu Gln His Gly Leu Pro Trp Ala Ile
                155                 160                 165

Ile Ser Ile Pro Val Asn Val Thr Ser Ile Pro Thr Phe Glu Leu
                170                 175                 180

Leu Gln Pro Pro Trp Thr Phe Trp
                185
```

<210> SEQ ID NO 41
<211> LENGTH: 1777
<212> TYPE: DNA
<213> ORGANISM: Homo sapiens

<400> SEQUENCE: 41

```
ggagagccgc ggctgggacc ggagtgggga gcgcggcgtg gaggtgccac        50

ccggcgcggg tggcggagag atcagaagcc tcttccccaa gccgagccaa       100

cctcagcggg gacccgggct cagggacgcg gcggcggcgg cggcgactgc       150

agtggctgga cgatggcagc gtccgccgga gccggggcgg tgattgcagc       200

cccagacagc cggcgctggc tgtggtcggt gctggcggcg gcgcttgggc       250

tcttgacagc tggagtatca gccttggaag tatatacgcc aaaagaaatc       300

ttcgtggcaa atggtacaca agggaagctg acctgcaagt tcaagtctac       350

tagtacgact ggcgggttga cctcagtctc ctggagcttc cagccagagg       400

gggccgacac tactgtgtcg tttttccact actcccaagg gcaagtgtac       450

cttgggaatt atccaccatt taaagacaga atcagctggg ctggagacct       500

tgacaagaaa gatgcatcaa tcaacataga aaatatgcag tttatacaca       550

atggcaccta tatctgtgat gtcaaaaacc ctcctgacat cgttgtccag       600

cctggacaca ttaggctcta tgtcgtagaa aaagagaatt tgcctgtgtt       650

tccagtttgg gtagtggtgg gcatagttac tgctgtggtc ctaggtctca       700

ctctgctcat cagcatgatt ctggctgtcc tctatagaag gaaaaactct       750

aaacgggatt acactggctg cagtacatca gagagtttgt caccagttaa       800

gcaggctcct cggaagtccc cctccgacac tgagggtctt gtaaagagtc       850

tgccttctgg atctcaccag ggcccagtca tatatgcaca gttagaccac       900

tccggcggac atcacagtga caagattaac aagtcagagt ctgtggtgta       950

tgcggatatc cgaaagaatt aagagaatac ctagaacata tcctcagcaa      1000

gaaacaaaac caaactggac tctcgtgcag aaaatgtagc ccattaccac      1050

atgtagcctt ggagacccag gcaaggacaa gtacacgtgt actcacagag      1100

ggagagaaag atgtgtacaa aggatatgta taaatattct atttagtcat      1150

cctgatatga ggagccagtg ttgcatgatg aaaagatggt atgattctac      1200

atatgtaccc attgtcttgc tgtttttgta ctttcttttc aggtcattta      1250

caattgggag atttcagaaa cattcctttc accatcattt agaaatggtt      1300

tgccttaatg gagacaatag cagatcctgt agtatttcca gtagacatgg      1350

ccttttaatc taagggctta agactgatta gtcttagcat ttactgtagt      1400

tggaggatgg agatgctatg atggaagcat acccagggtg gcctttagca      1450

cagtatcagt accatttatt tgtctgccgc ttttaaaaaa tacccattgg      1500

ctatgccact tgaaaacaat ttgagaagtt tttttgaagt ttttctcact      1550
```

aaaatatggg gcaattgtta gccttacatg ttgtgtagac ttactttaag 1600
tttgcaccct tgaaatgtgt catatcaatt tctggattca taatagcaag 1650
attagcaaag gataaatgcc gaaggtcact tcattctgga cacagttgga 1700
tcaatactga ttaagtagaa aatccaagct ttgcttgaga acttttgtaa 1750
cgtggagagt aaaaagtatc ggtttta 1777

<210> SEQ ID NO 42
<211> LENGTH: 269
<212> TYPE: PRT
<213> ORGANISM: Homo sapiens

<400> SEQUENCE: 42

Met Ala Ala Ser Ala Gly Ala Gly Ala Val Ile Ala Ala Pro Asp
1 5 10 15

Ser Arg Arg Trp Leu Trp Ser Val Leu Ala Ala Ala Leu Gly Leu
20 25 30

Leu Thr Ala Gly Val Ser Ala Leu Glu Val Tyr Thr Pro Lys Glu
35 40 45

Ile Phe Val Ala Asn Gly Thr Gln Gly Lys Leu Thr Cys Lys Phe
50 55 60

Lys Ser Thr Ser Thr Thr Gly Gly Leu Thr Ser Val Ser Trp Ser
65 70 75

Phe Gln Pro Glu Gly Ala Asp Thr Thr Val Ser Phe Phe His Tyr
80 85 90

Ser Gln Gly Gln Val Tyr Leu Gly Asn Tyr Pro Pro Phe Lys Asp
95 100 105

Arg Ile Ser Trp Ala Gly Asp Leu Asp Lys Lys Asp Ala Ser Ile
110 115 120

Asn Ile Glu Asn Met Gln Phe Ile His Asn Gly Thr Tyr Ile Cys
125 130 135

Asp Val Lys Asn Pro Pro Asp Ile Val Val Gln Pro Gly His Ile
140 145 150

Arg Leu Tyr Val Val Glu Lys Glu Asn Leu Pro Val Phe Pro Val
155 160 165

Trp Val Val Val Gly Ile Val Thr Ala Val Val Leu Gly Leu Thr
170 175 180

Leu Leu Ile Ser Met Ile Leu Ala Val Leu Tyr Arg Arg Lys Asn
185 190 195

Ser Lys Arg Asp Tyr Thr Gly Cys Ser Thr Ser Glu Ser Leu Ser
200 205 210

Pro Val Lys Gln Ala Pro Arg Lys Ser Pro Ser Asp Thr Glu Gly
215 220 225

Leu Val Lys Ser Leu Pro Ser Gly Ser His Gln Gly Pro Val Ile
230 235 240

Tyr Ala Gln Leu Asp His Ser Gly Gly His His Ser Asp Lys Ile
245 250 255

Asn Lys Ser Glu Ser Val Val Tyr Ala Asp Ile Arg Lys Asn
260 265

<210> SEQ ID NO 43
<211> LENGTH: 3554
<212> TYPE: DNA
<213> ORGANISM: Homo sapiens

<400> SEQUENCE: 43

```
gggactacaa gccgcgccgc gctgccgctg gcccctcagc aaccctcgac      50
atggcgctga ggcggccacc gcgactccgg ctctgcgctc ggctgcctga     100
cttcttcctg ctgctgcttt tcaggggctg cctgataggg gctgtaaatc     150
tcaaatccag caatcgaacc ccagtggtac aggaatttga aagtgtggaa     200
ctgtcttgca tcattacgga ttcgcagaca agtgacccca ggatcgagtg     250
gaagaaaatt caagatgaac aaaccacata tgtgtttttt gacaacaaaa     300
ttcagggaga cttggcgggt cgtgcagaaa tactggggaa gacatccctg     350
aagatctgga atgtgacacg gagagactca gccctttatc gctgtgaggt     400
cgttgctcga aatgaccgca aggaaattga tgagattgtg atcgagttaa     450
ctgtgcaagt gaagccagtg acccctgtct gtagagtgcc gaaggctgta     500
ccagtaggca agatggcaac actgcactgc caggagagtg agggccaccc     550
ccggcctcac tacagctggt atcgcaatga tgtaccactg cccacggatt     600
ccagagccaa tcccagattt cgcaattctt ctttccactt aaactctgaa     650
acaggcactt tggtgttcac tgctgttcac aaggacgact ctgggcagta     700
ctactgcatt gcttccaatg acgcaggctc agccaggtgt gaggagcagg     750
agatggaagt ctatgacctg aacattggcg gaattattgg gggggttctg     800
gttgtccttg ctgtactggc cctgatcacg ttgggcatct gctgtgcata     850
cagacgtggc tacttcatca acaataaaca ggatggagaa agttacaaga     900
acccagggaa accagatgga gttaactaca tccgcactga cgaggagggc     950
gacttcagac acaagtcatc gtttgtgatc tgagacccgc ggtgtggctg    1000
agagcgcaca gagcgcacgt gcacatacct ctgctagaaa ctcctgtcaa    1050
ggcagcgaga gctgatgcac tcggacagag ctagacactc attcagaagc    1100
ttttcgtttt ggccaaagtt gaccactact cttcttactc taacaagcca    1150
catgaataga agaattttcc tcaagatgga cccggtaaat ataaccacaa    1200
ggaagcgaaa ctgggtgcgt tcactgagtt gggttcctaa tctgtttctg    1250
gcctgattcc cgcatgagta ttagggtgat cttaaagagt ttgctcacgt    1300
aaacgcccgt gctgggccct gtgaagccag catgttcacc actggtcgtt    1350
cagcagccac gacagcacca tgtgagatgg cgaggtggct ggacagcacc    1400
agcagcgcat cccggcggga acccagaaaa ggcttcttac acagcagcct    1450
tacttcatcg gcccacagac accaccgcag tttcttctta aaggctctgc    1500
tgatcggtgt tgcagtgtcc attgtggaga agctttttgg atcagcattt    1550
tgtaaaaaca accaaaatca ggaaggtaaa ttggttgctg gaagagggat    1600
cttgcctgag gaaccctgct tgtccaacag ggtgtcagga tttaaggaaa    1650
accttcgtct taggctaagt ctgaaatggt actgaaatat gcttttctat    1700
gggtcttgtt tattttataa aattttacat ctaaattttt gctaaggatg    1750
tattttgatt attgaaaaga aaatttctat ttaaactgta aatatattgt    1800
catacaatgt taaataacct attttttaa aaaagttcaa cttaaggtag    1850
aagttccaag ctactagtgt taaattggaa aatatcaata attaagagta    1900
ttttacccaa ggaatcctct catggaagtt tactgtgatg ttccttttct    1950
cacacaagtt ttagcctttt tcacaaggga actcatactg tctacacatc    2000
```

```
agaccatagt tgcttaggaa acctttaaaa attccagtta agcaatgttg      2050
aaatcagttt gcatctcttc aaaagaaacc tctcaggtta gctttgaact      2100
gcctcttcct gagatgacta ggacagtctg tacccagagg ccacccagaa      2150
gccctcagat gtacatacac agatgccagt cagctcctgg ggttgcgcca      2200
ggcgcccccg ctctagctca ctgttgcctc gctgtctgcc aggaggccct      2250
gccatccttg ggccctggca gtggctgtgt cccagtgagc tttactcacg      2300
tggcccttgc ttcatccagc acagctctca ggtgggcact gcagggacac      2350
tggtgtcttc catgtagcgt cccagctttg ggctcctgta acagacctct      2400
ttttggttat ggatggctca caaaataggg cccccaatgc tattttttttt      2450
ttttaagttt gtttaattat ttgttaagat tgtctaaggc caaaggcaat      2500
tgcgaaatca agtctgtcaa gtacaataac atttttaaaa gaaaatggat      2550
cccactgttc ctctttgcca cagagaaagc acccagacgc cacaggctct      2600
gtcgcatttc aaaacaaacc atgatggagt ggcggccagt ccagcctttt      2650
aaagaacgtc aggtggagca gccaggtgaa aggcctggcg gggaggaaag      2700
tgaaacgcct gaatcaaaag cagttttcta attttgactt taaatttttc      2750
atccgccgga gacactgctc ccatttgtgg ggggacatta gcaacatcac      2800
tcagaagcct gtgttcttca agagcaggtg ttctcagcct cacatgccct      2850
gccgtgctgg actcaggact gaagtgctgt aaagcaagga gctgctgaga      2900
aggagcactc cactgtgtgc ctggagaatg gctctcacta ctcaccttgt      2950
ctttcagctt ccagtgtctt gggtttttta tactttgaca gcttttttttt      3000
aattgcatac atgagactgt gttgactttt tttagttatg tgaaacactt      3050
tgccgcaggc cgcctggcag aggcaggaaa tgctccagca gtggctcagt      3100
gctccctggt gtctgctgca tggcatcctg gatgcttagc atgcaagttc      3150
cctccatcat tgccaccttg gtagagaggg atggctcccc accctcagcg      3200
ttggggattc acgctccagc ctccttcttg gttgtcatag tgatagggta      3250
gccttattgc cccctcttct tataccctaa aaccttctac actagtgcca      3300
tgggaaccag gtctgaaaaa gtagagagaa gtgaaagtag agtctgggaa      3350
gtagctgcct ataactgaga ctagacggaa aaggaatact cgtgtatttt      3400
aagatatgaa tgtgactcaa gactcgaggc cgatacgagg ctgtgattct      3450
gcctttggat ggatgttgct gtacacagat gctacagact tgtactaaca      3500
caccgtaatt tggcatttgt ttaacctcat ttataaaagc ttcaaaaaaa      3550
ccca                                                        3554
```

<210> SEQ ID NO 44
<211> LENGTH: 310
<212> TYPE: PRT
<213> ORGANISM: Homo sapiens

<400> SEQUENCE: 44

```
Met Ala Leu Arg Arg Pro Pro Arg Leu Arg Leu Cys Ala Arg Leu
  1               5                  10                  15

Pro Asp Phe Phe Leu Leu Leu Leu Phe Arg Gly Cys Leu Ile Gly
                 20                  25                  30

Ala Val Asn Leu Lys Ser Ser Asn Arg Thr Pro Val Val Gln Glu
```

35 40 45

Phe Glu Ser Val Glu Leu Ser Cys Ile Ile Thr Asp Ser Gln Thr
50 55 60

Ser Asp Pro Arg Ile Glu Trp Lys Lys Ile Gln Asp Glu Gln Thr
65 70 75

Thr Tyr Val Phe Phe Asp Asn Lys Ile Gln Gly Asp Leu Ala Gly
80 85 90

Arg Ala Glu Ile Leu Gly Lys Thr Ser Leu Lys Ile Trp Asn Val
95 100 105

Thr Arg Arg Asp Ser Ala Leu Tyr Arg Cys Glu Val Val Ala Arg
110 115 120

Asn Asp Arg Lys Glu Ile Asp Glu Ile Val Ile Glu Leu Thr Val
125 130 135

Gln Val Lys Pro Val Thr Pro Val Cys Arg Val Pro Lys Ala Val
140 145 150

Pro Val Gly Lys Met Ala Thr Leu His Cys Gln Glu Ser Glu Gly
155 160 165

His Pro Arg Pro His Tyr Ser Trp Tyr Arg Asn Asp Val Pro Leu
170 175 180

Pro Thr Asp Ser Arg Ala Asn Pro Arg Phe Arg Asn Ser Ser Phe
185 190 195

His Leu Asn Ser Glu Thr Gly Thr Leu Val Phe Thr Ala Val His
200 205 210

Lys Asp Asp Ser Gly Gln Tyr Tyr Cys Ile Ala Ser Asn Asp Ala
215 220 225

Gly Ser Ala Arg Cys Glu Glu Gln Glu Met Glu Val Tyr Asp Leu
230 235 240

Asn Ile Gly Gly Ile Ile Gly Gly Val Leu Val Val Leu Ala Val
245 250 255

Leu Ala Leu Ile Thr Leu Gly Ile Cys Cys Ala Tyr Arg Arg Gly
260 265 270

Tyr Phe Ile Asn Asn Lys Gln Asp Gly Glu Ser Tyr Lys Asn Pro
275 280 285

Gly Lys Pro Asp Gly Val Asn Tyr Ile Arg Thr Asp Glu Glu Gly
290 295 300

Asp Phe Arg His Lys Ser Ser Phe Val Ile
305 310

<210> SEQ ID NO 45
<211> LENGTH: 3884
<212> TYPE: DNA
<213> ORGANISM: Homo sapiens

<400> SEQUENCE: 45
gccggctagg gcgccggagc cgcacgcagc cgcggggctc cgagaggcgc 50
gcactggggc tgggactgcg cggcgccgcc gctgcgagcg ccactgagcg 100
gtcgcgcaac ttcggaggca cagcgccgga gccaggcgag cgctcagaga 150
cccggagcca gaggggcgcg ccggagcctc gttcgagagc cggcgccagg 200
cacccaccgc gctccgagtg ccaggcggcc ctccgcgcag cgtggcttcc 250
gctgccccca cggaaggcac gggctggcgc tgccgggcgc cggggaggac 300
ggcgaggagg aggcggcggc ggcggagacg gcggcggcga gactggggcc 350
agggagacag ccctggggga gaggcgcccg aaccaggccg cgggagcatg 400

-continued

```
ggggcccgga gcggagctcg gggcgcgctg ctgctggcac tgctgctctg         450
ctgggacccg aggctgagcc aagcaggcac tgattctggc agcgaggtgc         500
tccctgactc cttcccgtca gcgccagcag agccgctgcc ctacttcctg         550
caggagccac aggacgccta cattgtgaag aacaagcctg tggagctccg         600
ctgccgcgcc ttccccgcca cacagatcta cttcaagtgc aacggcgagt         650
gggtcagcca gaacgaccac gtcacacagg aaggcctgga tgaggccacc         700
ggcctgcggg tgcgcgaggt gcagatcgag gtgtcgcggc agcaggtgga         750
ggagctcttt gggctggagg attactggtg ccagtgcgtg gcctggagct         800
ccgcaggcac caccaagagt cgccgagcct acgtccgcat cgcctacctg         850
cgcaagaact tcgatcagga gcctctgggc aaggaggtgc ccctggacca         900
tgaggttctc ctgcagtgcc gcccgccgga gggggtgcct gtggccgagg         950
tggaatggct caagaatgag gatgtcatcg accccaccca ggacaccaac        1000
ttcctgctca ccatcgacca caacctcatc atccgccagg cccgcctgtc        1050
ggacactgcc aactatacct gcgtggccaa gaacatcgtg gccaaacgcc        1100
ggagcaccac tgccaccgtc atcgtctacg tgaatggcgg ctggtccagc        1150
tgggcagagt ggtcaccctg ctccaaccgc tgtggccgag gctggcagaa        1200
gcgcacccgg acctgcacca accccgctcc actcaacgga ggggccttct        1250
gcgagggcca ggcattccag aagaccgcct gcaccaccat ctgcccagtc        1300
gatggggcgt ggacggagtg gagcaagtgg tcagcctgca gcactgagtg        1350
tgcccactgg cgtagccgcg agtgcatggc gcccccaccc cagaacggag        1400
gccgtgactg cagcgggacg ctgctcgact ctaagaactg cacagatggg        1450
ctgtgcatgc aaaataagaa aactctaagc gaccccaaca gccacctgct        1500
ggaggcctca ggggatgcgg cgctgtatgc ggggctcgtg gtggccatct        1550
tcgtggtcgt ggcaatcctc atggcggtgg gggtggtggt gtaccgccgc        1600
aactgccgtg acttcgacac agacatcact gactcatctg ctgccctgac        1650
tggtggtttc caccccgtca actttaagac ggcaaggccc agcaacccgc        1700
agctcctaca cccctctgtg cctcctgacc tgacagccag cgccggcatc        1750
taccgcggac ccgtgtatgc cctgcaggac tccaccgaca aaatccccat        1800
gaccaactct cctctgctgg acccccttacc cagccttaag gtcaaggtct        1850
acagctccag caccacgggc tctgggccag gcctggcaga tggggctgac        1900
ctgctggggg tcttgccgcc tggcacatac cctagcgatt tcgcccggga        1950
cacccacttc ctgcacctgc gcagcgccag cctcggttcc cagcagctct        2000
tgggcctgcc ccgagaccca gggagcagcg tcagcggcac ctttggctgc        2050
ctgggtggga ggctcagcat ccccggcaca ggggtcagct tgctggtgcc        2100
caatggagcc attccccagg gcaagttcta cgagatgtat ctactcatca        2150
acaaggcaga aagtaccctc ccgctttcag aagggaccca gacagtattg        2200
agcccctcgg tgacctgtgg acccacaggc ctcctgctgt gccgccccgt        2250
catcctcacc atgccccact gtgccgaagt cagtgcccgt gactggatct        2300
ttcagctcaa gacccaggcc caccagggcc actgggagga ggtggtgacc        2350
ctggatgagg agaccctgaa cacaccctgc tactgccagc tggagcccag        2400
```

-continued ggcctgtcac atcctgctgg accagctggg cacctacgtg ttcacgggcg 2450
agtcctattc ccgctcagca gtcaagcggc tccagctggc cgtcttcgcc 2500
cccgccctct gcacctccct ggagtacagc ctccgggtct actgcctgga 2550
ggacacgcct gtagcactga aggaggtgct ggagctggag cggactctgg 2600
gcggatactt ggtggaggag ccgaaaccgc taatgttcaa ggacagttac 2650
cacaacctgc gcctctccct ccatgacctc ccccatgccc attggaggag 2700
caagctgctg gccaaatacc aggagatccc cttctatcac atttggagtg 2750
gcagccagaa ggccctccac tgcactttca ccctggagag gcacagcttg 2800
gcctccacag agctcacctg caagatctgc gtgcggcaag tggaaggggga 2850 gggccagata ttccagctgc ataccactct ggcagagaca cctgctggct 2900
ccctggacac tctctgctct gcccctggca gcactgtcac cacccagctg 2950
ggaccttatg ccttcaagat cccactgtcc atccgccaga agatatgcaa 3000
cagcctagat gcccccaact cacggggcaa tgactggcgg atgttagcac 3050
agaagctctc tatggaccgg tacctgaatt actttgccac caaagcgagc 3100
cccacgggtg tgatcctgga cctctgggaa gctctgcagc aggacgatgg 3150
ggacctcaac agcctggcga gtgccttgga ggagatgggc aagagtgaga 3200
tgctggtggc tgtggccacc gacggggact gctgagcctc ctgggacagc 3250
gggctggcag ggactggcag gaggcaggtg cagggaggcc tggggcagcc 3300
tcctgatggg gatgtttggc ctctgcttcc tcccagttca cagccagagt 3350
tgcctctcct cctcctcttc cccaaccccc agaccatgac cagccttaga 3400
aaatccatgt actctgttgt tagagggccc agagttcctt ctccaccccc 3450
gctctctctc tcttggcctg agatctctgt gcaggaacca agatggggct 3500
gaagcctctg gaggcagttg gttgggggcg ggcaggcagg aggccctccc 3550
tccacccccc caccctcagc ccggcaactt ctgggttccg tgggttttag 3600
ttccgttctt cgttttcttc ctccgttatt gatttctcct ttctccctaa 3650 gccccccttct gcttccacgc ccttttcctc tttgaagagt caagtacaat 3700
tcagacaaac tgctttctcc tgtccaaaag caaaaaggca aaggaaagaa 3750
agaaagcttc agaccgctag taaggctcaa agaagaagaa aaacaccaaa 3800
accacaaggg aaaagaaaaa cccagtttct taggaaacgc aaacgattta 3850
ttatccagat tatttggata agtccttttt aaaa 3884

<210> SEQ ID NO 46
<211> LENGTH: 945
<212> TYPE: PRT
<213> ORGANISM: Homo sapiens

<400> SEQUENCE: 46

Met Gly Ala Arg Ser Gly Ala Arg Gly Ala Leu Leu Leu Ala Leu
1 5 10 15

Leu Leu Cys Trp Asp Pro Arg Leu Ser Gln Ala Gly Thr Asp Ser
20 25 30

Gly Ser Glu Val Leu Pro Asp Ser Phe Pro Ser Ala Pro Ala Glu
35 40 45

Pro Leu Pro Tyr Phe Leu Gln Glu Pro Gln Asp Ala Tyr Ile Val
50 55 60

```
Lys Asn Lys Pro Val Glu Leu Arg Cys Arg Ala Phe Pro Ala Thr
                65                  70                  75

Gln Ile Tyr Phe Lys Cys Asn Gly Glu Trp Val Ser Gln Asn Asp
                80                  85                  90

His Val Thr Gln Glu Gly Leu Asp Glu Ala Thr Gly Leu Arg Val
                95                  100                 105

Arg Glu Val Gln Ile Glu Val Ser Arg Gln Gln Val Glu Glu Leu
                110                 115                 120

Phe Gly Leu Glu Asp Tyr Trp Cys Gln Cys Val Ala Trp Ser Ser
                125                 130                 135

Ala Gly Thr Thr Lys Ser Arg Arg Ala Tyr Val Arg Ile Ala Tyr
                140                 145                 150

Leu Arg Lys Asn Phe Asp Gln Glu Pro Leu Gly Lys Glu Val Pro
                155                 160                 165

Leu Asp His Glu Val Leu Leu Gln Cys Arg Pro Pro Glu Gly Val
                170                 175                 180

Pro Val Ala Glu Val Glu Trp Leu Lys Asn Glu Asp Val Ile Asp
                185                 190                 195

Pro Thr Gln Asp Thr Asn Phe Leu Leu Thr Ile Asp His Asn Leu
                200                 205                 210

Ile Ile Arg Gln Ala Arg Leu Ser Asp Thr Ala Asn Tyr Thr Cys
                215                 220                 225

Val Ala Lys Asn Ile Val Ala Lys Arg Arg Ser Thr Thr Ala Thr
                230                 235                 240

Val Ile Val Tyr Val Asn Gly Gly Trp Ser Ser Trp Ala Glu Trp
                245                 250                 255

Ser Pro Cys Ser Asn Arg Cys Gly Arg Gly Trp Gln Lys Arg Thr
                260                 265                 270

Arg Thr Cys Thr Asn Pro Ala Pro Leu Asn Gly Gly Ala Phe Cys
                275                 280                 285

Glu Gly Gln Ala Phe Gln Lys Thr Ala Cys Thr Thr Ile Cys Pro
                290                 295                 300

Val Asp Gly Ala Trp Thr Glu Trp Ser Lys Trp Ser Ala Cys Ser
                305                 310                 315

Thr Glu Cys Ala His Trp Arg Ser Arg Glu Cys Met Ala Pro Pro
                320                 325                 330

Pro Gln Asn Gly Gly Arg Asp Cys Ser Gly Thr Leu Leu Asp Ser
                335                 340                 345

Lys Asn Cys Thr Asp Gly Leu Cys Met Gln Asn Lys Lys Thr Leu
                350                 355                 360

Ser Asp Pro Asn Ser His Leu Leu Glu Ala Ser Gly Asp Ala Ala
                365                 370                 375

Leu Tyr Ala Gly Leu Val Val Ala Ile Phe Val Val Val Ala Ile
                380                 385                 390

Leu Met Ala Val Gly Val Val Val Tyr Arg Arg Asn Cys Arg Asp
                395                 400                 405

Phe Asp Thr Asp Ile Thr Asp Ser Ser Ala Ala Leu Thr Gly Gly
                410                 415                 420

Phe His Pro Val Asn Phe Lys Thr Ala Arg Pro Ser Asn Pro Gln
                425                 430                 435

Leu Leu His Pro Ser Val Pro Pro Asp Leu Thr Ala Ser Ala Gly
                440                 445                 450

Ile Tyr Arg Gly Pro Val Tyr Ala Leu Gln Asp Ser Thr Asp Lys
                455                 460                 465
```

Ile Pro Met Thr Asn Ser Pro Leu Leu Asp Pro Leu Pro Ser Leu
470 475 480

Lys Val Lys Val Tyr Ser Ser Ser Thr Thr Gly Ser Gly Pro Gly
485 490 495

Leu Ala Asp Gly Ala Asp Leu Leu Gly Val Leu Pro Pro Gly Thr
500 505 510

Tyr Pro Ser Asp Phe Ala Arg Asp Thr His Phe Leu His Leu Arg
515 520 525

Ser Ala Ser Leu Gly Ser Gln Gln Leu Leu Gly Leu Pro Arg Asp
530 535 540

Pro Gly Ser Ser Val Ser Gly Thr Phe Gly Cys Leu Gly Gly Arg
545 550 555

Leu Ser Ile Pro Gly Thr Gly Val Ser Leu Leu Val Pro Asn Gly
560 565 570

Ala Ile Pro Gln Gly Lys Phe Tyr Glu Met Tyr Leu Leu Ile Asn
575 580 585

Lys Ala Glu Ser Thr Leu Pro Leu Ser Glu Gly Thr Gln Thr Val
590 595 600

Leu Ser Pro Ser Val Thr Cys Gly Pro Thr Gly Leu Leu Leu Cys
605 610 615

Arg Pro Val Ile Leu Thr Met Pro His Cys Ala Glu Val Ser Ala
620 625 630

Arg Asp Trp Ile Phe Gln Leu Lys Thr Gln Ala His Gln Gly His
635 640 645

Trp Glu Glu Val Val Thr Leu Asp Glu Glu Thr Leu Asn Thr Pro
650 655 660

Cys Tyr Cys Gln Leu Glu Pro Arg Ala Cys His Ile Leu Leu Asp
665 670 675

Gln Leu Gly Thr Tyr Val Phe Thr Gly Glu Ser Tyr Ser Arg Ser
680 685 690

Ala Val Lys Arg Leu Gln Leu Ala Val Phe Ala Pro Ala Leu Cys
695 700 705

Thr Ser Leu Glu Tyr Ser Leu Arg Val Tyr Cys Leu Glu Asp Thr
710 715 720

Pro Val Ala Leu Lys Glu Val Leu Glu Leu Glu Arg Thr Leu Gly
725 730 735

Gly Tyr Leu Val Glu Glu Pro Lys Pro Leu Met Phe Lys Asp Ser
740 745 750

Tyr His Asn Leu Arg Leu Ser Leu His Asp Leu Pro His Ala His
755 760 765

Trp Arg Ser Lys Leu Leu Ala Lys Tyr Gln Glu Ile Pro Phe Tyr
770 775 780

His Ile Trp Ser Gly Ser Gln Lys Ala Leu His Cys Thr Phe Thr
785 790 795

Leu Glu Arg His Ser Leu Ala Ser Thr Glu Leu Thr Cys Lys Ile
800 805 810

Cys Val Arg Gln Val Glu Gly Glu Gly Gln Ile Phe Gln Leu His
815 820 825

Thr Thr Leu Ala Glu Thr Pro Ala Gly Ser Leu Asp Thr Leu Cys
830 835 840

Ser Ala Pro Gly Ser Thr Val Thr Thr Gln Leu Gly Pro Tyr Ala
845 850 855

Phe Lys Ile Pro Leu Ser Ile Arg Gln Lys Ile Cys Asn Ser Leu

```
                860                 865                 870

Asp Ala Pro Asn Ser Arg Gly Asn Asp Trp Arg Met Leu Ala Gln
                875                 880                 885

Lys Leu Ser Met Asp Arg Tyr Leu Asn Tyr Phe Ala Thr Lys Ala
                890                 895                 900

Ser Pro Thr Gly Val Ile Leu Asp Leu Trp Glu Ala Leu Gln Gln
                905                 910                 915

Asp Asp Gly Asp Leu Asn Ser Leu Ala Ser Ala Leu Glu Glu Met
                920                 925                 930

Gly Lys Ser Glu Met Leu Val Ala Val Ala Thr Asp Gly Asp Cys
                935                 940                 945


<210> SEQ ID NO 47
<211> LENGTH: 872
<212> TYPE: DNA
<213> ORGANISM: Homo sapiens

<400> SEQUENCE: 47

gctgacaatc cccttgacgt tctatcccgg aagctccacc tggggcccaa             50

tgttgggcgt gatgttcctc gcctgtctct gcctggaaaa ctggtcttcc            100

caagctccac tggcagccac ttctccatgt tgggcatcgg agacatcgtt            150

atgcctggtc tcctactatg ctttgtcctt cgctatgaca actacaaaaa            200

gcaagccagt ggggactcct gtggggcccc tggacctgcc aacatctccg            250

ggcgcatgca gaaggtctcc tactctcact gcaccctcat cggatacttt            300

gtaggcctgc tcactgctac tgtggcgtct cgcattcacc gggccgccca            350

gcccgccctt ctctatttgg tgccatttac tttattgcca ctcctcacga            400

tggcctattt aaagggcgac ctccggcgga tgtggtctga gcctttccac            450

tccaagtcca gcagctcccg attcctggaa gtatgatgga tcacgtggaa            500

agtgaccaga tggccgtcat agtccttttc tctcaactca tggtttgttt            550

cctcttagag ctggcctggt actcagaaat gtacctgtgt ttaaggaact            600

gccgtgtgac tggatttggc attgaaaggg agctcgtttg caggagagag            650

gtgctggagc cctgtttggt tccttctctt cctgcggatg tagaggtggg            700

gccccttcca agagggacag gcctctcccc agcgcgcctt cctcccacgt            750

ttttatggat ctgcaccaga ctgttacctt ctgggggaga tggagatttg            800

actgtttaaa aactgaaaac agcgaggagt ctttctagaa cttttgaaca            850

ctaaaaggat gaaaaaatta  gc                                         872


<210> SEQ ID NO 48
<211> LENGTH: 108
<212> TYPE: PRT
<213> ORGANISM: Homo sapiens

<400> SEQUENCE: 48

Met Met Asp His Val Glu Ser Asp Gln Met Ala Val Ile Val Leu
  1               5                  10                  15

Phe Ser Gln Leu Met Val Cys Phe Leu Leu Glu Leu Ala Trp Tyr
                 20                  25                  30

Ser Glu Met Tyr Leu Cys Leu Arg Asn Cys Arg Val Thr Gly Phe
                 35                  40                  45

Gly Ile Glu Arg Glu Leu Val Cys Arg Arg Glu Val Leu Glu Pro
                 50                  55                  60
```

Cys Leu Val Pro Ser Leu Pro Ala Asp Val Glu Val Gly Pro Leu
65 70 75

Pro Arg Gly Thr Gly Leu Ser Pro Ala Arg Leu Pro Pro Thr Phe
80 85 90

Leu Trp Ile Cys Thr Arg Leu Leu Pro Ser Gly Gly Asp Gly Asp
95 100 105

Leu Thr Val

<210> SEQ ID NO 49
<211> LENGTH: 3479
<212> TYPE: DNA
<213> ORGANISM: Homo sapiens

<400> SEQUENCE: 49
cggacgcgtg gggaagatgg gataaataat tctgtcacac gtgccctggc 50
ctctggagct cagctgccag tccacgtcta gggaatctta gcatctggga 100
ccaagacact ttacagcaat catcaccctt tgcagaggag gtgagctcac 150
caggactcat ctgccatttc agaccttttg ctgctacctg ccaggtggcc 200
cccactgctg acgagagatg gtggatctct cagtctcccc ggactccttg 250
aagccagtat cgctgaccag cagtcttgtc ttcctcatgc acctcctcct 300
ccttcagcct ggggagccga gctcagaggt caaggtgcta ggccctgagt 350
atcccatcct ggccctcgtc ggggaggagg tggagttccc gtgccaccta 400
tggccacagc tggatgccca gcaaatggag atccgctggt tccggagtca 450
gaccttcaat gtggtacacc tgtaccagga gcagcaggag ctccctggca 500
ggcagatgcc ggcgttccgg aacaggacca agttggtcaa ggacgacatc 550
gcctatggca gcgtggtcct gcagcttcac agcatcatcc cctctgacaa 600
gggcacatat ggctgccgct tccactccga caacttctct ggcgaagctc 650
tctgggaact ggaggtagca gggctgggct cagaccctca cctctccctt 700
gagggcttca aggaaggagg cattcagctg aggctcagat ccagtggctg 750
gtaccccaag cctaaggttc agtggagaga ccaccaggga cagtgcctgc 800
ctccagagtt tgaagccatc gtctgggatg cccaggacct gttcagtctg 850
gaaacatctg tggttgtccg agcgggagcc ctcagcaatg tgtccgtctc 900
catccagaat ctcctcttga gccagaagaa agagttggtg gtccagatag 950
cagacgtgtt cgtacccgga gcctctgcgt ggaagagcgc gttcgtcgcg 1000
accctgccgc tgctgttggt cctcgcggcg ctggcgctgg gcgtcctccg 1050
gaagcagcgg agaagccgag aaaagctgag gaagcaggcg gagaagagac 1100
aagagaaact cactgcagag ctggaaaagc ttcagacaga gcttgactgg 1150
agacgggctg aaggccaggc tgagtggaga gcagcccaaa aatatgcagt 1200
ggatgtgacg ctggacccgg cctcggcgca ccccagcctg gaggtgtcgg 1250
aggatggcaa gagcgtgtct tcccgcgggg cgccgccagg cccggcgcct 1300
ggccacccgc agcggttctc ggagcagacg tgcgcgctga gcctggagcg 1350
gttctccgcc ggccgccact actgggaggt gcacgtgggc cgccgcagcc 1400
gctggttcct gggcgcctgc ctggccgcgg tgccgcgcgc ggggcctgcg 1450
cgcctgagcc ctgcggccgg ctactgggtg ctggggctgt ggaacggctg 1500

-continued

```
cgagtacttc gtcctggccc cgcaccgcgt cgcgctcacc ctgcgcgtgc    1550
ccccgcggcg cctgggcgtc ttcctggact acgaggccgg agagctgtcc    1600
ttcttcaacg tgtccgacgg ctcccacatc ttcaccttcc acgacacctt    1650
ctcgggcgcg ctctgtgcgt acttcaggcc cagggcccac gacggcggcg    1700
aacatccgga tcccctgacc atctgcccgc tgccggttag agggacgggc    1750
gtccccgaag agaacgacag tgacacctgg ctacagccct atgagcccgc    1800
ggaccccgcc ctggactggt ggtgaggcgc cctcgtggcc gcgggactgg    1850
ccccgggggg ccccctggat cccaggccag cgctttgctc tcctgctccg    1900
tctgaaggga gcaggtgcac cagccaaaat gtcagcgagg gggacaaaga    1950
gagggacctt tgcctacgta gatgtgtatg tgtagtgcga ttttcttcaa    2000
ggaaaggaga caagtccaaa gctcgtttgt ggattgtggg actgagcgaa    2050
ggagtacaaa tatatccacg tcgctcagag ctggggtgct cacggtgggc    2100
ggtgggcaag aagccagcat ggaagaaaga agggagaaaa ctttggtgac    2150
tgccttagag ggatcagtta atttgtatag ttttatattt tttgtatatg    2200
tttgctagct ctaaaaaggt cgagatgcaa taacacttcg taagcaacga    2250
gttcacctaa gtaaggctca gatcctagtt ttaaaaacca tttcccatta    2300
aaatgaagtt ggaggaacag ctgcttctga gccggggcaa aaatttcaag    2350
gtgagcctgg agcattgtgt gtggtgaagt aaaataaagg ctcaaaacgt    2400
gacggcaacc cggcaaaagg gtagggagcc aggccgaagg ggcctcactg    2450
accaattgtg ggacaatttg aacatcagga tgaataatga caggagagat    2500
tataacacac tgaataaaaa cataatccat gagttcatgc tgatactcaa    2550
atttcttttt aaaaaggaga aacaggaagg tttcttttgg aggtgaaatc    2600
taattattgg tgagagtctt ggagaacagg ctgtttccag tctcaaagca    2650
gtaaccttat acactactta taagtttgaa aggggaaagg ttacctttac    2700
aatggagaca tctaccagat catccaagtg attaaattta acatcatcaa    2750
tgatgggacc aaggacatta ttagtttgac aactggggaa agaagtgttc    2800
ttcacccccct acccccaaga cattctctct gtcggccagg ctggagtgca    2850
gcctcaacct cctgggccca agtgatcctc ccacctcagc acacaacacc    2900
atgcccaatt ttaagtgcgt tatagagacg ggggtctcac tttgttaccc    2950
aggctggtct caaactcctg cgctcaagca atcctcccac ctgggcctcc    3000
caaaatgctg ggtgtacagg catgagccgc tgtgcctggc ttcattttca    3050
gagtgagaca tttgtactgt ggctatgtag gagaacattc ttgttcttag    3100
caaacatact gaagttttta gatattaatt accacagtgt ctgccactga    3150
atttccagtg actaagtgga aaaatataaa acatatgaat ataaagaaag    3200
aaagagacaa gtcaaatgta gtaaaatgac aacacttggt gactctaggt    3250
gactggtcga cagatgttca ttgtactatc aatgtggctt tgctgtgggt    3300
ttgaaatttt gcaaactaag agttgggtgg cggggagaag gatacaccaa    3350
aaaactaagt gattatcttt ggatgggaaa atgtttggta attgcattct    3400
taaaatgtct tctttgtatt ttttaatgtt caataatgta tatgtatcag    3450
ttctgtaata aaggggaaaa  cacttttca                           3479
```

<210> SEQ ID NO 50
<211> LENGTH: 535
<212> TYPE: PRT
<213> ORGANISM: Homo sapiens

<400> SEQUENCE: 50

```
Met Val Asp Leu Ser Val Ser Pro Asp Ser Leu Lys Pro Val Ser
  1               5                  10                  15

Leu Thr Ser Ser Leu Val Phe Leu Met His Leu Leu Leu Leu Gln
                 20                  25                  30

Pro Gly Glu Pro Ser Ser Glu Val Lys Val Leu Gly Pro Glu Tyr
                 35                  40                  45

Pro Ile Leu Ala Leu Val Gly Glu Glu Val Glu Phe Pro Cys His
                 50                  55                  60

Leu Trp Pro Gln Leu Asp Ala Gln Gln Met Glu Ile Arg Trp Phe
                 65                  70                  75

Arg Ser Gln Thr Phe Asn Val Val His Leu Tyr Gln Glu Gln Gln
                 80                  85                  90

Glu Leu Pro Gly Arg Gln Met Pro Ala Phe Arg Asn Arg Thr Lys
                 95                 100                 105

Leu Val Lys Asp Asp Ile Ala Tyr Gly Ser Val Val Leu Gln Leu
                110                 115                 120

His Ser Ile Ile Pro Ser Asp Lys Gly Thr Tyr Gly Cys Arg Phe
                125                 130                 135

His Ser Asp Asn Phe Ser Gly Glu Ala Leu Trp Glu Leu Glu Val
                140                 145                 150

Ala Gly Leu Gly Ser Asp Pro His Leu Ser Leu Glu Gly Phe Lys
                155                 160                 165

Glu Gly Gly Ile Gln Leu Arg Leu Arg Ser Ser Gly Trp Tyr Pro
                170                 175                 180

Lys Pro Lys Val Gln Trp Arg Asp His Gln Gly Gln Cys Leu Pro
                185                 190                 195

Pro Glu Phe Glu Ala Ile Val Trp Asp Ala Gln Asp Leu Phe Ser
                200                 205                 210

Leu Glu Thr Ser Val Val Val Arg Ala Gly Ala Leu Ser Asn Val
                215                 220                 225

Ser Val Ser Ile Gln Asn Leu Leu Leu Ser Gln Lys Lys Glu Leu
                230                 235                 240

Val Val Gln Ile Ala Asp Val Phe Val Pro Gly Ala Ser Ala Trp
                245                 250                 255

Lys Ser Ala Phe Val Ala Thr Leu Pro Leu Leu Leu Val Leu Ala
                260                 265                 270

Ala Leu Ala Leu Gly Val Leu Arg Lys Gln Arg Arg Ser Arg Glu
                275                 280                 285

Lys Leu Arg Lys Gln Ala Glu Lys Arg Gln Glu Lys Leu Thr Ala
                290                 295                 300

Glu Leu Glu Lys Leu Gln Thr Glu Leu Asp Trp Arg Arg Ala Glu
                305                 310                 315

Gly Gln Ala Glu Trp Arg Ala Ala Gln Lys Tyr Ala Val Asp Val
                320                 325                 330

Thr Leu Asp Pro Ala Ser Ala His Pro Ser Leu Glu Val Ser Glu
                335                 340                 345

Asp Gly Lys Ser Val Ser Ser Arg Gly Ala Pro Pro Gly Pro Ala
                350                 355                 360
```

Pro Gly His Pro Gln Arg Phe Ser Glu Gln Thr Cys Ala Leu Ser
365 370 375

Leu Glu Arg Phe Ser Ala Gly Arg His Tyr Trp Glu Val His Val
380 385 390

Gly Arg Arg Ser Arg Trp Phe Leu Gly Ala Cys Leu Ala Ala Val
395 400 405

Pro Arg Ala Gly Pro Ala Arg Leu Ser Pro Ala Ala Gly Tyr Trp
410 415 420

Val Leu Gly Leu Trp Asn Gly Cys Glu Tyr Phe Val Leu Ala Pro
425 430 435

His Arg Val Ala Leu Thr Leu Arg Val Pro Pro Arg Arg Leu Gly
440 445 450

Val Phe Leu Asp Tyr Glu Ala Gly Glu Leu Ser Phe Phe Asn Val
455 460 465

Ser Asp Gly Ser His Ile Phe Thr Phe His Asp Thr Phe Ser Gly
470 475 480

Ala Leu Cys Ala Tyr Phe Arg Pro Arg Ala His Asp Gly Gly Glu
485 490 495

His Pro Asp Pro Leu Thr Ile Cys Pro Leu Pro Val Arg Gly Thr
500 505 510

Gly Val Pro Glu Glu Asn Asp Ser Asp Thr Trp Leu Gln Pro Tyr
515 520 525

Glu Pro Ala Asp Pro Ala Leu Asp Trp Trp
530 535

<210> SEQ ID NO 51
<211> LENGTH: 1840
<212> TYPE: DNA
<213> ORGANISM: Homo sapiens

<400> SEQUENCE: 51
gtgggccgcc cctgctgctg ccgtccatgc tgatgtttgc ggtgatcgtg 50
gcctccagcg ggctgctgct catgatcgag cggggcatcc tggccgagat 100
gaagcccctg cccctgcacc cgcccggccg cgagggcaca gcctggcgcg 150
ggaaagcccc caagcctggg ggcctgtccc tcagggctgg ggacgcggac 200
ttgcaagtgc ggcaggacgt ccggaacagg accctgcggg cggtgtgcgg 250
acagccaggc atgccccggg acccctggga cttgccggtg gggcagcggc 300
gcaccctgct gcgccacatc ctcgtaagtg accgttaccg cttcctctac 350
tgctacgtcc ccaaggtggc ctgctctaac tggaagcggg tgatgaaggt 400
gctggcaggc gtcctggaca gcgtggacgt ccgcctcaag atggaccacc 450
gcagtgacct ggtgttcctg gccgacctgc ggcctgagga gattcgctac 500
cgcctgcagc actactttaa gttcctgttt gtgcgggagc ccttggaacg 550
cctcctctct gcctaccgca acaagtttgg cgagatccga gagtaccagc 600
aacgctatgg ggctgagata gtgaggcggt acagggctgg agcggggccc 650
agccctgcag gcgacgatgt cacattcccc gagttcctga gatacctggt 700
ggatgaggac cctgagcgca tgaatgagca ttggatgccc gtgtaccacc 750
tgtgccagcc ttgtgccgtg cactatgact ttgtgggctc ctatgagagg 800
ctggaggctg atgcaaatca ggtgctggag tgggtacggg caccacctca 850
cgtccgattt ccagctcgcc aggcctggta ccggccagcc agccccgaaa 900

```
gcctgcatta ccacttgtgc agtgcccccc gggccctgct gcaggatgtg          950

ctgcctaagt atatcctgga cttctccctc tttgcctacc cactgcctaa         1000

tgtcaccaag gaggcgtgtc agcagtgacc atgggtgtgg ggccagcagc         1050

tggtggggac tggtttcaac gccagctttc tgtgcttctg cctgtcattc         1100

ggagaaactc tggctctggg gcttggggct tctcaggatc ctggatggca         1150

gagactgccc tcagaagttc cttgtccagg gtgggcaccc acagtgactc         1200

agaggacagg gctaggcagg agacctgctg ctcctcattg gggggatctc         1250

ttgggggggca gacaccagtt tgccaatgaa gcaacacatc tgatctaaag        1300

actggctcca gaccccgggc tgccaggatt atgcagtcca cttggtctac         1350

cttaatttaa cctgtggcca aactcagaga tggtaccagc caggggcaag         1400

catgaccaga gccagggacc ctgtggctct gatcccccat ttatccaccc         1450

catgtgcctc aggactagag tgagcaatca taccttataa atgacttttg         1500

tgcctttctg ctccagtctc aaaatttcct acacctgcca gttctttaca         1550

tttttccaag gaaaggaaaa cggaagcagg gttcttgcct ggtagctcca         1600

ggacccagct ctgcaggcac ccaaagaccc tctgtgccca gcctcttcct         1650

tgagttctcg gaacctcctc cctaattctc ccttccttcc ccacaaggcc         1700

tttgaggttg tgactgtggc tggtatatct ggctgccatt tttctgatgc         1750

atttatttaa aatttgtact ttttgataga acccttgtaa gggctttgtt         1800

ttcctaatag ctgacttttt aataaagcag ttttatatat                    1840
```

<210> SEQ ID NO 52
<211> LENGTH: 333
<212> TYPE: PRT
<213> ORGANISM: Homo sapiens

<400> SEQUENCE: 52

```
Met Leu Met Phe Ala Val Ile Val Ala Ser Ser Gly Leu Leu Leu
  1               5                  10                  15

Met Ile Glu Arg Gly Ile Leu Ala Glu Met Lys Pro Leu Pro Leu
                 20                  25                  30

His Pro Pro Gly Arg Glu Gly Thr Ala Trp Arg Gly Lys Ala Pro
                 35                  40                  45

Lys Pro Gly Gly Leu Ser Leu Arg Ala Gly Asp Ala Asp Leu Gln
                 50                  55                  60

Val Arg Gln Asp Val Arg Asn Arg Thr Leu Arg Ala Val Cys Gly
                 65                  70                  75

Gln Pro Gly Met Pro Arg Asp Pro Trp Asp Leu Pro Val Gly Gln
                 80                  85                  90

Arg Arg Thr Leu Leu Arg His Ile Leu Val Ser Asp Arg Tyr Arg
                 95                 100                 105

Phe Leu Tyr Cys Tyr Val Pro Lys Val Ala Cys Ser Asn Trp Lys
                110                 115                 120

Arg Val Met Lys Val Leu Ala Gly Val Leu Asp Ser Val Asp Val
                125                 130                 135

Arg Leu Lys Met Asp His Arg Ser Asp Leu Val Phe Leu Ala Asp
                140                 145                 150

Leu Arg Pro Glu Glu Ile Arg Tyr Arg Leu Gln His Tyr Phe Lys
                155                 160                 165

Phe Leu Phe Val Arg Glu Pro Leu Glu Arg Leu Leu Ser Ala Tyr
```

-continued

```
                170                 175                 180

Arg Asn Lys Phe Gly Glu Ile Arg Glu Tyr Gln Gln Arg Tyr Gly
                185                 190                 195

Ala Glu Ile Val Arg Arg Tyr Arg Ala Gly Ala Gly Pro Ser Pro
                200                 205                 210

Ala Gly Asp Asp Val Thr Phe Pro Glu Phe Leu Arg Tyr Leu Val
                215                 220                 225

Asp Glu Asp Pro Glu Arg Met Asn Glu His Trp Met Pro Val Tyr
                230                 235                 240

His Leu Cys Gln Pro Cys Ala Val His Tyr Asp Phe Val Gly Ser
                245                 250                 255

Tyr Glu Arg Leu Glu Ala Asp Ala Asn Gln Val Leu Glu Trp Val
                260                 265                 270

Arg Ala Pro Pro His Val Arg Phe Pro Ala Arg Gln Ala Trp Tyr
                275                 280                 285

Arg Pro Ala Ser Pro Glu Ser Leu His Tyr His Leu Cys Ser Ala
                290                 295                 300

Pro Arg Ala Leu Leu Gln Asp Val Leu Pro Lys Tyr Ile Leu Asp
                305                 310                 315

Phe Ser Leu Phe Ala Tyr Pro Leu Pro Asn Val Thr Lys Glu Ala
                320                 325                 330

Cys Gln Gln


<210> SEQ ID NO 53
<211> LENGTH: 2594
<212> TYPE: DNA
<213> ORGANISM: Homo sapiens

<400> SEQUENCE: 53

gccctaacct tcccagggct cagctctttg gagctgccca ttcctccggc         50

tgcgagaaag gacgcgcgcc ctgcgtcggg cgaagaaaag aagcaaaact        100

tgtcgggagg gtttcgtcat caacctcctt cccgcaaacc taaacctcct        150

gccggggcca tccctagaca gaggaaagtt cctgcagagc cgaccagccc        200

tagtggatct ggggcaggca gcggcgctgg ctgtggaatt agatctgttt        250

tgaacccagt ggagcgcatc gctggggctc ggaagtcacc gtccgcgggc        300

accgggttgg cgctgcccga gtggaaccga cagtttgcga gcctcggctg        350

caagtggcct ctcctccccg cggttgttgt tcagtgtcgg gtgagggctg        400

cgagtgtggc aagttgcaaa gagagcctca gaggtccgaa gagcgctgcg        450

ctcctactcg cgttcgcttc ttcctcttct cggttcccta ctgtgaaatc        500

gcagcgacat ttacaaaggc ctccgggtcc taccgagacc gatccgcagc        550

gtttggcccg gtcgtgccta ttgcatcggg agcccccgag caccggcgaa        600

ggactggcgg gtggggtagg gaggtggcgg cggcggcatg gcgaggttcc        650

cgaaggccga cctggccgct gcaggagtta tgttactttg ccacttcttc        700

acggaccagt ttcagttcgc cgatgggaaa cccggagacc aaatccttga        750

ttggcagtat ggagttactc aggccttccc tcacacagag gaggaggtgg        800

aagttgattc acacgcgtac agccacaggt ggaaaagaaa cttggacttt        850

ctcaaggcgg tagacacgaa ccgagcaagc gtcggccaag actctcctga        900

gcccagaagc ttcacagacc tgctgctgga tgatgggcag gacaataaca        950
```

-continued

```
ctcagatcga ggaggataca gaccacaatt actatatatc tcgaatatat      1000

ggtccatctg attctgccag ccgggattta tgggtgaaca tagaccaaat      1050

ggaaaaagat aaagtgaaga ttcatggaat attgtccaat actcatcggc      1100

aagctgcaag agtgaatctg tccttcgatt ttccatttta tggccacttc      1150

ctacgtgaaa tcactgtggc aaccgggggt ttcatataca ctggagaagt      1200

cgtacatcga atgctaacag ccacacagta catagcacct ttaatggcaa      1250

atttcgatcc cagtgtatcc agaaattcaa ctgtcagata ttttgataat      1300

ggcacagcac ttgtggtcca gtgggaccat gtacatctcc aggataatta      1350

taacctggga agcttcacat tccaggcaac cctgctcatg gatggacgaa      1400

tcatctttgg atacaaagaa attcctgtct tggtcacaca gataagttca      1450

accaatcatc cagtgaaagt cggactgtcc gatgcatttg tcgttgtcca      1500

caggatccaa caaattccca atgttcgaag aagaacaatt tatgaatacc      1550

accgagtaga gctacaaatg tcaaaaatta ccaacatttc ggctgtggag      1600

atgaccccat tacccacatg cctccagttt aacagatgtg gcccctgtgt      1650

atcttctcag attggcttca actgcagttg gtgtagtaaa cttcaaagat      1700

gttccagtgg atttgatcgt catcggcagg actgggtgga cagtggatgc      1750

cctgaagagt caaaagagaa gatgtgtgag aatacagaac cagtggaaac      1800

ttcttctcga accaccacaa ccgtaggagc gacaaccacc cagttcaggg      1850

tcctaactac caccagaaga gcagtgactt ctcagtttcc caccagcctc      1900

cctacagaag atgataccaa gatagcacta catctaaaag ataatggagc      1950

ttctacagat gacagtgcag ctgagaagaa agggggaacc ctccacgctg      2000

gcctcatcat tggaatcctc atcctggtcc tcattgtagc cacagccatt      2050

cttgtgacag tctatatgta tcaccaccca acatcagcag ccagcatctt      2100

ctttattgag agacgcccaa gcagatggcc tgcgatgaag tttagaagag      2150

gctctggaca tcctgcctat gctgaagttg aaccagttgg agagaaagaa      2200

ggctttattg tatcagagca gtgctaaaat ttctaggaca gaacaacacc      2250

agtactggtt tacaggtgtt aagactaaaa ttttgcctat acctttaaga      2300

caaacaaaca aacacacaca caaacaagct ctaagctgct gtagcctgaa      2350

gaagacaaga tttctggaca agctcagccc aggaaacaaa gggtaaacaa      2400

aaaactaaaa cttatacaag ataccattta cactgaacat agaattccct      2450

agtggaatgt catctatagt tcactcggaa catctcccgt ggacttatct      2500

gaagtatgac aagattataa tgcttttggc ttaggtgcag ggttgcaaag      2550

ggatcagaaa aaaaaaatca taataaagct ttagttcatg  aggg           2594
```

<210> SEQ ID NO 54
<211> LENGTH: 529
<212> TYPE: PRT
<213> ORGANISM: Homo sapiens

<400> SEQUENCE: 54

```
Met Ala Arg Phe Pro Lys Ala Asp Leu Ala Ala Ala Gly Val Met
  1               5                  10                  15

Leu Leu Cys His Phe Phe Thr Asp Gln Phe Gln Phe Ala Asp Gly
                 20                  25                  30
```

-continued

```
Lys Pro Gly Asp Gln Ile Leu Asp Trp Gln Tyr Gly Val Thr Gln
                35                  40                  45

Ala Phe Pro His Thr Glu Glu Glu Val Glu Val Asp Ser His Ala
                50                  55                  60

Tyr Ser His Arg Trp Lys Arg Asn Leu Asp Phe Leu Lys Ala Val
                65                  70                  75

Asp Thr Asn Arg Ala Ser Val Gly Gln Asp Ser Pro Glu Pro Arg
                80                  85                  90

Ser Phe Thr Asp Leu Leu Leu Asp Asp Gly Gln Asp Asn Asn Thr
                95                  100                 105

Gln Ile Glu Glu Asp Thr Asp His Asn Tyr Tyr Ile Ser Arg Ile
                110                 115                 120

Tyr Gly Pro Ser Asp Ser Ala Ser Arg Asp Leu Trp Val Asn Ile
                125                 130                 135

Asp Gln Met Glu Lys Asp Lys Val Lys Ile His Gly Ile Leu Ser
                140                 145                 150

Asn Thr His Arg Gln Ala Ala Arg Val Asn Leu Ser Phe Asp Phe
                155                 160                 165

Pro Phe Tyr Gly His Phe Leu Arg Glu Ile Thr Val Ala Thr Gly
                170                 175                 180

Gly Phe Ile Tyr Thr Gly Glu Val Val His Arg Met Leu Thr Ala
                185                 190                 195

Thr Gln Tyr Ile Ala Pro Leu Met Ala Asn Phe Asp Pro Ser Val
                200                 205                 210

Ser Arg Asn Ser Thr Val Arg Tyr Phe Asp Asn Gly Thr Ala Leu
                215                 220                 225

Val Val Gln Trp Asp His Val His Leu Gln Asp Asn Tyr Asn Leu
                230                 235                 240

Gly Ser Phe Thr Phe Gln Ala Thr Leu Leu Met Asp Gly Arg Ile
                245                 250                 255

Ile Phe Gly Tyr Lys Glu Ile Pro Val Leu Val Thr Gln Ile Ser
                260                 265                 270

Ser Thr Asn His Pro Val Lys Val Gly Leu Ser Asp Ala Phe Val
                275                 280                 285

Val Val His Arg Ile Gln Gln Ile Pro Asn Val Arg Arg Arg Thr
                290                 295                 300

Ile Tyr Glu Tyr His Arg Val Glu Leu Gln Met Ser Lys Ile Thr
                305                 310                 315

Asn Ile Ser Ala Val Glu Met Thr Pro Leu Pro Thr Cys Leu Gln
                320                 325                 330

Phe Asn Arg Cys Gly Pro Cys Val Ser Ser Gln Ile Gly Phe Asn
                335                 340                 345

Cys Ser Trp Cys Ser Lys Leu Gln Arg Cys Ser Ser Gly Phe Asp
                350                 355                 360

Arg His Arg Gln Asp Trp Val Asp Ser Gly Cys Pro Glu Glu Ser
                365                 370                 375

Lys Glu Lys Met Cys Glu Asn Thr Glu Pro Val Glu Thr Ser Ser
                380                 385                 390

Arg Thr Thr Thr Thr Val Gly Ala Thr Thr Thr Gln Phe Arg Val
                395                 400                 405

Leu Thr Thr Thr Arg Arg Ala Val Thr Ser Gln Phe Pro Thr Ser
                410                 415                 420

Leu Pro Thr Glu Asp Asp Thr Lys Ile Ala Leu His Leu Lys Asp
                425                 430                 435
```

Asn Gly Ala Ser Thr Asp Asp Ser Ala Ala Glu Lys Lys Gly Gly
440 445 450

Thr Leu His Ala Gly Leu Ile Ile Gly Ile Leu Ile Leu Val Leu
455 460 465

Ile Val Ala Thr Ala Ile Leu Val Thr Val Tyr Met Tyr His His
470 475 480

Pro Thr Ser Ala Ala Ser Ile Phe Phe Ile Glu Arg Arg Pro Ser
485 490 495

Arg Trp Pro Ala Met Lys Phe Arg Arg Gly Ser Gly His Pro Ala
500 505 510

Tyr Ala Glu Val Glu Pro Val Gly Glu Lys Glu Gly Phe Ile Val
515 520 525

Ser Glu Gln Cys

<210> SEQ ID NO 55
<211> LENGTH: 3461
<212> TYPE: DNA
<213> ORGANISM: Homo sapiens

<400> SEQUENCE: 55
gcgcccggcg cagctcggcc agagcgaccg cggggctgag cgcgcgtccg 50
cccagggggc tccggaagct gccccggccc gcggcctcct ccctcgctcc 100
cgcttcccct ttctcgctca ccgccgccct ccttccccag ctccctcgcc 150
gtccgcccgc cccacagcca gcggctccgc gccccctgca gccacgatgc 200
ccgcggcccg gccgcccgcc gcgggactcc gcgggatctc gctgttcctc 250
gctctgctcc tggggagccc ggcggcagcg ctggagcgag atgctcttcc 300
cgagggagat gctagccctt tggtccttta cctcctgccc tcaggagccc 350
cggagagagg cagtcctggc aaagagcacc ctgaagagag agtggtaaca 400
gcgcccccca gttcctcaca gtcggcggaa gtgctgggcg agctggtgct 450
ggatgggacc gcaccctctg cacatcacga catcccagcc ctgtcaccgc 500
tgcttccaga ggaggcccgc cccaagcacg ccttgccccc caagaagaaa 550
ctgccttcgc tcaagcaggt gaactctgcc aggaagcagc tgaggcccaa 600
ggccacctcc gcagccactg tccaaagggc agggtcccag ccagcgtccc 650
agggcctaga tctcctctcc tcctccacgg agaagcctgg cccaccgggg 700
gacccggacc ccatcgtggc ctccgaggag gcatcagaag tgccccctttg 750 gctggatcga aaggagagtg cggtccctac aacacccgca cccctgcaaa 800
tctccccctt cacttcgcag ccctatgtgg cccacacact cccccagagg 850
ccagaacccg gggagcctgg gcctgacatg gcccaggagg ccccccagga 900
ggacaccagc cccatggccc tgatggacaa aggtgagaat gagctgactg 950
ggtcagcctc agaggagagc caggagacca ctacctccac cattatcacc 1000
accacggtca tcaccaccga gcaagcacca gctctctgca gtgtgagctt 1050
ctccaatcct gaggggtaca ttgactccag cgactaccca ctgctgcccc 1100
tcaacaactt tctggagtgc acatacaacg tgacagtcta cactggctat 1150
ggggtggagc tccaggtgaa gagtgtgaac ctgtccgatg gggaactgct 1200
ctccatccgc ggggtggacg gccctaccct gaccgtcctg gccaaccaga 1250
cactcctggt ggaggggcag gtaatccgaa gccccaccaa caccatctcc 1300

-continued

```
gtctacttcc ggaccttcca ggacgacggc cttgggacct tccagcttca    1350
ctaccaggcc ttcatgctga gctgcaactt tccccgccgg cctgactctg    1400
gggatgtcac ggtgatggac ctgcactcag gtggggtggc ccactttcac    1450
tgccacctgg gctatgagct ccagggcgct aagatgctga catgcatcaa    1500
tgcctccaag ccgcactgga gcagccagga gcccatctgc tcagctcctt    1550
gtggaggggc agtgcacaat gccaccatcg gccgcgtcct ctccccaagt    1600
taccctgaaa acacaaatgg gagccaattc tgcatctgga cgattgaagc    1650
tccagagggc cagaagctgc acctgcactt tgagaggctg ttgctgcatg    1700
acaaggacag gatgacggtt cacagcgggc agaccaacaa gtcagctctt    1750
ctctacgact cccttcaaac cgagagtgtc ccttttgagg gcctgctgag    1800
cgaaggcaac accatccgca tcgagttcac gtccgaccag gcccgggcgg    1850
cctccacctt caacatccga tttgaagcgt ttgagaaagg ccactgctat    1900
gagccctaca tccagaatgg gaacttcact acatccgacc cgacctataa    1950
cattgggact atagtggagt tcacctgcga ccccggccac tccctggagc    2000
agggcccggc catcatcgaa tgcatcaatg tgcgggaccc atactggaat    2050
gacacagagc ccctgtgcag agccatgtgt ggtggggagc tctctgctgt    2100
ggctggggtg gtattgtccc caaactggcc cgagccctac gtggaaggtg    2150
aagattgtat ctggaagatc cacgtgggag aagagaaacg gatcttctta    2200
gatatccagt tcctgaatct gagcaacagt gacatcttga ccatctacga    2250
tggcgacgag gtcatgcccc acatcttggg gcagtacctt gggaacagtg    2300
gcccccagaa actgtactcc tccacgccag acttaaccat ccagttccat    2350
tcggaccctg ctggcctcat ctttggaaag ggccagggat ttatcatgaa    2400
ctacatagag gtatcaagga atgactcctg ctcggattta cccgagatcc    2450
agaatggctg gaaaaccact tctcacacgg agttggtgcg gggagccaga    2500
atcacctacc agtgtgaccc cggctatgac atcgtgggga gtgacaccct    2550
cacctgccag tgggacctca gctggagcag cgaccccca ttttgtgaga    2600
aaattatgta ctgcaccgac cccggagagg tggatcactc gacccgctta    2650
atttcggatc ctgtgctgct ggtggggacc accatccaat acacctgcaa    2700
ccccggtttt gtgcttgaag ggagttctct tctgacctgc tacagccgtg    2750
aaacagggac tcccatctgg acgtctcgcc tgccccactg cgtttcggag    2800
gagtccctgg catgtgacaa cccagggctg cctgaaaatg gataccaaat    2850
cctgtacaag cgactctacc tgccaggaga gtccctcacc ttcatgtgct    2900
acgaaggctt tgagctcatg ggtgaagtga ccatccgctg catcctggga    2950
cagccatccc actggaacgg gcccctgccc gtgtgtaaag ttaatcaaga    3000
cagttttgaa catgctttag aagcagaagc ggcagcagag acgtcgctgg    3050
aagggggggaa catggccctg gctatcttca tcccggtcct catcatctcc    3100
ttactgctgg gaggagccta catttacatc acaagatgtc gctactattc    3150
caacctccgc ctgcctctga tgtactccca cccctacagc cagatcaccg    3200
tggaaaccga gtttgacaac cccatttacg agacagggga aaccagagag    3250
tatgaggttt ctatctaaag agagctacac ttgagaaggg gacttgtgaa    3300
```

-continued

```
ctcaaccaca atctcctcga gacattcatc cagagaccat gtggcacttg            3350

attgaaaccc cagaatgtcg actgtctttt gtttagactc tttatcaaag            3400

gtttactgtt ttcttccctg tatttattat atttaaaagt gaaaaaaaaa            3450

aaaaaaaaaa  a                                                     3461
```

<210> SEQ ID NO 56
<211> LENGTH: 1023
<212> TYPE: PRT
<213> ORGANISM: Homo sapiens

<400> SEQUENCE: 56

```
Met Pro Ala Ala Arg Pro Pro Ala Ala Gly Leu Arg Gly Ile Ser
  1               5                  10                  15

Leu Phe Leu Ala Leu Leu Leu Gly Ser Pro Ala Ala Ala Leu Glu
                 20                  25                  30

Arg Asp Ala Leu Pro Glu Gly Asp Ala Ser Pro Leu Gly Pro Tyr
                 35                  40                  45

Leu Leu Pro Ser Gly Ala Pro Glu Arg Gly Ser Pro Gly Lys Glu
                 50                  55                  60

His Pro Glu Glu Arg Val Val Thr Ala Pro Pro Ser Ser Ser Gln
                 65                  70                  75

Ser Ala Glu Val Leu Gly Glu Leu Val Leu Asp Gly Thr Ala Pro
                 80                  85                  90

Ser Ala His His Asp Ile Pro Ala Leu Ser Pro Leu Leu Pro Glu
                 95                 100                 105

Glu Ala Arg Pro Lys His Ala Leu Pro Pro Lys Lys Lys Leu Pro
                110                 115                 120

Ser Leu Lys Gln Val Asn Ser Ala Arg Lys Gln Leu Arg Pro Lys
                125                 130                 135

Ala Thr Ser Ala Ala Thr Val Gln Arg Ala Gly Ser Gln Pro Ala
                140                 145                 150

Ser Gln Gly Leu Asp Leu Leu Ser Ser Ser Thr Glu Lys Pro Gly
                155                 160                 165

Pro Pro Gly Asp Pro Asp Pro Ile Val Ala Ser Glu Glu Ala Ser
                170                 175                 180

Glu Val Pro Leu Trp Leu Asp Arg Lys Glu Ser Ala Val Pro Thr
                185                 190                 195

Thr Pro Ala Pro Leu Gln Ile Ser Pro Phe Thr Ser Gln Pro Tyr
                200                 205                 210

Val Ala His Thr Leu Pro Gln Arg Pro Glu Pro Gly Glu Pro Gly
                215                 220                 225

Pro Asp Met Ala Gln Glu Ala Pro Gln Glu Asp Thr Ser Pro Met
                230                 235                 240

Ala Leu Met Asp Lys Gly Glu Asn Glu Leu Thr Gly Ser Ala Ser
                245                 250                 255

Glu Glu Ser Gln Glu Thr Thr Thr Ser Thr Ile Ile Thr Thr Thr
                260                 265                 270

Val Ile Thr Thr Glu Gln Ala Pro Ala Leu Cys Ser Val Ser Phe
                275                 280                 285

Ser Asn Pro Glu Gly Tyr Ile Asp Ser Ser Asp Tyr Pro Leu Leu
                290                 295                 300

Pro Leu Asn Asn Phe Leu Glu Cys Thr Tyr Asn Val Thr Val Tyr
                305                 310                 315
```

-continued

```
Thr Gly Tyr Gly Val Glu Leu Gln Val Lys Ser Val Asn Leu Ser
                320                 325                 330

Asp Gly Glu Leu Leu Ser Ile Arg Gly Val Asp Gly Pro Thr Leu
                335                 340                 345

Thr Val Leu Ala Asn Gln Thr Leu Leu Val Glu Gly Gln Val Ile
                350                 355                 360

Arg Ser Pro Thr Asn Thr Ile Ser Val Tyr Phe Arg Thr Phe Gln
                365                 370                 375

Asp Asp Gly Leu Gly Thr Phe Gln Leu His Tyr Gln Ala Phe Met
                380                 385                 390

Leu Ser Cys Asn Phe Pro Arg Arg Pro Asp Ser Gly Asp Val Thr
                395                 400                 405

Val Met Asp Leu His Ser Gly Gly Val Ala His Phe His Cys His
                410                 415                 420

Leu Gly Tyr Glu Leu Gln Gly Ala Lys Met Leu Thr Cys Ile Asn
                425                 430                 435

Ala Ser Lys Pro His Trp Ser Ser Gln Glu Pro Ile Cys Ser Ala
                440                 445                 450

Pro Cys Gly Gly Ala Val His Asn Ala Thr Ile Gly Arg Val Leu
                455                 460                 465

Ser Pro Ser Tyr Pro Glu Asn Thr Asn Gly Ser Gln Phe Cys Ile
                470                 475                 480

Trp Thr Ile Glu Ala Pro Glu Gly Gln Lys Leu His Leu His Phe
                485                 490                 495

Glu Arg Leu Leu Leu His Asp Lys Asp Arg Met Thr Val His Ser
                500                 505                 510

Gly Gln Thr Asn Lys Ser Ala Leu Leu Tyr Asp Ser Leu Gln Thr
                515                 520                 525

Glu Ser Val Pro Phe Glu Gly Leu Leu Ser Glu Gly Asn Thr Ile
                530                 535                 540

Arg Ile Glu Phe Thr Ser Asp Gln Ala Arg Ala Ala Ser Thr Phe
                545                 550                 555

Asn Ile Arg Phe Glu Ala Phe Glu Lys Gly His Cys Tyr Glu Pro
                560                 565                 570

Tyr Ile Gln Asn Gly Asn Phe Thr Thr Ser Asp Pro Thr Tyr Asn
                575                 580                 585

Ile Gly Thr Ile Val Glu Phe Thr Cys Asp Pro Gly His Ser Leu
                590                 595                 600

Glu Gln Gly Pro Ala Ile Ile Glu Cys Ile Asn Val Arg Asp Pro
                605                 610                 615

Tyr Trp Asn Asp Thr Glu Pro Leu Cys Arg Ala Met Cys Gly Gly
                620                 625                 630

Glu Leu Ser Ala Val Ala Gly Val Val Leu Ser Pro Asn Trp Pro
                635                 640                 645

Glu Pro Tyr Val Glu Gly Glu Asp Cys Ile Trp Lys Ile His Val
                650                 655                 660

Gly Glu Glu Lys Arg Ile Phe Leu Asp Ile Gln Phe Leu Asn Leu
                665                 670                 675

Ser Asn Ser Asp Ile Leu Thr Ile Tyr Asp Gly Asp Glu Val Met
                680                 685                 690

Pro His Ile Leu Gly Gln Tyr Leu Gly Asn Ser Gly Pro Gln Lys
                695                 700                 705

Leu Tyr Ser Ser Thr Pro Asp Leu Thr Ile Gln Phe His Ser Asp
                710                 715                 720
```

Pro Ala Gly Leu Ile Phe Gly Lys Gly Gln Gly Phe Ile Met Asn
725 730 735

Tyr Ile Glu Val Ser Arg Asn Asp Ser Cys Ser Asp Leu Pro Glu
740 745 750

Ile Gln Asn Gly Trp Lys Thr Thr Ser His Thr Glu Leu Val Arg
755 760 765

Gly Ala Arg Ile Thr Tyr Gln Cys Asp Pro Gly Tyr Asp Ile Val
770 775 780

Gly Ser Asp Thr Leu Thr Cys Gln Trp Asp Leu Ser Trp Ser Ser
785 790 795

Asp Pro Pro Phe Cys Glu Lys Ile Met Tyr Cys Thr Asp Pro Gly
800 805 810

Glu Val Asp His Ser Thr Arg Leu Ile Ser Asp Pro Val Leu Leu
815 820 825

Val Gly Thr Thr Ile Gln Tyr Thr Cys Asn Pro Gly Phe Val Leu
830 835 840

Glu Gly Ser Ser Leu Leu Thr Cys Tyr Ser Arg Glu Thr Gly Thr
845 850 855

Pro Ile Trp Thr Ser Arg Leu Pro His Cys Val Ser Glu Glu Ser
860 865 870

Leu Ala Cys Asp Asn Pro Gly Leu Pro Glu Asn Gly Tyr Gln Ile
875 880 885

Leu Tyr Lys Arg Leu Tyr Leu Pro Gly Glu Ser Leu Thr Phe Met
890 895 900

Cys Tyr Glu Gly Phe Glu Leu Met Gly Glu Val Thr Ile Arg Cys
905 910 915

Ile Leu Gly Gln Pro Ser His Trp Asn Gly Pro Leu Pro Val Cys
920 925 930

Lys Val Asn Gln Asp Ser Phe Glu His Ala Leu Glu Ala Glu Ala
935 940 945

Ala Ala Glu Thr Ser Leu Glu Gly Gly Asn Met Ala Leu Ala Ile
950 955 960

Phe Ile Pro Val Leu Ile Ile Ser Leu Leu Leu Gly Gly Ala Tyr
965 970 975

Ile Tyr Ile Thr Arg Cys Arg Tyr Tyr Ser Asn Leu Arg Leu Pro
980 985 990

Leu Met Tyr Ser His Pro Tyr Ser Gln Ile Thr Val Glu Thr Glu
995 1000 1005

Phe Asp Asn Pro Ile Tyr Glu Thr Gly Glu Thr Arg Glu Tyr Glu
1010 1015 1020

Val Ser Ile

<210> SEQ ID NO 57
<211> LENGTH: 1997
<212> TYPE: DNA
<213> ORGANISM: Homo sapiens

<400> SEQUENCE: 57
gcgagccggg tcccaccatg gccgcgaatt attccagtac cagtacccgg 50
agagaacatg tcaaagttaa aaccagctcc cagccaggct tcctggaacg 100
gctgagcgag acctcgggtg ggatgtttgt ggggctcatg gccttcctgc 150
tctccttcta cctaattttc accaatgagg gccgcgcatt gaagacggca 200
acctcattgg ctgaggggct ctcgcttgtg gtgtctcccg acagcatcca 250

```
cagtgtggct ccggagaatg aaggaaggct ggtgcacatc attggcgcct          300

tacggacatc caagcttttg tctgatccaa actatggggt ccatcttccg          350

gctgtgaaac tgcggaggca cgtggagatg taccaatggg tagaaactga          400

ggagtccagg gagtacaccg aggatgggca ggtgaagaag gagacgaggt          450

attcctacaa cactgaatgg aggtcagaaa tcatcaacag caaaaacttc          500

gaccgagaga ttggccacaa aaaccccagt gccatggcag tggagtcatt          550

catggcaaca gcccccttttg tccaaattgg caggtttttc ctctcgtcag         600

gcctcatcga caaagtcgac aacttcaagt ccctgagcct atccaagctg          650

gaggaccctc atgtggacat cattcgccgt ggagactttt tctaccacag          700

cgaaaatccc aagtatccag aggtgggaga cttgcgtgtc tccttttcct          750

atgctggact gagcggcgat gaccctgacc tgggcccagc tcacgtggtc          800

actgtgattg cccggcagcg gggtgaccag ctagtcccat tctccaccaa          850

gtctggggat accttactgc tcctgcacca cggggacttc tcagcagagg          900

aggtgtttca tagagaacta aggagcaact ccatgaagac ctggggcctg          950

cgggcagctg gctggatggc catgttcatg ggcctcaacc ttatgacacg         1000

gatcctctac accttggtgg actggtttcc tgttttccga gacctggtca         1050

acattggcct gaaagccttt gccttctgtg tggccacctc gctgaccctg         1100

ctgaccgtgg cggctggctg gctcttctac cgacccctgt gggccctcct         1150

cattgccggc ctggcccttg tgcccatcct tgttgctcgg acacgggtgc         1200

cagccaaaaa gttggagtga aaagaccctg gcacccgccc gacacctgcg         1250

tgagccctga ggctggttgt acaatgccca cgcctgcctg gctgctttca         1300

cctgggagtg ctttcgatgt gggcacctgg gcttcctagg gctgcttctg         1350

agtggttctt tcacgtgttg tgtccatagc tttagtcttc ctaaataaga         1400

tccacccaca cctaagtcac agaatttcta agttccccaa ctactctcac         1450

acccttttaa agataaagta tgttgtaacc aggacgtctt aaatgattct         1500

ttgtgtacct tttctgtcat attcagaaac cgttctgtgc ctgctgggag         1550

taattccttt agcaattaag tatttggtag ctgaataagg ggtcagaact         1600

tctgaaacca gagatctgta atcatctcta ttggcctggg gtgcctgtgc         1650

tataaatgag tttcttcaca tgaaaaacac agccagccca agatgactta         1700

tctgggttta ggattcaata gtattcacta actgcttatt acatgagcaa         1750

tttcatcaaa tctccaaact cttaaaggat gctttcggaa aacacgctgt         1800

atacctagat gatgactaaa tgcaaaatcc ttgggctttg gtttttttct         1850

agtaaggatt ttaaataact gccgacttca aaagtgttct taaaacgaaa         1900

gataatgtta agaaaaattt gaaagctttg gaaaaccaaa tttgtaatat         1950

cattgtattt tttattaaaa gttttgtaat aaatttctaa  attatca           1997
```

<210> SEQ ID NO 58
<211> LENGTH: 400
<212> TYPE: PRT
<213> ORGANISM: Homo sapiens

<400> SEQUENCE: 58

Met Ala Ala Asn Tyr Ser Ser Thr Ser Thr Arg Arg Glu His Val

-continued

```
                1               5                   10                  15

Lys Val Lys Thr Ser Ser Gln Pro Gly Phe Leu Glu Arg Leu Ser
                20                  25                  30

Glu Thr Ser Gly Gly Met Phe Val Gly Leu Met Ala Phe Leu Leu
                35                  40                  45

Ser Phe Tyr Leu Ile Phe Thr Asn Glu Gly Arg Ala Leu Lys Thr
                50                  55                  60

Ala Thr Ser Leu Ala Glu Gly Leu Ser Leu Val Val Ser Pro Asp
                65                  70                  75

Ser Ile His Ser Val Ala Pro Glu Asn Glu Gly Arg Leu Val His
                80                  85                  90

Ile Ile Gly Ala Leu Arg Thr Ser Lys Leu Leu Ser Asp Pro Asn
                95                  100                 105

Tyr Gly Val His Leu Pro Ala Val Lys Leu Arg Arg His Val Glu
                110                 115                 120

Met Tyr Gln Trp Val Glu Thr Glu Glu Ser Arg Glu Tyr Thr Glu
                125                 130                 135

Asp Gly Gln Val Lys Lys Glu Thr Arg Tyr Ser Tyr Asn Thr Glu
                140                 145                 150

Trp Arg Ser Glu Ile Ile Asn Ser Lys Asn Phe Asp Arg Glu Ile
                155                 160                 165

Gly His Lys Asn Pro Ser Ala Met Ala Val Glu Ser Phe Met Ala
                170                 175                 180

Thr Ala Pro Phe Val Gln Ile Gly Arg Phe Phe Leu Ser Ser Gly
                185                 190                 195

Leu Ile Asp Lys Val Asp Asn Phe Lys Ser Leu Ser Leu Ser Lys
                200                 205                 210

Leu Glu Asp Pro His Val Asp Ile Ile Arg Arg Gly Asp Phe Phe
                215                 220                 225

Tyr His Ser Glu Asn Pro Lys Tyr Pro Glu Val Gly Asp Leu Arg
                230                 235                 240

Val Ser Phe Ser Tyr Ala Gly Leu Ser Gly Asp Asp Pro Asp Leu
                245                 250                 255

Gly Pro Ala His Val Val Thr Val Ile Ala Arg Gln Arg Gly Asp
                260                 265                 270

Gln Leu Val Pro Phe Ser Thr Lys Ser Gly Asp Thr Leu Leu Leu
                275                 280                 285

Leu His His Gly Asp Phe Ser Ala Glu Glu Val Phe His Arg Glu
                290                 295                 300

Leu Arg Ser Asn Ser Met Lys Thr Trp Gly Leu Arg Ala Ala Gly
                305                 310                 315

Trp Met Ala Met Phe Met Gly Leu Asn Leu Met Thr Arg Ile Leu
                320                 325                 330

Tyr Thr Leu Val Asp Trp Phe Pro Val Phe Arg Asp Leu Val Asn
                335                 340                 345

Ile Gly Leu Lys Ala Phe Ala Phe Cys Val Ala Thr Ser Leu Thr
                350                 355                 360

Leu Leu Thr Val Ala Ala Gly Trp Leu Phe Tyr Arg Pro Leu Trp
                365                 370                 375

Ala Leu Leu Ile Ala Gly Leu Ala Leu Val Pro Ile Leu Val Ala
                380                 385                 390

Arg Thr Arg Val Pro Ala Lys Lys Leu Glu
                395                 400
```

<210> SEQ ID NO 59
<211> LENGTH: 2016
<212> TYPE: DNA
<213> ORGANISM: Homo sapiens

<400> SEQUENCE: 59
gatcaagcgc cttcctttcc cttcctctcc ctacttggcc tttgccctaa 50
gccaagacct ggccatcagc ctggctgcag gggcctgcag agccagctgc 100
actttttcag gtatggggga gggccaggca ccatgaagcc agtgtgggtc 150
gccacccttc tgtggatgct actgctggtg cccaggctgg gggccgcccg 200
gaaggggtcc ccagaagagg cctccttcta ctatggaacc ttccctcttg 250
gcttctcctg ggcgtgggc agttctgcct accagacgga gggcgcctgg 300
gaccaggacg ggaaagggcc tagcatctgg gacgtcttca cacacagtgg 350
gaaggggaaa gtgcttggga atgagacggc agatgtagcc tgtgacggct 400
actacaaggt ccaggaggac atcattctgc tgagggaact gcacgtcaac 450
cactaccgat tctccctgtc ttggccccgg ctcctgccca caggcatccg 500
agccgagcag gtgaacaaga agggaatcga attctacagt gatcttatcg 550
atgcccttct gagcagcaac atcactccca tcgtgacctt gcaccactgg 600
gatctgccac agctgctcca ggtcaaatac ggtgggtggc agaatgtgag 650
catggccaac tacttcagag actacgccaa cctgtgcttt gaggcctttg 700
gggaccgtgt gaagcactgg atcacgttca gtgatcctcg ggcaatggca 750
gaaaaaggct atgagacggg ccaccatgcg ccgggcctga agctccgcgg 800
caccggcctg tacaaggcag cacaccacat cattaaggcc cacgccaaaa 850
cctggcattc ttataacacc acgtggcgca gcaagcagca aggtctggtg 900
ggaatttcac tgaactgtga ctgggggaa cctgtggaca ttagtaaccc 950
caaggaccta gaggctgccg agagatacct acagttctgt ctgggctggt 1000
ttgccaaccc catttatgcc ggtgactacc cccaagtcat gaaggactac 1050
attggaagaa agagtgcaga gcaaggcctg gagatgtcga ggttaccggt 1100
gttctcactc caggagaaga gctacattaa aggcacatcc gatttcttgg 1150
gattaggtca ttttactact cggtacatca cggaaaggaa ctacccctcc 1200
cgccaggggc ccagctacca gaacgatcgt gacttgatag agctggttga 1250
cccaaactgg ccagatctgg ggtctaaatg gctatattct gtgccatggg 1300
gatttaggag gctccttaac tttgctcaga ctcaatacgg tgatcctccc 1350
atatatgtga tggaaaatgg agcatctcaa aaattccact gtactcaatt 1400
atgtgatgag tggagaattc aataccttaa aggatacata aatgaaatgc 1450
taaaagctat aaaagatggt gctaatataa aggggtatac ttcctggtct 1500
ctgttggata agtttgaatg ggagaaagga tactcagata gatatggatt 1550
ctactatgtt gaatttaacg acagaaataa gcctcgctat ccaaaggctt 1600
cagttcaata ttacaagaag attatcattg ccaatgggtt tcccaatcca 1650
agagaggtgg aaagttggta cctcaaagct ttggaaactt gctctatcaa 1700
caatcagatg cttgctgcag agcctttgct aagtcacatg caaatggtta 1750
cggagatcgt ggtacccact gtctgctccc tctgtgtcct catcactgct 1800
gttctactaa tgctcctcct gaggaggcag agctgagaca ggattatcaa 1850
ttttggagct tcataagaga atcttcagga tcttcctccc ttttctgctt 1900
tgagggtttc catacattgc tgttttcagg ttctacaata attacctttt 1950
tttctctttc tctttttggc ttgtgctggg atttaagaat tagaaaataa 2000
aaataagcag aaatta 2016

<210> SEQ ID NO 60
<211> LENGTH: 567
<212> TYPE: PRT
<213> ORGANISM: Homo sapiens

<400> SEQUENCE: 60

Met Lys Pro Val Trp Val Ala Thr Leu Leu Trp Met Leu Leu Leu
1 5 10 15

Val Pro Arg Leu Gly Ala Ala Arg Lys Gly Ser Pro Glu Glu Ala
20 25 30

Ser Phe Tyr Tyr Gly Thr Phe Pro Leu Gly Phe Ser Trp Gly Val
35 40 45

Gly Ser Ser Ala Tyr Gln Thr Glu Gly Ala Trp Asp Gln Asp Gly
50 55 60

Lys Gly Pro Ser Ile Trp Asp Val Phe Thr His Ser Gly Lys Gly
65 70 75

Lys Val Leu Gly Asn Glu Thr Ala Asp Val Ala Cys Asp Gly Tyr
80 85 90

Tyr Lys Val Gln Glu Asp Ile Ile Leu Leu Arg Glu Leu His Val
95 100 105

Asn His Tyr Arg Phe Ser Leu Ser Trp Pro Arg Leu Leu Pro Thr
110 115 120

Gly Ile Arg Ala Glu Gln Val Asn Lys Lys Gly Ile Glu Phe Tyr
125 130 135

Ser Asp Leu Ile Asp Ala Leu Leu Ser Ser Asn Ile Thr Pro Ile
140 145 150

Val Thr Leu His His Trp Asp Leu Pro Gln Leu Leu Gln Val Lys
155 160 165

Tyr Gly Gly Trp Gln Asn Val Ser Met Ala Asn Tyr Phe Arg Asp
170 175 180

Tyr Ala Asn Leu Cys Phe Glu Ala Phe Gly Asp Arg Val Lys His
185 190 195

Trp Ile Thr Phe Ser Asp Pro Arg Ala Met Ala Glu Lys Gly Tyr
200 205 210

Glu Thr Gly His His Ala Pro Gly Leu Lys Leu Arg Gly Thr Gly
215 220 225

Leu Tyr Lys Ala Ala His His Ile Ile Lys Ala His Ala Lys Thr
230 235 240

Trp His Ser Tyr Asn Thr Thr Trp Arg Ser Lys Gln Gln Gly Leu
245 250 255

Val Gly Ile Ser Leu Asn Cys Asp Trp Gly Glu Pro Val Asp Ile
260 265 270

Ser Asn Pro Lys Asp Leu Glu Ala Ala Glu Arg Tyr Leu Gln Phe
275 280 285

Cys Leu Gly Trp Phe Ala Asn Pro Ile Tyr Ala Gly Asp Tyr Pro
290 295 300

Gln Val Met Lys Asp Tyr Ile Gly Arg Lys Ser Ala Glu Gln Gly
305 310 315

Leu Glu Met Ser Arg Leu Pro Val Phe Ser Leu Gln Glu Lys Ser
320 325 330

Tyr Ile Lys Gly Thr Ser Asp Phe Leu Gly Leu Gly His Phe Thr
335 340 345

Thr Arg Tyr Ile Thr Glu Arg Asn Tyr Pro Ser Arg Gln Gly Pro
350 355 360

Ser Tyr Gln Asn Asp Arg Asp Leu Ile Glu Leu Val Asp Pro Asn
365 370 375

Trp Pro Asp Leu Gly Ser Lys Trp Leu Tyr Ser Val Pro Trp Gly
380 385 390

Phe Arg Arg Leu Leu Asn Phe Ala Gln Thr Gln Tyr Gly Asp Pro
395 400 405

Pro Ile Tyr Val Met Glu Asn Gly Ala Ser Gln Lys Phe His Cys
410 415 420

Thr Gln Leu Cys Asp Glu Trp Arg Ile Gln Tyr Leu Lys Gly Tyr
425 430 435

Ile Asn Glu Met Leu Lys Ala Ile Lys Asp Gly Ala Asn Ile Lys
440 445 450

Gly Tyr Thr Ser Trp Ser Leu Leu Asp Lys Phe Glu Trp Glu Lys
455 460 465

Gly Tyr Ser Asp Arg Tyr Gly Phe Tyr Tyr Val Glu Phe Asn Asp
470 475 480

Arg Asn Lys Pro Arg Tyr Pro Lys Ala Ser Val Gln Tyr Tyr Lys
485 490 495

Lys Ile Ile Ile Ala Asn Gly Phe Pro Asn Pro Arg Glu Val Glu
500 505 510

Ser Trp Tyr Leu Lys Ala Leu Glu Thr Cys Ser Ile Asn Asn Gln
515 520 525

Met Leu Ala Ala Glu Pro Leu Leu Ser His Met Gln Met Val Thr
530 535 540

Glu Ile Val Val Pro Thr Val Cys Ser Leu Cys Val Leu Ile Thr
545 550 555

Ala Val Leu Leu Met Leu Leu Leu Arg Arg Gln Ser
560 565

<210> SEQ ID NO 61
<211> LENGTH: 996
<212> TYPE: DNA
<213> ORGANISM: Homo sapiens

<400> SEQUENCE: 61
cccgtgccaa gagtgacgta agtaccgcct atagagtcta taggcccact 50
tggcttcgtt agaacgcggc tacaattaat acataacctt atgtatcata 100
cacatacgat ttaggtgaca ctatagaata acatccactt tgcctttctc 150
tccacaggtg tccactccca ggtccaactg cacctcggtt ctatcgataa 200
tctcagcacc agccactcag agcagggcac gatgttgggg gcccgcctca 250
ggctctgggt ctgtgccttg tgcagcgtct gcagcatgag cgtcctcaga 300
gcctatccca atgcctcccc actgctcggc tccagctggg gtggcctgat 350
ccacctgtac acagccacag ccaggaacag ctaccacctg cagatccaca 400
agaatggcca tgtggatggc gcaccccatc agaccatcta cagtgccctg 450
atgatcagat cagaggatgc tggctttgtg gtgattacag gtgtgatgag 500

```
cagaagatac ctctgcatgg atttcagagg caacattttt ggatcacact          550

atttcgaccc ggagaactgc aggttccaac accagacgct ggaaaacggg          600

tacgacgtct accactctcc tcagtatcac ttcctggtca gtctgggccg          650

ggcgaagaga gccttcctgc caggcatgaa cccacccccg tactcccagt          700

tcctgtcccg gaggaacgag atccccctaa ttcacttcaa cacccccata          750

ccacggcggc acacccggag cgccgaggac gactcggagc gggacccccct         800

gaacgtgctg aagccccggg cccggatgac cccggccccg gcctcctgtt          850

cacaggagct cccgagcgcc gaggacaaca gcccgatggc cagtgaccca          900

ttaggggtgg tcaggggcgg tcgagtgaac acgcacgctg ggggaacggg          950

cccggaaggc tgccgcccct tcgccaagtt catctagggt  cgctgg             996


<210> SEQ ID NO 62
<211> LENGTH: 251
<212> TYPE: PRT
<213> ORGANISM: Homo sapiens

<400> SEQUENCE: 62

Met Leu Gly Ala Arg Leu Arg Leu Trp Val Cys Ala Leu Cys Ser
  1               5                  10                  15

Val Cys Ser Met Ser Val Leu Arg Ala Tyr Pro Asn Ala Ser Pro
                 20                  25                  30

Leu Leu Gly Ser Ser Trp Gly Gly Leu Ile His Leu Tyr Thr Ala
                 35                  40                  45

Thr Ala Arg Asn Ser Tyr His Leu Gln Ile His Lys Asn Gly His
                 50                  55                  60

Val Asp Gly Ala Pro His Gln Thr Ile Tyr Ser Ala Leu Met Ile
                 65                  70                  75

Arg Ser Glu Asp Ala Gly Phe Val Val Ile Thr Gly Val Met Ser
                 80                  85                  90

Arg Arg Tyr Leu Cys Met Asp Phe Arg Gly Asn Ile Phe Gly Ser
                 95                 100                 105

His Tyr Phe Asp Pro Glu Asn Cys Arg Phe Gln His Gln Thr Leu
                110                 115                 120

Glu Asn Gly Tyr Asp Val Tyr His Ser Pro Gln Tyr His Phe Leu
                125                 130                 135

Val Ser Leu Gly Arg Ala Lys Arg Ala Phe Leu Pro Gly Met Asn
                140                 145                 150

Pro Pro Pro Tyr Ser Gln Phe Leu Ser Arg Arg Asn Glu Ile Pro
                155                 160                 165

Leu Ile His Phe Asn Thr Pro Ile Pro Arg Arg His Thr Arg Ser
                170                 175                 180

Ala Glu Asp Asp Ser Glu Arg Asp Pro Leu Asn Val Leu Lys Pro
                185                 190                 195

Arg Ala Arg Met Thr Pro Ala Pro Ala Ser Cys Ser Gln Glu Leu
                200                 205                 210

Pro Ser Ala Glu Asp Asn Ser Pro Met Ala Ser Asp Pro Leu Gly
                215                 220                 225

Val Val Arg Gly Gly Arg Val Asn Thr His Ala Gly Gly Thr Gly
                230                 235                 240

Pro Glu Gly Cys Arg Pro Phe Ala Lys Phe Ile
                245                 250
```

<210> SEQ ID NO 63
<211> LENGTH: 2067
<212> TYPE: DNA
<213> ORGANISM: Homo sapiens

<400> SEQUENCE: 63

```
catgtctaga ctgggagccc tgggtggtgc ccgtgccggg ctgggactgt      50
tgctgggtac cgccgccggc cttggattcc tgtgcctcct ttacagccag     100
cgatggaaac ggacccagcg tcatggccgc agccagagcc tgcccaactc     150
cctggactat acgcagactt cagatcccgg acgccacgtg atgctcctgc     200
gggctgtccc aggtggggct ggagatgcct cagtgctgcc cagccttcca     250
cgggaaggac aggagaaggt gctggaccgc ctggactttg tgctgaccag     300
ccttgtggcg ctgcggcggg aggtggagga gctgagaagc agcctgcgag     350
ggcttgcggg ggagattgtt ggggaggtcc gatgccacat ggaagagaac     400
cagagagtgg ctcggcggcg aaggtttccg tttgtccggg agaggagtga     450
ctccactggc tccagctctg tctacttcac ggcctcctcg ggagccacgt     500
tcacagatgc tgagagtgaa gggggttaca caacagccaa tgcggagtct     550
gacaatgagc gggactctga caaagaaagt gaggacgggg aagatgaagt     600
gagctgtgag actgtgaaga tggggagaaa ggattctctt gacttggagg     650
aagaggcagc ttcaggtgcc tccagtgccc tggaggctgg aggttcctca     700
ggcttggagg atgtgctgcc cctcctgcag caggccgacg agctgcacag     750
gggtgatgag caaggcaagc gggagggctt ccagctgctg ctcaacaaca     800
agctggtgta tggaagccgg caggactttc tctggcgcct ggcccgagcc     850
tacagtgaca tgtgtgagct cactgaggag gtgagcgaga agaagtcata     900
tgccctagat ggaaaagaag aagcagaggc tgctctggag aagggggatg     950
agagtgctga ctgtcacctg tggtatgcgg tgctttgtgg tcagctggct    1000
gagcatgaga gcatccagag gcgcatccag agtggcttta gcttcaagga    1050
gcatgtggac aaagccattg ctctccagcc agaaaacccc atggctcact    1100
ttcttcttgg caggtggtgc tatcaggtct ctcacctgag ctggctagaa    1150
aaaaaaactg ctacagcctt gcttgaaagc cctctcagtg ccactgtgga    1200
agatgccctc cagagcttcc taaaggctga agaactacag ccaggatttt    1250
ccaaagcagg aagggtatat atttccaagt gctacagaga actagggaaa    1300
aactctgaag ctagatggtg gatgaagttg gccctggagc tgccagatgt    1350
cacgaaggag gatttggcta tccagaagga cctggaagaa ctggaagtca    1400
ttttacgaga ctaaccacgt ttcactggcc ttcatgactt gatgccacta    1450
tttaaggtgg gggggcgggg aggctttttt ccttagacct tgctgagatc    1500
aggaaaccac acaaatctgt ctcctgggtc tgactgctac ccactaccac    1550
tccccattag ttaatttatt ctaacctcta acctaatcta gaattggggc    1600
agtactcatg gcttccgttt ctgttgttct ctcccttgag taatctctta    1650
aaaaaatcaa gattcacacc tgccccagga ttacacatgg gtagagcctg    1700
caagacctga gaccttccaa ttgctggtga ggtggatgaa cttcaaagct    1750
ataggaacaa agcacataac ttgtcacttt aatctttttc actgactaat    1800
aggactcagt acatatagtc ttaagatcat accttaccta ccaaggtaaa    1850
```

aagagggatc agagtggccc acagacattg ctttcttatc acctatcatg 1900
tgaattctac ctgtattcct gggctggacc acttgataac ttccagtgtc 1950
ctggcagctt ttggaatgac agcagtggta tggggtttat gatgctataa 2000
aacaatgtct gaaaagttgc ctagaatata ttttgttaca aacttgaaat 2050
aaaccaaatt tgatgtt 2067

<210> SEQ ID NO 64
<211> LENGTH: 470
<212> TYPE: PRT
<213> ORGANISM: Homo sapiens

<400> SEQUENCE: 64

Met Ser Arg Leu Gly Ala Leu Gly Gly Ala Arg Ala Gly Leu Gly
1 5 10 15

Leu Leu Leu Gly Thr Ala Ala Gly Leu Gly Phe Leu Cys Leu Leu
20 25 30

Tyr Ser Gln Arg Trp Lys Arg Thr Gln Arg His Gly Arg Ser Gln
35 40 45

Ser Leu Pro Asn Ser Leu Asp Tyr Thr Gln Thr Ser Asp Pro Gly
50 55 60

Arg His Val Met Leu Leu Arg Ala Val Pro Gly Gly Ala Gly Asp
65 70 75

Ala Ser Val Leu Pro Ser Leu Pro Arg Glu Gly Gln Glu Lys Val
80 85 90

Leu Asp Arg Leu Asp Phe Val Leu Thr Ser Leu Val Ala Leu Arg
95 100 105

Arg Glu Val Glu Glu Leu Arg Ser Ser Leu Arg Gly Leu Ala Gly
110 115 120

Glu Ile Val Gly Glu Val Arg Cys His Met Glu Glu Asn Gln Arg
125 130 135

Val Ala Arg Arg Arg Arg Phe Pro Phe Val Arg Glu Arg Ser Asp
140 145 150

Ser Thr Gly Ser Ser Ser Val Tyr Phe Thr Ala Ser Ser Gly Ala
155 160 165

Thr Phe Thr Asp Ala Glu Ser Glu Gly Gly Tyr Thr Thr Ala Asn
170 175 180

Ala Glu Ser Asp Asn Glu Arg Asp Ser Asp Lys Glu Ser Glu Asp
185 190 195

Gly Glu Asp Glu Val Ser Cys Glu Thr Val Lys Met Gly Arg Lys
200 205 210

Asp Ser Leu Asp Leu Glu Glu Glu Ala Ala Ser Gly Ala Ser Ser
215 220 225

Ala Leu Glu Ala Gly Gly Ser Ser Gly Leu Glu Asp Val Leu Pro
230 235 240

Leu Leu Gln Gln Ala Asp Glu Leu His Arg Gly Asp Glu Gln Gly
245 250 255

Lys Arg Glu Gly Phe Gln Leu Leu Leu Asn Asn Lys Leu Val Tyr
260 265 270

Gly Ser Arg Gln Asp Phe Leu Trp Arg Leu Ala Arg Ala Tyr Ser
275 280 285

Asp Met Cys Glu Leu Thr Glu Glu Val Ser Glu Lys Lys Ser Tyr
290 295 300

Ala Leu Asp Gly Lys Glu Glu Ala Glu Ala Ala Leu Glu Lys Gly

```
                305                 310                 315

Asp Glu Ser Ala Asp Cys His Leu Trp Tyr Ala Val Leu Cys Gly
                320                 325                 330

Gln Leu Ala Glu His Glu Ser Ile Gln Arg Arg Ile Gln Ser Gly
                335                 340                 345

Phe Ser Phe Lys Glu His Val Asp Lys Ala Ile Ala Leu Gln Pro
                350                 355                 360

Glu Asn Pro Met Ala His Phe Leu Leu Gly Arg Trp Cys Tyr Gln
                365                 370                 375

Val Ser His Leu Ser Trp Leu Glu Lys Lys Thr Ala Thr Ala Leu
                380                 385                 390

Leu Glu Ser Pro Leu Ser Ala Thr Val Glu Asp Ala Leu Gln Ser
                395                 400                 405

Phe Leu Lys Ala Glu Glu Leu Gln Pro Gly Phe Ser Lys Ala Gly
                410                 415                 420

Arg Val Tyr Ile Ser Lys Cys Tyr Arg Glu Leu Gly Lys Asn Ser
                425                 430                 435

Glu Ala Arg Trp Trp Met Lys Leu Ala Leu Glu Leu Pro Asp Val
                440                 445                 450

Thr Lys Glu Asp Leu Ala Ile Gln Lys Asp Leu Glu Glu Leu Glu
                455                 460                 465

Val Ile Leu Arg Asp
                470


<210> SEQ ID NO 65
<211> LENGTH: 925
<212> TYPE: DNA
<213> ORGANISM: Homo sapiens

<400> SEQUENCE: 65

tgaaggcctg tgagtgagga atgcctctca ccagctgtgc ctgagctgca               50

gcactccagc cactgctgtc tccttagctg ctcacatatg gatactttca              100

cagttcagga ttccactgca atgagctggt ggaggaataa tttctggatc              150

atcttagctg tggccatcat tgttgtctct gtgggcctgg gcctcatcct              200

gtactgtgtc tgtaagtggc agcttagacg aggcaagaaa tgggaaattg              250

ccaagcccct gaaacacaag caagtagatg aagaaaagat gtatgagaat              300

gttcttaatg agtcgccagt tcaattaccg cctctgccac cgaggaattg              350

gccttctcta gaagactctt ccccacagga agccccaagt cagccgcccg              400

ctacatactc actggtaaat aaagttaaaa ataagaagac tgtttccatc              450

ccaagctaca ttgagcctga agatgactat gacgatgttg aaatccctgc              500

aaatactgaa aaagcatcat tttgaaacag ccatttcttc tttttggcaa              550

aactgaagag ggttcacaca acttatttta aaacaatcaa gaatggttga              600

acttcagtag gtctctgggc cctgaaagcc agtggtgatt ttatgaagct              650

ctataagata aagcacttcc caaaccttag atgaagacac ccctgcgatc              700

ggatgactgc agccagagga gacacatggg tgctcggctc tgaggactta              750

gaggggtcag ccttgtgctg ttgaggaaac tttccatggg aaggaccacg              800

gggctccatg gctcccacct gtgggaaact actcatttct tggcattctt              850

tccccccttca ttccctttgg tttgcatggt tctgagtgat attaaatctc             900

agcatttggt tgtgcaaaaa  aaaaa                                         925
```

<210> SEQ ID NO 66
<211> LENGTH: 145
<212> TYPE: PRT
<213> ORGANISM: Homo sapiens

<400> SEQUENCE: 66

Met Asp Thr Phe Thr Val Gln Asp Ser Thr Ala Met Ser Trp Trp
1 5 10 15

Arg Asn Asn Phe Trp Ile Ile Leu Ala Val Ala Ile Ile Val Val
20 25 30

Ser Val Gly Leu Gly Leu Ile Leu Tyr Cys Val Cys Lys Trp Gln
35 40 45

Leu Arg Arg Gly Lys Lys Trp Glu Ile Ala Lys Pro Leu Lys His
50 55 60

Lys Gln Val Asp Glu Glu Lys Met Tyr Glu Asn Val Leu Asn Glu
65 70 75

Ser Pro Val Gln Leu Pro Pro Leu Pro Pro Arg Asn Trp Pro Ser
80 85 90

Leu Glu Asp Ser Ser Pro Gln Glu Ala Pro Ser Gln Pro Pro Ala
95 100 105

Thr Tyr Ser Leu Val Asn Lys Val Lys Asn Lys Lys Thr Val Ser
110 115 120

Ile Pro Ser Tyr Ile Glu Pro Glu Asp Asp Tyr Asp Asp Val Glu
125 130 135

Ile Pro Ala Asn Thr Glu Lys Ala Ser Phe
140 145

<210> SEQ ID NO 67
<211> LENGTH: 3399
<212> TYPE: DNA
<213> ORGANISM: Homo sapiens

<400> SEQUENCE: 67
ctccagttcg ccgactgtaa catgtttcat ccagttcagt atgttttgta 50
tgcaagttgg aaataaataa acgtcctgaa ctggatgaaa catgttacag 100
tcggccgaaa catgagaggc tgtgtgagaa gctgcagccg ccggcagagg 150
agacctcagc atcatctaga gcccagcgct ggccctgcct ccgcctgcgc 200
cgccgccgcc gtcgccgttt ctgttcctgc tactgtccca cctaaacaac 250
tcccgttaca cggacaagtg aacatctgtg gctgtcctct ccttttcttc 300
ctcctcttcc aactccttct cctcctccca cttcccagcc gcagcagaaa 350
gcccccaacc caactgacgc tggcacaact gcaaacggtg tcatccgcac 400
aactttatct cgctcctcgg gctcccctaa ggcattggac ccatcgccgc 450
gtcttttatt tttgcaaagt tgcatcgctg tacatatttt tgtccccgcc 500
acctccctct gtctctggag tgccctacag ccccgcaaac tcctcctgga 550
gctgcgccct agtgcccctg ctgggcagtg gcgttccccc ccatcctccc 600
gcgcccagcc cctgctgctc tgggcagacg atgctgaaga tgctctcctt 650
taagctgctg ctgctggccg tggctctggg cttctttgaa ggagatgcta 700
agtttgggga aagaaacgaa gggagcggag caaggaggag aaggtgcctg 750
aatgggaacc ccccgaagcg cctgaaaagg agagacagga ggatgatgtc 800
ccagctggag ctgctgagtg ggggagagat gctgtgcggt ggcttctacc 850
ctcggctgtc ctgctgcctg cggagtgaca gcccggggct agggcgcctg 900
gagaataaga tattttctgt taccaacaac acagaatgtg ggaagttact 950
ggaggaaatc aaatgtgcac tttgctctcc acattctcaa agcctgttcc 1000
actcacctga gagagaagtc ttggaaagag acctagtact tcctctgctc 1050
tgcaaagact attgcaaaga attcttttac acttgccgag gccatattcc 1100
aggtttcctt caaacaactg cggatgagtt ttgcttttac tatgcaagaa 1150
aagatggtgg gttgtgcttt ccagattttc caagaaaaca agtcagagga 1200
ccagcatcta actacttgga ccagatggaa gaatatgaca aagtggaaga 1250
gatcagcaga aagcacaaac acaactgctt ctgtattcag gaggttgtga 1300
gtgggctgcg gcagcccgtt ggtgccctgc atagtgggga tggctcgcaa 1350
cgtctcttca ttctggaaaa agaaggttat gtgaagatac ttacccctga 1400
aggagaaatt ttcaaggagc cttatttgga cattcacaaa cttgttcaaa 1450
gtggaataaa gggaggagat gaaagaggac tgctaagcct cgcattccat 1500
cccaattaca agaaaaatgg aaagttgtat gtgtcctata ccaccaacca 1550
agaacggtgg gctatcgggc ctcatgacca cattcttagg gttgtggaat 1600
acacagtatc cagaaaaaat ccacaccaag ttgatttgag aacagccaga 1650
gtctttcttg aagttgcaga actccacaga aagcatctgg gaggacaact 1700
gctctttggc cctgacggct tttgtacat cattcttggt gatgggatga 1750
ttacactgga tgatatggaa gaaatggatg ggttaagtga tttcacaggc 1800
tcagtgctac ggctggatgt ggacacagac atgtgcaacg tgccttattc 1850
cataccaagg agcaacccac acttcaacag caccaaccag cccccgaag 1900
tgtttgctca tgggctccac gatccaggca gatgtgctgt ggatagacat 1950
cccactgata taaacatcaa tttaacgata ctgtgttcag actccaatgg 2000
aaaaaacaga tcatcagcca gaattctaca gataataaag gggaaagatt 2050
atgaaagtga gccatcactt ttagaattca agccattcag taatggtcct 2100
ttggttggtg gatttgtata ccggggctgc cagtcagaaa gattgtatgg 2150
aagctacgtg tttggagatc gtaatgggaa tttcctaact ctccagcaaa 2200
gtcctgtgac aaagcagtgg caagaaaaac cactctgtct cggcactagt 2250
gggtcctgta gaggctactt ttccggtcac atcttgggat ttggagaaga 2300
tgaactaggt gaagtttaca ttttatcaag cagtaaaagt atgacccaga 2350
ctcacaatgg aaaactctac aaaattgtag atcccaaaag acctttaatg 2400
cctgaggaat gcagagccac ggtacaacct gcacagacac tgacttcaga 2450
gtgctccagg ctctgtcgaa acggctactg cacccccacg ggaaagtgct 2500
gctgcagtcc aggctgggag ggggacttct gcagaactgc aaaatgtgag 2550
ccagcatgtc gtcatggagg tgtctgtgtt agaccgaaca agtgcctctg 2600
taaaaaagga tatcttggtc ctcaatgtga acaagtggac agaaacatcc 2650
gcagagtgac cagggcaggt attcttgatc agatcattga catgacatct 2700
tacttgctgg atctaacaag ttacattgta tagtttctgg gactgtttga 2750
atattctatt ccaatgggca tttatttttt atcctgtcat taaaaaaaaa 2800
aagactgtta tcctgctaca cactcctgtg atttcattct cttttattaa 2850

```
tttaaaaata atttccagaa atgtgcagat cctctgtgtg tatgtcagca        2900

tgtttgttca catatgcaca tacacatact cataacccct atatgcgttg        2950

ttgcataaca gatgattttt taaaatatat acttccttat gcaaagtaat        3000

ttacacagaa attccattgt aaattgataa tggatttttt atgttactag        3050

aagagattat ttgacttccc aggaattttc tgtctgtaat cactaaagtc        3100

aactttaata gagttttgaa acagtactgt gcaatccgat ggatctaatt        3150

aaaaaaaagg caatattttt atattaaagt actatactag gagagaatgt        3200

ttcagaactc cctgatgaat ttctaagtga gcaacttgat ataaaattgt        3250

aatcttcatt tttgtcagtg tatccagtta cagaatgcta cacacttacc        3300

tttttattgg ctgagaaatc tggttatttc atcttaatct caagattgtt        3350

ttcaagtgtt ttataattaa atcataatag catattttaa  aatcaaaaa        3399
```

<210> SEQ ID NO 68
<211> LENGTH: 882
<212> TYPE: PRT
<213> ORGANISM: Homo sapiens

<400> SEQUENCE: 68

```
Met Lys His Val Thr Val Gly Arg Asn Met Arg Gly Cys Val Arg
  1               5                  10                  15

Ser Cys Ser Arg Arg Gln Arg Arg Pro Gln His His Leu Glu Pro
                 20                  25                  30

Ser Ala Gly Pro Ala Ser Ala Cys Ala Ala Ala Ala Val Ala Val
                 35                  40                  45

Ser Val Pro Ala Thr Val Pro Pro Lys Gln Leu Pro Leu His Gly
                 50                  55                  60

Gln Val Asn Ile Cys Gly Cys Pro Leu Leu Phe Phe Leu Leu Phe
                 65                  70                  75

Gln Leu Leu Leu Leu Leu Pro Leu Pro Ser Arg Ser Arg Lys Pro
                 80                  85                  90

Pro Thr Gln Leu Thr Leu Ala Gln Leu Gln Thr Val Ser Ser Ala
                 95                 100                 105

Gln Leu Tyr Leu Ala Pro Arg Ala Pro Leu Arg His Trp Thr His
                110                 115                 120

Arg Arg Val Phe Tyr Phe Cys Lys Val Ala Ser Leu Tyr Ile Phe
                125                 130                 135

Leu Ser Pro Pro Pro Pro Ser Val Ser Gly Val Pro Tyr Ser Pro
                140                 145                 150

Ala Asn Ser Ser Trp Ser Cys Ala Leu Val Pro Leu Leu Gly Ser
                155                 160                 165

Gly Val Pro Pro His Pro Pro Ala Pro Ser Pro Cys Cys Ser Gly
                170                 175                 180

Gln Thr Met Leu Lys Met Leu Ser Phe Lys Leu Leu Leu Leu Ala
                185                 190                 195

Val Ala Leu Gly Phe Phe Glu Gly Asp Ala Lys Phe Gly Glu Arg
                200                 205                 210

Asn Glu Gly Ser Gly Ala Arg Arg Arg Arg Cys Leu Asn Gly Asn
                215                 220                 225

Pro Pro Lys Arg Leu Lys Arg Arg Asp Arg Arg Met Met Ser Gln
                230                 235                 240

Leu Glu Leu Leu Ser Gly Gly Glu Met Leu Cys Gly Gly Phe Tyr
```

-continued

```
                245                 250                 255

Pro Arg Leu Ser Cys Cys Leu Arg Ser Asp Ser Pro Gly Leu Gly
                260                 265                 270

Arg Leu Glu Asn Lys Ile Phe Ser Val Thr Asn Asn Thr Glu Cys
                275                 280                 285

Gly Lys Leu Leu Glu Glu Ile Lys Cys Ala Leu Cys Ser Pro His
                290                 295                 300

Ser Gln Ser Leu Phe His Ser Pro Glu Arg Glu Val Leu Glu Arg
                305                 310                 315

Asp Leu Val Leu Pro Leu Leu Cys Lys Asp Tyr Cys Lys Glu Phe
                320                 325                 330

Phe Tyr Thr Cys Arg Gly His Ile Pro Gly Phe Leu Gln Thr Thr
                335                 340                 345

Ala Asp Glu Phe Cys Phe Tyr Tyr Ala Arg Lys Asp Gly Gly Leu
                350                 355                 360

Cys Phe Pro Asp Phe Pro Arg Lys Gln Val Arg Gly Pro Ala Ser
                365                 370                 375

Asn Tyr Leu Asp Gln Met Glu Glu Tyr Asp Lys Val Glu Glu Ile
                380                 385                 390

Ser Arg Lys His Lys His Asn Cys Phe Cys Ile Gln Glu Val Val
                395                 400                 405

Ser Gly Leu Arg Gln Pro Val Gly Ala Leu His Ser Gly Asp Gly
                410                 415                 420

Ser Gln Arg Leu Phe Ile Leu Glu Lys Glu Gly Tyr Val Lys Ile
                425                 430                 435

Leu Thr Pro Glu Gly Glu Ile Phe Lys Glu Pro Tyr Leu Asp Ile
                440                 445                 450

His Lys Leu Val Gln Ser Gly Ile Lys Gly Gly Asp Glu Arg Gly
                455                 460                 465

Leu Leu Ser Leu Ala Phe His Pro Asn Tyr Lys Lys Asn Gly Lys
                470                 475                 480

Leu Tyr Val Ser Tyr Thr Thr Asn Gln Glu Arg Trp Ala Ile Gly
                485                 490                 495

Pro His Asp His Ile Leu Arg Val Val Glu Tyr Thr Val Ser Arg
                500                 505                 510

Lys Asn Pro His Gln Val Asp Leu Arg Thr Ala Arg Val Phe Leu
                515                 520                 525

Glu Val Ala Glu Leu His Arg Lys His Leu Gly Gly Gln Leu Leu
                530                 535                 540

Phe Gly Pro Asp Gly Phe Leu Tyr Ile Ile Leu Gly Asp Gly Met
                545                 550                 555

Ile Thr Leu Asp Asp Met Glu Glu Met Asp Gly Leu Ser Asp Phe
                560                 565                 570

Thr Gly Ser Val Leu Arg Leu Asp Val Asp Thr Asp Met Cys Asn
                575                 580                 585

Val Pro Tyr Ser Ile Pro Arg Ser Asn Pro His Phe Asn Ser Thr
                590                 595                 600

Asn Gln Pro Pro Glu Val Phe Ala His Gly Leu His Asp Pro Gly
                605                 610                 615

Arg Cys Ala Val Asp Arg His Pro Thr Asp Ile Asn Ile Asn Leu
                620                 625                 630

Thr Ile Leu Cys Ser Asp Ser Asn Gly Lys Asn Arg Ser Ser Ala
                635                 640                 645
```

```
Arg Ile Leu Gln Ile Ile Lys Gly Lys Asp Tyr Glu Ser Glu Pro
                650                 655                 660

Ser Leu Leu Glu Phe Lys Pro Phe Ser Asn Gly Pro Leu Val Gly
                665                 670                 675

Gly Phe Val Tyr Arg Gly Cys Gln Ser Glu Arg Leu Tyr Gly Ser
                680                 685                 690

Tyr Val Phe Gly Asp Arg Asn Gly Asn Phe Leu Thr Leu Gln Gln
                695                 700                 705

Ser Pro Val Thr Lys Gln Trp Gln Glu Lys Pro Leu Cys Leu Gly
                710                 715                 720

Thr Ser Gly Ser Cys Arg Gly Tyr Phe Ser Gly His Ile Leu Gly
                725                 730                 735

Phe Gly Glu Asp Glu Leu Gly Glu Val Tyr Ile Leu Ser Ser Ser
                740                 745                 750

Lys Ser Met Thr Gln Thr His Asn Gly Lys Leu Tyr Lys Ile Val
                755                 760                 765

Asp Pro Lys Arg Pro Leu Met Pro Glu Glu Cys Arg Ala Thr Val
                770                 775                 780

Gln Pro Ala Gln Thr Leu Thr Ser Glu Cys Ser Arg Leu Cys Arg
                785                 790                 795

Asn Gly Tyr Cys Thr Pro Thr Gly Lys Cys Cys Cys Ser Pro Gly
                800                 805                 810

Trp Glu Gly Asp Phe Cys Arg Thr Ala Lys Cys Glu Pro Ala Cys
                815                 820                 825

Arg His Gly Gly Val Cys Val Arg Pro Asn Lys Cys Leu Cys Lys
                830                 835                 840

Lys Gly Tyr Leu Gly Pro Gln Cys Glu Gln Val Asp Arg Asn Ile
                845                 850                 855

Arg Arg Val Thr Arg Ala Gly Ile Leu Asp Gln Ile Ile Asp Met
                860                 865                 870

Thr Ser Tyr Leu Leu Asp Leu Thr Ser Tyr Ile Val
                875                 880


<210> SEQ ID NO 69
<211> LENGTH: 2601
<212> TYPE: DNA
<213> ORGANISM: Homo sapiens

<400> SEQUENCE: 69

ccggggcctc cggagaacgc tgtcccatga acgtgcgggg agcggccccc          50

ggcgtccgcg cgtccccgcg tccctggcaa ttcccgactt cccaacggct         100

tcccgctggc agccccgaag ccgcaccatg ttccgcctct ggttgctgct         150

ggccgggctc tgcggcctcc tggcgtcaag acccggtttt caaaattcac         200

ttctacagat cgtaattcca gagaaaatcc aaacaaatac aaatgacagt         250

tcagaaatag aatatgaaca aatatcctat attattccaa tagatgagaa         300

actgtacact gtgcacctta aacaaagata ttttttagca gataatttta         350

tgatctattt gtacaatcaa ggatctatga atacttattc ttcagatatt         400

cagactcaat gctactatca aggaaatatt gaaggatatc cagattccat         450

ggtcacactc agcacgtgct ctggactaag aggaatactg caatttgaaa         500

atgtttctta tggaattgag cctctggaat ctgcagttga atttcagcat         550

gttctttaca aattaaagaa tgaagacaat gatattgcaa tttttattga         600
```

-continued

```
cagaagcctg aaagaacaac caatggatga caacattttt ataagtgaaa       650
aatcagaacc agctgttcca gatttatttc ctctttatct agaaatgcat       700
attgtggtgg acaaaacttt gtatgattac tggggctctg atagcatgat       750
agtaacaaat aaagtcatcg aaattgttgg ccttgcaaat tcaatgttca       800
cccaatttaa agttactatt gtgctgtcat cattggagtt atggtcagat       850
gaaaataaga tttctacagt tggtgaggca gatgaattat tgcaaaaatt       900
tttagaatgg aaacaatctt atcttaacct aaggcctcat gatattgcat       950
atctactaat ttatatggat tatcctcgtt atttgggagc agtgtttcct      1000
ggaacaatgt gtattactcg ttattctgca ggagttgcat tgtaccccaa      1050
ggagataact ctggaggcat ttgcagttat tgtcacccag atgctggcac      1100
tcagtctggg aatatcatat gacgacccaa agaaatgtca atgttcagaa      1150
tccacctgta taatgaatcc agaagttgtg caatccaatg gtgtgaagac      1200
ttttagcagt tgcagtttga ggagctttca aaatttcatt tcaaatgtgg      1250
gtgtcaaatg tcttcagaat aagccacaaa tgcaaaaaaa atctccgaaa      1300
ccagtctgtg gcaatggcag attggaggga aatgaaatct gtgattgtgg      1350
tactgaggct caatgtggac ctgcaagctg ttgtgatttt cgaacttgtg      1400
tactgaaaga cggagcaaaa tgttataaag gactgtgctg caaagactgt      1450
caaattttac aatcaggcgt tgaatgtagg ccgaaagcac atcctgaatg      1500
tgacatcgct gaaaattgta atggaagctc accagaatgt ggtcctgaca      1550
taactttaat caatggactt tcatgcaaaa ataataagtt tatttgttat      1600
gacggagact gccatgatct cgatgcacgt tgtgagagtg tatttggaaa      1650
aggttcaaga aatgctccat ttgcctgcta tgaagaaata caatctcaat      1700
cagacagatt tgggaactgt ggtagggata gaaataacaa atatgtgttc      1750
tgtggatgga ggaatcttat atgtggaaga ttagtttgta cctaccctac      1800
tcgaaagcct ttccatcaag aaaatggtga tgtgatttat gctttcgtac      1850
gagattctgt atgcataact gtagactaca aattgcctcg aacagttcca      1900
gatccactgg ctgtcaaaaa tggctctcag tgtgatattg ggagggtttg      1950
tgtaaatcgt gaatgtgtag aatcaaggat aattaaggct tcagcacatg      2000
tttgttcaca acagtgttct ggacatggag tgtgtgattc cagaaacaag      2050
tgccattgtt cgccaggcta taagcctcca aactgccaaa tacgttccaa      2100
aggattttcc atatttcctg aggaagatat gggttcaatc atggaaagag      2150
catctgggaa gactgaaaac acctggcttc taggtttcct cattgctctt      2200
cctattctca ttgtaacaac cgcaatagtt ttggcaagga aacagttgaa      2250
aaagtggttc gccaaggaag aggaattccc aagtagcgaa tctaaatcgg      2300
aaggtagcac acagacatat gccagccaat ccagctcaga aggcagcact      2350
cagacatatg ccagccaaac cagatcagaa agcagcagtc aagctgatac      2400
tagcaaatcc aaatcagaag atagtgctga agcatatact agcagatcca      2450
aatcacagga cagtacccaa acacaaagca gtagtaacta gtgattcctt      2500
cagaaggcaa cggataacat cgagagtctc gctaagaaat gaaaattctg      2550
tctttccttc cgtggtcaca gctgaaagaa acaataaatt gagtgtggat      2600
```

c 2601

<210> SEQ ID NO 70
<211> LENGTH: 787
<212> TYPE: PRT
<213> ORGANISM: Homo sapiens

<400> SEQUENCE: 70

Met Phe Arg Leu Trp Leu Leu Leu Ala Gly Leu Cys Gly Leu Leu
1 5 10 15

Ala Ser Arg Pro Gly Phe Gln Asn Ser Leu Leu Gln Ile Val Ile
20 25 30

Pro Glu Lys Ile Gln Thr Asn Thr Asn Asp Ser Ser Glu Ile Glu
35 40 45

Tyr Glu Gln Ile Ser Tyr Ile Ile Pro Ile Asp Glu Lys Leu Tyr
50 55 60

Thr Val His Leu Lys Gln Arg Tyr Phe Leu Ala Asp Asn Phe Met
65 70 75

Ile Tyr Leu Tyr Asn Gln Gly Ser Met Asn Thr Tyr Ser Ser Asp
80 85 90

Ile Gln Thr Gln Cys Tyr Tyr Gln Gly Asn Ile Glu Gly Tyr Pro
95 100 105

Asp Ser Met Val Thr Leu Ser Thr Cys Ser Gly Leu Arg Gly Ile
110 115 120

Leu Gln Phe Glu Asn Val Ser Tyr Gly Ile Glu Pro Leu Glu Ser
125 130 135

Ala Val Glu Phe Gln His Val Leu Tyr Lys Leu Lys Asn Glu Asp
140 145 150

Asn Asp Ile Ala Ile Phe Ile Asp Arg Ser Leu Lys Glu Gln Pro
155 160 165

Met Asp Asp Asn Ile Phe Ile Ser Glu Lys Ser Glu Pro Ala Val
170 175 180

Pro Asp Leu Phe Pro Leu Tyr Leu Glu Met His Ile Val Val Asp
185 190 195

Lys Thr Leu Tyr Asp Tyr Trp Gly Ser Asp Ser Met Ile Val Thr
200 205 210

Asn Lys Val Ile Glu Ile Val Gly Leu Ala Asn Ser Met Phe Thr
215 220 225

Gln Phe Lys Val Thr Ile Val Leu Ser Ser Leu Glu Leu Trp Ser
230 235 240

Asp Glu Asn Lys Ile Ser Thr Val Gly Glu Ala Asp Glu Leu Leu
245 250 255

Gln Lys Phe Leu Glu Trp Lys Gln Ser Tyr Leu Asn Leu Arg Pro
260 265 270

His Asp Ile Ala Tyr Leu Leu Ile Tyr Met Asp Tyr Pro Arg Tyr
275 280 285

Leu Gly Ala Val Phe Pro Gly Thr Met Cys Ile Thr Arg Tyr Ser
290 295 300

Ala Gly Val Ala Leu Tyr Pro Lys Glu Ile Thr Leu Glu Ala Phe
305 310 315

Ala Val Ile Val Thr Gln Met Leu Ala Leu Ser Leu Gly Ile Ser
320 325 330

Tyr Asp Asp Pro Lys Lys Cys Gln Cys Ser Glu Ser Thr Cys Ile
335 340 345

Met Asn Pro Glu Val Val Gln Ser Asn Gly Val Lys Thr Phe Ser

-continued

```
                    350                 355                 360

Ser Cys Ser Leu Arg Ser Phe Gln Asn Phe Ile Ser Asn Val Gly
                    365                 370                 375

Val Lys Cys Leu Gln Asn Lys Pro Gln Met Gln Lys Lys Ser Pro
                    380                 385                 390

Lys Pro Val Cys Gly Asn Gly Arg Leu Glu Gly Asn Glu Ile Cys
                    395                 400                 405

Asp Cys Gly Thr Glu Ala Gln Cys Gly Pro Ala Ser Cys Cys Asp
                    410                 415                 420

Phe Arg Thr Cys Val Leu Lys Asp Gly Ala Lys Cys Tyr Lys Gly
                    425                 430                 435

Leu Cys Cys Lys Asp Cys Gln Ile Leu Gln Ser Gly Val Glu Cys
                    440                 445                 450

Arg Pro Lys Ala His Pro Glu Cys Asp Ile Ala Glu Asn Cys Asn
                    455                 460                 465

Gly Ser Ser Pro Glu Cys Gly Pro Asp Ile Thr Leu Ile Asn Gly
                    470                 475                 480

Leu Ser Cys Lys Asn Asn Lys Phe Ile Cys Tyr Asp Gly Asp Cys
                    485                 490                 495

His Asp Leu Asp Ala Arg Cys Glu Ser Val Phe Gly Lys Gly Ser
                    500                 505                 510

Arg Asn Ala Pro Phe Ala Cys Tyr Glu Glu Ile Gln Ser Gln Ser
                    515                 520                 525

Asp Arg Phe Gly Asn Cys Gly Arg Asp Arg Asn Asn Lys Tyr Val
                    530                 535                 540

Phe Cys Gly Trp Arg Asn Leu Ile Cys Gly Arg Leu Val Cys Thr
                    545                 550                 555

Tyr Pro Thr Arg Lys Pro Phe His Gln Glu Asn Gly Asp Val Ile
                    560                 565                 570

Tyr Ala Phe Val Arg Asp Ser Val Cys Ile Thr Val Asp Tyr Lys
                    575                 580                 585

Leu Pro Arg Thr Val Pro Asp Pro Leu Ala Val Lys Asn Gly Ser
                    590                 595                 600

Gln Cys Asp Ile Gly Arg Val Cys Val Asn Arg Glu Cys Val Glu
                    605                 610                 615

Ser Arg Ile Ile Lys Ala Ser Ala His Val Cys Ser Gln Gln Cys
                    620                 625                 630

Ser Gly His Gly Val Cys Asp Ser Arg Asn Lys Cys His Cys Ser
                    635                 640                 645

Pro Gly Tyr Lys Pro Pro Asn Cys Gln Ile Arg Ser Lys Gly Phe
                    650                 655                 660

Ser Ile Phe Pro Glu Glu Asp Met Gly Ser Ile Met Glu Arg Ala
                    665                 670                 675

Ser Gly Lys Thr Glu Asn Thr Trp Leu Leu Gly Phe Leu Ile Ala
                    680                 685                 690

Leu Pro Ile Leu Ile Val Thr Thr Ala Ile Val Leu Ala Arg Lys
                    695                 700                 705

Gln Leu Lys Lys Trp Phe Ala Lys Glu Glu Glu Phe Pro Ser Ser
                    710                 715                 720

Glu Ser Lys Ser Glu Gly Ser Thr Gln Thr Tyr Ala Ser Gln Ser
                    725                 730                 735

Ser Ser Glu Gly Ser Thr Gln Thr Tyr Ala Ser Gln Thr Arg Ser
                    740                 745                 750
```

Glu Ser Ser Ser Gln Ala Asp Thr Ser Lys Ser Lys Ser Glu Asp
755 760 765

Ser Ala Glu Ala Tyr Thr Ser Arg Ser Lys Ser Gln Asp Ser Thr
770 775 780

Gln Thr Gln Ser Ser Ser Asn
785

<210> SEQ ID NO 71
<211> LENGTH: 1952
<212> TYPE: DNA
<213> ORGANISM: Homo sapiens

<400> SEQUENCE: 71
ggcacgagag atctgtggtc catctgccct aaggacttga gctgcacctg 50
tctcaaaggg agctacttgc ctcgagtctc atgcctctgt gcttgctgct 100
tctggtcttc gctcctgtcg gagtccagtc cgactggttg agcatcagcc 150
ttccacaccg ttcttatgaa ggagaccaag tagttataag ctgcacaggg 200
aaaaataatg gtgacataaa gagactgaag tacttcaagg atggatatca 250
catagaaact tacagcagtg cttcaagcta caccattagg aatgcaagac 300
gcggtgacag tggctcctat tcctgtaagg cagataggaa atttttccta 350
tttatagaca caacagaaga aacaggatct aagtggctga atgtccaaga 400
gctgtttcca gcacctgggc tgacagccag ccccctgcag cccgtagagg 450
ggagttcagt gaccctgtcc tgcaacacct ggctcccttc agatagggca 500
acgacccagc tacgctattc cttcttcaaa gatggccaca ctttgcaatc 550
gggctggacc tcatcaaaat ttaccatctc agcaatatcg aaggaagact 600
caggaaatta ctggtgtgaa gcaatgactg cctctcgcag tgtctcaaag 650
cagagtcacc ggtcctacat agatgtagag aggatccctg tatctcaagt 700
caccatggag atccagcctt caagaggctg gggagttgaa ggggagccac 750
tggtcgttga aggggagccc ctggtccttg cttgttctgt ggctaaaggc 800
actgggctaa tcacattctc ctggcatagg caggacacta aggaaagtgt 850
ggggaagaaa agtcagcgtt cccagagagt ggagctggag atccctacta 900
tcagggaaag ccatgctggg gggtactact gcacagcaga caacaactac 950
ggcctgatcc agagtgcaat cgtgaacatc accgtgaaaa ttccagtgtt 1000
gaacccgctc ctctccatca gtgttcctgg ggtcttgccc ttcatcggag 1050
atgtggcgga gcttcactgt gaagacaaga gagcatctcc tccggttctc 1100
tactggtttt atcatgaaaa tatcactctg gctaacacct cggcaccttt 1150
tggaggaaag gcatccttta agctctctct gactgcaggg cattctggga 1200
actactcttg tgaggctgaa aacgcctggg gtaccaagcg cagtgaggtg 1250
gtaacgctca atgtcacaga gcccccaccc aaagtgcgtt tggtgaatgg 1300
cccccaccac tgtgaaggac gcgtagaggt tgaacaggaa ggtcgctggg 1350
gcactgtatg tgatgatggc tgggacatga gggatgtggc tgtggtgtgc 1400
cgagagctgg gctgtggagc agcccaacac acacctatag ccatgctgta 1450
tccaccagca gttgatgaag ctctgcctgt gctcattcag gtagccctgt 1500
gcaatggcac agaaaagacc ctggctgaat gtgaccaggt tgaggccttt 1550
gattgtggac atgatgagga tgctggagct gtgtgtgaag tcttacccag 1600

-continued

```
cactttctga agatctagag accagagacc atcagacctc ctactttctg            1650

cactgggcct cacagccctc acggtctgca gctcccagtg gacttccaga            1700

cttcagctgt ggcttatcat tcaagaggac tcaaaactat attaatctgc            1750

tctgagataa tgttccaaaa gctccaaaga aagcccgagt cccttgcccc            1800

cagaggccaa gcttggaaaa attgttcccc tgtccaggtt ccctgccttt            1850

ctagctcctt cttgctatct ccttgggcag acgtgcgcag aggtggcgca            1900

agtgaggatc acatacatgt gcctgggctt ccatctggta gaatgtggtc            1950

ta                                                                1952


<210> SEQ ID NO 72
<211> LENGTH: 526
<212> TYPE: PRT
<213> ORGANISM: Homo sapiens

<400> SEQUENCE: 72

Met Pro Leu Cys Leu Leu Leu Leu Val Phe Ala Pro Val Gly Val
  1               5                  10                  15

Gln Ser Asp Trp Leu Ser Ile Ser Leu Pro His Arg Ser Tyr Glu
                 20                  25                  30

Gly Asp Gln Val Val Ile Ser Cys Thr Gly Lys Asn Asn Gly Asp
                 35                  40                  45

Ile Lys Arg Leu Lys Tyr Phe Lys Asp Gly Tyr His Ile Glu Thr
                 50                  55                  60

Tyr Ser Ser Ala Ser Ser Tyr Thr Ile Arg Asn Ala Arg Arg Gly
                 65                  70                  75

Asp Ser Gly Ser Tyr Ser Cys Lys Ala Asp Arg Lys Phe Phe Leu
                 80                  85                  90

Phe Ile Asp Thr Thr Glu Glu Thr Gly Ser Lys Trp Leu Asn Val
                 95                 100                 105

Gln Glu Leu Phe Pro Ala Pro Gly Leu Thr Ala Ser Pro Leu Gln
                110                 115                 120

Pro Val Glu Gly Ser Ser Val Thr Leu Ser Cys Asn Thr Trp Leu
                125                 130                 135

Pro Ser Asp Arg Ala Thr Thr Gln Leu Arg Tyr Ser Phe Phe Lys
                140                 145                 150

Asp Gly His Thr Leu Gln Ser Gly Trp Thr Ser Ser Lys Phe Thr
                155                 160                 165

Ile Ser Ala Ile Ser Lys Glu Asp Ser Gly Asn Tyr Trp Cys Glu
                170                 175                 180

Ala Met Thr Ala Ser Arg Ser Val Ser Lys Gln Ser His Arg Ser
                185                 190                 195

Tyr Ile Asp Val Glu Arg Ile Pro Val Ser Gln Val Thr Met Glu
                200                 205                 210

Ile Gln Pro Ser Arg Gly Trp Gly Val Glu Gly Glu Pro Leu Val
                215                 220                 225

Val Glu Gly Glu Pro Leu Val Leu Ala Cys Ser Val Ala Lys Gly
                230                 235                 240

Thr Gly Leu Ile Thr Phe Ser Trp His Arg Gln Asp Thr Lys Glu
                245                 250                 255

Ser Val Gly Lys Lys Ser Gln Arg Ser Gln Arg Val Glu Leu Glu
                260                 265                 270

Ile Pro Thr Ile Arg Glu Gly His Ala Gly Gly Tyr Tyr Cys Thr
```

-continued

```
                275                 280                 285

Ala Asp Asn Asn Tyr Gly Leu Ile Gln Ser Ala Ile Val Asn Ile
                290                 295                 300

Thr Val Lys Ile Pro Val Leu Asn Pro Leu Leu Ser Ile Ser Val
                305                 310                 315

Pro Gly Val Leu Pro Phe Ile Gly Asp Val Ala Glu Leu His Cys
                320                 325                 330

Glu Asp Lys Arg Ala Ser Pro Pro Val Leu Tyr Trp Phe Tyr His
                335                 340                 345

Glu Asn Ile Thr Leu Ala Asn Thr Ser Ala Pro Phe Gly Gly Lys
                350                 355                 360

Ala Ser Phe Lys Leu Ser Leu Thr Ala Gly His Ser Gly Asn Tyr
                365                 370                 375

Ser Cys Glu Ala Glu Asn Ala Trp Gly Thr Lys Arg Ser Glu Val
                380                 385                 390

Val Thr Leu Asn Val Thr Glu Pro Pro Pro Lys Val Arg Leu Val
                395                 400                 405

Asn Gly Pro His His Cys Glu Gly Arg Val Glu Val Glu Gln Glu
                410                 415                 420

Gly Arg Trp Gly Thr Val Cys Asp Asp Gly Trp Asp Met Arg Asp
                425                 430                 435

Val Ala Val Val Cys Arg Glu Leu Gly Cys Gly Ala Ala Gln His
                440                 445                 450

Thr Pro Ile Ala Met Leu Tyr Pro Pro Ala Val Asp Glu Ala Leu
                455                 460                 465

Pro Val Leu Ile Gln Val Ala Leu Cys Asn Gly Thr Glu Lys Thr
                470                 475                 480

Leu Ala Glu Cys Asp Gln Val Glu Ala Phe Asp Cys Gly His Asp
                485                 490                 495

Glu Asp Ala Glu Phe Gly Gly Gly Leu Asn Asp Ile Phe Glu Ala
                500                 505                 510

Gln Lys Ile Glu Trp His Glu Gly Arg Ala His His His His His
                515                 520                 525

His


<210> SEQ ID NO 73
<211> LENGTH: 1322
<212> TYPE: DNA
<213> ORGANISM: Homo sapiens

<400> SEQUENCE: 73

atatatcgat atgctgccga ggctgttgct gttgatctgt gctccactct              50

gtgaacctgc cgagctgttt ttgatagcca gcccctccca tcccacagag             100

gggagcccag tgaccctgac gtgtaagatg ccctttctac agagttcaga             150

tgcccagttc cagttctgct tttcagaga cacccgggcc ttgggcccag              200

gctggagcag ctcccccaag ctccagatcg ctgccatgtg gaaagaagac             250

acagggtcat actggtgcga ggcacagaca atggcgtcca aagtcttgag             300

gagcaggaga tcccagataa atgtgcacag ggtccctgtc gctgatgtga             350

gcttggagac tcagccccca ggaggacagg tgatggaggg agacaggctg             400

gtcctcatct gctcagttgc tatgggcaca ggagacatca ccttcctttg             450

gtacaaaggg gctgtaggtt taaaccttca gtcaaagacc cagcgttcac             500
```

-continued

```
tgacagcaga gtatgagatt ccttcagtga gggagagtga tgctgagcaa    550
tattactgtg tagctgaaaa tggctatggt cccagcccca gtgggctggt    600
gagcatcact gtcagaatcc cggtgtctcg cccaatcctc atgctcaggg    650
ctcccagggc ccaggctgca gtggaggatg tgctggagct tcactgtgag    700
gccctgagag gctctcctcc gatcctgtac tggttttatc acgaggatat    750
caccctgggg agcaggtcgg ccccctctgg aggaggagcc tccttcaacc    800
tttccctgac tgaagaacat tctggaaact actcctgtga ggccaacaat    850
ggcctggggg cccagcgcag tgaggcggtg acactcaact tcacagtgcc    900
tactggggcc agaagcaatc atcttacctc aggagtcatt gaggggctgc    950
tcagcaccct tggtccagcc accgtggcct tattattttg ctacggcctc   1000
aaaagaaaaa taggaagacg ttcagccagg gatccactca ggagccttcc   1050
cagccctcta ccccaagagt tcacgtacct caactcacct accccagggc   1100
agctacagcc tatatatgaa aatgtgaatg ttgtaagtgg ggatgaggtt   1150
tattcactgg cgtactataa ccagccggag caggaatcag tagcagcaga   1200
aaccctgggg acacatatgg aggacaaggt ttccttagac atctattcca   1250
ggctgaggaa agcaaacatt acagatgtgg actatgaaga tgctatgtaa   1300
ggttatggaa gattctgctc  tt                                1322
```

<210> SEQ ID NO 74
<211> LENGTH: 429
<212> TYPE: PRT
<213> ORGANISM: Homo sapiens

<400> SEQUENCE: 74

```
Met Leu Pro Arg Leu Leu Leu Leu Ile Cys Ala Pro Leu Cys Glu
  1               5                  10                  15

Pro Ala Glu Leu Phe Leu Ile Ala Ser Pro Ser His Pro Thr Glu
                 20                  25                  30

Gly Ser Pro Val Thr Leu Thr Cys Lys Met Pro Phe Leu Gln Ser
                 35                  40                  45

Ser Asp Ala Gln Phe Gln Phe Cys Phe Phe Arg Asp Thr Arg Ala
                 50                  55                  60

Leu Gly Pro Gly Trp Ser Ser Ser Pro Lys Leu Gln Ile Ala Ala
                 65                  70                  75

Met Trp Lys Glu Asp Thr Gly Ser Tyr Trp Cys Glu Ala Gln Thr
                 80                  85                  90

Met Ala Ser Lys Val Leu Arg Ser Arg Arg Ser Gln Ile Asn Val
                 95                 100                 105

His Arg Val Pro Val Ala Asp Val Ser Leu Glu Thr Gln Pro Pro
                110                 115                 120

Gly Gly Gln Val Met Glu Gly Asp Arg Leu Val Leu Ile Cys Ser
                125                 130                 135

Val Ala Met Gly Thr Gly Asp Ile Thr Phe Leu Trp Tyr Lys Gly
                140                 145                 150

Ala Val Gly Leu Asn Leu Gln Ser Lys Thr Gln Arg Ser Leu Thr
                155                 160                 165

Ala Glu Tyr Glu Ile Pro Ser Val Arg Glu Ser Asp Ala Glu Gln
                170                 175                 180

Tyr Tyr Cys Val Ala Glu Asn Gly Tyr Gly Pro Ser Pro Ser Gly
                185                 190                 195
```

Leu Val Ser Ile Thr Val Arg Ile Pro Val Ser Arg Pro Ile Leu
200 205 210

Met Leu Arg Ala Pro Arg Ala Gln Ala Ala Val Glu Asp Val Leu
215 220 225

Glu Leu His Cys Glu Ala Leu Arg Gly Ser Pro Pro Ile Leu Tyr
230 235 240

Trp Phe Tyr His Glu Asp Ile Thr Leu Gly Ser Arg Ser Ala Pro
245 250 255

Ser Gly Gly Gly Ala Ser Phe Asn Leu Ser Leu Thr Glu Glu His
260 265 270

Ser Gly Asn Tyr Ser Cys Glu Ala Asn Asn Gly Leu Gly Ala Gln
275 280 285

Arg Ser Glu Ala Val Thr Leu Asn Phe Thr Val Pro Thr Gly Ala
290 295 300

Arg Ser Asn His Leu Thr Ser Gly Val Ile Glu Gly Leu Leu Ser
305 310 315

Thr Leu Gly Pro Ala Thr Val Ala Leu Leu Phe Cys Tyr Gly Leu
320 325 330

Lys Arg Lys Ile Gly Arg Arg Ser Ala Arg Asp Pro Leu Arg Ser
335 340 345

Leu Pro Ser Pro Leu Pro Gln Glu Phe Thr Tyr Leu Asn Ser Pro
350 355 360

Thr Pro Gly Gln Leu Gln Pro Ile Tyr Glu Asn Val Asn Val Val
365 370 375

Ser Gly Asp Glu Val Tyr Ser Leu Ala Tyr Tyr Asn Gln Pro Glu
380 385 390

Gln Glu Ser Val Ala Ala Glu Thr Leu Gly Thr His Met Glu Asp
395 400 405

Lys Val Ser Leu Asp Ile Tyr Ser Arg Leu Arg Lys Ala Asn Ile
410 415 420

Thr Asp Val Asp Tyr Glu Asp Ala Met
425

<210> SEQ ID NO 75
<211> LENGTH: 3265
<212> TYPE: DNA
<213> ORGANISM: Homo sapiens

<400> SEQUENCE: 75
gccaggaata actagagagg aacaatgggg ttattcagag gttttgtttt 50
cctcttagtt ctgtgcctgc tgcaccagtc aaatacttcc ttcattaagc 100
tgaataataa tggctttgaa gatattgtca ttgttataga tcctagtgtg 150
ccagaagatg aaaaaataat tgaacaaata gaggatatgg tgactacagc 200
ttctacgtac ctgtttgaag ccacagaaaa aagatttttt ttcaaaaatg 250
tatctatatt aattcctgag aattggaagg aaaatcctca gtacaaaagg 300
ccaaaacatg aaaaccataa acatgctgat gttatagttg caccacctac 350
actcccaggt agagatgaac catacaccaa gcagttcaca gaatgtggag 400
agaaaggcga atacattcac ttcacccctg accttctact tggaaaaaaa 450
caaaatgaat atggaccacc aggcaaactg tttgtccatg agtgggctca 500
cctccggtgg ggagtgtttg atgagtacaa tgaagatcag cctttctacc 550
gtgctaagtc aaaaaaaatc gaagcaacaa ggtgttccgc aggtatctct 600

-continued

```
ggtagaaata gagtttataa gtgtcaagga ggcagctgtc ttagtagagc        650
atgcagaatt gattctacaa caaaactgta tggaaaagat tgtcaattct        700
ttcctgataa agtacaaaca gaaaaagcat ccataatgtt tatgcaaagt        750
attgattctg ttgttgaatt ttgtaacgaa aaaacccata atcaagaagc        800
tccaagccta caaaacataa agtgcaattt tagaagtaca tgggaggtga        850
ttagcaattc tgaggatttt aaaaacacca tacccatggt gacaccacct        900
cctccacctg tcttctcatt gctgaagatc agtcaaagaa ttgtgtgctt        950
agttcttgat aagtctggaa gcatgggggg taaggaccgc ctaaatcgaa       1000
tgaatcaagc agcaaaacat ttcctgctgc agactgttga aaatggatcc       1050
tgggtgggga tggttcactt tgatagtact gccactattg taaataagct       1100
aatccaaata aaaagcagtg atgaaagaaa cacactcatg gcaggattac       1150
ctacatatcc tctgggagga acttccatct gctctggaat taaatatgca       1200
tttcaggtga ttggagagct acattcccaa ctcgatggat ccgaagtact       1250
gctgctgact gatggggagg ataacactgc aagttcttgt attgatgaag       1300
tgaaacaaag tggggccatt gttcatttta ttgctttggg aagagctgct       1350
gatgaagcag taatagagat gagcaagata acaggaggaa gtcattttta       1400
tgtttcagat gaagctcaga acaatggcct cattgatgct tttggggctc       1450
ttacatcagg aaatactgat ctctcccaga agtcccttca gctcgaaagt       1500
aagggattaa cactgaatag taatgcctgg atgaacgaca ctgtcataat       1550
tgatagtaca gtgggaaagg acacgttctt tctcatcaca tggaacagtc       1600
tgcctcccag tatttctctc tggatcccca gtggaacaat aatggaaaat       1650
ttcacagtgg atgcaacttc caaaatggcc tatctcagta ttccaggaac       1700
tgcaaaggtg ggcacttggg catacaatct tcaagccaaa gcgaacccag       1750
aaacattaac tattacagta acttctcgag cagcaaattc ttctgtgcct       1800
ccaatcacag tgaatgctaa aatgaataag gacgtaaaca gtttccccag       1850
cccaatgatt gtttacgcag aaattctaca aggatatgta cctgttcttg       1900
gagccaatgt gactgctttc attgaatcac agaatggaca tacagaagtt       1950
ttggaacttt tggataatgg tgcaggcgct gattctttca agaatgatgg       2000
agtctactcc aggtatttta cagcatatac agaaaatggc agatatagct       2050
taaaagttcg ggctcatgga ggagcaaaca ctgccaggct aaaattacgg       2100
cctccactga atagagccgc gtacatacca ggctgggtag tgaacgggga       2150
aattgaagca aacccgccaa gacctgaaat tgatgaggat actcagacca       2200
ccttggagga tttcagccga acagcatccg gaggtgcatt tgtggtatca       2250
caagtcccaa gccttccctt gcctgaccaa tacccaccaa gtcaaatcac       2300
agaccttgat gccacagttc atgaggataa gattattctt acatggacag       2350
caccaggaga taattttgat gttggaaaag ttcaacgtta tatcataaga       2400
ataagtgcaa gtattcttga tctaagagac agttttgatg atgctcttca       2450
agtaaatact actgatctgt caccaaagga ggccaactcc aaggaaagct       2500
ttgcatttaa accagaaaat atctcagaag aaaatgcaac ccacatattt       2550
attgccatta aaagtataga taaaagcaat ttgacatcaa aagtatccaa       2600
```

```
cattgcacaa gtaactttgt ttatccctca agcaaatcct gatgacattg        2650
atcctacacc tactcctact cctactccta ctcctgataa aagtcataat        2700
tctggagtta atatttctac gctggtattg tctgtgattg ggtctgttgt        2750
aattgttaac tttattttaa gtaccaccat ttgaacctta acgaagaaaa        2800
aaatcttcaa gtagacctag aagagagttt taaaaaacaa aacaatgtaa        2850
gtaaaggata tttctgaatc ttaaaattca tcccatgtgt gatcataaac        2900
tcataaaaat aattttaaga tgtcggaaaa ggatactttg attaaataaa        2950
aacactcatg gatatgtaaa aactgtcaag attaaaattt aatagtttca        3000
tttatttgtt attttatttg taagaaatag tgatgaacaa agatcctttt        3050
tcatactgat acctggttgt atattatttg atgcaacagt tttctgaaat        3100
gatatttcaa attgcatcaa gaaattaaaa tcatctatct gagtagtcaa        3150
aatacaagta aaggagagca aataaacaac atttggaaaa aaaaaaaaaa        3200
aaaaaaaaaa aaaaaaaaaa aaaaaaaaaa aaaaaaaaaa aaaaaaaaaa        3250
aaaaaaaaaa  aaaaa                                             3265
```

<210> SEQ ID NO 76
<211> LENGTH: 919
<212> TYPE: PRT
<213> ORGANISM: Homo sapiens

<400> SEQUENCE: 76

```
Met Gly Leu Phe Arg Gly Phe Val Phe Leu Leu Val Leu Cys Leu
  1               5                  10                  15

Leu His Gln Ser Asn Thr Ser Phe Ile Lys Leu Asn Asn Asn Gly
                 20                  25                  30

Phe Glu Asp Ile Val Ile Val Ile Asp Pro Ser Val Pro Glu Asp
                 35                  40                  45

Glu Lys Ile Ile Glu Gln Ile Glu Asp Met Val Thr Thr Ala Ser
                 50                  55                  60

Thr Tyr Leu Phe Glu Ala Thr Glu Lys Arg Phe Phe Phe Lys Asn
                 65                  70                  75

Val Ser Ile Leu Ile Pro Glu Asn Trp Lys Glu Asn Pro Gln Tyr
                 80                  85                  90

Lys Arg Pro Lys His Glu Asn His Lys His Ala Asp Val Ile Val
                 95                 100                 105

Ala Pro Pro Thr Leu Pro Gly Arg Asp Glu Pro Tyr Thr Lys Gln
                110                 115                 120

Phe Thr Glu Cys Gly Glu Lys Gly Glu Tyr Ile His Phe Thr Pro
                125                 130                 135

Asp Leu Leu Leu Gly Lys Lys Gln Asn Glu Tyr Gly Pro Pro Gly
                140                 145                 150

Lys Leu Phe Val His Glu Trp Ala His Leu Arg Trp Gly Val Phe
                155                 160                 165

Asp Glu Tyr Asn Glu Asp Gln Pro Phe Tyr Arg Ala Lys Ser Lys
                170                 175                 180

Lys Ile Glu Ala Thr Arg Cys Ser Ala Gly Ile Ser Gly Arg Asn
                185                 190                 195

Arg Val Tyr Lys Cys Gln Gly Gly Ser Cys Leu Ser Arg Ala Cys
                200                 205                 210

Arg Ile Asp Ser Thr Thr Lys Leu Tyr Gly Lys Asp Cys Gln Phe
```

-continued

```
                215                 220                 225

Phe Pro Asp Lys Val Gln Thr Glu Lys Ala Ser Ile Met Phe Met
                230                 235                 240

Gln Ser Ile Asp Ser Val Val Glu Phe Cys Asn Glu Lys Thr His
                245                 250                 255

Asn Gln Glu Ala Pro Ser Leu Gln Asn Ile Lys Cys Asn Phe Arg
                260                 265                 270

Ser Thr Trp Glu Val Ile Ser Asn Ser Glu Asp Phe Lys Asn Thr
                275                 280                 285

Ile Pro Met Val Thr Pro Pro Pro Pro Pro Val Phe Ser Leu Leu
                290                 295                 300

Lys Ile Ser Gln Arg Ile Val Cys Leu Val Leu Asp Lys Ser Gly
                305                 310                 315

Ser Met Gly Gly Lys Asp Arg Leu Asn Arg Met Asn Gln Ala Ala
                320                 325                 330

Lys His Phe Leu Leu Gln Thr Val Glu Asn Gly Ser Trp Val Gly
                335                 340                 345

Met Val His Phe Asp Ser Thr Ala Thr Ile Val Asn Lys Leu Ile
                350                 355                 360

Gln Ile Lys Ser Ser Asp Glu Arg Asn Thr Leu Met Ala Gly Leu
                365                 370                 375

Pro Thr Tyr Pro Leu Gly Gly Thr Ser Ile Cys Ser Gly Ile Lys
                380                 385                 390

Tyr Ala Phe Gln Val Ile Gly Glu Leu His Ser Gln Leu Asp Gly
                395                 400                 405

Ser Glu Val Leu Leu Leu Thr Asp Gly Glu Asp Asn Thr Ala Ser
                410                 415                 420

Ser Cys Ile Asp Glu Val Lys Gln Ser Gly Ala Ile Val His Phe
                425                 430                 435

Ile Ala Leu Gly Arg Ala Ala Asp Glu Ala Val Ile Glu Met Ser
                440                 445                 450

Lys Ile Thr Gly Gly Ser His Phe Tyr Val Ser Asp Glu Ala Gln
                455                 460                 465

Asn Asn Gly Leu Ile Asp Ala Phe Gly Ala Leu Thr Ser Gly Asn
                470                 475                 480

Thr Asp Leu Ser Gln Lys Ser Leu Gln Leu Glu Ser Lys Gly Leu
                485                 490                 495

Thr Leu Asn Ser Asn Ala Trp Met Asn Asp Thr Val Ile Ile Asp
                500                 505                 510

Ser Thr Val Gly Lys Asp Thr Phe Phe Leu Ile Thr Trp Asn Ser
                515                 520                 525

Leu Pro Pro Ser Ile Ser Leu Trp Asp Pro Ser Gly Thr Ile Met
                530                 535                 540

Glu Asn Phe Thr Val Asp Ala Thr Ser Lys Met Ala Tyr Leu Ser
                545                 550                 555

Ile Pro Gly Thr Ala Lys Val Gly Thr Trp Ala Tyr Asn Leu Gln
                560                 565                 570

Ala Lys Ala Asn Pro Glu Thr Leu Thr Ile Thr Val Thr Ser Arg
                575                 580                 585

Ala Ala Asn Ser Ser Val Pro Pro Ile Thr Val Asn Ala Lys Met
                590                 595                 600

Asn Lys Asp Val Asn Ser Phe Pro Ser Pro Met Ile Val Tyr Ala
                605                 610                 615
```

Glu Ile Leu Gln Gly Tyr Val Pro Val Leu Gly Ala Asn Val Thr
620 625 630

Ala Phe Ile Glu Ser Gln Asn Gly His Thr Glu Val Leu Glu Leu
635 640 645

Leu Asp Asn Gly Ala Gly Ala Asp Ser Phe Lys Asn Asp Gly Val
650 655 660

Tyr Ser Arg Tyr Phe Thr Ala Tyr Thr Glu Asn Gly Arg Tyr Ser
665 670 675

Leu Lys Val Arg Ala His Gly Gly Ala Asn Thr Ala Arg Leu Lys
680 685 690

Leu Arg Pro Pro Leu Asn Arg Ala Ala Tyr Ile Pro Gly Trp Val
695 700 705

Val Asn Gly Glu Ile Glu Ala Asn Pro Pro Arg Pro Glu Ile Asp
710 715 720

Glu Asp Thr Gln Thr Thr Leu Glu Asp Phe Ser Arg Thr Ala Ser
725 730 735

Gly Gly Ala Phe Val Val Ser Gln Val Pro Ser Leu Pro Leu Pro
740 745 750

Asp Gln Tyr Pro Pro Ser Gln Ile Thr Asp Leu Asp Ala Thr Val
755 760 765

His Glu Asp Lys Ile Ile Leu Thr Trp Thr Ala Pro Gly Asp Asn
770 775 780

Phe Asp Val Gly Lys Val Gln Arg Tyr Ile Ile Arg Ile Ser Ala
785 790 795

Ser Ile Leu Asp Leu Arg Asp Ser Phe Asp Asp Ala Leu Gln Val
800 805 810

Asn Thr Thr Asp Leu Ser Pro Lys Glu Ala Asn Ser Lys Glu Ser
815 820 825

Phe Ala Phe Lys Pro Glu Asn Ile Ser Glu Glu Asn Ala Thr His
830 835 840

Ile Phe Ile Ala Ile Lys Ser Ile Asp Lys Ser Asn Leu Thr Ser
845 850 855

Lys Val Ser Asn Ile Ala Gln Val Thr Leu Phe Ile Pro Gln Ala
860 865 870

Asn Pro Asp Asp Ile Asp Pro Thr Pro Thr Pro Thr Pro Thr Pro
875 880 885

Thr Pro Asp Lys Ser His Asn Ser Gly Val Asn Ile Ser Thr Leu
890 895 900

Val Leu Ser Val Ile Gly Ser Val Val Ile Val Asn Phe Ile Leu
905 910 915

Ser Thr Thr Ile

<210> SEQ ID NO 77
<211> LENGTH: 1164
<212> TYPE: DNA
<213> ORGANISM: Homo sapiens

<400> SEQUENCE: 77
cttctgtagg acagtcacca ggccagatcc agaagcctct ctaggctcca 50
gctttctctg tggaagatga cagcaattat agcaggaccc tgccaggctg 100
tcgaaaagat tccgcaataa aactttgcca gtgggaagta cctagtgaaa 150
cggcctaaga tgccacttct tctcatgtcc caggcttgag gccctgtggt 200
ccccatcctt gggagaagtc agctccagca ccatgaaggg catcctcgtt 250
gctggtatca ctgcagtgct tgttgcagct gtagaatctc tgagctgcgt 300
gcagtgtaat tcatgggaaa aatcctgtgt caacagcatt gcctctgaat 350
gtccctcaca tgccaacacc agctgtatca gctcctcagc cagctcctct 400
ctagagacac cagtcagatt ataccagaat atgttctgct cagcggagaa 450
ctgcagtgag gagacacaca ttacagcctt cactgtccac gtgtctgctg 500
aagaacactt tcattttgta agccagtgct gccaaggaaa ggaatgcagc 550
aacaccagcg atgccctgga ccctcccctg aagaacgtgt ccagcaacgc 600
agagtgccct gcttgttatg aatctaatgg aacttcctgt cgtgggaagc 650
cctggaaatg ctatgaagaa gaacagtgtg tctttctagt tgcagaactt 700
aagaatgaca ttgagtctaa gagtctcgtg ctgaaaggct gttccaacgt 750
cagtaacgcc acctgtcagt tcctgtctgg tgaaaacaag actcttggag 800
gagtcatctt tcgaaagttt gagtgtgcaa atgtaaacag cttaaccccc 850
acgtctgcac caaccacttc ccacaacgtg ggctccaaag cttccctcta 900
cctcttggcc cttgccagcc tccttcttcg gggactgctg ccctgaggtc 950
ctggggctgc actttgccca gcaccccatt tctgcttctc tgaggtccag 1000 agcacccccct gcggtgctga caccctcttt ccctgctctg ccccgtttaa 1050
ctgcccagta agtgggagtc acaggtctcc aggcaatgcc gacagctgcc 1100
ttgttcttca ttattaaagc actggttcat tcactgccaa aaaaaaaaaa 1150
aaaaaaaaaa aaaa 1164

<210> SEQ ID NO 78
<211> LENGTH: 237
<212> TYPE: PRT
<213> ORGANISM: Homo sapiens

<400> SEQUENCE: 78

Met Lys Gly Ile Leu Val Ala Gly Ile Thr Ala Val Leu Val Ala
1 5 10 15

Ala Val Glu Ser Leu Ser Cys Val Gln Cys Asn Ser Trp Glu Lys
20 25 30

Ser Cys Val Asn Ser Ile Ala Ser Glu Cys Pro Ser His Ala Asn
35 40 45

Thr Ser Cys Ile Ser Ser Ser Ala Ser Ser Ser Leu Glu Thr Pro
50 55 60

Val Arg Leu Tyr Gln Asn Met Phe Cys Ser Ala Glu Asn Cys Ser
65 70 75

Glu Glu Thr His Ile Thr Ala Phe Thr Val His Val Ser Ala Glu
80 85 90

Glu His Phe His Phe Val Ser Gln Cys Cys Gln Gly Lys Glu Cys
95 100 105

Ser Asn Thr Ser Asp Ala Leu Asp Pro Pro Leu Lys Asn Val Ser
110 115 120

Ser Asn Ala Glu Cys Pro Ala Cys Tyr Glu Ser Asn Gly Thr Ser
125 130 135

Cys Arg Gly Lys Pro Trp Lys Cys Tyr Glu Glu Glu Gln Cys Val
140 145 150

Phe Leu Val Ala Glu Leu Lys Asn Asp Ile Glu Ser Lys Ser Leu
155 160 165

Val Leu Lys Gly Cys Ser Asn Val Ser Asn Ala Thr Cys Gln Phe

```
                170                 175                 180

Leu Ser Gly Glu Asn Lys Thr Leu Gly Gly Val Ile Phe Arg Lys
                185                 190                 195

Phe Glu Cys Ala Asn Val Asn Ser Leu Thr Pro Thr Ser Ala Pro
                200                 205                 210

Thr Thr Ser His Asn Val Gly Ser Lys Ala Ser Leu Tyr Leu Leu
                215                 220                 225

Ala Leu Ala Ser Leu Leu Leu Arg Gly Leu Leu Pro
                230                 235
```

<210> SEQ ID NO 79
<211> LENGTH: 1643
<212> TYPE: DNA
<213> ORGANISM: Homo sapiens

<400> SEQUENCE: 79

```
ggaattccct gatatacacc tggaccacca ccaatggata tacaaatggc        50

aaacaatttt actccgccct ctgcaactcc tcagggaaat gactgtgacc       100

tctatgcaca tcacagcacg gccaggatag taatgcctct gcattacagc       150

ctcgtcttca tcattgggct cgtgggaaac ttactagcct tggtcgtcat       200

tgttcaaaac aggaaaaaaa tcaactctac caccctctat tcaacaaatt       250

tggtgatttc tgatatactt tttaccacgg ctttgcctac acgaatagcc       300

tactatgcaa tgggctttga ctggagaatc ggagatgcct tgtgtaggat       350

aactgcgcta gtgttttaca tcaacacata tgcaggtgtg aactttatga       400

cctgcctgag tattgaccgc ttcattgctg tggtgcaccc tctacgctac       450

aacaagataa aaaggattga acatgcaaaa ggcgtgtgca tatttgtctg       500

gattctagta tttgctcaga cactcccact cctcatcaac cctatgtcaa       550

agcaggaggc tgaaaggatt acatgcatgg agtatccaaa ctttgaagaa       600

actaaatctc ttccctggat tctgcttggg gcatgtttca taggatatgt       650

acttccactt ataatcattc tcatctgcta ttctcagatc tgctgcaaac       700

tcttcagaac tgccaaacaa aacccactca ctgagaaatc tggtgtaaac       750

aaaaaggctc tcaacacaat tattcttatt attgttgtgt ttgttctctg       800

tttcacacct taccatgttg caattattca acatatgatt aagaagcttc       850

gtttctctaa tttcctggaa tgtagccaaa gacattcgtt ccagatttct       900

ctgcacttta cagtatgcct gatgaacttc aattgctgca tggacccttt       950

tatctacttc tttgcatgta aagggtataa gagaaaggtt atgaggatgc      1000

tgaaacggca agtcagtgta tcgatttcta gtgctgtgaa gtcagcccct      1050

gaagaaaatt cacgtgaaat gacagaaacg cagatgatga tacattccaa      1100

gtcttcaaat ggaaagtgaa atggattgta ttttggttta tagtgacgta      1150

aactgtatga caaactttgc aggacttccc ttataaagca aaataattgt      1200

tcagcttcca attagtattc ttttatattt ctttcattgg gcgctttccc      1250

atctccaact cggaagtaag cccaagagaa caacataaag caaacaacat      1300

aaagcacaat aaaaatgcaa ataaatattt tcatttttat ttgtaaacga      1350

atacaccaaa aggaggcgct cttaataact cccaatgtaa aaagttttgt      1400

tttaataaaa aattaattat tattcttgcc aacaaatggc tagaaaggac      1450
```

```
tgaatagatt atatattgcc agatgttaat actgtaacat actttttaaa          1500

taacatattt cttaaatcca aatttctctc aatgttagat ttaattccct          1550

caataacacc aatgttttgt tttgtttcgt tctgggtcat aaaactttgt          1600

taaggaactc ttttggaata aagagcagga tgctgcggaa  ttc                1643


<210> SEQ ID NO 80
<211> LENGTH: 361
<212> TYPE: PRT
<213> ORGANISM: Homo sapiens

<400> SEQUENCE: 80

Met Asp Ile Gln Met Ala Asn Asn Phe Thr Pro Pro Ser Ala Thr
  1               5                  10                  15

Pro Gln Gly Asn Asp Cys Asp Leu Tyr Ala His His Ser Thr Ala
                 20                  25                  30

Arg Ile Val Met Pro Leu His Tyr Ser Leu Val Phe Ile Ile Gly
                 35                  40                  45

Leu Val Gly Asn Leu Leu Ala Leu Val Val Ile Val Gln Asn Arg
                 50                  55                  60

Lys Lys Ile Asn Ser Thr Thr Leu Tyr Ser Thr Asn Leu Val Ile
                 65                  70                  75

Ser Asp Ile Leu Phe Thr Thr Ala Leu Pro Thr Arg Ile Ala Tyr
                 80                  85                  90

Tyr Ala Met Gly Phe Asp Trp Arg Ile Gly Asp Ala Leu Cys Arg
                 95                 100                 105

Ile Thr Ala Leu Val Phe Tyr Ile Asn Thr Tyr Ala Gly Val Asn
                110                 115                 120

Phe Met Thr Cys Leu Ser Ile Asp Arg Phe Ile Ala Val Val His
                125                 130                 135

Pro Leu Arg Tyr Asn Lys Ile Lys Arg Ile Glu His Ala Lys Gly
                140                 145                 150

Val Cys Ile Phe Val Trp Ile Leu Val Phe Ala Gln Thr Leu Pro
                155                 160                 165

Leu Leu Ile Asn Pro Met Ser Lys Gln Glu Ala Glu Arg Ile Thr
                170                 175                 180

Cys Met Glu Tyr Pro Asn Phe Glu Glu Thr Lys Ser Leu Pro Trp
                185                 190                 195

Ile Leu Leu Gly Ala Cys Phe Ile Gly Tyr Val Leu Pro Leu Ile
                200                 205                 210

Ile Ile Leu Ile Cys Tyr Ser Gln Ile Cys Cys Lys Leu Phe Arg
                215                 220                 225

Thr Ala Lys Gln Asn Pro Leu Thr Glu Lys Ser Gly Val Asn Lys
                230                 235                 240

Lys Ala Leu Asn Thr Ile Ile Leu Ile Ile Val Val Phe Val Leu
                245                 250                 255

Cys Phe Thr Pro Tyr His Val Ala Ile Ile Gln His Met Ile Lys
                260                 265                 270

Lys Leu Arg Phe Ser Asn Phe Leu Glu Cys Ser Gln Arg His Ser
                275                 280                 285

Phe Gln Ile Ser Leu His Phe Thr Val Cys Leu Met Asn Phe Asn
                290                 295                 300

Cys Cys Met Asp Pro Phe Ile Tyr Phe Phe Ala Cys Lys Gly Tyr
                305                 310                 315

Lys Arg Lys Val Met Arg Met Leu Lys Arg Gln Val Ser Val Ser
```

```
                320                 325                 330

Ile Ser Ser Ala Val Lys Ser Ala Pro Glu Glu Asn Ser Arg Glu
                335                 340                 345

Met Thr Glu Thr Gln Met Met Ile His Ser Lys Ser Ser Asn Gly
                350                 355                 360

Lys


<210> SEQ ID NO 81
<211> LENGTH: 43
<212> TYPE: DNA
<213> ORGANISM: Artificial sequence
<220> FEATURE:
<223> OTHER INFORMATION: oligonucleotide probe

<400> SEQUENCE: 81

tgtaaaacga cggccagtta aatagacctg caattattaa  tct                       43


<210> SEQ ID NO 82
<211> LENGTH: 41
<212> TYPE: DNA
<213> ORGANISM: Artificial sequence
<220> FEATURE:
<223> OTHER INFORMATION: oligonucleotide probe

<400> SEQUENCE: 82

caggaaacag ctatgaccac ctgcacacct gcaaatccat  t                         41


<210> SEQ ID NO 83
<211> LENGTH: 22
<212> TYPE: DNA
<213> ORGANISM: Artificial sequence
<220> FEATURE:
<223> OTHER INFORMATION: oligonucleotide probe

<400> SEQUENCE: 83

tcacctggag cctttattgg  cc                                              22


<210> SEQ ID NO 84
<211> LENGTH: 23
<212> TYPE: DNA
<213> ORGANISM: Artificial sequence
<220> FEATURE:
<223> OTHER INFORMATION: oligonucleotide probe

<400> SEQUENCE: 84

ataccagcta taaccaggct  gcg                                             23


<210> SEQ ID NO 85
<211> LENGTH: 52
<212> TYPE: DNA
<213> ORGANISM: Artificial sequence
<220> FEATURE:
<223> OTHER INFORMATION: oligonucleotide probe

<400> SEQUENCE: 85

caacagtaag tggtttgatg ctcttccaaa tctagagatt ctgatgattg                 50

gg                                                                     52


<210> SEQ ID NO 86
<211> LENGTH: 20
<212> TYPE: DNA
<213> ORGANISM: Artificial sequence
<220> FEATURE:
<223> OTHER INFORMATION: oligonucleotide probe
```

<400> SEQUENCE: 86
ggaaatgagt gcaaaccctc 20

<210> SEQ ID NO 87
<211> LENGTH: 24
<212> TYPE: DNA
<213> ORGANISM: Artificial sequence
<220> FEATURE:
<223> OTHER INFORMATION: oligonucleotide probe

<400> SEQUENCE: 87
tcccaagctg aacactcatt ctgc 24

<210> SEQ ID NO 88
<211> LENGTH: 50
<212> TYPE: DNA
<213> ORGANISM: Artificial sequence
<220> FEATURE:
<223> OTHER INFORMATION: oligonucleotide probe

<400> SEQUENCE: 88
gggtgacggt gttccatatc agaattgcag aagcaaaact gacctcagtt 50

<210> SEQ ID NO 89
<211> LENGTH: 20
<212> TYPE: DNA
<213> ORGANISM: Artificial sequence
<220> FEATURE:
<223> OTHER INFORMATION: oligonucleotide probe

<400> SEQUENCE: 89
tcgtacagtt acgctctccc 20

<210> SEQ ID NO 90
<211> LENGTH: 20
<212> TYPE: DNA
<213> ORGANISM: Artificial sequence
<220> FEATURE:
<223> OTHER INFORMATION: oligonucleotide probe

<400> SEQUENCE: 90
cttgaggagc gtcagaagcg 20

<210> SEQ ID NO 91
<211> LENGTH: 20
<212> TYPE: DNA
<213> ORGANISM: Artificial sequence
<220> FEATURE:
<223> OTHER INFORMATION: oligonucleotide probe

<400> SEQUENCE: 91
ataacgaatg aagcctcgtg 20

<210> SEQ ID NO 92
<211> LENGTH: 40
<212> TYPE: DNA
<213> ORGANISM: Artificial sequence
<220> FEATURE:
<223> OTHER INFORMATION: oligonucleotide probe

<400> SEQUENCE: 92
gctaatatct gtaagacggc agctacagca ggcatcattg 40

<210> SEQ ID NO 93
<211> LENGTH: 28
<212> TYPE: DNA

<213> ORGANISM: Artificial sequence
<220> FEATURE:
<223> OTHER INFORMATION: oligonucleotide probe

<400> SEQUENCE: 93
gcctttgaca accttcagtc actagtgg 28

<210> SEQ ID NO 94
<211> LENGTH: 24
<212> TYPE: DNA
<213> ORGANISM: Artificial sequence
<220> FEATURE:
<223> OTHER INFORMATION: oligonucleotide probe

<400> SEQUENCE: 94
ccccatgtgt ccatgactgt tccc 24

<210> SEQ ID NO 95
<211> LENGTH: 45
<212> TYPE: DNA
<213> ORGANISM: Artificial sequence
<220> FEATURE:
<223> OTHER INFORMATION: oligonucleotide probe

<400> SEQUENCE: 95
tactgcctca tgacctcttc actcccttgc atcatcttag agcgg 45

<210> SEQ ID NO 96
<211> LENGTH: 24
<212> TYPE: DNA
<213> ORGANISM: Artificial sequence
<220> FEATURE:
<223> OTHER INFORMATION: oligonucleotide probe

<400> SEQUENCE: 96
gtgggaacca aactccggca gacc 24

<210> SEQ ID NO 97
<211> LENGTH: 18
<212> TYPE: DNA
<213> ORGANISM: Artificial sequence
<220> FEATURE:
<223> OTHER INFORMATION: oligonucleotide probe

<400> SEQUENCE: 97
cacatcgagc gtctctgg 18

<210> SEQ ID NO 98
<211> LENGTH: 24
<212> TYPE: DNA
<213> ORGANISM: Artificial sequence
<220> FEATURE:
<223> OTHER INFORMATION: oligonucleotide probe

<400> SEQUENCE: 98
agccgctcct tctccggttc atcg 24

<210> SEQ ID NO 99
<211> LENGTH: 48
<212> TYPE: DNA
<213> ORGANISM: Artificial sequence
<220> FEATURE:
<223> OTHER INFORMATION: oligonucleotide probe

<400> SEQUENCE: 99
tggaaggacc acttgatatc agtcactcca gacagcatca gggatggg 48

<210> SEQ ID NO 100
<211> LENGTH: 24
<212> TYPE: DNA
<213> ORGANISM: Artificial sequence
<220> FEATURE:
<223> OTHER INFORMATION: oligonucleotide probe

<400> SEQUENCE: 100
ggcttctgct gttgctcttc tccg 24

<210> SEQ ID NO 101
<211> LENGTH: 20
<212> TYPE: DNA
<213> ORGANISM: Artificial sequence
<220> FEATURE:
<223> OTHER INFORMATION: oligonucleotide probe

<400> SEQUENCE: 101
gtacactgtg accagtcagc 20

<210> SEQ ID NO 102
<211> LENGTH: 20
<212> TYPE: DNA
<213> ORGANISM: Artificial sequence
<220> FEATURE:
<223> OTHER INFORMATION: oligonucleotide probe

<400> SEQUENCE: 102
atcatcacag attcccgagc 20

<210> SEQ ID NO 103
<211> LENGTH: 24
<212> TYPE: DNA
<213> ORGANISM: Artificial sequence
<220> FEATURE:
<223> OTHER INFORMATION: oligonucleotide probe

<400> SEQUENCE: 103
ttcaatctcc tcaccttcca ccgc 24

<210> SEQ ID NO 104
<211> LENGTH: 24
<212> TYPE: DNA
<213> ORGANISM: Artificial sequence
<220> FEATURE:
<223> OTHER INFORMATION: Oligonucleotide probe

<400> SEQUENCE: 104
atagctgtgt ctgcgtctgc tgcg 24

<210> SEQ ID NO 105
<211> LENGTH: 50
<212> TYPE: DNA
<213> ORGANISM: Artificial sequence
<220> FEATURE:
<223> OTHER INFORMATION: oligonucleiotide probe

<400> SEQUENCE: 105
cgcggcactg atccccacag gtgatgggca gaatctgttt acgaaagacg 50

<210> SEQ ID NO 106
<211> LENGTH: 26
<212> TYPE: DNA
<213> ORGANISM: Artificial sequence
<220> FEATURE:
<223> OTHER INFORMATION: oligonucleotide probe

<400> SEQUENCE: 106
atccgcccag atggctacaa tgtgta 26

<210> SEQ ID NO 107
<211> LENGTH: 42
<212> TYPE: DNA
<213> ORGANISM: Artificial sequence
<220> FEATURE:
<223> OTHER INFORMATION: oligonucleotide probe

<400> SEQUENCE: 107
gcctcccggt ctccctgagc agtgccaaac agcggcagtg ta 42

<210> SEQ ID NO 108
<211> LENGTH: 22
<212> TYPE: DNA
<213> ORGANISM: Artificial sequence
<220> FEATURE:
<223> OTHER INFORMATION: oligonucleotide probe

<400> SEQUENCE: 108
ccagtccggt gacaagccca aa 22

<210> SEQ ID NO 109
<211> LENGTH: 24
<212> TYPE: DNA
<213> ORGANISM: Artificial sequence
<220> FEATURE:
<223> OTHER INFORMATION: oligonucleotide probe

<400> SEQUENCE: 109
ggacagaatt tgggagcaca ctgg 24

<210> SEQ ID NO 110
<211> LENGTH: 20
<212> TYPE: DNA
<213> ORGANISM: Artificial sequence
<220> FEATURE:
<223> OTHER INFORMATION: oligonucleotide probe

<400> SEQUENCE: 110
ccaagagtat actgtcctcg 20

<210> SEQ ID NO 111
<211> LENGTH: 25
<212> TYPE: DNA
<213> ORGANISM: Artificial sequence
<220> FEATURE:
<223> OTHER INFORMATION: oligonucleotide probe

<400> SEQUENCE: 111
agcacagatt ttctctacag ccccc 25

<210> SEQ ID NO 112
<211> LENGTH: 24
<212> TYPE: DNA
<213> ORGANISM: Artificial sequence
<220> FEATURE:
<223> OTHER INFORMATION: oligonucleotide probe

<400> SEQUENCE: 112
aaccactcca gcatgtactg ctgc 24

<210> SEQ ID NO 113
<211> LENGTH: 50
<212> TYPE: DNA

<213> ORGANISM: Artificial sequence
<220> FEATURE:
<223> OTHER INFORMATION: oligonucleotide probe

<400> SEQUENCE: 113
ccattcaggt gttctggccc tgtatgtaca cattatacac aggtcgtgtg 50

<210> SEQ ID NO 114
<211> LENGTH: 25
<212> TYPE: DNA
<213> ORGANISM: Artificial sequence
<220> FEATURE:
<223> OTHER INFORMATION: oligonucleotide probe

<400> SEQUENCE: 114
ccaaactcac ccagtgagtg tgagc 25

<210> SEQ ID NO 115
<211> LENGTH: 25
<212> TYPE: DNA
<213> ORGANISM: Artificial sequence
<220> FEATURE:
<223> OTHER INFORMATION: oligonucleotide probe

<400> SEQUENCE: 115
tgggaaatca ggaatggtgt tctcc 25

<210> SEQ ID NO 116
<211> LENGTH: 50
<212> TYPE: DNA
<213> ORGANISM: Artificial sequence
<220> FEATURE:
<223> OTHER INFORMATION: oligonucleotide probe

<400> SEQUENCE: 116
cttgttttca ccattgggct aactttgctg ctaggagttc aagccatgcc 50

<210> SEQ ID NO 117
<211> LENGTH: 23
<212> TYPE: DNA
<213> ORGANISM: Artificial sequence
<220> FEATURE:
<223> OTHER INFORMATION: oligonucleotide probe

<400> SEQUENCE: 117
ctccgtggta aaccccacag ccc 23

<210> SEQ ID NO 118
<211> LENGTH: 24
<212> TYPE: DNA
<213> ORGANISM: Artificial sequence
<220> FEATURE:
<223> OTHER INFORMATION: oligonucleotide probe

<400> SEQUENCE: 118
tcacatcgat gggatccatg accg 24

<210> SEQ ID NO 119
<211> LENGTH: 50
<212> TYPE: DNA
<213> ORGANISM: Artificial sequence
<220> FEATURE:
<223> OTHER INFORMATION: oligonucleotide probe

<400> SEQUENCE: 119
ggtctcgtga ctgtgaagcc atgttacaac tactgctcaa acatcatgag 50

<210> SEQ ID NO 120
<211> LENGTH: 19
<212> TYPE: DNA
<213> ORGANISM: Artificial sequence
<220> FEATURE:
<223> OTHER INFORMATION: oligonucleotide probe

<400> SEQUENCE: 120
gaagccggct gtctgaatc 19

<210> SEQ ID NO 121
<211> LENGTH: 18
<212> TYPE: DNA
<213> ORGANISM: Artificial sequence
<220> FEATURE:
<223> OTHER INFORMATION: oligonucleotide probe

<400> SEQUENCE: 121
ggccagctat ctccgcag 18

<210> SEQ ID NO 122
<211> LENGTH: 18
<212> TYPE: DNA
<213> ORGANISM: Artificial sequence
<220> FEATURE:
<223> OTHER INFORMATION: oligonucleotide probe

<400> SEQUENCE: 122
aagggcctgc aagagaag 18

<210> SEQ ID NO 123
<211> LENGTH: 18
<212> TYPE: DNA
<213> ORGANISM: Artificial sequence
<220> FEATURE:
<223> OTHER INFORMATION: oligonucleotide probe

<400> SEQUENCE: 123
cactgggaca actgtggg 18

<210> SEQ ID NO 124
<211> LENGTH: 18
<212> TYPE: DNA
<213> ORGANISM: Artificial sequence
<220> FEATURE:
<223> OTHER INFORMATION: oligonucleotide probe

<400> SEQUENCE: 124
cagaggcaac gtggagag 18

<210> SEQ ID NO 125
<211> LENGTH: 21
<212> TYPE: DNA
<213> ORGANISM: Artificial sequence
<220> FEATURE:
<223> OTHER INFORMATION: oligonucleotide probe

<400> SEQUENCE: 125
aagtattgtc atacagtgtt c 21

<210> SEQ ID NO 126
<211> LENGTH: 24
<212> TYPE: DNA
<213> ORGANISM: Artificial sequence
<220> FEATURE:
<223> OTHER INFORMATION: oligonucleotide probe

<400> SEQUENCE: 126
tagtacttgg gcacgaggtt ggag 24

<210> SEQ ID NO 127
<211> LENGTH: 24
<212> TYPE: DNA
<213> ORGANISM: Artificial sequence
<220> FEATURE:
<223> OTHER INFORMATION: oligonucleotide probe

<400> SEQUENCE: 127
tcataccaac tgctggtcat tggc 24

<210> SEQ ID NO 128
<211> LENGTH: 45
<212> TYPE: DNA
<213> ORGANISM: Artificial sequence
<220> FEATURE:
<223> OTHER INFORMATION: oligonucleotide probe

<400> SEQUENCE: 128
ctcaagctgc tggacacgga gcggccggtg aatcggtttc acttg 45

<210> SEQ ID NO 129
<211> LENGTH: 20
<212> TYPE: DNA
<213> ORGANISM: Artificial sequence
<220> FEATURE:
<223> OTHER INFORMATION: oligonucleotide probe

<400> SEQUENCE: 129
acggctcacc atgggctccg 20

<210> SEQ ID NO 130
<211> LENGTH: 24
<212> TYPE: DNA
<213> ORGANISM: Artificial sequence
<220> FEATURE:
<223> OTHER INFORMATION: oligonucleotide probe

<400> SEQUENCE: 130
aggaagagga gcccttggag tccg 24

<210> SEQ ID NO 131
<211> LENGTH: 24
<212> TYPE: DNA
<213> ORGANISM: Artificial sequence
<220> FEATURE:
<223> OTHER INFORMATION: oligonecleotide probe

<400> SEQUENCE: 131
aggaagagga gcccttggag tccg 24

<210> SEQ ID NO 132
<211> LENGTH: 23
<212> TYPE: DNA
<213> ORGANISM: Artificial sequence
<220> FEATURE:
<223> OTHER INFORMATION: oligoneucleotide probe

<400> SEQUENCE: 132
cgaggtgcag atcgaggtgt cgc 23

<210> SEQ ID NO 133
<211> LENGTH: 25
<212> TYPE: DNA

<213> ORGANISM: Artificial sequence
<220> FEATURE:
<223> OTHER INFORMATION: oligoneucleotide probe

<400> SEQUENCE: 133
ggcactgcag gagaacctca tggtc 25

<210> SEQ ID NO 134
<211> LENGTH: 42
<212> TYPE: DNA
<213> ORGANISM: Artificial sequence
<220> FEATURE:
<223> OTHER INFORMATION: oligoneucleotide probe

<400> SEQUENCE: 134
cagcaggtgg aggagctctt tgggctggag gattactggt gc 42

<210> SEQ ID NO 135
<211> LENGTH: 24
<212> TYPE: DNA
<213> ORGANISM: Artificial sequence
<220> FEATURE:
<223> OTHER INFORMATION: oligoneucleotide probe

<400> SEQUENCE: 135
gacatatgct gccgcttcca ctcc 24

<210> SEQ ID NO 136
<211> LENGTH: 25
<212> TYPE: DNA
<213> ORGANISM: Artificial sequence
<220> FEATURE:
<223> OTHER INFORMATION: oligoneucleotide probe

<400> SEQUENCE: 136
tctcttctcc gcctgcttcc tcagc 25

<210> SEQ ID NO 137
<211> LENGTH: 44
<212> TYPE: DNA
<213> ORGANISM: Artificial sequence
<220> FEATURE:
<223> OTHER INFORMATION: oligoneucleotide probe

<400> SEQUENCE: 137
gacaacttct ctggcgaagc tctctgggaa ctggaggtag cagg 44

<210> SEQ ID NO 138
<211> LENGTH: 22
<212> TYPE: DNA
<213> ORGANISM: Artificial sequence
<220> FEATURE:
<223> OTHER INFORMATION: oligoneucleotide probe

<400> SEQUENCE: 138
gctgctgccg tccatgctga tg 22

<210> SEQ ID NO 139
<211> LENGTH: 23
<212> TYPE: DNA
<213> ORGANISM: Artificial sequence
<220> FEATURE:
<223> OTHER INFORMATION: oligoneucleotide probe

<400> SEQUENCE: 139
ctcggggaat gtgacatcgt cgc 23

<210> SEQ ID NO 140
<211> LENGTH: 35
<212> TYPE: DNA
<213> ORGANISM: Artificial sequence
<220> FEATURE:
<223> OTHER INFORMATION: oligoneucleotide probe

<400> SEQUENCE: 140
gctgccgtcc atgctgatgt ttgcggtgat cgtgg 35

<210> SEQ ID NO 141
<211> LENGTH: 23
<212> TYPE: DNA
<213> ORGANISM: Artificial sequence
<220> FEATURE:
<223> OTHER INFORMATION: oligoneucleotide probe

<400> SEQUENCE: 141
ggagaggtgg atcactcgac ccg 23

<210> SEQ ID NO 142
<211> LENGTH: 24
<212> TYPE: DNA
<213> ORGANISM: Artificial sequence
<220> FEATURE:
<223> OTHER INFORMATION: oligoneucleotide probe

<400> SEQUENCE: 142
acatgccagg gactcctccg aaac 24

<210> SEQ ID NO 143
<211> LENGTH: 42
<212> TYPE: DNA
<213> ORGANISM: Artificial sequence
<220> FEATURE:
<223> OTHER INFORMATION: oligoneucleotide probe

<400> SEQUENCE: 143
gtggatcact cgacccgctt aatttcggat cctgtgctgc tg 42

<210> SEQ ID NO 144
<211> LENGTH: 26
<212> TYPE: DNA
<213> ORGANISM: Artificial sequence
<220> FEATURE:
<223> OTHER INFORMATION: oligoneucleotide probe

<400> SEQUENCE: 144
aatctcagca ccagccactc agagca 26

<210> SEQ ID NO 145
<211> LENGTH: 25
<212> TYPE: DNA
<213> ORGANISM: Artificial sequence
<220> FEATURE:
<223> OTHER INFORMATION: oligoneuclotide probe

<400> SEQUENCE: 145
gttaaagagg gtgcccttcc agcga 25

<210> SEQ ID NO 146
<211> LENGTH: 24
<212> TYPE: DNA
<213> ORGANISM: Artificial sequence
<220> FEATURE:
<223> OTHER INFORMATION: oligoneucleotide probe -continued

```
<400> SEQUENCE: 146

tatcccaatg cctccccact  gctc                                    24


<210> SEQ ID NO 147
<211> LENGTH: 24
<212> TYPE: DNA
<213> ORGANISM: Artificial sequence
<220> FEATURE:
<223> OTHER INFORMATION: oligoneucleotide probe

<400> SEQUENCE: 147

gatgaacttg gcgaaggggc  ggca                                    24
```